United States Patent
Venkatraman et al.

(10) Patent No.: US 7,718,691 B2
(45) Date of Patent: May 18, 2010

(54) COMPOUNDS AS INHIBITORS OF HEPATITIS C VIRUS NS3 SERINE PROTEASE

(75) Inventors: Srikanth Venkatraman, Woodbridge, NJ (US); F. George Njoroge, Warren, NJ (US); Melissa L. Blackman, Ocean, NJ (US); Wanil Wu, Edison, NJ (US); Latha G. Nair, Edison, NJ (US); Ashok Arasappan, Bridgewater, NJ (US); Stephane L. Bogen, Somerset, NJ (US); Kevin X. Chen, Edison, NJ (US); Mousumi Sannigrahi, Summit, NJ (US); Frank Bennett, Cranford, NJ (US); Viyyor M. Girijavallabhan, Parsippany, NJ (US)

(73) Assignee: Schering Corporation, Kenilworth, NJ (US)

( * ) Notice: Subject to any disclaimer, the term of this patent is extended or adjusted under 35 U.S.C. 154(b) by 194 days.

(21) Appl. No.: 11/542,228

(22) Filed: Oct. 3, 2006

(65) Prior Publication Data

US 2007/0049536 A1 Mar. 1, 2007

Related U.S. Application Data

(62) Division of application No. 11/065,509, filed on Feb. 24, 2005, now Pat. No. 7,192,957.

(60) Provisional application No. 60/548,507, filed on Feb. 27, 2004.

(51) Int. Cl.
*A61K 31/403* (2006.01)
*C07D 209/02* (2006.01)
*C07D 403/12* (2006.01)

(52) U.S. Cl. .................. 514/422; 514/423; 548/465; 548/515

(58) Field of Classification Search ................ 548/515, 548/465

See application file for complete search history.

(56) References Cited

U.S. PATENT DOCUMENTS

| 5,712,145 | A | 1/1998 | Houghton et al. | |
|---|---|---|---|---|
| 6,608,027 | B1 | 8/2003 | Tsantrizos et al. | |
| 6,894,072 | B2 * | 5/2005 | Arasappan et al. | .......... 514/422 |
| 2003/0216325 | A1 | 11/2003 | Saksena et al. | |
| 2005/0197301 | A1 | 9/2005 | Njoroge et al. | |
| 2005/0222047 | A1 | 10/2005 | Chen et al. | |

FOREIGN PATENT DOCUMENTS

| EP | 0 381 216 B1 | 12/1995 |
|---|---|---|
| WO | WO 89/04669 A1 | 6/1989 |
| WO | WO 98/14181 A1 | 4/1998 |
| WO | WO 98/17679 A1 | 4/1998 |
| WO | WO 98/22496 A2 | 5/1998 |
| WO | WO 99/07734 A2 | 2/1999 |
| WO | WO 00/09543 A2 | 2/2000 |
| WO | WO 00/09558 A1 | 2/2000 |
| WO | WO 00/59929 A1 | 10/2000 |
| WO | WO 01/07713 A2 | 10/2001 |
| WO | WO 01/74768 A2 | 10/2001 |
| WO | WO 01/81325 A2 | 11/2001 |
| WO | WO 02/08187 A1 | 1/2002 |
| WO | WO 02/08198 A2 | 1/2002 |
| WO | WO 02/08244 A2 | 1/2002 |
| WO | WO 02/08251 A2 | 1/2002 |
| WO | WO 02/08256 A2 | 1/2002 |
| WO | WO 02/48172 A2 | 6/2002 |
| WO | WO 03/035060 A1 | 5/2003 |
| WO | WO 03/062228 A1 | 7/2003 |

OTHER PUBLICATIONS

"Chronic Hepatitis C: Current Disease Management". National Digestive Diseases Information Clearinghouse. retrieved on Nov. 5, 2007 from http://www.digestive.niddk.nih.gov.*
Advanced Drug Delivery Reviews 48 (2001) 3-26.*
Berenguer, Marina, et al., "Hepatitis B and C Viruses: Molecular Identification and Targeted Antiviral Therapies", *Proceedings of the Association of American Physicians*, 110(2):98-112 (1998).
Dimasi, Nazzareno, et al., "Characterization of Engineered Hepatitis C Virus NS3 Protease Inhibitors Affinity Selected from Human Pancreatic Secretory Trypsin Inhibitor and Minibody Repertoires", *Journal of Virology*, 71(10):7461-7469 (1997).
Elzouki, Abdul-Nasser, et al., "Serine Protease Inhibitors In Patients with Chronic Viral Hepatitis", *Journal of Hepatology*, 27:42-48 (1997).
Failla, Cristina Maria, et al., "Redesigning the Substrate Specificity of the Hepatitis C Virus NS3 Protease", *Folding & Design*, 1(1):35-42 (Jan. 10, 1996).
Han, Wei, et al., "α-Ketoamides, α-Ketoesters and α-Diketones as HCV NS3 Protease Inhibitors", *Bioorganic & Medicinal Chemistry Letters*, 10:711-713 (2000).
Hoofnagle, Jay H., et al., "The Treatment of Chronic Viral Hepatitis", *Drug Therapy*, 336(5):347-356 (1997).
Ingallinella, Paolo, et al. "Potent Peptide Inhibitors of Human Hepatitis C Virus NS3 Protease Are Obtained by Optimizing the Cleavage Products", *Biochemistry*, 37:8906-8914 (1998).
Kolykhalov, Alexander A., et al., "Specificity of the Hepatitis C Virus NS3 Serine Protease: Effects of Substitutions at the 3/4A, 4A/4B, 4B/5A, and 5A/5B Cleavage Sites on Polyprotein Processing", *Journal of Virology*, 68(11):7525-7533 (Nov. 1994).

(Continued)

*Primary Examiner*—Rebecca L Anderson
*Assistant Examiner*—Shawquia Young
(74) *Attorney, Agent, or Firm*—Palaiyur S. Kalyanaraman; Serena Farquharson-Torres

(57) ABSTRACT

The present invention discloses novel compounds which have HCV protease inhibitory activity as well as methods for preparing such compounds. In another embodiment, the invention discloses pharmaceutical compositions comprising such compounds as well as methods of using them to treat disorders associated with the HCV protease.

33 Claims, No Drawings

OTHER PUBLICATIONS

Komoda, Yasumasa, et al., "Substrate Requirements of Hepatitis C Virus Serine Proteinase for Intermolecular Polypeptide Cleavage in *Escherichia coli*", *Journal of Virology*, 68(11):7351-7357 (Nov. 1994).

Landro, James A., et al., "Mechanistic Role of an NS4A Peptide Cofactor with the Truncated NS3 Protease of Hepatitis C Virus: Elucidation of the NS4A Stimulatory Effect via Kinetic Analysis and Inhibitor Mapping", *Biochemistry*, 36:9340-9348 (1997).

Llinas-Brunet, Montse, et al., "Peptide-Based Inhibitors of the Hepatitis C Virus Serine Protease", *Bioorganic & Medicinal Chemistry Letters* 8:1713-1718 (1998).

Marchetti, Antonella, et al., "Synthesis of Two Novel Cyclic Biphenyl Ether Analogs of an Inhibitor of HCV NS3 Protease", *Synlett*, S1:1000-1002 (1999).

Martin, F., et al., "Affinity selection of a camelized $V_H$ domain antibody inhibitor of hepatitis C virus NS3 protease", *Protein Engineering*, 10(5):607-614 (1997).

Martin, Franck, et al., "Design of Selective Eglin Inhibitors of HCV NS3 Proteinase", *Biochemistry*, 37:11459-11468 (1998).

Pizzi, Elisabetta, et al., "Molecular model of the specificity pocket of the hepatitis C virus protease: Implications for substrate recognition", *Proc. Natl. Acad. Sci. USA*, 91:888-892 (Feb. 1994).

Lamar, Jason, et al., "Novel P4 truncated tripeptidyl α-ketoamides as HCV protease inhibitors", *Bioorganic & Medicinal Chemistry Letters*, 14:263-266 (2004).

BioWorld Today, 9(217):1-5, (Nov. 10, 1998).

U.S. Appl. No. 10/052,386, filed Jan 18, 2002.

PCT International Search Report dated Sep. 15, 2005 for corresponding PCT Application No. PCT/US2005/005772.

* cited by examiner

COMPOUNDS AS INHIBITORS OF HEPATITIS C VIRUS NS3 SERINE PROTEASE

This application is a divisional of U.S. application Ser. No. 11/065,509, filed Feb. 24, 2005, and claims the benefit of U.S. Provisional Application Ser. No. 60/548,507 filed Feb. 27, 2004.

FIELD OF THE INVENTION

Background of the Invention

Hepatitis C virus (HCV) is a (+)-sense single-stranded RNA virus that has been implicated as the major causative agent in non-A, non-B hepatitis (NANBH), particularly in blood-associated NANBH (BB-NANBH) (see, International Patent Application Publication No. WO 89/04669 and European Patent Application Publication No. EP 381 216). NANBH is to be distinguished from other types of viral-induced liver disease, such as hepatitis A virus (HAV), hepatitis B virus (HBV), delta hepatitis virus (HDV), cytomegalovirus (CMV) and Epstein-Barr virus (EBV), as well as from other forms of liver disease such as alcoholism and primary biliar cirrhosis.

Recently, an HCV protease necessary for polypeptide processing and viral replication has been identified, cloned and expressed. (See, e.g. U.S. Pat. No. 5,712,145). This approximately 3000 amino acid polyprotein contains, from the amino terminus to the carboxy terminus, a nucleocapsid protein (C), envelope proteins (E1 and E2) and several non-structural proteins (NS1, 2, 3, 4a, 5a and 5b). NS3 is an approximately 68 kda protein, encoded by approximately 1893 nucleotides of the HCV genome, and has two distinct domains: (a) a serine protease domain consisting of approximately 200 of the N-terminal amino acids; and (b) an RNA-dependent ATPase domain at the C-terminus of the protein. The NS3 protease is considered a member of the chymotrypsin family because of similarities in protein sequence, overall three-dimensional structure and mechanism of catalysis. Other chymotrypsin-like enzymes are elastase, factor Xa, thrombin, trypsin, plasmin, urokinase, tPA and PSA. The HCV NS3 serine protease is responsible for proteolysis of the polypeptide (polyprotein) at the NS3/NS4a, NS4a/NS4b, NS4b/NS5a and NS5a/NS5b junctions and is thus responsible for generating four viral proteins during viral replication. This has made the HCV NS3 serine protease an attractive target for antiviral chemotherapy. The inventive compounds can inhibit such protease. They also can modulate the processing of hepatitis C virus (HCV) polypeptide.

It has been determined that the NS4a protein, an approximately 6 kda polypeptide, is a co-factor for the serine protease activity of NS3. Autocleavage of the NS3/NS4a junction by the NS3/NS4a serine protease occurs intramolecularly (i.e., cis) while the other cleavage sites are processed intermolecularly (i.e., trans).

Analysis of the natural cleavage sites for HCV protease revealed the presence of cysteine at P1 and serine at P1' and that these residues are strictly conserved in the NS4a/NS4b, NS4b/NS5a and NS5a/NS5b junctions. The NS3/NS4a junction contains a threonine at P1 and a serine at P1'. The Cys→Thr substitution at NS3/NS4a is postulated to account for the requirement of cis rather than trans processing at this junction. See, e.g., Pizzi et al. (1994) *Proc. Natl. Acad. Sci.* (USA) 91:888-892, Failla et al. (1996) *Folding &Design* 1:35-42. The NS3/NS4a cleavage site is also more tolerant of mutagenesis than the other sites. See, e.g., Kollykhalov et al. (1994) *J. Virol.* 68:7525-7533. It has also been found that acidic residues in the region upstream of the cleavage site are required for efficient cleavage. See, e.g., Komoda et al. (1994) *J. Virol.* 68:7351-7357.

Inhibitors of HCV protease that have been reported include antioxidants (see, International Patent Application Publication No. WO 98/14181), certain peptides and peptide analogs (see, International Patent Application Publication No. WO 98/17679, Landro et al. (1997) *Biochem.* 36:9340-9348, Ingallinella et al. (1998) *Biochem.* 37:8906-8914, Llinàs-Brunet et al. (1998) *Bioorg. Med. Chem. Lett.* 8:1713-1718), inhibitors based on the 70-amino acid polypeptide eglin c (Martin et al. (1998) *Biochem.* 37:11459-11468, inhibitors affinity selected from human pancreatic secretory trypsin inhibitor (hPSTI-C3) and minibody repertoires (MBip) (Dimasi et al. (1997) *J. Virol.* 71:7461-7469), $cV_HE2$ (a "camelized" variable domain antibody fragment) (Martin et al. (1997) *Protein Eng.* 10:607-614), and α1-antichymotrypsin (ACT) (Elzouki et al.) (1997) *J. Hepat.* 27:42-28). A ribozyme designed to selectively destroy hepatitis C virus RNA has recently been disclosed (see, *BioWorld Today* 9(217): 4 (Nov. 10, 1998)).

Reference is also made to the PCT Publications, No. WO 98/17679, published Apr. 30, 1998 (Vertex Pharmaceuticals Incorporated); WO 98/22496, published May 28, 1998 (F. Hoffmann-La Roche A G); and WO 99/07734, published Feb. 18, 1999 (Boehringer Ingelheim Canada Ltd.).

HCV has been implicated in cirrhosis of the liver and in induction of hepatocellular carcinoma. The prognosis for patients suffering from HCV infection is currently poor. HCV infection is more difficult to treat than other forms of hepatitis due to the lack of immunity or remission associated with HCV infection. Current data indicates a less than 50% survival rate at four years post cirrhosis diagnosis. Patients diagnosed with localized resectable hepatocellular carcinoma have a five-year survival rate of 10-30%, whereas those with localized unresectable hepatocellular carcinoma have a five-year survival rate of less than 1%.

Reference is made to WO 00/59929 (U.S. Pat. No. 6,608,027, Assignee: Boehringer Ingelheim (Canada) Ltd.; Published Oct. 12, 2000) which discloses peptide derivatives of the formula:

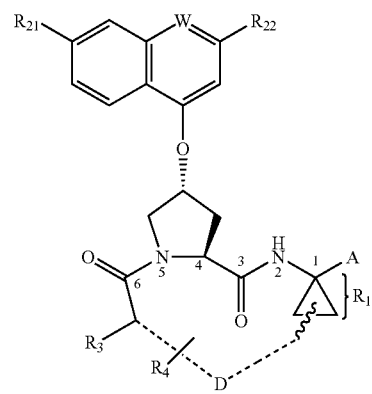

Reference is made to A. Marchetti et al, *Synlett,* S1, 1000-1002 (1999) describing the synthesis of bicylic analogs of an inhibitor of HCV NS3 protease. A compound disclosed therein has the formula:

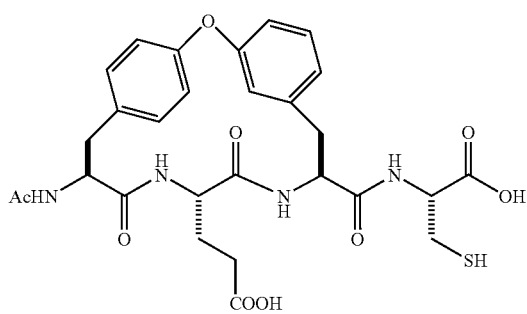

Reference is also made to W. Han et al, *Bioorganic & Medicinal Chem. Lett*, (2000) 10, 711-713, which describes the preparation of certain α-ketoamides, α-ketoesters and α-diketones containing allyl and ethyl functionalities.

Reference is also made to WO 00/09558 (Assignee: Boehringer Ingelheim Limited; Published Feb. 24, 2000) which discloses peptide derivatives of the formula:

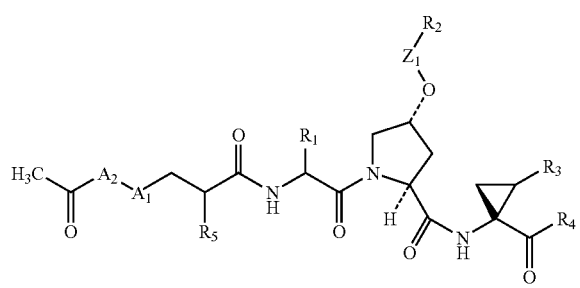

where the various elements are defined therein. An illustrative compound of that series is:

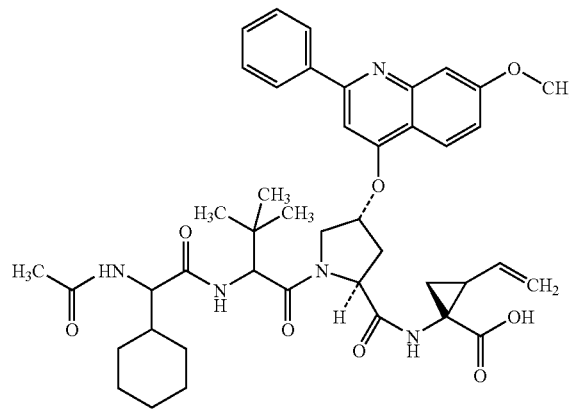

Reference is also made to WO 00/09543 (Assignee: Boehringer Ingelheim Limited; Published Feb. 24, 2000) which discloses peptide derivatives of the formula:

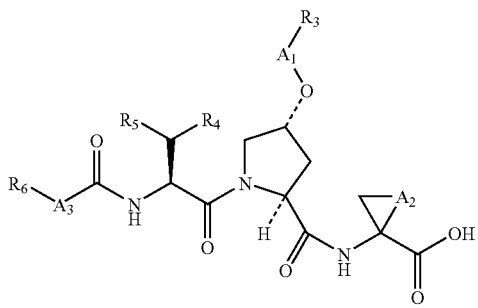

where the various elements are defined therein. An illustrative compound of that series is:

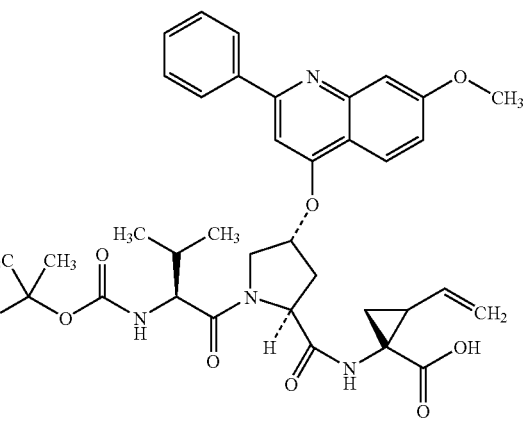

Reference is also made to U.S. Pat. No. 6,608,027 (Boehringer Ingelheim, Canada) which discloses NS3 protease inhibitors of the type:

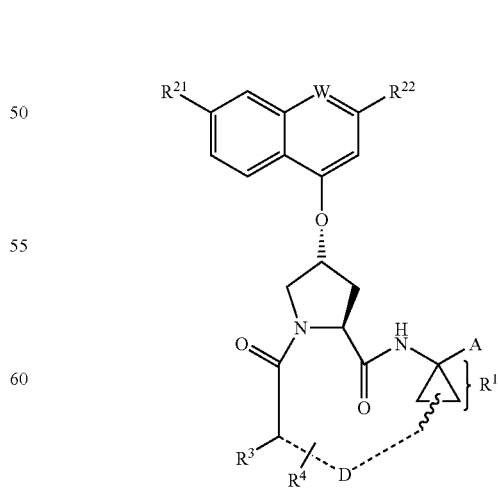

wherein the various moieties are defined therein.

Current therapies for hepatitis C include interferon-α (INF$_α$) and combination therapy with ribavirin and interferon. See, e.g. Beremguer et al. (1998) *Proc. Assoc. Am. Physicians* 110(2):98-112. These therapies suffer from a low sustained response rate and frequent side effects. See, e.g., Hoofnagle et al. (1997) *N. Engl. J. Med.* 336:347. Currently, no vaccine is available for HCV infection.

Reference is further made to WO 01/74768 (Assignee: Vertex Pharmaceuticals Inc) published Oct. 11, 2001, which discloses certain compounds of the following general formula (R is defined therein) as NS3-serine protease inhibitors of Hepatitis C virus:

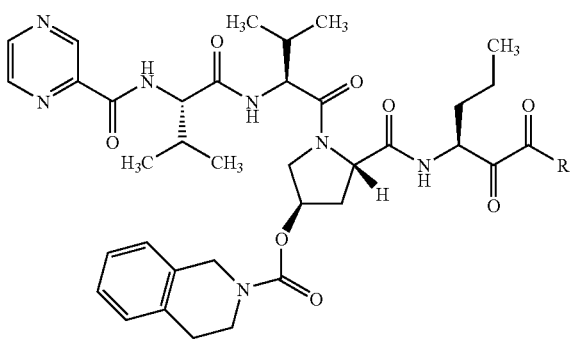

A specific compound disclosed in the afore-mentioned WO 01/74768 has the following

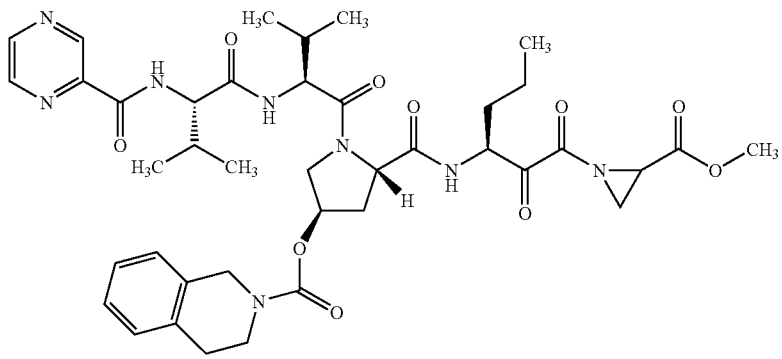

PCT Publications WO 01/77113; WO 01/081325; WO 02/08198; WO 02/08256; WO 02/08187; WO 02/08244; WO 02/48172; WO 02/08251; and pending U.S. patent application Ser. No. 10/052,386, filed Jan. 18, 2002, disclose various types of peptides and/or other compounds as NS-3 serine protease inhibitors of hepatitis C virus. The disclosures of those applications are incorporated herein by reference thereto.

There is a need for new treatments and therapies for HCV infection. There is a need for compounds useful in the treatment or prevention or amelioration of one or more symptoms of hepatitis C.

There is a need for methods of treatment or prevention or amelioration of one or more symptoms of hepatitis C.

There is a need for methods for modulating the activity of serine proteases, particularly the HCV NS3/NS4a serine protease, using the compounds provided herein.

There is a need for methods of modulating the processing of the HCV polypeptide using the compounds provided herein.

SUMMARY OF THE INVENTION

In its many embodiments, the present invention provides a novel class of inhibitors of the HCV protease, pharmaceutical compositions containing one or more of the compounds, methods of preparing pharmaceutical formulations comprising one or more such compounds, and methods of treatment or prevention of HCV or amelioration of one or more of the symptoms of hepatitis C using one or more such compounds or one or more such formulations. Also provided are methods of modulating the interaction of an HCV polypeptide with HCV protease. Among the compounds provided herein, compounds that inhibit HCV NS3/NS4a serine protease activity are preferred. The present invention discloses compounds, or enantiomers, stereoisomers, rotamers, tautomers, diastereomers and racemates of said compounds, or a pharmaceutically acceptable salt, solvate or ester of said compounds, said compounds having the having the general structure shown in structural Formula 1:

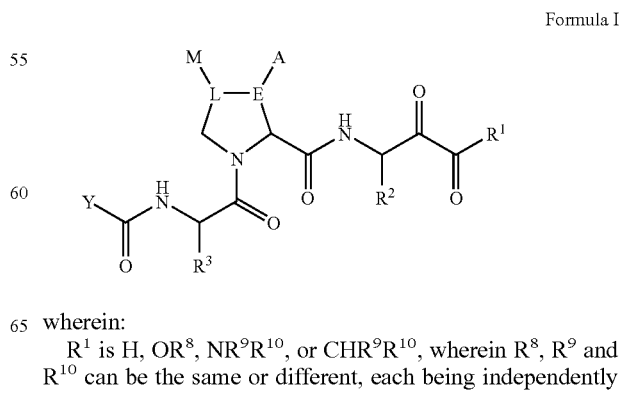

Formula I wherein:
R$^1$ is H, OR$^8$, NR$^9$R$^{10}$, or CHR$^9$R$^{10}$, wherein R$^8$, R$^9$ and R$^{10}$ can be the same or different, each being independently selected from the group consisting of H, alkyl-, alkenyl-, alkynyl-, aryl-, heteroalkyl-, heteroaryl-, cycloalkyl-, heterocyclyl-, arylalkyl-, and heteroarylalkyl;

A and M can be the same or different, each being independently selected from R, $NR^9R^{10}$, SR, $SO_2R$, and halo; or A and M are connected to each other such that the moiety:

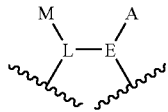

shown above in Formula I (i.e., M-L-E-A taken together) forms either a three, four, six, seven or eight-membered cycloalkyl, a four to eight-membered heterocyclyl, a six to ten-membered aryl, or a five to ten-membered heteroaryl;

E is C(H) or C(R);

L is C(H), C(R), $CH_2C(R)$, or $C(R)CH_2$;

R, R', $R^2$, and $R^3$ can be the same or different, each being independently selected from the group consisting of H, alkyl-, alkenyl-, alkynyl-, cycloalkyl-, heteroalkyl-, heterocyclyl-, aryl-, heteroaryl-, (cycloalkyl)alkyl-, (heterocyclyl)alkyl-, aryl-alkyl-, and heteroaryl-alkyl-; or alternately R and R' in NRR' are connected to each other such that $NR^9R^{10}$ forms a four to eight-membered heterocyclyl;

Y is selected from the following moieties:

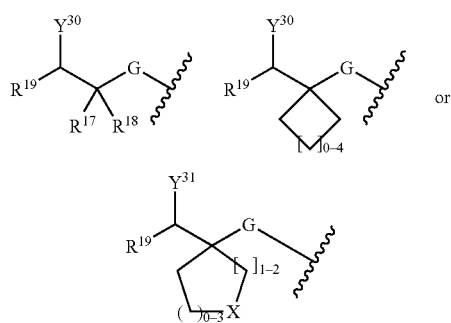

wherein $Y^{30}$ and $Y^{31}$ are selected from

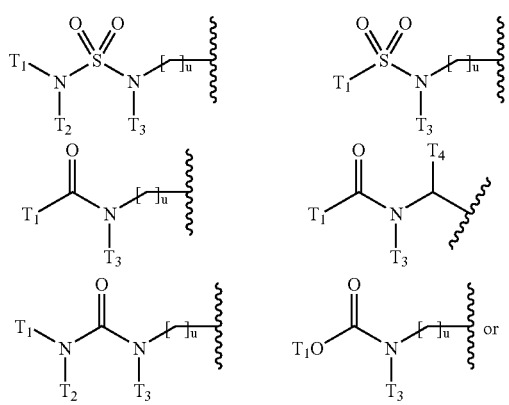

-continued

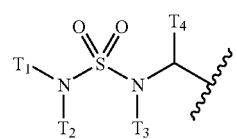

where u is a number 0-6;

X is selected from O, $NR^{15}$, $NC(O)R^{16}$, S, S(O) and $SO_2$;

G is NH or O; and $R^{15}$, $R^{16}$, $R^{17}$, $R^{18}$, $R^{19}$, $T_1$, $T_2$, $T_3$ and $T_4$ can be the same or different, each being independently selected from the group consisting of H, alkyl, heteroalkyl, alkenyl, heteroalkenyl, alkynyl, heteroalkynyl, cycloalkyl, heterocyclyl, aryl, arylalkyl, heteroaryl, and heteroarylalkyl, or alternately, $R^{17}$ and $R^{18}$ are connected to each other to form a three to eight-membered cycloalkyl or heterocyclyl;

wherein each of said alkyl, aryl, heteroaryl, cycloalkyl or heterocyclyl can be unsubstituted or optionally independently substituted with one or more moieties selected from the group consisting of: hydroxy, alkoxy, aryloxy, thio, alkylthio, arylthio, amino, amido, alkylamino, arylamino, alkylsulfonyl, arylsulfonyl, sulfonamido, alkyl, aryl, heteroaryl, alkylsulfonamido, arylsulfonamido, keto, carboxy, carbalkoxy, carboxamido, alkoxycarbonylamino, alkoxycarbonyloxy, alkylureido, arylureido, halo, cyano, and nitro.

The above-noted statement "A and M are connected to each other such that the moiety:

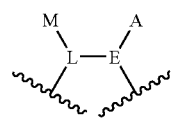

shown above in Formula I forms either a three, four, six, seven or eight-membered cycloalkyl, a four to eight-membered heterocyclyl, a six to ten-membered aryl, or a five to ten-membered heteroaryl" can be illustrated in a non-limiting matter as follows. Thus, for example, in the case where A and M are connected such that the oiety:

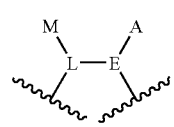

shown above in Formula I forms a six-membered cycloalkyl (cyclohexyl), Formula I can be depicted as:

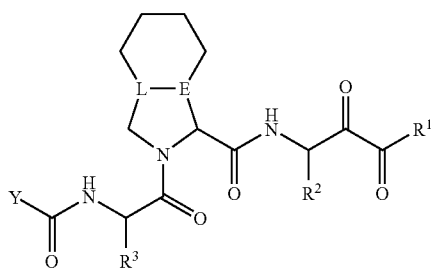

One with ordinary skill in the art will appreciate that similar depictions for Formula I can be arrived at when A and M shown above in the moiety:

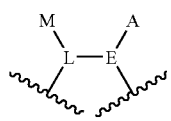

(M-L-E-A taken together) are connected to form a three, four, seven or eight-membered cycloalkyl, a four to eight-membered heterocyclyl, a six to ten-membered aryl, or a five to ten-membered heteroaryl.

In the above-noted definitions of R, R', $R^2$, and $R^3$ preferred alkyl is made of one to ten carbon atoms, preferred alkenyl or alkynyl is made of two to ten carbon atoms, preferred cycloalkyl is made of three to eight carbon atoms, and preferred heteroalkyl, heteroaryl or heterocycloalkyl(heterocyclyl) has one to six oxygen, nitrogen, sulfur, or phosphorus atoms.

The compounds represented by Formula I, by themselves or in combination with one or more other suitable agents disclosed herein, can be useful for treating diseases such as, for example, HCV, HIV, AIDS (Acquired Immune Deficiency Syndrome), and related disorders, as well as for modulating the activity of hepatitis C virus (HCV) protease, preventing HCV, or ameliorating one or more symptoms of hepatitis C. Such modulation, treatment, prevention or amelioration can be done with the inventive compounds as well as with pharmaceutical compositions or formulations comprising such compounds. Without being limited to theory, it is believed that the HCV protease may be the NS3 or NS4a protease. The inventive compounds can inhibit such protease. They can also modulate the processing of hepatitis C virus (HCV) polypeptide.

DETAILED DESCRIPTION

In an embodiment, the present invention discloses compounds which are represented by structural Formula 1 or a pharmaceutically acceptable salt, solvate or ester thereof, wherein the various moieties are as defined above.

In another embodiment, $R^1$ is $NR^9R^{10}$, and $R^9$ is H, $R^{10}$ is H, or $R^{14}$ wherein $R^{14}$ is H, alkyl, aryl, heteroalkyl, heteroaryl, cycloalkyl, alkyl-aryl, alkyl-heteroaryl, aryl-alkyl, alkenyl, alkynyl or heteroaryl-alkyl.

In another embodiment, $R^{14}$ is selected from the group consisting of:

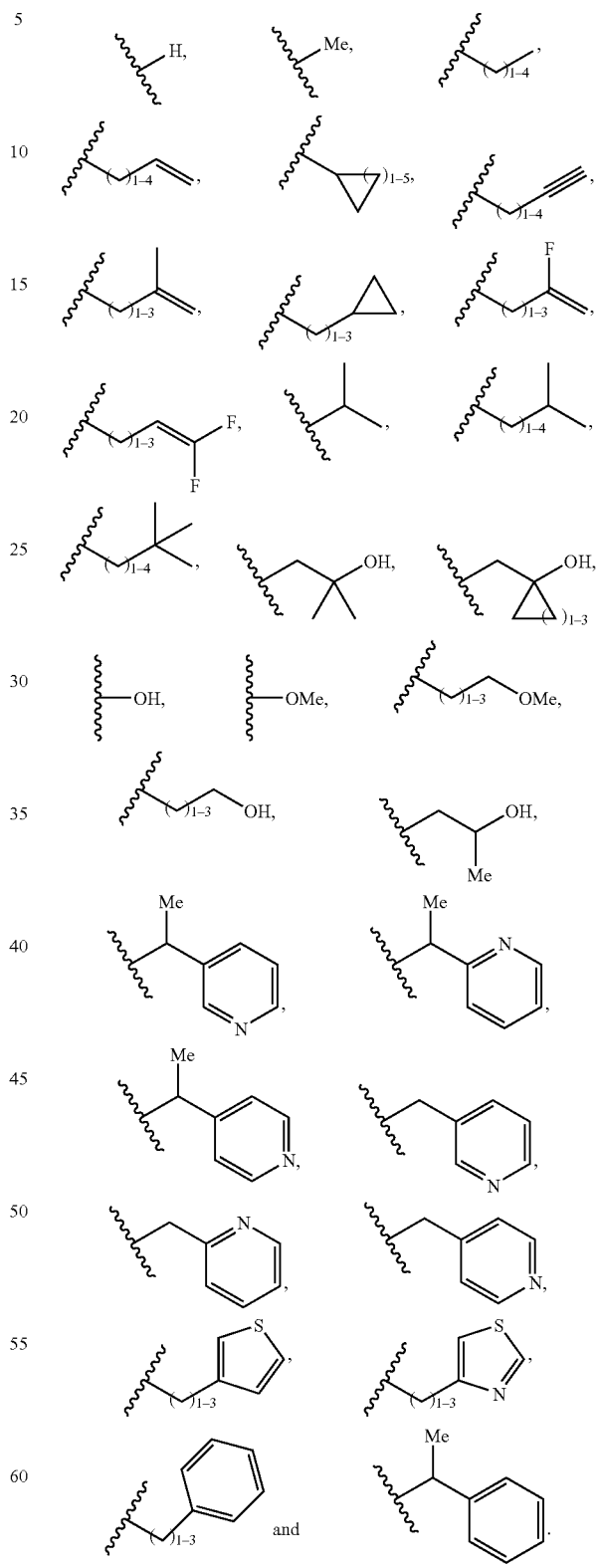

In another embodiment, $R^2$ is selected from the group consisting of the following moieties:

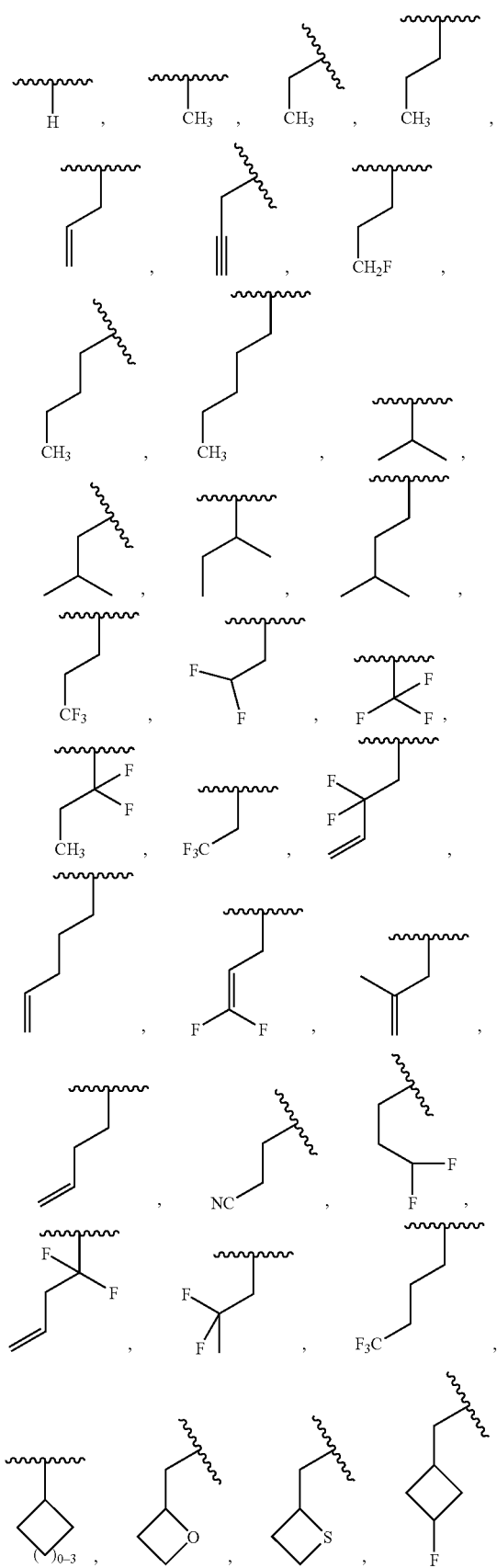
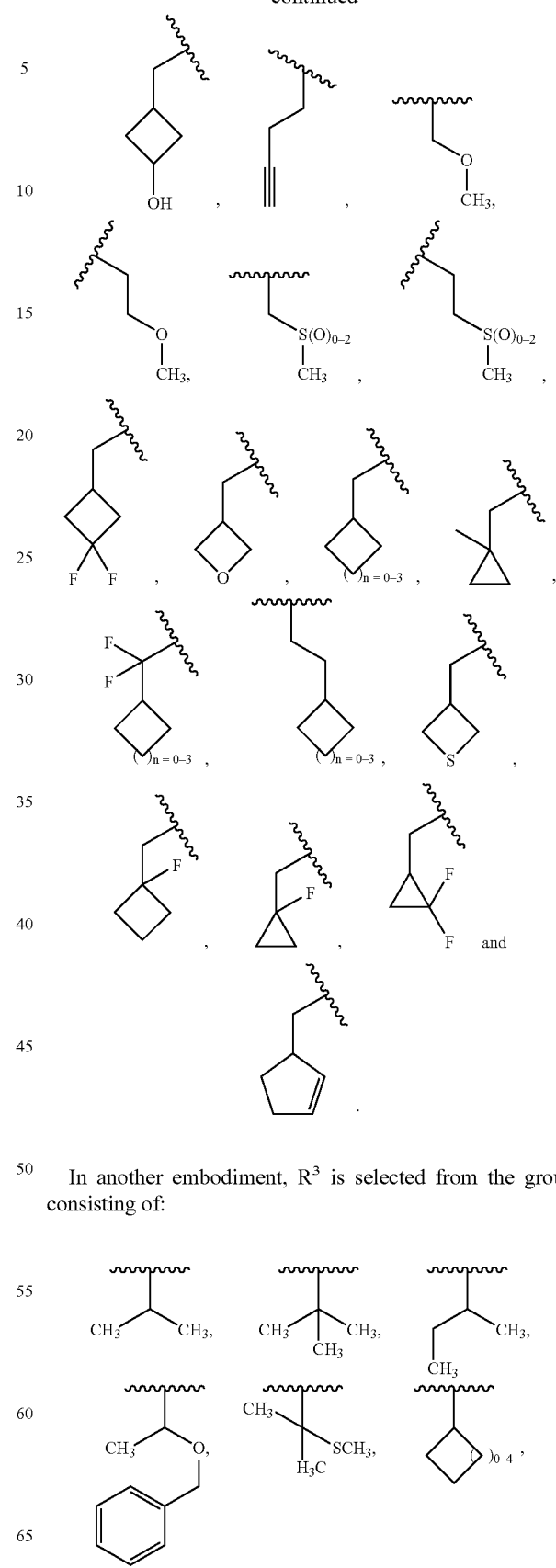
In another embodiment, $R^3$ is selected from the group consisting of:
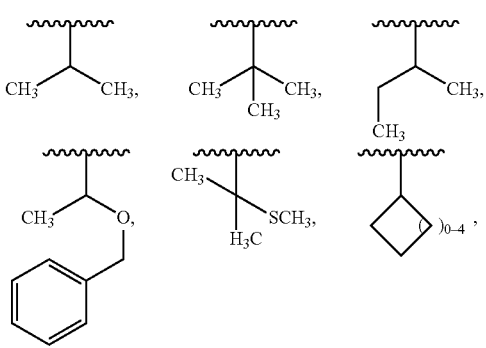

-continued
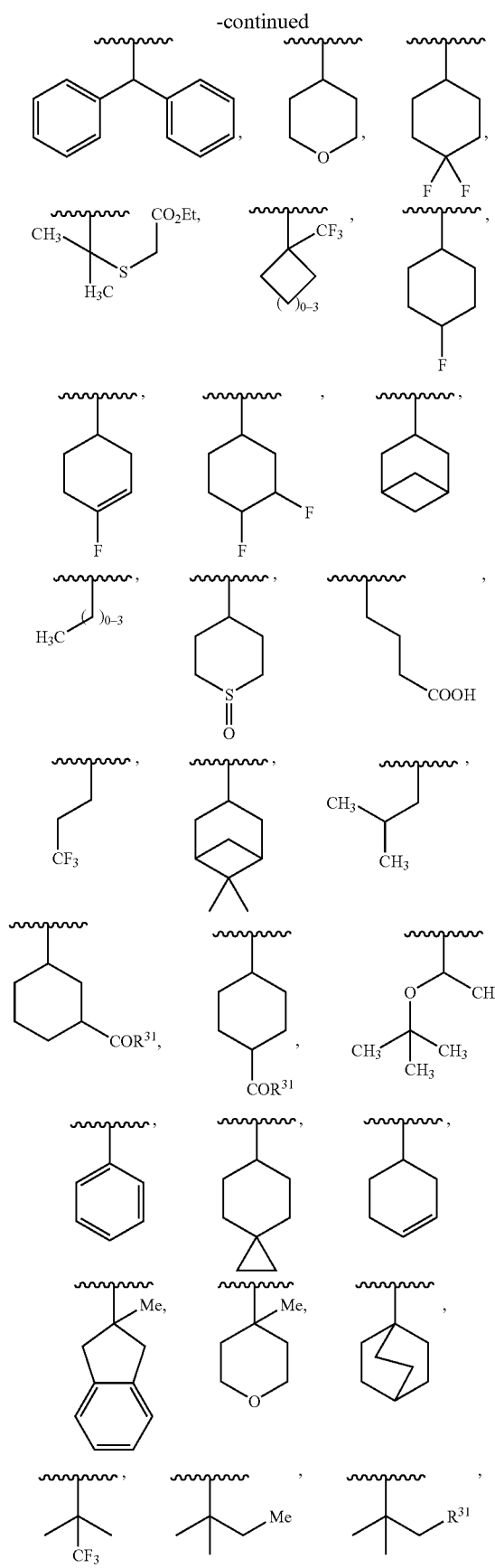
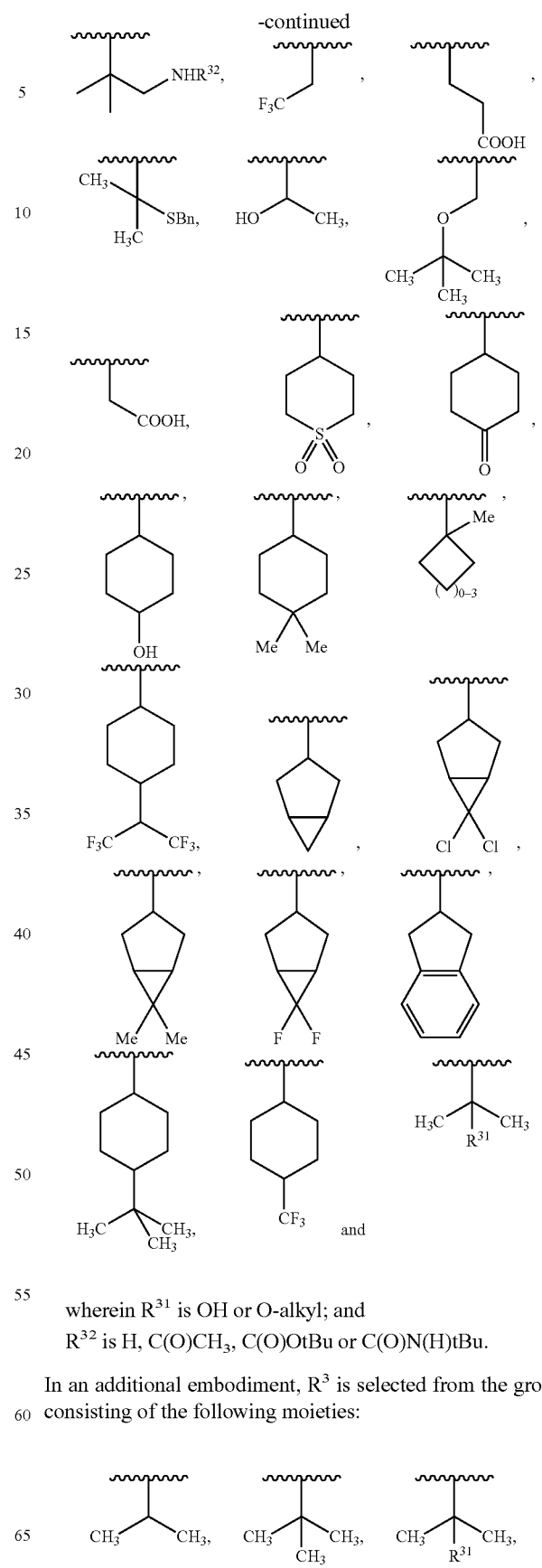
wherein $R^{31}$ is OH or O-alkyl; and
$R^{32}$ is H, C(O)CH$_3$, C(O)OtBu or C(O)N(H)tBu.
In an additional embodiment, $R^3$ is selected from the group consisting of the following moieties:

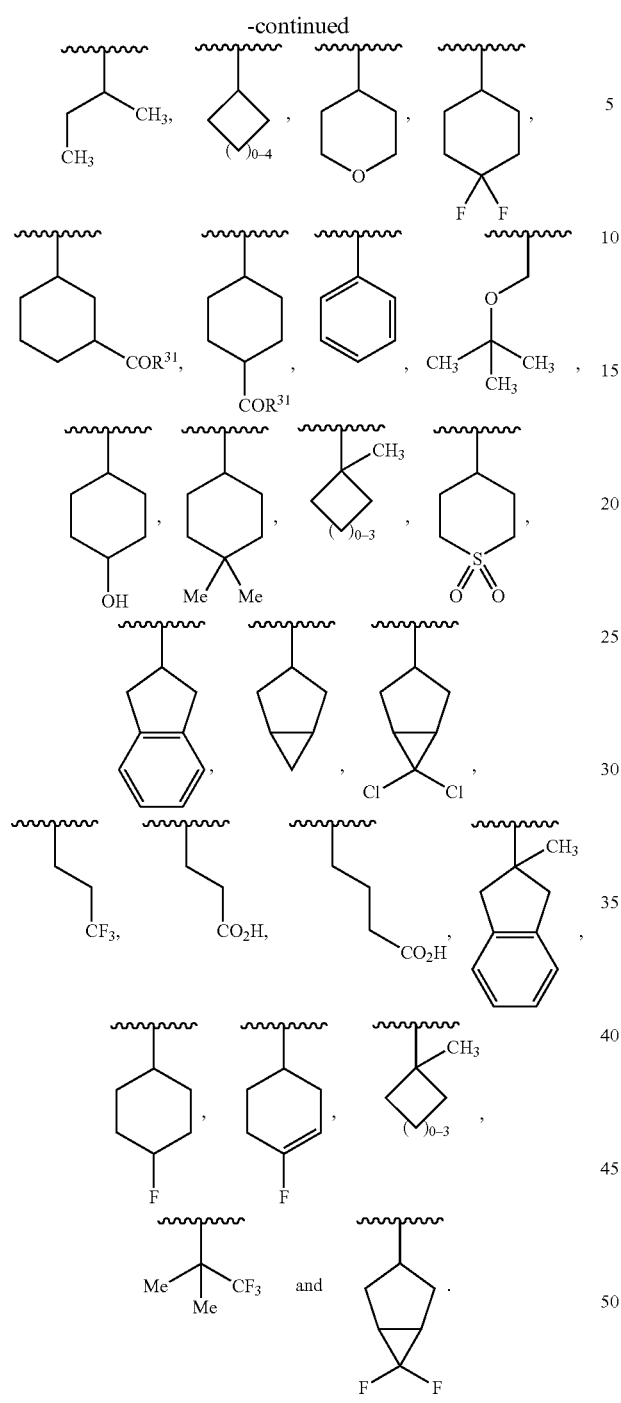
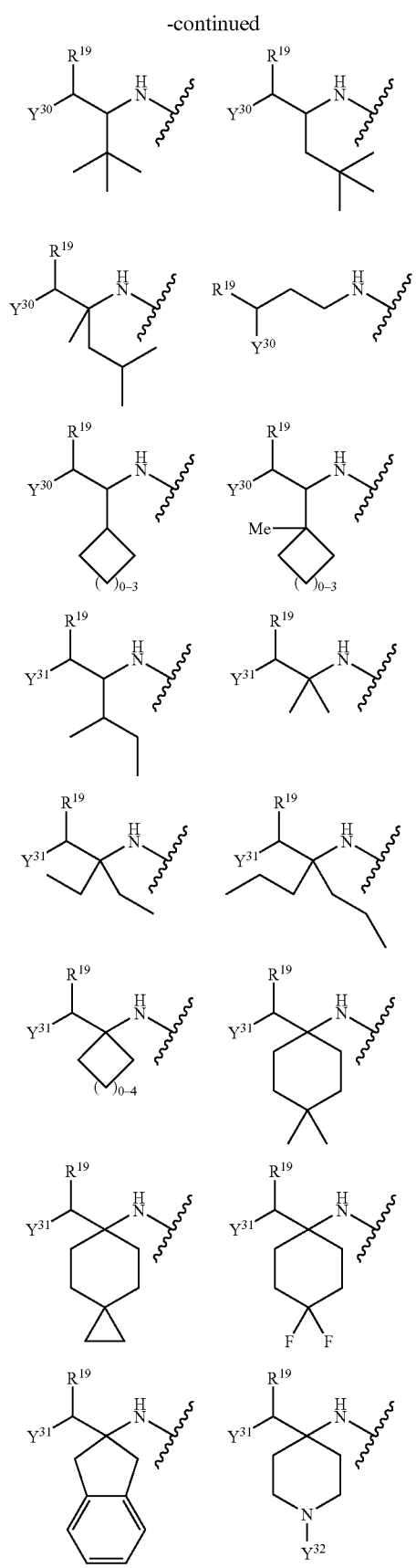
In another embodiment, G is NH.
In another embodiment, Y is selected from the following moieties:
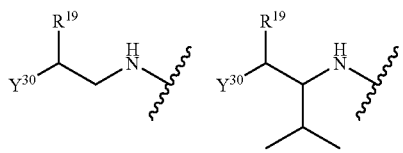
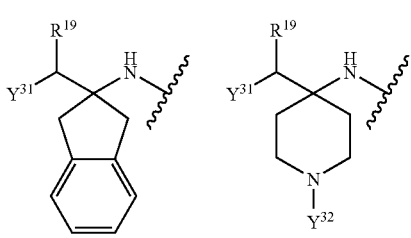

-continued

wherein Y³² is selected from the group consisting of:

Y³⁰ and Y³¹ is selected from

wherein u is a number 0-6; and
and R¹⁹ is selected from H, alkyl, phenyl or benzyl.

In another embodiment, T₁ and T₂ can be the same or different, each being independently selected from the group consisting of:

-continued

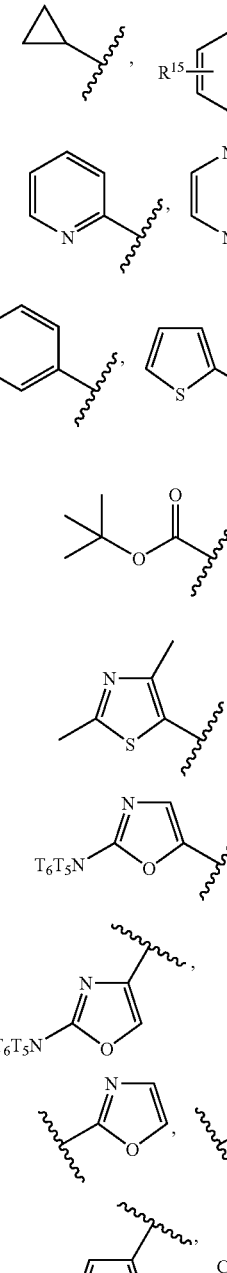

wherein T₅ and T₆ can be the same or different, each being independently selected from the group consisting of alkyl, aryl, cycloalkyl, heteroaryl and heterocyclyl;

or the moiety:

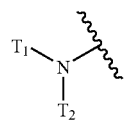

taken together represents

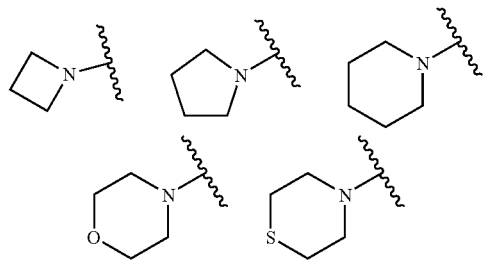

and
T₃ and T₄ can be the same or different, each being independently selected from:

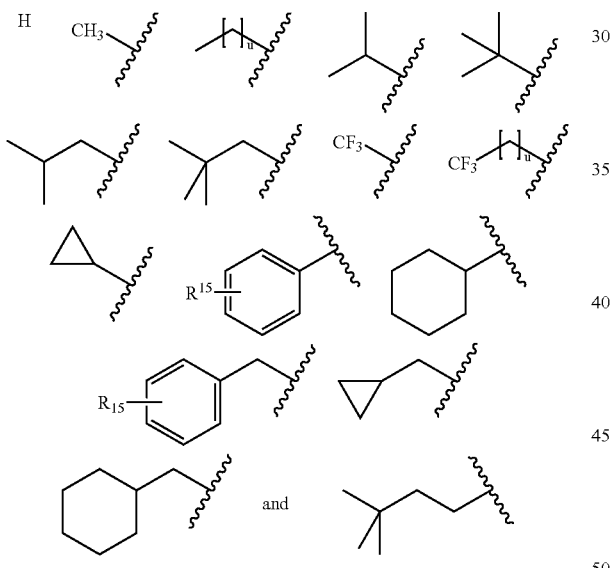

or T₃ and T₄ taken together may form part of a four to seven membered heterocyclic ring; in other words, the moiety T₃-N—C-T₄ may form part of a four to seven membered heterocyclic ring.
In another embodiment, the moiety:

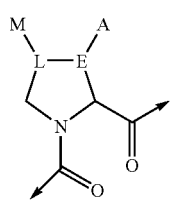

is selected from the following structures:

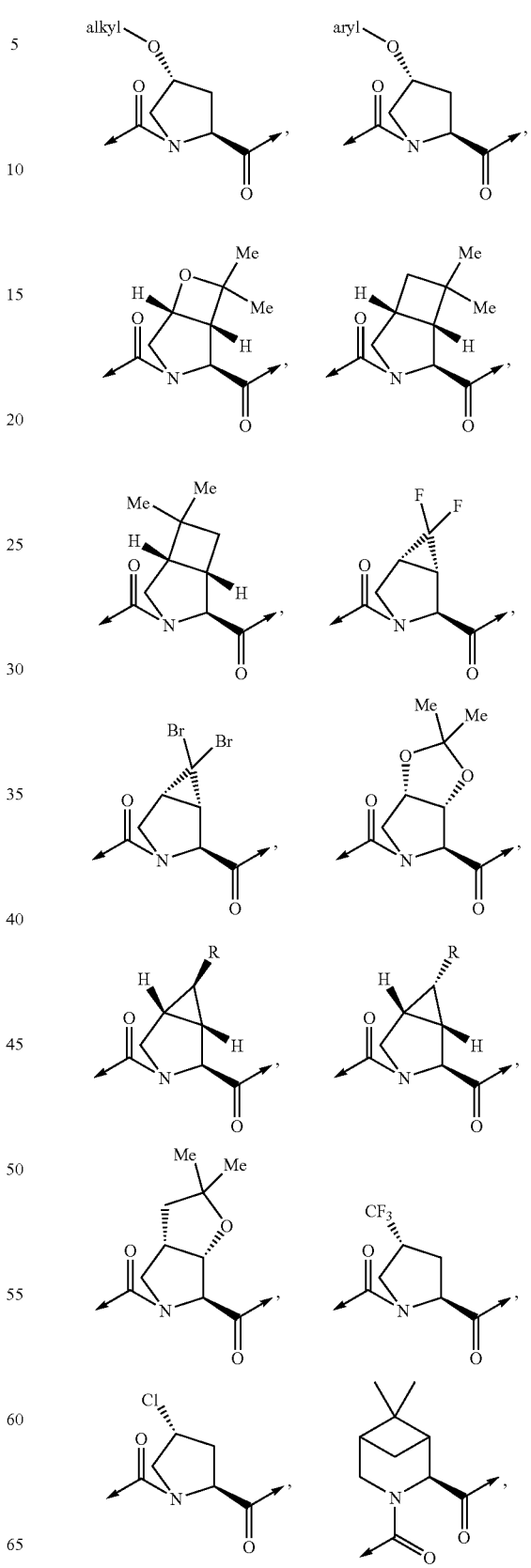

-continued
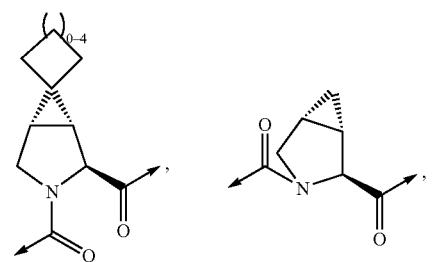
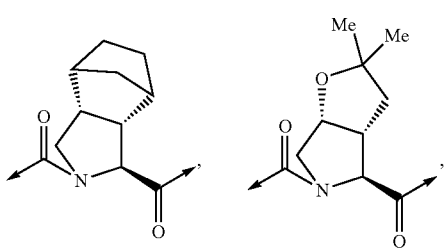
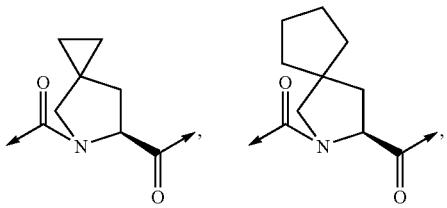
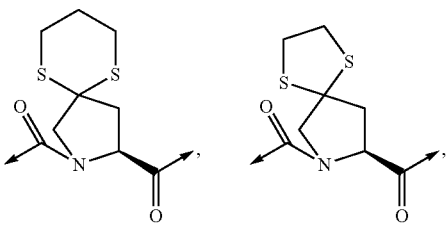
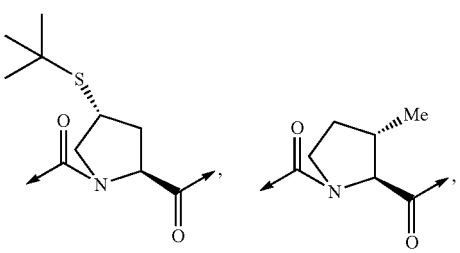
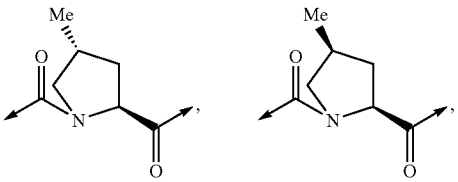
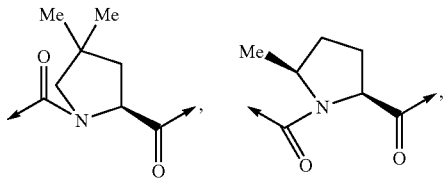
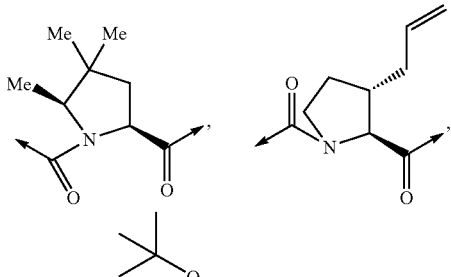
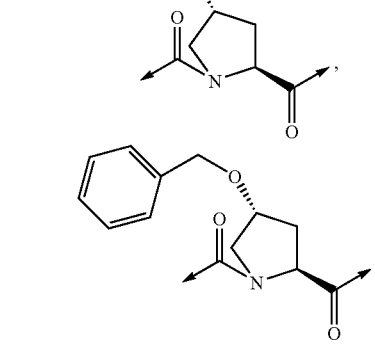
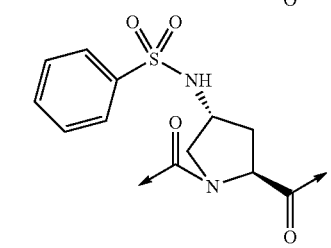
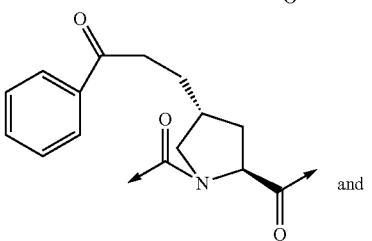
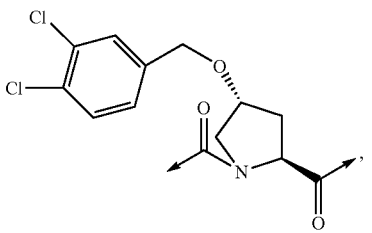
and
In an additional embodiment, the moiety:
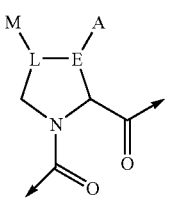

is selected from the following structures:
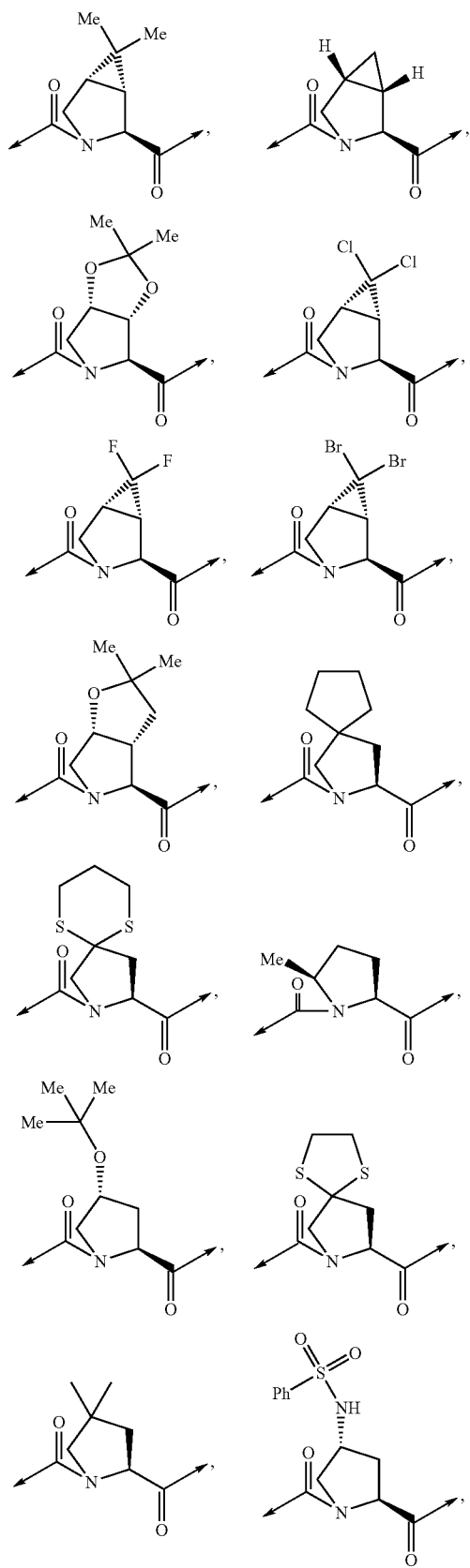
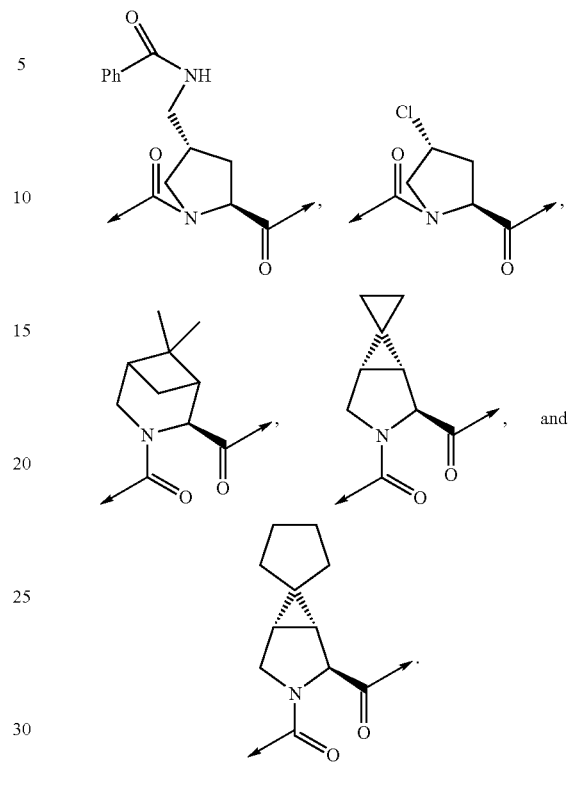
In a still additional embodiment, the moiety:
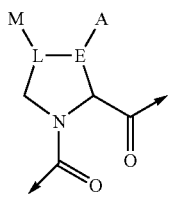
is selected from the following structures:
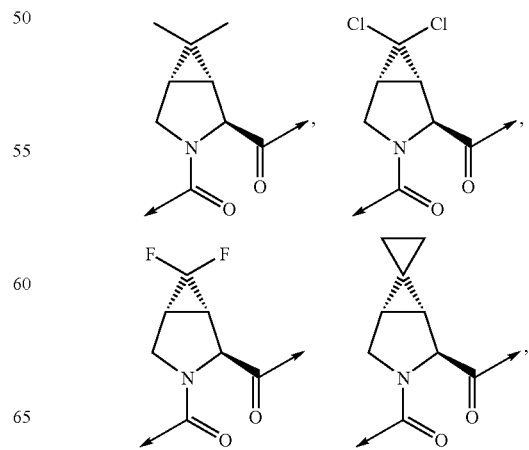

-continued
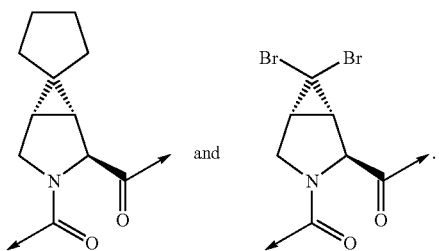 and 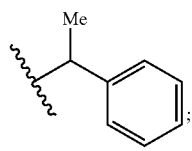
In a further additional embodiment, $R^1$ is $NHR^{14}$, where $R^{14}$ is selected from the group consisting of:
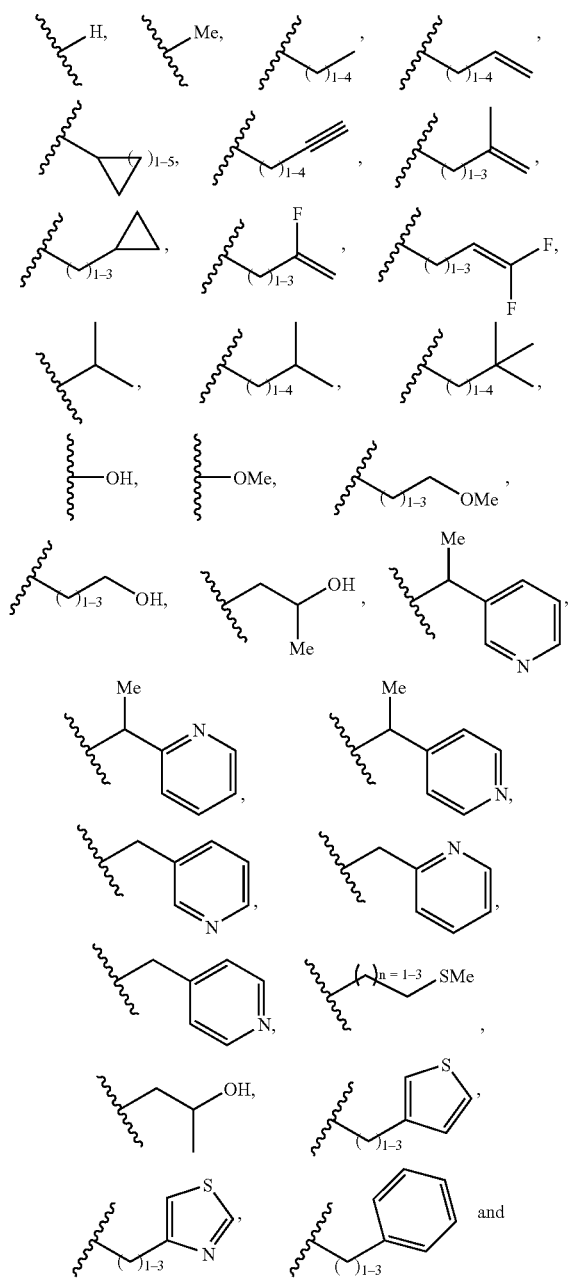
-continued
$R^2$ is selected from the group consisting of the following moieties:
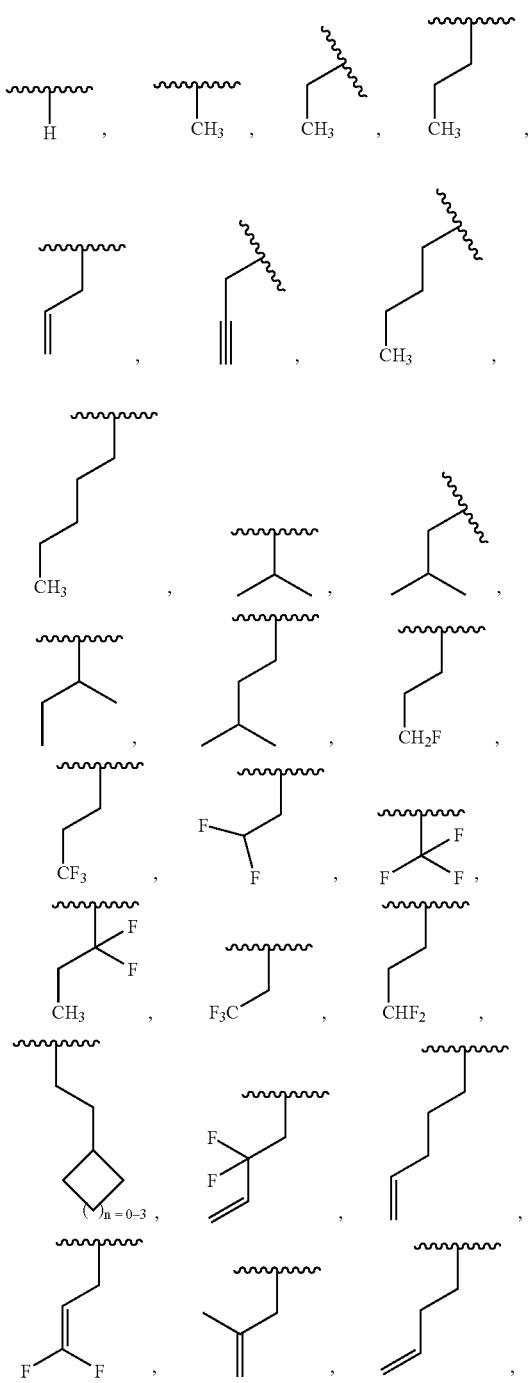

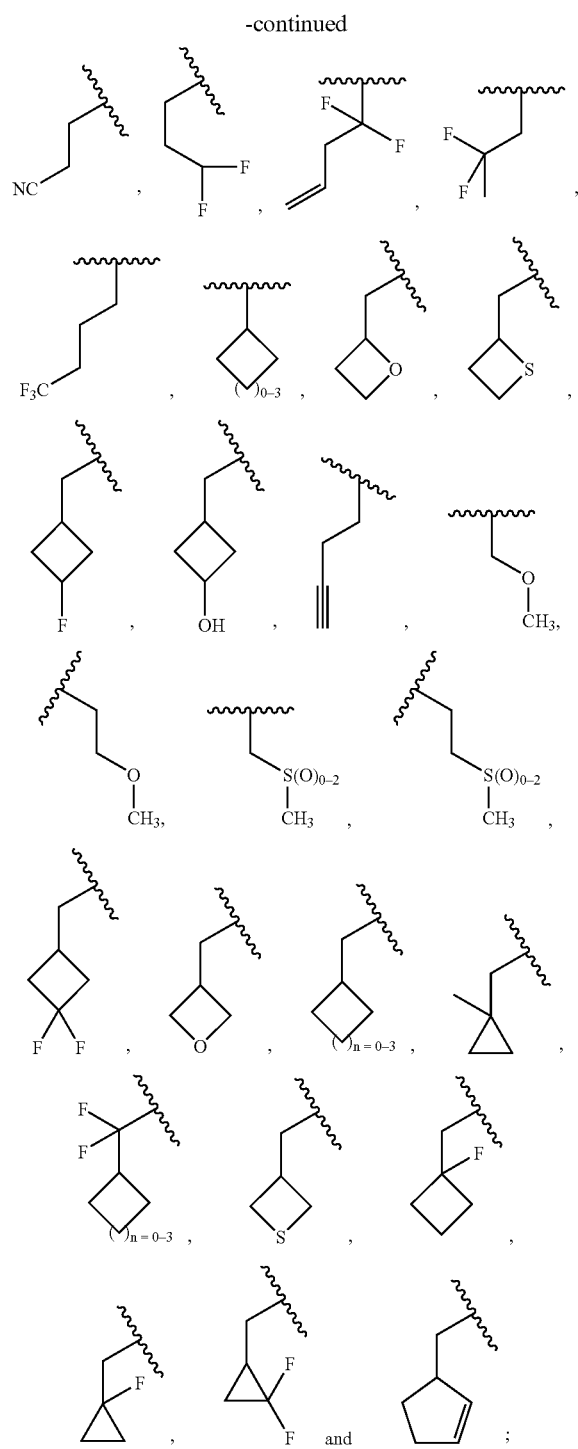
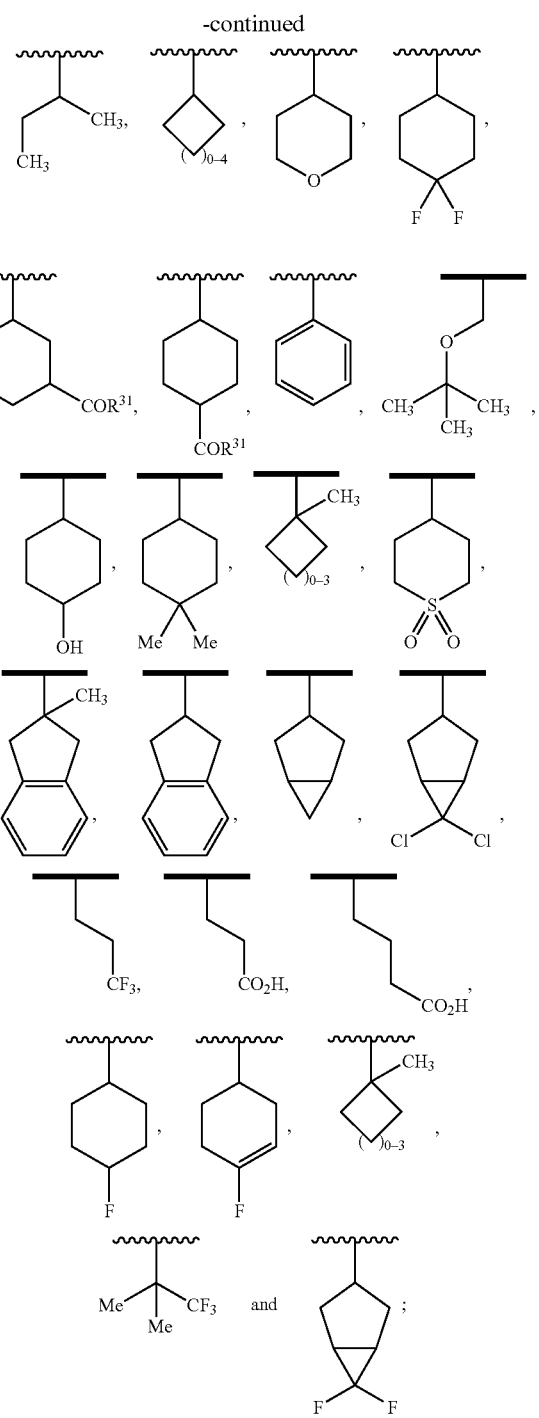
$R^3$ is selected from the group consisting of the following moieties:
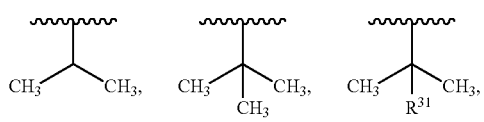
Y is selected from the group consisting of:
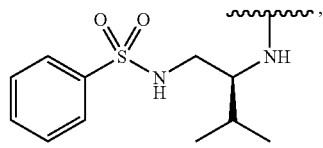

-continued
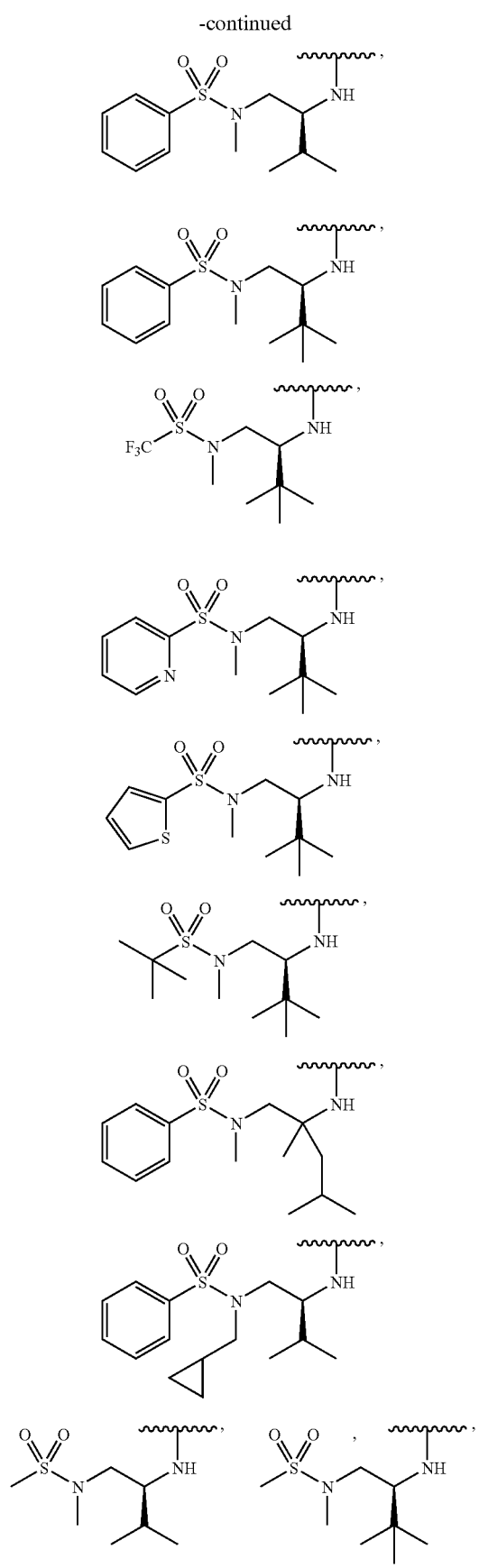
-continued
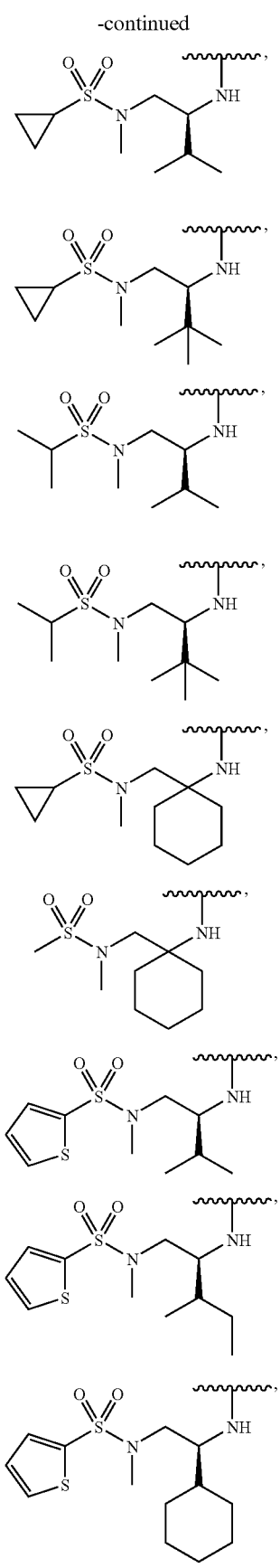

-continued
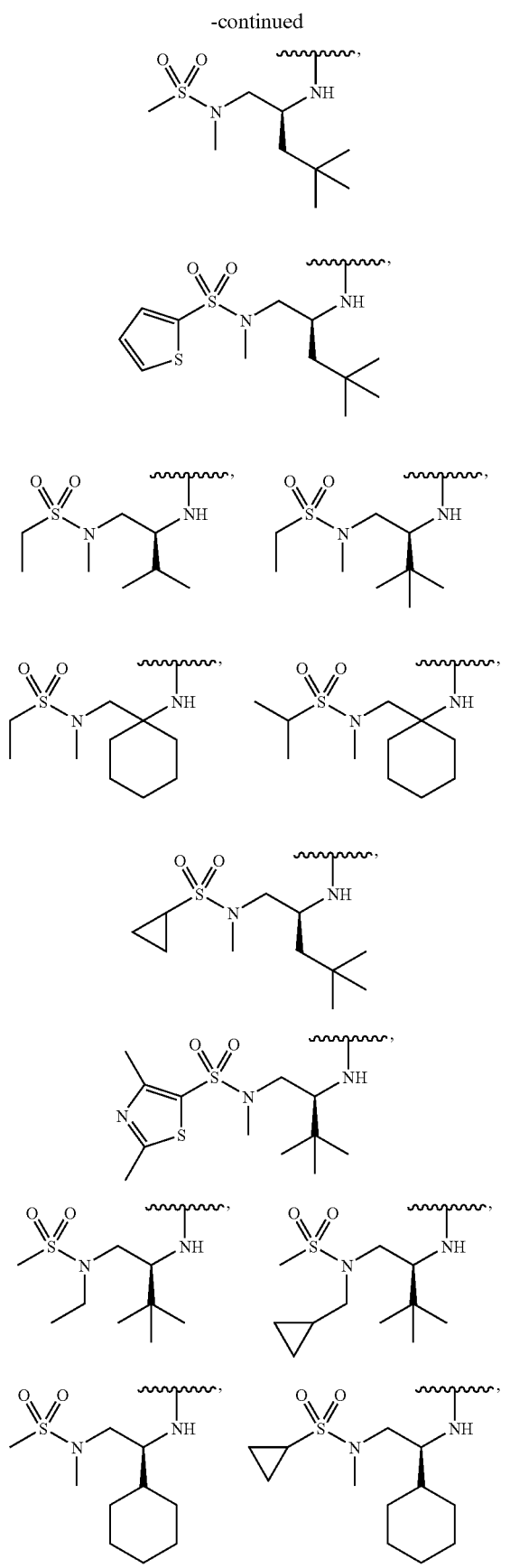
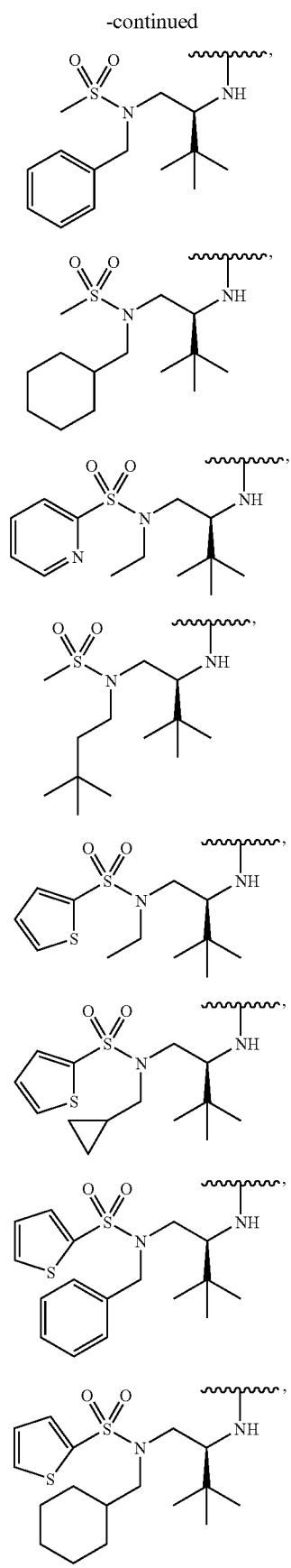

-continued
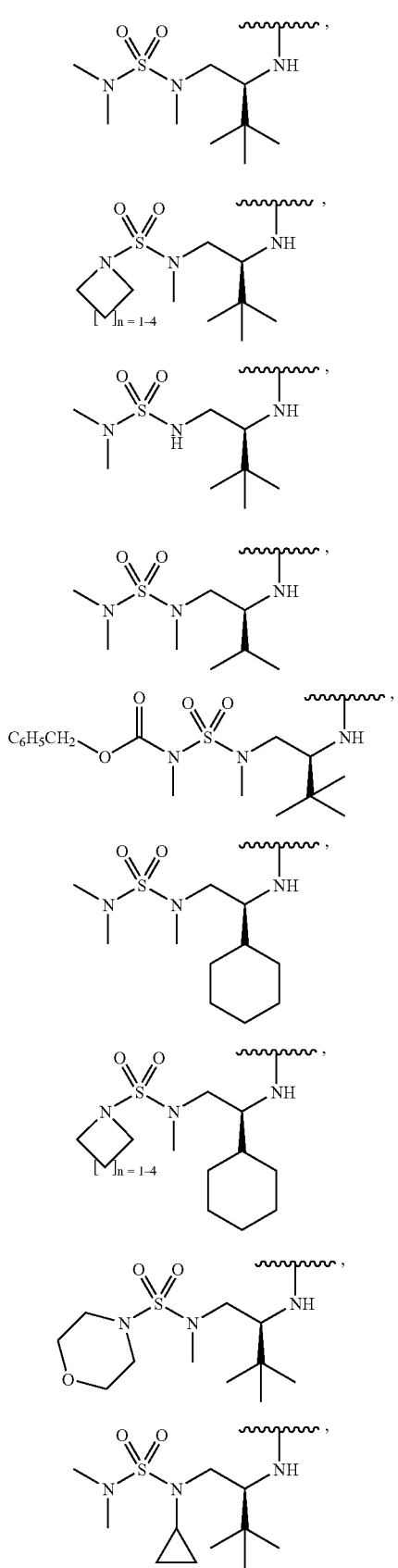
-continued
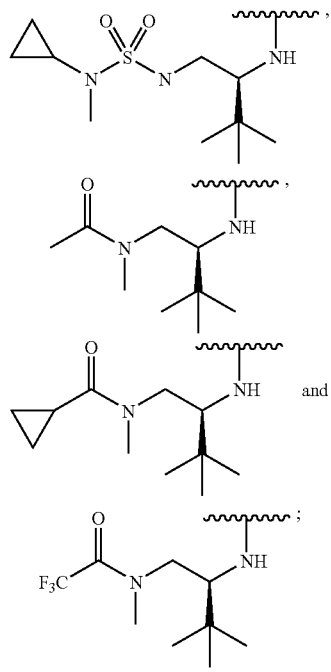
and the moiety:
and the moiety is:

-continued

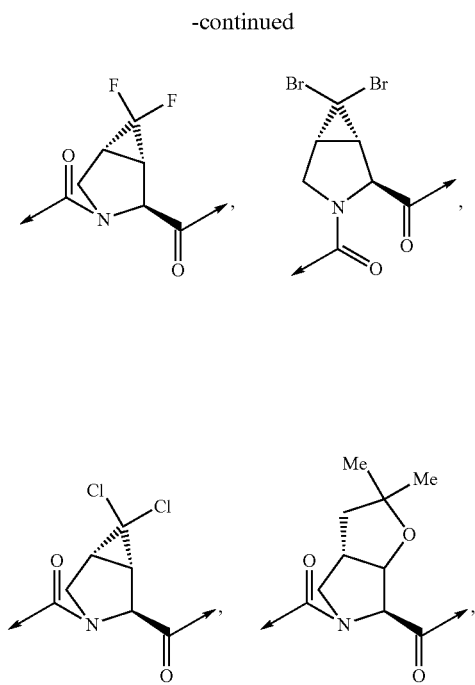

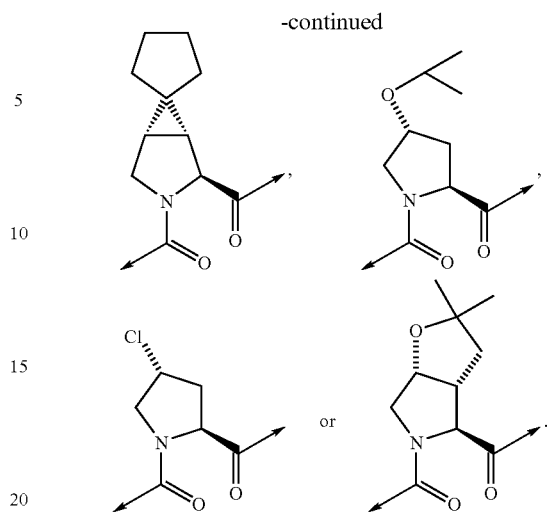

Yet another embodiment of the invention discloses compounds shown in Table 1, Table 2, Table 3, Table 4 and Table 5 later in this Description. Also shown in the Tables are the biological activities of several inventive compounds (as Ki* values in nanoMolar).

In a still additional embodiment, this invention discloses the following compounds in Table 6:

TABLE 6

| Structure | Ki* (nM) |
|---|---|
| 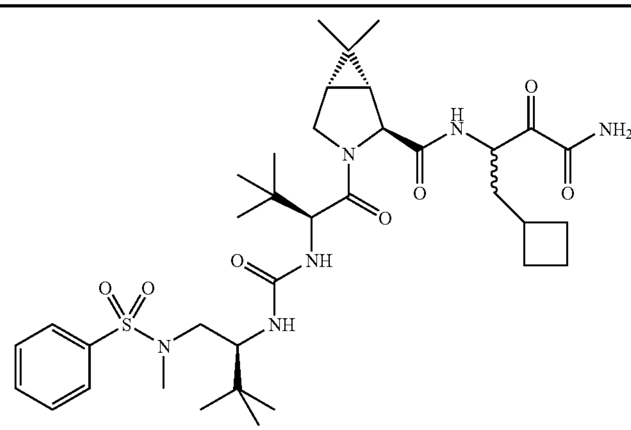 | 5 |
| 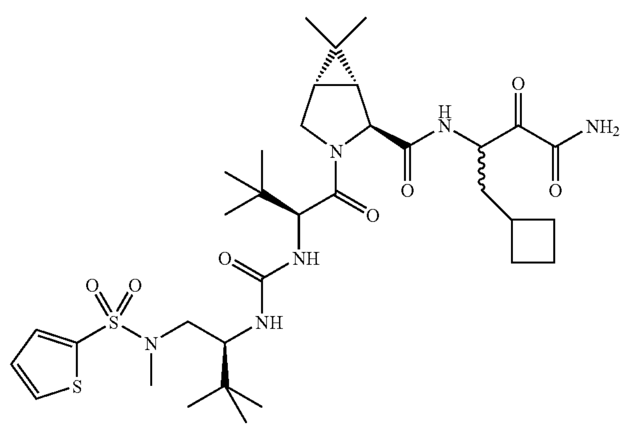 | 3.7 |

TABLE 6-continued
| Structure | Ki* (nM) |
|---|---|
| 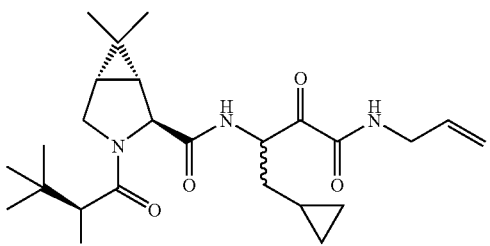 | 30 |
| 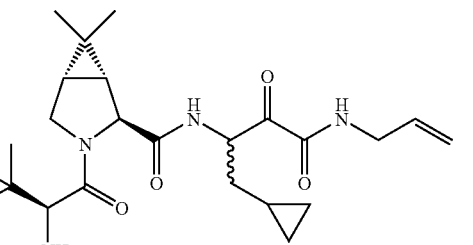 | 19 |
| 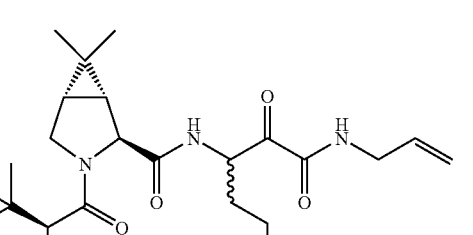 | 9 |

TABLE 6-continued

| Structure | Ki* (nM) |
| --- | --- |
| 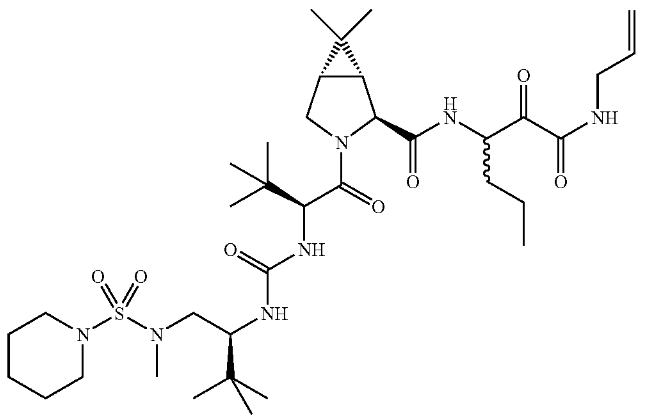 | 15 |
| 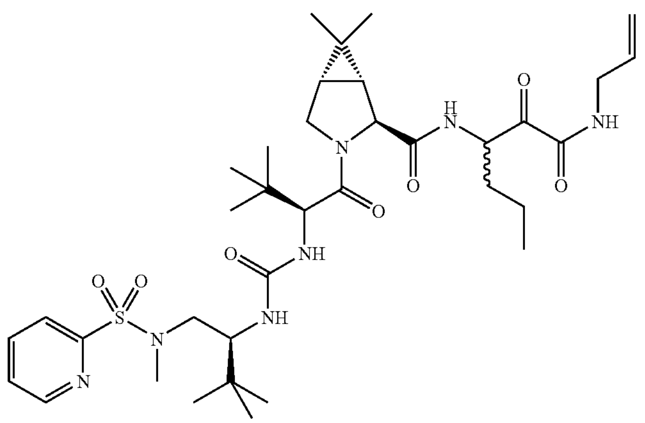 | 14 |
| 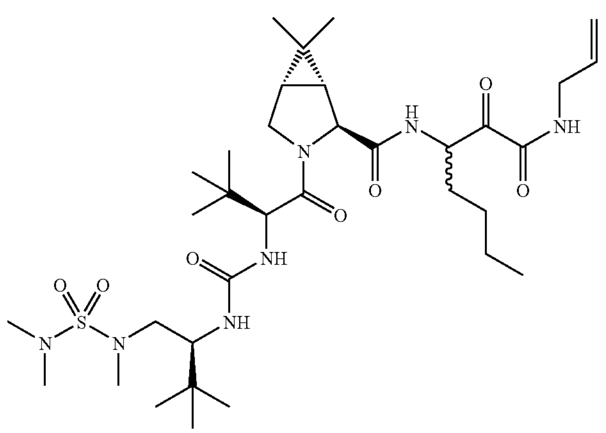 | 11 |

TABLE 6-continued

| Structure | Ki* (nM) |
|---|---|
| 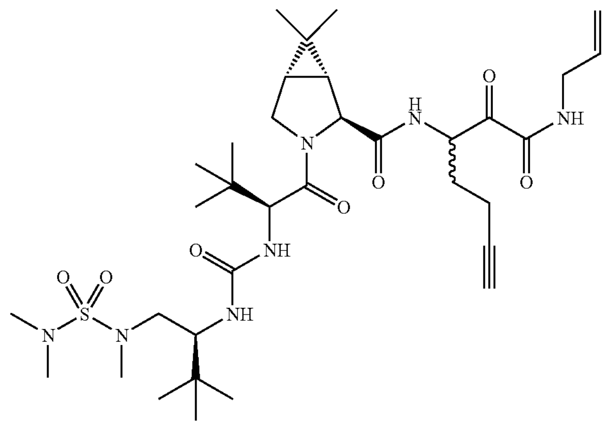 | 2.6 |
| 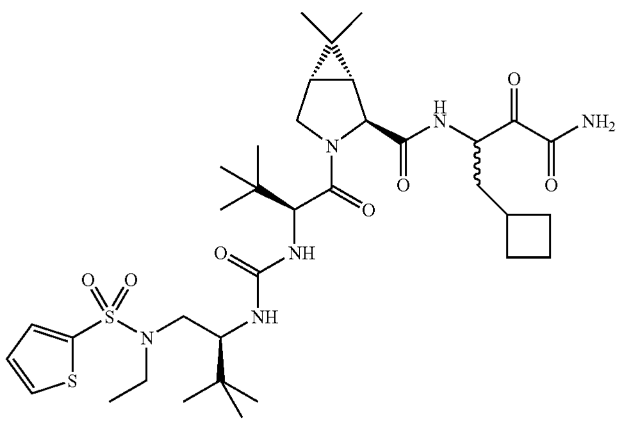 | 9 |
| 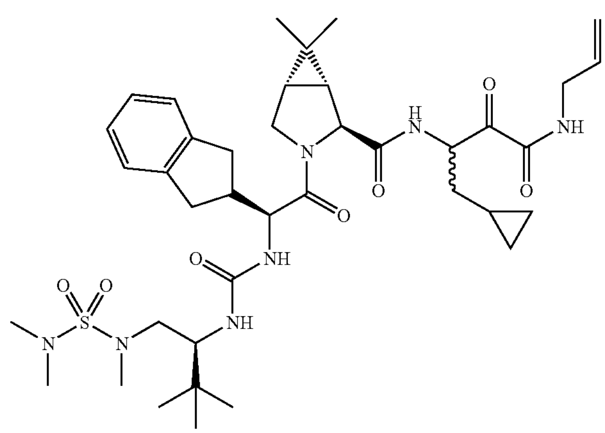 | 12 |

TABLE 6-continued
| Structure | Ki* (nM) |
| --- | --- |
| 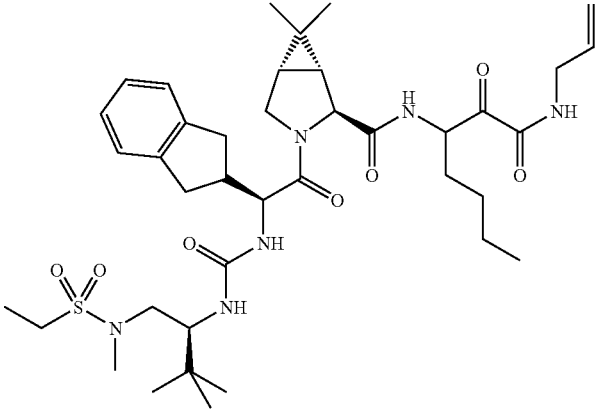 | 5.8 |
| 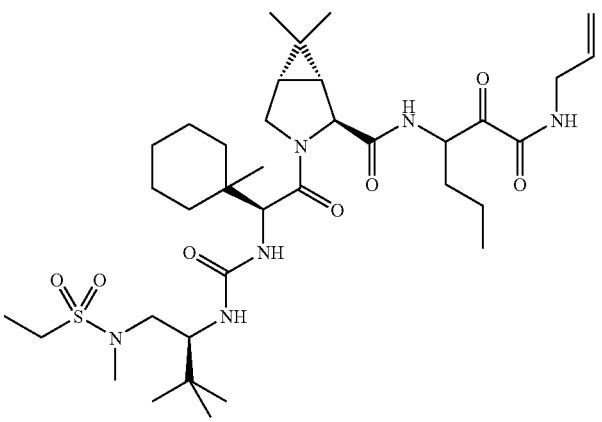 | 10 |
| 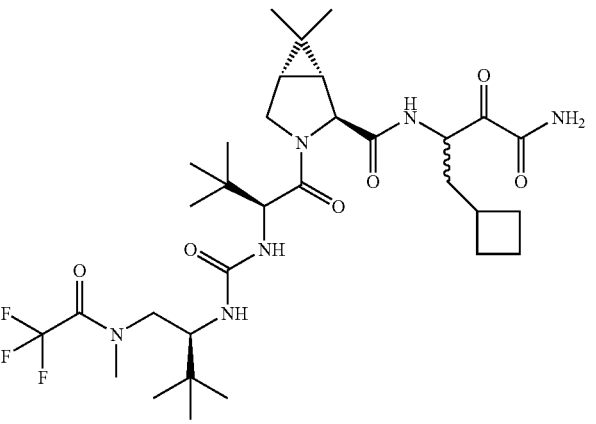 | 2 |

TABLE 6-continued

| | Structure | Ki* (nM) |
|---|---|---|
| 11399 | 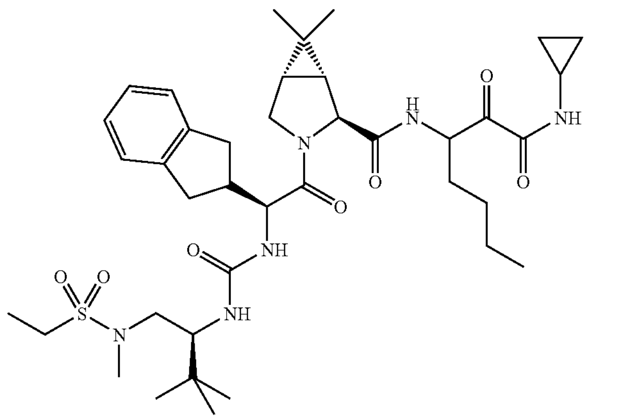 | 4 |
| 11405 | 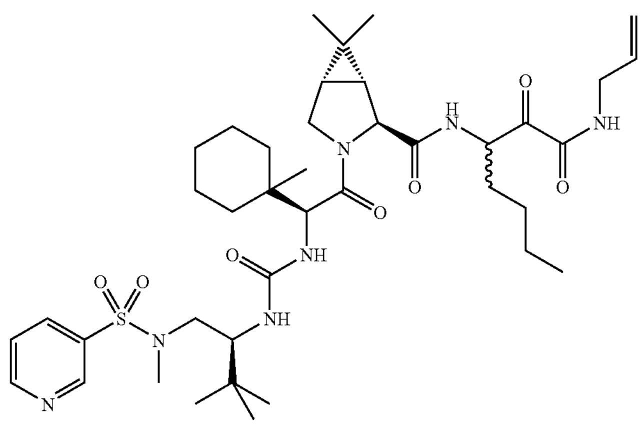 | 4 |
| 11411 | 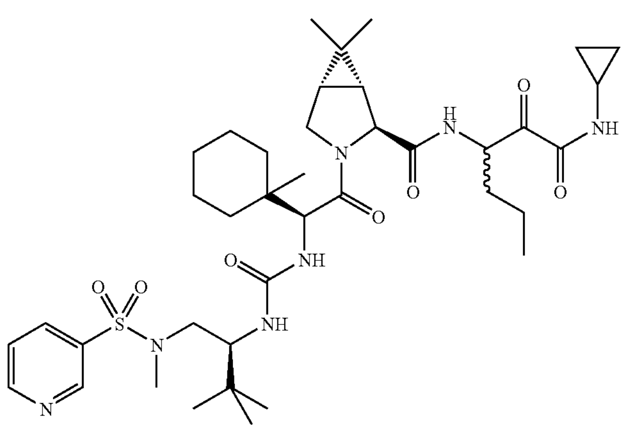 | 5 |

TABLE 6-continued

| | Structure | Ki* (nM) |
|---|---|---|
| 11417 | 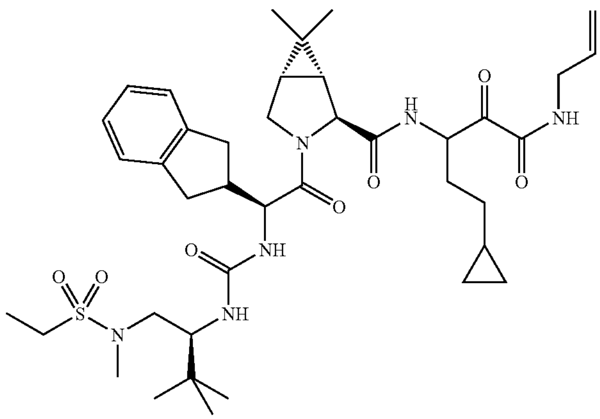 | 6 |
| 11401 | 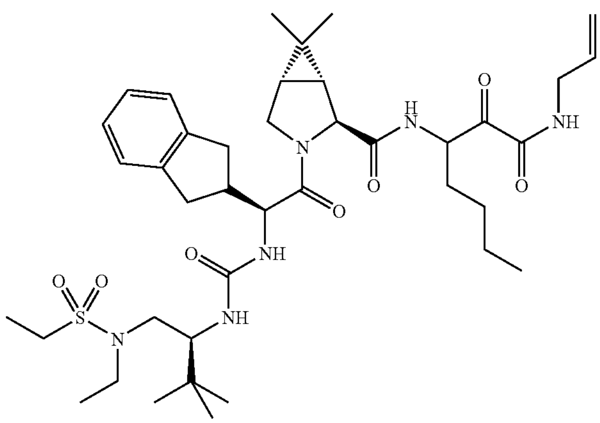 | 6 |
| 11412 | 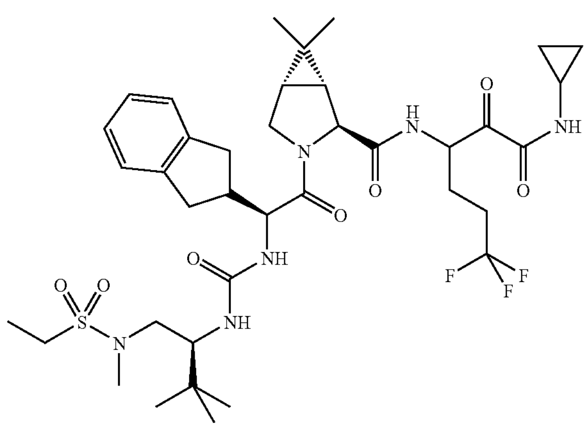 | 7 |

TABLE 6-continued

| | Structure | Ki* (nM) |
|---|---|---|
| 11418 | 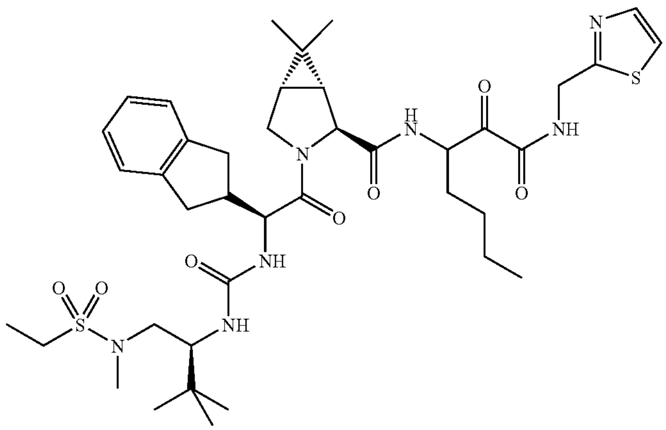 | 7 |
| 11421 | 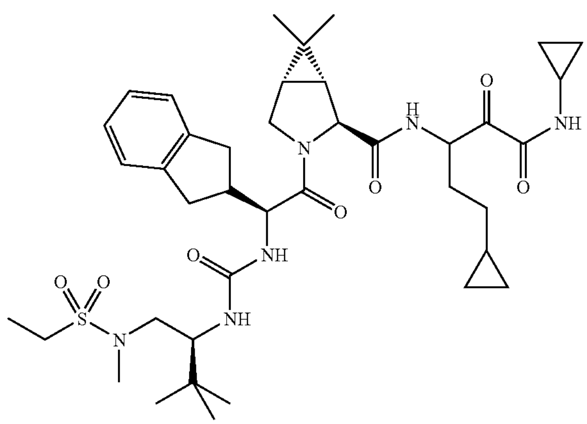 | 7 |
| 11395 | 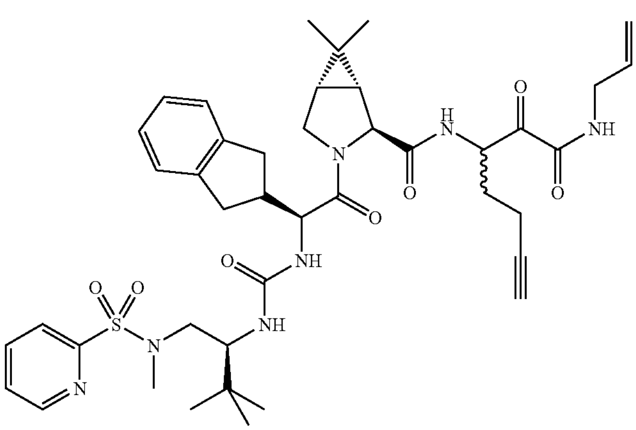 | 8 |

TABLE 6-continued
| | Structure | Ki* (nM) |
|---|---|---|
| 11420 | 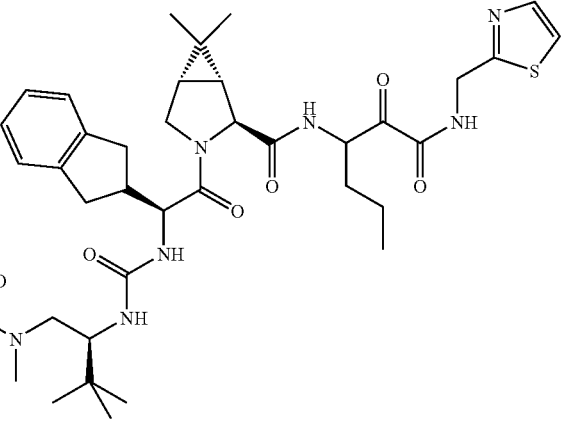 | 8 |
| 11400 | 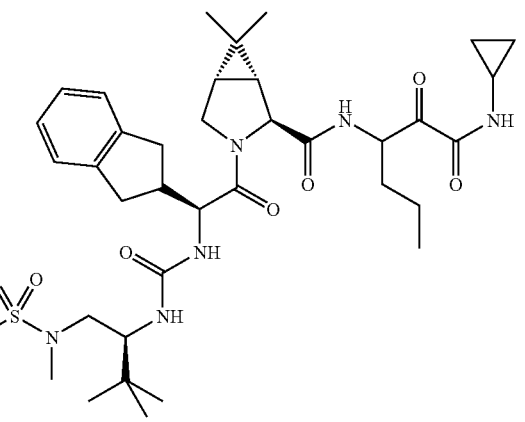 | 9 |
| 11410 | 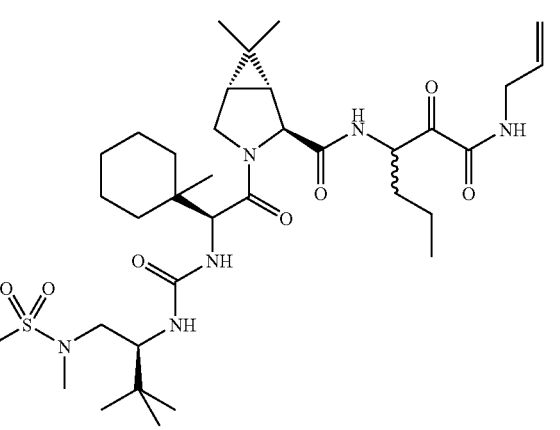 | 9 |

TABLE 6-continued

| Structure | Ki* (nM) |
|---|---|
| 11402 | 10 |

As used above, and throughout this disclosure, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, —N(alkyl)$_2$, carboxy and —(O)O-alkyl. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. The term "substituted alkenyl" means that the alkenyl group may be substituted by one or more substituents which may be the same or different, each substituent being independently selected from the group consisting of halo, alkyl. aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. The term "substituted alkynyl" means that the alkynyl group may be substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl-group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like, as well as partially saturated species such as, for example, indanyl, tetrahydronaphthyl and the like.

"Halogen" or "halo" means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—NH$_2$, —C(=NH)—NH$_2$, —C(=NH)—NH(alkyl), Y$_1$Y$_2$N—, Y$_1$Y$_2$N-alkyl-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

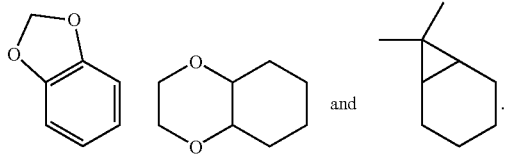

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

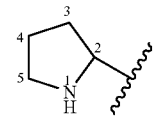

there is no —OH attached directly to carbons marked 2 and 5.

It should also be noted that tautomeric forms such as, for example, the moieties:

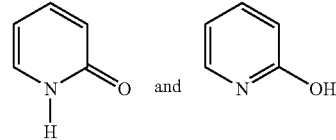

are considered equivalent in certain embodiments of this invention.

"Alkynylalkyl" means an alkynyl-alkyl-group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S($O_2$)— group. Preferred groups are those in which the alkyl group is lower alkyl. The bond to the parent moiety is through the sulfonyl.

"Arylsulfonyl" means an aryl-S($O_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "one or more" or "at least one", when indicating the number of substituents, compounds, combination agents and the like, refers to at least one, and up to the maximum number of chemically and physically permissible, substituents, compounds, combination agents and the like, that are present or added, depending on the context. Such techniques and knowledge are well known within the skills of the concerned artisan.

The term "optionally substituted" means optional substitution with the specified groups, radicals or moieties.

The term "isolated" or "in isolated form" for a compound refers to the physical state of said compound after being isolated from a synthetic process or natural source or combination thereof. The term "purified" or "in purified form" for a compound refers to the physical state of said compound after being obtained from a purification process or processes described herein or well known to the skilled artisan, in sufficient purity to be characterizable by standard analytical techniques described herein or well known to the skilled artisan.

It should also be noted that any heteroatom with unsatisfied valences in the text, schemes, examples and Tables herein is assumed to have the hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formula 1, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of Formula 1 or a salt and/or solvate thereof. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound or a composition of the present invention effective in inhibiting the CDK(s) and thus producing the desired therapeutic, ameliorative, inhibitory or preventative effect.

The compounds of Formula 1 can form salts which are also within the scope of this invention. Reference to a compound of Formula 1 herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula 1 contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula 1 may be formed, for example, by reacting a compound of Formula 1 with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

Compounds of Formula 1, and salts, solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate" "prodrug" and the like, is intended to equally apply to the salt, solvate and prodrug of enantiomers, stereoisomers, rotamers, tautomers, positional isomers, racemates or prodrugs of the inventive compounds.

Polymorphic forms of the compounds of Formula I, and of the salts, solvates and prodrugs of the compounds of Formula I, are intended to be included in the present invention.

It is to be understood that the utility of the compounds of Formula 1 for the therapeutic applications discussed herein is applicable to each compound by itself or to the combination or combinations of one or more compounds of Formula 1 as illustrated, for example, in the next immediate paragraph. The same understanding also applies to pharmaceutical composition(s) comprising such compound or compounds and method(s) of treatment involving such compound or compounds.

The compounds according to the invention can have pharmacological properties; in particular, the compounds of Formula 1 can be inhibitors of HCV protease, each compound by itself or one or more compounds of Formula 1 can be combined with one or more compounds selected from within Formula 1. The compound(s) can be useful for treating diseases such as, for example, HCV, HIV, (AIDS, Acquired Immune Deficiency Syndrome), and related disorders, as well as for modulating the activity of hepatitis C virus (HCV) protease, preventing HCV, or ameliorating one or more symptoms of hepatitis C.

The compounds of Formula 1 may be used for the manufacture of a medicament to treat disorders associated with the HCV protease, for example, the method comprising bringing into intimate contact a compound of Formula 1 and a pharmaceutically acceptable carrier.

In another embodiment, this invention provides pharmaceutical compositions comprising the inventive compound or compounds as an active ingredient. The pharmaceutical compositions generally additionally comprise at least one pharmaceutically acceptable carrier diluent, excipient or carrier (collectively referred to herein as carrier materials). Because of their HCV inhibitory activity, such pharmaceutical compositions possess utility in treating hepatitis C and related disorders.

In yet another embodiment, the present invention discloses methods for preparing pharmaceutical compositions comprising the inventive compounds as an active ingredient. In the pharmaceutical compositions and methods of the present invention, the active ingredients will typically be administered in admixture with suitable carrier materials suitably selected with respect to the intended form of administration, i.e. oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Moreover, when desired or needed, suitable binders, lubricants, disintegrating agents and coloring agents may also be incorporated in the mixture. Powders and tablets may be comprised of from about 5 to about 95 percent inventive composition.

Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum and the like.

Sweetening and flavoring agents and preservatives may also be included where appropriate. Some of the terms noted above, namely disintegrants, diluents, lubricants, binders and the like, are discussed in more detail below.

Additionally, the compositions of the present invention may be formulated in sustained release form to provide the rate controlled release of any one or more of the components or active ingredients to optimize the therapeutic effects, i.e. HCV inhibitory activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions. As an example may be mentioned water or water-propylene glycol solutions for parenteral injections or addition of sweeteners and pacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool and thereby solidify.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions may take the form of creams, lotions, aerosols and/or emulsions and can be included in a transdermal patch of the matrix or reservoir type as are conventional in the art for this purpose.

The compounds of the invention may also be administered orally, intravenously, intranasally or subcutaneously.

The compounds of the invention may also comprise preparations which are in a unit dosage form. In such form, the preparation is subdivided into suitably sized unit doses containing appropriate quantities of the active components, e.g., an effective amount to achieve the desired purpose.

The quantity of the inventive active composition in a unit dose of preparation may be generally varied or adjusted from about 1.0 milligram to about 1,000 milligrams, preferably from about 1.0 to about 950 milligrams, more preferably from about 1.0 to about 500 milligrams, and typically from about 1 to about 250 milligrams, according to the particular application. The actual dosage employed may be varied depending upon the patient's age, sex, weight and severity of the condition being treated. Such techniques are well known to those skilled in the art.

Generally, the human oral dosage form containing the active ingredients can be administered 1 or 2 times per day. The amount and frequency of the administration will be regulated according to the judgment of the attending clinician. A generally recommended daily dosage regimen for oral administration may range from about 1.0 milligram to about 1,000 milligrams per day, in single or divided doses.

Some useful terms are described below:

Capsule—refers to a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

Tablet—refers to a compressed or molded solid dosage form containing the active ingredients with suitable diluents. The tablet can be prepared by compression of mixtures or granulations obtained by wet granulation, dry granulation or by compaction.

Oral gel—refers to the active ingredients dispersed or solubilized in a hydrophillic semi-solid matrix.

Powder for constitution refers to powder blends containing the active ingredients and suitable diluents which can be suspended in water or juices.

Diluent—refers to substances that usually make up the major portion of the composition or dosage form. Suitable diluents include sugars such as lactose, sucrose, mannitol and sorbitol; starches derived from wheat, corn, rice and potato; and celluloses such as microcrystalline cellulose. The amount of diluent in the composition can range from about 10 to about 90% by weight of the total composition, preferably from about 25 to about 75%, more preferably from about 30 to about 60% by weight, even more preferably from about 12 to about 60%.

Disintegrant—refers to materials added to the composition to help it break apart (disintegrate) and release the medicaments. Suitable disintegrants include starches; "cold water soluble" modified starches such as sodium carboxymethyl starch; natural and synthetic gums such as locust bean, karaya, guar, tragacanth and agar; cellulose derivatives such as methylcellulose and sodium carboxymethylcellulose; microcrystalline celluloses and cross-linked microcrystalline celluloses such as sodium croscarmellose; alginates such as alginic acid and sodium alginate; clays such as bentonites; and effervescent mixtures. The amount of disintegrant in the composition can range from about 2 to about 15% by weight of the composition, more preferably from about 4 to about 10% by weight.

Binder—refers to substances that bind or "glue" powders together and make them cohesive by forming granules, thus serving as the "adhesive" in the formulation. Binders add cohesive strength already available in the diluent or bulking agent. Suitable binders include sugars such as sucrose; starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropylmethylcellulose; polyvinylpyrrolidone; and inorganics such as magnesium aluminum silicate. The amount of binder in the composition can range from about 2 to about 20% by weight of the composition, more preferably from about 3 to about 10% by weight, even more preferably from about 3 to about 6% by weight.

Lubricant—refers to a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and d'l-leucine. Lubricants are usually added at the very last step before compression, since they must be present on the surfaces of the granules and in between them and the parts of the tablet press. The amount of lubricant in the composition can range from about 0.2 to about 5% by weight of the composition, preferably from about 0.5 to about 2%, more preferably from about 0.3 to about 1.5% by weight.

Glident—material that prevents caking and improve the flow characteristics of granulations, so that flow is smooth and uniform. Suitable glidents include silicon dioxide and talc. The amount of glident in the composition can range from about 0.1% to about 5% by weight of the total composition, preferably from about 0.5 to about 2% by weight.

Coloring agents—excipients that provide coloration to the composition or the dosage form. Such excipients can include food grade dyes and food grade dyes adsorbed onto a suitable adsorbent such as clay or aluminum oxide. The amount of the coloring agent can vary from about 0.1 to about 5% by weight of the composition, preferably from about 0.1 to about 1%.

Bioavailability—refers to the rate and extent to which the active drug ingredient or therapeutic moiety is absorbed into the systemic circulation from an administered dosage form as compared to a standard or control.

Conventional methods for preparing tablets are known. Such methods include dry methods such as direct compression and compression of granulation produced by compaction, or wet methods or other special procedures. Conventional methods for making other forms for administration such as, for example, capsules, suppositories and the like are also well known.

Another embodiment of the invention discloses the use of the inventive compounds or pharmaceutical compositions disclosed above for treatment of diseases such as, for example, hepatitis C and the like. The method comprises administering a therapeutically effective amount of the inventive compound or pharmaceutical composition to a patient having such a disease or diseases and in need of such a treatment.

In yet another embodiment, the compounds of the invention may be used for the treatment of HCV in humans in monotherapy mode or in a combination therapy (e.g., dual combination, triple combination etc.) mode such as, for example, in combination with antiviral and/or immunomodulatory agents. Examples of such antiviral and/or immunomodulatory agents include Ribavirin (from Schering-Plough Corporation, Madison, N.J.) and Levovirin™ (from ICN Pharmaceuticals, Costa Mesa, Calif.), VP 50406™ (from Viropharma, Incorporated, Exton, Pa.), ISIS 14803™ (from ISIS Pharmaceuticals, Carlsbad, Calif.), Heptazyme™ (from Ribozyme Pharmaceuticals, Boulder, Colo.), VX 497™ (from Vertex Pharmaceuticals, Cambridge, Mass.), Thymosin™ (from SciClone Pharmaceuticals, San Mateo, Calif.), Maxamine™ (Maxim Pharmaceuticals, San Diego, Calif.), mycophenolate mofetil (from Hoffman-LaRoche, Nutley, N.J.), interferon (such as, for example, interferon-alpha, PEG-interferon alpha conjugates) and the like. "PEG-interferon alpha conjugates" are interferon alpha molecules covalently attached to a PEG molecule. Illustrative PEG-interferon alpha conjugates include interferon alpha-2a (Roferon™, from Hoffman La-Roche, Nutley, N.J.) in the form of pegylated interferon alpha-2a (e.g., as sold under the trade name Pegasys™), interferon alpha-2b (Intron™, from Schering-Plough Corporation) in the form of pegylated interferon alpha-2b (e.g., as sold under the trade name PEG-Intron™), interferon alpha-2c (Berofor Alpha™, from Boehringer Ingelheim, Ingelheim, Germany) or consensus interferon as defined by determination of a consensus sequence of naturally occurring interferon alphas (Infergen™, from Amgen, Thousand Oaks, Calif.).

As stated earlier, the invention includes tautomers, rotamers, enantiomers and other stereoisomers of the inventive compounds also. Thus, as one skilled in the art appreciates, some of the inventive compounds may exist in suitable isomeric forms. Such variations are contemplated to be within the scope of the invention.

Another embodiment of the invention discloses a method of making the compounds disclosed herein. The compounds may be prepared by several techniques known in the art. Illustrative procedures are outlined in the following reaction schemes. The illustrations should not be construed to limit the scope of the invention which is defined in the appended claims. Alternative mechanistic pathways and analogous structures will be apparent to those skilled in the art.

It is to be understood that while the following illustrative schemes describe the preparation of a few representative inventive compounds, suitable substitution of any of both the natural and unnatural amino acids will result in the formation of the desired compounds based on such substitution. Such variations are contemplated to be within the scope of the invention.

For the procedures described below, the following abbreviations are used:

Abbreviations

Abbreviations which are used in the descriptions of the schemes, preparations and the examples that follow are:

THF: Tetrahydrofuran

DMF: N,N-Dimethylformamide

EtOAc: Ethyl acetate

AcOH: Acetic acid

HOOBt: 3-Hydroxy-1,2,3-benzotriazin-4(3H)-one

EDCl: 1-(3-dimethylaminopropyl)-3-ethylcarbodiimide hydrochloride

NMM: N-Methylmorpholine

ADDP: 1,1'-(Azodicarbobyl)dipiperidine

DEAD: Diethylazodicarboxylate

MeOH: Methanol

EtOH: Ethanol

Et$_2$O: Diethyl ether

DMSO: Dimethylsulfoxide

HOBt: N-Hydroxybenzotriazole

PyBrOP: Bromo-tris-pyrrolidinophosphonium hexafluorophosphate

DCM: Dichloromethane

DCC: 1,3-Dicyclohexylcarbodiimide

TEMPO: 2,2,6,6-Tetramethyl-1-piperidinyloxy

Phg: Phenylglycine

Chg: Cyclohexylglycine

Bn: Benzyl

Bzl: Benzyl

Et: Ethyl

Ph: Phenyl iBoc: isobutoxycarbonyl iPr: isopropyl $^t$Bu or Bu$^t$: tert-Butyl

Boc: tert-Butyloxycarbonyl

Cbz: Benzyloxycarbonyl

Cp: Cylcopentyldienyl

Ts: p-toluenesulfonyl

MCPBA: 3-chloroperbenzoic acid.

Me: Methyl

HATU: O-(7-azabenzotriazol-1-yl)-1,1,3,3-tetramethyluronium hexafluorophosphate

DMAP: 4-N,N-Dimethylaminopyridine

Bop: Benzotriazol-1-yl-oxy-tris(dimethylamino)hexafluorophosphate

PCC: Pyridiniumchlorochromate

Other abbreviations are commonly used abbreviations Such as according to the guidelines published by *Journal of Organic Chemistry*.

General Schemes for Preparation of Target Compounds

Compounds of the present invention were synthesized using the general schemes (Methods A-E) described below.

Method A

Deprotection of the N-Boc functionality of 1.01 under acidic conditions provided the hydrochloride salt 1.02 which was subsequently coupled with N-Boc-tert-leucine under peptide coupling methodology (Louis A Carpino et al. "Preparation of uronium and immonium salts for peptide coupling", WO 2002094822, pp. 76) to afford 1.03. N-Boc deprotection followed by treatment with appropriate isocyanate gave the urea 1.05. Hydrolysis of the methyl ester provided the acid 1.06. Peptide coupling of the acid 1.06 with the appropriate $P_1$—P' primary amide moiety afforded the hydroxyl amide 1.07. Oxidation (Moffatt, or Dess-Martin's) resulted in the target compound 1.08.

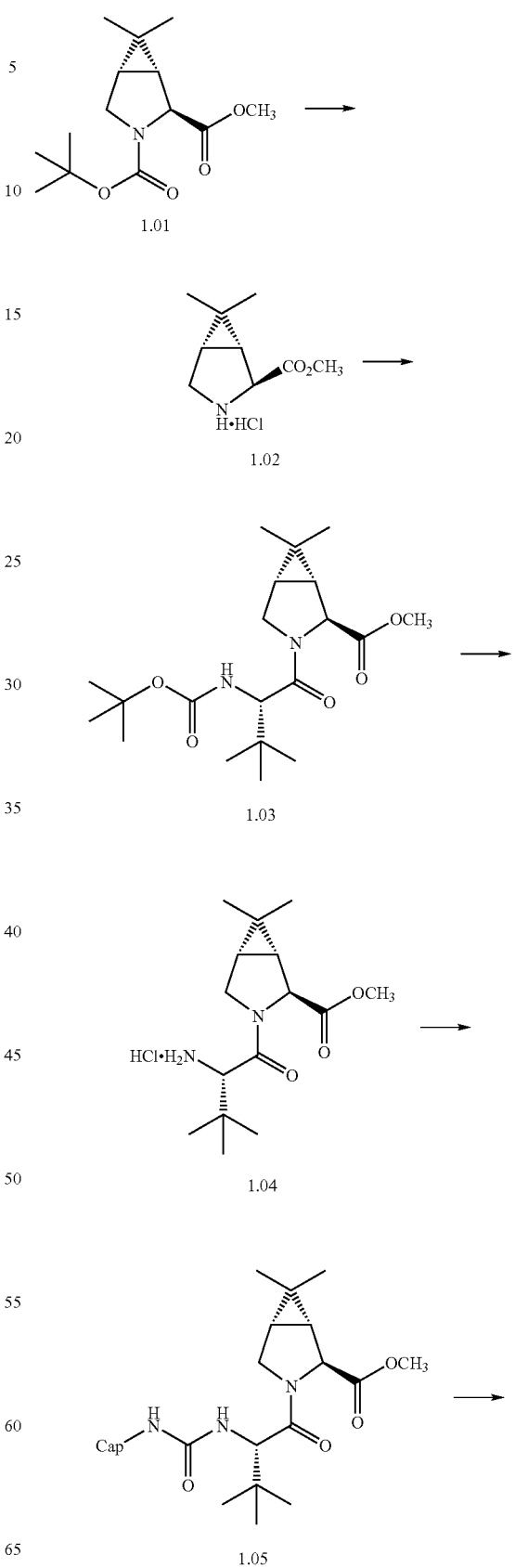

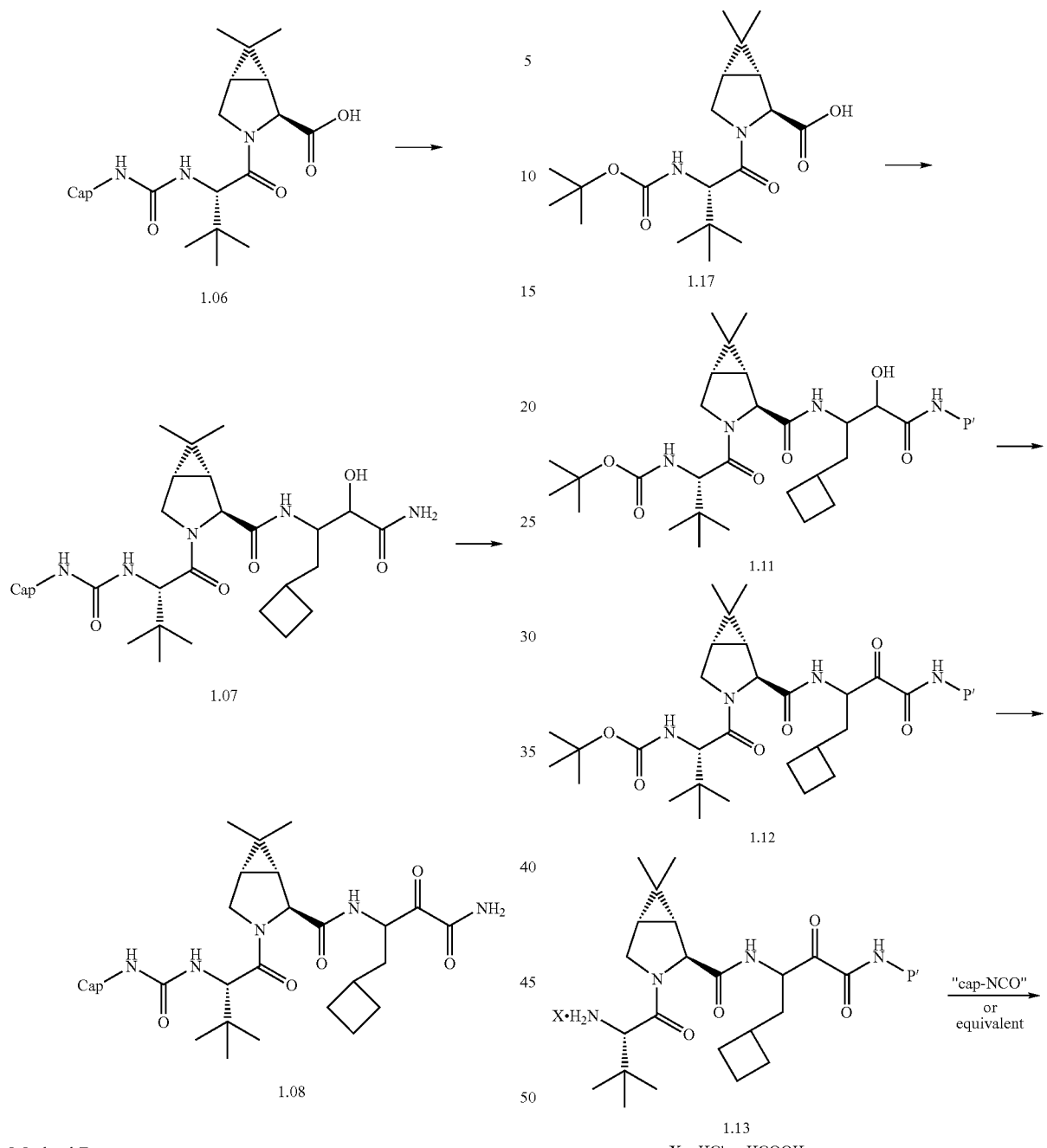

Method B

Peptide coupling of the acid 1.06 with the appropriate P$_1$—P' secondary amide moiety afforded the hydroxyl amide 1.09. Oxidation (Moffatt or Dess-Martin's) resulted in the target compound 1.10.

Method C

In another variation, peptide coupling of the N-Boc-P2-P$_3$- acid 1.03 with the appropriate P$_1$—P' amide moiety afforded the hydroxyl amide 1.11. Oxidation (Moffatt or Dess-Martin's) resulted in the keto-amide 1.12. Deprotection of the N-Boc using either formic acid or 4 M HCl in dioxane gave the formate or hydrochloride salt 1.13. Treatment with a suitable isocyanate (or isocyanate equivalent) resulted in the target compound 1.14.

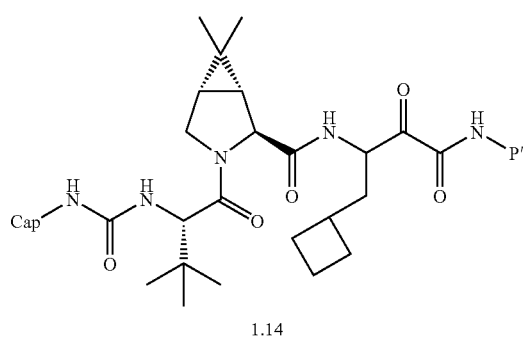

Method D

In yet another variation, the hydrochloride salt 1.13 was converted to the 4-nitrophenyl carbamate 1.15 by reaction with 4-nitrophenyl chloroformate. Subsequent treatment with an amine (or amine hydrochloride salt) of choice provided the target compound 1.14.

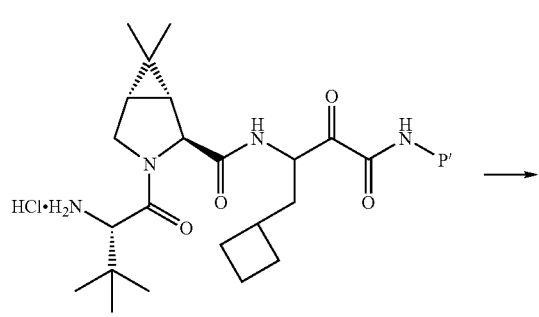

1.13

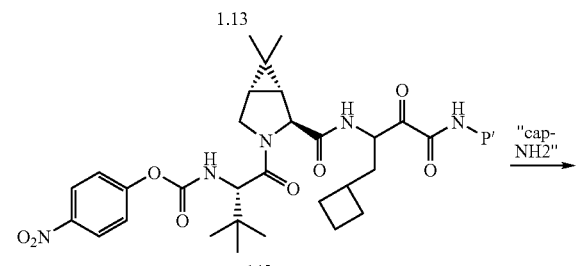

1.15

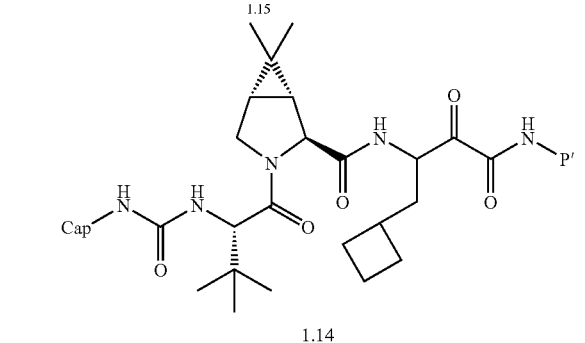

1.14

Method E

In yet another variation, the dipeptide hydrochloride salt 1.04 was converted to the 4-nitrophenyl carbamate as described above. Treatment with an amine (or amine hydrochloride salt) of choice provided the urea derivative 1.05. Hydrolysis and further elaboration as described in Methods A/B provided the target compounds 1.14.

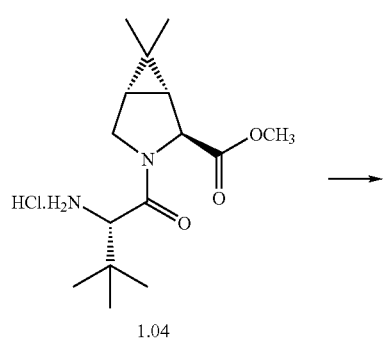

1.04

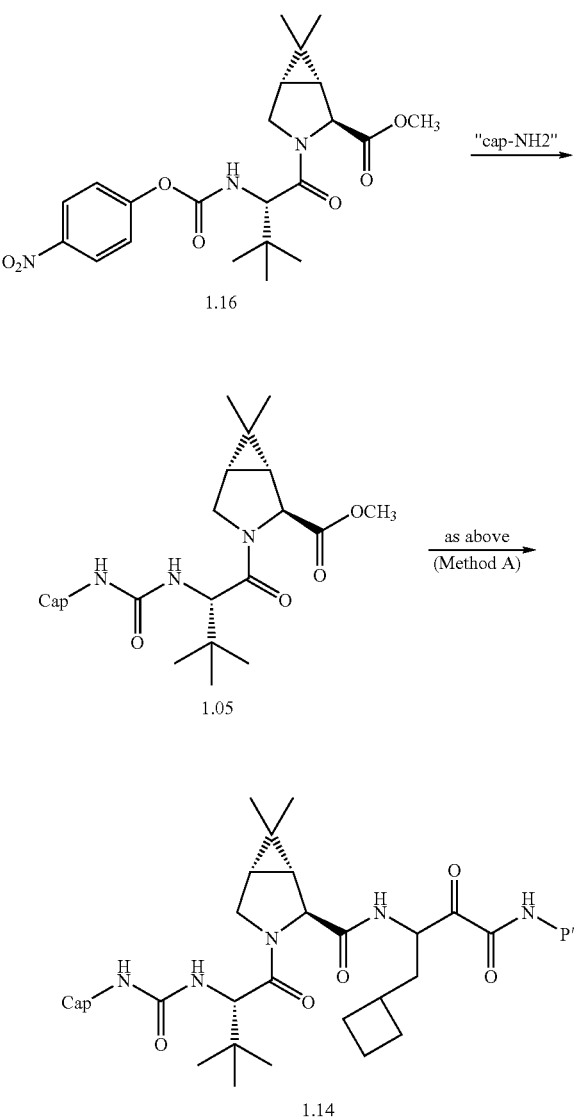

Preparation of Intermediates

Preparation of P1-P' moieties

Preparation of Intermediates 10.11 and 10.12

Step 1

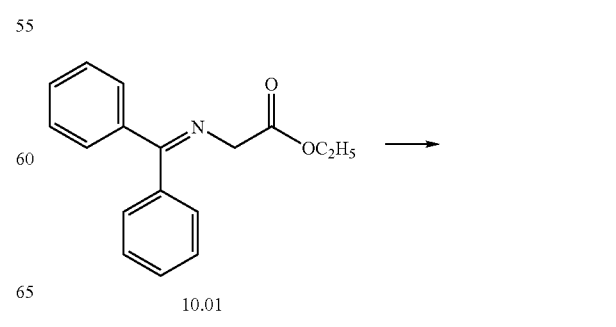

10.01

-continued

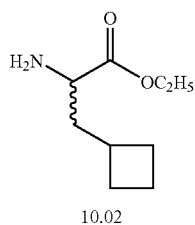

10.02

A stirred solution of ketimine 10.01 (50 g, 187.1 mmol) under $N_2$ in dry THF (400 mL) was cooled to −78° C. and treated with 1 M solution of K-$^t$BuO (220 mL, 1.15 equiv.) in THF. The reaction mixture was warmed to 0° C. and stirred for 1 h and treated with bromomethyl cyclobutane (28 mL, 249 mmol). The reaction mixture was stirred at room temperature for 48 h and concentrated in vacuo. The residue was dissolved in $Et_2O$ (300 mL) and treated with aq. HCl (2 M, 300 mL) The resulting solution was stirred at room temperature for 5 h and extracted with $Et_2O$ (1 L). The aqueous layer was made basic to pH ~12-14 with NaOH (50% aq.) and extracted with $CH_2Cl_2$ (3×300 mL). The combined organic layers were dried ($MgSO_4$), filtered, and concentrated to give the pure amine (10.02, 18 g) as a colorless oil.

Step 2.

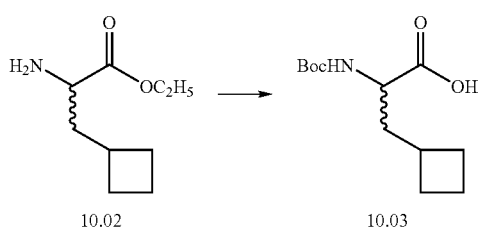

A solution of the amine 10.02 (18 g, 105.2 mmol) at 0° C. in $CH_2Cl_2$ (350 mL) was treated with di-tert-butyldicarbonate (23 g, 105.4 mmol) and stirred at rt. for 12 h. After the completion of the reaction (TLC), the reaction mixture was concentrated in vacuo and the residue was dissolved in THF/$H_2O$ (200 ml, 1:1) and treated with $LiOH.H_2O$ (6.5 g, 158.5 mmol) and stirred at room temperature for 3 h. The reaction mixture was concentrated and the basic aqueous layer was extracted with $Et_2O$. The aqueous layer was acidified with conc. HCl to pH ~1-2 and extracted with $CH_2Cl_2$. The combined organic layers were dried ($MgSO_4$), filtered, and concentrated in vacuo to yield 10.03 as a colorless viscous oil which was used for the next step without any further purification.

Step 3.

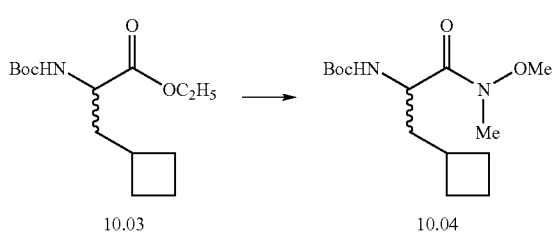

A solution of the acid 10.03 (15.0 g, 62 mmol) in $CH_2Cl_2$ (250 mL) was treated with BOP reagent (41.1 g, 93 mmol), N-methyl morpholine (27 mL), N,O-dimethyl hydroxylamine hydrochloride (9.07 g, 93 mmol) and stirred overnight at rt. The reaction mixture was diluted with 1 N aq. HCl (250 mL), and the layers were separated and the aqueous layer was extracted with $CH_2Cl_2$ (3×300 ml). The combined organic layers were dried ($MgSO_4$), filtered and concentrated in vacuo and purified by chromatography ($SiO_2$, EtOAc/Hex 2:3) to yield the amide 10.04 (15.0 g) as a colorless solid.

Step 4.

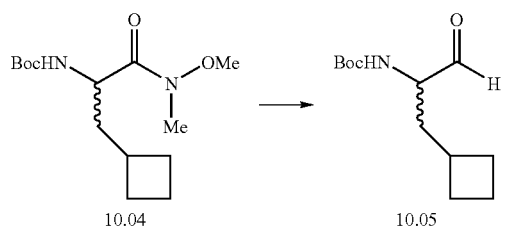

A solution of the amide 10.04 (15 g, 52.1 mmol) in dry THF (200 mL) was treated dropwise with a solution of $LiAlH_4$ (1M, 93 mL, 93 mmol) at 0° C. The reaction mixture was stirred at room temperature for 1 h and carefully quenched at 0° C. with a solution of $KHSO_4$ (10% aq.) and stirred for 0.5 h. The reaction mixture was diluted with aq. HCl (1 M, 150 mL) and extracted with $CH_2Cl_2$ (3×200 mL), The combined organic layers were washed with aq. HCl (1 M), saturated $NaHCO_3$, brine, and dried ($MgSO_4$). The mixture was filtered and concentrated in vacuo to yield 10.05 as a viscous colorless oil (14 g).

Step 5.

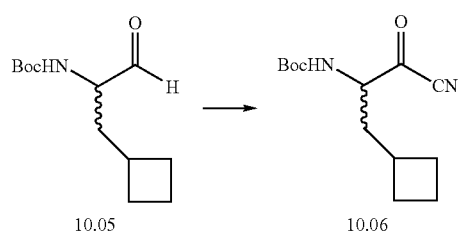

A solution of the aldehyde 10.05 (14 g, 61.6 mmol) in $CH_2Cl_2$ (50 mL), was treated with $Et_3N$ (10.73 mL, 74.4 mmol), and acetone cyanohydrin (10.86 g, 127.57 mmol) and stirred at room temperature for 24 hrs. The reaction mixture was concentrated in vacuo and diluted with aq. HCl (1 M, 200 mL) and extracted into $CH_2Cl_2$ (3×200 mL). The combined organic layer were washed with $H_2O$, brine, dried ($MgSO_4$), filtered, concentrated in vacuo and purified by chromatography ($SiO_2$, EtOAc/Hex 1:4) to yield 10.06 (10.3 g) as a colorless liquid Step 6.

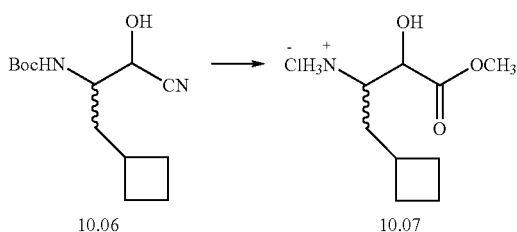

Methanol saturated with HCl*, prepared by bubbling HCl gas through CH$_3$OH (700 ml) at 0° C., was treated with the cyanohydrin 10.06 and heated to reflux for 24 h. The reaction was concentrated in vacuo to yield 10.07, which was used in the next step without purification.

*Alternatively 6M HCl prepared by addition of AcCl to dry methanol can also be used.

Step 7.

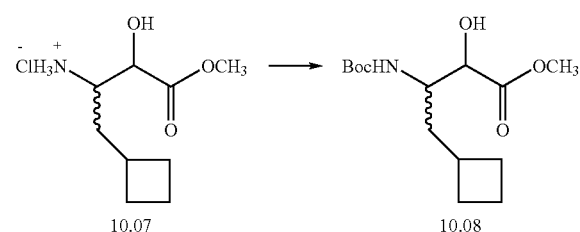

A solution of the amine hydrochloride 10.07 in CH$_2$Cl$_2$ (200 mL) was treated with Et$_3$N (45.0 mL, 315 mmol) and Boc$_2$O (45.7 g, 209 mmol) at −78° C. The reaction mixture was then stirred at room temperature overnight and diluted with HCl (2 M, 200 mL) and extracted into CH$_2$Cl$_2$. The combined organic layers were dried (MgSO$_4$) filtered, concentrated in vacuo and purified by chromatography (EtOAc/Hex 1:4) to yield hydroxy ester 10.08.

Step 8.

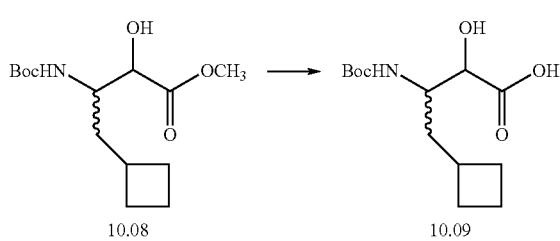

A solution of methyl ester 10.08 (3 g, 10.5 mmol) in THF/H$_2$O (1:1) was treated with LiOH.H$_2$O (645 mg, 15.75 mmol) and stirred at rt. for 2 h. The reaction mixture was acidified with aq HCl (1 M, 15 mL) and concentrated in vacuo. The residue was dried in vacuum to afford 10.09 in quantitative yield.

Step 9

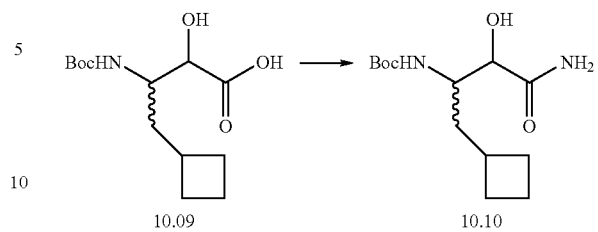

A solution of the acid 10.09 (from above) in CH$_2$Cl$_2$ (50 mL) and DMF (25 mL) was treated with NH$_4$Cl (2.94 g, 55.5 mmol), EDCl (3.15 g, 16.5 mmol), HOOBt (2.69 g, 16.5 mmol), and NMM (4.4 g, 44 mmol). The reaction mixture was stirred at room temperature for 3 d. The solvents were removed under vacuo and the residue was diluted with aq. HCl (250 mL) and extracted with CH$_2$Cl$_2$. The combined organic layers were washed with aq. Sat'd. NaHCO$_3$, dried (MgSO$_4$) filtered concentrated in vacuo to obtain 10.10, which was used as it was in the following steps. (Alternatively 10.10 can also be obtained directly by the reaction of 10.06 (4.5 g, 17.7 mmol) with aq. H$_2$O$_2$ (10 mL), LiOH.H$_2$O (820 mg, 20.8 mmol) at 0° C. in 50 mL of CH$_3$OH for 0.5 h.)

Step 10.

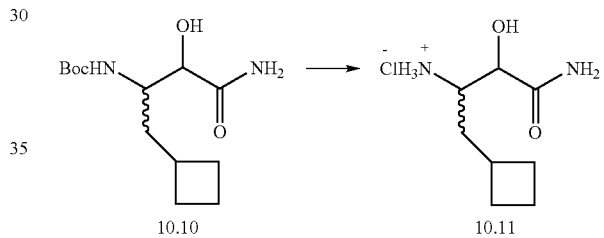

A solution of 10.10 obtained in the previous step was dissolved in 4 N HCl in dioxane and stirred at rt. for 2 h. The reaction mixture was concentrated in vacuo to give the intermediate 10.11 as a solid, which was used without further purification.

Step 11.

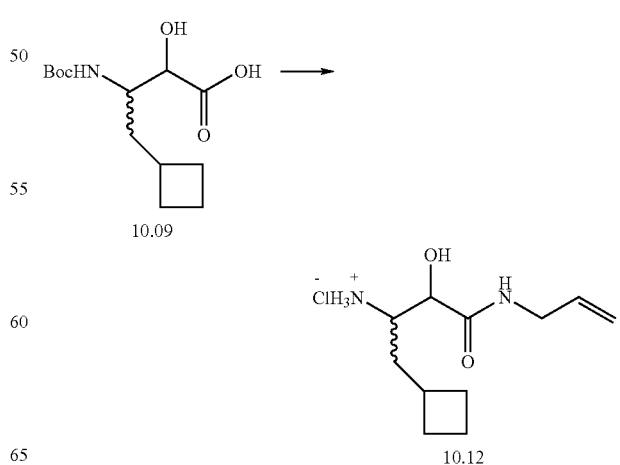

The required intermediate 10.12 was obtained from compound 10.09 using essentially the procedures described above in Steps 9, 10 using 2.0 equivalents of allylamine instead of ammonium chloride.

Preparation of Intermediate 11.01

Step 1

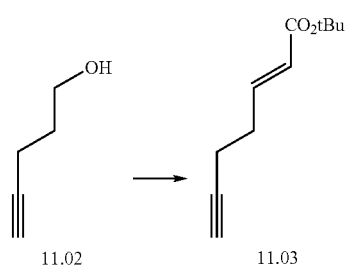

To a solution of 4-pentyn-1-ol, 11.02 (4.15 g; Aldrich) was added Dess-Martin Periodinane (30.25 g; Aldrich) and the resulting mixture was stirred for 45 min. before the addition of (tert-Butoxycarbonylmethylene)triphenylphosphorane (26.75 g; Aldrich). The resulting dark reaction was stirred overnight, diluted with EtOAc), washed with aq. sodium sulfite. sat. aq. NaHCO3, water, brine and dried. The volatiles were removed under reduced pressure and the residue was purified by silica gel column chromatography using 1% EtOAc in hexanes as eluent to give the desired compound, 11.03 (3.92 g). Some impure fractions were also obtained but set aside at this time.

Step 2

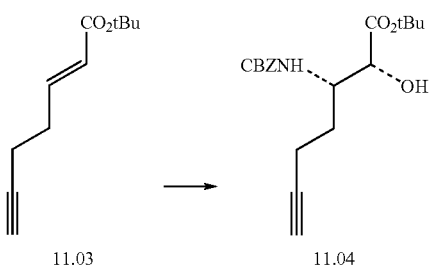

Using the alkene 11.03 (1.9 g) in n-propanol (20 ml; Aldrich)), benzyl carbamate (4.95 g; Aldrich) in n-propanol (40 ml), NaOH (1.29 g) in water (79 ml), tert-butyl hypochlorite (3.7 ml), (DHQ)2PHAL (0.423 g; Aldrich)) in n-propanol (37.5 ml), and potassium osmate:dehydrate (0.1544 g; Aldrich) and the procedure set forth in *Angew. Chem. Int. Ed. Engl* (1998), 35, (23/24), pp. 2813-7 gave a crude product which was purified by silica gel column chromatography using EtOAc:Hexanes (1:5) to give the desired amino alcohol 11.04 (1.37 g, 37%) as a white solid.

Step 3

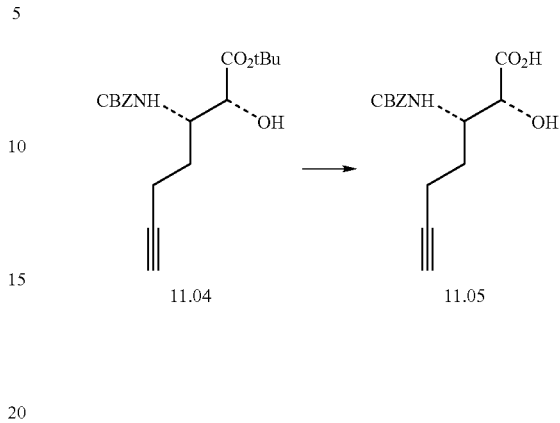

To the ester 11.04 (0.700 g) was added 4M HCl in dioxane (20 ml; Aldrich) and the resulting mixture was allowed to stand at room temperature overnight. The volatiles were removed under reduced pressure to give the acid 11.05 (0.621 g) as a white solid.

Step 4

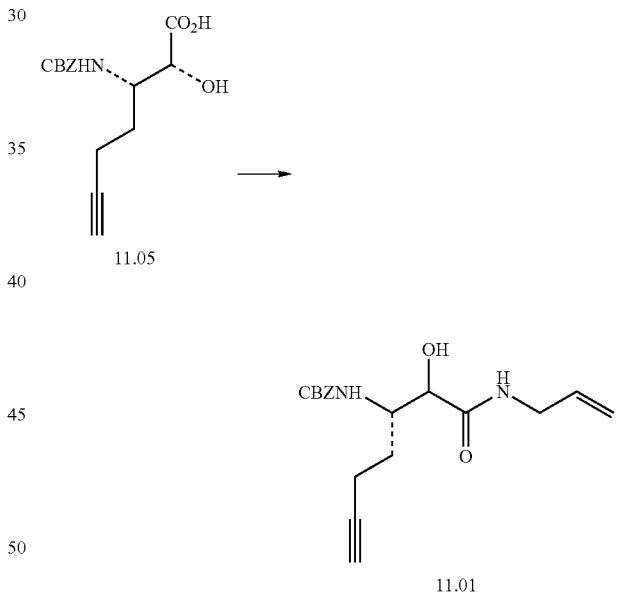

BOP reagent (3.65 g; Sigma) followed by triethylamine (3.45 ml) were added to a dichloromethane (20 ml) solution of the carboxylic acid 11.05 (2.00 g) and allyl amine (0.616 ml) at room temperature and the resulting mixture was stirred overnight. The reaction mixture was partitioned between EtOAc and 10% aq. HCl. The organic phase was separated, washed with sat. aq. sodium bicarbonate, water, dried (magnesium sulfate). The crude reaction product was purified by silica gel column chromatography using (EtOAc:Hexanes; 70:30) as eluent to provide the desired amide 11.01 (1.73 g) as a viscous yellow oil.

Preparation of Intermediates 12.03 and 12.04

Step 1

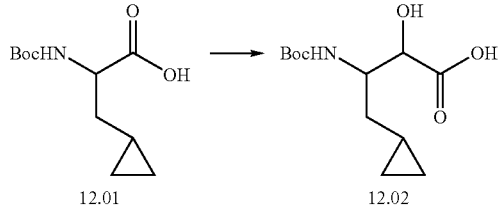

Compound 12.01 (Compound 12.01 was obtained commercially or can be synthesized using similar chemistry as outlined for the synthesis of 10.11 using bromomethyl cyclopropane instead of bromomethylcyclobutane) was converted to the required material 12.02 using essentially the procedures described for Intermediate 10.11, Steps 3-8.

Step 2

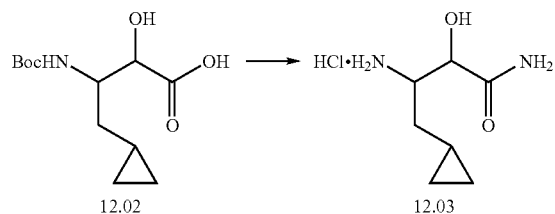

Compound 12.02 was converted to the required intermediate 12.03 using essentially the procedures described for Intermediate 10.11, Steps 9, 10.

Step 3

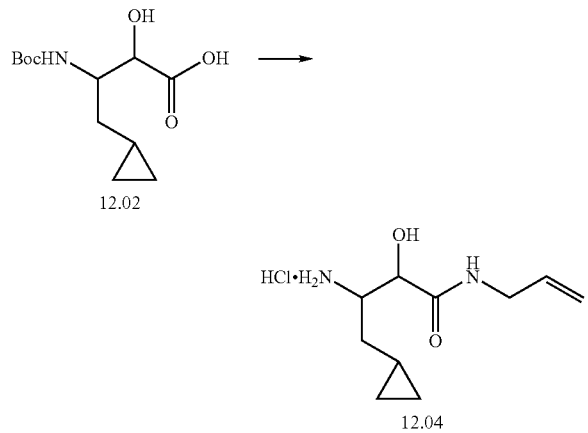

Compound 12.02 was converted to the required intermediate 12.03 using essentially the procedures described for Intermediate 10.12, Step 11.

Preparation of Intermediate 13.01

Step 1

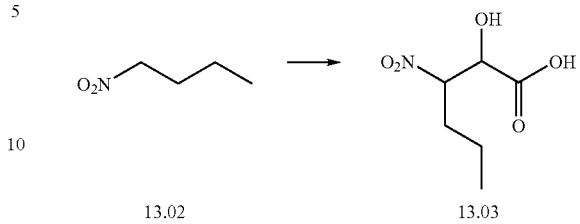

To a stirred solution of 1-nitrobutane, 13.02 (16.5 g, 0.16 mol) and glyoxylic acid in $H_2O$ (28.1 g, 0.305 mol) and MeOH (122 mL) at 0° C.-5° C., was added dropwise triethylamine (93 mL, 0.667 mol) over 2 hrs. The solution was warmed to room temperature, stirred overnight and concentrated to dryness to give an oil. The oil was then dissolved in $H_2O$ and acidified to pH=1 with 10% HCl, followed by extraction with EtOAc. The combined organic solution was washed with brine, dried over $Na_2SO_4$, filtered and concentrated to dryness to give the product 13.03 (28.1 g, 99% yield).

Step 2

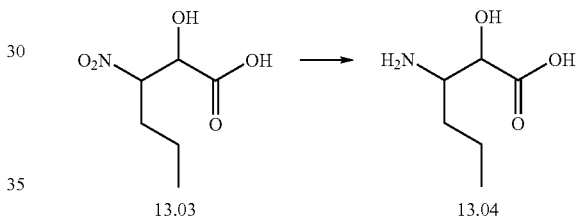

To a stirred solution of compound 13.03 (240 g, 1.35 mol) in acetic acid (1.25 L) was added 10% Pd/C (37 g). The resulting solution was hydrogenated at 59 psi for 3 hrs and then at 60 psi overnight. The acetic acid was then evaporated and azeotroped 3 times with toluene, then triturated with MeOH and ether. The solution was then filtered and azeotroped twice with toluene to afford 13.04 as an off white solid (131 g, 0.891 mol, 66%).

Step 3

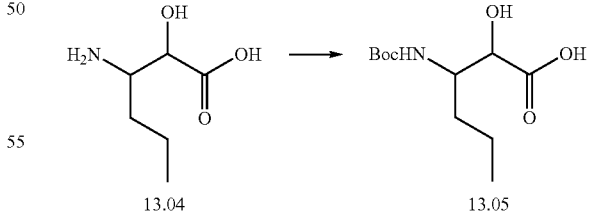

To a stirred solution of the amino acid 13.04 (2.0 g, 13.6 mmol) in dioxane (10 mL) and $H_2O$ (5 mL) at 0° C., was added 1N NaOH solution (4.3 mL, 14.0 mmol). The resulting solution was stirred for 10 minutes, followed by addition of di-t-butyldicarbonate (0.110 g, 14.0 mmol) and stirred at 0° C. for 15 minutes. The solution was then warmed to room temperature, stirred for 45 minutes and kept at refrigerator overnight and concentrated to dryness to give a crude material. To the solution of this crude material in EtOAc (100 mL) and ice, was added KHSO₄ (3.36 g) and H₂O (32 mL) and stirred for 4-6 minutes. The organic layer was then separated and the aqueous layer was extracted twice with EtOAc and the combined organic layer was washed with water, brine, dried over Na₂SO₄, filtered and concentrated to dryness to give the product 13.05 as a clear gum (3.0 g, 89% yield).

Step 4

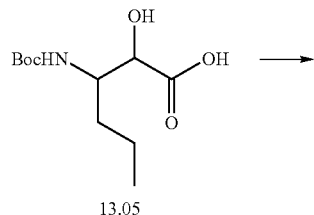

13.05

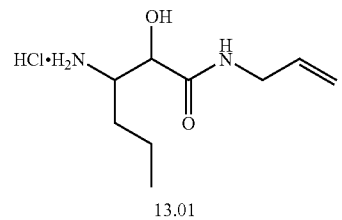

13.01

Compound 13.05 was converted to the required intermediate 13.01 using essentially the procedures described for Intermediate 10.12, Step 11.

Preparation of Intermediate 14.01

Step 1

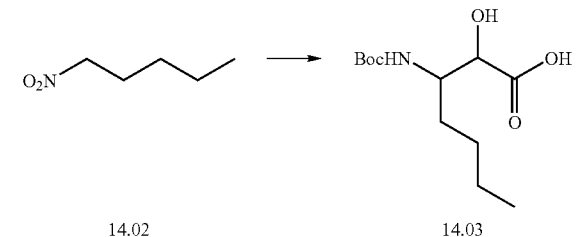

14.02                 14.03

Compound 14.02 was converted to the required material 14.03 using essentially the procedures described for Intermediate 13.01, Steps 1-3.

Step 2

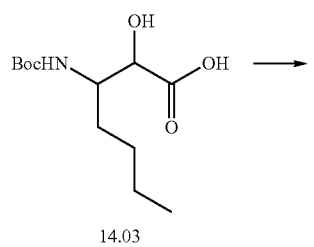

14.03

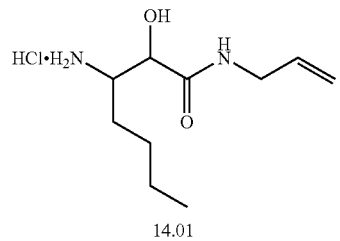

14.01

Compound 14.03 was converted to the required intermediate 14.01 using essentially the procedures described for Intermediate 10.12, Step 11.

Preparation of Intermediate 15.01

Step 1

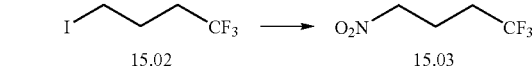

15.02                 15.03

To a suspension of silver nitrite (9 g, 58.5 mmol) in diethyl ether (25 mL) at 0° C. was added a solution of 4-iodo-1,1,1-trifluorobutane, 15.02 (10 g, 42.0 mmol) in diethyl ether (25 mL) slowly through an addition funnel (approx. 15 min). The resulting mixture was vigorously stirred at 0° C. and warmed to rt. After 50 h, the solid material was filtered off through a celite pad. The resulting diethyl ether solution was concentrated in vacuo to give 15.03 as colorless oil, which was used without further purification.

Step 2

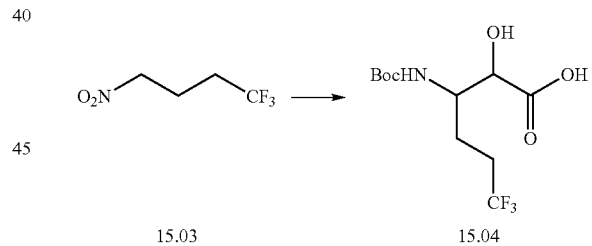

15.03                 15.04

Compound 15.03 was converted to the required material 15.04 using essentially the procedures described for Intermediate 13.01, Steps 1-3.

Step 3

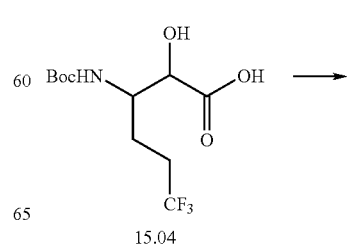

15.04

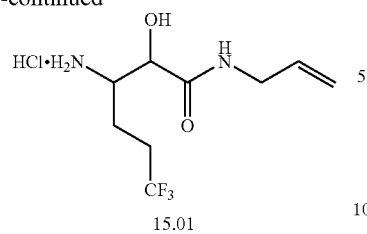

15.01

Compound 15.04 was converted to the required intermediate 15.01 using essentially the procedures described for Intermediate 10.12, Step 11.

Preparation of Intermediate 16.01

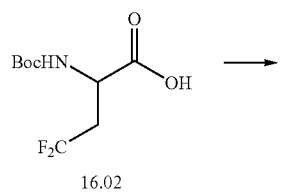

16.02

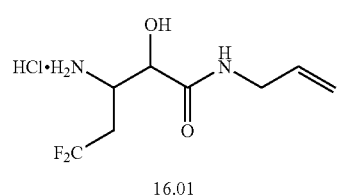

16.01

The acid 16.02 (Winkler, D.; Burger, K., *Synthesis*, 1996, 1419) is processed as described above (preparation of Intermediate 10.12) to give the expected intermediate 16.01.

Preparation of P2/P3-P2 Moieties

Preparation of Intermediate 20.01

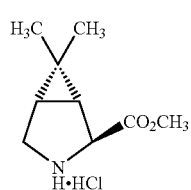

20.01

The amino ester 20.01 was prepared following the method of R. Zhang and J. S. Madalengoitia (*J. Org. Chem.* 1999, 64, 330), with the exception that the Boc group was cleaved by the reaction of the Boc-protected amino acid with methanolic HCl. (Note: In a variation of the reported synthesis, the sulfonium ylide used for the construction of 3,4-dimethylcyclopropyl ring was replaced with the corresponding phosphonium ylide)

Preparation of Intermediate 21.01

Step 1:

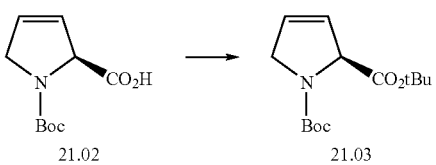

To a stirred solution of N-Boc-3,4-dehydroproline 21.02 (5.0 g, 23.5 mmol), di-tert-butyl dicarbonate (7.5 g, 34.4 mmol), and 4-N,N-dimethylaminopyridine (0.40 g, 3.33 mmol) in acetonitrile (100 mL) at room temperature was added triethylamine (5.0 mL, 35.6 mmol). The resulting solution was stirred at this temperature for 18 h before it was concentrated in vacuo. The dark brown residue was purified by flash column chromatography eluting with 10-25% EtOAc/hexane to give the product 21.03 as a pale yellow oil (5.29 g, 84%).

Step 2:

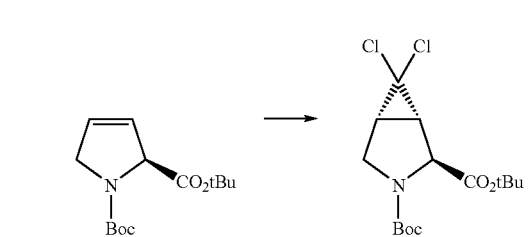

To a stirred solution of the dehydroproline derivative 21.03 (10.1 g, 37.4 mmol), benzyltriethylammonium chloride (1.60 g, 7.02 mmol) in chloroform (120 mL) at room temperature was added 50% aqueous sodium hydroxide (120 g). After vigorously stirred at this temperature for 24 h, the dark mixture was diluted with $CH_2Cl_2$ (200 mL) and diethyl ether (600 mL). After the layers were separated, the aqueous solution was extracted with $CH_2Cl_2/Et_2O$ (1:2, 3×600 mL). The organic solution was dried ($MgSO_4$) and concentrated. The residue was purified by flash column chromatography using 5-20% EtOAc/hexane to afford 9.34 g (71%) of 21.04 as an off-white solid.

Step 3:

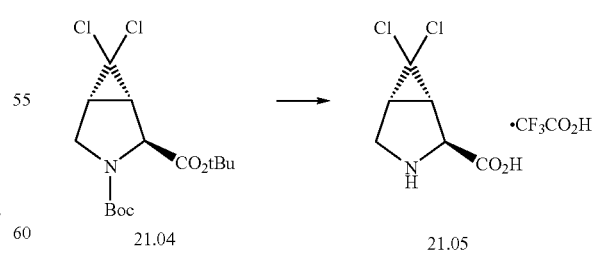

The solution of 21.04 (9.34 g, 26.5 mmol) in $CH_2Cl_2$ (25 mL) and $CF_3CO_2H$ (50 mL) was stirred at room temperature for 4.5 h before it was concentrated in vacuo to give a brown residue, 21.05 which was used in Step 4 without further purification.

Step 4

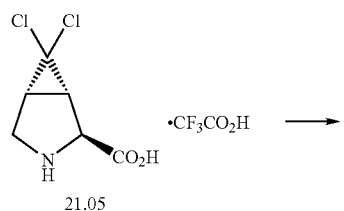

Concentrated hydrochloric acid (4.5 mL) was added to a solution of the residue 21.05 from Step 3 in methanol (70 mL) and the resulting mixture was warmed to 65° C. in an oil bath. After 18 h, the mixture was concentrated in vacuo to give a brown oil 21.01, which was used further without purification.

Preparation of Intermediate 22.01

Step 1

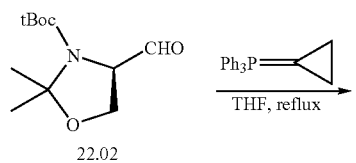

Potassium bis(trimethylsilyl)amide (158 ml of a 0.5M solution in toluene; 79 mmol) was added to a stirred suspension of cyclopropyltriphenylphosphonium bromide (33.12 g; 86.4 mmol) in anhydrous tetrahydrofuran (130 ml) and the resulting orange mixture was stirred under an atmosphere of nitrogen at room temperature for a period of 1 h., before the addition of the aldehyde 22.02 (9.68 g; 42.2 mmol) in THF (8 ml). The reaction was then refluxed under an atmosphere of nitrogen for a period of 2 h. After cooling, methanol, diethyl ether and Rochelles salt were added. The organic phase was separated, washed with brine, dried and concentrated under reduced pressure. The crude reaction product was purified by silica gel column chromatography using EtOAc-hexane (1:99) to EtOAc-hexane (5:95) to provide the alkene 22.03 (8.47 g) as a yellow oil.

Step 2

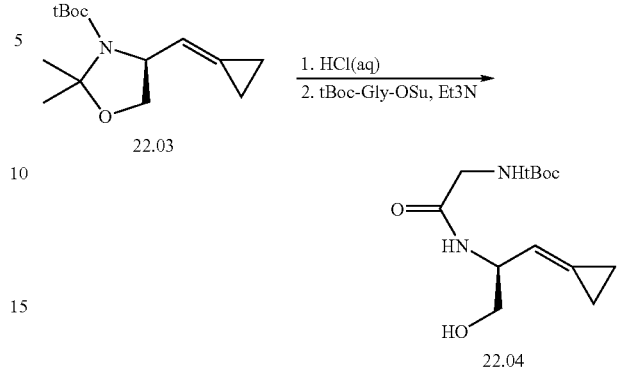

A solution of 1M HCl in MeOH/MeOAc was prepared by adding 14.2 ml of acetyl chloride dropwise into cold methanol and diluting the resulting solution to 200 ml at room temperature. The carbamate 22.03 (9.49 g; 37.5 mmol) was dissolved in methanol (12 ml) and added to 1M HCl in MeOH/MeOAc (150 ml) while cooled in an ice bath. The resulting mixture was maintained at this temperature for 1 h., then the ice bath was removed and stirring continued overnight at room temperature. The volatiles were removed under reduced pressure to yield a yellow oil which was used in the next step without purification. The yellow oil was dissolved in a mixture of THF (30 ml) and MeOH (20 ml) and treated with triethylamine (15 ml; 108 mmol) until the solution was pH=9-10. After placing in an ice bath, the mixture was treated with N-Boc-Gly-OSu (11.22 g; 41 mmol). The ice bath was withdrawn and the reaction stirred at room temp. for 1 h. The volatiles were removed under reduced pressure and the residue was purified by silica gel column chromatography using methanol (1-3%) in dichloromethane providing the desired amide 22.04 (9.09 g).

Step 3

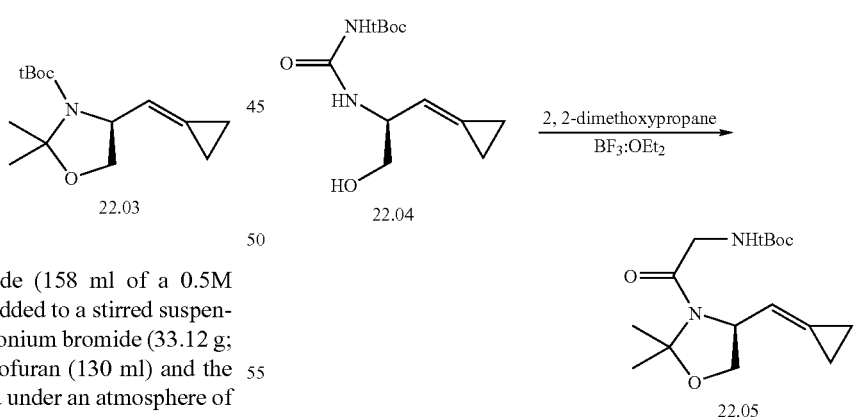

The alcohol 22.04 (9.09 g; 33.6 mmol) was dissolved in acetone (118.5 ml) and treated with 2,2-dimethoxypropane (37.4 ml; 304 mmol) and $BF_3:Et_2O$ (0.32 ml; 2.6 mmol) and the resulting mixture was stirred at room temperature for a period of 5.5 h The reaction solution was treated with a few drops of triethylamine and the volatiles were removed under reduced pressure. The residue was purified by silica gel column chromatography using 5-25% EtOAc in hexanes to provide the N,O-acetal 22.05 (8.85 g).

Step 4

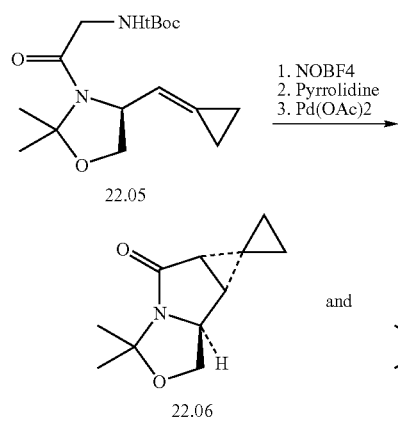

The carbamate 22.05 (8.81 g; 28.4 mmol) was dissolved in acetonitrile (45 ml) and the solution was cooled to −40° C. under an atmosphere of nitrogen. Pyridine (6.9 ml; 85.3 mmol) followed by nitrosium tetrafluoroborate (6.63 g; 56.8 mmol) were added and the resulting reaction mixture maintained below 0° C. until TLC indicated that no starting material remained (approx. 2.25 h.). Pyrrolidine (20 ml; 240 mmol) was added and the cooling bath was withdrawn and stirring was continued at room temperature for 1 h. and then the volatiles were removed under reduced pressure. The residue was quickly passed through a pad of silica gel to provide a yellow oil. The yellow oil was dissolved in anhydrous benzene (220 ml) and palladium acetate (0.317 g; 1.41 mmol) was added before heating the resulting mixture to reflux, under an atmosphere of nitrogen for a period of 1.5 h. After cooling, the volatiles were removed under reduced pressure and the dark residue was purified by silica gel column chromatography using EtOAc-hexane (1:4) to provide the 1) the trans-pyrrolidinone 22.06 (1.94 g) followed by ii) the cis-pyrrolidinone 22.07 (1.97 g).

Step 5

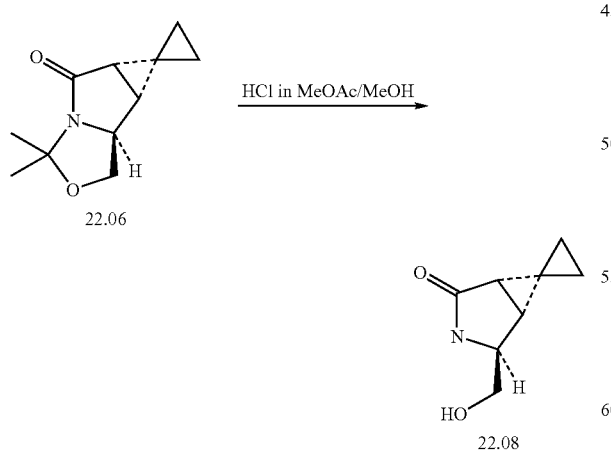

Freshly prepared 1M HCl in MeOAc/MeOH (10 ml; as described above) was added to the N,O-acetal 22.06 and stirred at room temperature for 1 h. The solvent was removed under reduced pressure and the residue was purified by silica gel column chromatography using 0-4% MeOH in dichloromethane as eluent to provide the desired alcohol 22.08 (1.42 g), a yellow oil.

Step 6

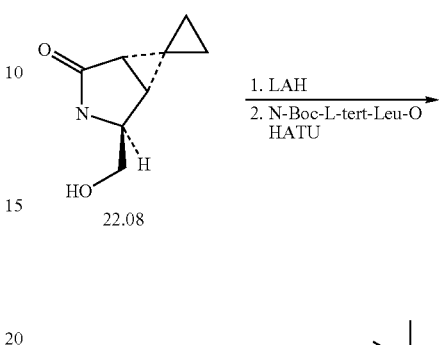

To a solution of the lactam 22.08 (1.29 g; 8.44 mmol) in anhydrous tetrahydrofuran (55 ml) was added lithium aluminum hydride (2.40 g; 63.2 mmol) and the resulting mixture was refluxed for 8 h. After cooling, water, followed by 15% aq. NaOH were added and the resulting mixture was filtered through celite and the solid was washed thoroughly with THF and MeOH. The solvent was removed under reduced pressure and the residue redissolved in dichloromethane, dried and concentrated under reduced pressure to provide the pyrrolidine, used without purification. Hunigs base (4.5 ml; 25.8 mmol) was added to a mixture of N-Boc-L-tert-Leu-OH (1.76 g; 7.6 mmol), The crude pyrrolidine and HATU (2.89 g; 7.6 mmol) in anhydrous dichloromethane (50 ml) at −60° C., under an atmosphere of nitrogen. The resulting reaction was allowed to come to room temperature slowly, overnight. EtOAc was added and the yellow solution was washed with dil. aq. HCl, sat. aq. sodium bicarbonate, water, brine. The organic layer was dried and concentrated under reduced pressure. The residue was purified by silica gel column chromatography using EtOAc:hexanes (1:3) to give the desired amide 22.09 (2.00 g).

Step 7

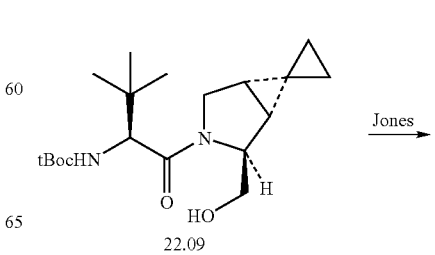

Step 2:

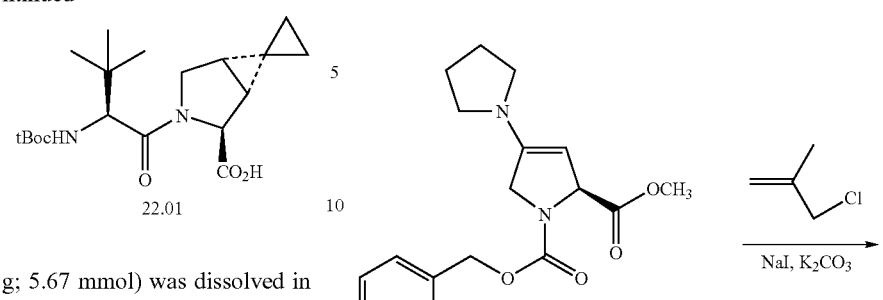

23.03

The alcohol 22.09 (2.00 g; 5.67 mmol) was dissolved in acetone (116 ml) and cooled in an ice bath for 10 min. This solution was then added to a cooled Jones reagent (14.2 ml; approx 2 mmol/ml) and the resulting mixture was stirred at 5 C for 0.5 h and the cooling bath was removed. The reaction was stirred for a further 2 h. at room temp., before adding to sodium sulfate (28.54 g), celite (15 g) in EtOAc (100 ml). Isopropanol (15 ml) was added after 1 min and then stirred for a further 10 min. and filtered. The filtrate was concentrated under reduced pressure, providing a brown oil which was dissolved in EtOAc. This solution was washed with water, 3% aq. citric acid, brine, dried and concentrated to provide the desired carboxylic acid 22.01 (1.64 g) as a white solid.

Preparation of Intermediate 23.01

Step 1:

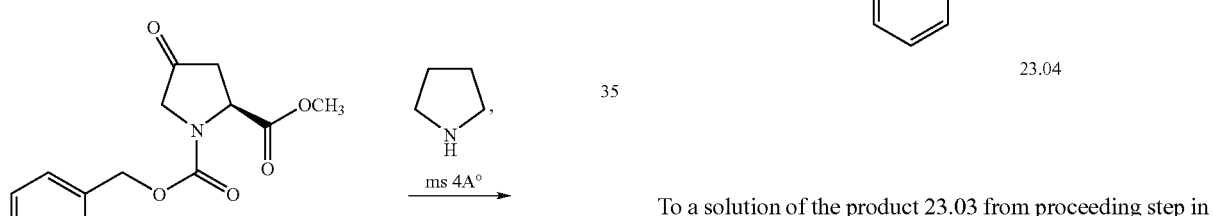

23.02

23.03

To the mixture of ester 23.02 (6.0 g) and molecular sieve (5.2 g) in anhydrous methylene chloride (35 mL) was added pyrrolidine (5.7 mL, 66.36 mmoL). The resulting brown slurry was stirred at room temperature under $N_2$ for 24 h, filtered and washed with anhydrous $CH_3CN$. The combined filtrate was concentrated to yield the desired product, 23.03.

23.04

To a solution of the product 23.03 from proceeding step in $CH_3CN$ (35 mL) was added anhydrous $K_2CO_3$, methallyl chloride (2.77 g, 30.5 mmoL), NaI (1.07 g, 6.7 mmoL). The resulting slurry was stirred at ambient temperature under $N_2$ for 24 h. 50 mL of ice-cold water was added followed by 2N $KHSO_4$ solution until pH was 1. EtOAc (100 mL) was added and the mixture was stirred for 0.75 h. Combined organic layer was collected and washed with brine, dried over $MgSO_4$, and evaporated to yield the desired product, 23.04.

Step 3:

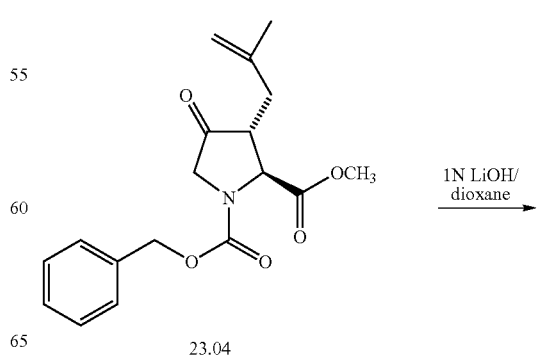

23.04

Step 5:

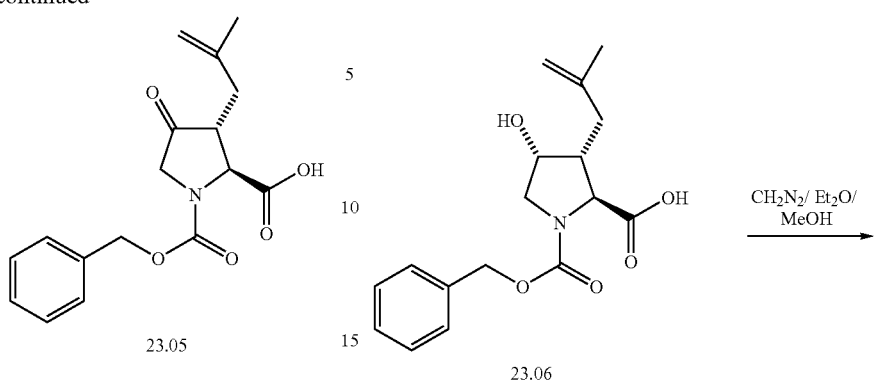

The product 23.04 from the preceding step (2.7 g, 8.16 mmoL) was dissolved in dioxane (20 mL) and treated with freshly prepared 1N LiOH (9 mL). The reaction mixture was stirred at ambient temperature under $N_2$ for 20 h. The reaction mixture was taken in EtOAc and washed with $H_2O$. The combined aqueous phase was cooled to 0° C. and acidified to pH 1.65 using 1N HCl. The turbid mixture was extracted with EtOAc (2×100 mL). Combined organic layer was washed with brine, dried over $MgSO_4$, and concentrated to give the desired acid, 23.05 (3.40 g).

Step 4:

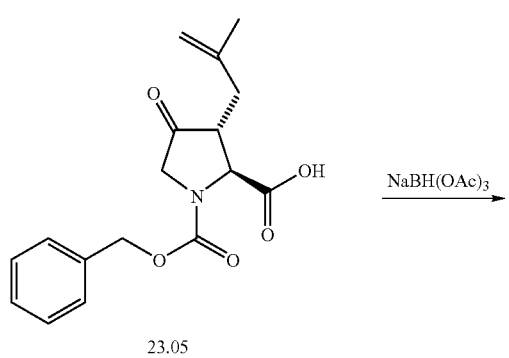

To a solution of the product 23.06 from preceding step (1.9 g) in MeOH (40 mL) was treated with excess of $CH_2N_2/Et_2O$ solution and stirred for overnight. The reaction mixture was concentrated to dryness to yield a crude residue. The residue was chromatographed on silica gel, eluting with a gradient of EtOAc/hexane to afford 1.07 g of the pure desired product, 23.07.

Step 6:

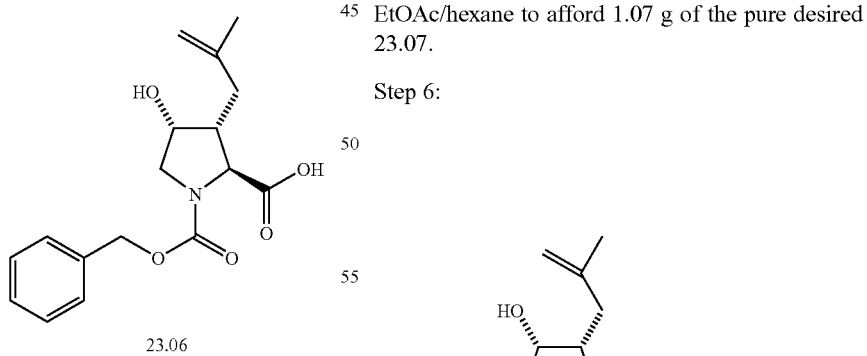

To a suspension of $NaBH(OAc)_3$ (3.93 g, 18.5 mmoL) in $CH_2Cl_2$ (55 mL) was added a solution of product 23.05 from preceding step in anhydrous $CH_2Cl_2$ (20 mL) and acetic acid (2 mL). The slurry was stirred at ambient temperature for 20 h. Ice cold water (100 mL) was added to the slurry and stirred for ½ hr. Organic layer was separated, filtered, dried and evaporated to yield the desired product, 23.06.

-continued

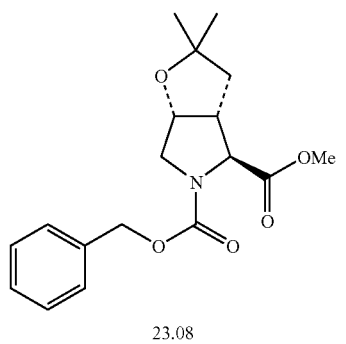

23.08

To a solution of product 23.07 from preceding step (1.36 g) in anhydrous CH$_2$Cl$_2$ (40 mL) was treated with BF$_3$. Me$_2$O (0.7 mL). The reaction mixture was stirred at ambient temperature for 20 h and quenched with sat. NaHCO$_3$ (30 mL) ad stirred for ½ hr. Organic layer was separated and combined organic layer was washed with brine, dried over MgSO$_4$, concentrated to give crude residue. The residue was chromatographed on silica gel eluting with a gradient of EtOAc/hexane to afford 0.88 g of the desired compound, 23.08.

Step 7:

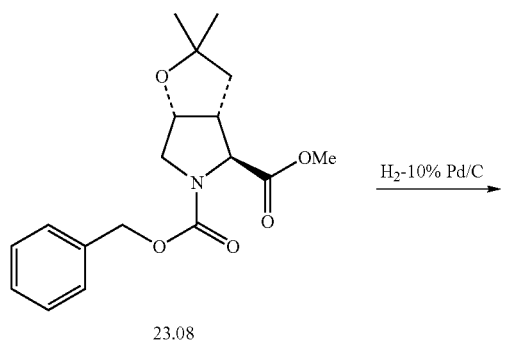

To a solution of the product 23.08 (0.92 g) from preceding step in MeOH (30 mL) was added 10% Pd/C (0.16 g) at room temperature and hydrogenated at ambient temperature under 1 atm. Pressure. The reaction mixture was stirred for 4 h and concentrated to dryness to yield the desired compound, 23.01.

Preparation of P3 Moieties

Preparation of Intermediate 50.01

Step 1

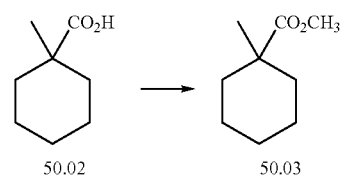

To a solution of 5.02 (15 g) in MeOH (150 mL) was added conc HCl (3-4 mL) and the mixture was refluxed for 16 h. The reaction mixture was cooled to room temperature and concentrated. The residue was taken in diethyl ether (250 mL) and washed with cold saturated sodium bicarbonate solution, and brine. The organic layer was dried (Na$_2$SO$_4$) and concentrated to afford the methyl ester 50.03 (12.98 g) which was carried forward without further purification.

Step 2

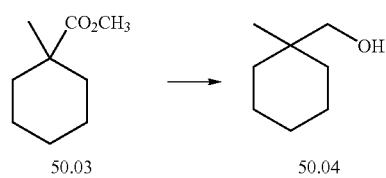

The methyl ester 50.03 from above was dissolved in methylene chloride (100 mL) and cooled to −78° C., under nitrogen atmosphere. DIBAL (1.0 M solution in methylene chloride, 200 mL) was added dropwise over 2 h period. The reaction mixture was warmed to room temperature over 16 h. The reaction mixture was cooled to 0° C. and MeOH (5-8 mL) was added dropwise. A solution of aqueous 10% sodium potassium tartarate (200 mL) was slowly added with stirring. Diluted with methylene chloride (100 mL) and separated the organic layer (along with some white precipitate). The organic layer was washed with 1 N HCl (250 mL), brine (200 mL), dried (Na$_2$SO$_4$) and concentrated to provide the alcohol 50.04 (11.00 g) as a clear oil.

Step 3

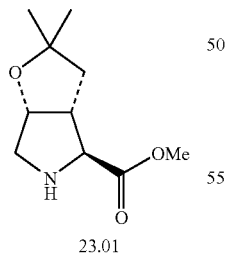

The alcohol 50.04 from above was dissolved in methylene chloride (400 mL) and cooled to 0° C. under nitrogen atmosphere. PCC (22.2 g) was added in portions and the reaction mixture was slowly warmed to room temperature over 16 h. The reaction mixture was diluted with diethyl ether (500 mL) and filtered through a pad of celite. The filtrate was concentrated and the residue was taken in diethyl ether (500 mL). This was passed through a pad of silica gel and the filtrate was concentrated to provide the aldehyde 50.05 which was carried forward without further purification.

Step 4

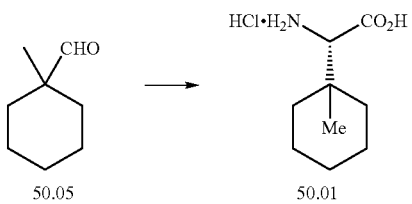

The aldehyde 50.05 from above was converted to the desired material 50.01 using essentially the method of Chakraborty et. al (Tetrahedron, 1995, 51(33), 9179-90).

PREPARATION OF SPECIFIC EXAMPLES

Example 1

Synthesis of Compound of Formula 10001

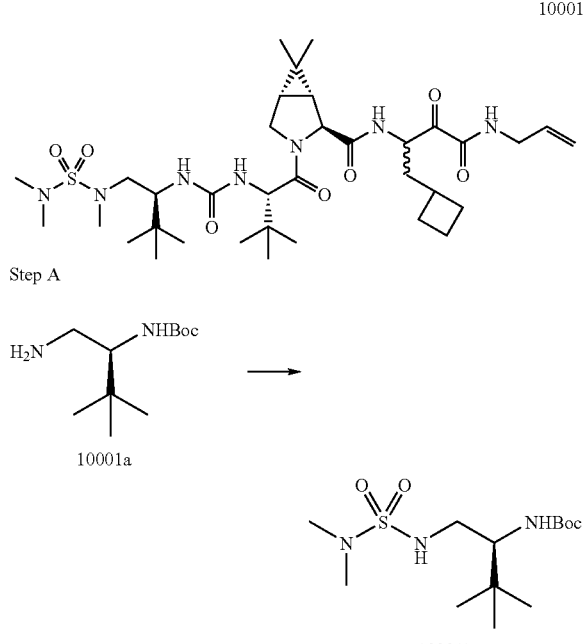

Step A

The amine, 10001a, (C. A. Busacca et al, *Tetrahedron: Asymmetry*; (2000) 9 1907) (1.5 g, 6.9 mmol, 1 equiv.) was dissolved in dry dichloromethane 20 ml) and cooled to −78° C. Added 3 ml (3 equiv.) of Et₃N followed by the slow addition of dimethylsulfamyl chloride (1.5 eq., Sigma-Aldrich) dissolved in DCM. The temperature was kept at −78° C. until the addition is complete and then stirred overnight allowing it to raise to room temperature. Diluted with methylene chloride and washed with water, aq. 1N HCl and finally brine. The organic layers were dried over anhydrous sodium sulfate, filtered and concentrated in vacuo. Crude product isolated was purified via flash column (10→30% EtOAc-Hexane) to afford 1.27 g (58%) of 10001b.

¹H NMR (CDCl₃, 300 MHz) δ, 4.6 (d, 1H), 3.45 (m, 1H), 3.25 (d, 1H), 2.89 (s, 6H), 1.89 (bs, NH), 1.22 (s, 9H), 0.98 (s, 9H).

MS (ESI), m/z, relative intensity 324 [(M+1) 85], 268 (100), 224 (50).

Step B:

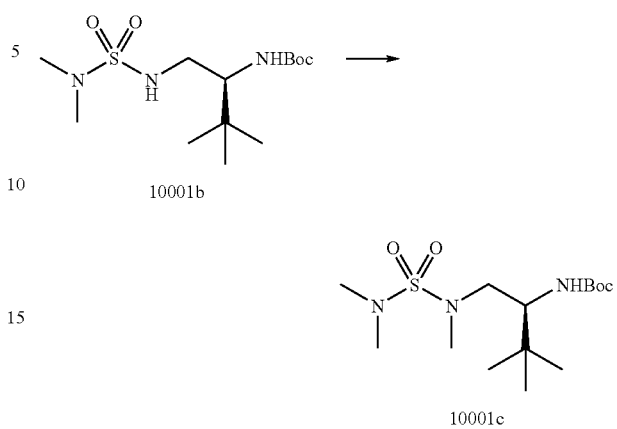

To the Boc protected sulfonyl urea 10001b (440 mg, 1.25 mmol, 1 equiv.) in DMF (10 mL) at 0° C. was added Cs₂CO₃ (613 mg, 1.5 equiv, 1.88 mmol) and MeI (6.36 mmol, 5 equiv., 0.601 mL) under inert atmosphere. The reaction mixture was stirred at room temperature for 90 min and quenched with water. The aqueous layers were extracted with EtOAc, washed 4 times with water and brine. The organic layers was dried over anhydrous sodium sulfate, filtered and evaporated off the solvent to afford 420 mg (91%) of 10001c that was used in the next reaction without further purification.

¹H NMR (CDCl₃, 300 MHz) δ, 4.59 (d, 1H), 3.62-3.58 (m, 1H), 3.29-3.22 (m, 1H), 2.80 (s, 3H), 2.79 (s, 6H), 1.89 (bs, NH), 1.22 (s, 9H), 0.98 (s, 9H).

MS (ESI), m/z, relative intensity 338 [(M+1) 60], 282 (100), 238 (90)

Step C:

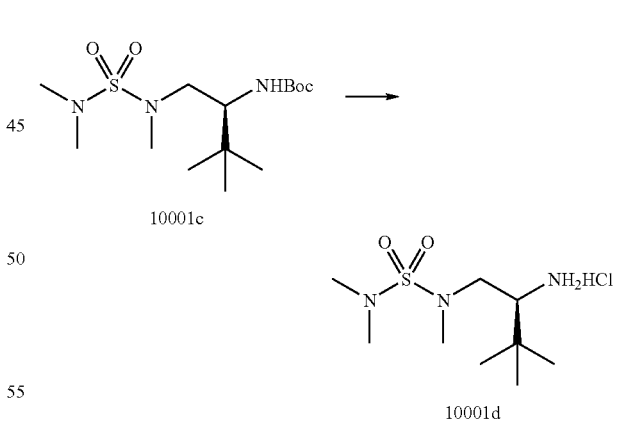

To the Boc-protected sulfonyl urea 10001c (890 mg, 1 equiv.) was added 4M solution of HCl in dioxane (25 mL) at room temp and stirred for 1 hr. After the disappearance of starting material (TLC), the reaction mixture was concentrated and azeotroped with hexanes and ether. The residue was triturated with ether and the solid separating out was filtered and dried in vacuum to afford a pale yellow solid (720 mg, ~100%). It was used in further reaction without purification.

Step D:

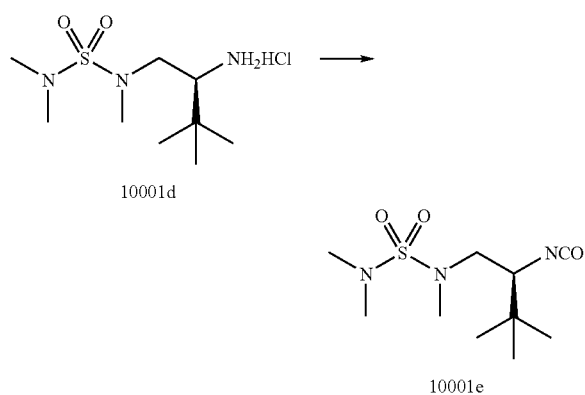

To the amine hydrochloride salt 10001d (720 mg, 2.63 mmol) in dichloromethane (15 ml) was added 15 ml of aq. saturated NaHCO₃ and stirred vigorously at 0° C. for 5 min. A solution of phosgene (2 equiv. 20% in toluene) was syringed out to the lower layer and restored the vigorous stirring immediately. Checked the TLC at times and after 2 hrs, it showed complete consumption of starting material. The methylene chloride layer was separated and the aqueous layer was extracted with dichloromethane (30 ml). The combined organic layers were dried over anhydrous sodium sulfate, filtered and concentrated using rotary evaporator under reduced pressure at rt. to half the volume and then flushed N₂ for 15 minutes. Diluted the solution to 130 mL with dichloromethane and used as 0.02 M solution in further reactions.

Step E:

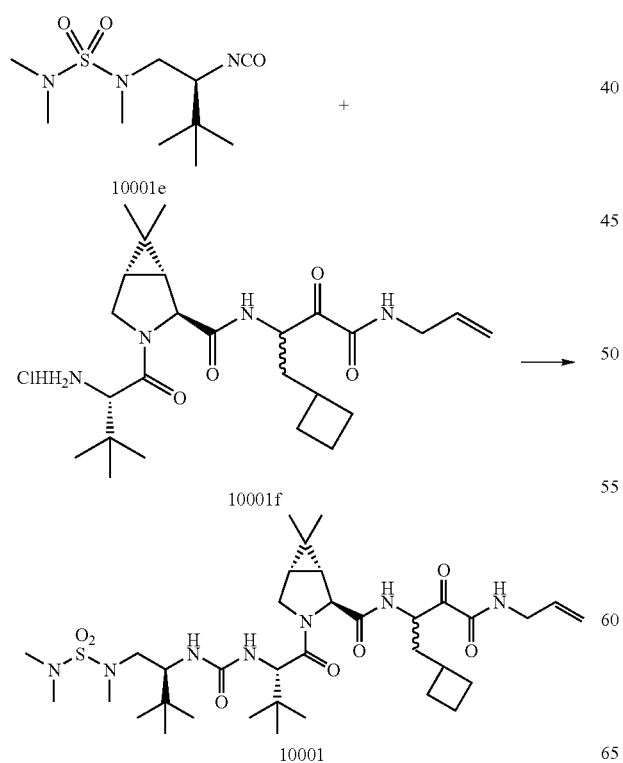

To the amine hydrochloride salt, 10001f (synthesized by coupling of intermediate 10.12 and 1.17 using HATU followed by Dess-Martin oxidation and Boc deprotection following method C or the procedure outlined for the synthesis of 13001h) (130 mg, 0.261 mmol, 1 equiv.) in dichloromethane (5 ml) was added DIPEA (6 equiv.) at 0° C. A solution of isocyanate 10001e (1 equiv, 13 ml of 0.02M soln.) under N₂ atmosphere and stirred for 30 min at ice temperature and 90 min at room temperature. The reaction mixture was quenched with citric acid and extracted with EtOAc. The organic layer was washed with brine, dried over anhydrous sodium sulfate, filtered and concentrated in vacuo. The crude product was purified using flash column chromatography (SiO₂, 10-40% acetone-hexane) to afford 110 mg (59%) of 10001 as a colorless solid.

MS (ESI), m/z, relative intensity 724[(M+1) 45], 377 (100).

Example 2

Synthesis of Compound of Formula 10002

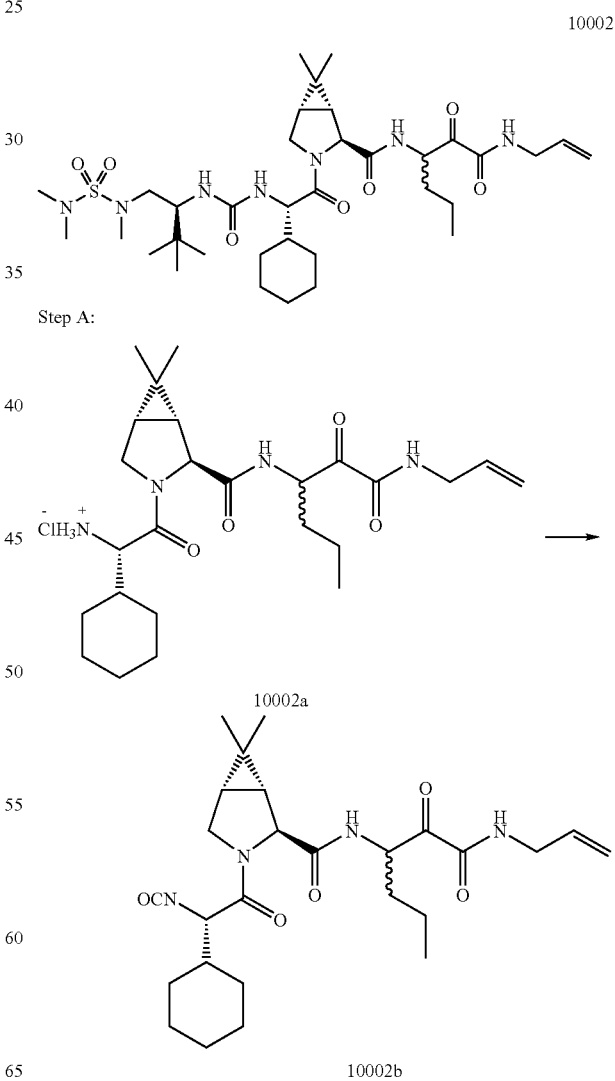

Step A:

To a solution of amine hydrochloride salt 10002a (500 mg, 1.00 mmol, 1 equiv.) in dichloromethane (15 ml) was added a solution of aq. sat. NaHCO$_3$ (15 mL). The reaction mixture was stirred vigorously at ice temperature for 5 min. A solution of phosgene (2 equiv. 20% in toluene) was syringed out to the lower layer and restored the vigorous stirring immediately. Checked the TLC at times and after 2 hrs it showed complete consumption of starting material and then separated the layers. Washed the water layer one more time with DCM (3 ml) and dried over sodium sulfate. Filtered and evaporated at high vacuum to half the volume and then purged N$_2$ for 15 minutes. Used 10002b as a stock solution of 0.02M by diluting with 50 mL of dichloromethane.

Step B:

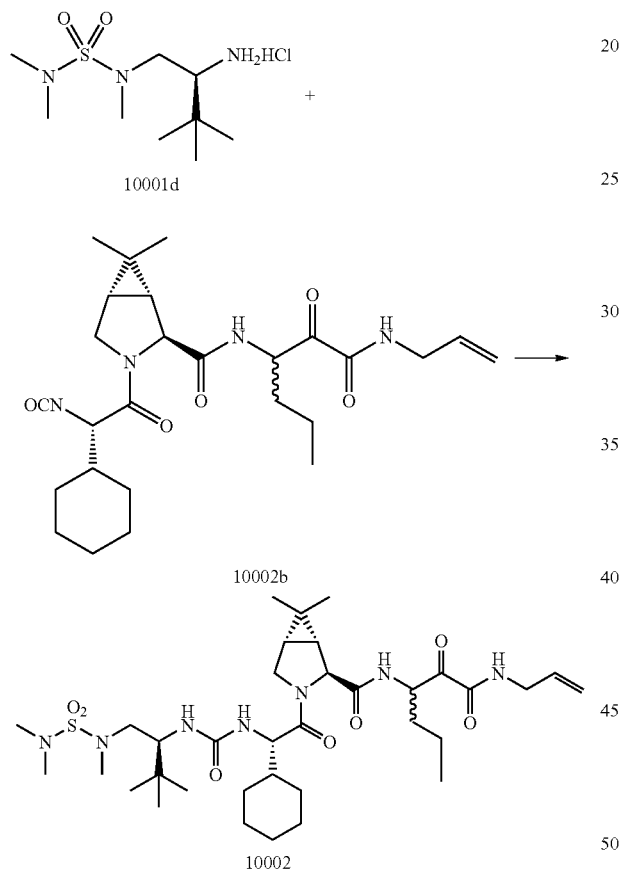

To the ammonium salt 10001d, (80 mg, 0.293 mmol, 1 equiv.) in dichloromethane (10 ml) was added DIPEA (6 equiv.) at ice temperature. Added isocyanate 10002b (1 equiv, 14.6 ml of 0.02M solution) under N$_2$ atm., and stirred for 30 min at ice temperature and 90 ml at room temperature. Quenched with citric acid and extracted with EtOAc and washed with brine. Dried over anhydrous sodium sulfate and filtered and evaporated off the solvent. The crude product was purified using silica gel flash chromatography (10-40% acetone-hexane) to afford 120 mg (57%) of 10002 as a colorless solid.

MS (ESI), m/z, relative intensity 724 [(M+1) 100], 461 (45), 403 (80).

Example 3

Synthesis of Compound of Formula 10003

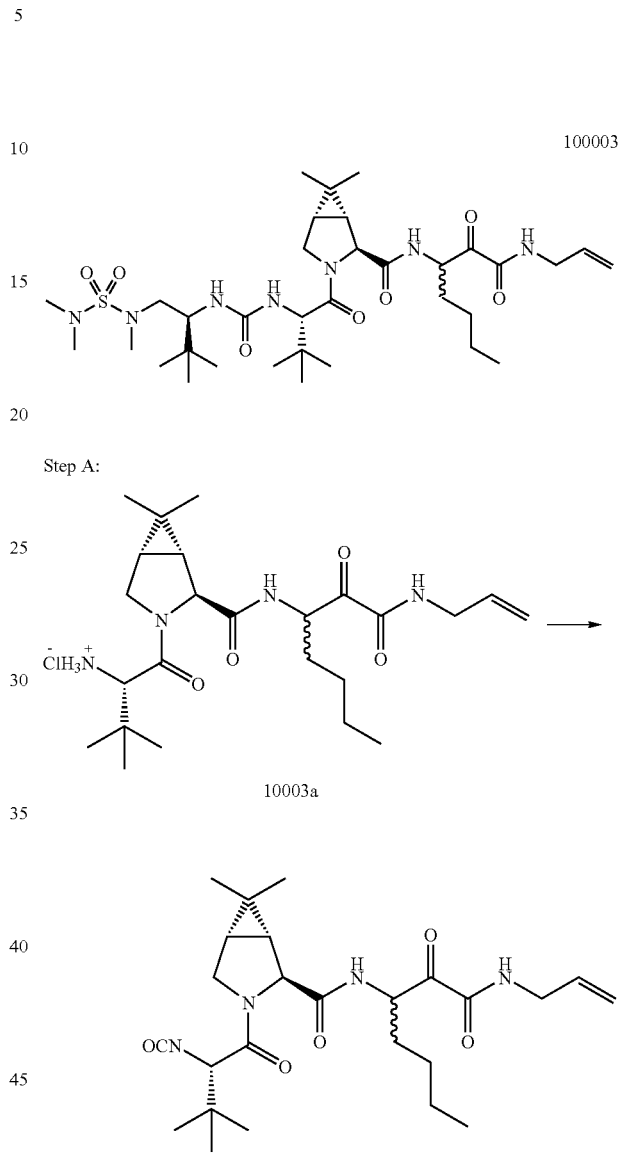

Step A:

To the amine hydrochloride 10003a, prepared as described before, (500 mg, 1.03 mmol, 1 equiv.) in DCM (15 ml) was added 15 ml of sat. NaHCO$_3$. Stirred vigorously at ice temperature for 5 min. Stopped stirring and phosgene (1.11 mL, 2 equiv., 20% in toluene) was syringed out to the lower layer and restored the vigorous stirring immediately. Checked the TLC at times and after 2 hrs it showed complete consumption of starting material and then separated the layers. Washed the water layer one more time with DCM (3 ml) and dried over sodium sulfate. Filtered and evaporated at high vacuum to half the volume and then purged N$_2$ for 15 minutes. Used as a stock solution of 10003b (0.02M) by diluting with 50 mL of dichloromethane.

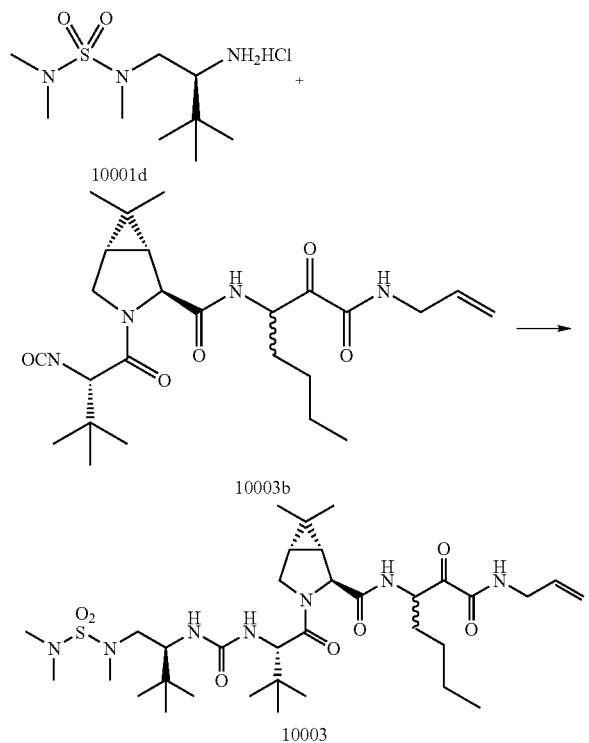

To a solution of ammonium salt, 10001d, (20 mg, 0.073 mmol, 1 equiv.) in DCM (5 ml) was added DIPEA (6 equiv.) at ice temperature was added isocyanate 10003b (1 equiv, 0.073 mmol, 3.66 mL of 0.02M soln) under N₂ atm. and stirred for 30 min at ice temperature and 90 min at room temperature. Quenched with citric acid and extracted with EtOAc and washed with brine. Dried over anhydrous sodium sulfate, filtered and evaporated off the solvent. The crude product was purified via flash silica column (10-40% acetone-hexane) to afford 28 mg, 55% of 10003.

MS (ESI), m/z, relative intensity 724 [(M+1) 100], 461 (45), 403 (80).

Example 4

Synthesis of Compound of Formula 10004

Step A:

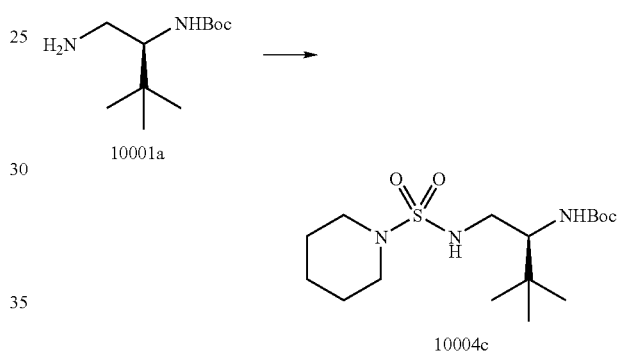

To 0.95 mL (11.7 mmol) of sulfuryl chloride in 20 mL ether was added dropwise 2.3 mL (23.4 mmol) of piperidine at −78° C. The reaction was stirred at rt for 3 hrs. The insoluble solid was removed by filtration and the filtrate was washed with 1N HCl, sat NaHCO₃ and brine. The organic layer was dried over MgSO₄, filtered and the filtrate was concentrated to dryness to give 1.00 g of 10004b. yield 46%.

Step B:

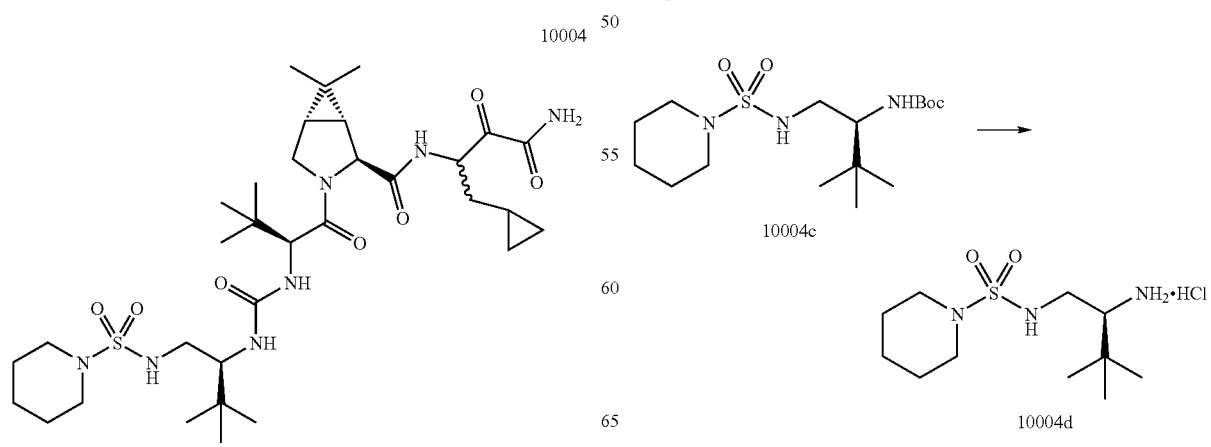

To 0.350 g (1.62 mmol) of 10001a in 10 mL CH₂Cl₂ was added 0.23 mL (1.62 mmol) of Et₃N, then 0.446 g (2.42 mmol) of 10004b in 5 mL CH₂Cl₂ drop wise at rt. The reaction mixture was stirred at rt overnight. The reaction mixture was diluted with EtOAc, washed with a solution of aq. NH₄Cl and brine. The organic layers was dried over MgSO₄, filtered, concentrated in vacuo and purified by silica gel chromatography with 6→24% EtOAc in Hexane to yield 0.353 g of product. Yield 60%.

Step C:

To 15 mg (0.041 mmol) of 10004c in a flask was added 2 ml (8 mmol) of 4M HCl (in dioxane) and stirred at RT for 50 min. The reaction mixture was concentrated to dryness in vacuo to give 32 mg of 2004d. Yield 100%.

Note: The conversion of 10004d to 10004 was identical to step B. in preparative example 3 Synthesis of compound of formula 10003.

Example 5

Synthesis of Compound of Formula 10005

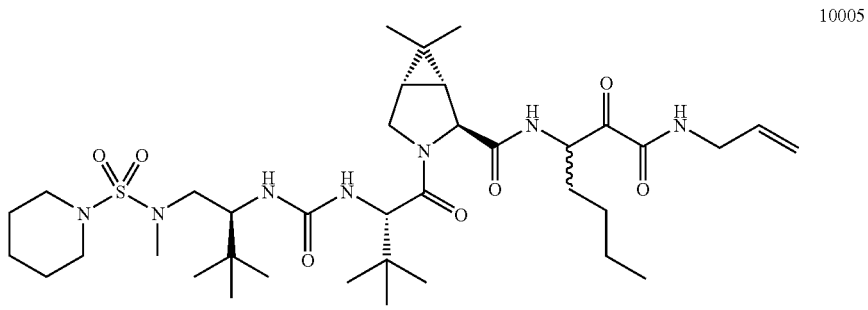

10005

Step A:

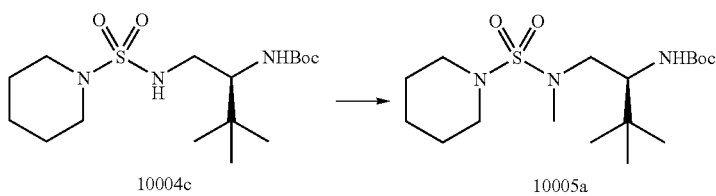

To a solution of 0.275 g (0.76 mmol) of 10004c in DMF was added 0.369 g (1.13 mmol) of Cs$_2$CO$_3$ and 0.085 mL (1.37 mmol) of MeI at 0° C. The reaction was stirred at rt. overnight. The reaction mixture was diluted with water and extracted with EtOAc. The organic layer was washed with brine, dried, concentrated in vacuo and the residue was purified by chromatography (SiO$_2$ 8~32% EtOAc in hexane) to give 0.256 g of product 10005a. Yield 89%.

Step B:

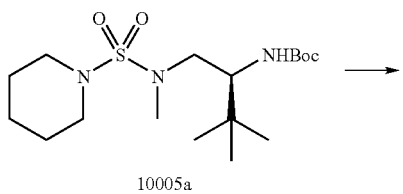

10005a

-continued

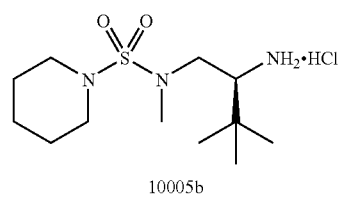

10005b

To a solution of 0.291 g (0.77 mmol) of 10005a in flask was added 3 mL (12 mmol) of 4M HCl (in dioxane). and stirred at rt. for 50 min. After the completion of reaction as indicated by TLC the reaction mixture was concentrated in vacuo to dryness to yield 0.241 g of 10005b.

Step C:

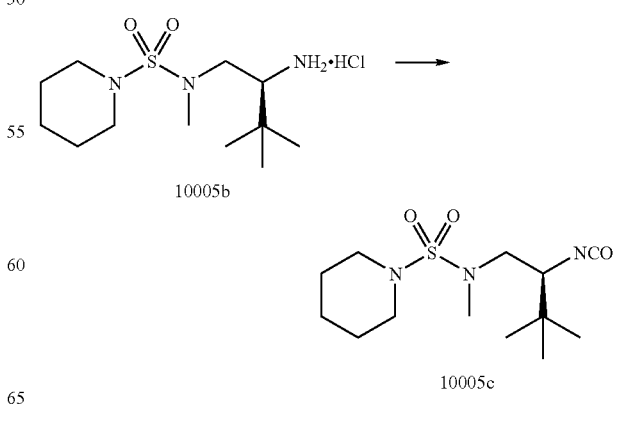

To 0.241 g (0.77 mol) of 10005c in CH$_2$Cl$_2$ at 0° C. was added 0.81 mL (1.54 mmol) of 1.9 M solution of phosgene in toluene and 10 mL of saturated aqueous NaHCO$_3$ solution. The reaction mixture was stirred at rt. for 1.0 h. The organic layer was separated and dried over (Na$_2$SO$_4$), filtered concentrated to half volume. It was further diluted with CH$_2$Cl$_2$ to afford a 0.07 M solution.

Note: The conversion of 10005c to 10005 was identical to step B in preparative example 3 Synthesis of compounds 10003.

Compounds indicated in the following Table 1 were synthesized using similar reactions as shown in Examples 1-5. Range of Ki* indicated: A≦75 nM; 75<B≦250 nM; C>250 nM.

TABLE 1

| Entry | Structure | K$_i$* |
|---|---|---|
| 10001 | 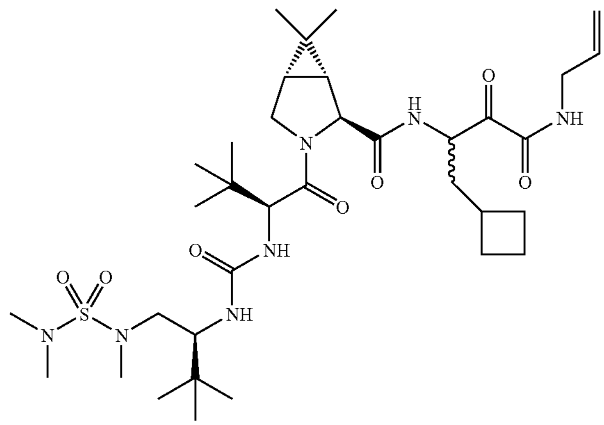 | A |
| 10002 | 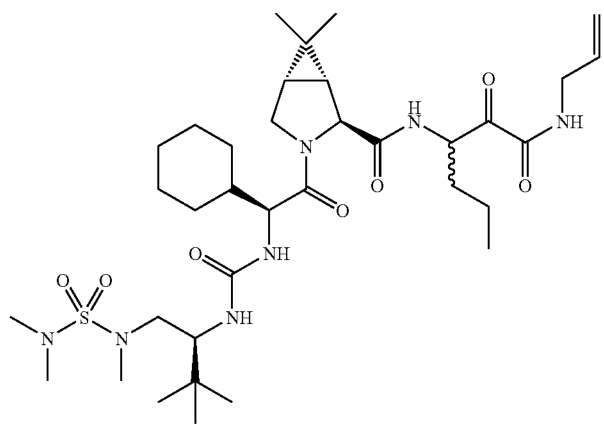 | A |
| 10003 | 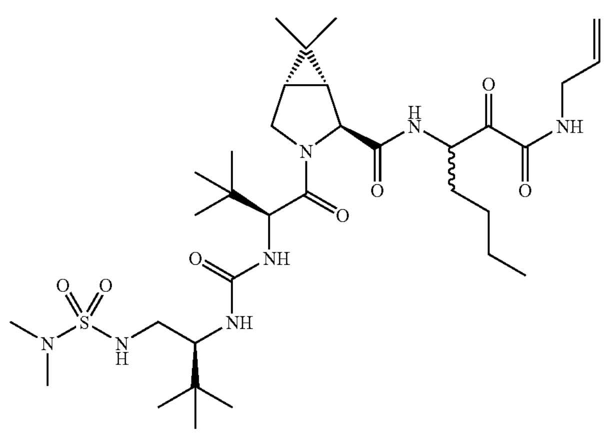 | A |

TABLE 1-continued
| Entry | Structure | $K_i$* |
|---|---|---|
| 10004 | 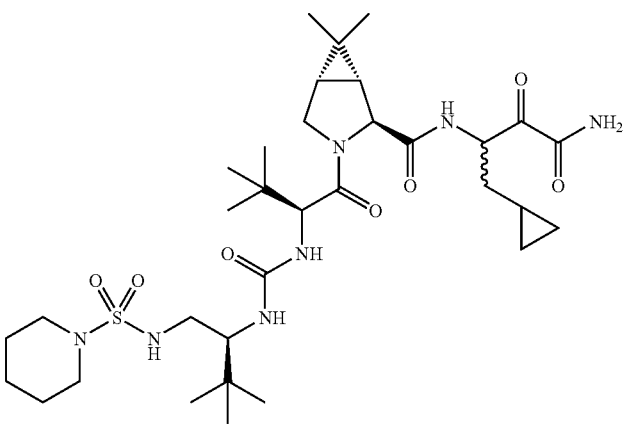 | A |
| 10005 | 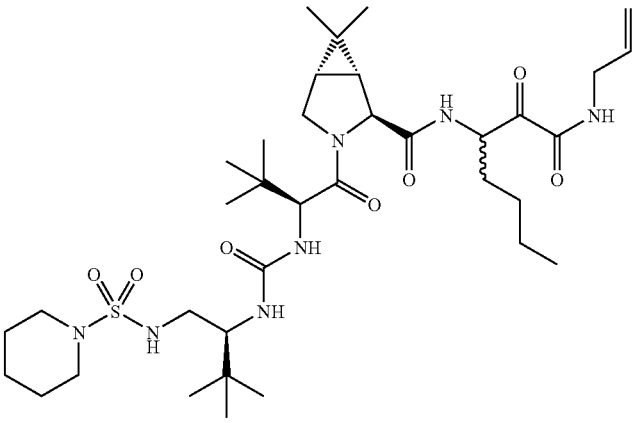 | A |
| 10006 | 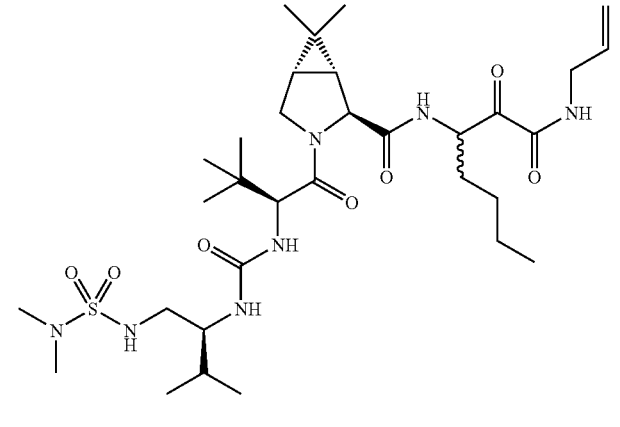 | B |

TABLE 1-continued

| Entry | Structure | $K_i$* |
|---|---|---|
| 10007 | 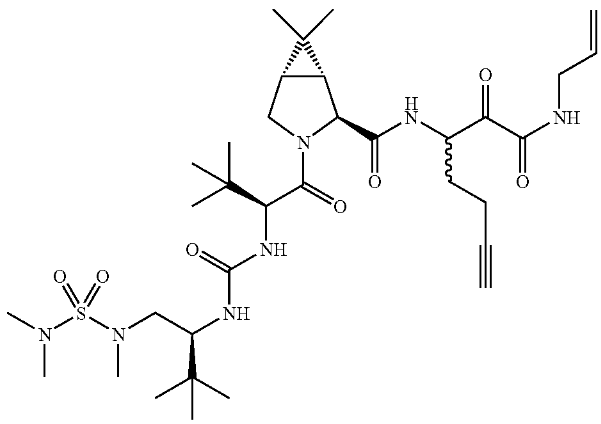 | A |
| 10008 | 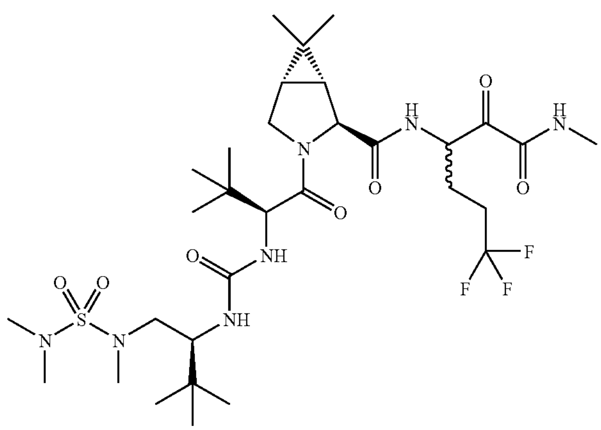 | A |
| 10009 | 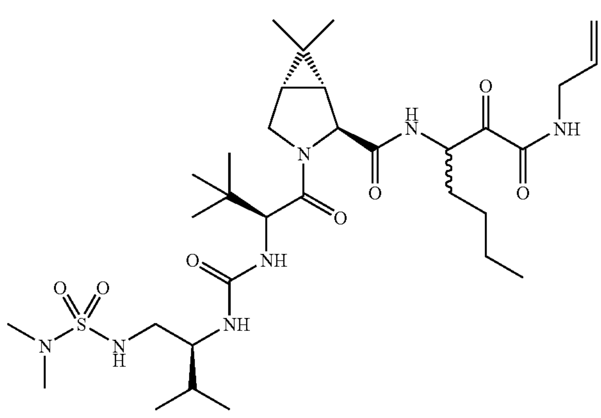 | B |

TABLE 1-continued

| Entry | Structure | $K_i$* |
|---|---|---|
| 10010 | 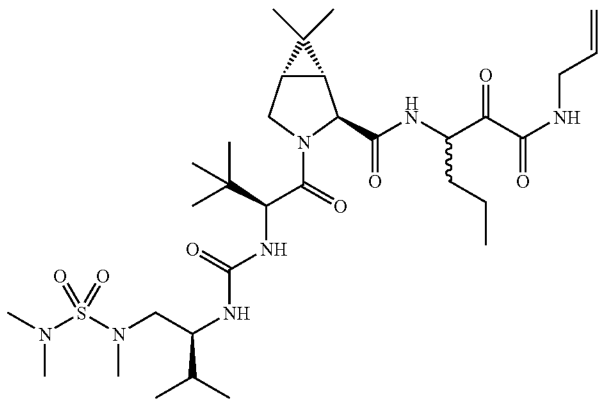 | A |
| 10011 | 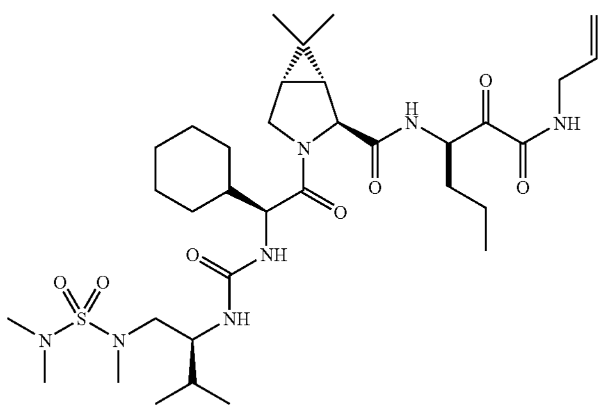 | A |
| 10012 | 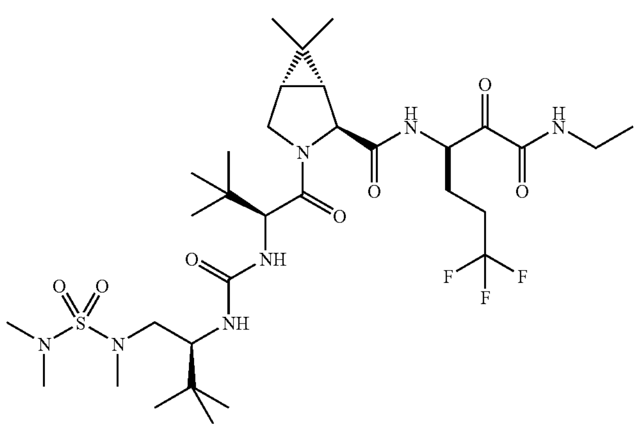 | A |

TABLE 1-continued

| Entry | Structure | $K_i^*$ |
|---|---|---|
| 10013 | 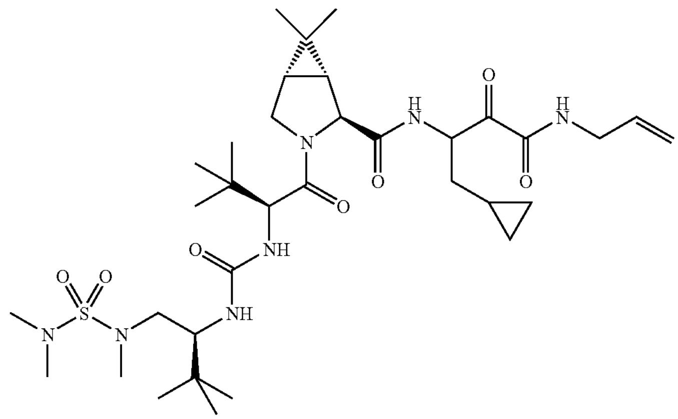 | A |
| 10014 | 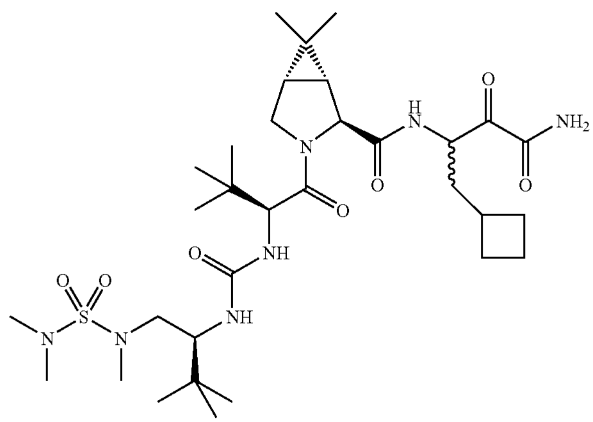 | A |
| 10015 | 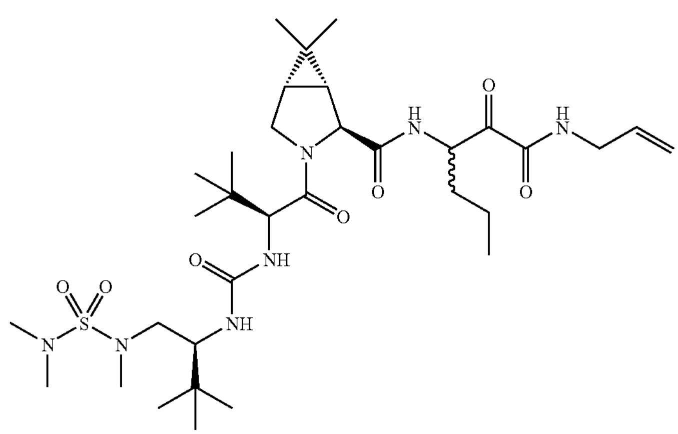 | A |

TABLE 1-continued
| Entry | Structure | $K_i$* |
|---|---|---|
| 10016 | 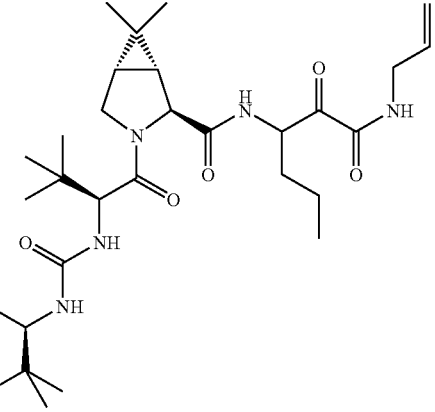 | A |
| 10017 | 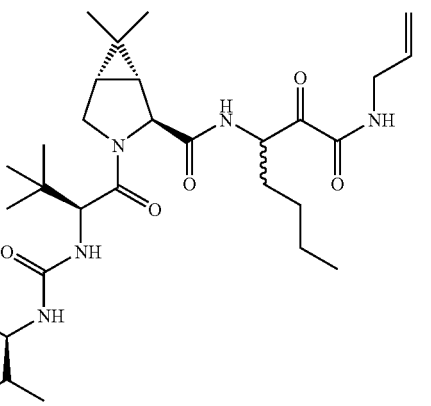 | A |
| 10018 | 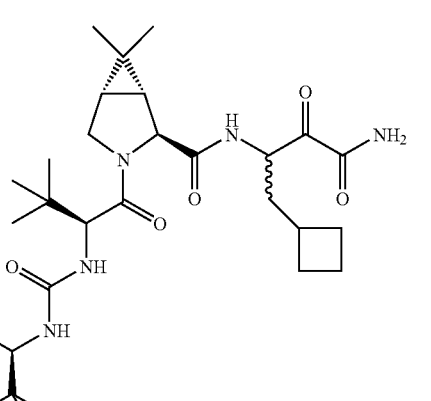 | B |

TABLE 1-continued

| Entry | Structure | $K_i{}^*$ |
|---|---|---|
| 10019 | 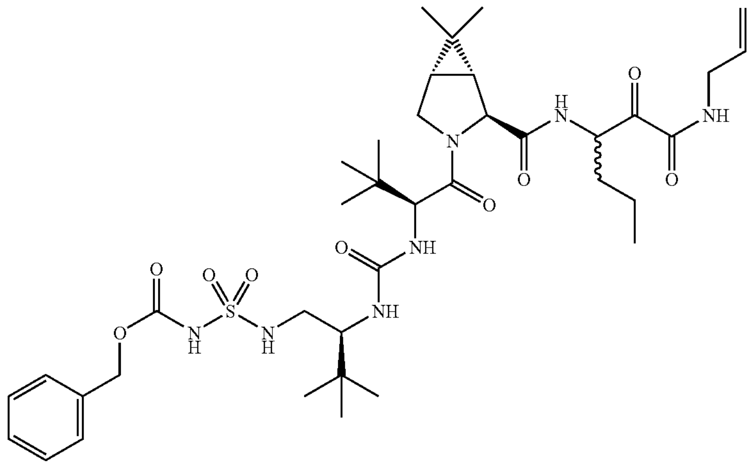 | A |
| 10020 | 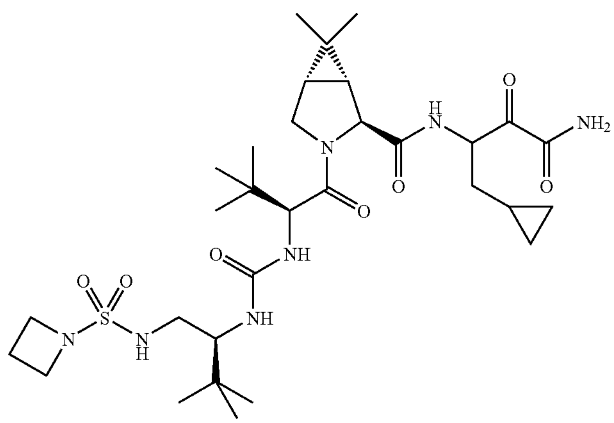 | A |
| 10021 | 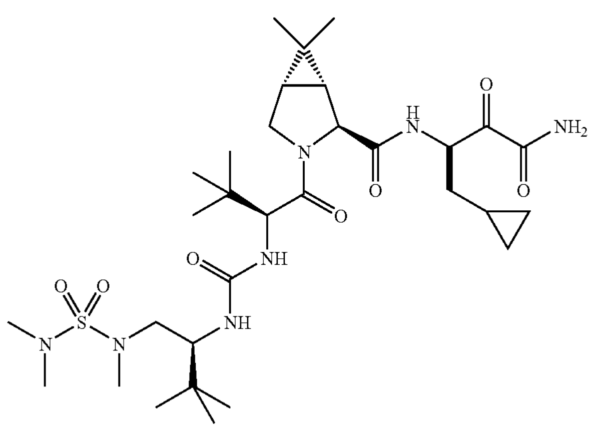 | A |

TABLE 1-continued

| Entry | Structure | K*ᵢ |
|---|---|---|
| 10022 | 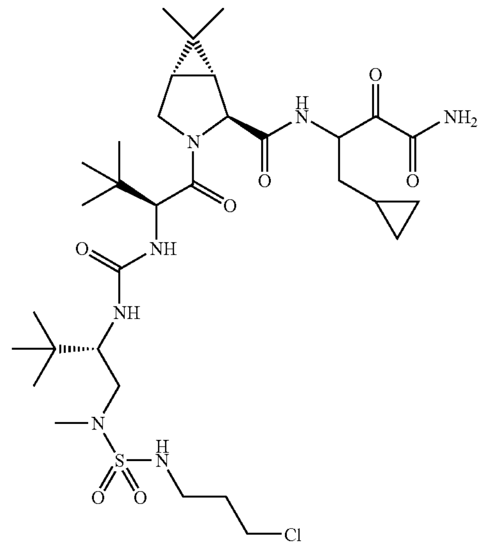 | A |
| 10023 | 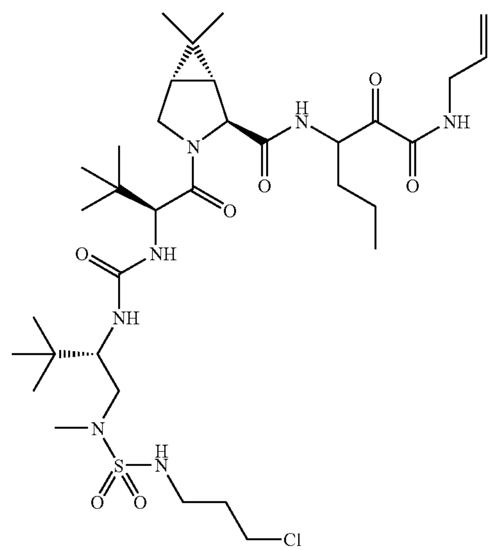 | A |
| 10024 | 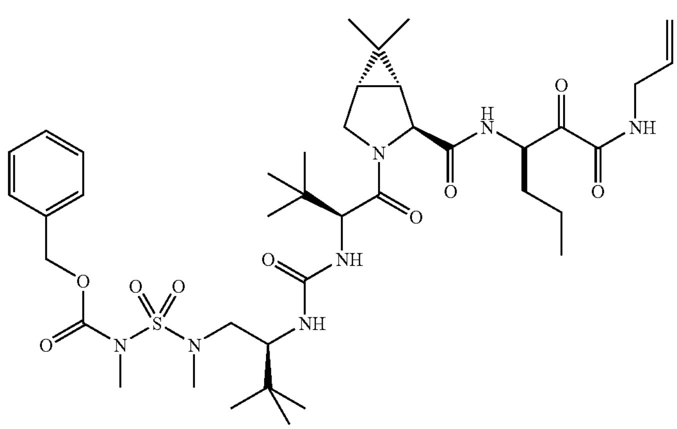 | A |

TABLE 1-continued

| Entry | Structure | $K_i$* |
|---|---|---|
| 10025 | 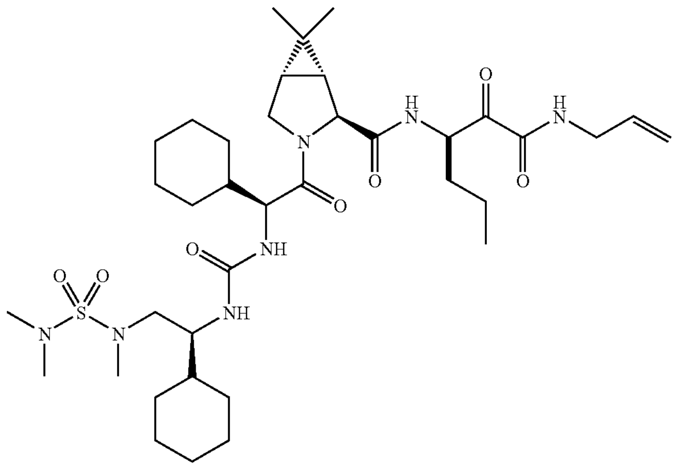 | A |
| 10026 | 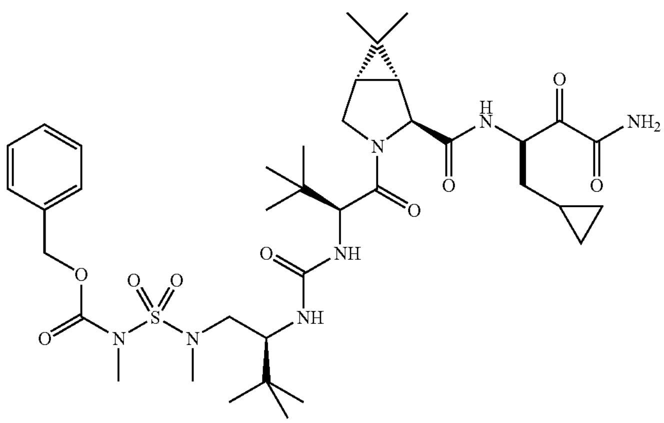 | A |
| 10027 | 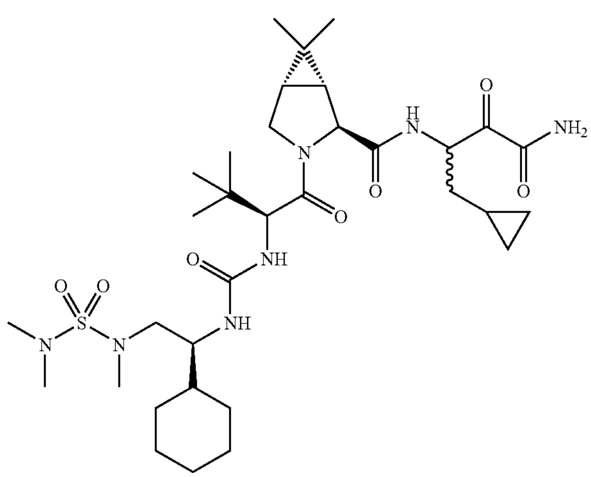 | A |

TABLE 1-continued

| Entry | Structure | $K_i$* |
|---|---|---|
| 10028 | 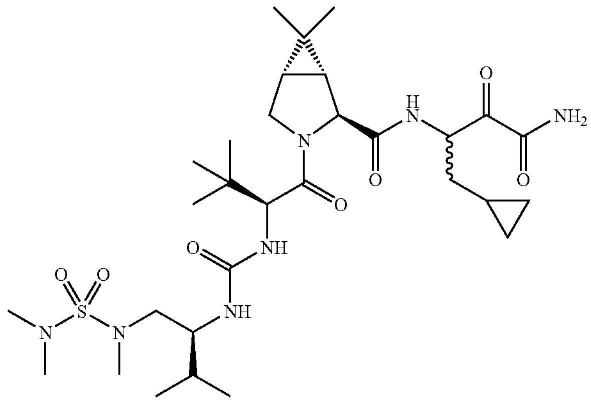 | A |
| 10229 | 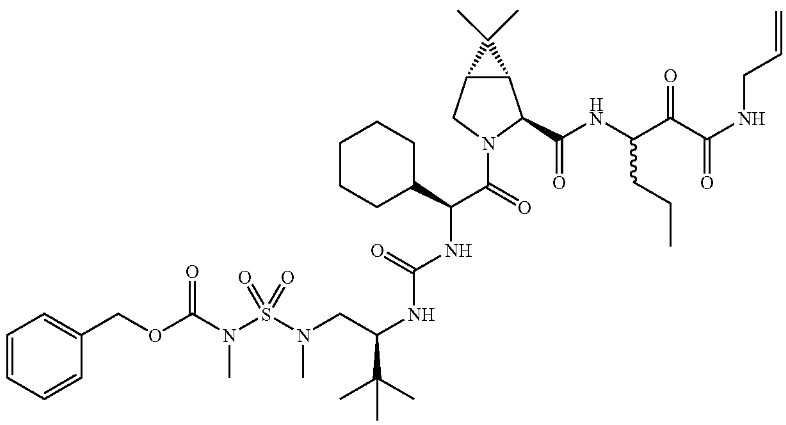 | A |
| 10030 | 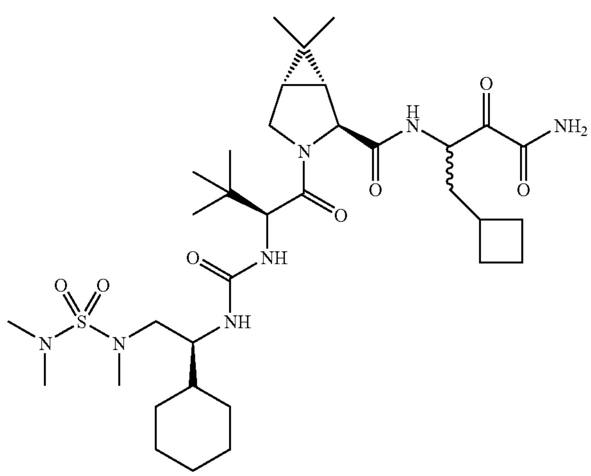 | A |

TABLE 1-continued
| Entry | Structure | $K_i$* |
|---|---|---|
| 10031 | 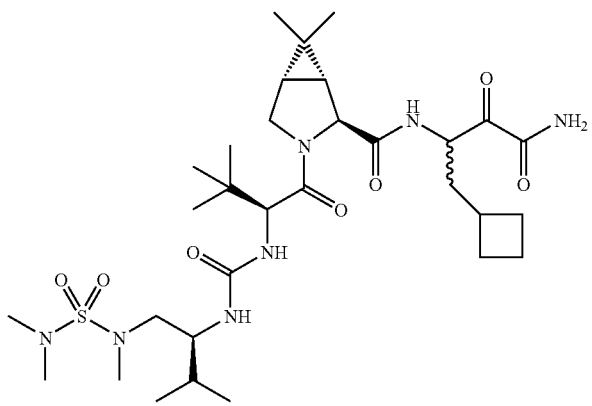 | A |
| 10032 | 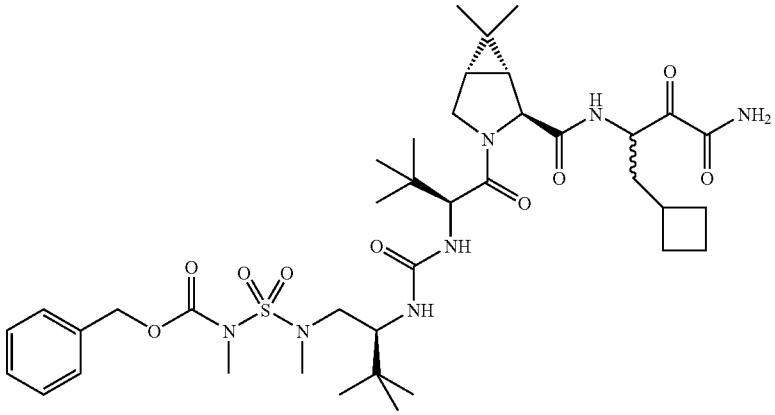 | A |
| 10033 | 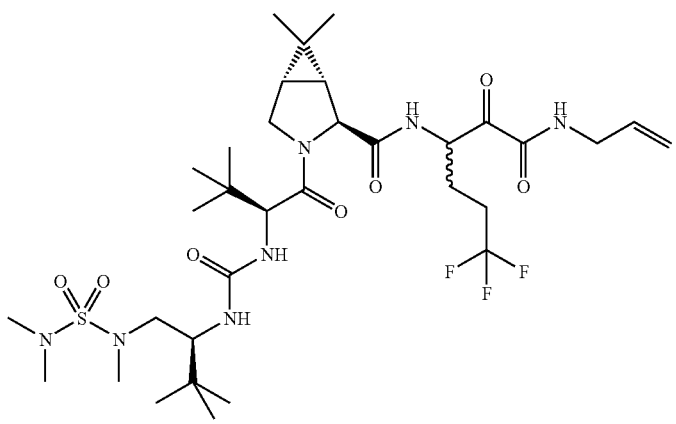 | A |

TABLE 1-continued

| Entry | Structure | $K_i^*$ |
|---|---|---|
| 10034 | 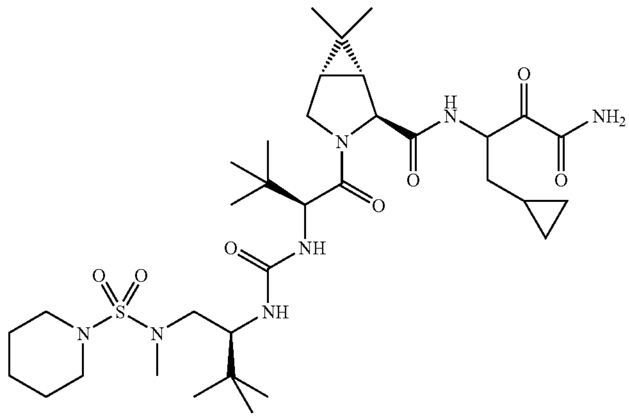 | A |
| 10035 | 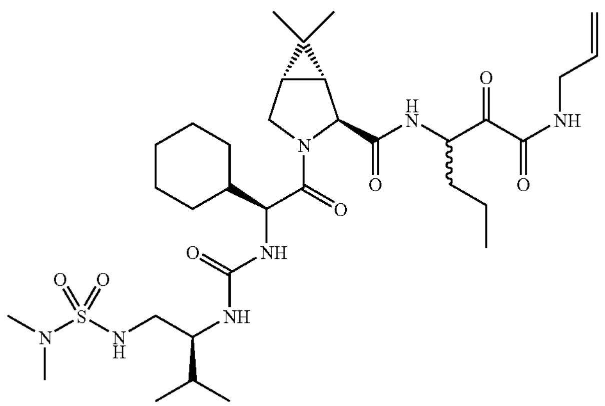 | B |
| 10036 | 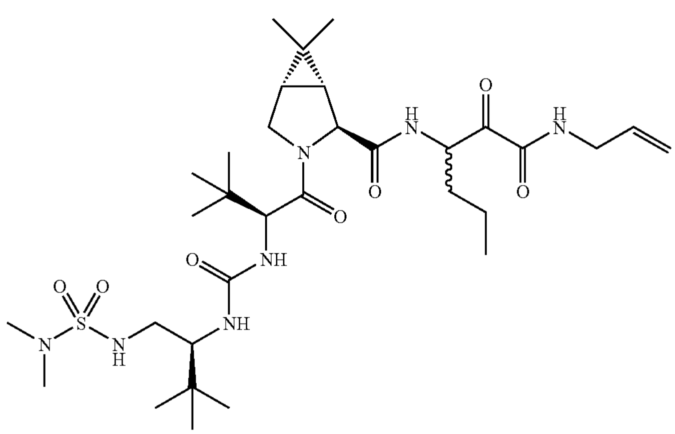 | A |

TABLE 1-continued
| Entry | Structure | $K_i$* |
|---|---|---|
| 10037 | 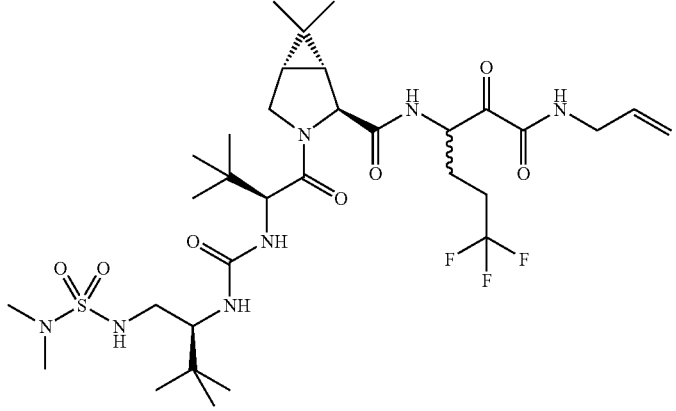 | A |
| 10038 | 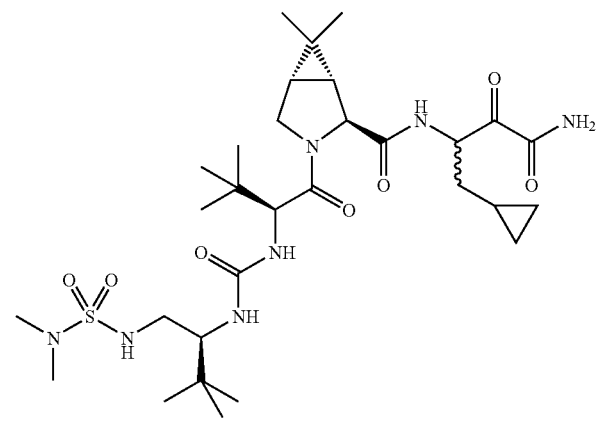 | A |
| 10039 | 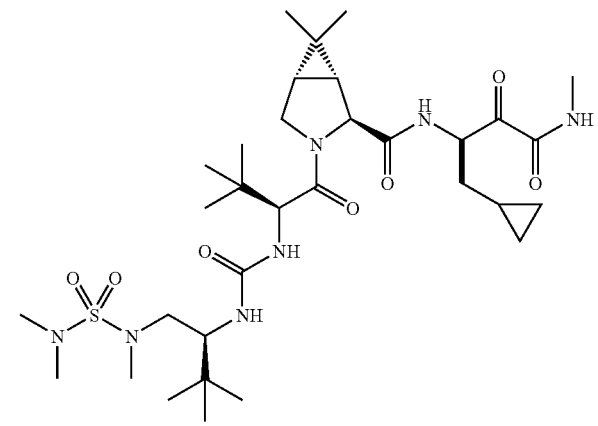 | A |

TABLE 1-continued

| Entry | Structure | $K_i^*$ |
|---|---|---|
| 10040 | 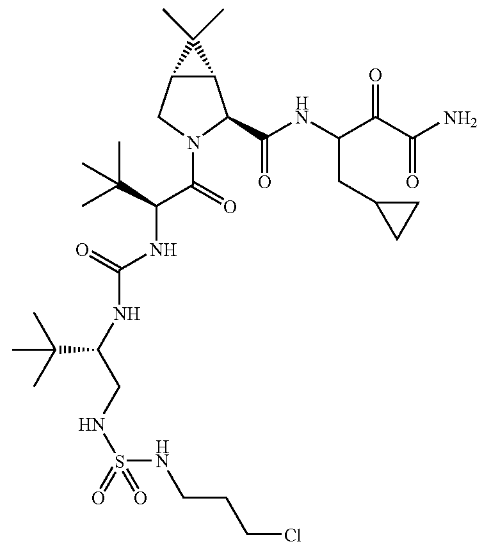 | A |
| 10041 | 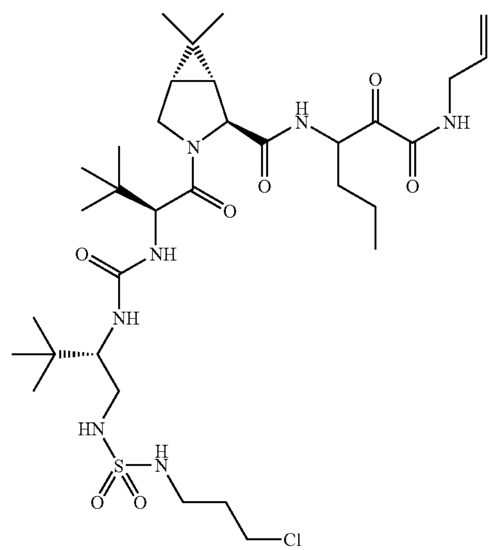 | A |
| 10042 | 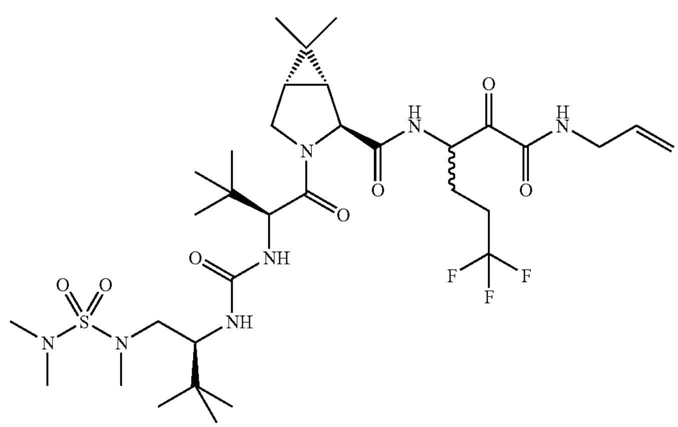 | A |

TABLE 1-continued
| Entry | Structure | $K_i$* |
|---|---|---|
| 10043 | 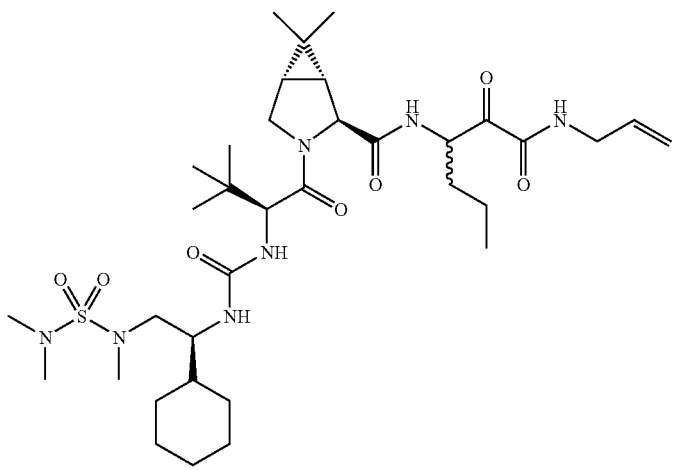 | A |
| 10044 | 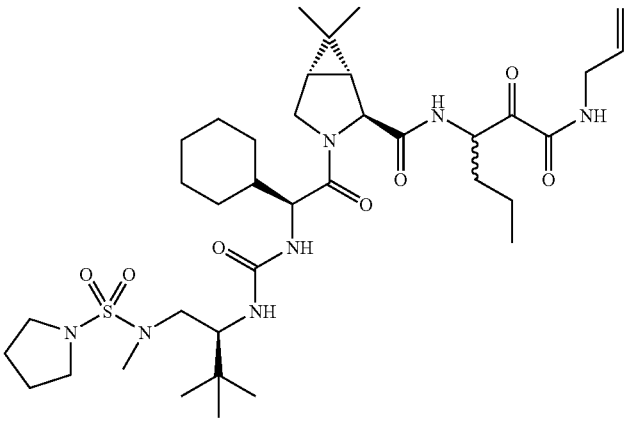 | A |
| 10045 | 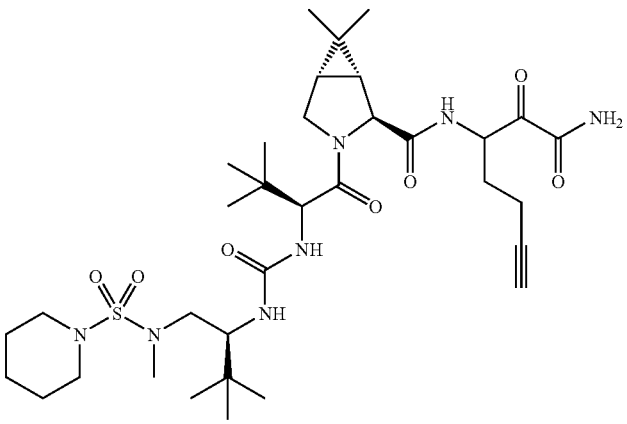 | A |

TABLE 1-continued

| Entry | Structure | $K_i$* |
|---|---|---|
| 10046 | 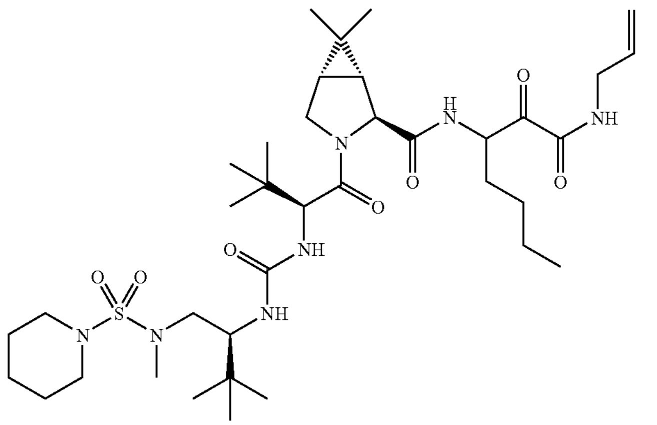 | A |
| 10047 | 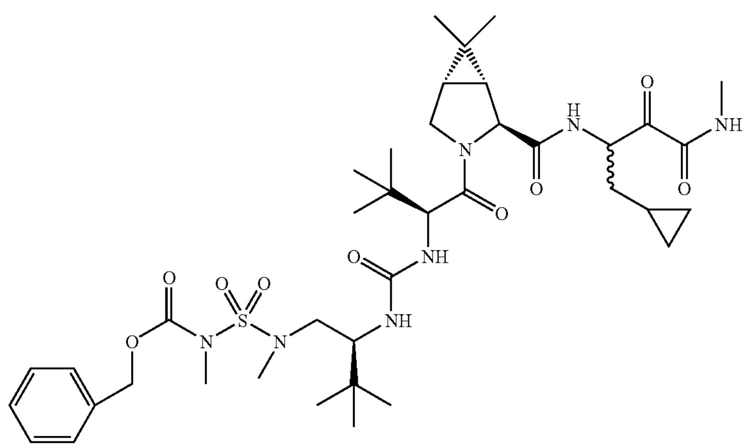 | A |
| 10048 | 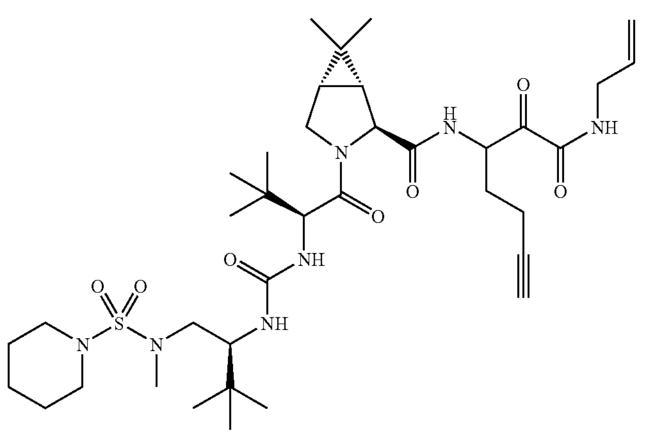 | A |

TABLE 1-continued
| Entry | Structure | $K_i$* |
|---|---|---|
| 10049 | 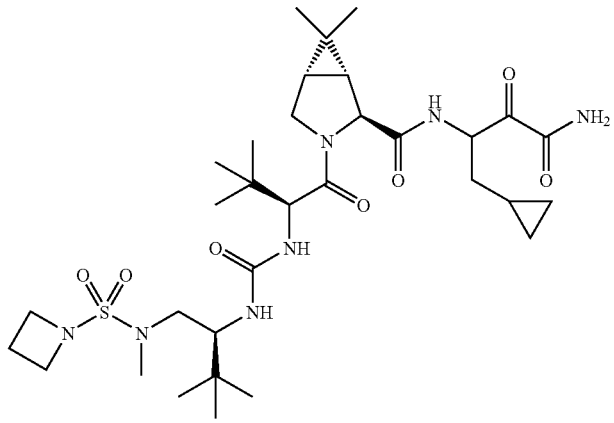 | A |
| 10050 | 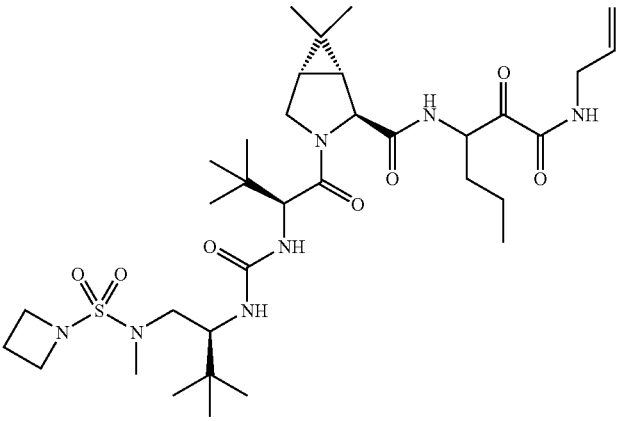 | A |
| 10051 | 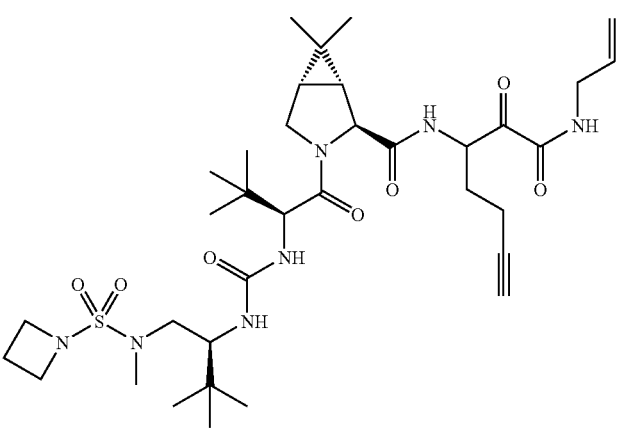 | A |

TABLE 1-continued
| Entry | Structure | $K_i^*$ |
|---|---|---|
| 10052 | 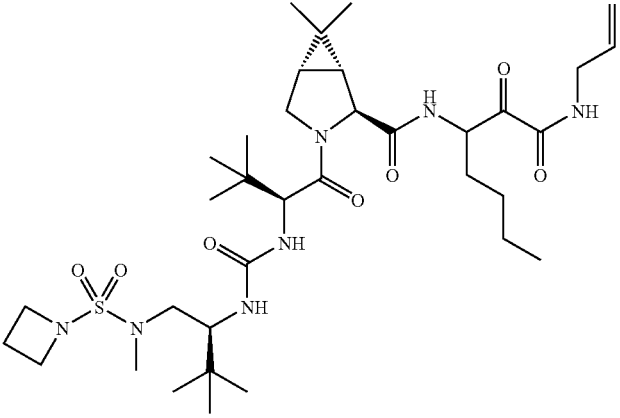 | A |
| 10053 | 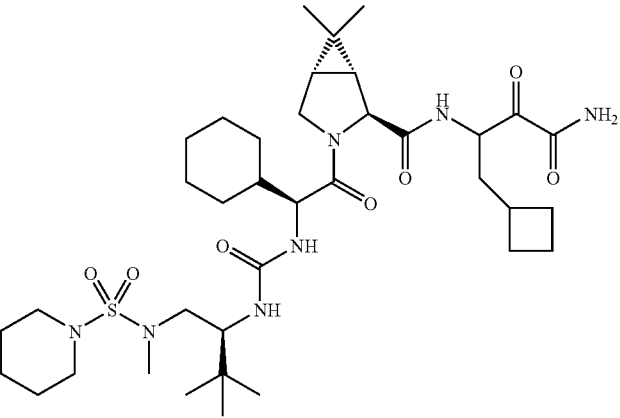 | A |
| 10054 | 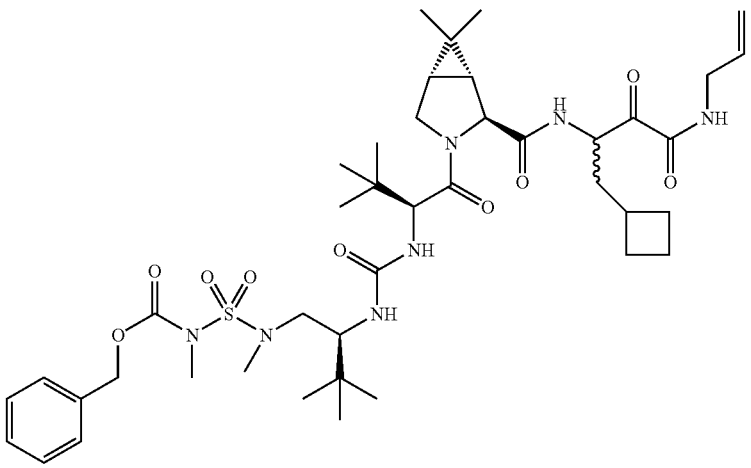 | A |

TABLE 1-continued
| Entry | Structure | $K_i$* |
|---|---|---|
| 10055 | 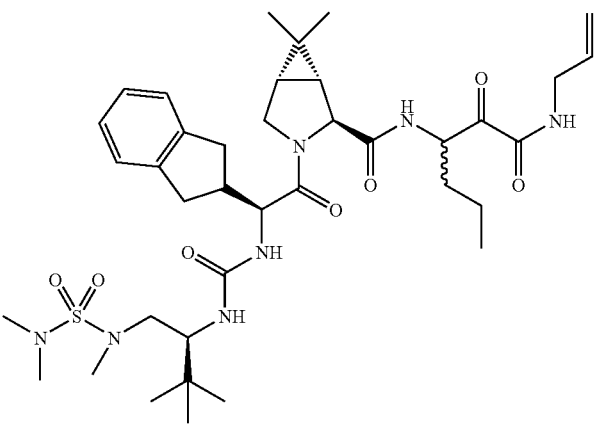 | A |
| 10056 | 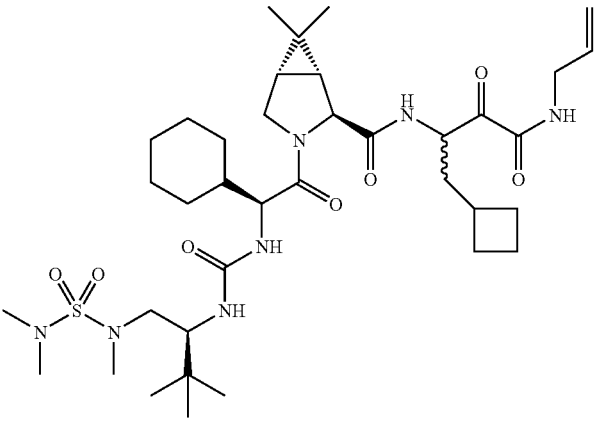 | A |
| 10057 | 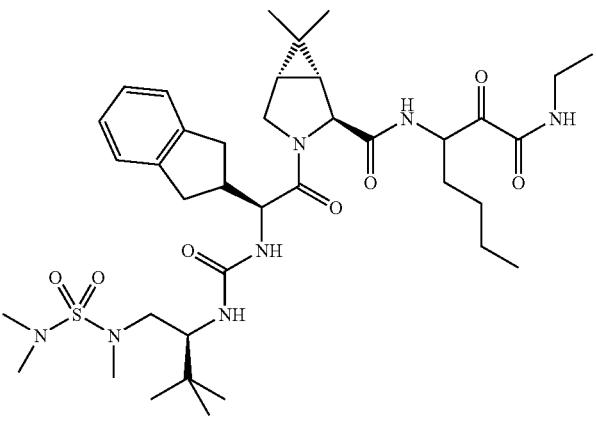 | A |

TABLE 1-continued

| Entry | Structure | $K_i$* |
|---|---|---|
| 10058 | 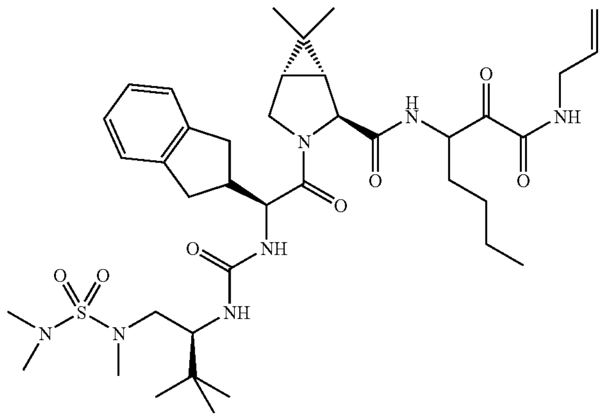 | A |
| 10059 | 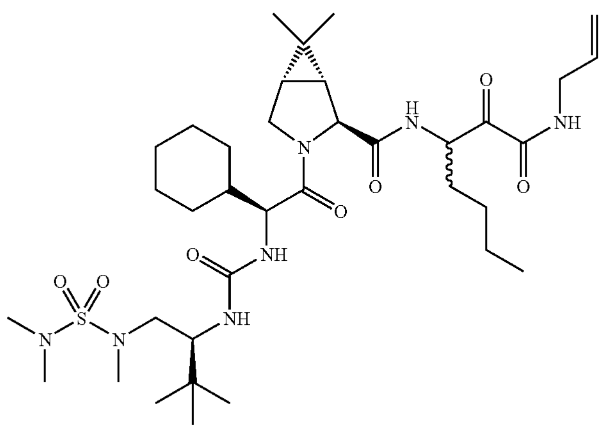 | A |
| 10060 | 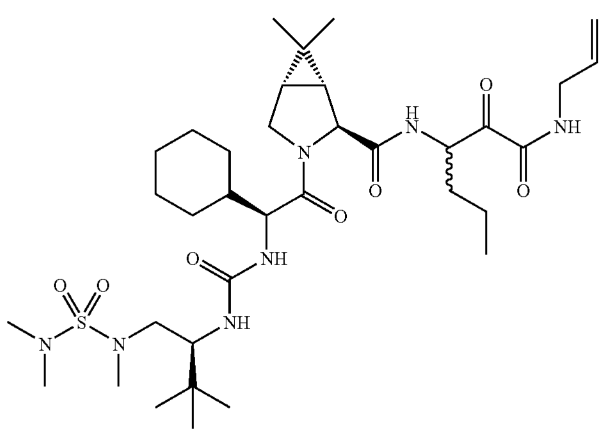 | A |

TABLE 1-continued

| Entry | Structure | $K_i^*$ |
|---|---|---|
| 10061 | 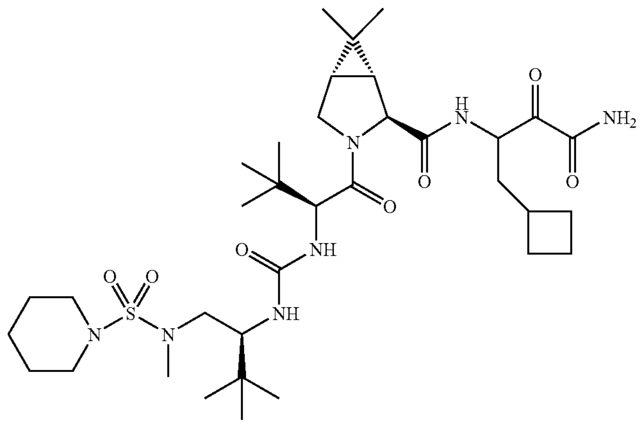 | A |
| 10062 | 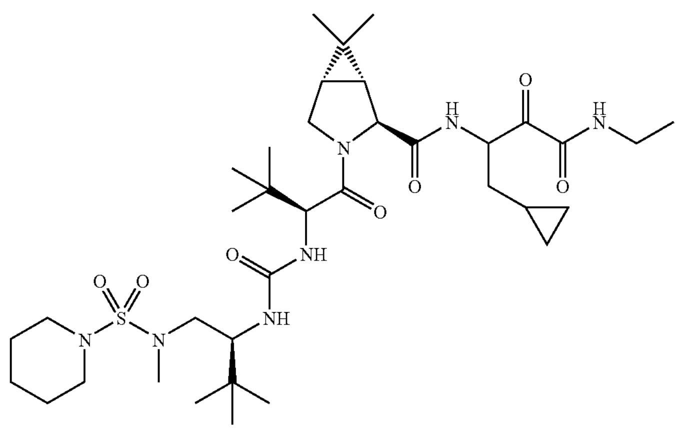 | A |
| 10063 | 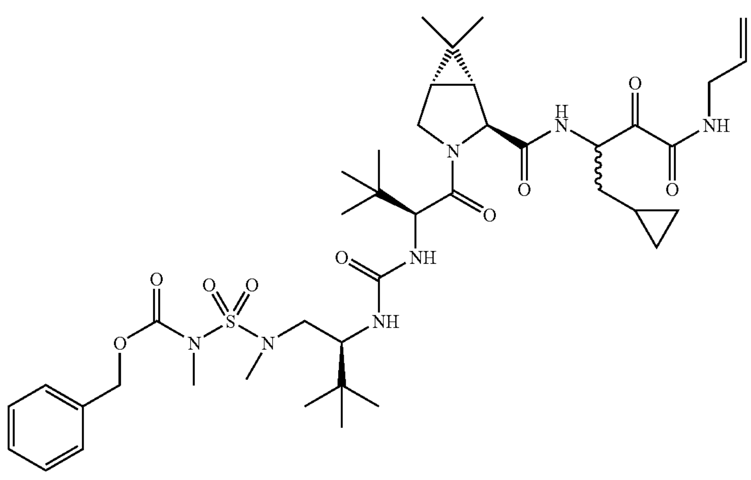 | A |

TABLE 1-continued

| Entry | Structure | $K_i$* |
|---|---|---|
| 10064 | 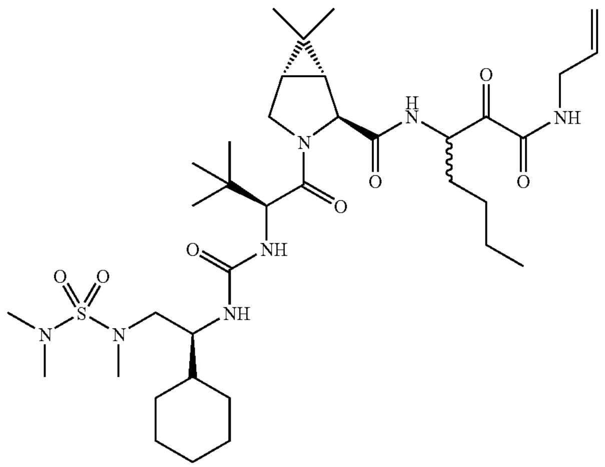 | A |
| 10065 | 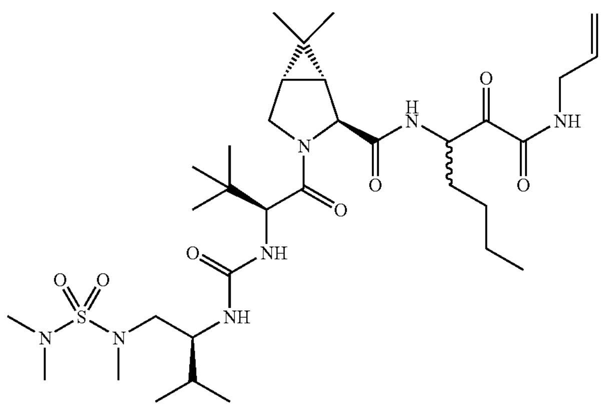 | A |
| 10066 | 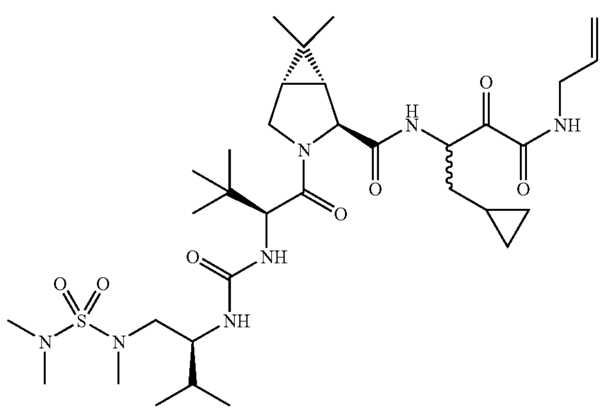 | A |

TABLE 1-continued

| Entry | Structure | $K_i$* |
|---|---|---|
| 10067 | 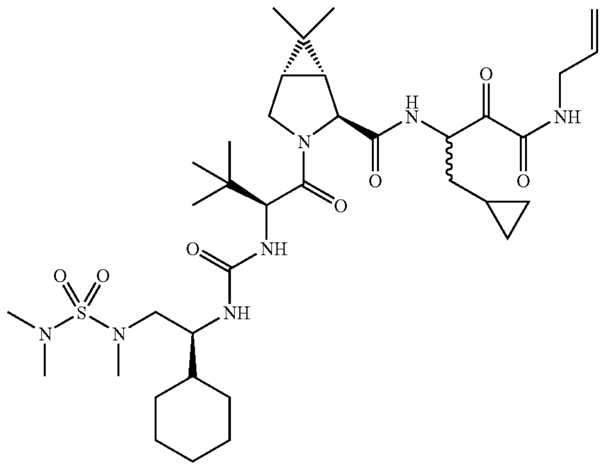 | A |
| 10068 | 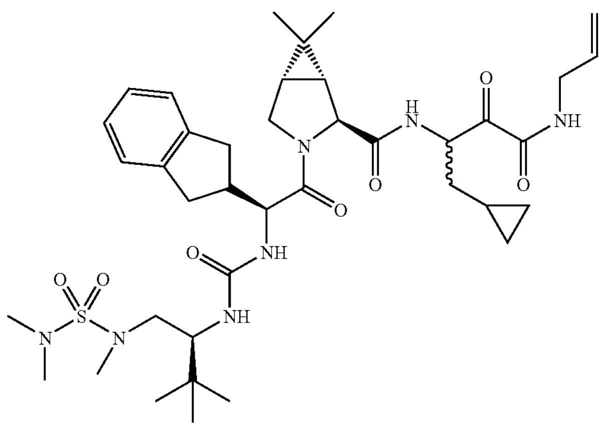 | A |
| 10069 | 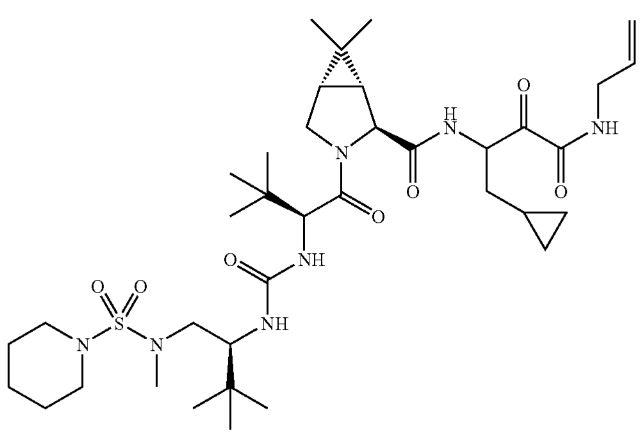 | A |

TABLE 1-continued

| Entry | Structure | $K_i$* |
|---|---|---|
| 10070 | 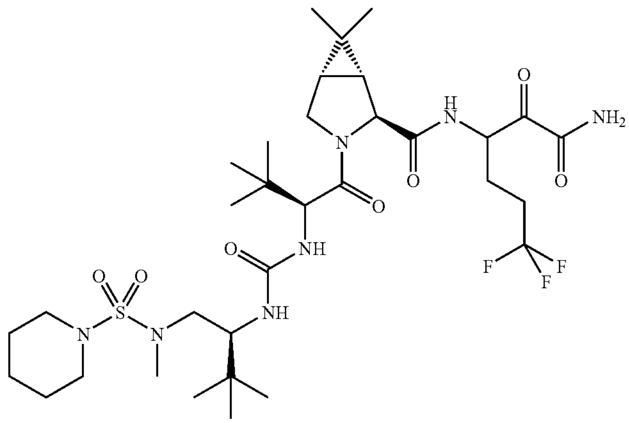 | A |
| 10071 | 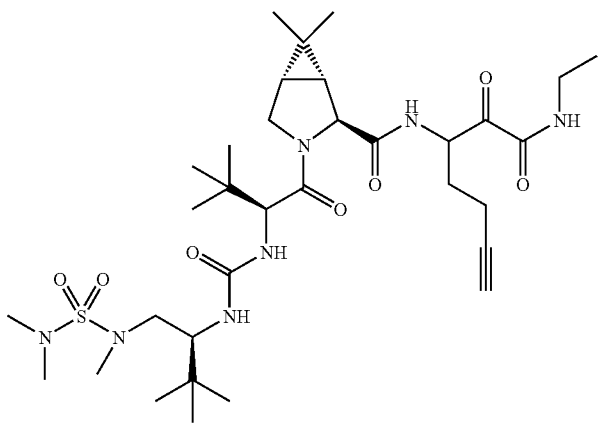 | A |
| 10072 | 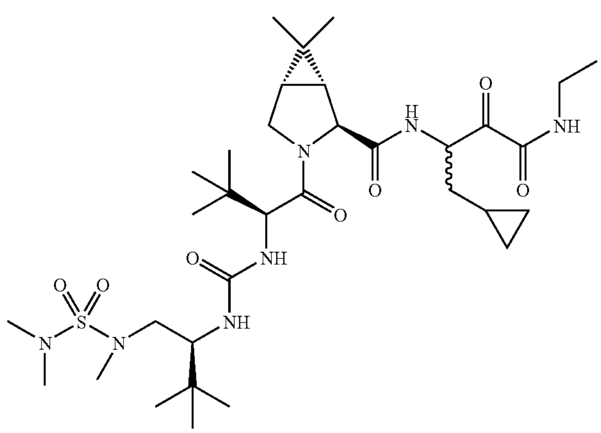 | A |

TABLE 1-continued
| Entry | Structure | $K_i$* |
|---|---|---|
| 10073 | 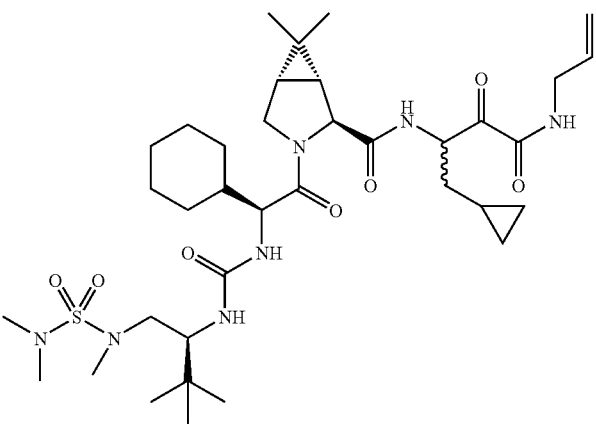 | A |
| 10074 | 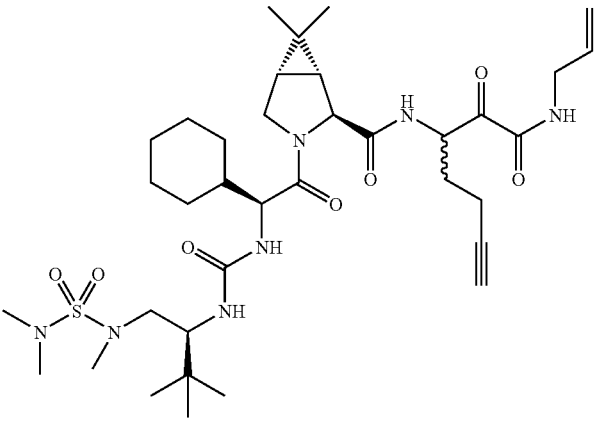 | A |
| 10075 | 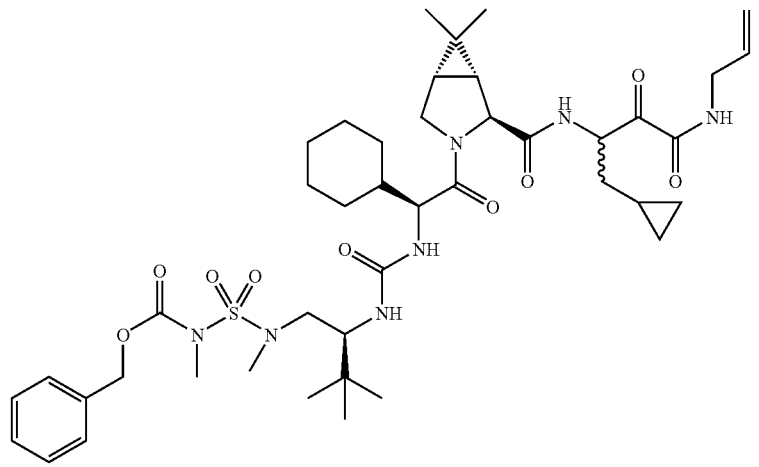 | A |

TABLE 1-continued
| Entry | Structure | $K_i$* |
|---|---|---|
| 10076 | 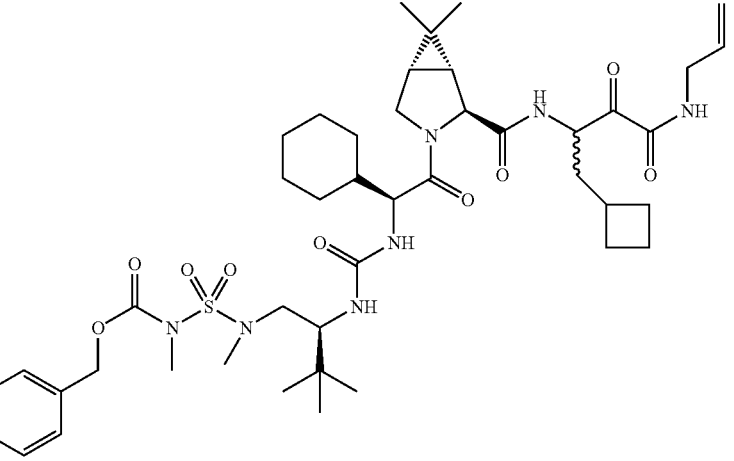 | A |
| 10077 | 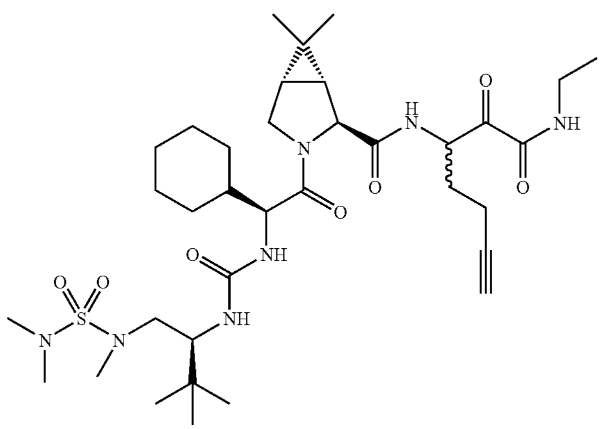 | A |
| 10078 | 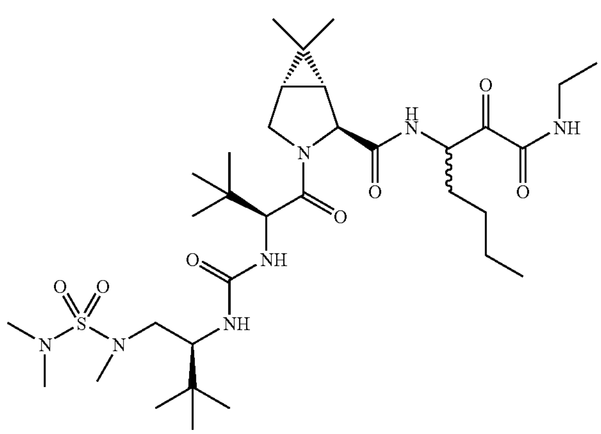 | A |

TABLE 1-continued
| Entry | Structure | $K_i$* |
|---|---|---|
| 10079 | 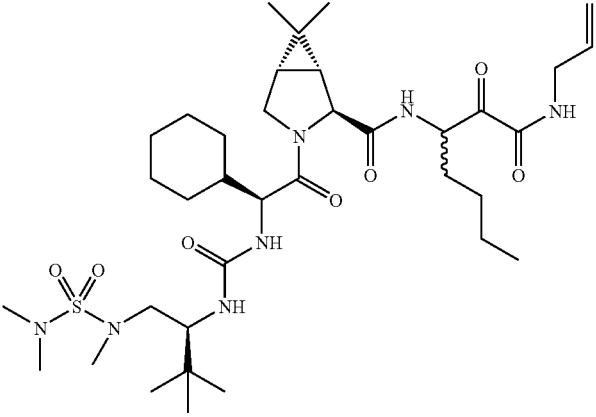 | A |
| 10080 | 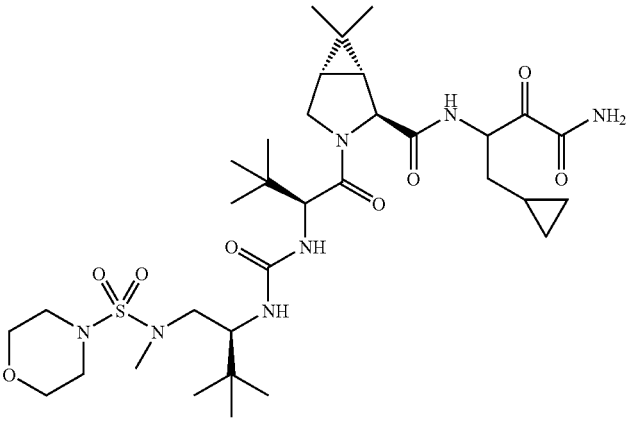 | A |
| 10081 | 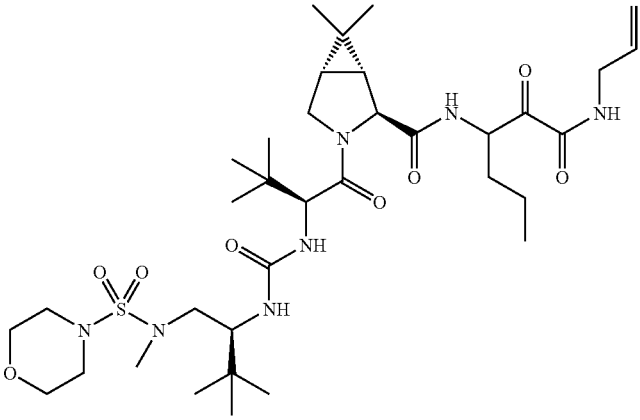 | A |

TABLE 1-continued
| Entry | Structure | $K_i$* |
|---|---|---|
| 10082 | 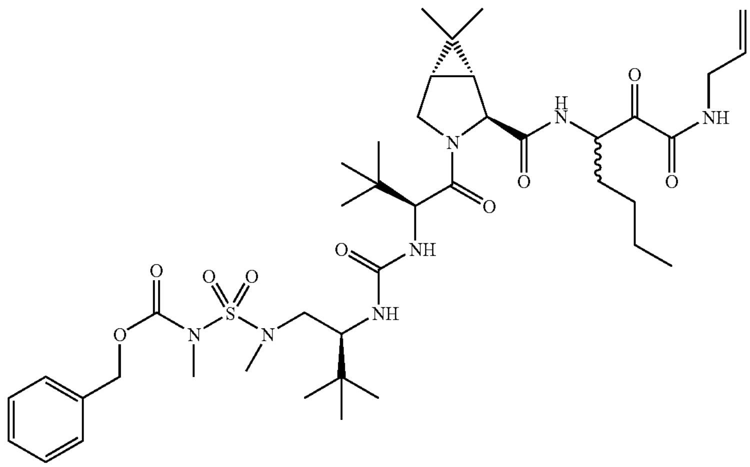 | A |
| 10083 | 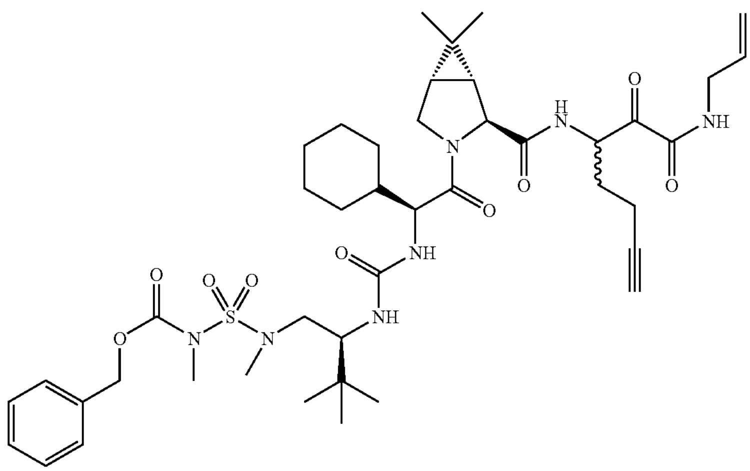 | A |
| 10084 | 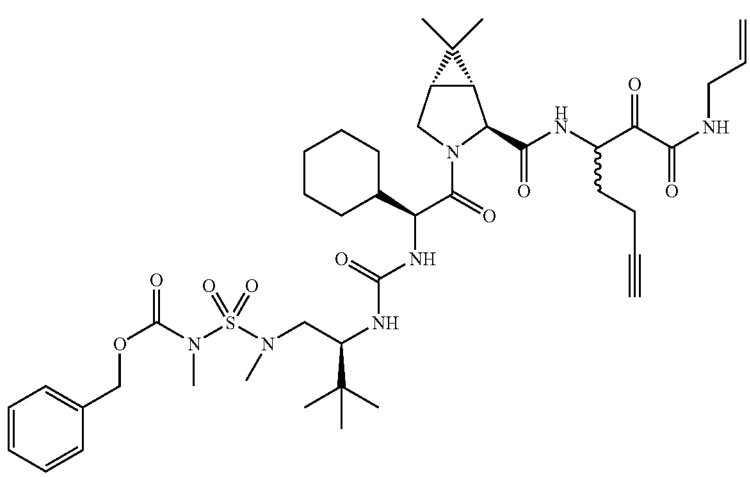 | A |

TABLE 1-continued
| Entry | Structure | $K_i$* |
|---|---|---|
| 10085 | 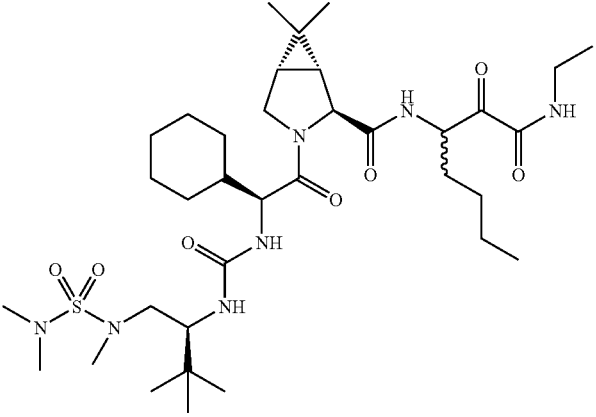 | A |
| 10086 | 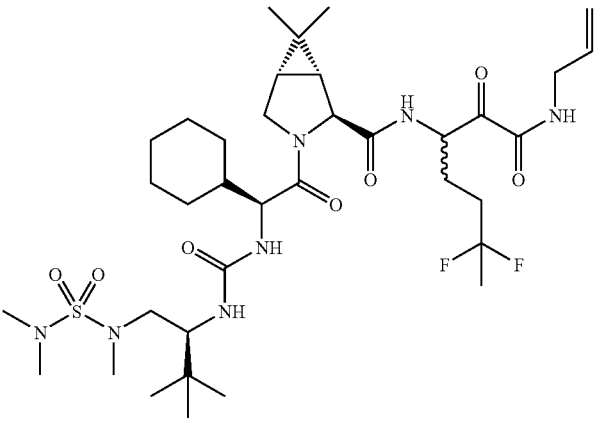 | A |
| 10087 | 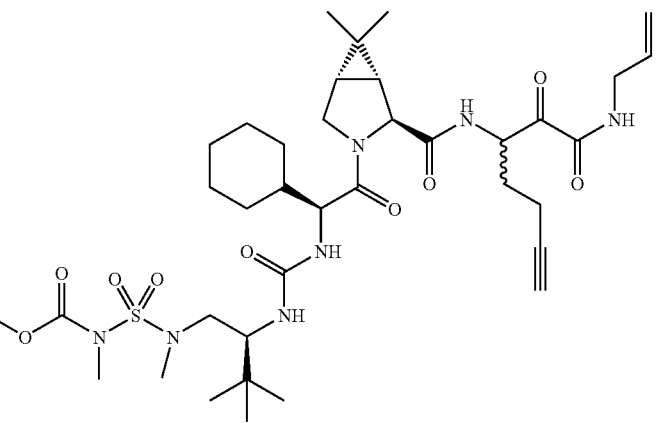 | A |

TABLE 1-continued

| Entry | Structure | $K_i$* |
|---|---|---|
| 10088 | 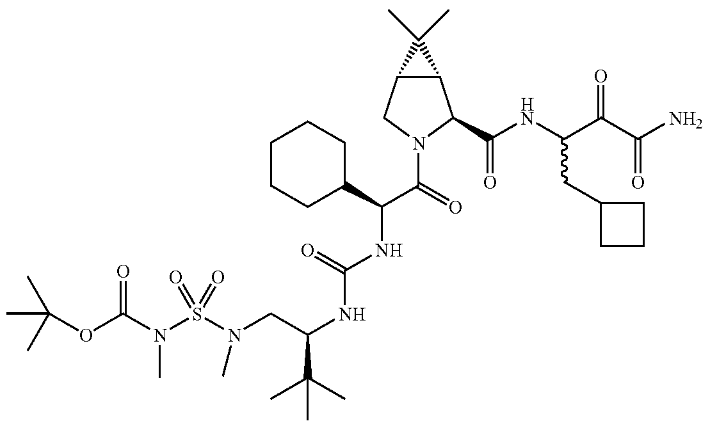 | A |
| 10089 | 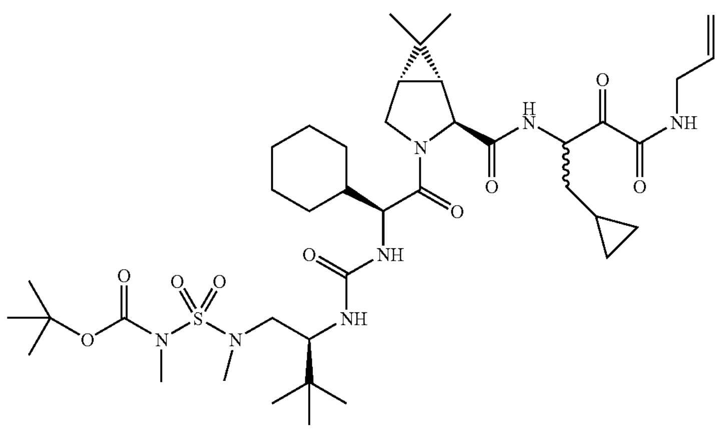 | A |
| 10090 | 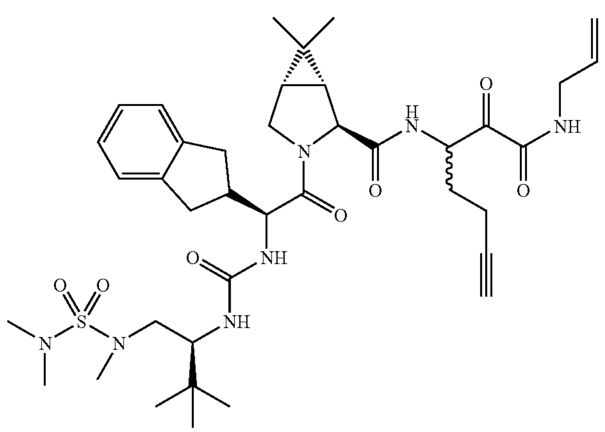 | A |

TABLE 1-continued
| Entry | Structure | $K_i$* |
|---|---|---|
| 10091 | 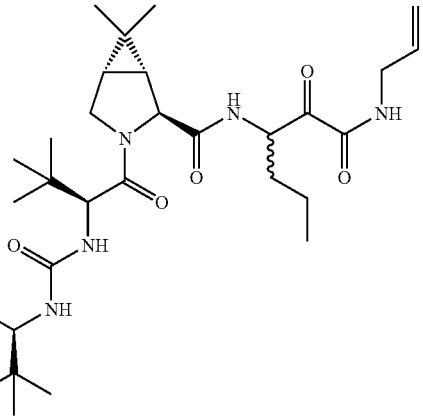 | A |
| 10092 | 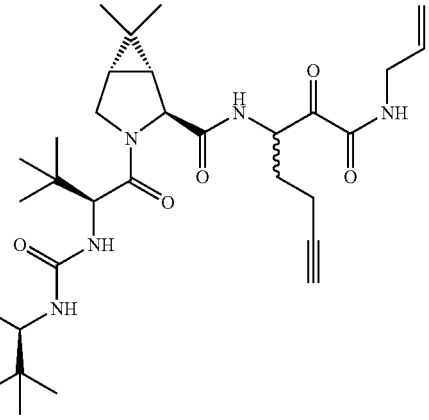 | A |
| 10093 | 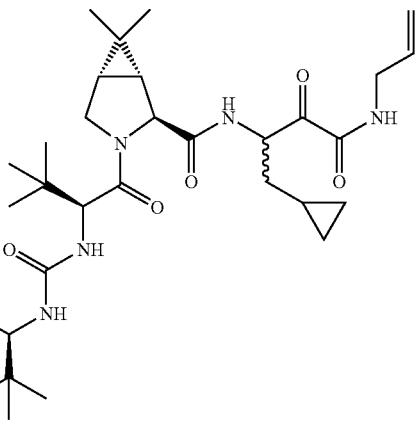 | A |

TABLE 1-continued
| Entry | Structure | $K_i$* |
|---|---|---|
| 10094 | 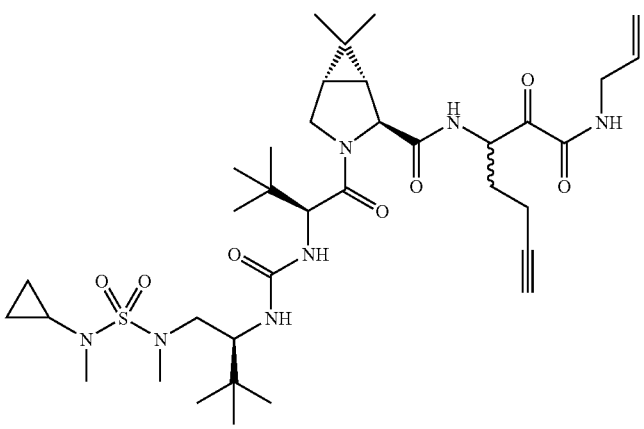 | A |
| 10095 | 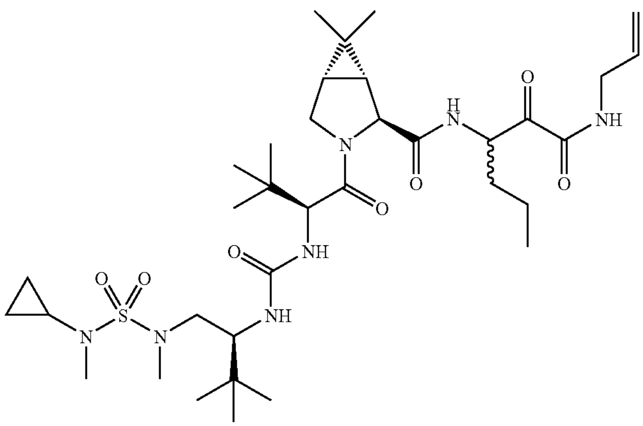 | A |
| 10096 | 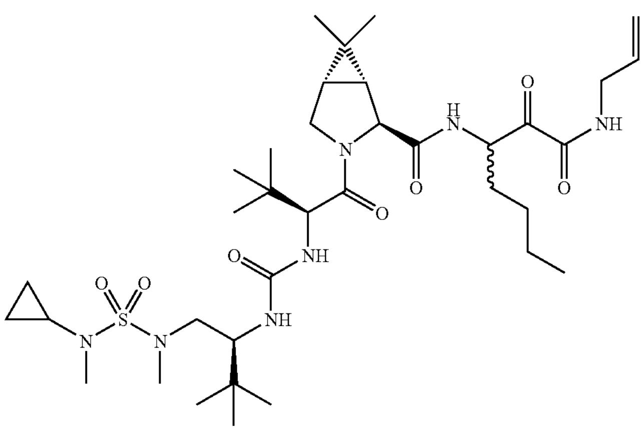 | A |

TABLE 1-continued
| Entry | Structure | K_i* |
|---|---|---|
| 10097 | 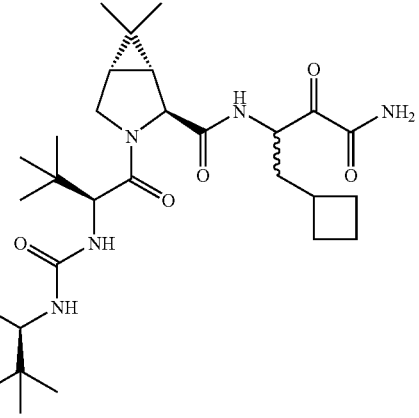 | A |
| 10098 | 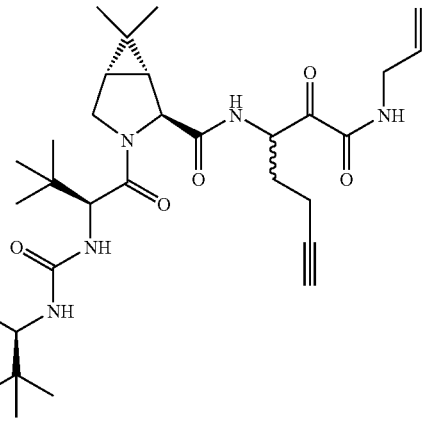 | A |
| 10099 | 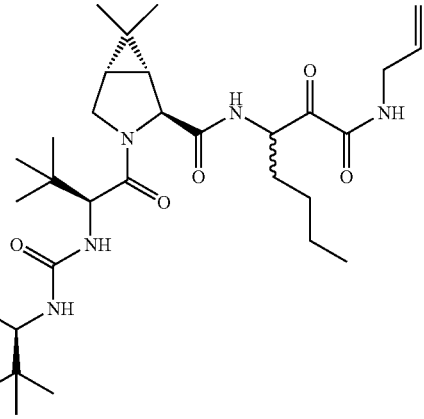 | A |

TABLE 1-continued

| Entry | Structure | $K_i$* |
|---|---|---|
| 10100 | 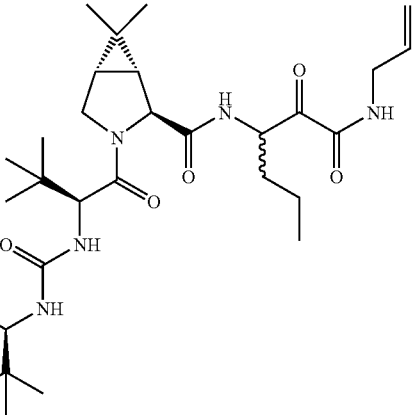 | A |
| 10101 | 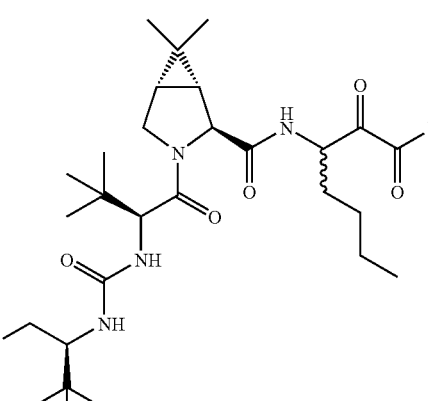 | A |

Example-6

Synthesis of Compound of Formula 11001

11001

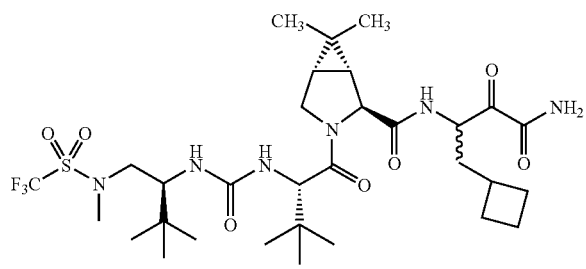

Step A:

A solution of amide 11001a (Obtained by Cbz protection of tert-butylglycine-N-methyl amide obtained from commercial source: TCI-Japan) 18 g, 64.67 mmol) in toluene (200 mL) was treated with $BH_3$.DMS (2 M soln. in THF, 65 mL, 130 mmol) and heated at 80° C. for 3 h. The reaction mixture was cooled to rt. and treated carefully with aq. NaOH (2 M solution) and extracted into $CH_2Cl_2$ (3×200 mL). The combined organic layers were extracted with aq. saturated $NaHCO_3$ (3×300 mL), brine (300 mL), dried ($MgSO_4$) and purified by chromatography ($SiO_2$, ammoniacal methanol (7M)/$CH_2Cl_2$ 1:20) to yield 11001 b as a colorless oil.

Step B:

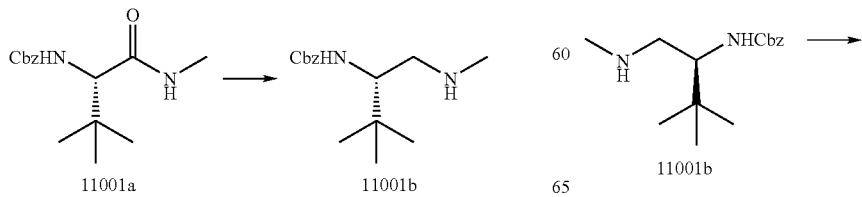

-continued

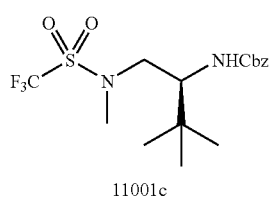
11001c

A solution of amine 11001b (900 mg, 3.40 mmol) in CH$_2$Cl$_2$ at 0° C. was treated with NMM (511 mg, 5.10 mmol) and triflic anhydride (585 mg, 5.10 mmol) and stirred at 0° C. for 12 h. The reaction mixture was diluted with CH$_2$Cl$_2$ (300 mL) and washed with excess aq. HCl (1M, 500 mL). The organic layer was dried (MgSO$_4$) filtered concentrated in vacuo and purified by chromatography (SiO$_2$, Hex/EtOAc 1:9-1:1) to yield trifluoromethane sulfonamide 11001c.

Step C:

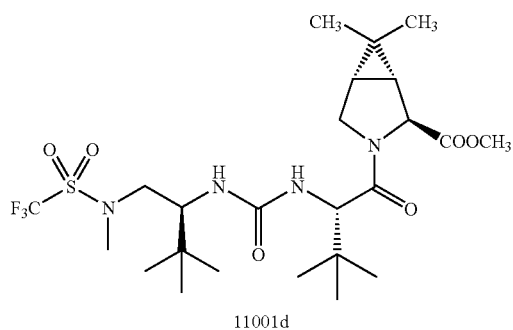

A solution of 11001c (1.28 g, 3.22 mmol) in methanol (30 mL) was treated with palladium hydroxide (200 mg, 10% wt/C) and hydrogenated at 60 psi for 3 h. The reaction mixture was filtered through a plug of Celite® and the filtrate was concentrated in vacuo. The residue was directly used in further reaction without purification. A solution of deprotected amine (200 mg, 0.763 mmol) in DMF (3 mL), CH$_2$Cl$_2$ (3 mL) was treated with 4-nitrophenylcarbamate 1.16 (409 mg, 0.915 mmol), NMM (308 mg, 3.05 mmol) at 0° C. and stirred at rt. overnight. The reaction mixture was concentrated in vacuo diluted with CH$_2$Cl$_2$ (150 mL) and washed with aq. HCl (1M, 2×125 mL), aq. saturated NaHCO$_3$ (2×125 mL), brine (100 mL), dried (MgSO$_4$), filtered and purified by chromatography (SiO$_2$, CH$_2$Cl$_2$/EtOAc 1:19) to yield 11001d.

Step D:

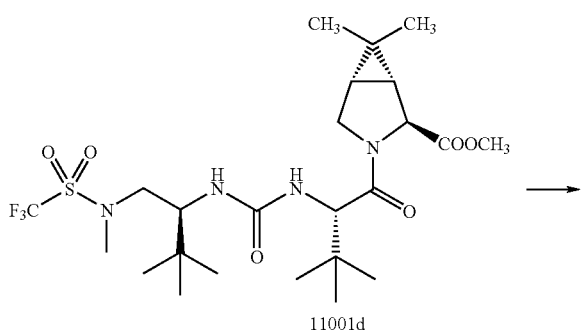

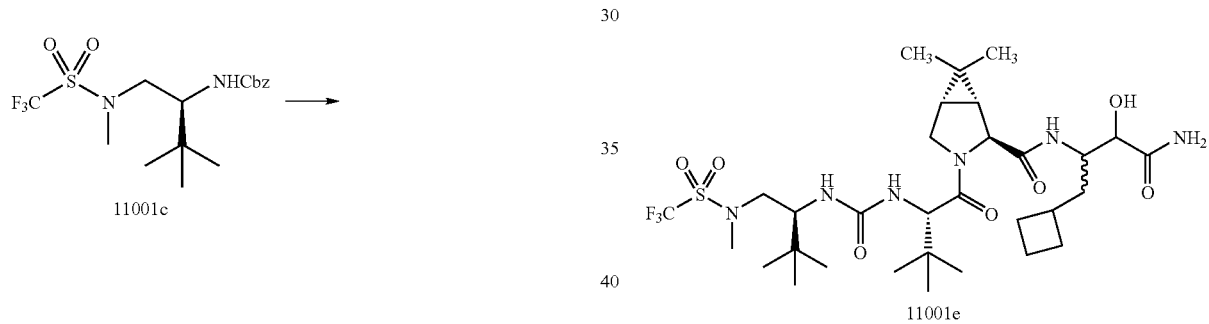

A solution of methyl ester 11001d (210 mg, 0.368 mmol) in dry THF (3 mL) was treated with H$_2$O (3 mL), methanol (3 mL) and treated with LiOH monohydrate (41.9 mg, 1 mmol) and stirred for 3 h at rt. The reaction mixture was acidified to pH-2 and extracted into CH$_2$Cl$_2$ (100 mL). The organic layer was washed with H$_2$O (100 mL), brine (100 mL) dried (MgSO$_4$) filtered concentrated in vacuo to yield acid that was used as it is in the next reaction.

A solution the acid (50 mg, 0.089 mmol) in dry CH$_2$Cl$_2$ (2 mL) and DMF (2 mL) was cooled to 0° C. and treated with amine 10.11 (20 mg, 0.116 mmol) HATU (57.03 mg, 0.15 mmol) and NMM (40.4 mg, 0.40 mmol). The reaction was stirred at 0° C. for 36 h and concentrated in vacuo. The residue was dissolved in CH$_2$Cl$_2$ (100 mL) and washed with aq HCl (1 M, 2×100 mL), aq. saturated NaHCO$_3$ (2×100 mL) brine (100 mL), dried (MgSO$_4$) filtered, concentrated in vacuo to yield 11001e that was used in the next reaction without further purification.

Step E:

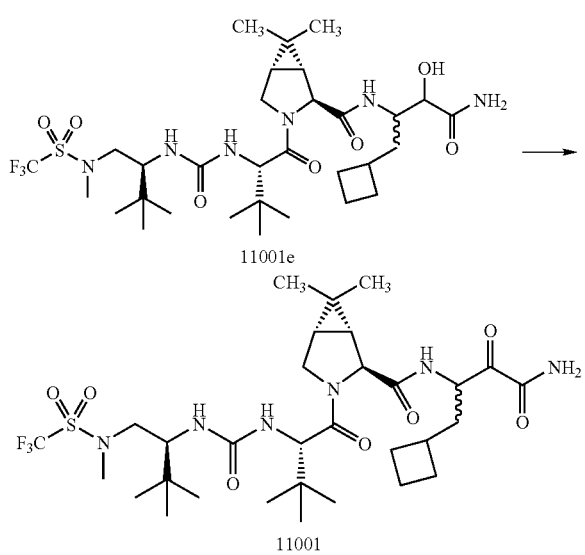

A solution of 11001e (50 mg, 0.075 mmol) in toluene (3 mL) and DMSO (3 mL) was treated with EDCl (134 mg, 0.703 mmol), and dichloroacetic acid (45.3 mg, 0.351 mmol, 30 μL) and stirred at rt. for 3 h. The reaction mixture was diluted with CH$_2$Cl$_2$ (60 mL) and washed with aq. saturated NaHCO$_3$ (30 mL), aq. HCl (1 M, 30 mL), brine (30 mL), dried (MgSO$_4$) filtered, concentrated in vacuo and purified by chromatography (SiO$_2$, acetone/Hexanes 20-50% linear gradient) to yield 11001.

Example-7

Synthesis of Compound of Formula 11002

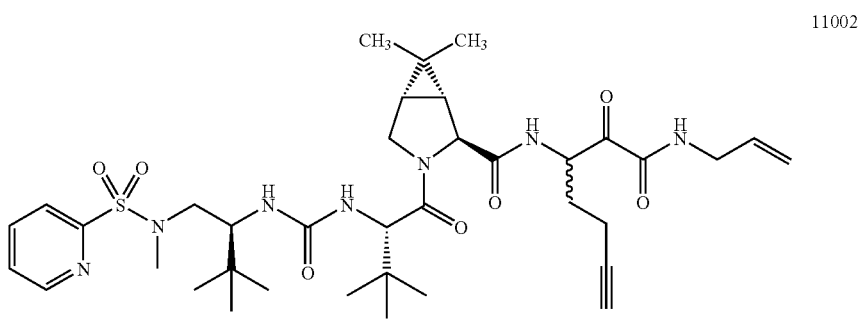

11002

Step A:

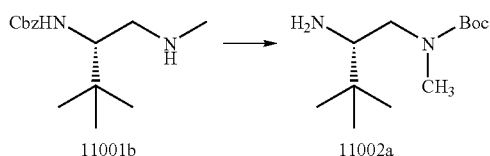

A solution of amine 11001b (4.0 g, 15.14 mmol) in CH$_2$Cl$_2$ (100 mL) was treated with di-tert-butyldicarbonate (4.13 g, 18.91 mmol) and stirred at rt. for 12 h. The reaction mixture was concentrated in vacuo and purified by chromatography (SiO$_2$, EtOAc/Hexanes 1:5) to yield Boc protected amine.

A solution of the Boc protected compound in methanol was treated with palladium hydroxide and hydrogenated at 60 psi for 12 h. The reaction mixture was filtered through a plug of Celite® and the filtrate was concentrated in vacuo. The residue 11002a was used in subsequent steps without further purification.

Step B:

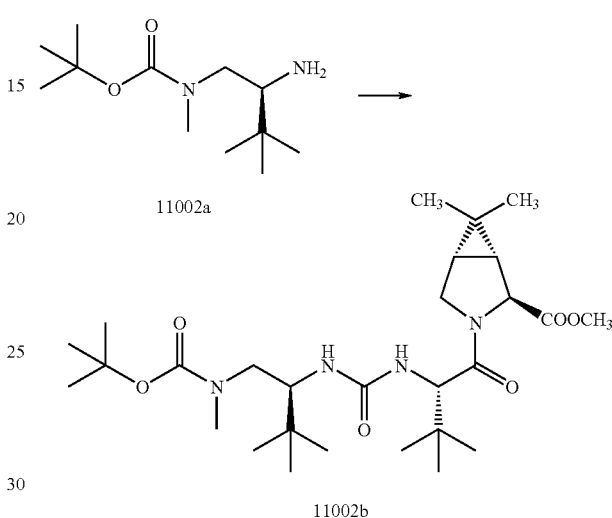

A solution of amine 11002a (134 mg, 0.58 mmol) in acetonitrile (20 mL) was treated with 4-nitrophenylcarbamate 1.16 (260 mg, 0.58 mmol), NMM (177 mg, 1.74 mmol) at 0° C. and stirred at rt. overnight. The reaction mixture was concentrated in vacuo, diluted with CH$_2$Cl$_2$ (250 mL) and washed with aq. HCl (1M, 2×125 mL), aq. saturated NaHCO$_3$ (2×125 mL), brine (100 mL), dried (MgSO$_4$) filtered and purified by chromatography (SiO$_2$, CH$_2$Cl$_2$/EtOAc 1:19) to yield 11002b (279 mg).

Step C:

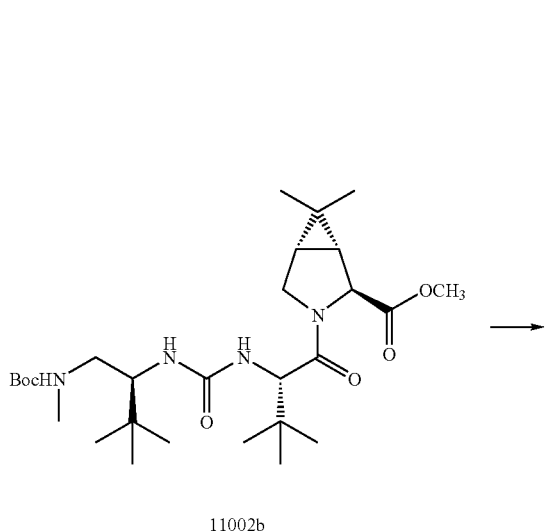

11002b

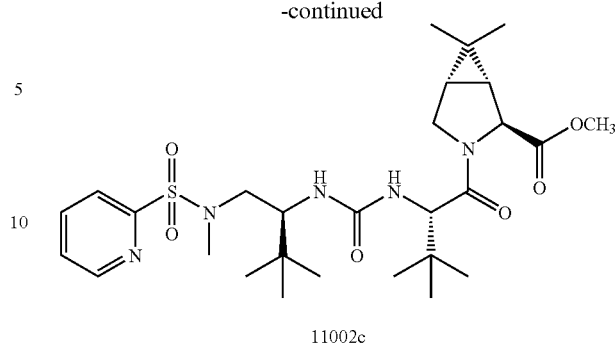

11002c

A solution of 11002b (279 mg, 0.52 mmol) in 4 M HCl dioxane was stirred at rt for 2 h and concentrated in vacuo. The residue was used in further reaction as it is.

The ammonium salt (274 mg, 0.58 mmol) was dissolved in $CH_2Cl_2$:DMF (1:1) and cooled to 0° C. The reaction mixture was treated with 4 eq of $Et_3N$ (233 mg, 2.33 mmol) and 2 eq of 2-pyridinesulfonyl chloride (248 mg, 1.2 mmol) and stirred at rt overnight. The reaction mixture was washed with saturated $NaHCO_3$, and the organic layer was extracted with $CH_2Cl_2$. The organic layer was dried with $MgSO_4$, filtered, and concentrated in vacuo. The crude product was purified using silica gel chromatography using a Horizon HPFC system (30%-->90% EtOAc/hexanes) to yield 240 mg of 11002c.

Step D:

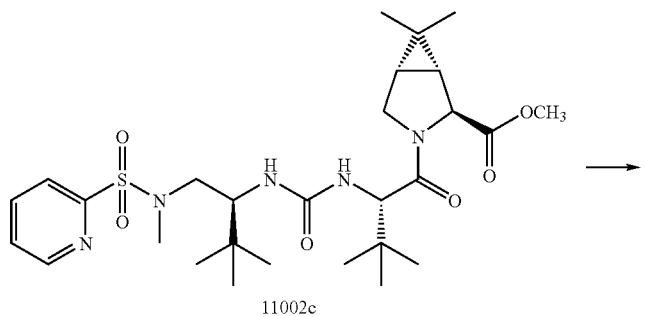

11002c

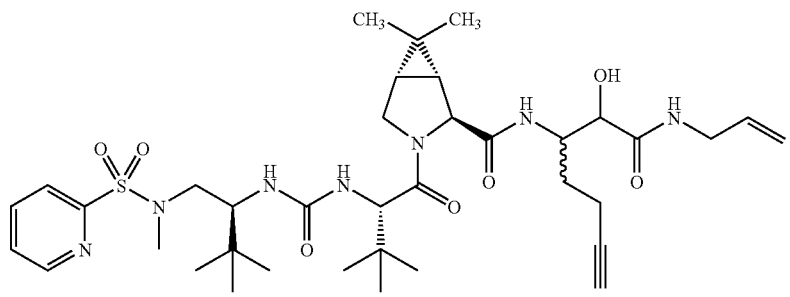

11002d 11002c (240 mg, 0.41 mmol) was dissolved in THF and H₂O (3:1) and treated with 2.5 eq of LiOH.H₂O. The reaction mixture was treated with MeOH until the solution turns homogeneous. The reaction mixture was stirred at rt for approximately 3 hr. The reaction mixture was treated with 1 M aq HCl and concentrated in vacuo. The aqueous layer was extracted with CH₂Cl₂, dried with MgSO₄, filtered, and concentrated in vacuo. The crude was used in further couplings without any purification.

The acid (179 mg, 0.32 mmol) was dissolved in 1:1 CH₂Cl₂/DMF and cooled to 0° C. The reaction mixture was treated with 1.3 eq of deprotected 11.01 (11.01 was deprotected by dissolving (200 mg, 0.61 mmol) in 10 mL of TFA and 3 mL of Me₂S and standing for 3 h. The reaction mixture was concentrated in vacuo and used as it is in further couplings) (238 mg, 0.41 mmol) 3.5 eq of NMM (112 mg 1.1 mmol), and 1.5 eq of HATU (180 mg, 0.47 mmol), and stored in the freezer (~0° C.) overnight. The reaction mixture was concentrated under high vacuum, and the residue was treated with saturated NaHCO₃. The aqueous layer was extracted with CH₂Cl₂, dried with MgSO₄, filtered, and concentrated in vacuo.

Step E:

11002d (313 mg, 0.42 mmol) was dissolved in CH₂Cl₂ and treated with 3 eq of Dess-Martin periodinane (535 mg, 1.3 mmol). The reaction mixture was stirred at rt for approximately 2 hr. The reaction mixture was diluted with 2:1 1 M NaHSO₃/saturated NaHCO₃, and the aqueous layer was extracted with CH₂Cl₂. The organic layer was washed with 1 M NaHSO₃ and saturated NaHCO₃, dried with MgSO₄, filtered, and concentrated in vacuo. The crude product was purified using silica gel chromatography with a Horizon HPFC system (20%-->60% acetone/hexanes) to yield 11002

Example-8

Synthesis of Compound of Formula 11003

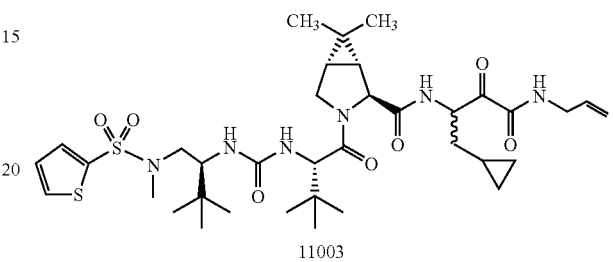

11003

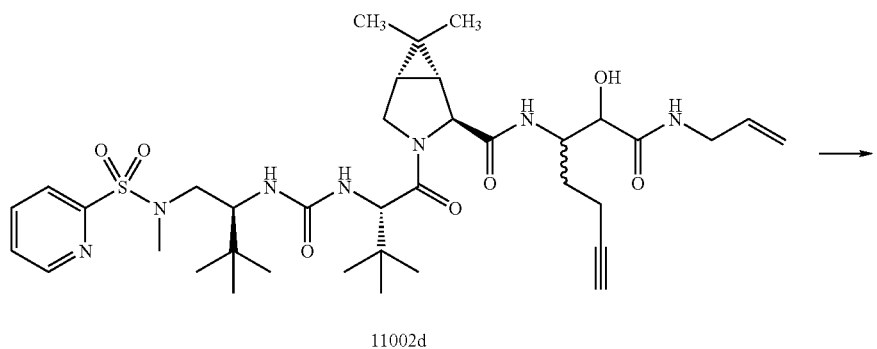

11002d

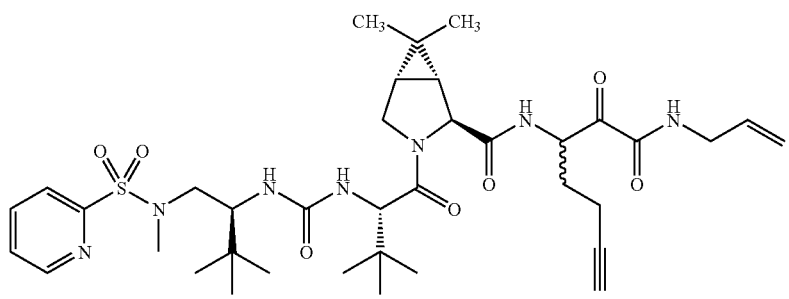

11002

Step A:

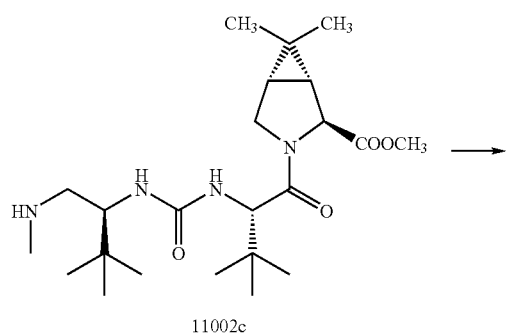

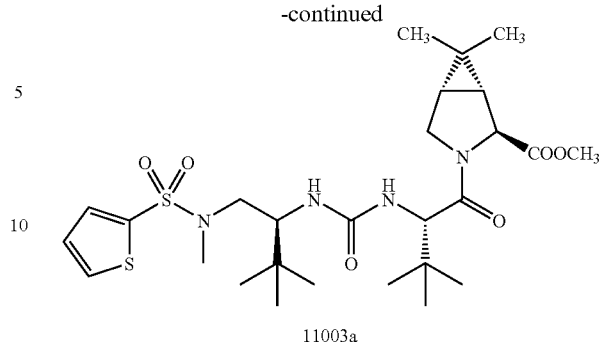

A solution of ammonium salt 11002c (880 mg, 1.86 mmol) in dry methylene chloride was cooled to 0° C. and treated with triethylamine (0.5 mL, 3.71 mmol) and 2-thiophenesulfonyl chloride (678 mg, 3.71 mmol) and stirred at 0° C. for 48 h. The reaction mixture was taken in methylene chloride and the organic layer was washed with aq. HCl (1 M soln.), and brine. The combined organic layers were dried (MgSO$_4$) filtered concentrated in vacuo and purified by chromatography (SiO$_2$, acetone/Hexanes 1:4) to yield 978 mg of 11003a as a colorless solid.

Step C:

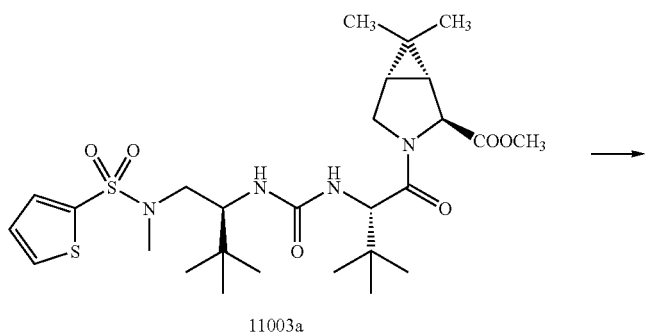

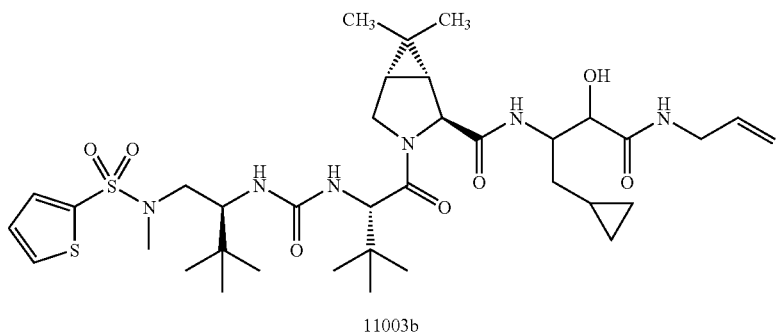

A solution of 11003a (1.2 g, 2.22 mmol) in THF/H$_2$O was treated with LiOH.H$_2$O and stirred at rt. for 3 h. The reaction mixture was acidified with 1 M aq. HCl and extracted with CH$_2$Cl$_2$. The combined organic layers were dried (MgSO$_4$), filtered concentrated in vacuo and used as it is in the next step.

A solution of acid (100 mg, 0.175 mmol) in dry CH$_2$Cl$_2$ (4 mL) and DMF (4 mL) was cooled to 0° C. and treated with amine 12.04 (100 mg, 0.263 mmol) HATU (100 mg, 0.263 mmol) and NMM (70.4 mg, 0.704 mmol). The reaction was stirred at 0° C. for 14 h and concentrated in vacuo. The residue was dissolved in CH$_2$Cl$_2$ (100 mL) and washed with aq. HCl (1 M, 2×100 mL), aq. saturated NaHCO$_3$ (2×100 mL) brine (100 mL), dried (MgSO$_4$), filtered, concentrated in vacuo to yield 11003b that was used in the next reaction without further purification.

Step D:

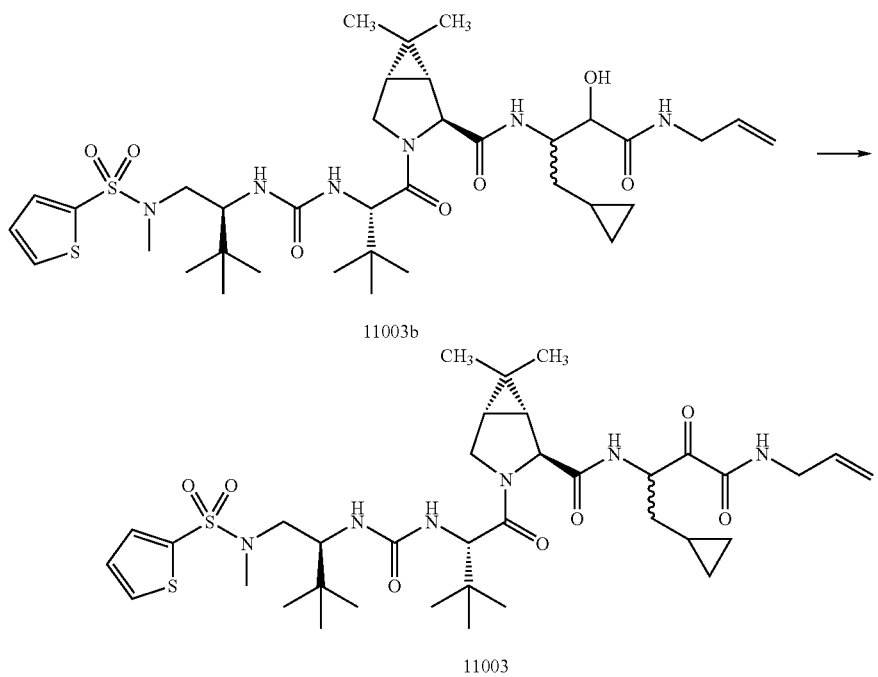

11003b

11003

A solution of alcohol 11003b (100 mg, 0.133 mmol) in dry CH$_2$Cl$_2$ (4 mL) was treated with Dess-Martin reagent (Dess, D. B.; Martin, J. C. *J. Am. Chem. Soc.* 1991, 113, 7277.) (150 mg, 0.345 mmol) and stirred at rt for 2 h. The reaction mixture was diluted with aq. Na$_2$S$_2$O$_3$ (5%, 30 mL) and aq. saturated NaHCO$_3$ (30 mL) and stirred at rt. for 15 min. The reaction mixture was extracted with CH$_2$Cl$_2$ (100 mL) and the combined organic layers were dried (MgSO$_4$), filtered, concentrated in vacuo and purified by chromatography (SiO$_2$, acetone/Hexanes 20%-55% linear gradient) to yield 11003.

Example-9

Synthesis of Compound of Formula 11004

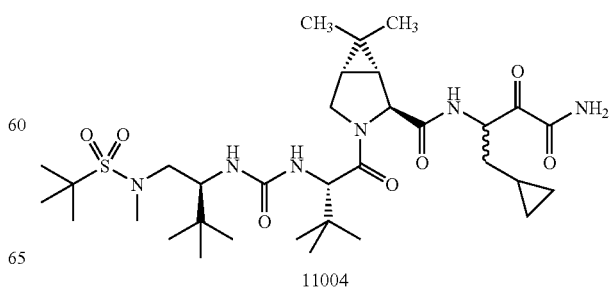

11004

Step A:

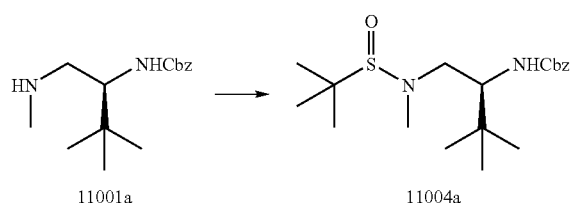

A solution of amine 11001a (150 mg, 0.567 mmol) in CH$_2$Cl$_2$ (5 mL) was cooled to 0° C. and treated with NMM (100 mg, 100 mL). The reaction was treated with tert-butyl sulfenylchloride (Sun, P; Weinreb, S. M.; Shang, M. *J. Org. Chem.* 1997, 62, 8604) (0.5 mL, 1.3 M soln in CH$_2$Cl$_2$) and stirred at rt. overnight. The reaction mixture was diluted with aq. HCl (1M, 30 mL) and extracted with CH$_2$Cl$_2$ (3×30 mL). The combined organic layer was extracted with brine (30 mL) dried (MgSO$_4$) filtered concentrated in vacuo and purified by chromatography (SiO$_2$, acetone/Hexanes) to yield 11004a.

Step B:

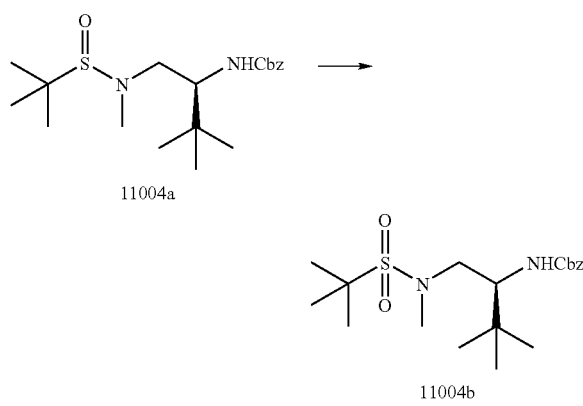

A solution of sulfenamide 11004a (2.00 g, 5.43 mmol) in CH$_2$Cl$_2$ (60 mL) was treated with MCPBA (2.34 g, 8.145 mmol, 60%) and stirred at rt. for 1 h. The reaction mixture was diluted with aq. Na$_2$S$_2$O$_3$ (10%, 50 mL) and aq NaHCO$_3$ (saturated, 100 mL) and stirred at rt. for 30 min. The reaction mixture was extracted with CH$_2$Cl$_2$ (150 mL) and the combined organic layers were washed with water, brine, dried (MgSO$_4$) filtered concentrated in vacuo and purified by chromatography (SiO$_2$, EtOAc/Hex 1:9→1:1) to yield 11004b.

Step C:

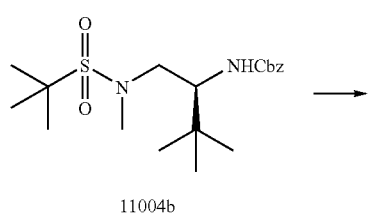

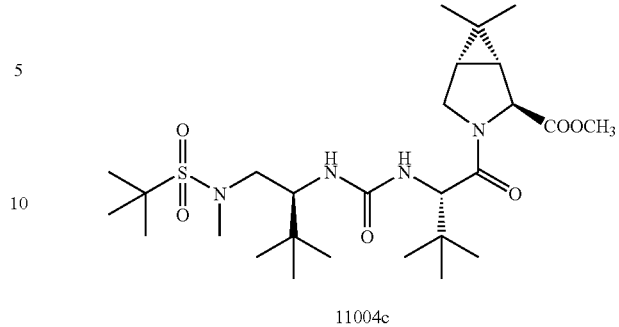

A solution of Cbz-protected compound 11004b (1.5 g, 3.90 mmol) in methanol (25 mL) was treated with palladium hydroxide (10% on C) and hydrogenated at 60 psi for 1 h. The reaction mixture was filtered through a plug of celite and concentrated in vacuo. It was used for further reaction without any purification.

A solution of deprotected amine (1.00 g, 4.00 mmol) in acetonitrile (20 mL) was treated with 4-nitrophenylcarbamate 1.16 (1.879 g, 4.20 mmol), NMM (1.062 g, 10.5 mmol) and stirred at rt. overnight. The reaction mixture was concentrated in vacuo diluted with CH$_2$Cl$_2$ (200 mL) and washed with aq. HCl (1M, 2×125 mL), aq. saturated NaHCO$_3$ (2×125 mL), brine (100 mL), dried (MgSO$_4$), filtered, and purified by chromatography (SiO$_2$, CH$_2$Cl$_2$/EtOAc 1:19) to yield 11004c.

Step D:

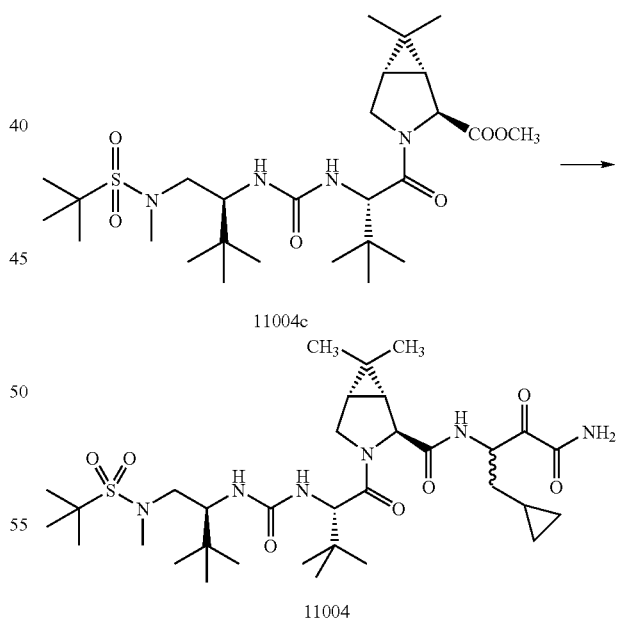

Intermediate 11004c was converted to 11004 by coupling to intermediate 12.03 followed by Moffett oxidation identical to the procedures described in preparative example-6 of synthesis of 11001, Step D and Step E. Compounds shown in the following Table 2 were synthesized using similar reactions as shown in Examples above. Range of Ki* Indicated A≦75 nM; 75<B≦250 nM; C>250 nM.

TABLE 2
| Entry | Structure | Ki* |
|---|---|---|
| 11001 | 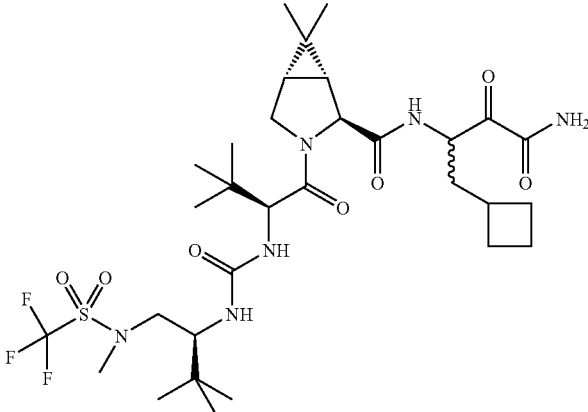 | A |
| 11002 | 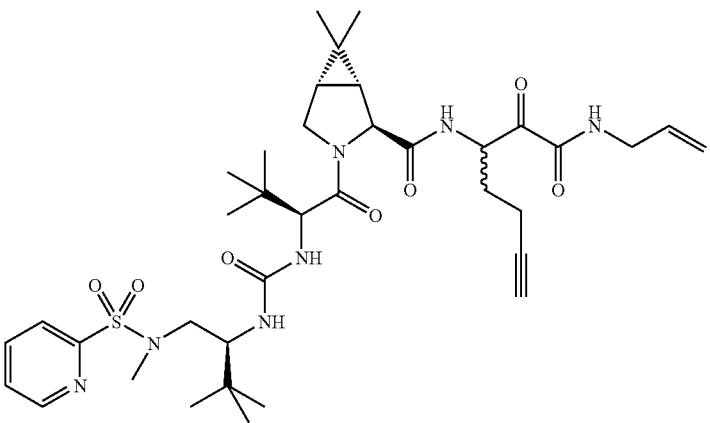 | A |
| 11003 | 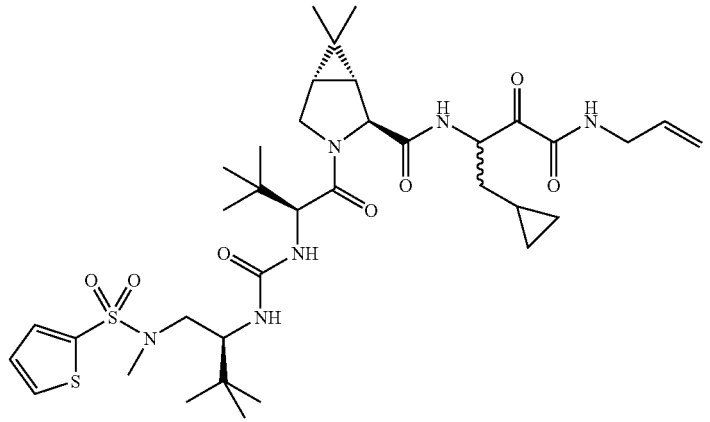 | A |

TABLE 2-continued

| Entry | Structure | Ki* |
|-------|-----------|-----|
| 11004 | 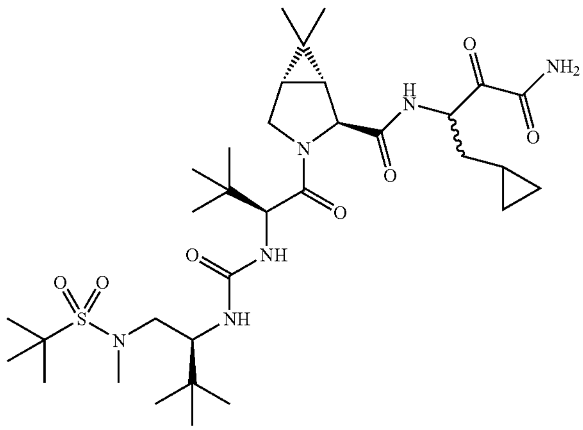 | A |
| 11005 | 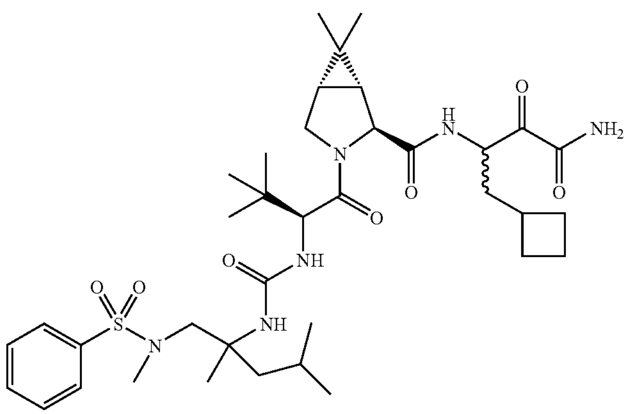 | B |
| 11006 | 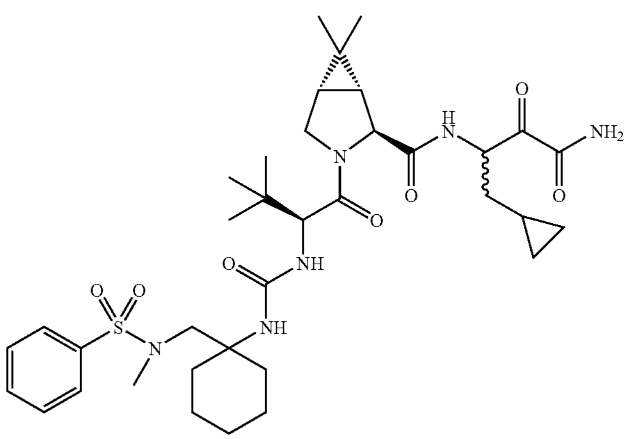 | A |

TABLE 2-continued

| Entry | Structure | Ki* |
|---|---|---|
| 11007 | 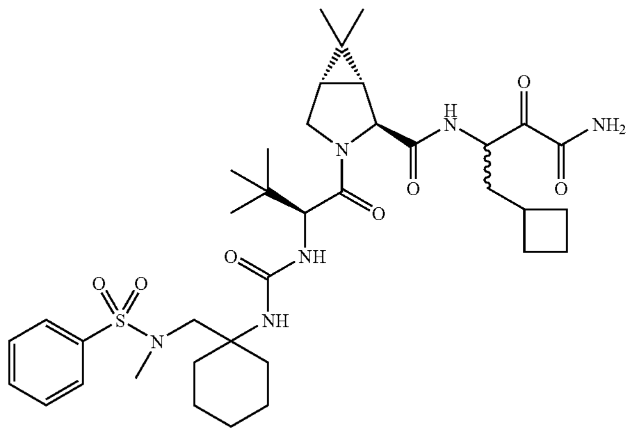 | A |
| 11008 | 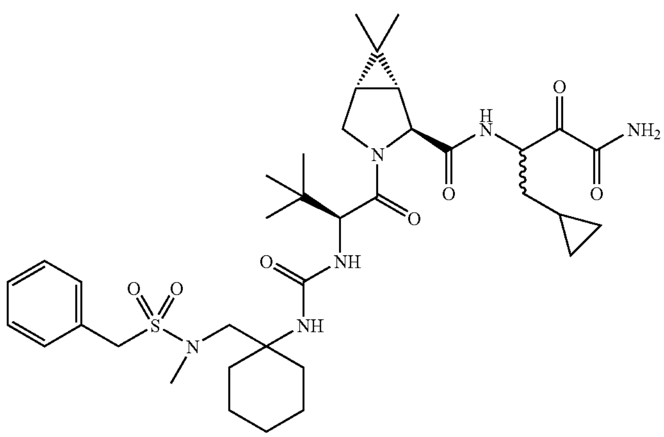 | A |
| 11009 | 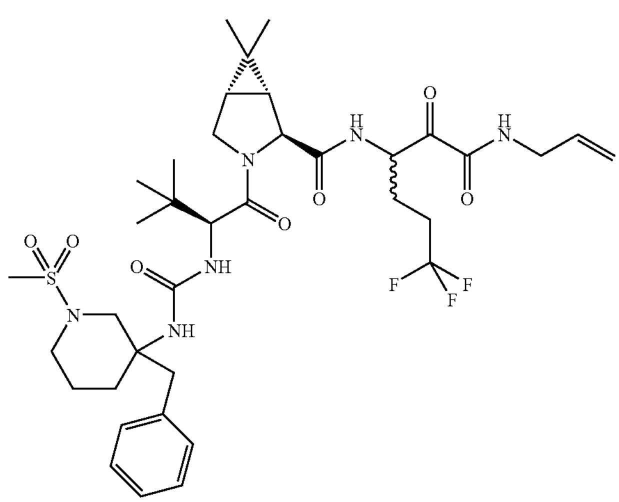 | C |

TABLE 2-continued
| Entry | Structure | Ki* |
|---|---|---|
| 11010 | 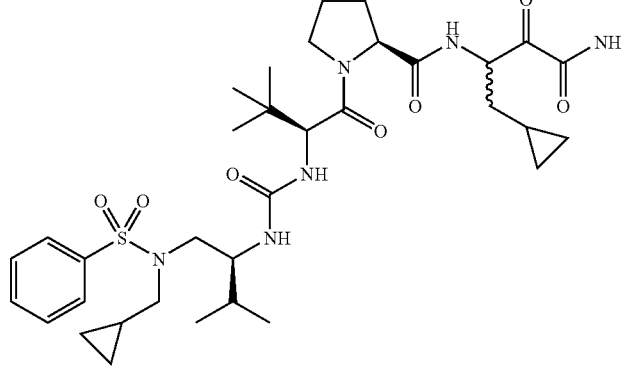 | A |
| 11011 | 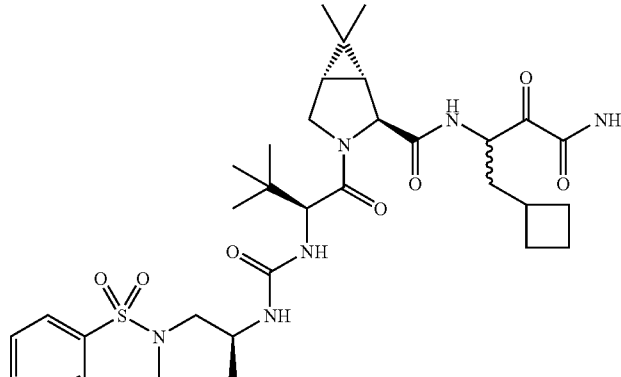 | |
| 11012 | 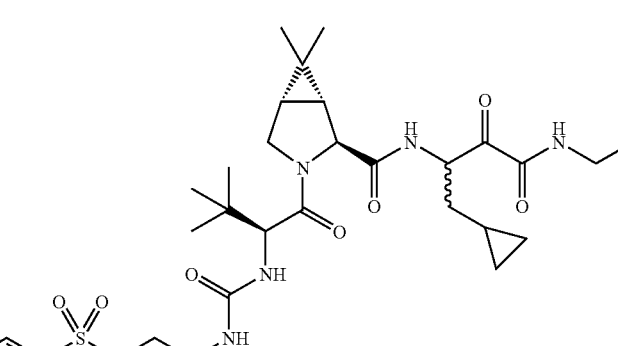 | A |

TABLE 2-continued

| Entry | Structure | Ki* |
|---|---|---|
| 11013 | 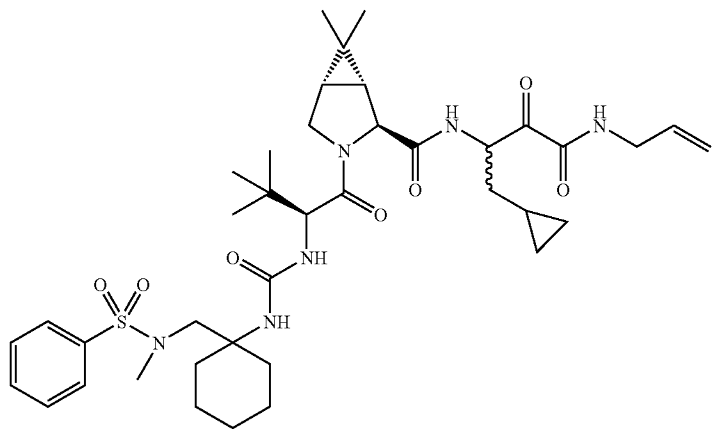 | A |
| 11014 | 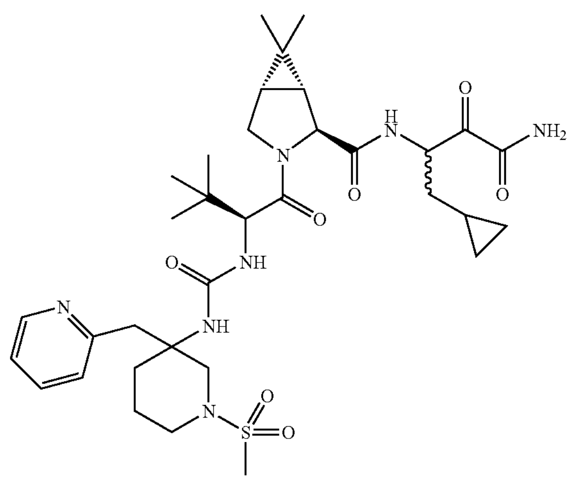 | C |
| 11015 | 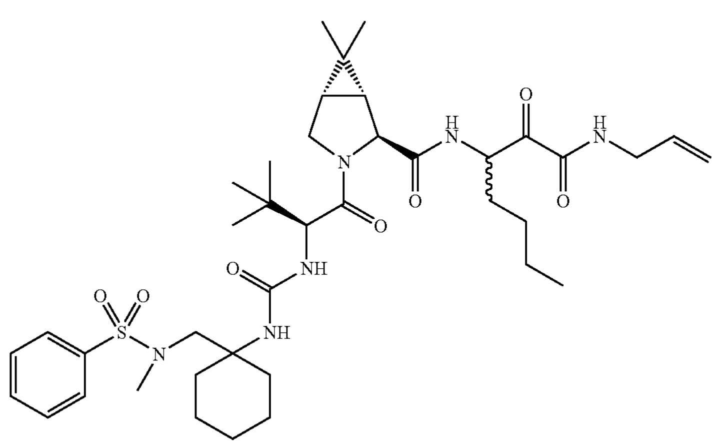 | A |

TABLE 2-continued

| Entry | Structure | Ki* |
|---|---|---|
| 11016 | 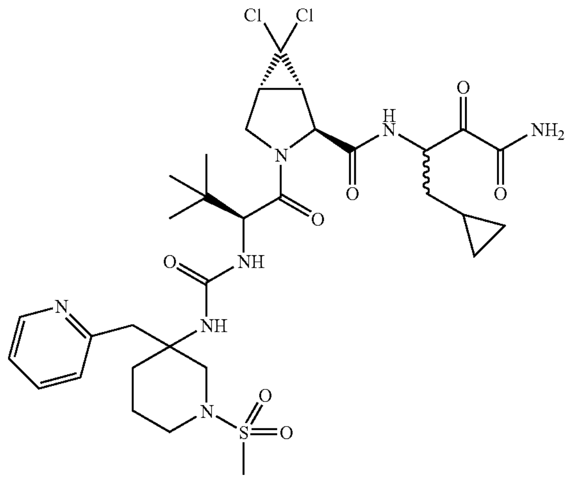 | C |
| 11017 | 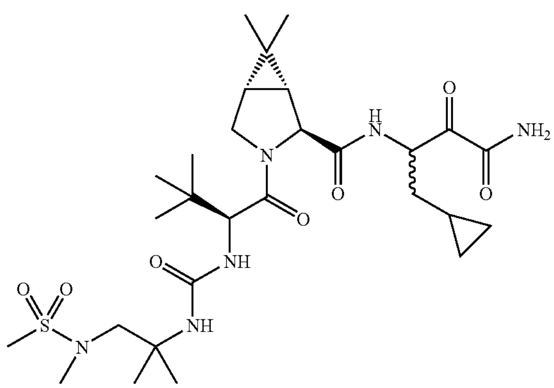 | B |
| 11018 | 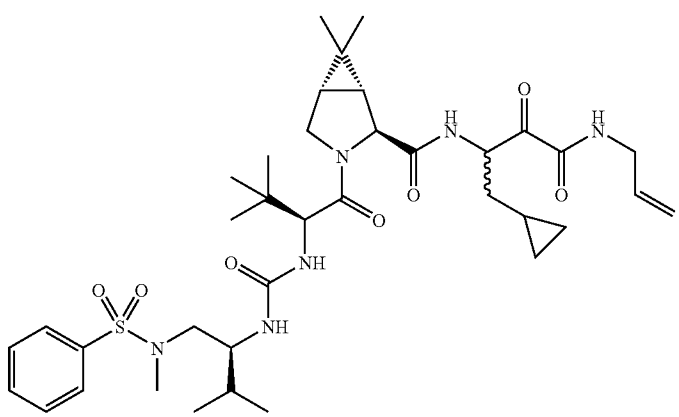 | A |

TABLE 2-continued

| Entry | Structure | Ki* |
|---|---|---|
| 11019 | 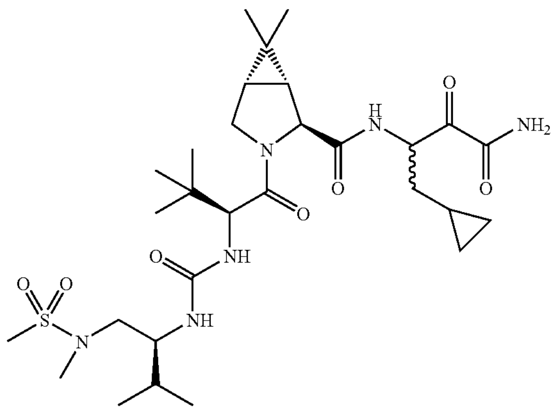 | A |
| 11020 | 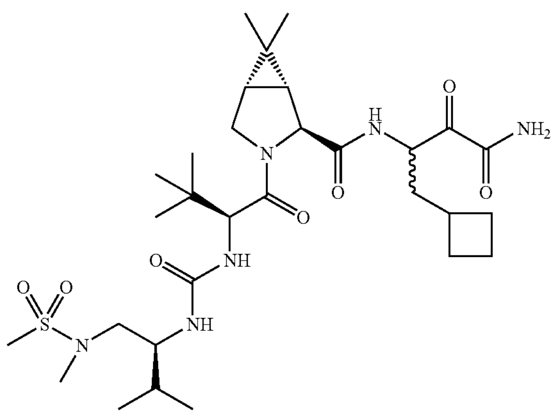 | A |
| 11021 | 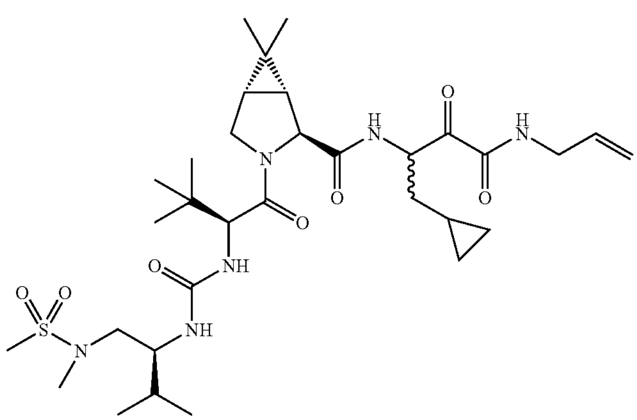 | A |

TABLE 2-continued
| Entry | Structure | Ki* |
|---|---|---|
| 11022 | 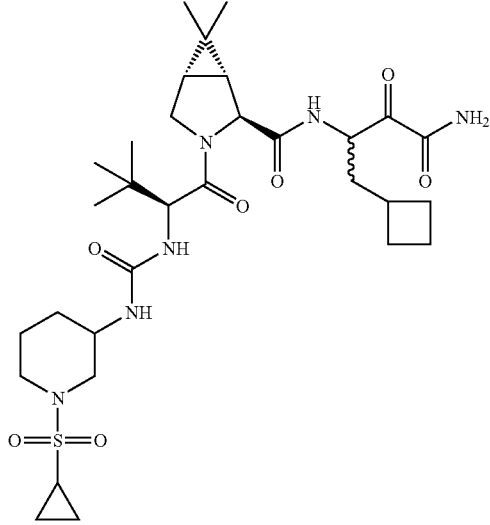 | B |
| 11023 | 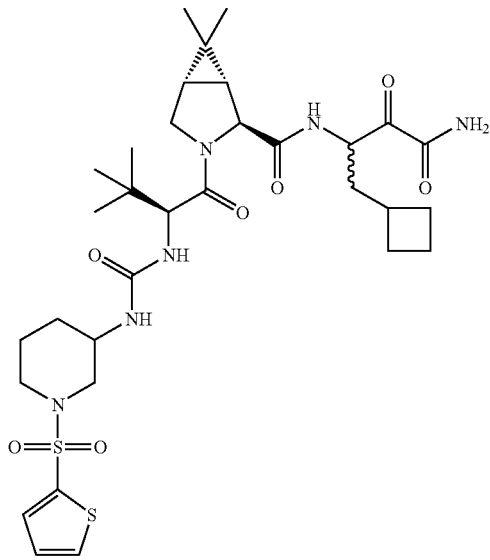 | B |

TABLE 2-continued

| Entry | Structure | Ki* |
|---|---|---|
| 11024 | 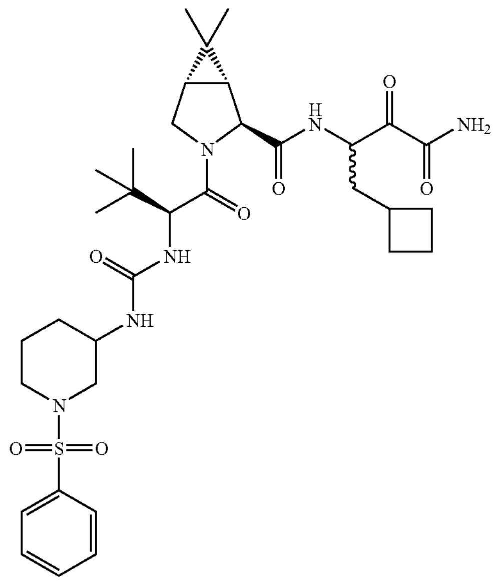 | B |
| 11025 | 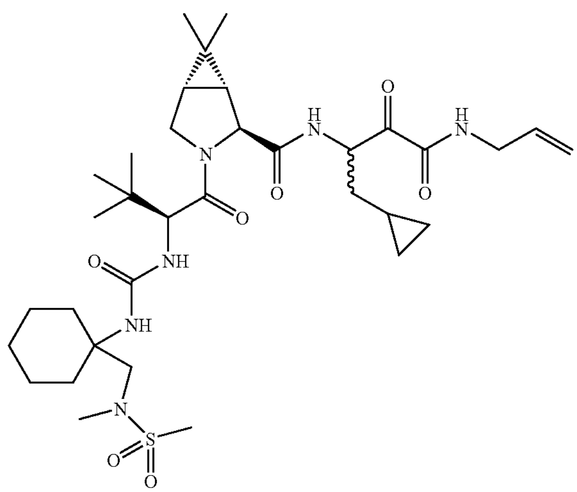 | A |
| 11026 | 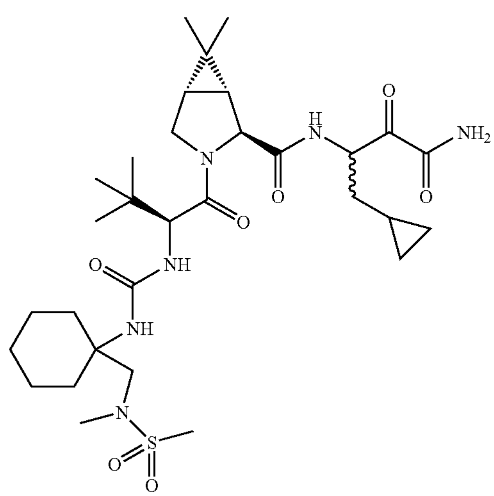 | A |

TABLE 2-continued

| Entry | Structure | Ki* |
|---|---|---|
| 11027 | 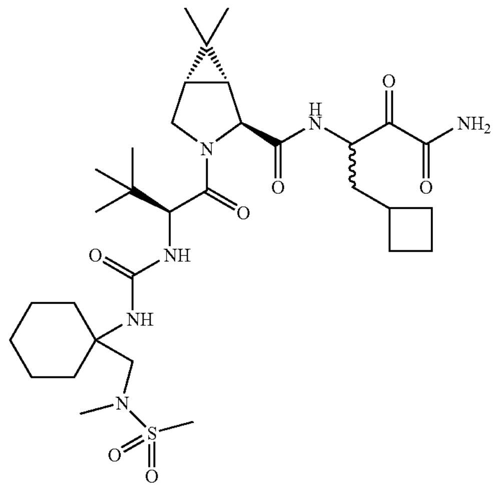 | A |
| 11028 | 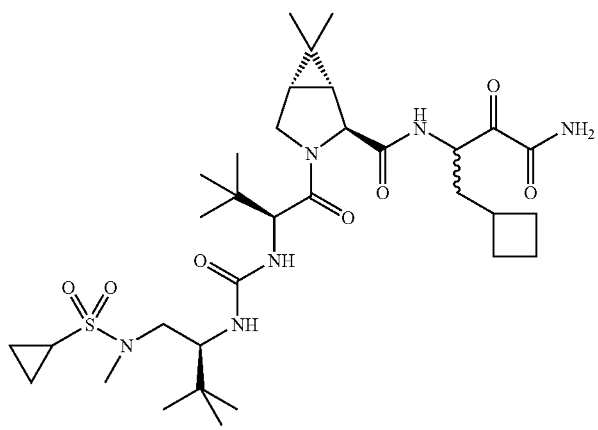 | A |
| 11029 | 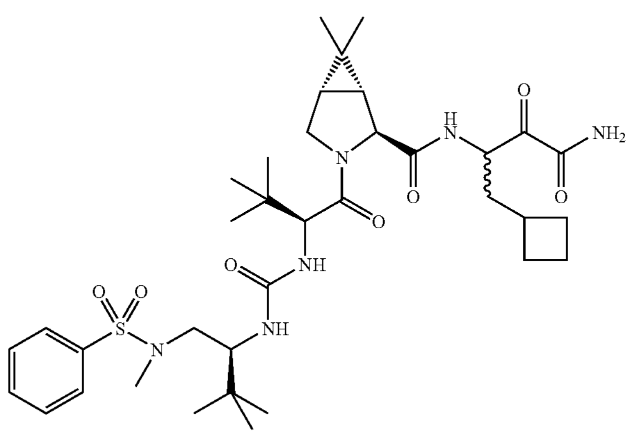 | A |

TABLE 2-continued
| Entry | Structure | Ki* |
|---|---|---|
| 11030 | 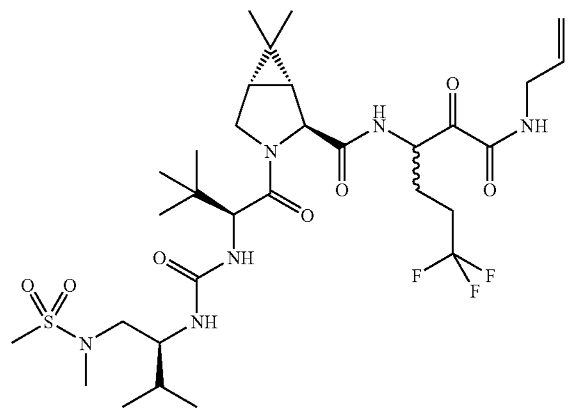 | A |
| 11031 | 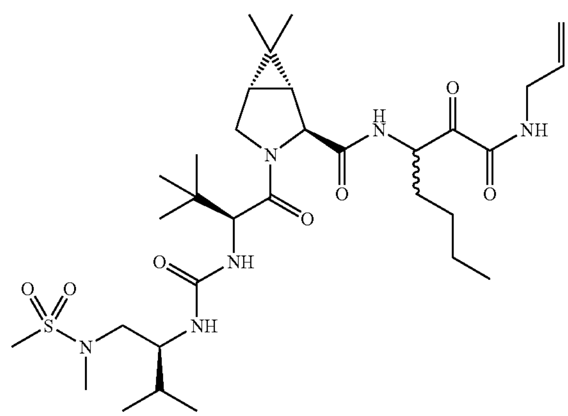 | A |
| 11032 | 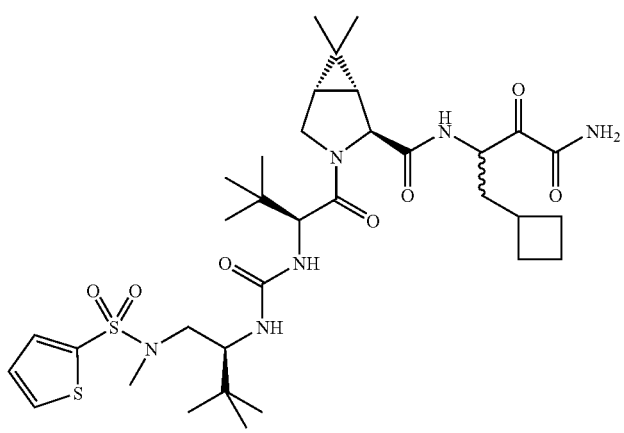 | A |

TABLE 2-continued

| Entry | Structure | Ki* |
|---|---|---|
| 11033 | 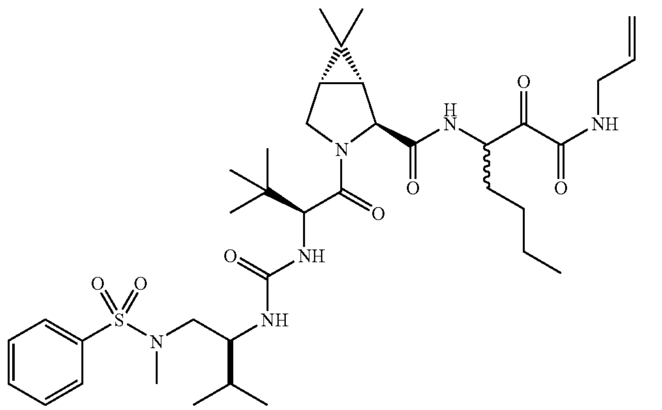 | A |
| 11034 | 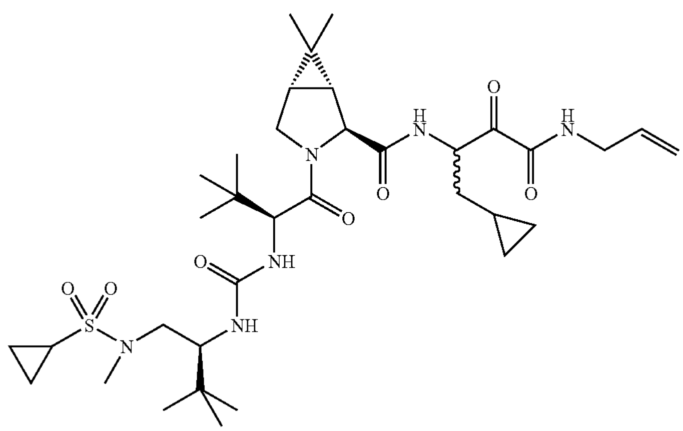 | A |
| 11035 | 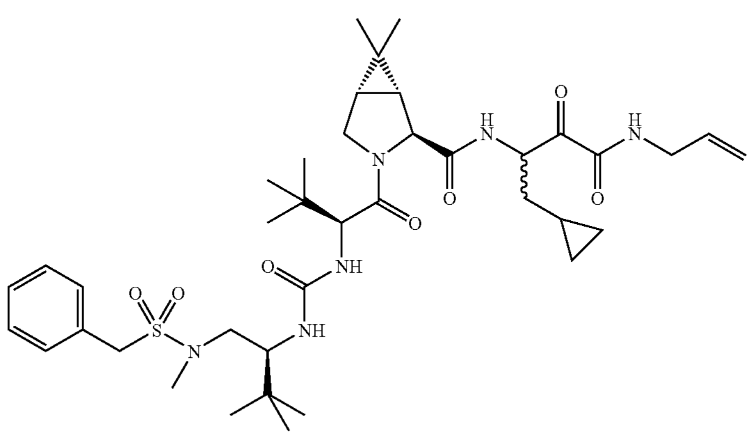 | A |

TABLE 2-continued

| Entry | Structure | Ki* |
|---|---|---|
| 11036 | 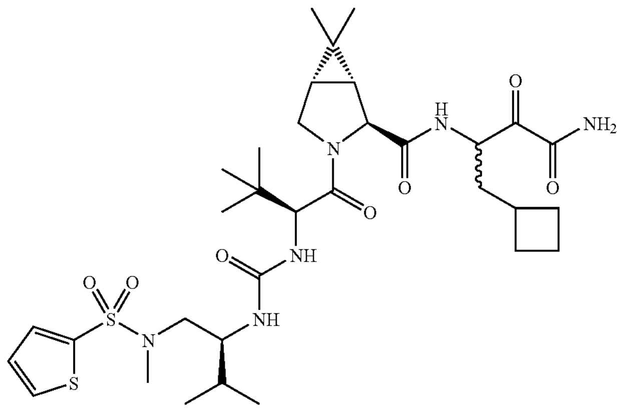 | A |
| 11037 | 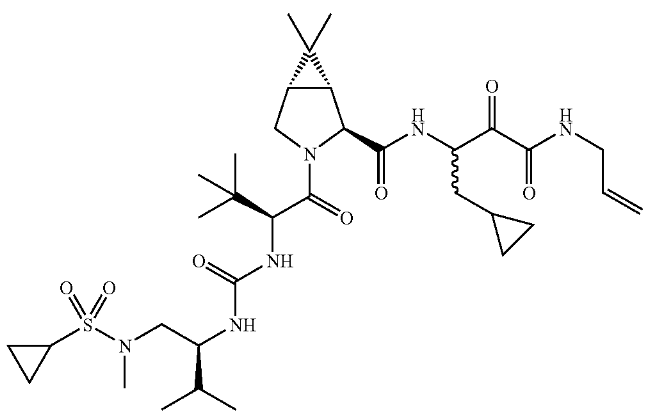 | B |
| 11038 | 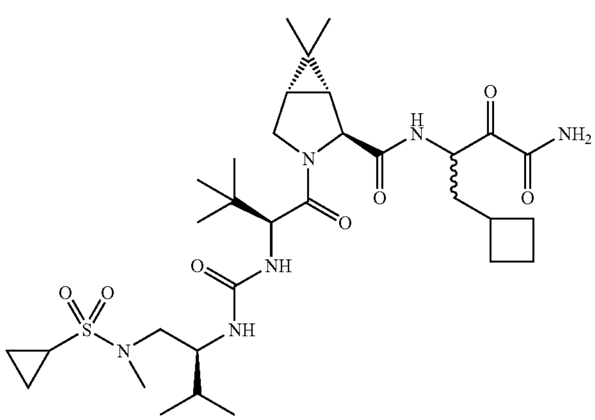 | A |

TABLE 2-continued
| Entry | Structure | Ki* |
|---|---|---|
| 11039 | 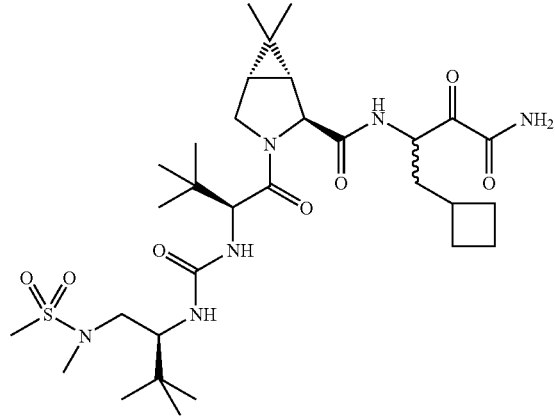 | A |
| 11040 | 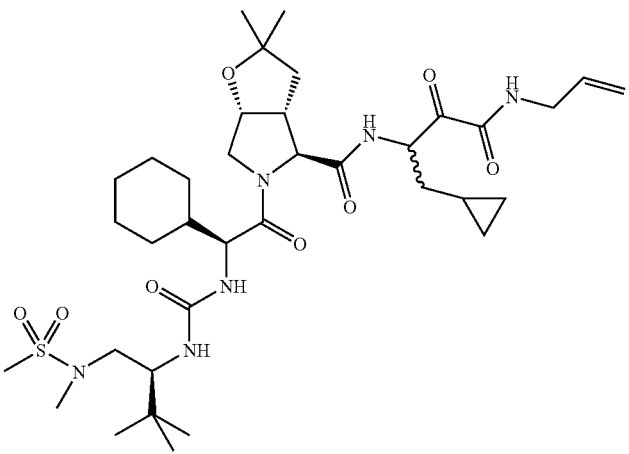 | B |
| 11041 | 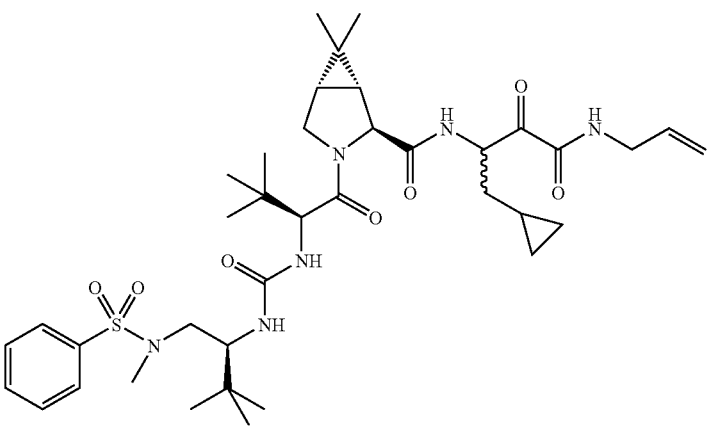 | A |

TABLE 2-continued
| Entry | Structure | Ki* |
|---|---|---|
| 11042 | 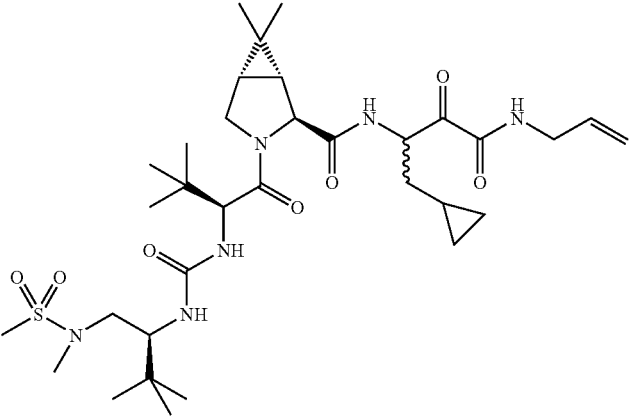 | A |
| 11043 | 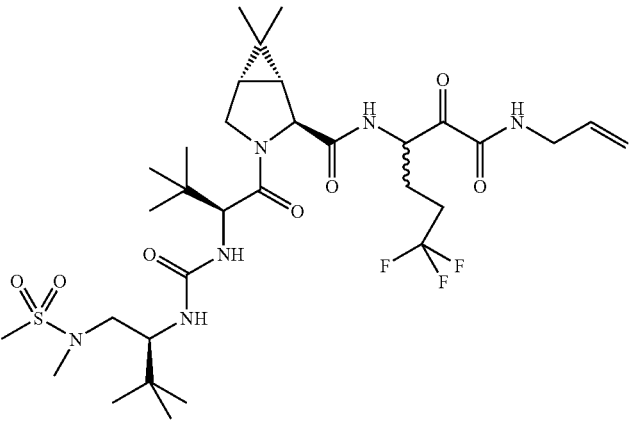 | A |
| 11044 | 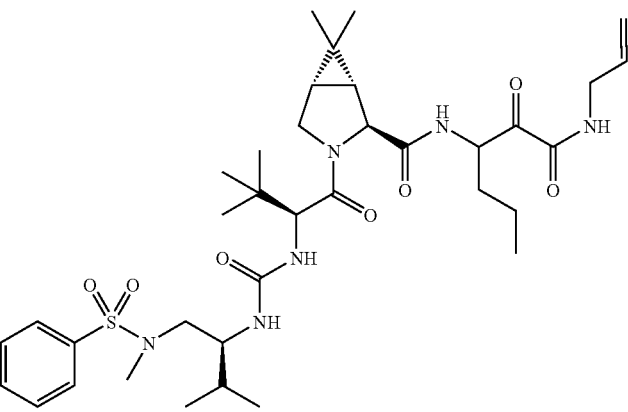 | A |

TABLE 2-continued

| Entry | Structure | Ki* |
|---|---|---|
| 11045 | 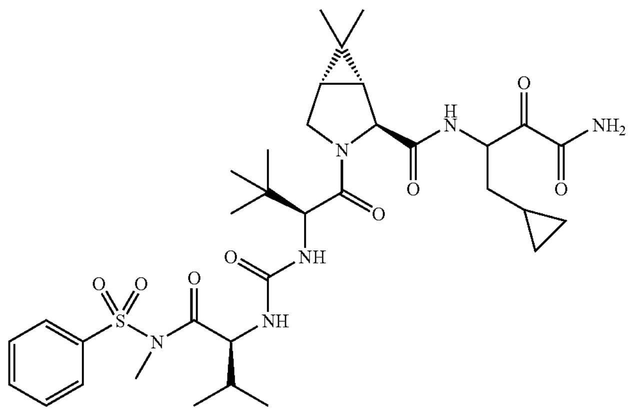 | A |
| 11046 | 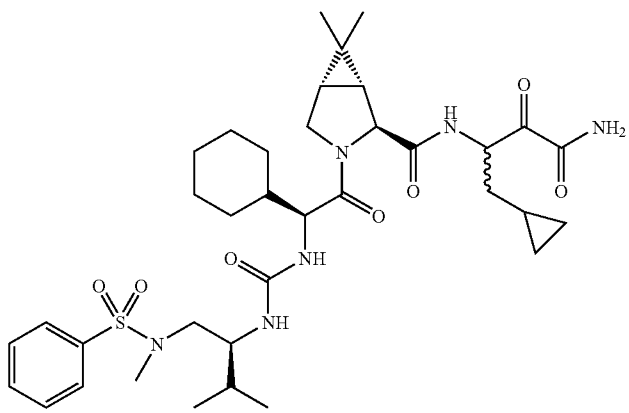 | A |
| 11047 | 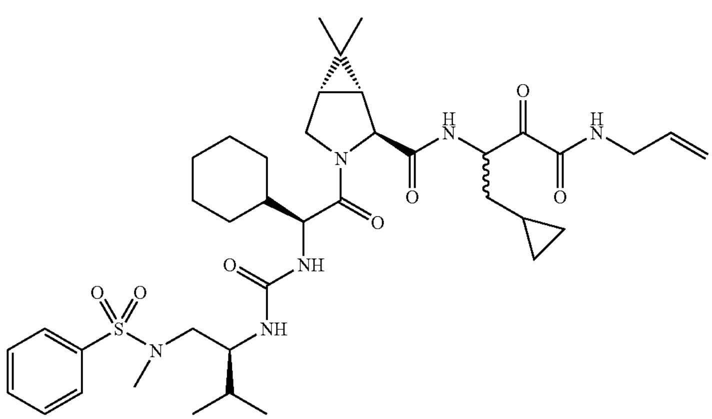 | A |

TABLE 2-continued

| Entry | Structure | Ki* |
|---|---|---|
| 11048 | 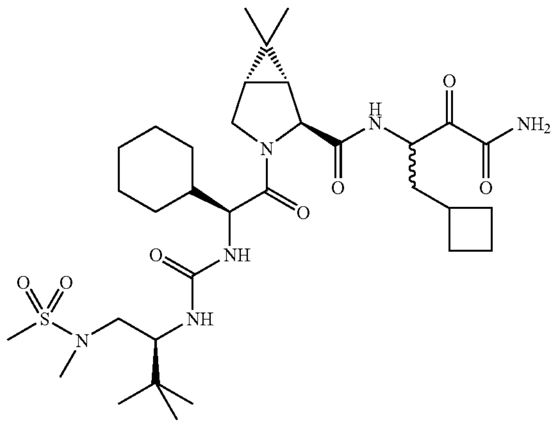 | A |
| 11049 | 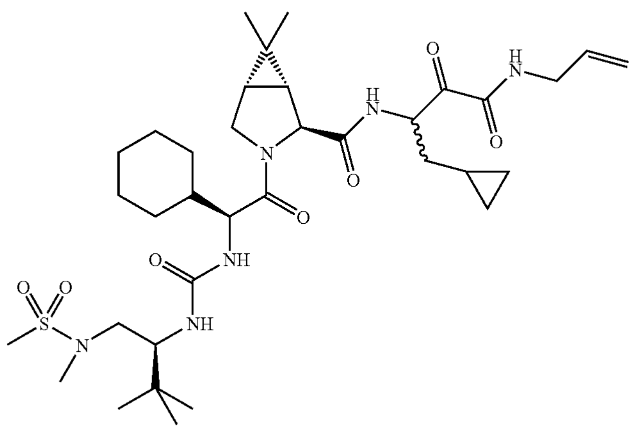 | A |
| 11050 | 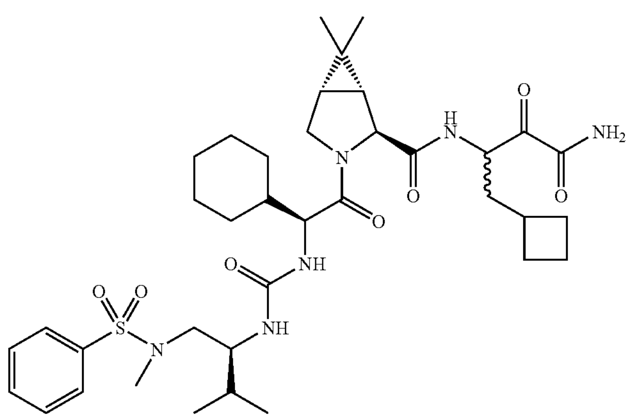 | A |

TABLE 2-continued

| Entry | Structure | Ki* |
|---|---|---|
| 11051 | 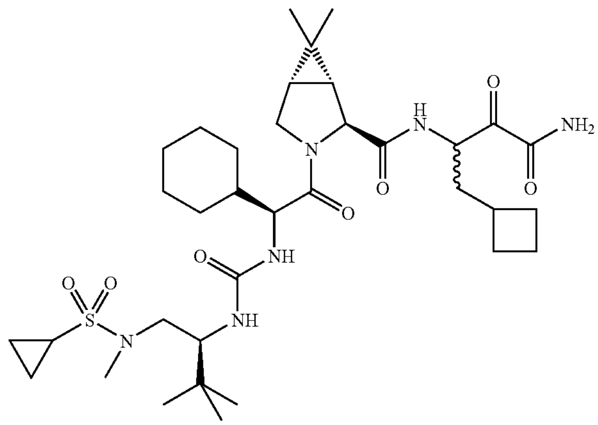 | |
| 11052 | 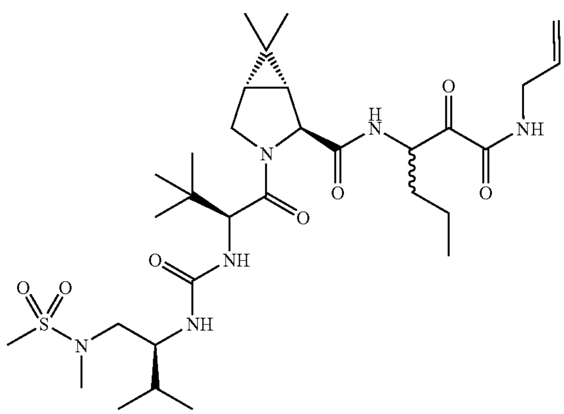 | A |
| 11053 | 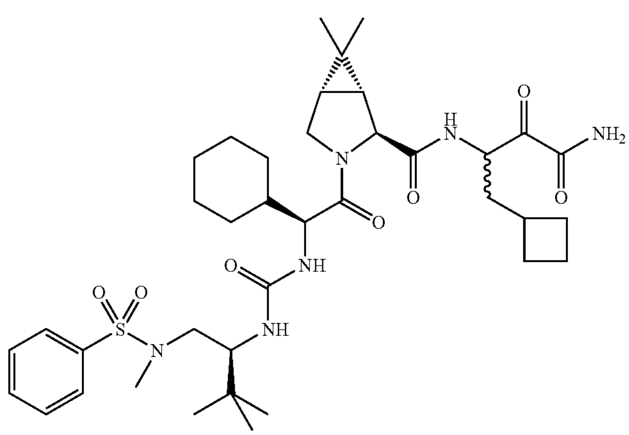 | A |

TABLE 2-continued

| Entry | Structure | Ki* |
|---|---|---|
| 11054 | 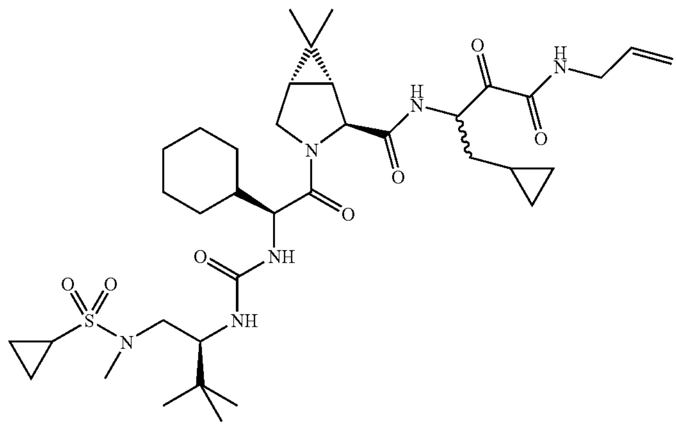 | A |
| 11055 | 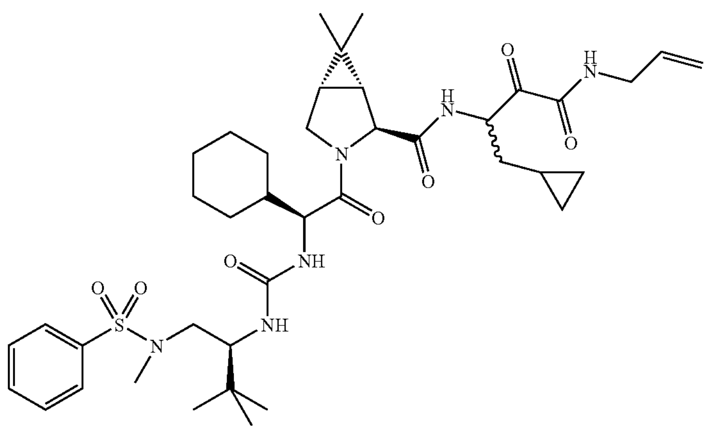 | A |
| 11057 | 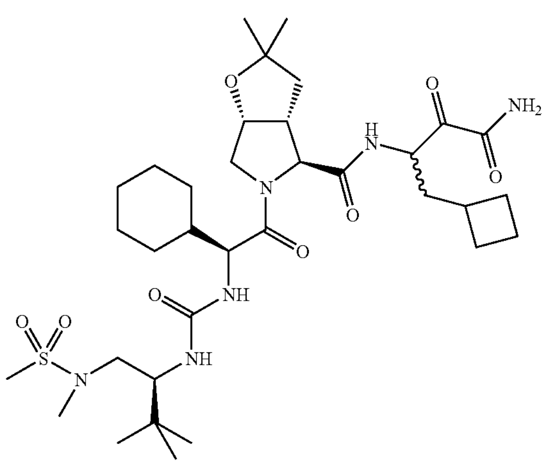 | A |

TABLE 2-continued

| Entry | Structure | Ki* |
|---|---|---|
| 11058 | 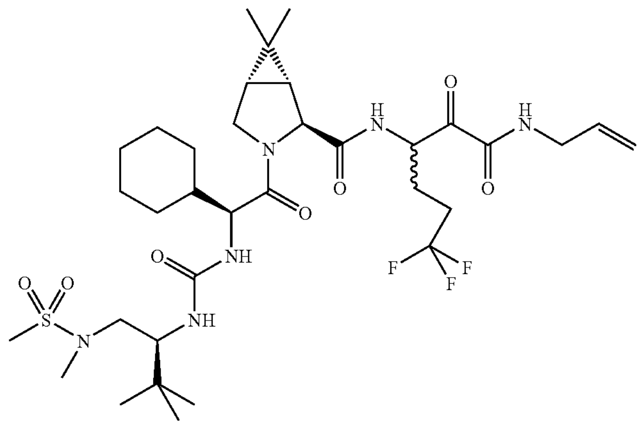 | A |
| 11059 | 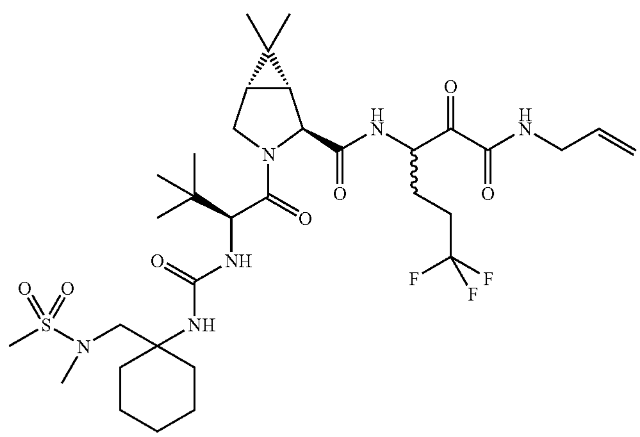 | A |
| 11060 | 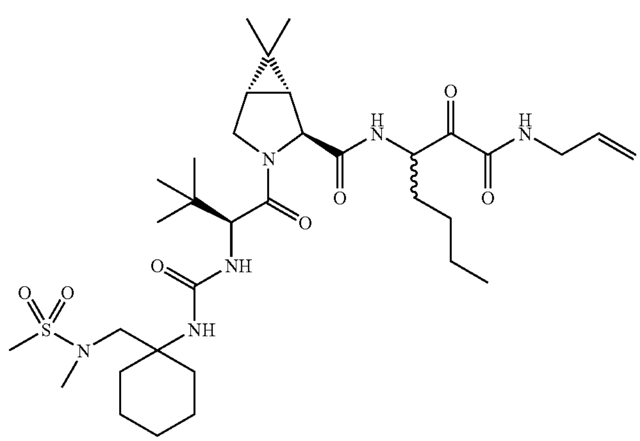 | A |

TABLE 2-continued

| Entry | Structure | Ki* |
|---|---|---|
| 11061 | 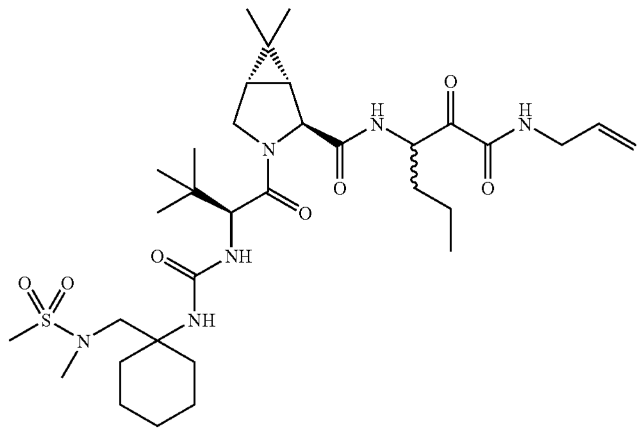 | A |
| 11062 | 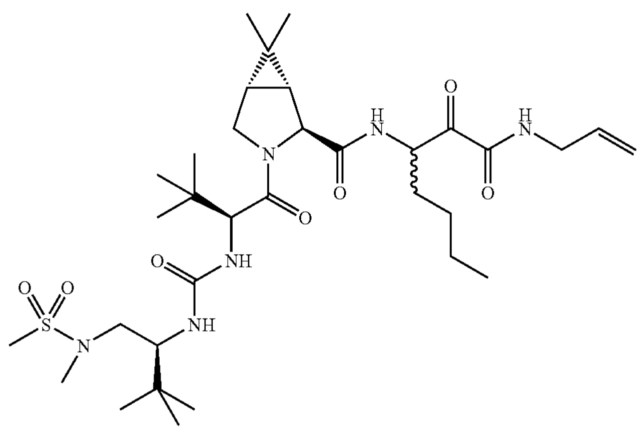 | A |
| 11063 | 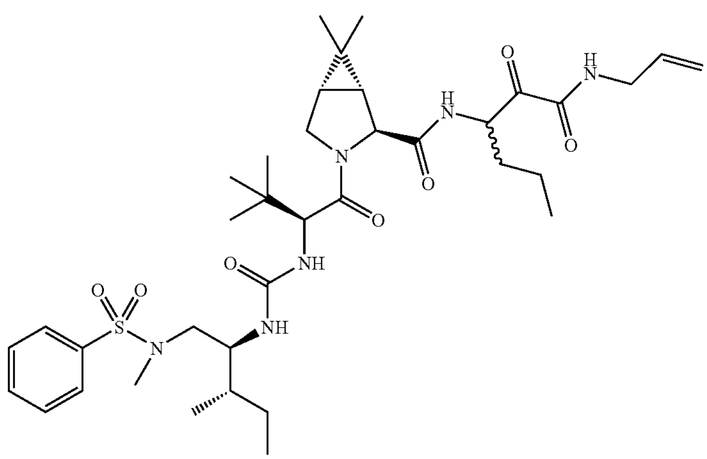 | A |

TABLE 2-continued
| Entry | Structure | Ki* |
|---|---|---|
| 11064 | 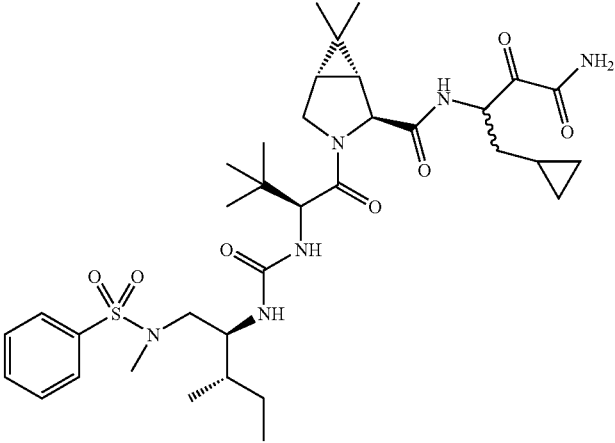 | A |
| 11065 | 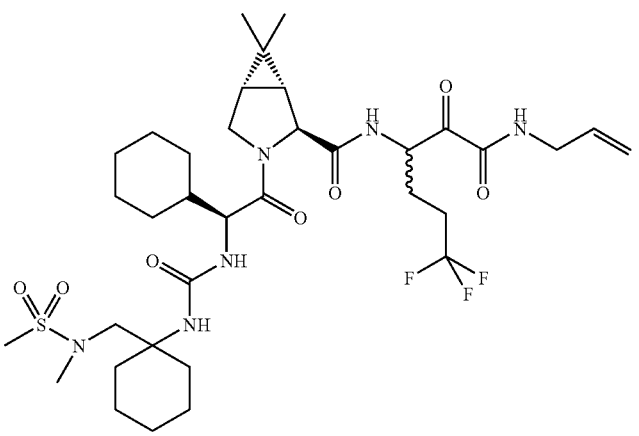 | A |
| 11066 | 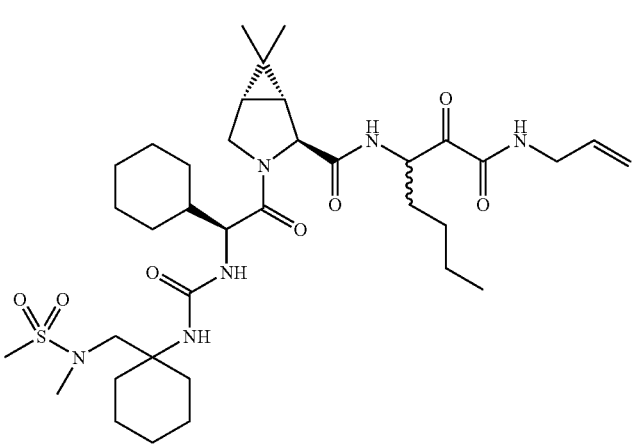 | A |

TABLE 2-continued

| Entry | Structure | Ki* |
|---|---|---|
| 11067 | 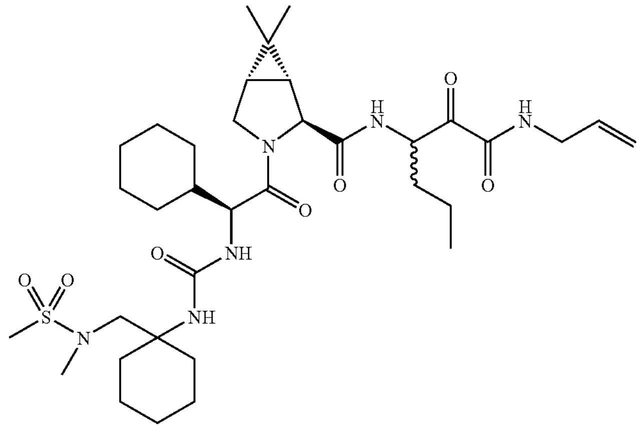 | A |
| 11068 | 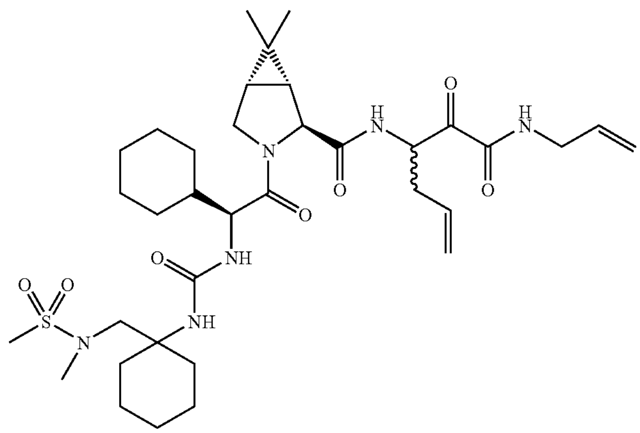 | A |
| 11069 | 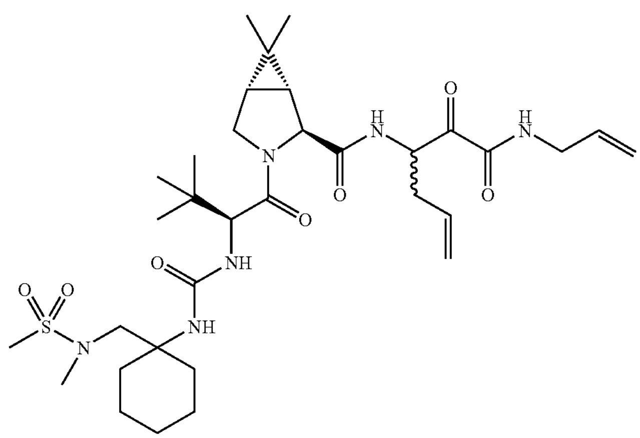 | A |

TABLE 2-continued

| Entry | Structure | Ki* |
|---|---|---|
| 11070 | 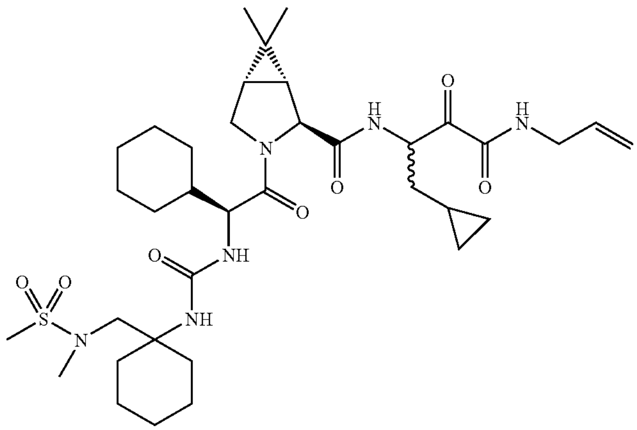 | A |
| 11071 | 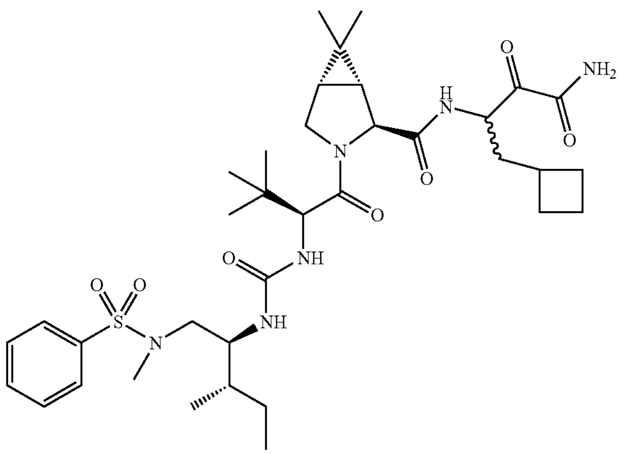 | A |
| 11072 | 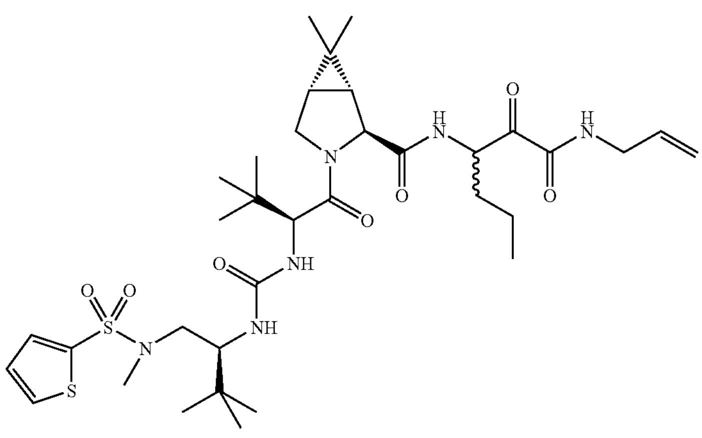 | A |

TABLE 2-continued
| Entry | Structure | Ki* |
|---|---|---|
| 11073 | 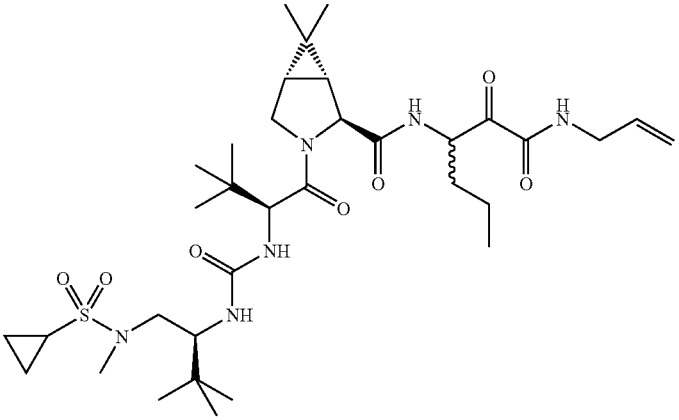 | A |
| 11074 | 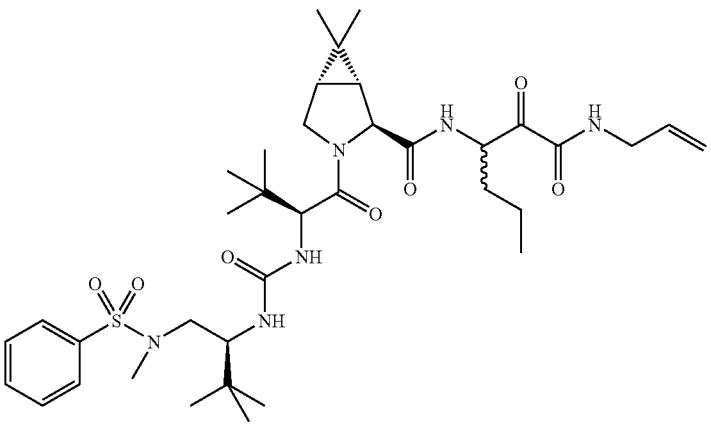 | A |
| 11075 | 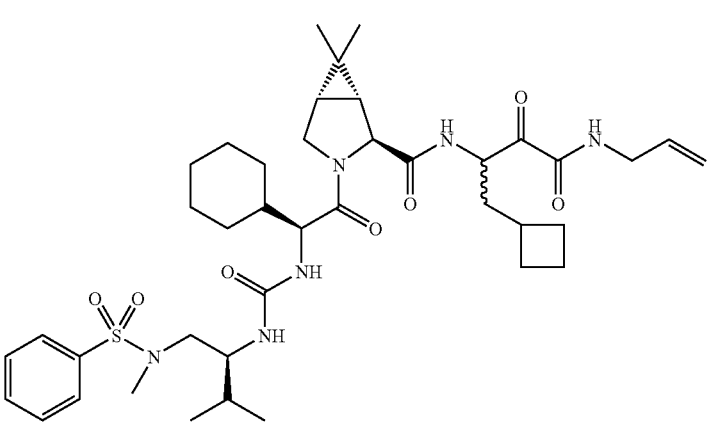 | A |

TABLE 2-continued
| Entry | Structure | Ki* |
|---|---|---|
| 11076 | 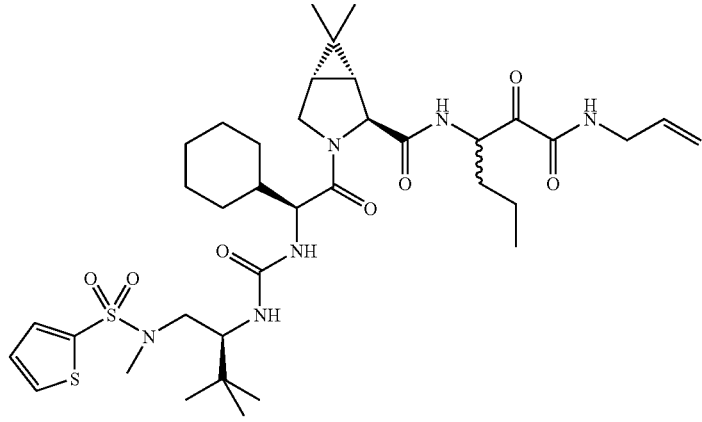 | A |
| 11077 | 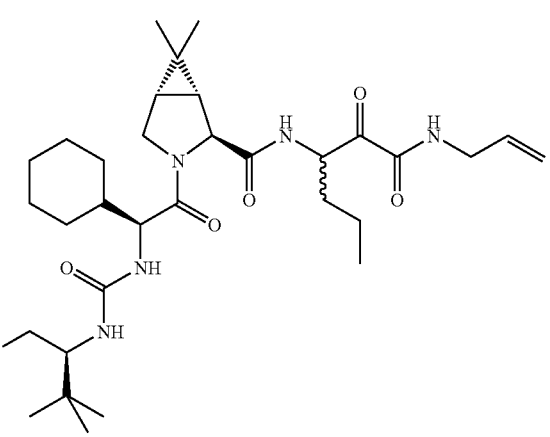 | A |
| 11078 | 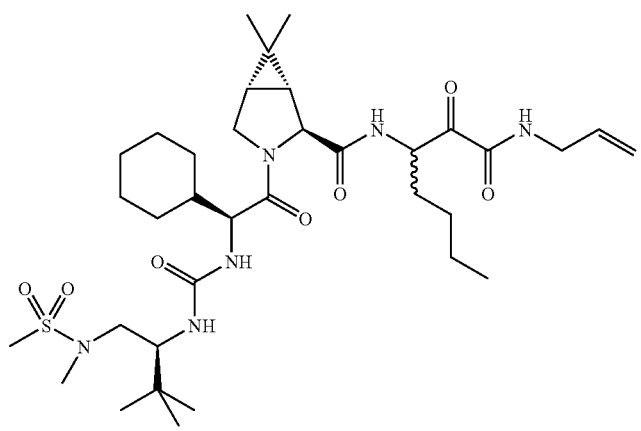 | A |

TABLE 2-continued

| Entry | Structure | Ki* |
|---|---|---|
| 11079 | 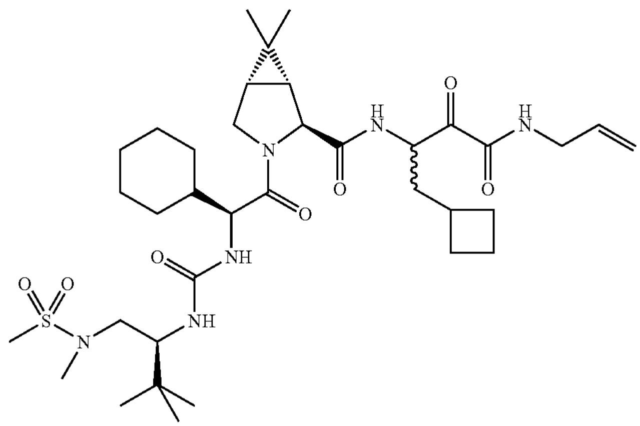 | A |
| 11080 | 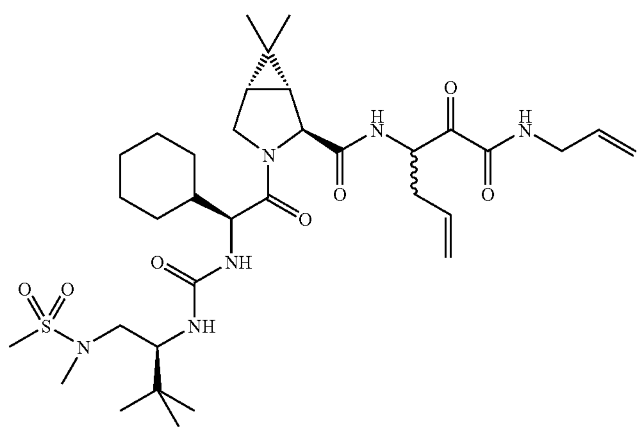 | A |
| 11081 | 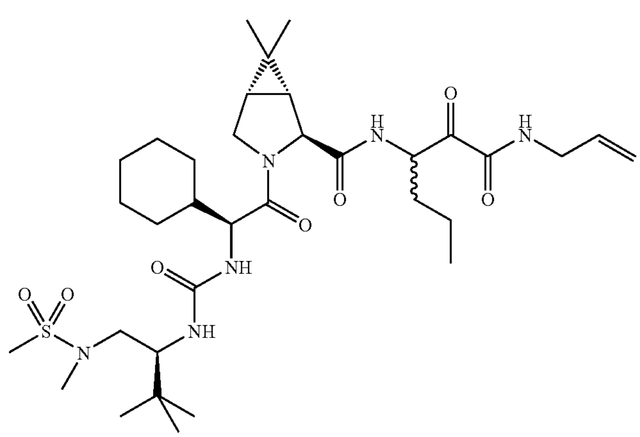 | A |

TABLE 2-continued
| Entry | Structure | Ki* |
|---|---|---|
| 11082 | 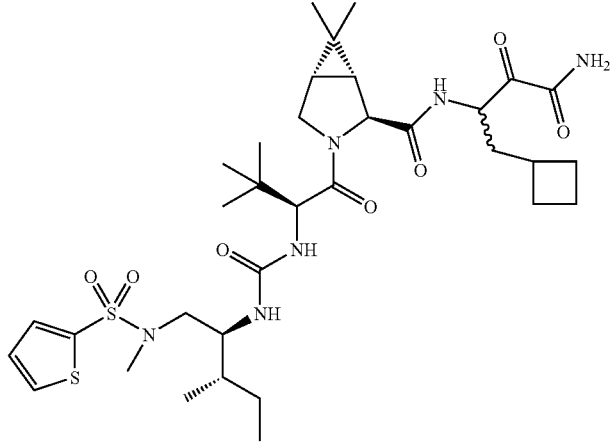 | A |
| 11083 | 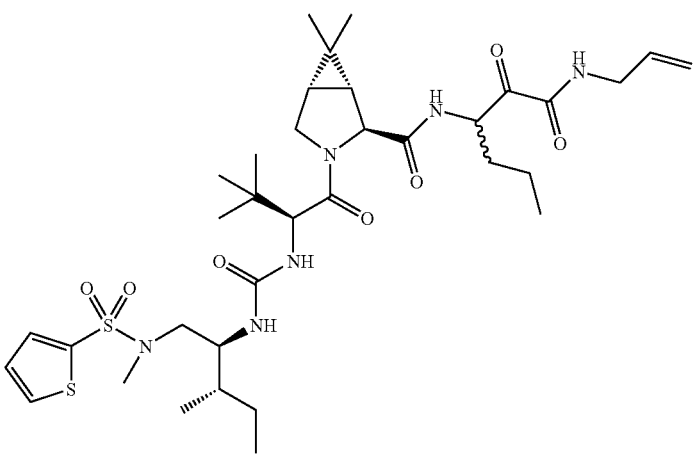 | A |
| 11084 | 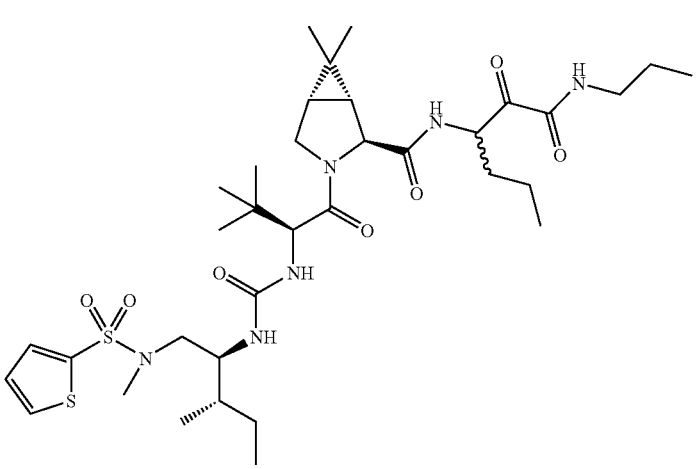 | C |

TABLE 2-continued
| Entry | Structure | Ki* |
|---|---|---|
| 11085 | 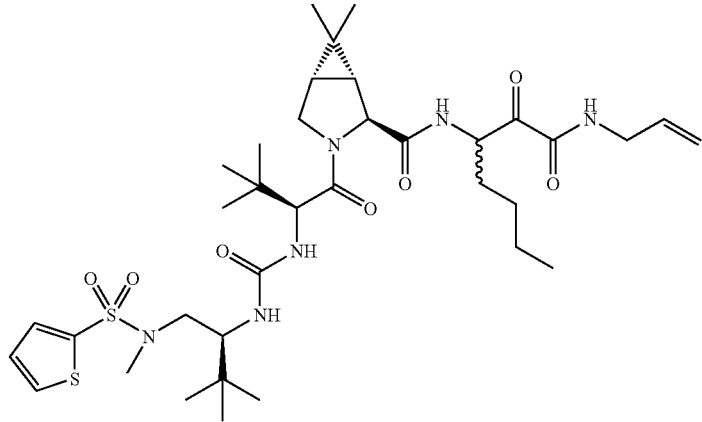 | A |
| 11086 | 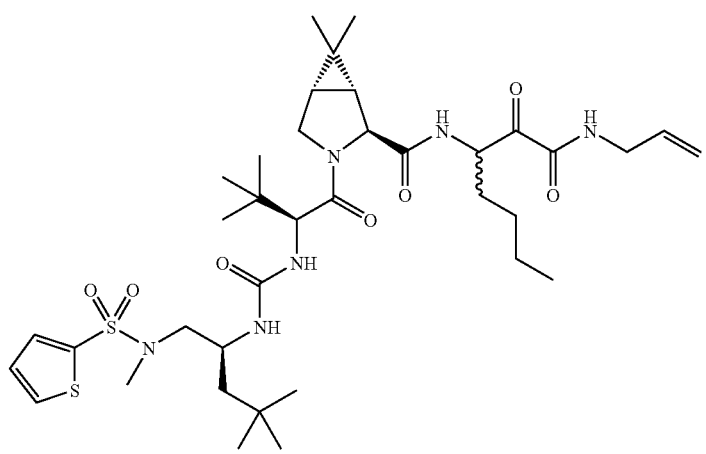 | B |
| 11087 | 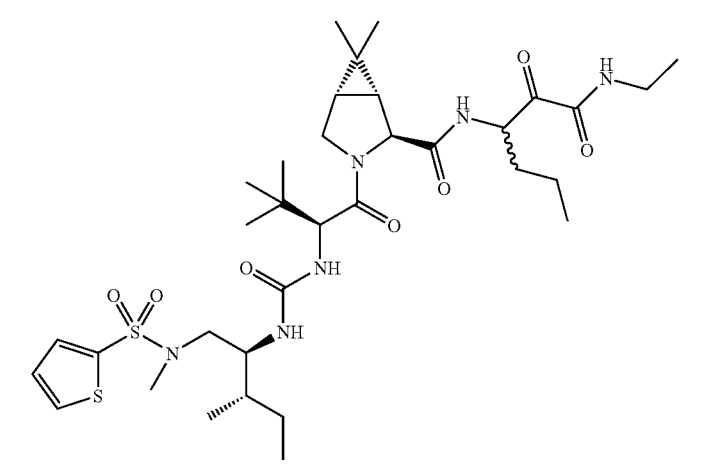 | B |

TABLE 2-continued

| Entry | Structure | Ki* |
|-------|-----------|-----|
| 11088 | 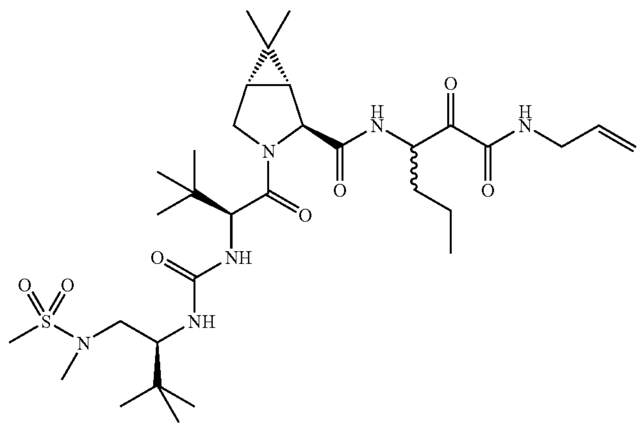 | A |
| 11089 | 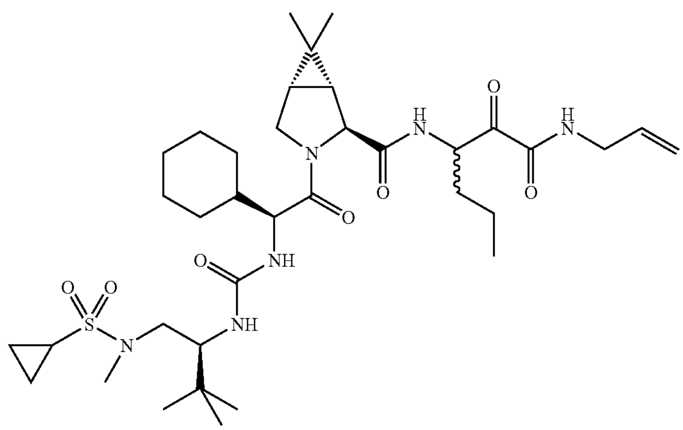 | A |
| 11090 | 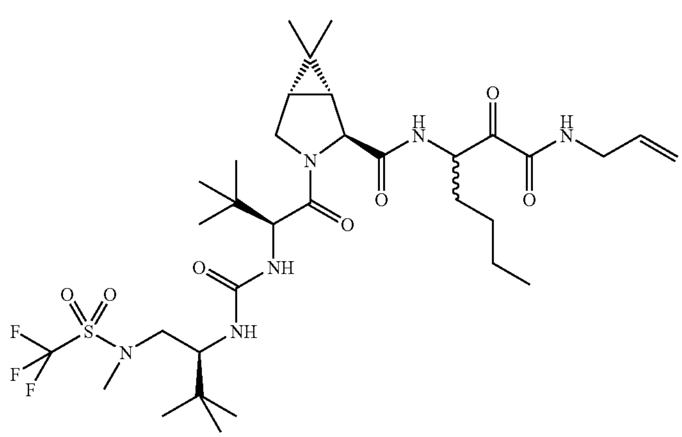 | A |

TABLE 2-continued

| Entry | Structure | Ki* |
|---|---|---|
| 11091 | 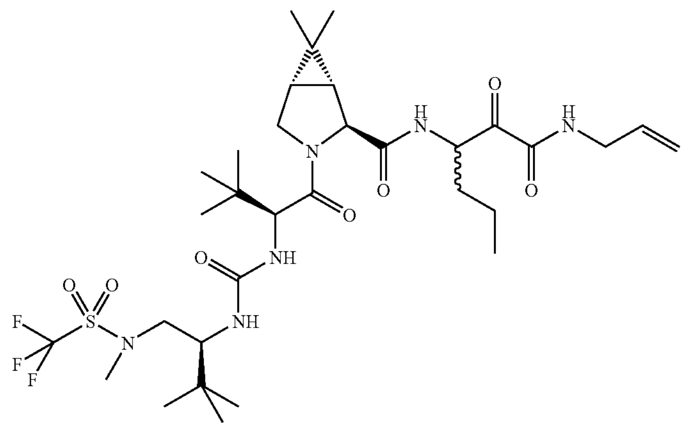 | A |
| 11092 | 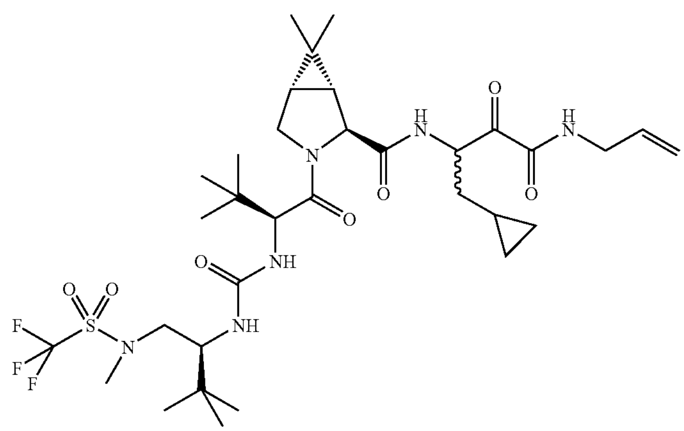 | A |
| 11093 | 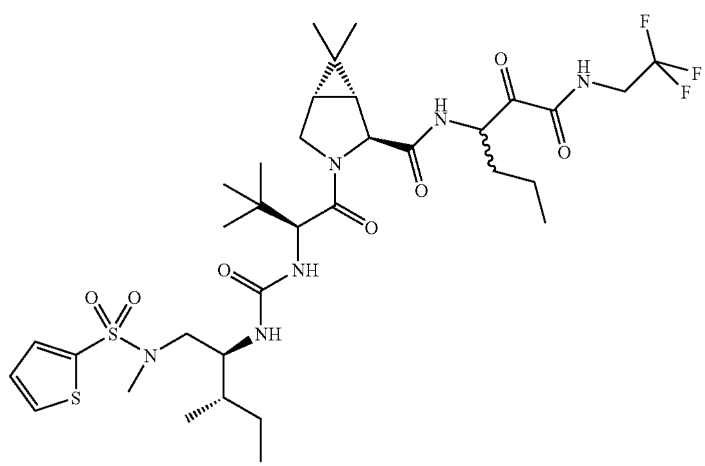 | C |

TABLE 2-continued
| Entry | Structure | Ki* |
|---|---|---|
| 11094 | 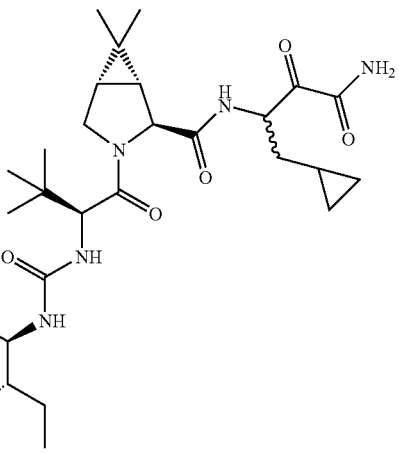 | A |
| 11095 | 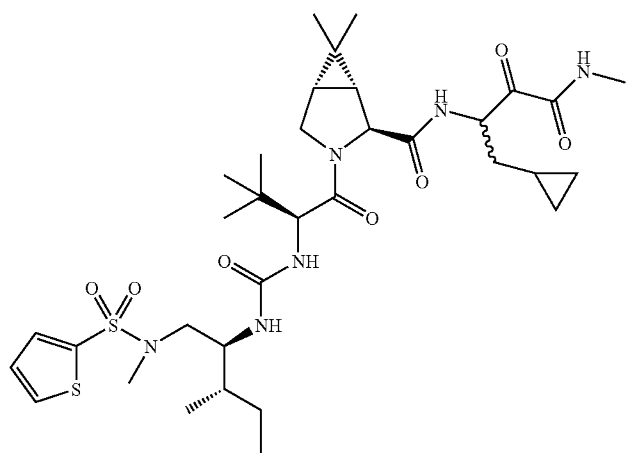 | B |
| 11096 | 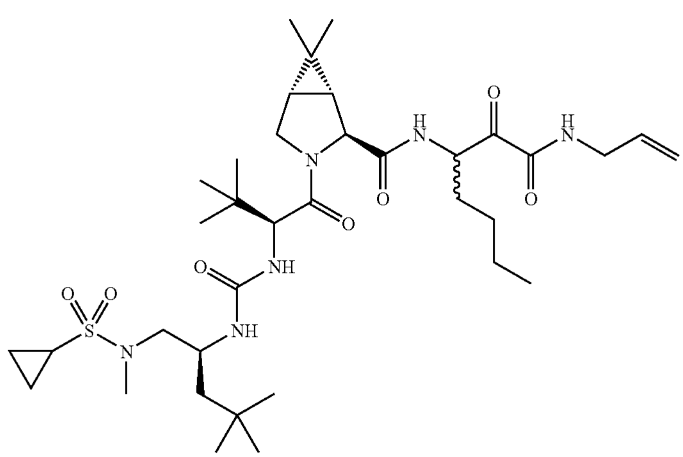 | B |

TABLE 2-continued

| Entry | Structure | Ki* |
|-------|-----------|-----|
| 11097 | 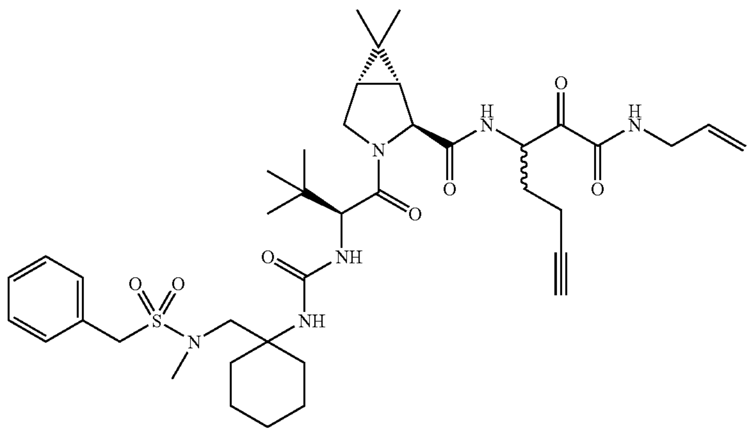 | A |
| 11098 | 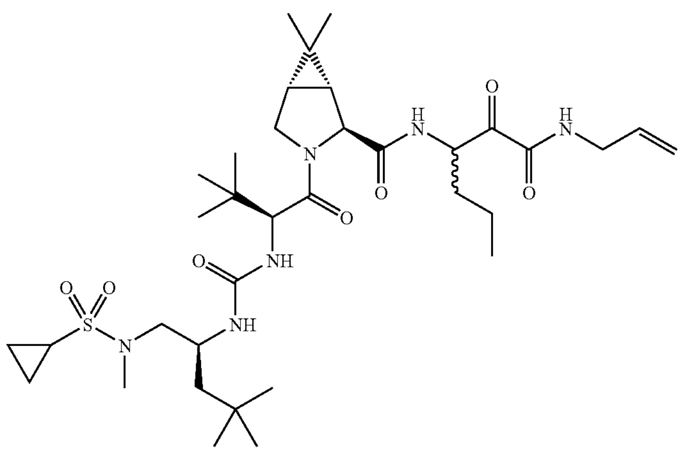 | B |
| 11099 | 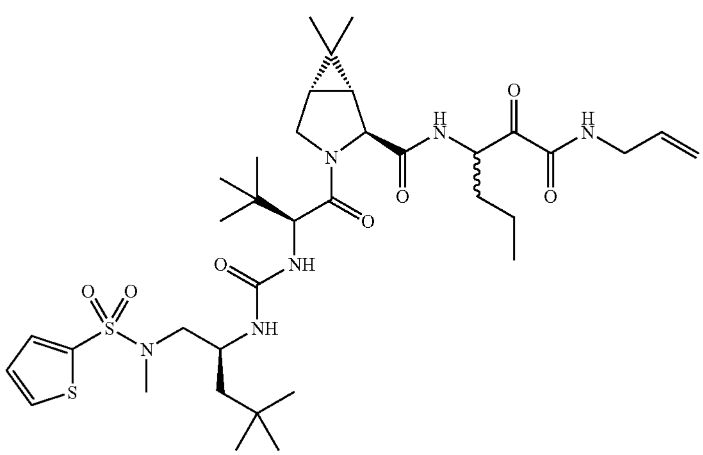 | B |

TABLE 2-continued

| Entry | Structure | Ki* |
|---|---|---|
| 11100 | 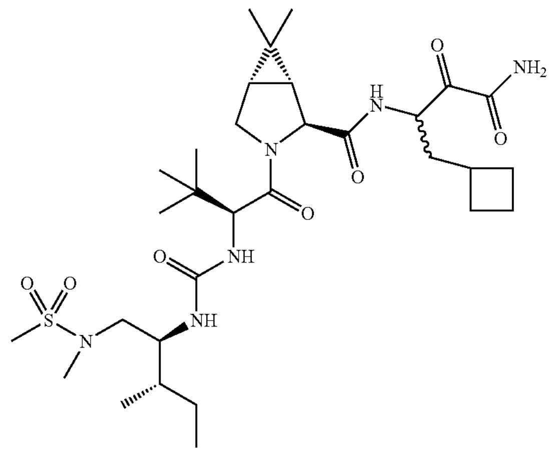 | A |
| 11101 | 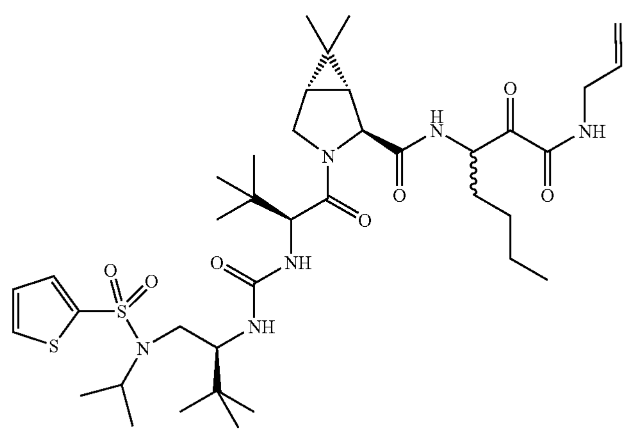 | A |
| 11102 | 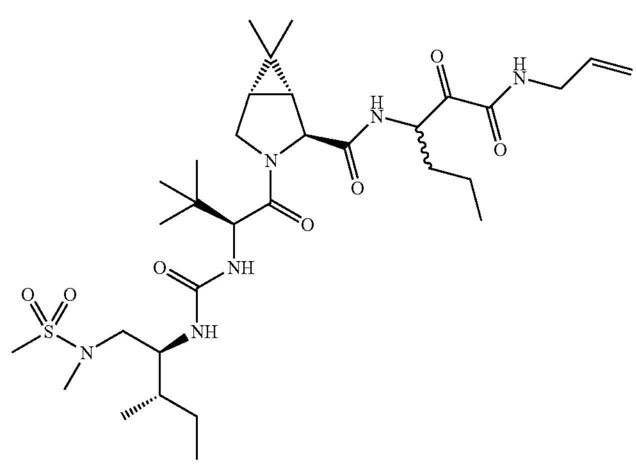 | A |

TABLE 2-continued
| Entry | Structure | Ki* |
|---|---|---|
| 11103 | 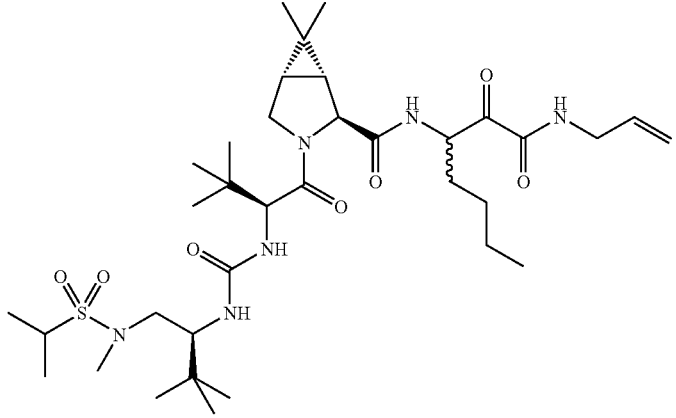 | A |
| 11104 | 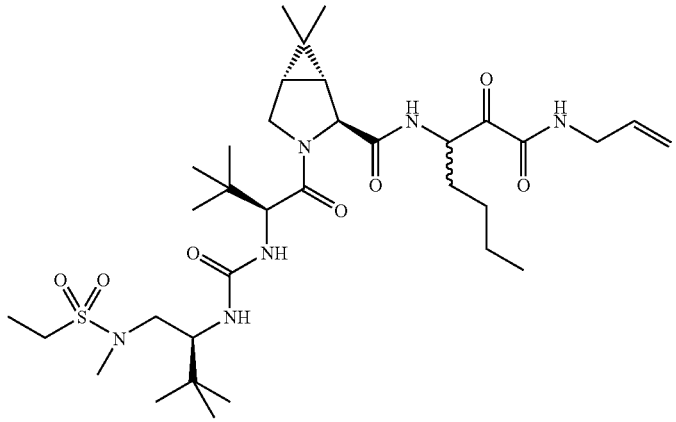 | A |
| 11105 | 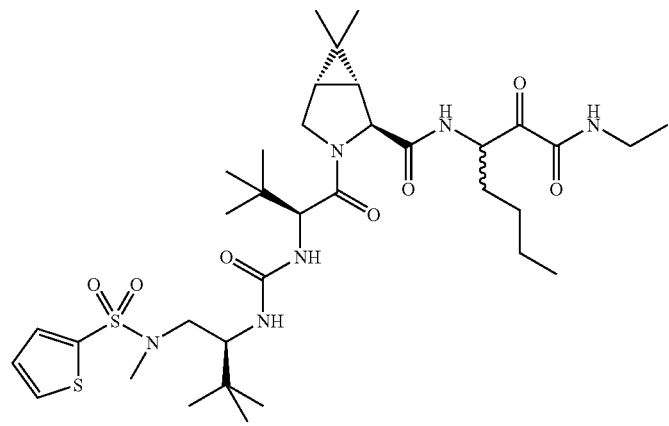 | A |

TABLE 2-continued
| Entry | Structure | Ki* |
|---|---|---|
| 11106 | 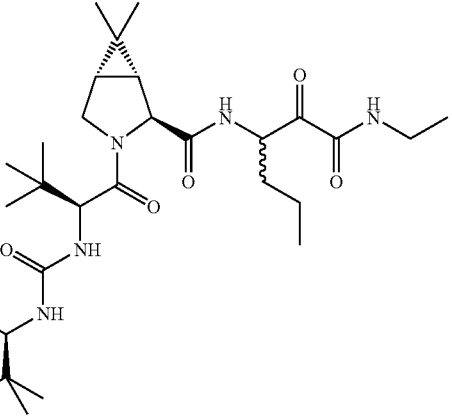 | A |
| 11107 | 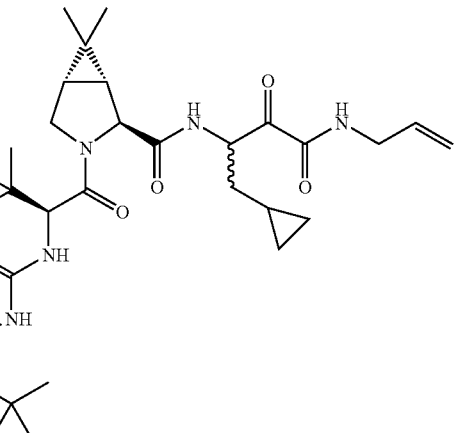 | B |
| 11108 | 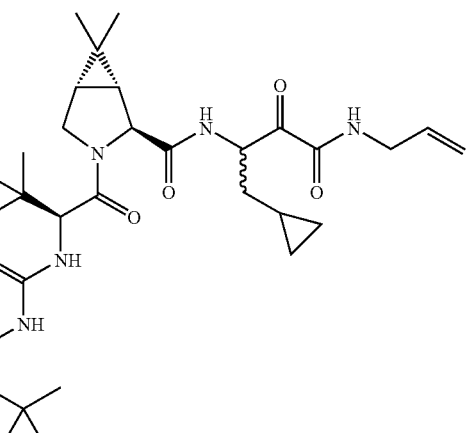 | A |

TABLE 2-continued

| Entry | Structure | Ki* |
|---|---|---|
| 11109 | 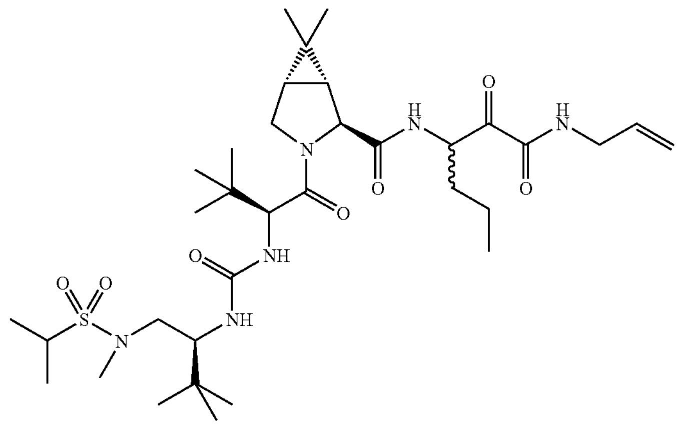 | A |
| 11110 | 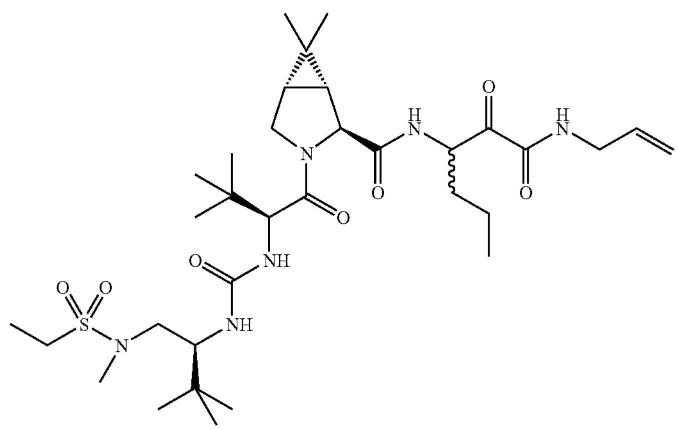 | A |
| 11111 | 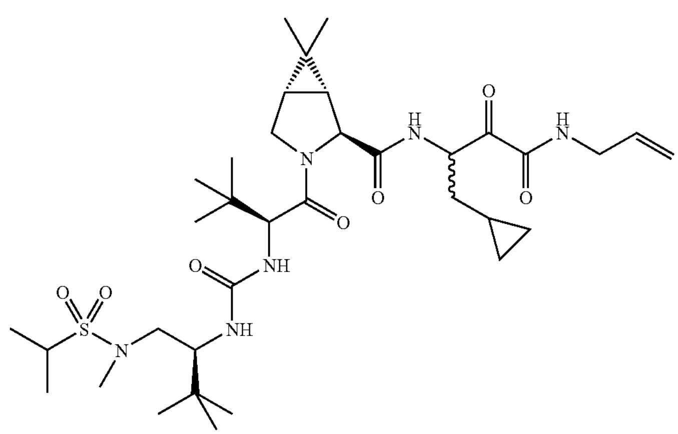 | A |

TABLE 2-continued
| Entry | Structure | Ki* |
|---|---|---|
| 11112 | 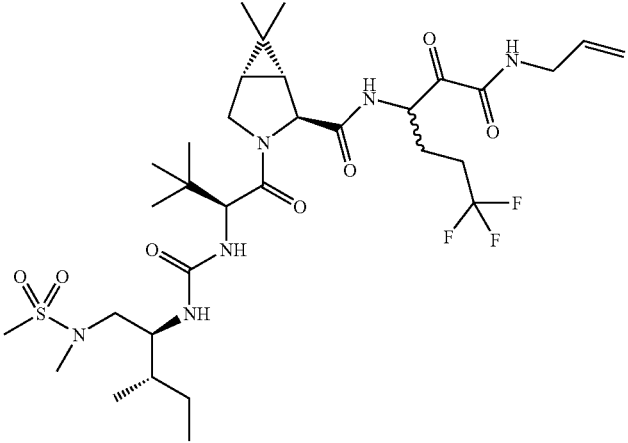 | A |
| 11113 | 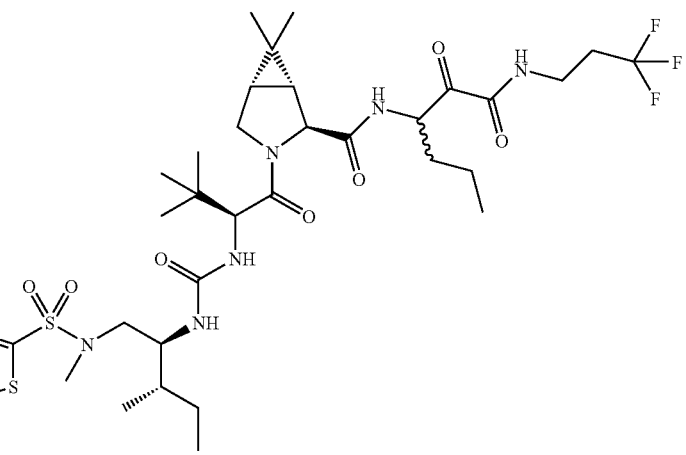 | B |
| 11114 | 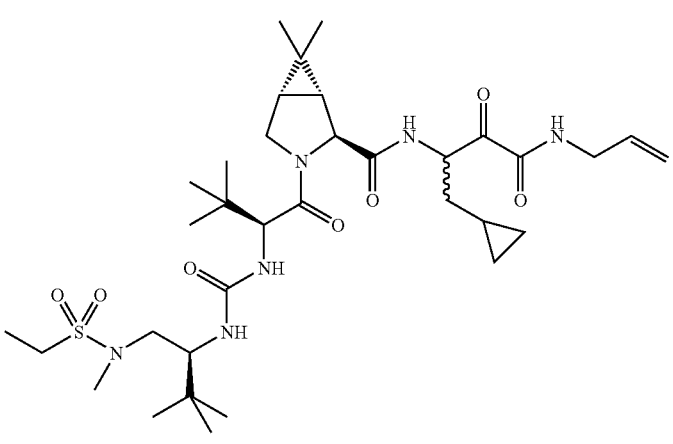 | A |

TABLE 2-continued

| Entry | Structure | Ki* |
|---|---|---|
| 11115 | 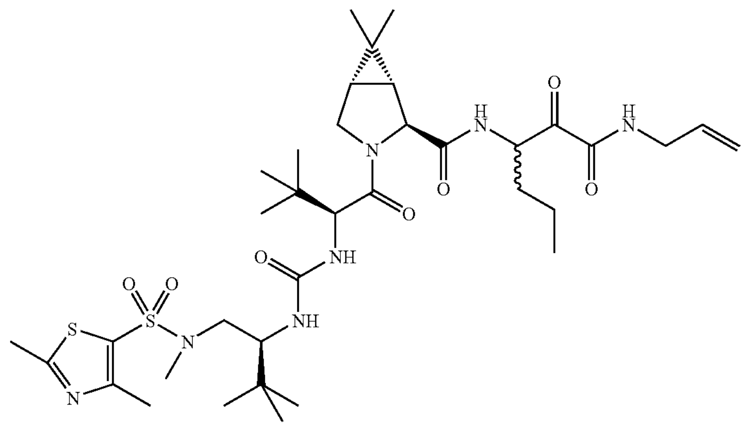 | A |
| 11116 | 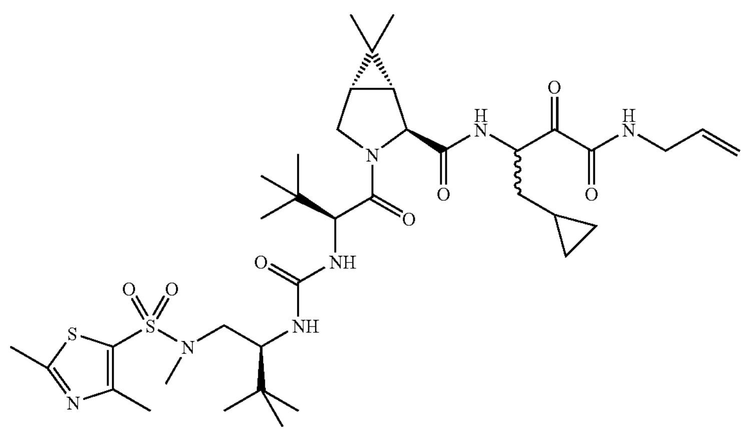 | A |
| 11117 | 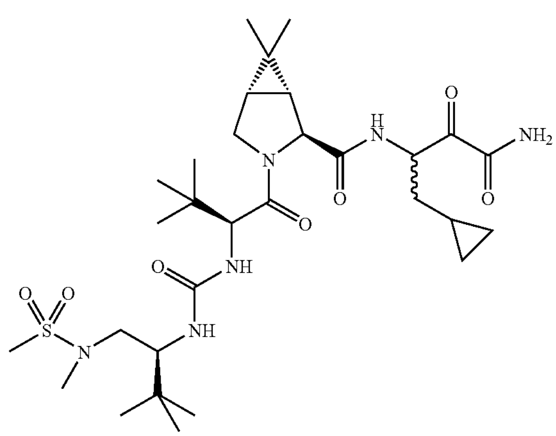 | A |

TABLE 2-continued
| Entry | Structure | Ki* |
|---|---|---|
| 11118 | 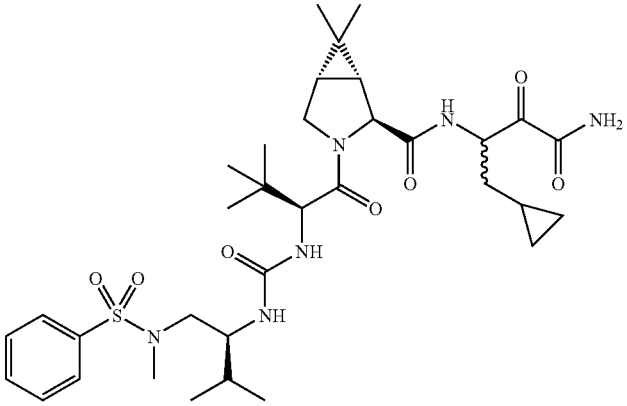 | A |
| 11119 | 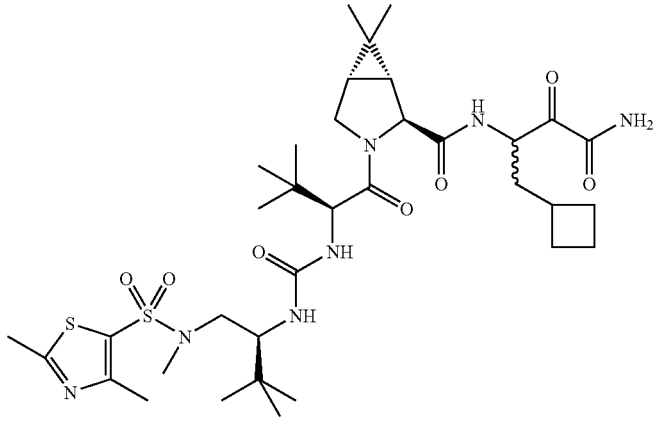 | A |
| 11120 | 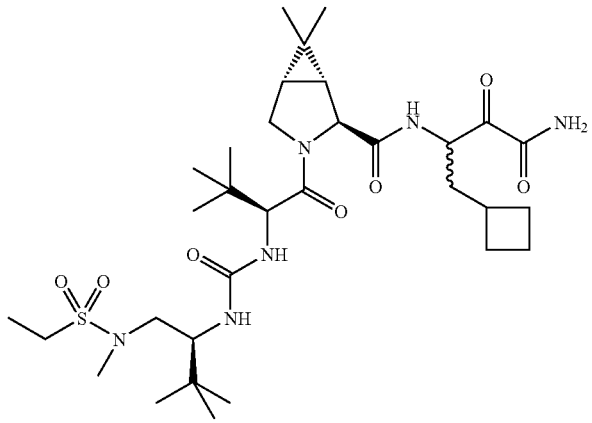 | A |

TABLE 2-continued
| Entry | Structure | Ki* |
|---|---|---|
| 11121 | 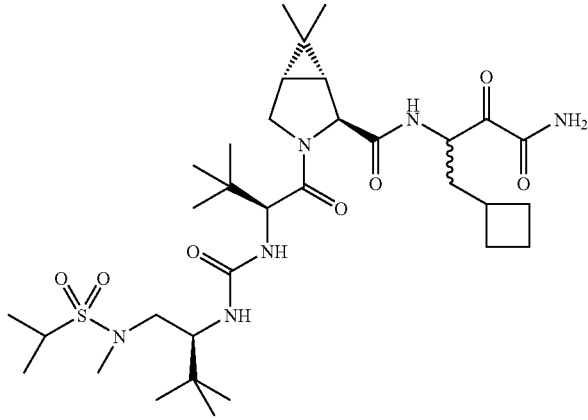 | A |
| 11122 | 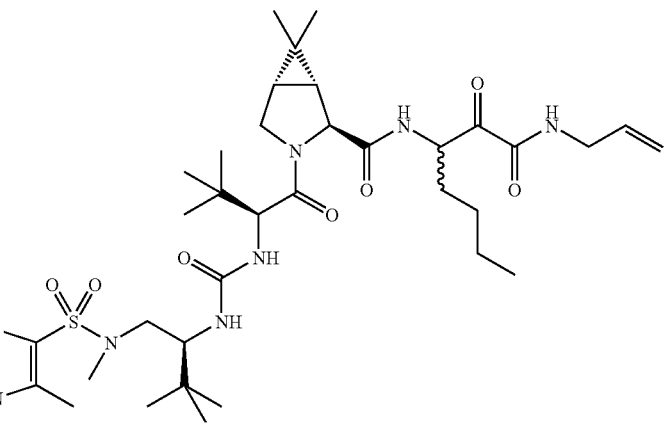 | A |
| 11123 | 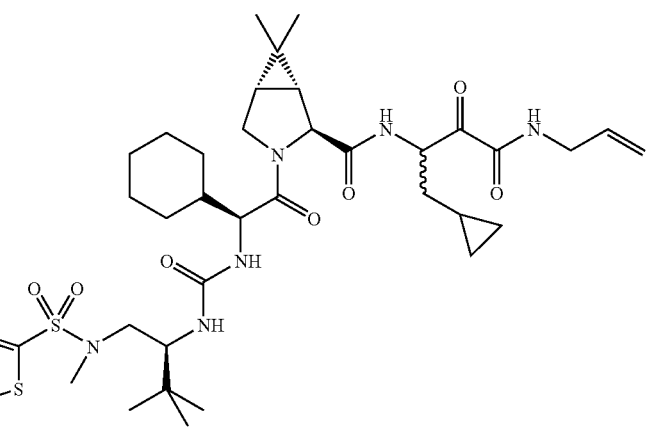 | A |

TABLE 2-continued

| Entry | Structure | Ki* |
|---|---|---|
| 11124 | 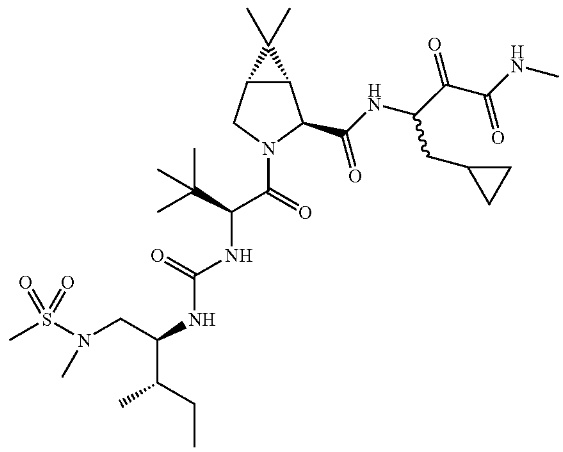 | A |
| 11125 | 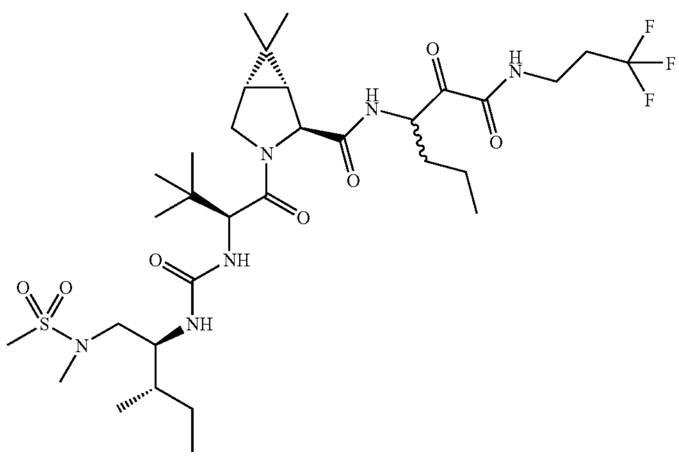 | A |
| 11126 | 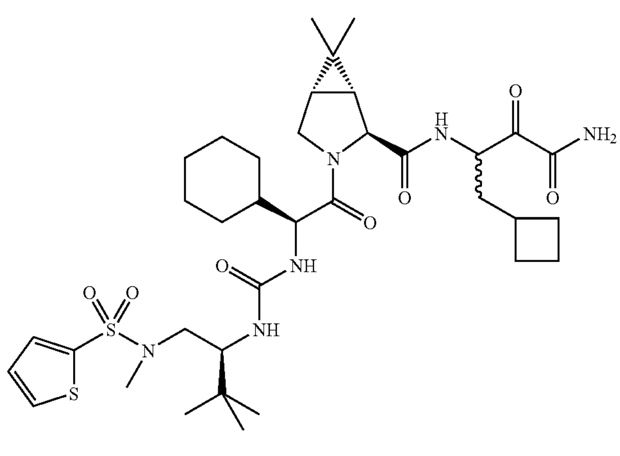 | A |

TABLE 2-continued

| Entry | Structure | Ki* |
|---|---|---|
| 11127 | 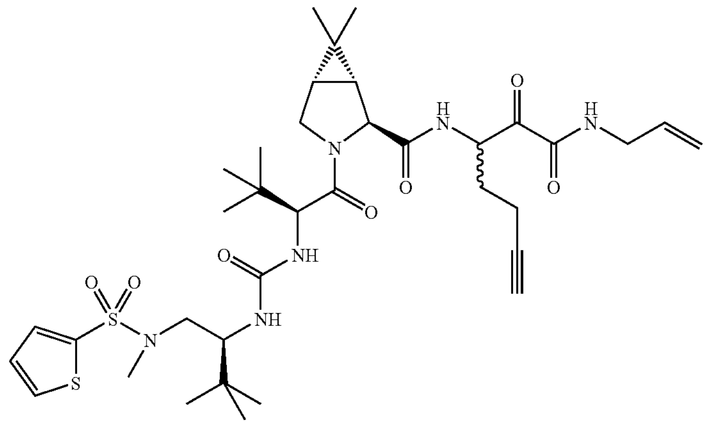 | A |
| 11128 | 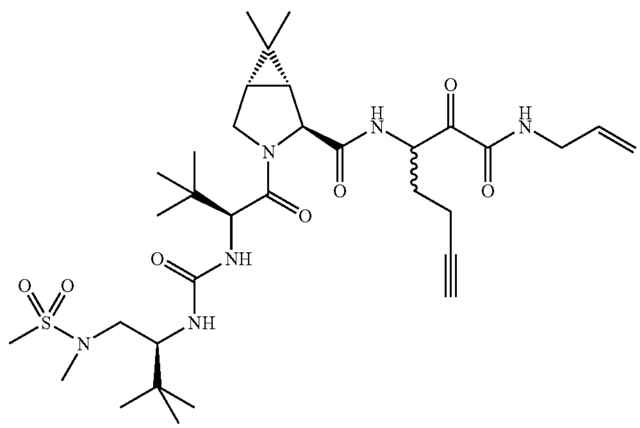 | A |
| 11129 | 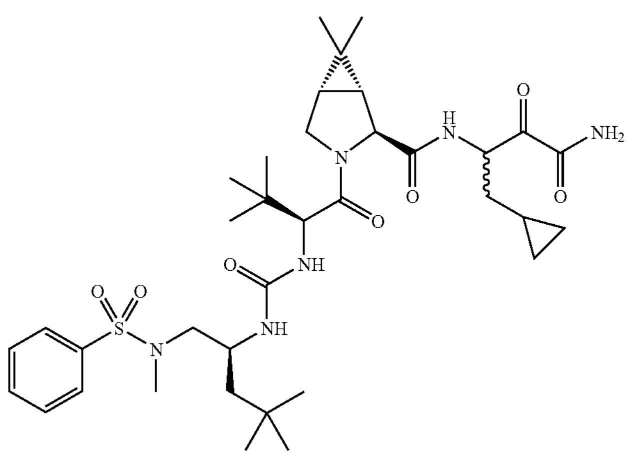 | A |

TABLE 2-continued

| Entry | Structure | Ki* |
|-------|-----------|-----|
| 11130 | 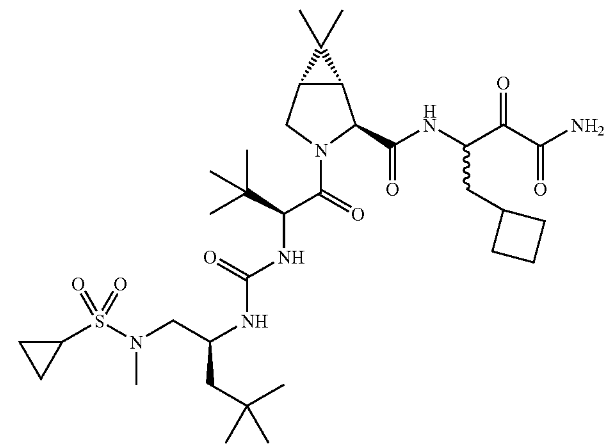 | A |
| 11131 | 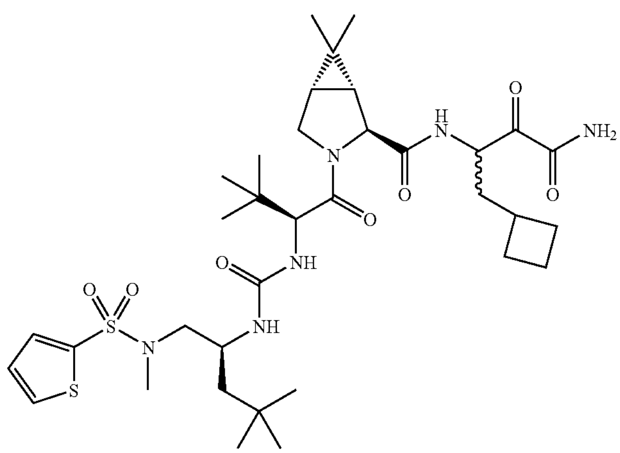 | A |
| 11132 | 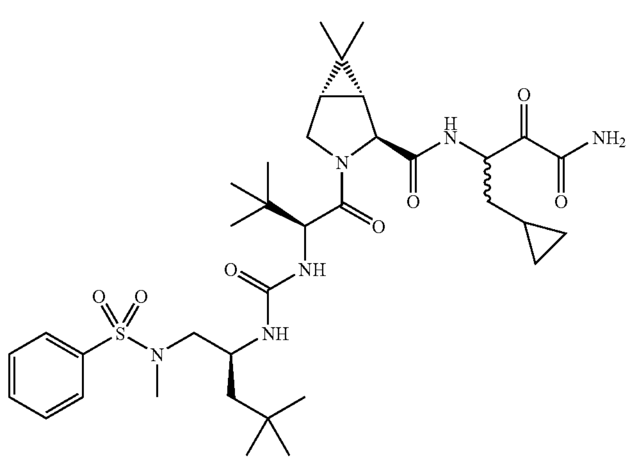 | B |

TABLE 2-continued

| Entry | Structure | Ki* |
|---|---|---|
| 11133 | 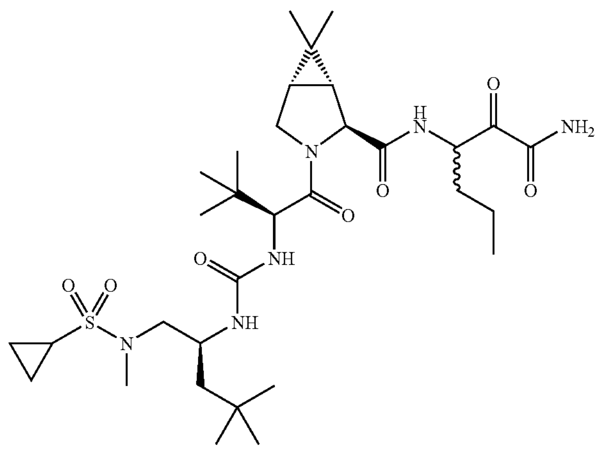 | A |
| 11134 | 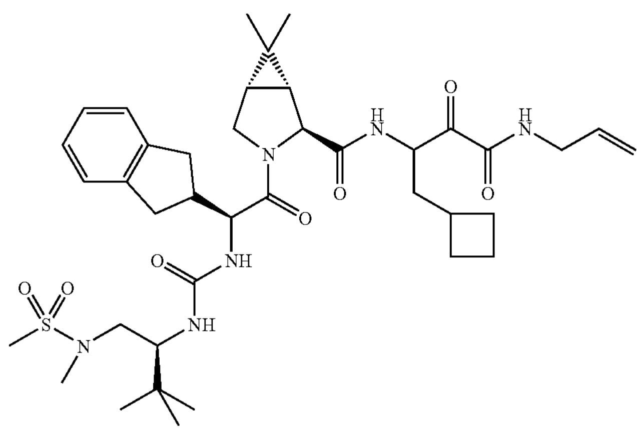 | A |
| 11135 | 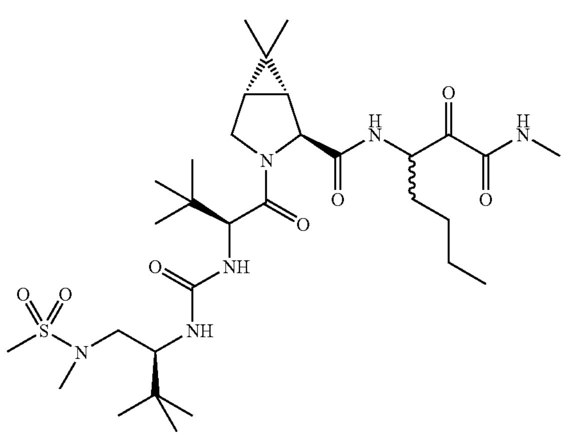 | A |

TABLE 2-continued
| Entry | Structure | Ki* |
|---|---|---|
| 11136 | 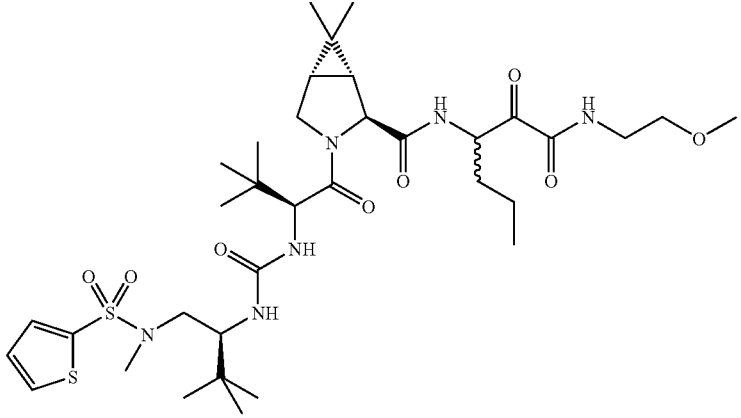 | B |
| 11137 | 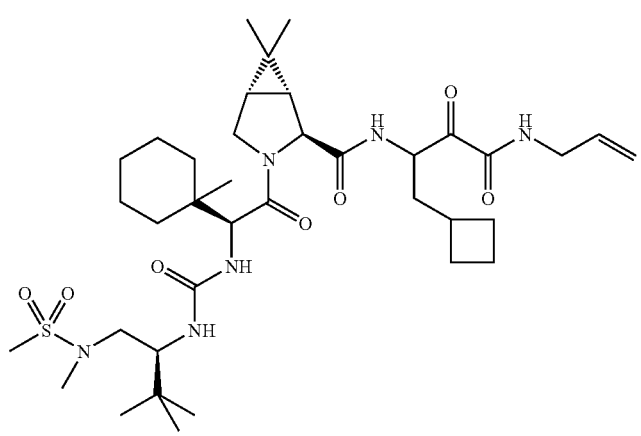 | A |
| 11138 | 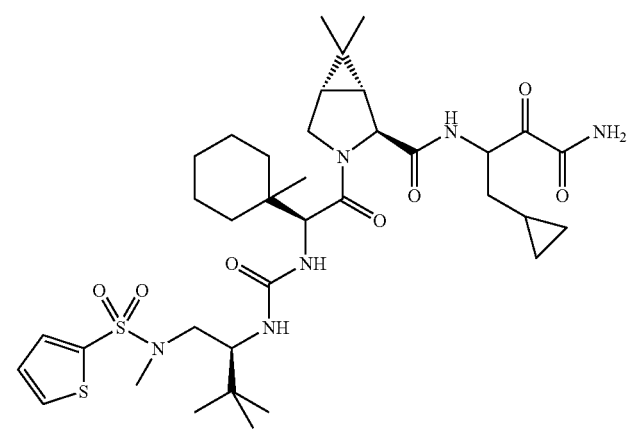 | A |

TABLE 2-continued

| Entry | Structure | Ki* |
|---|---|---|
| 11139 | 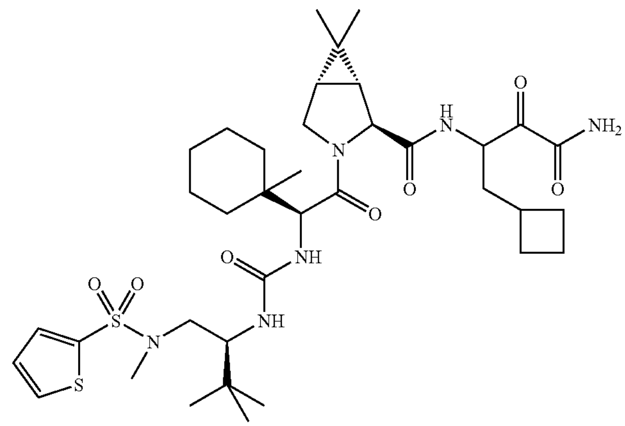 | A |
| 11140 | 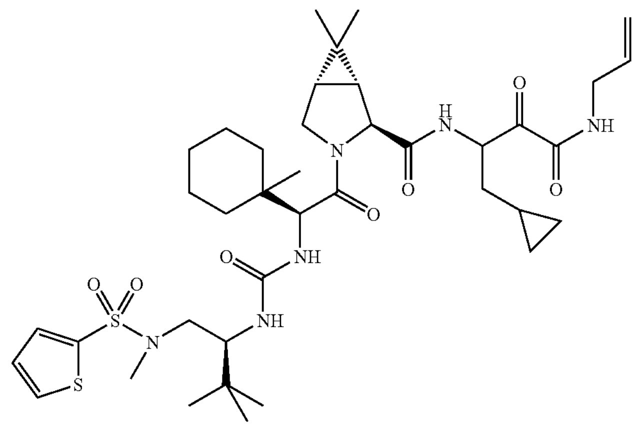 | A |
| 11141 | 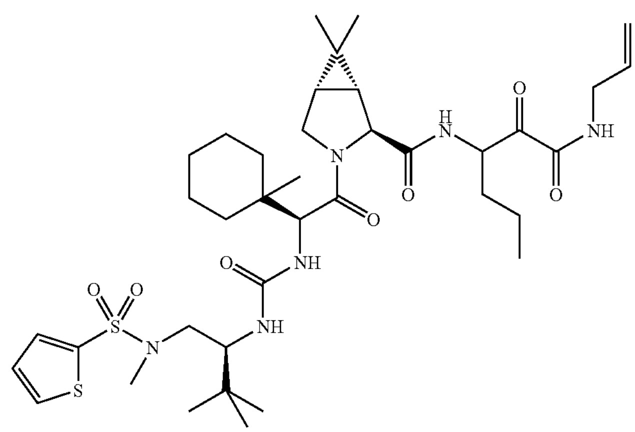 | A |

TABLE 2-continued
| Entry | Structure | Ki* |
|---|---|---|
| 11142 | 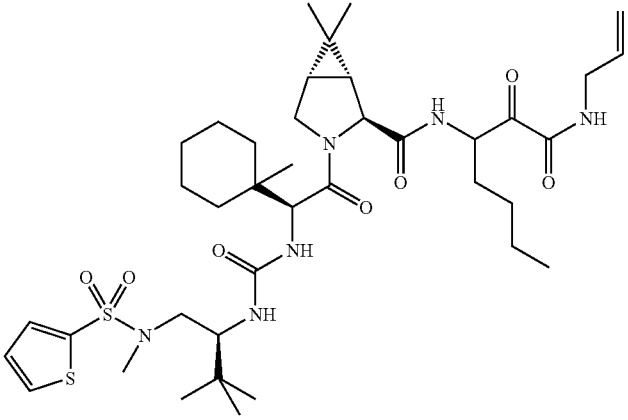 | A |
| 11143 | 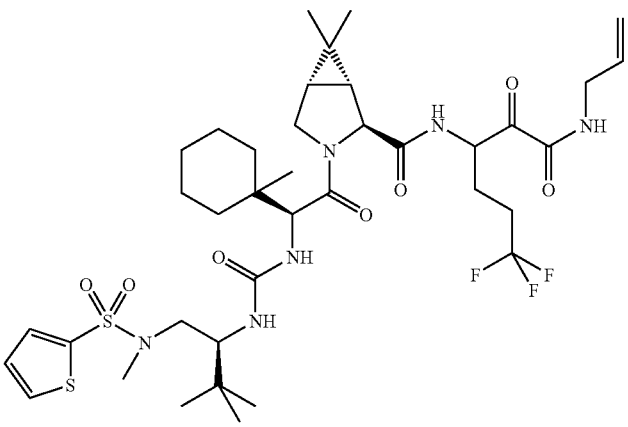 | A |
| 11144 | 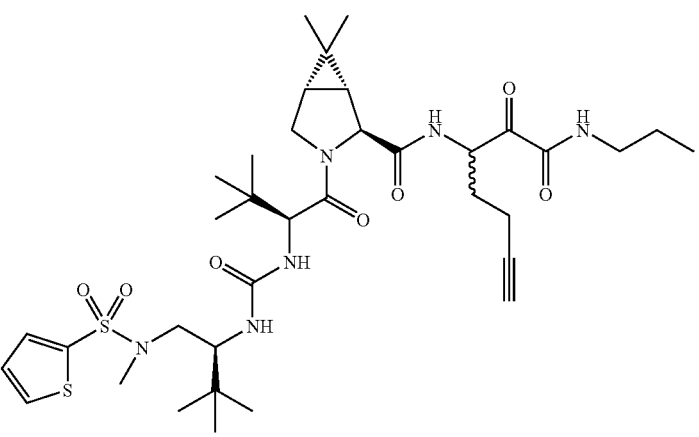 | A |

TABLE 2-continued

| Entry | Structure | Ki* |
|---|---|---|
| 11145 | 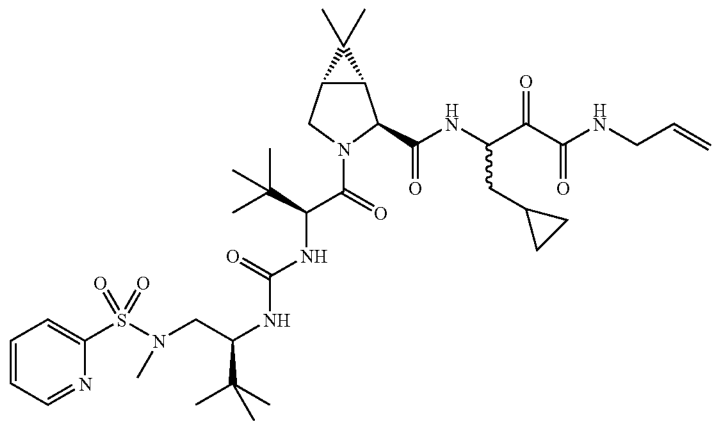 | A |
| 11146 | 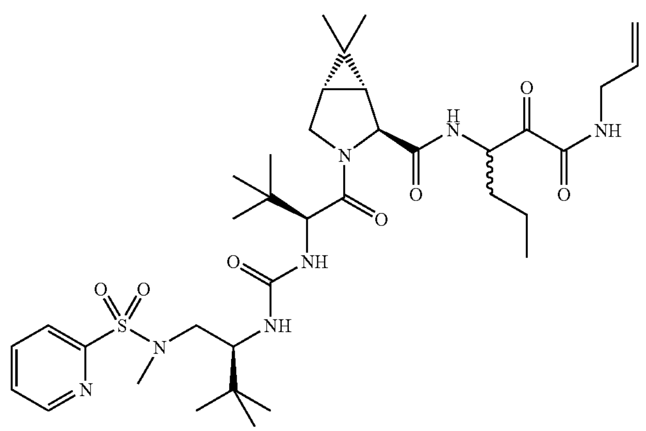 | A |
| 11147 | 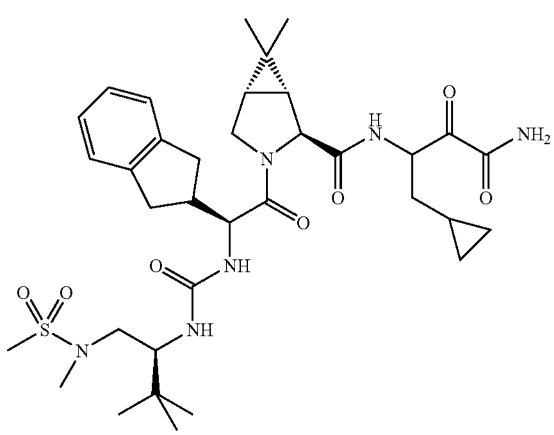 | A |

TABLE 2-continued
| Entry | Structure | Ki* |
|---|---|---|
| 11148 | 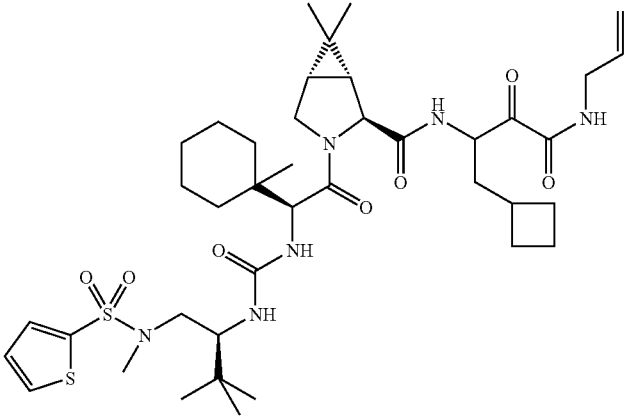 | A |
| 11149 | 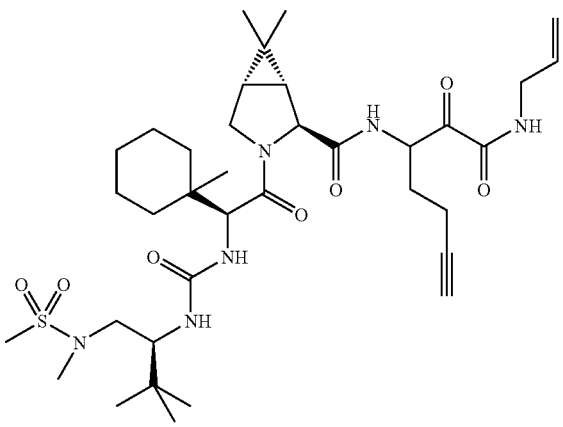 | A |
| 11150 | 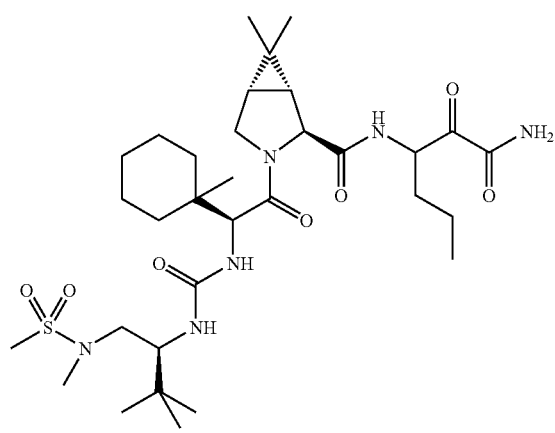 | A |

TABLE 2-continued

| Entry | Structure | Ki* |
|---|---|---|
| 11151 | 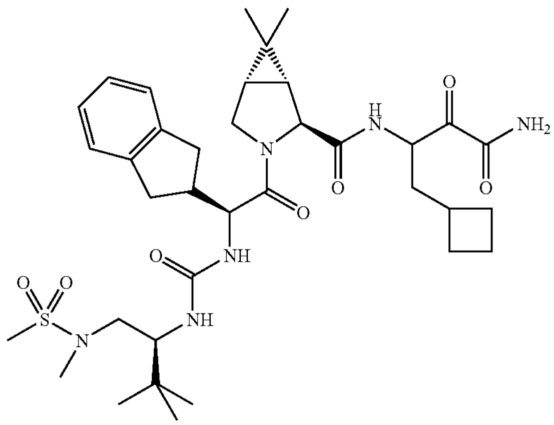 | A |
| 11152 | 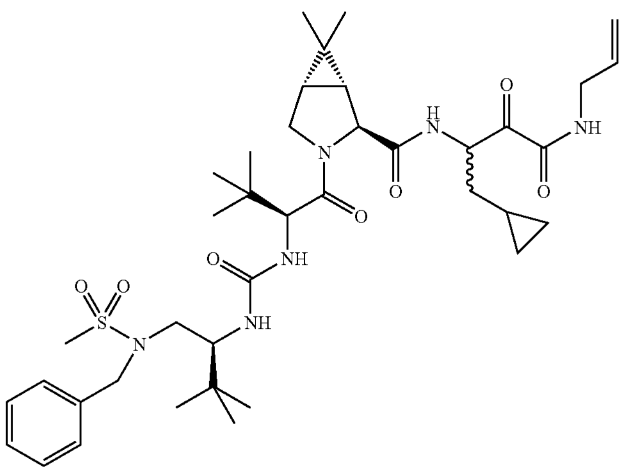 | A |
| 11153 | 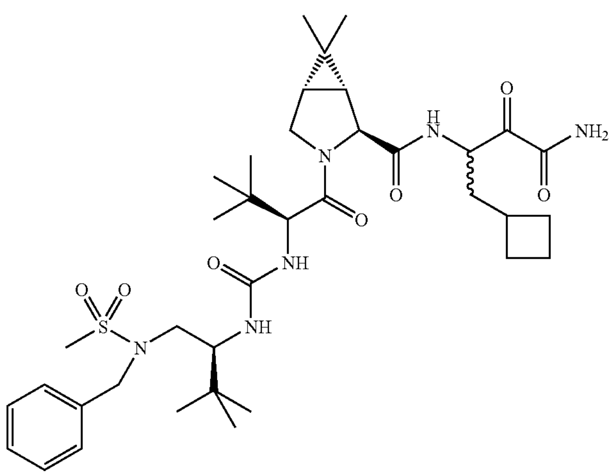 | A |

TABLE 2-continued

| Entry | Structure | Ki* |
|---|---|---|
| 11154 | 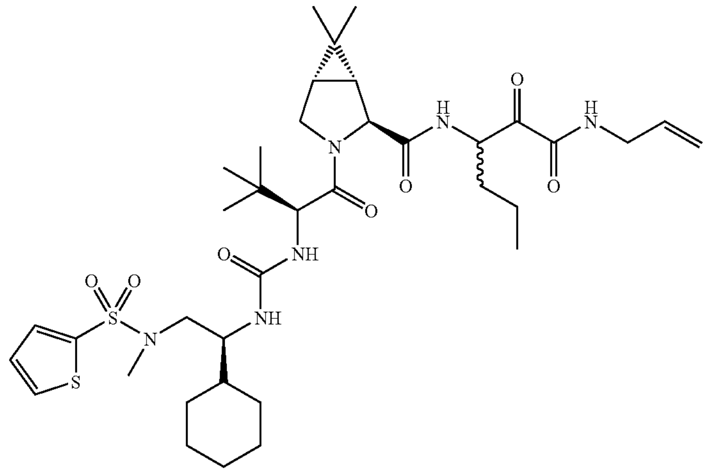 | A |
| 11155 | 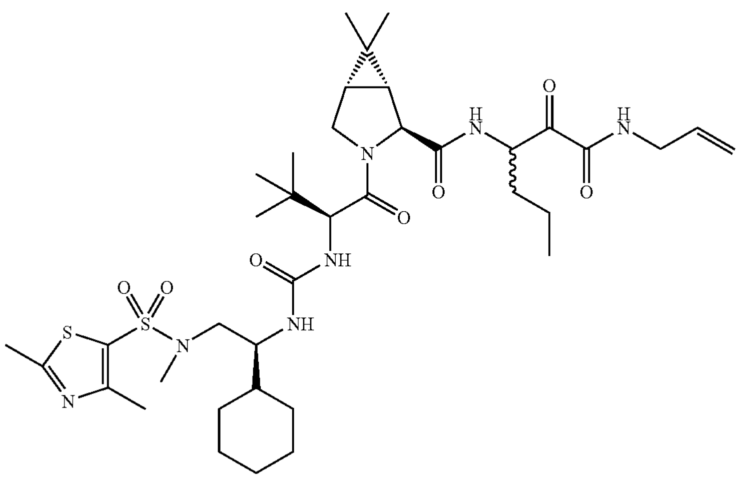 | A |
| 11156 | 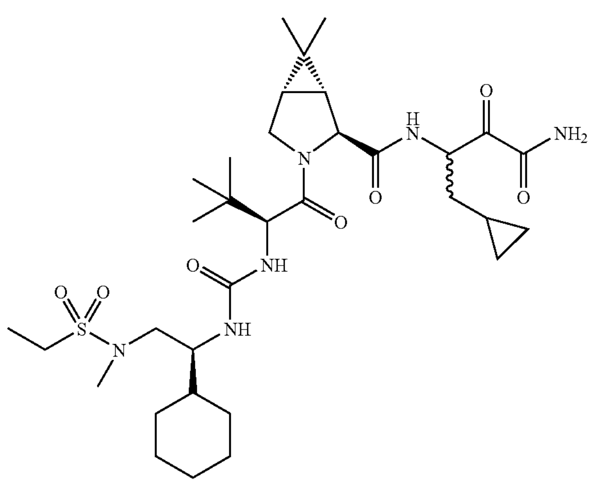 | A |

TABLE 2-continued

| Entry | Structure | Ki* |
|-------|-----------|-----|
| 11157 | 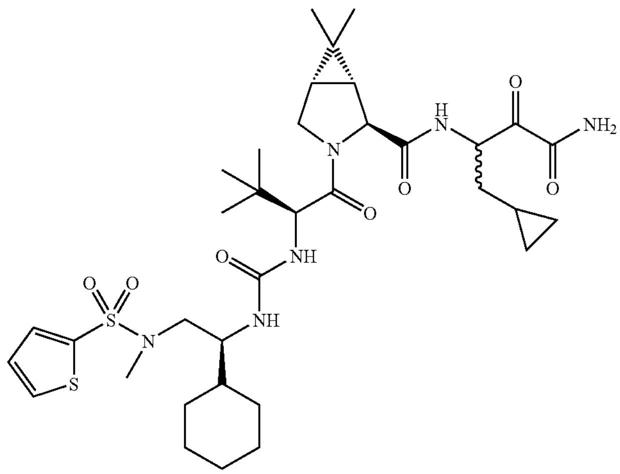 | A |
| 11158 | 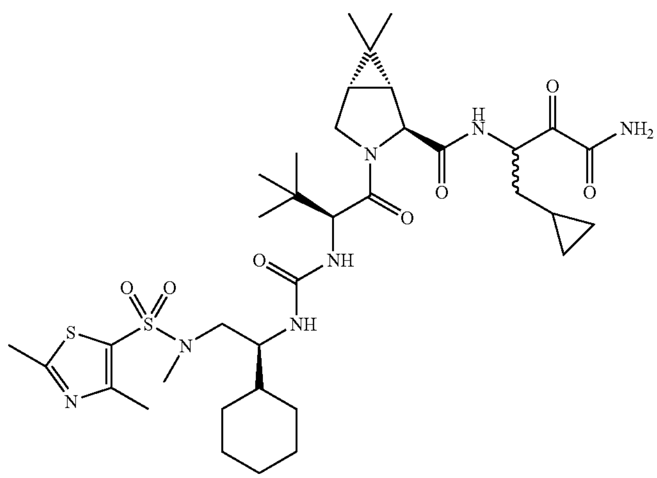 | A |
| 11159 | 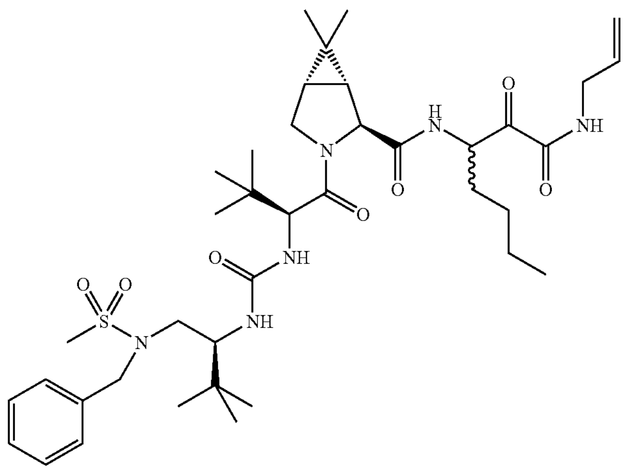 | A |

TABLE 2-continued

| Entry | Structure | Ki* |
|-------|-----------|-----|
| 11160 | 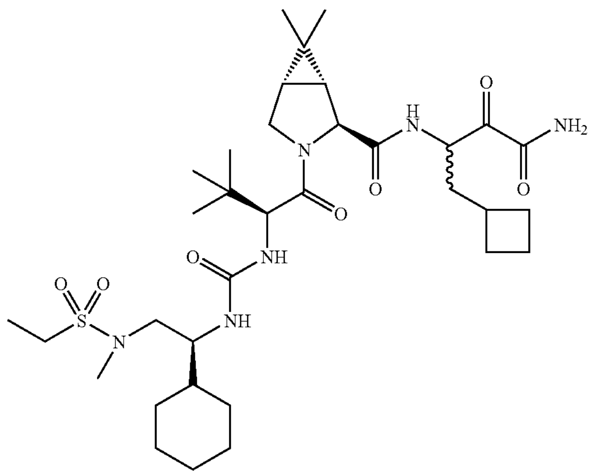 | A |
| 11161 | 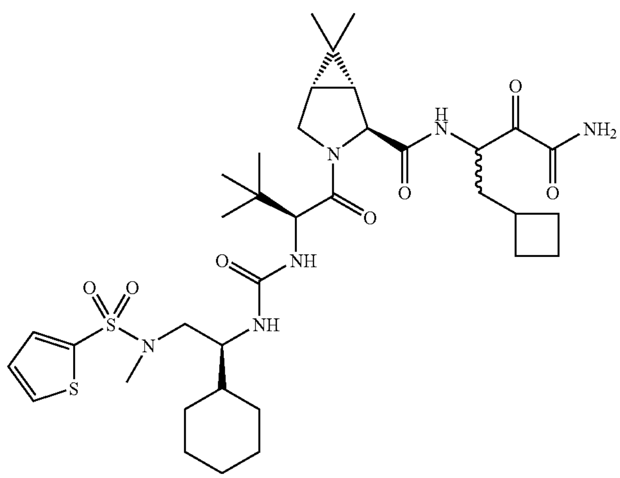 | A |
| 11162 | 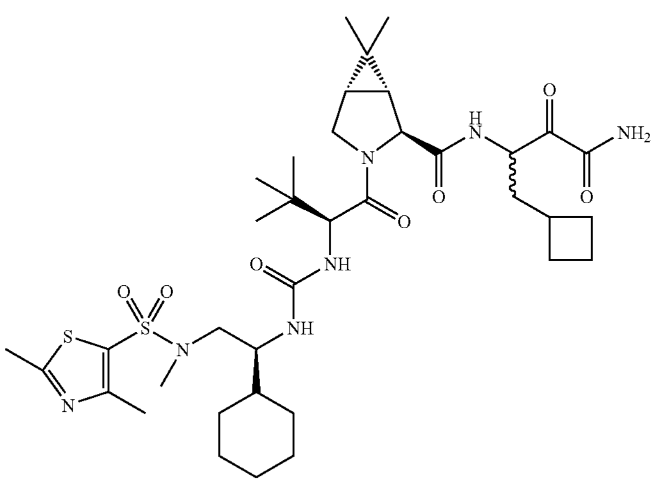 | A |

TABLE 2-continued
| Entry | Structure | Ki* |
|---|---|---|
| 11163 | 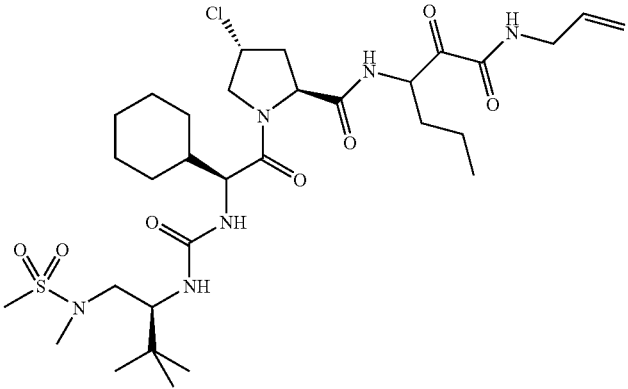 | A |
| 11164 | 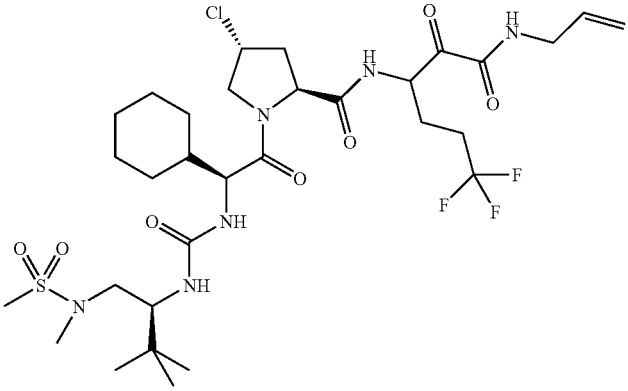 | A |
| 11165 | 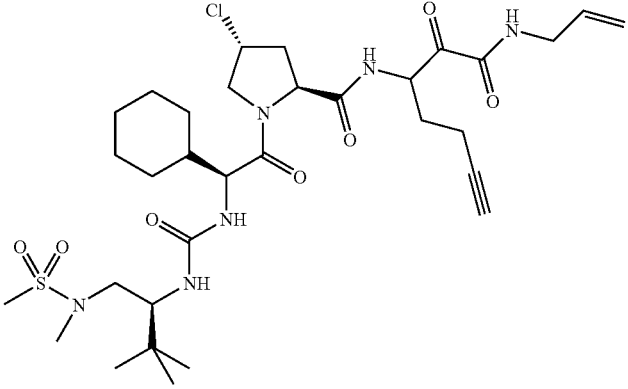 | A |
| 11166 | 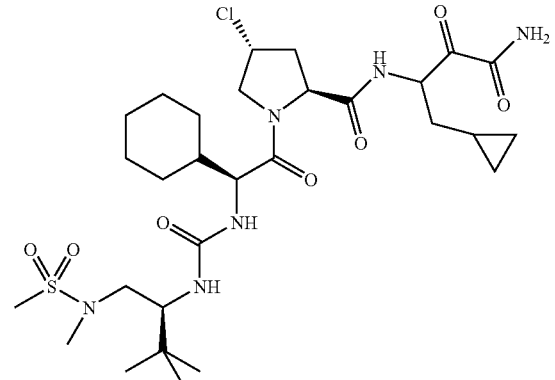 | A |

TABLE 2-continued

| Entry | Structure | Ki* |
|---|---|---|
| 11167 | 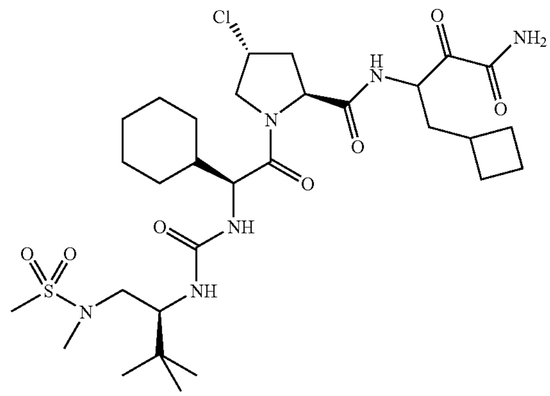 | A |
| 11168 | 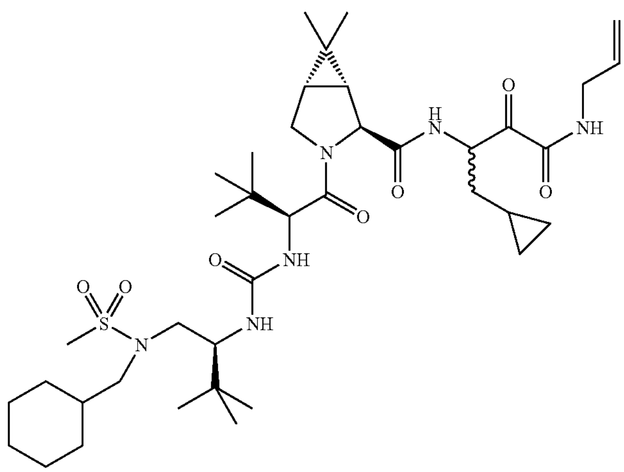 | A |
| 11169 | 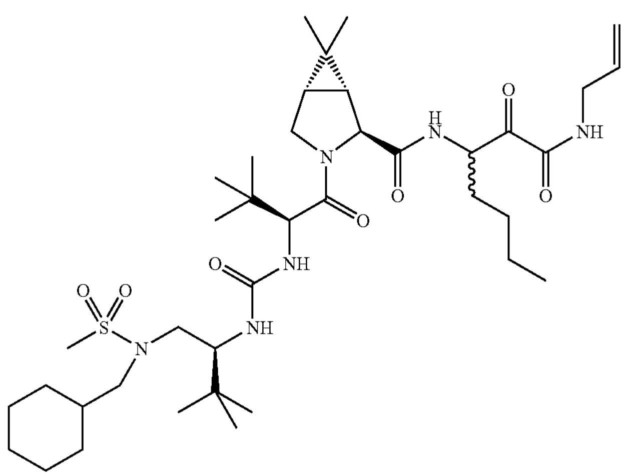 | A |

TABLE 2-continued
| Entry | Structure | Ki* |
|---|---|---|
| 11170 | 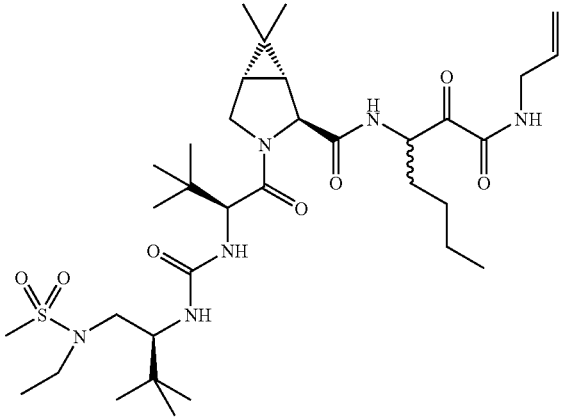 | A |
| 11171 | 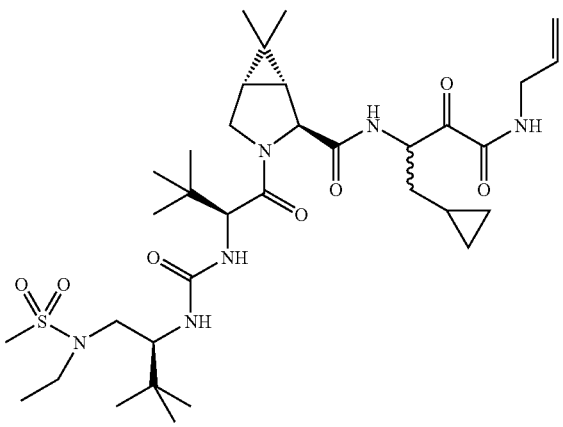 | A |
| 11172 | 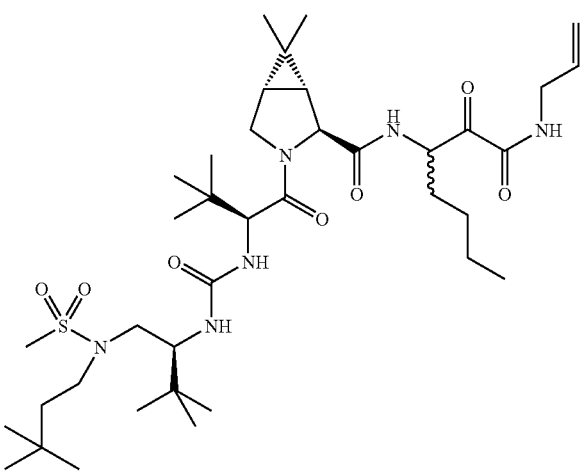 | A |

TABLE 2-continued
| Entry | Structure | Ki* |
|-------|-----------|-----|
| 11173 | 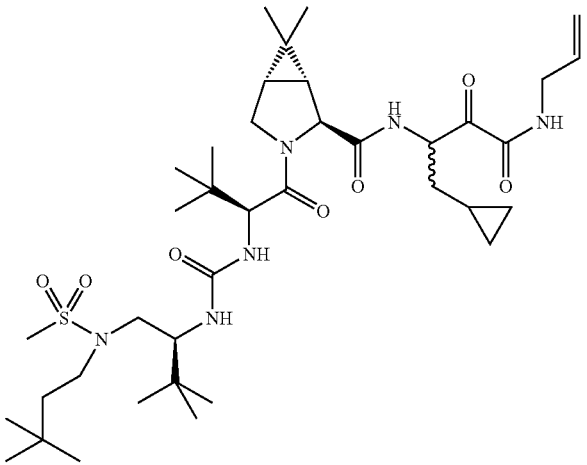 | A |
| 11174 | 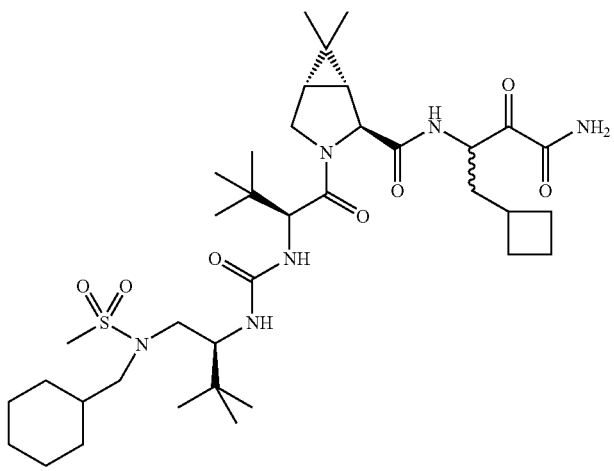 | A |
| 11175 | 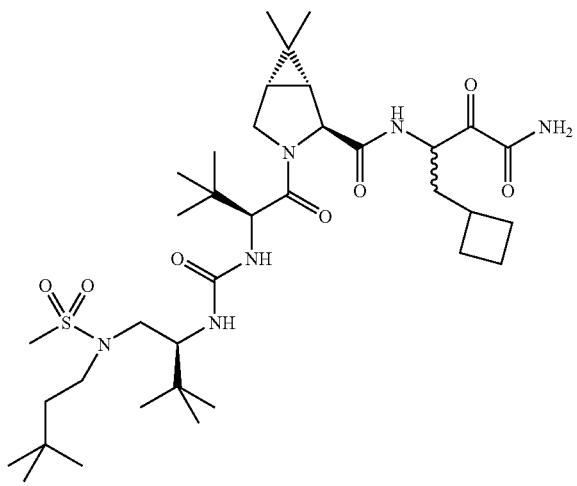 | A |

TABLE 2-continued

| Entry | Structure | Ki* |
|---|---|---|
| 11176 | 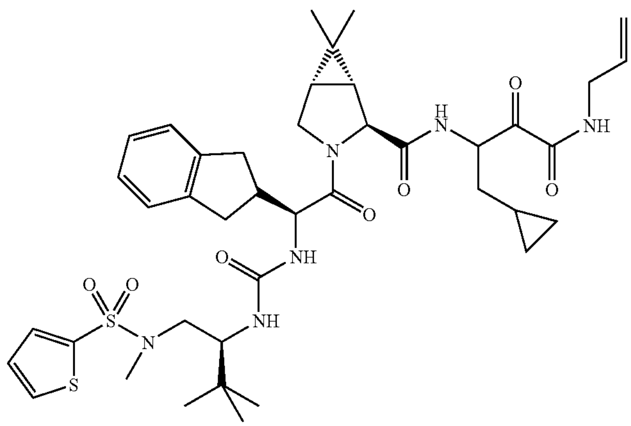 | A |
| 11177 | 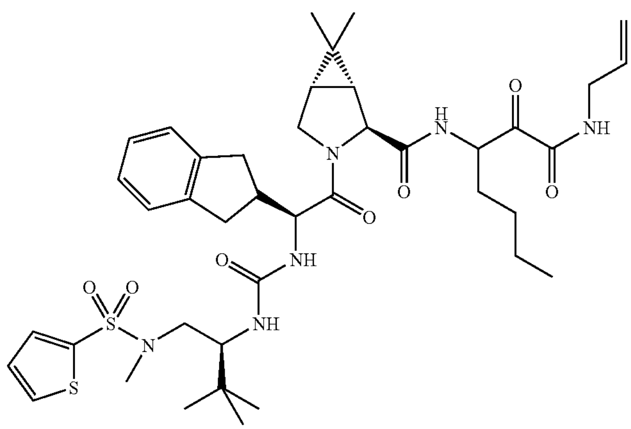 | A |
| 11178 | 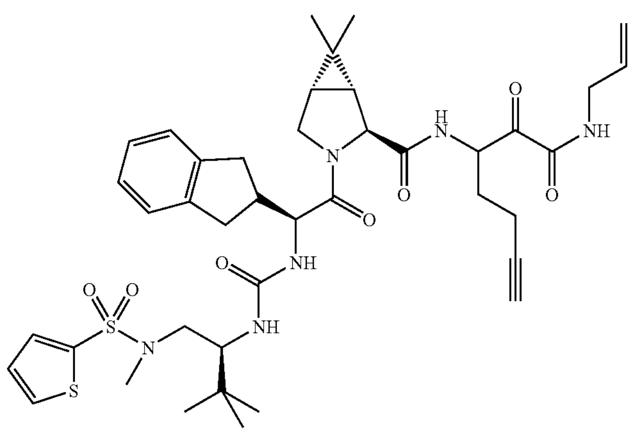 | A |

TABLE 2-continued

| Entry | Structure | Ki* |
|---|---|---|
| 11179 | 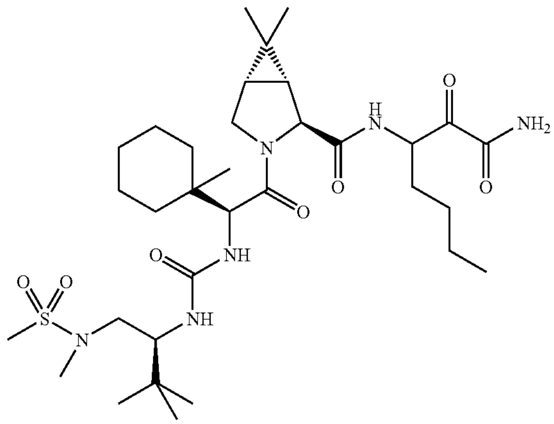 | A |
| 11180 | 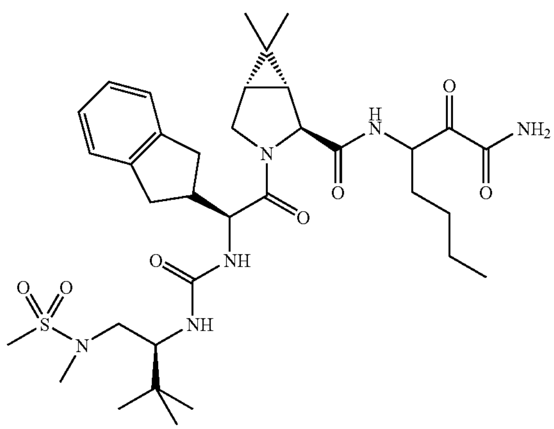 | A |
| 11181 | 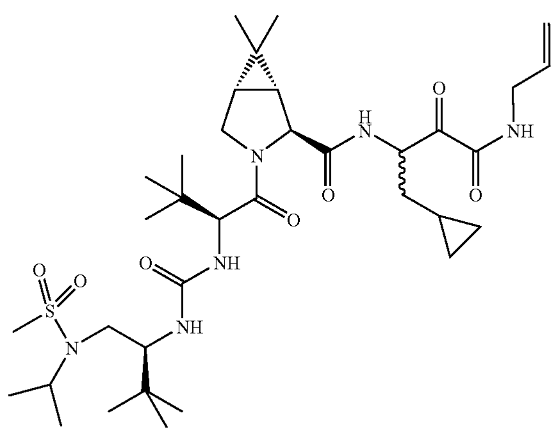 | A |

TABLE 2-continued

| Entry | Structure | Ki* |
|-------|-----------|-----|
| 11182 | 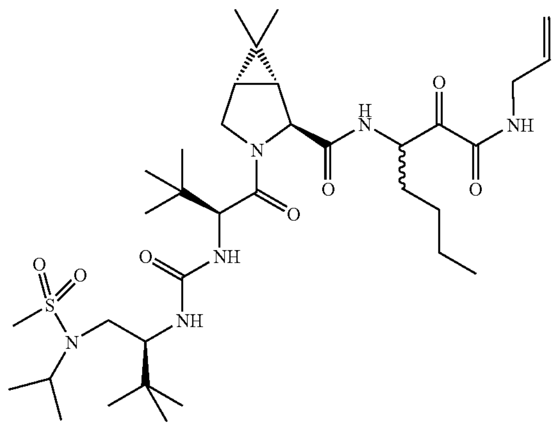 | A |
| 11183 | 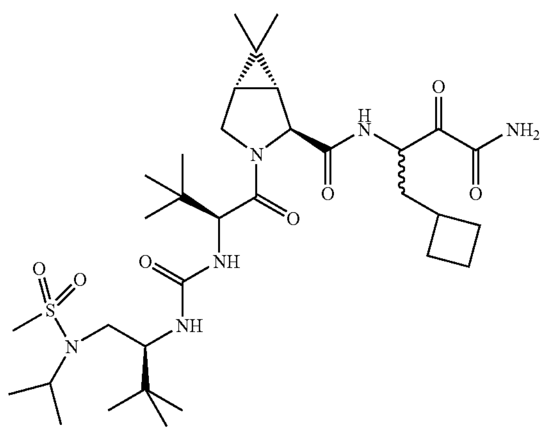 | A |
| 11184 | 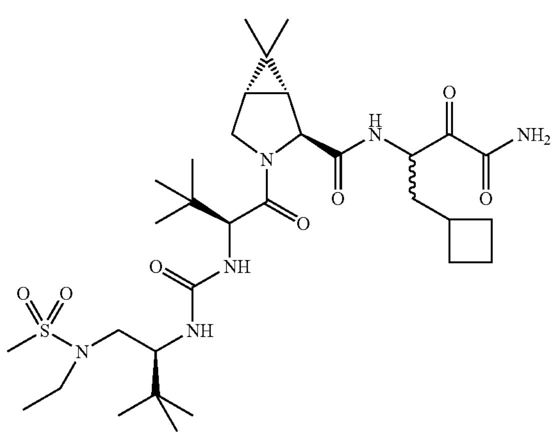 | A |

TABLE 2-continued
| Entry | Structure | Ki* |
|---|---|---|
| 11185 | 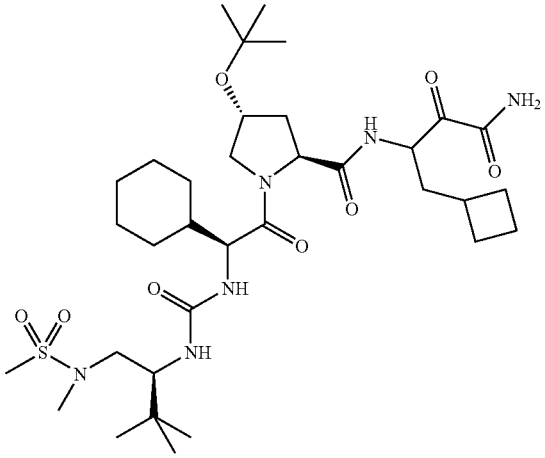 | A |
| 11186 | 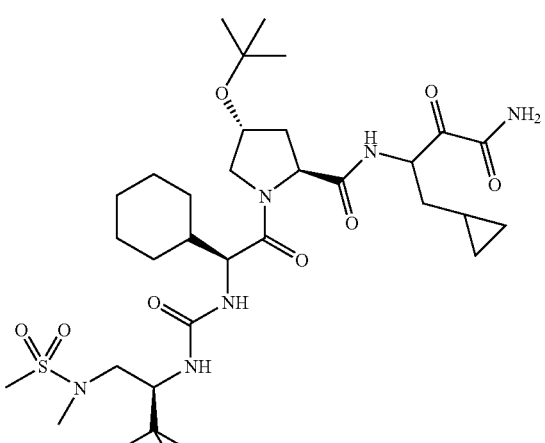 | A |
| 11187 | 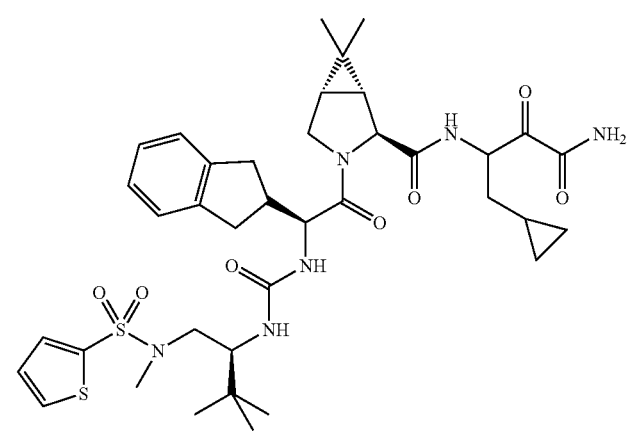 | A |

TABLE 2-continued
| Entry | Structure | Ki* |
|---|---|---|
| 11188 | 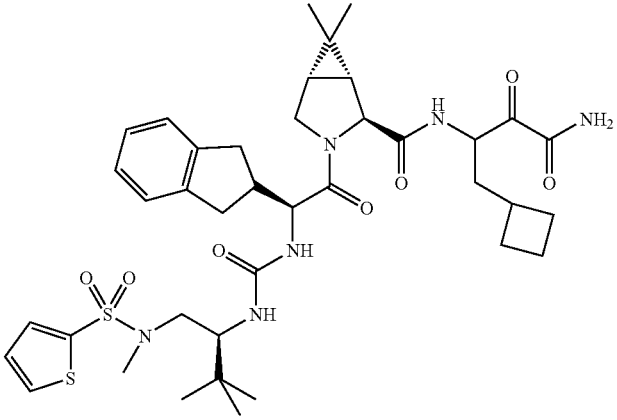 | A |
| 11189 | 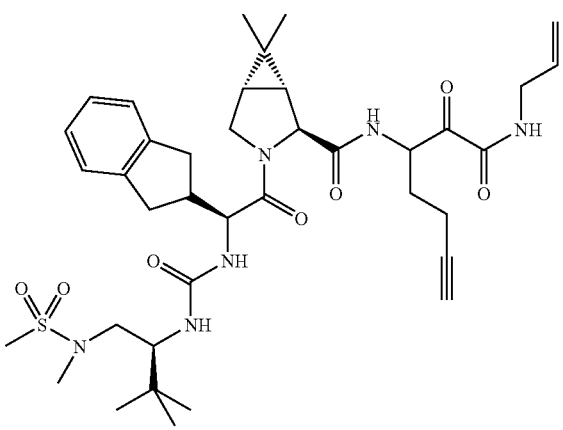 | A |
| 11190 | 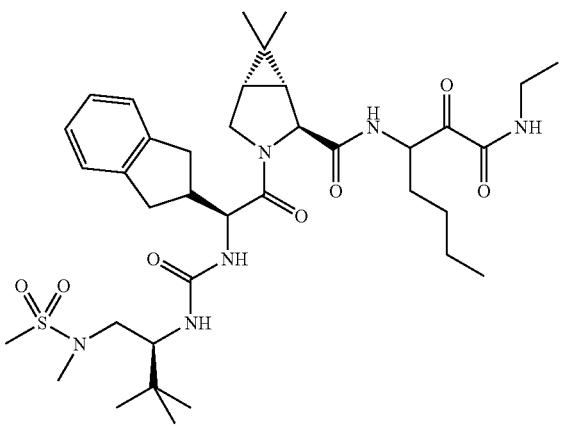 | A |

TABLE 2-continued
| Entry | Structure | Ki* |
|---|---|---|
| 11191 | 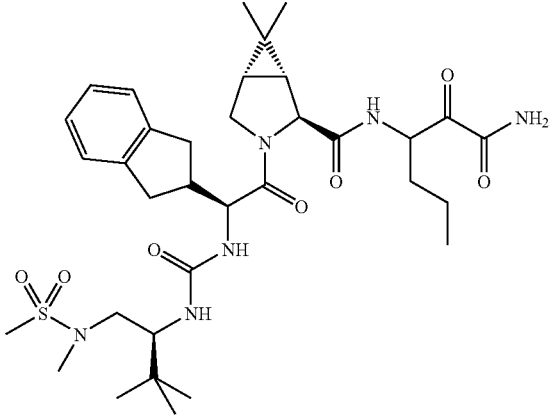 | A |
| 11192 | 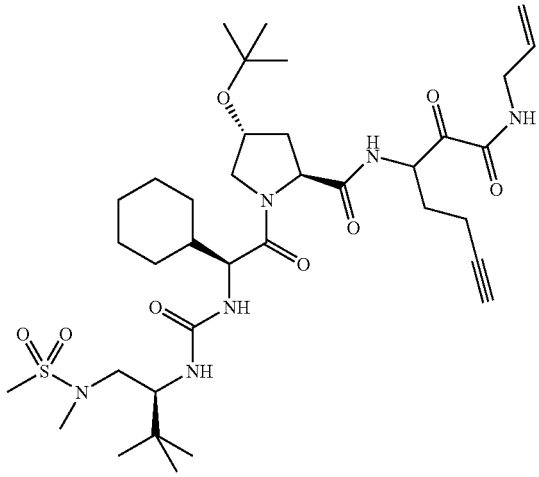 | A |
| 11193 | 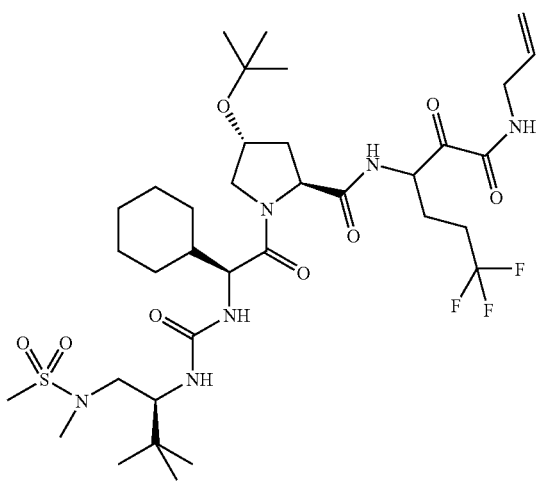 | B |

TABLE 2-continued

| Entry | Structure | Ki* |
|-------|-----------|-----|
| 11194 | 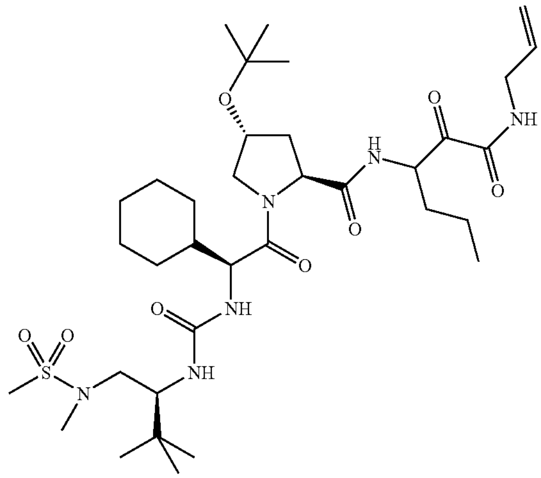 | B |
| 11195 | 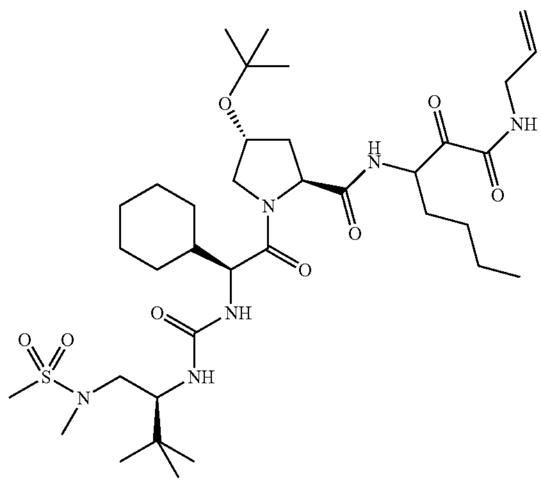 | B |
| 11196 | 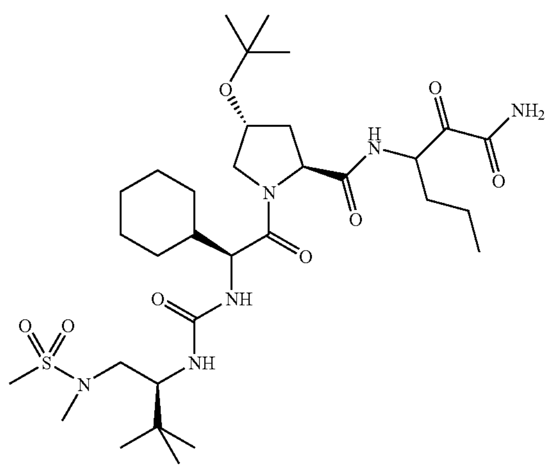 | A |

TABLE 2-continued
| Entry | Structure | Ki* |
|---|---|---|
| 11197 | 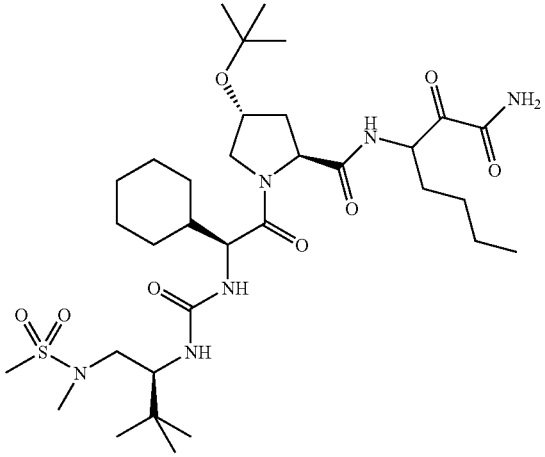 | A |
| 11198 | 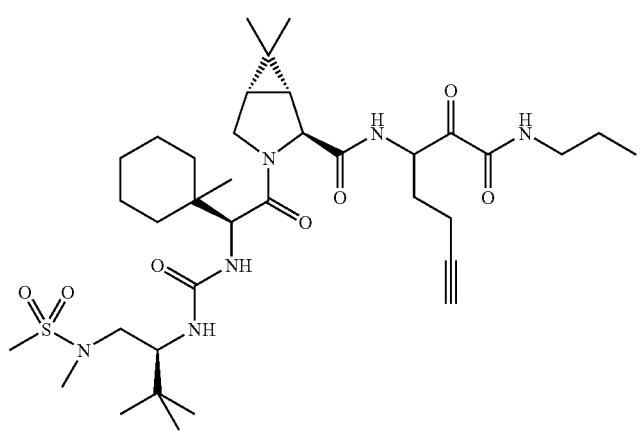 | A |
| 11199 | 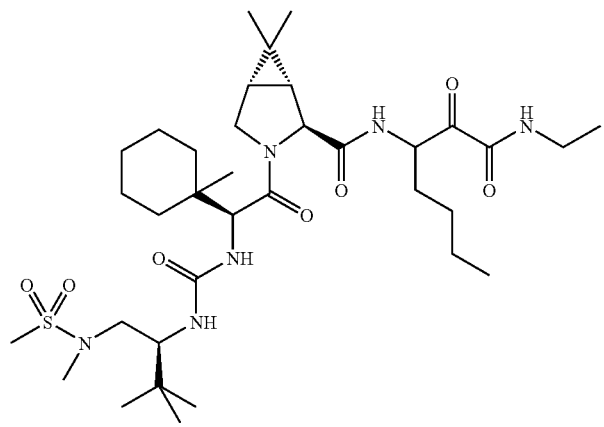 | A |

TABLE 2-continued
| Entry | Structure | Ki* |
|---|---|---|
| 11200 | 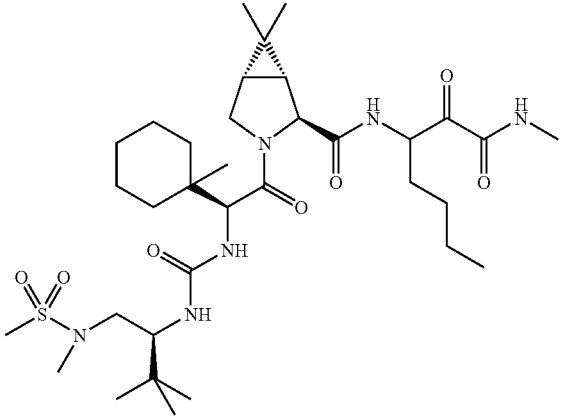 | A |
| 11201 | 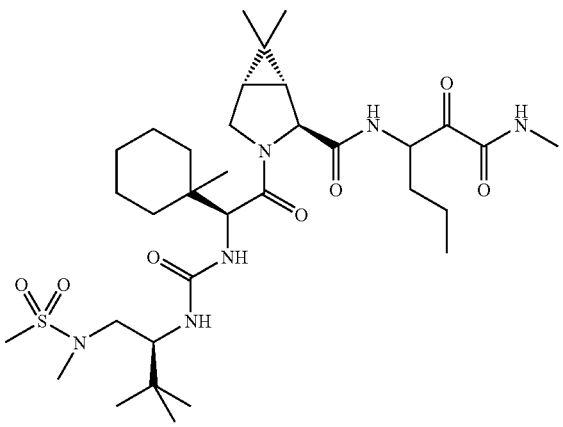 | A |
| 11202 | 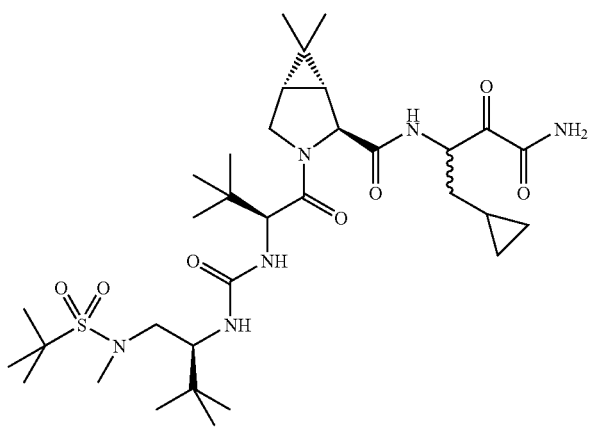 | A |

TABLE 2-continued
| Entry | Structure | Ki* |
|---|---|---|
| 11203 | 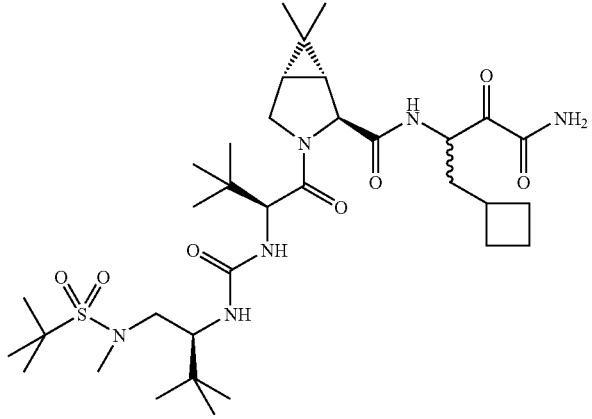 | A |
| 11204 | 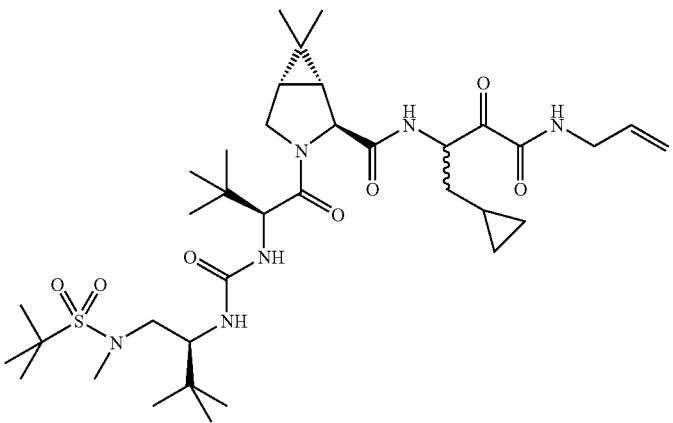 | B |
| 11205 | 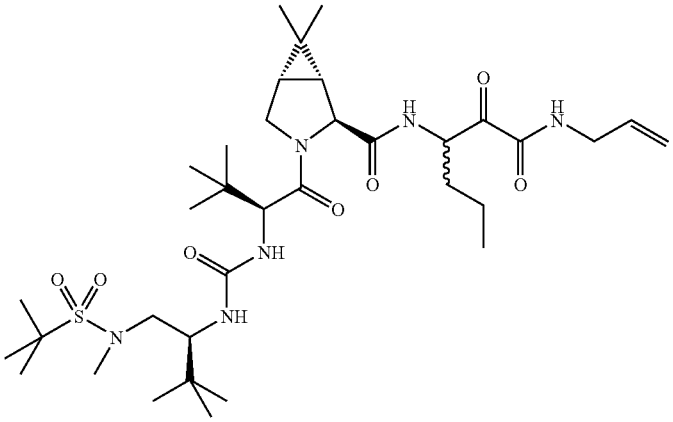 | A |

TABLE 2-continued

| Entry | Structure | Ki* |
|---|---|---|
| 11206 | 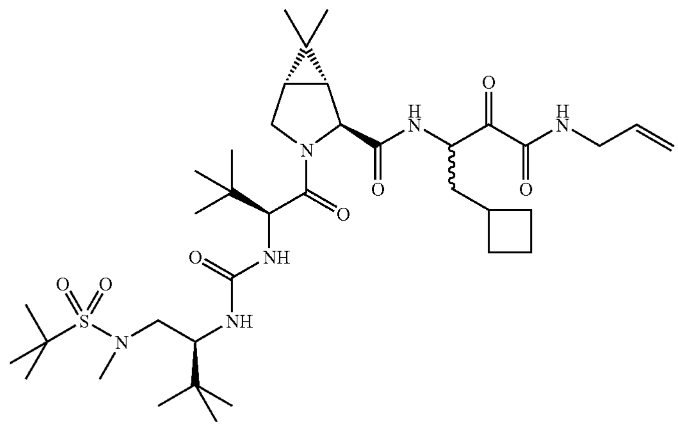 | B |
| 11207 | 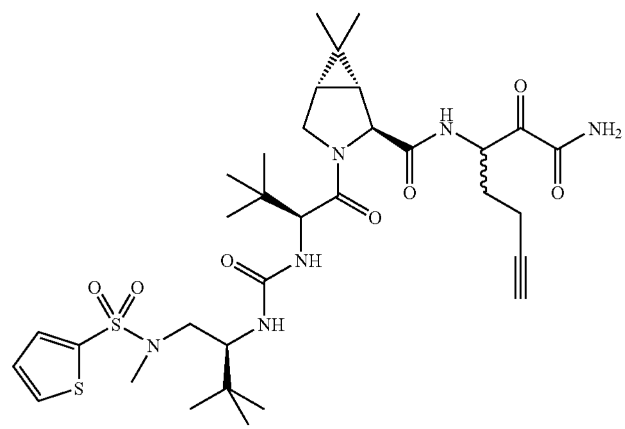 | A |
| 11208 | 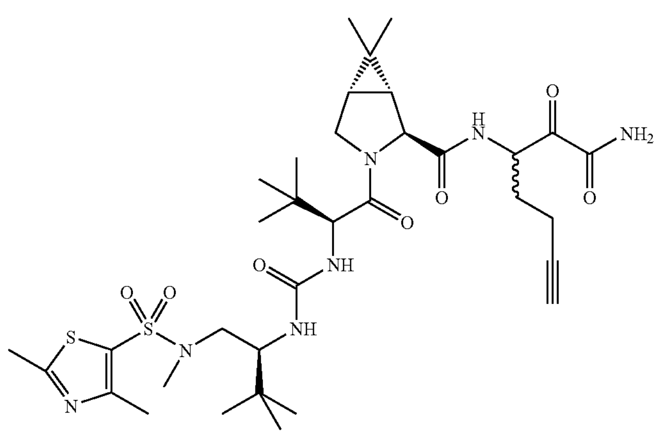 | A |

TABLE 2-continued

| Entry | Structure | Ki* |
|---|---|---|
| 11209 | 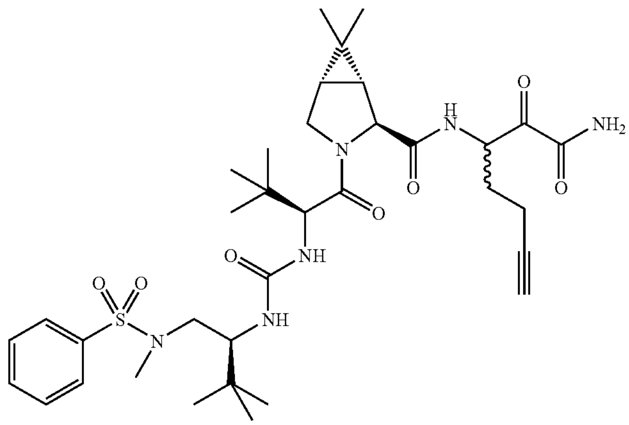 | A |
| 11210 | 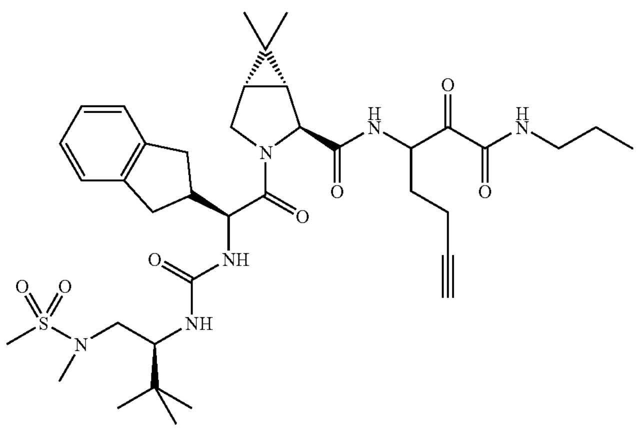 | A |
| 11211 | 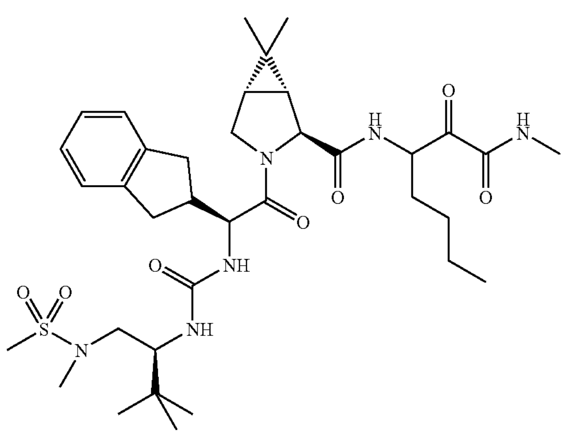 | A |

TABLE 2-continued
| Entry | Structure | Ki* |
|---|---|---|
| 11212 | 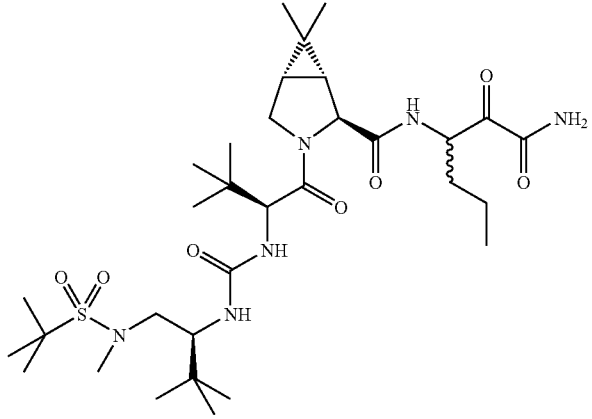 | A |
| 11213 | 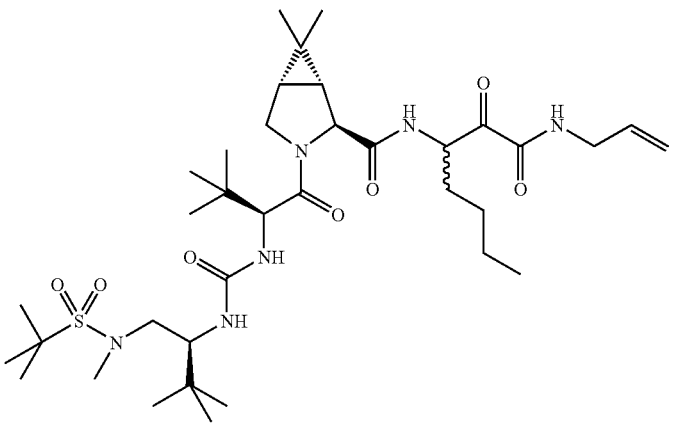 | B |
| 11214 | 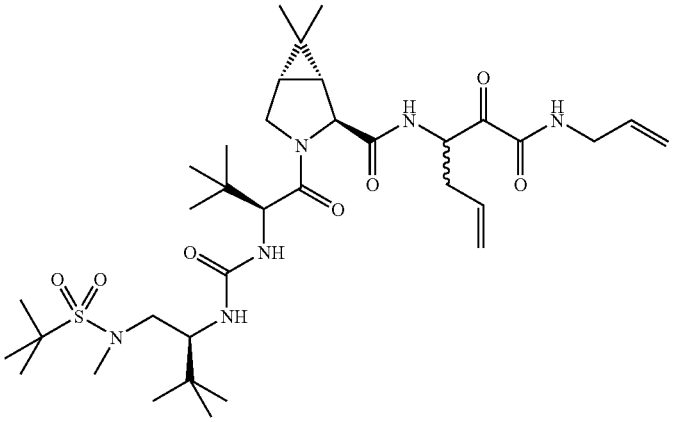 | A |

TABLE 2-continued

| Entry | Structure | Ki* |
|---|---|---|
| 11215 | 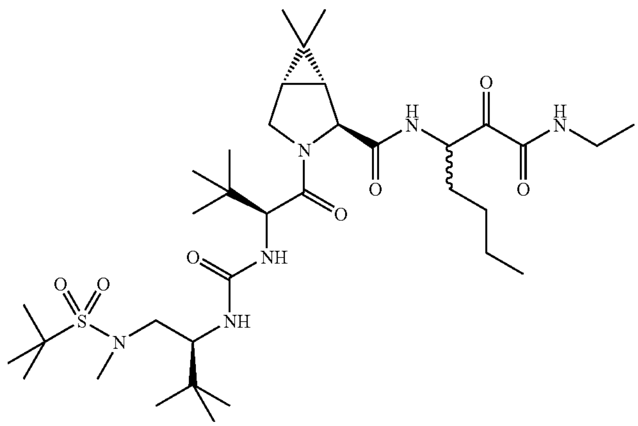 | B |
| 11216 | 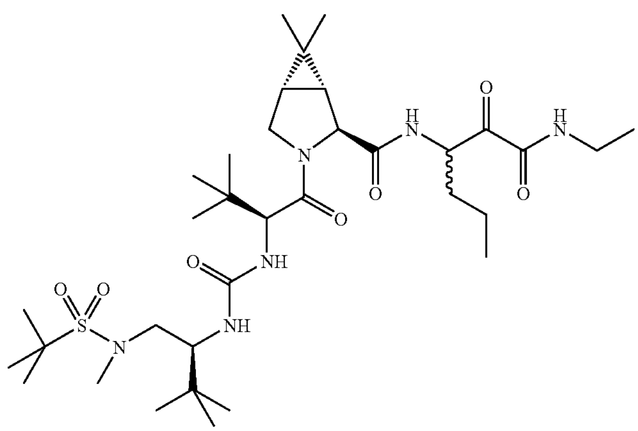 | B |
| 11217 | 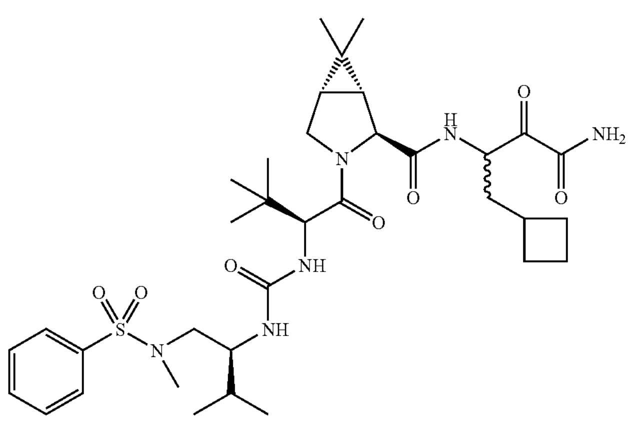 | A |

TABLE 2-continued

| Entry | Structure | Ki* |
|-------|-----------|-----|
| 11218 | 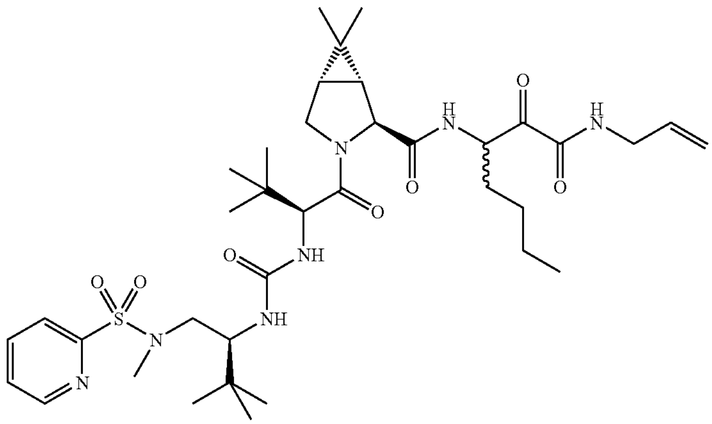 | A |
| 11219 | 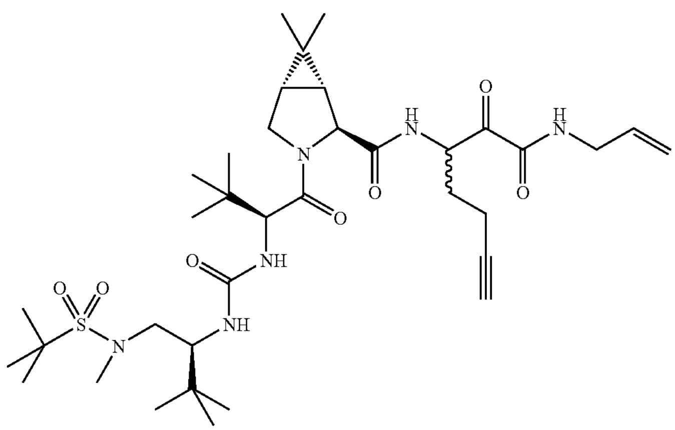 | A |
| 11220 | 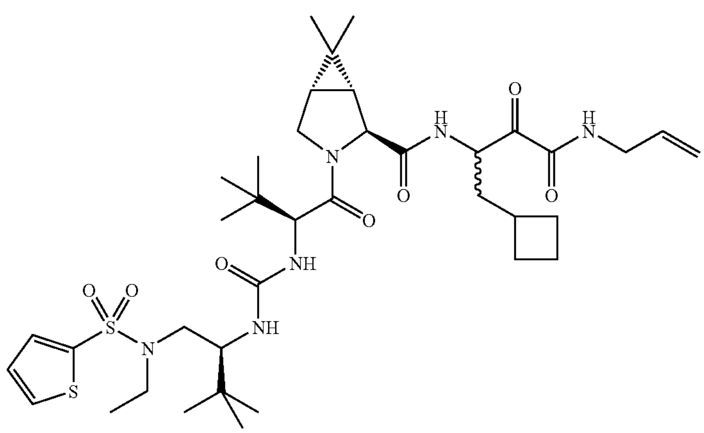 | A |

TABLE 2-continued
| Entry | Structure | Ki* |
|---|---|---|
| 11221 | 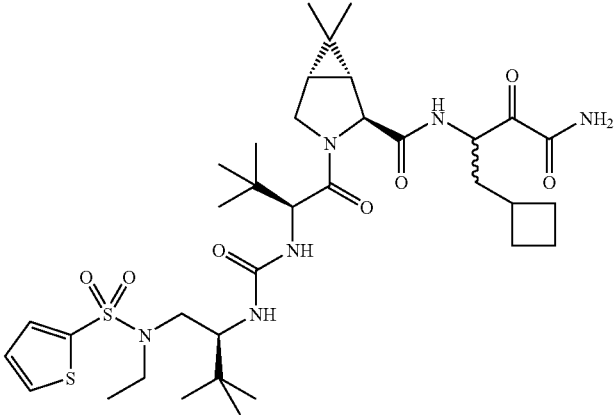 | A |
| 11222 | 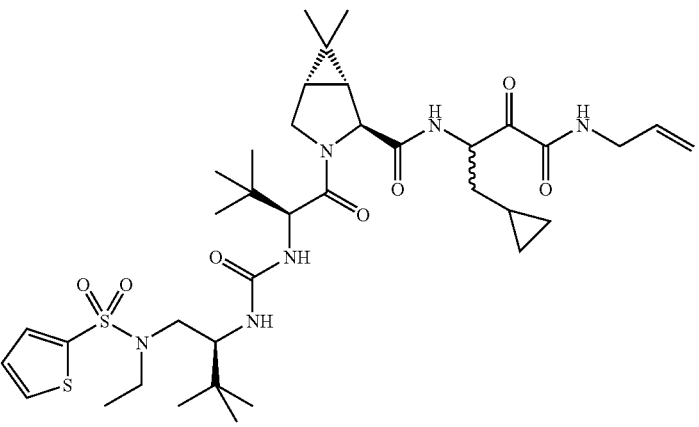 | A |
| 11223 | 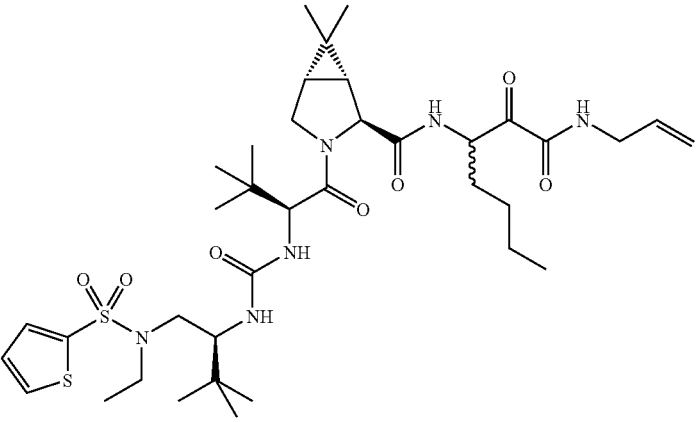 | A |

TABLE 2-continued

| Entry | Structure | Ki* |
|---|---|---|
| 11224 | 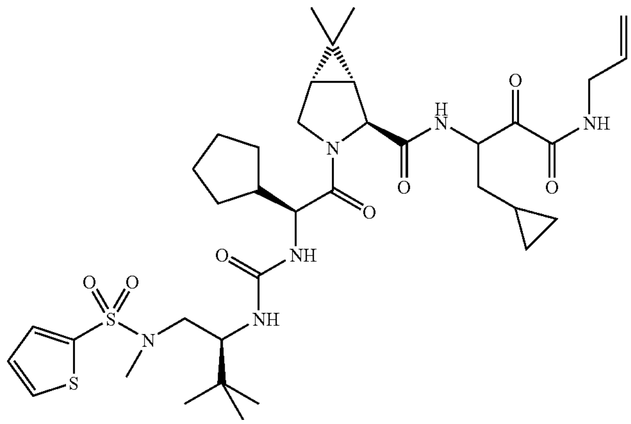 | B |
| 11225 | 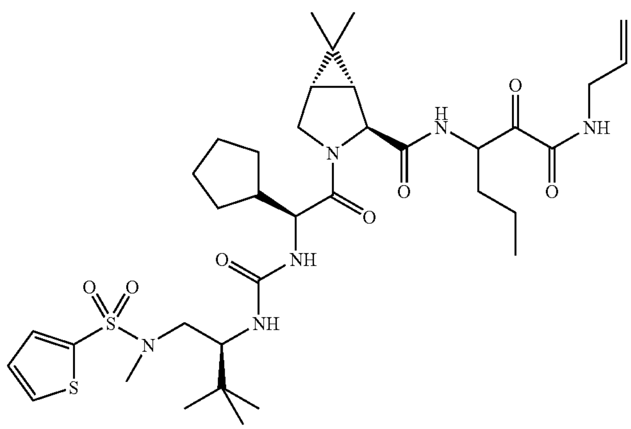 | A |
| 11226 | 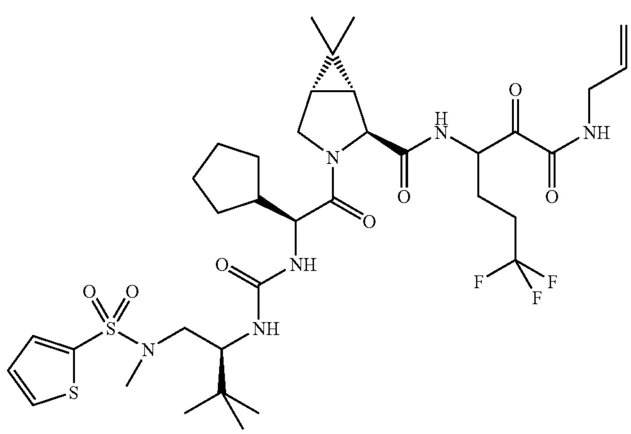 | A |

TABLE 2-continued

| Entry | Structure | Ki* |
|-------|-----------|-----|
| 11227 | 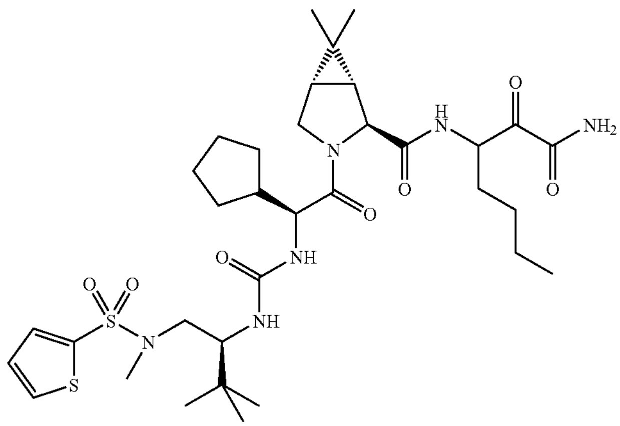 | A |
| 11228 | 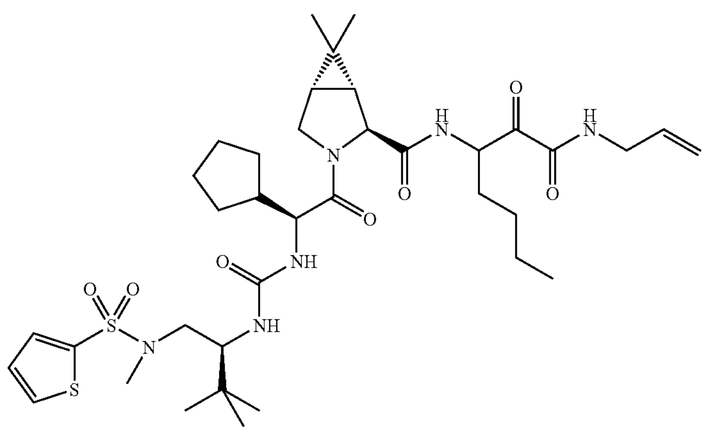 | A |
| 11229 | 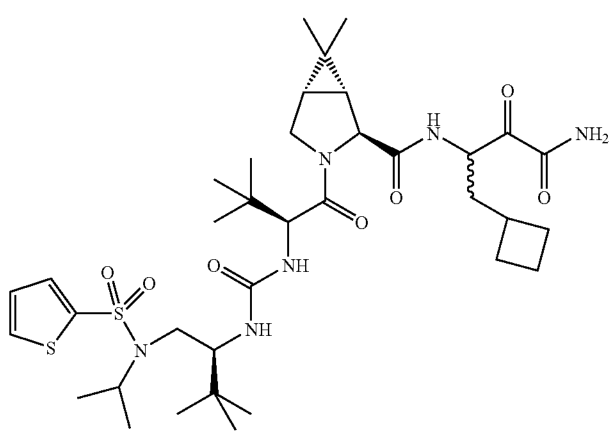 | A |

TABLE 2-continued

| Entry | Structure | Ki* |
|---|---|---|
| 11230 | 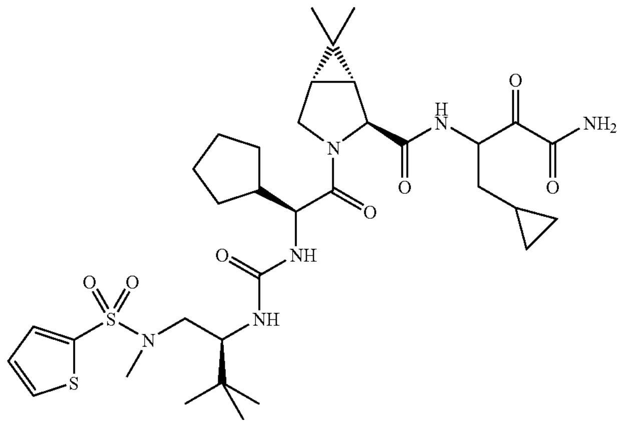 | A |
| 11231 | 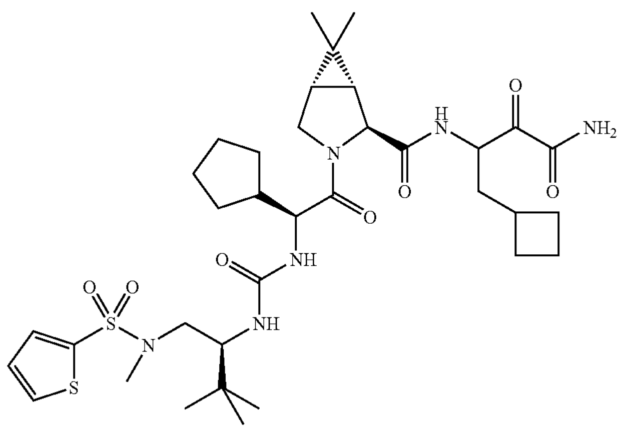 | A |
| 11232 | 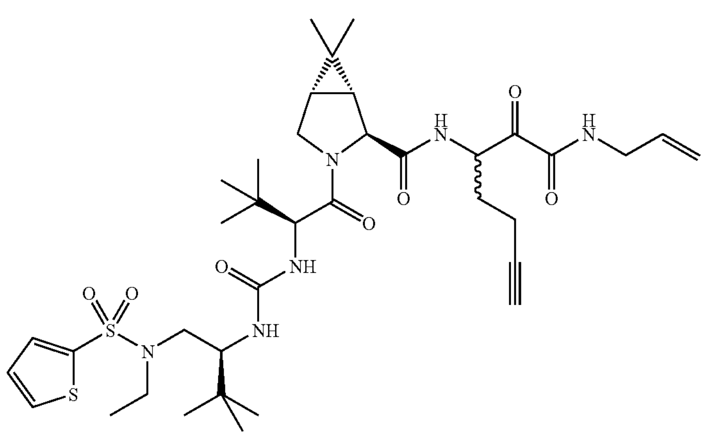 | A |

//

TABLE 2-continued

| Entry | Structure | Ki* |
|---|---|---|
| 11233 | 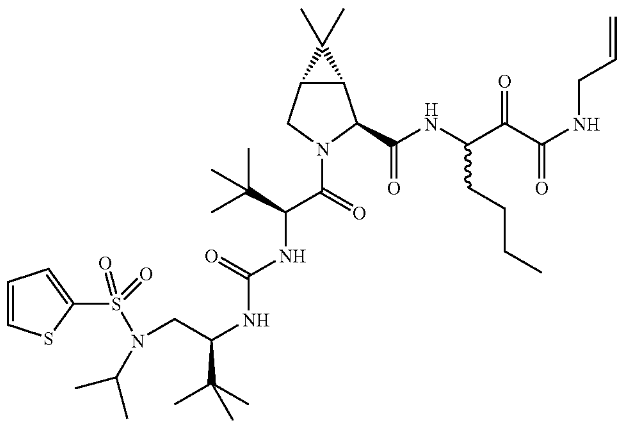 | A |
| 11234 | 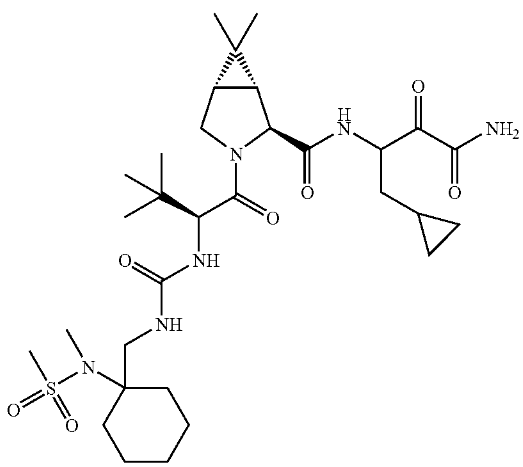 | A |
| 11235 | 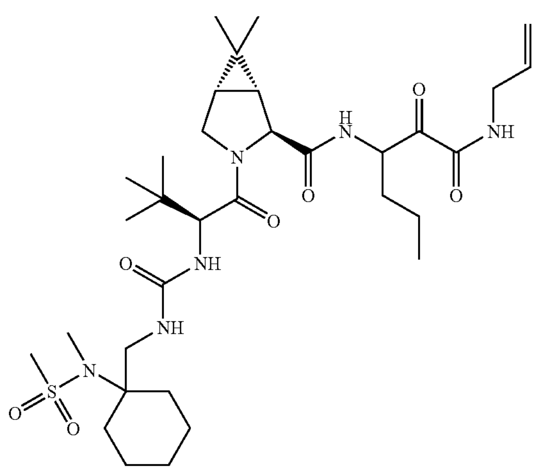 | A |

TABLE 2-continued

| Entry | Structure | Ki* |
|---|---|---|
| 11236 | 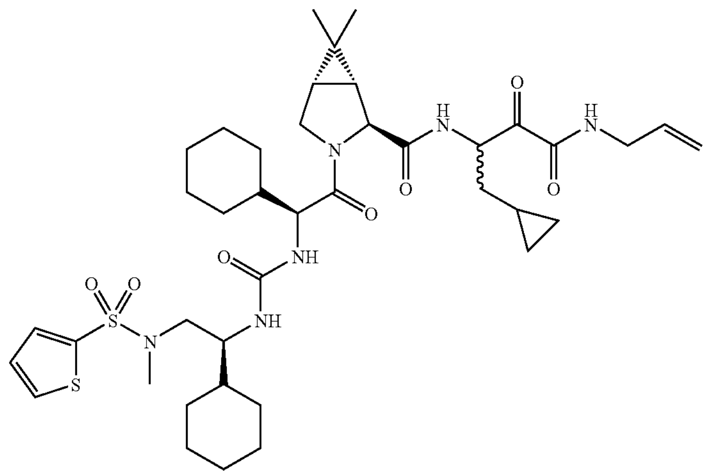 | A |
| 11237 | 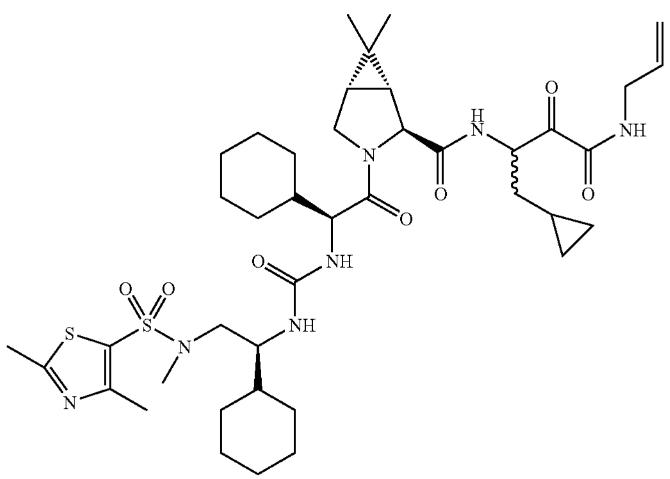 | A |
| 11238 | 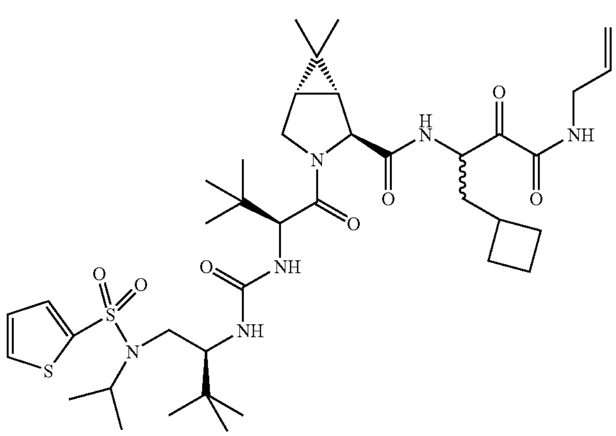 | A |

TABLE 2-continued
| Entry | Structure | Ki* |
|---|---|---|
| 11239 | 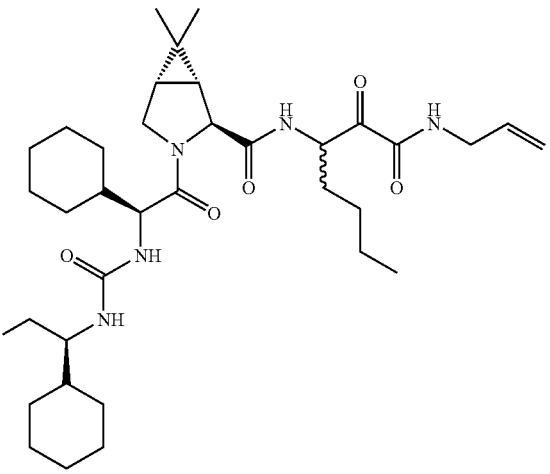 | A |
| 11240 | 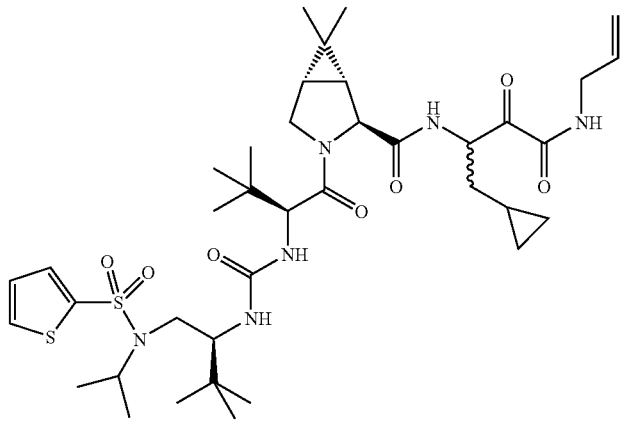 | A |
| 11242 | 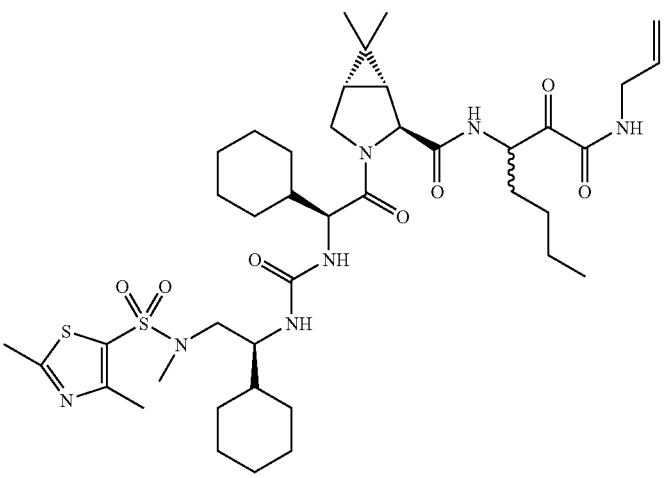 | A |

TABLE 2-continued

| Entry | Structure | Ki* |
|---|---|---|
| 11243 | 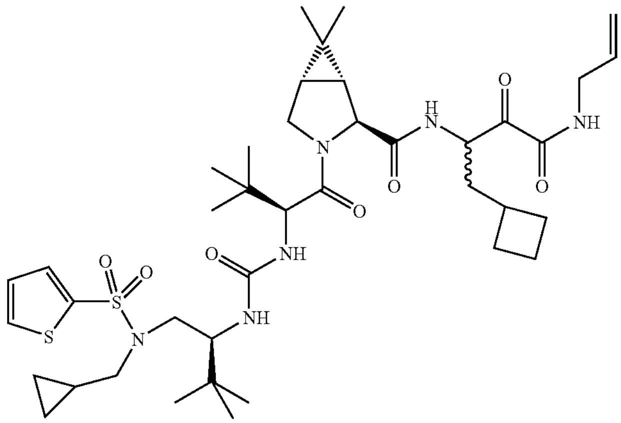 | B |
| 11244 | 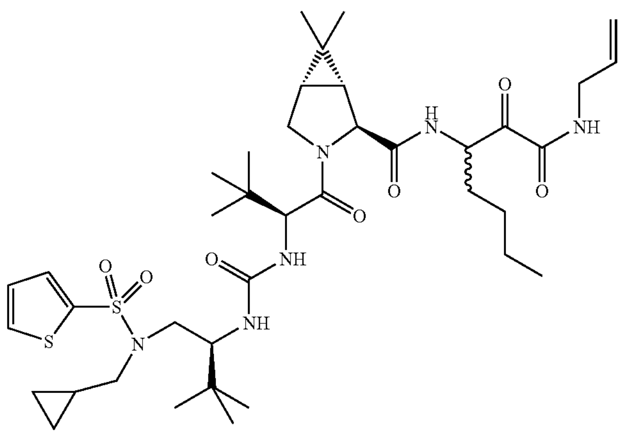 | A |
| 11245 | 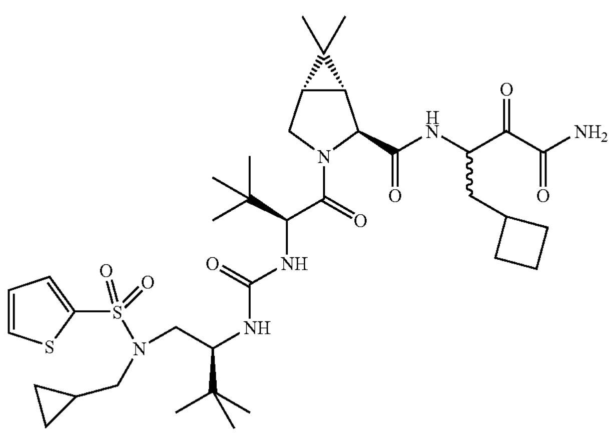 | A |

TABLE 2-continued
| Entry | Structure | Ki* |
|---|---|---|
| 11246 | 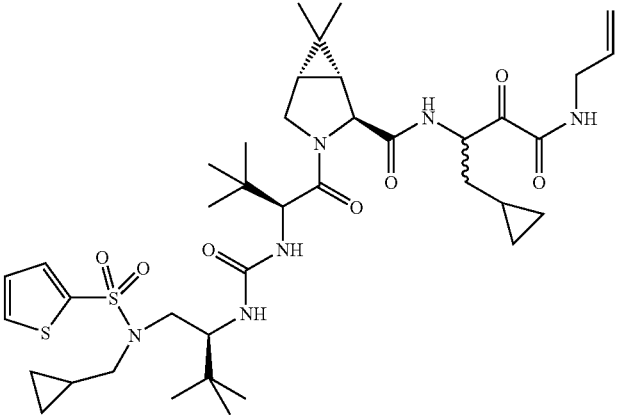 | A |
| 11247 | 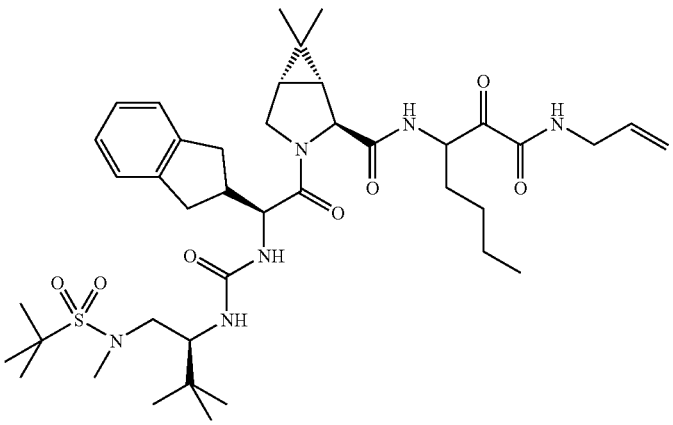 | A |
| 11248 | 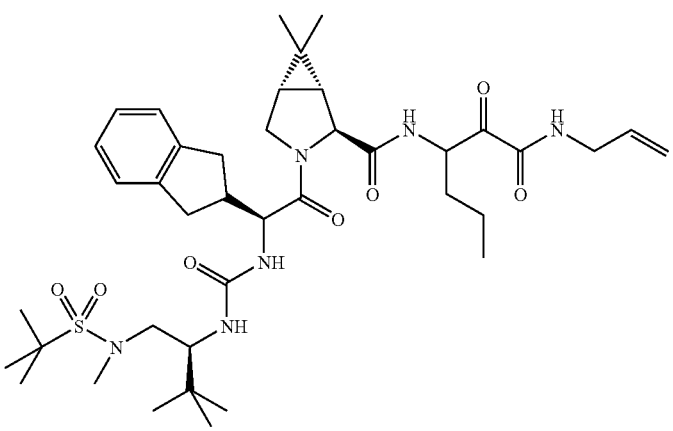 | A |

TABLE 2-continued

| Entry | Structure | Ki* |
|---|---|---|
| 11249 | 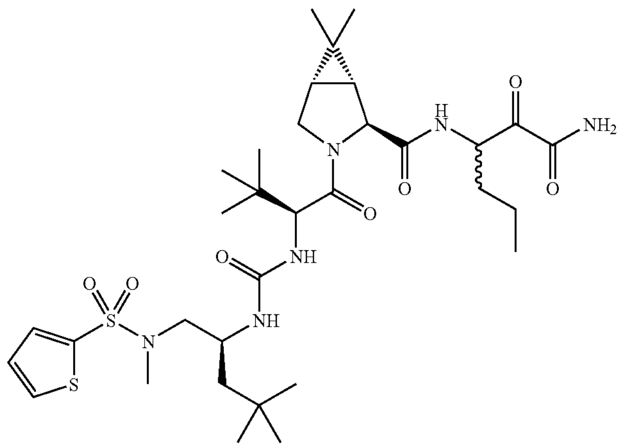 | A |
| 11250 | 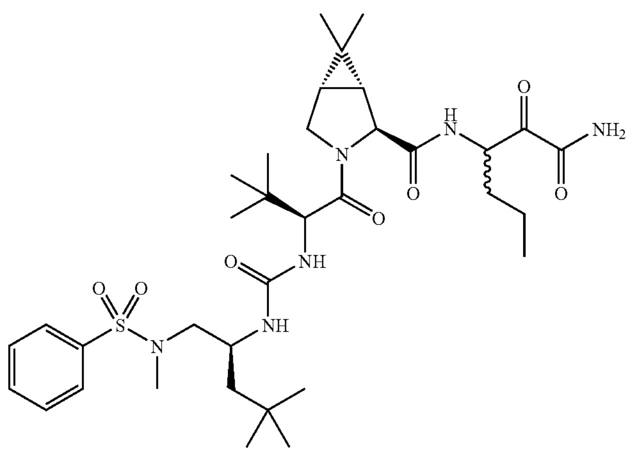 | A |
| 11251 | 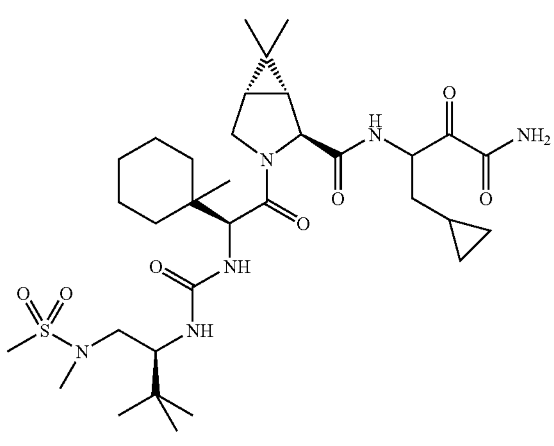 | A |

TABLE 2-continued
| Entry | Structure | Ki* |
|---|---|---|
| 11252 | 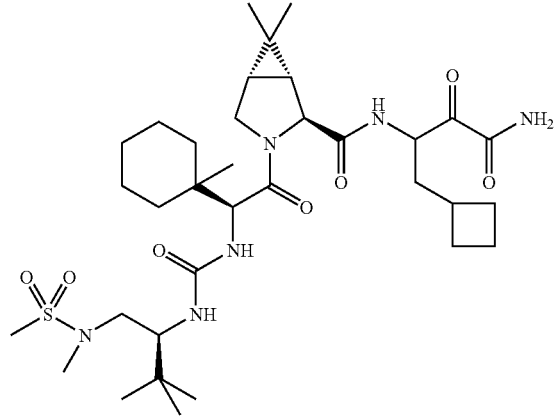 | A |
| 11253 | 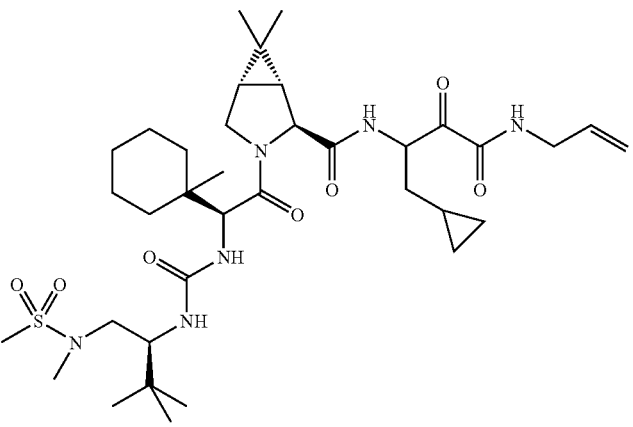 | A |
| 11254 | 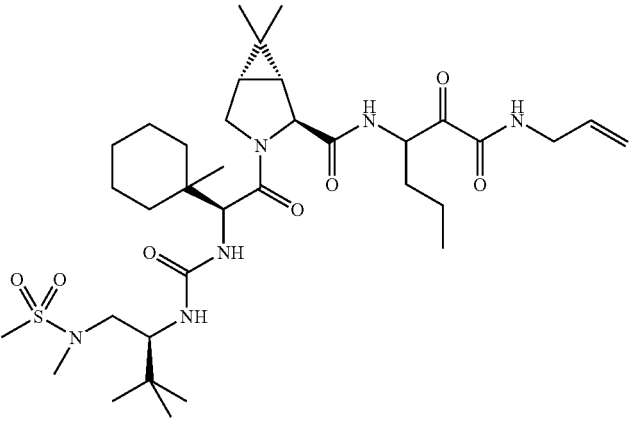 | A |

TABLE 2-continued
| Entry | Structure | Ki* |
|---|---|---|
| 11255 | 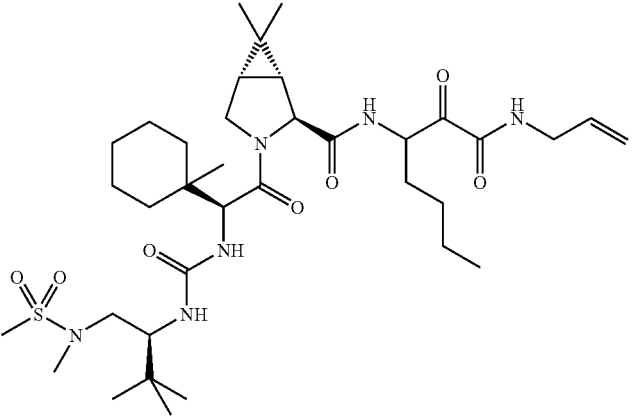 | A |
| 11256 | 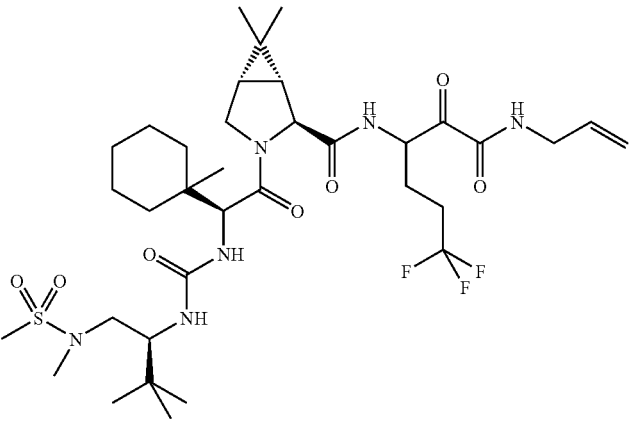 | A |
| 11257 | 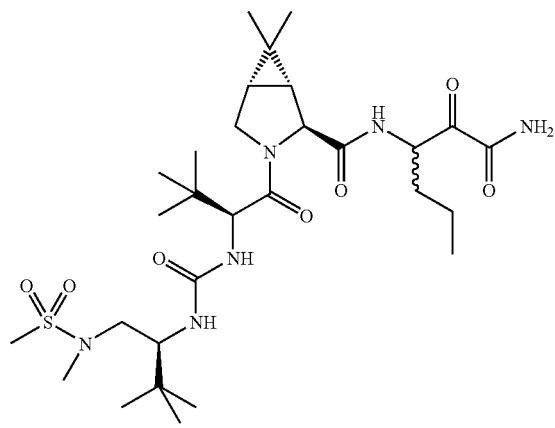 | A |

TABLE 2-continued

| Entry | Structure | Ki* |
|---|---|---|
| 11258 | 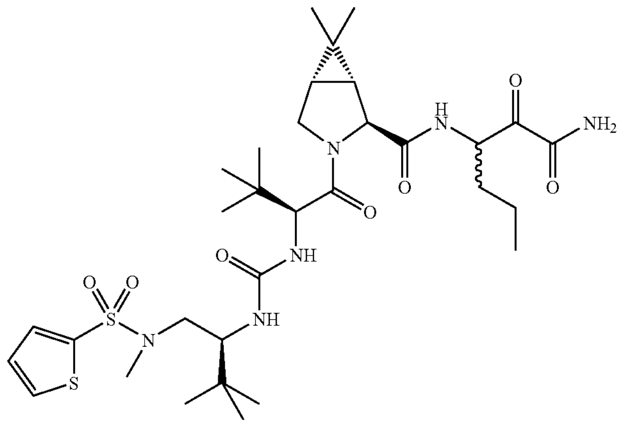 | A |
| 11259 | 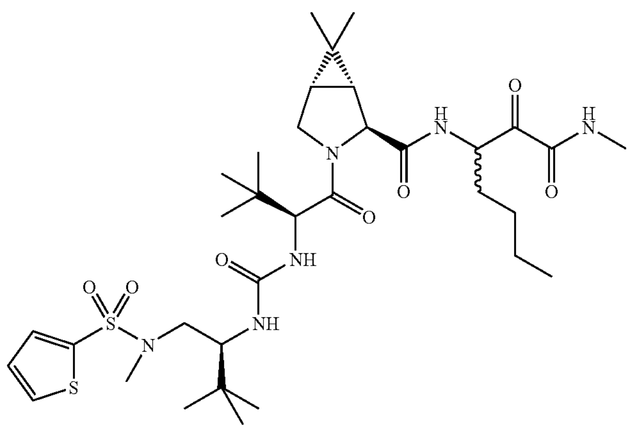 | A |
| 11260 | 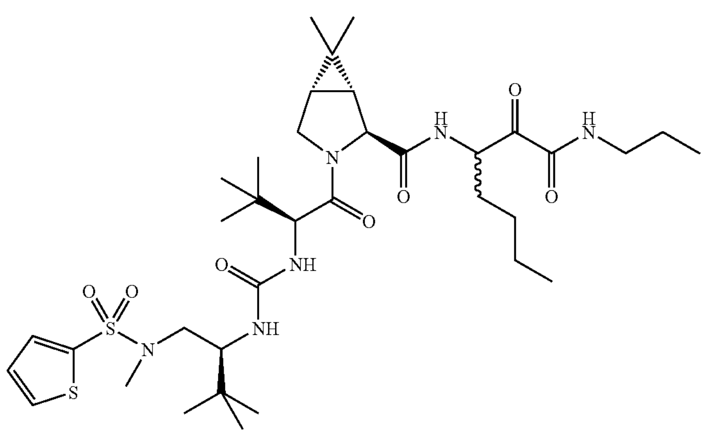 | A |

TABLE 2-continued
| Entry | Structure | Ki* |
|---|---|---|
| 11261 | 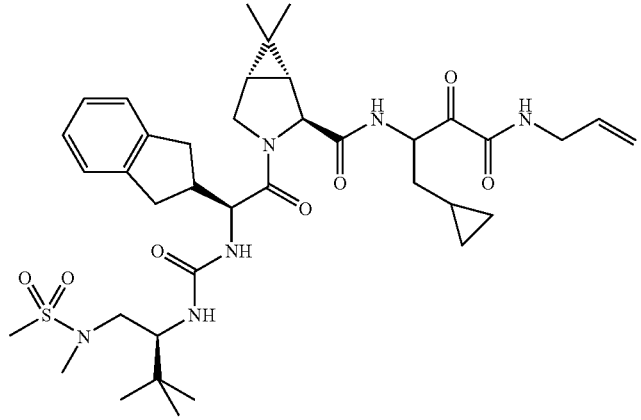 | A |
| 11262 | 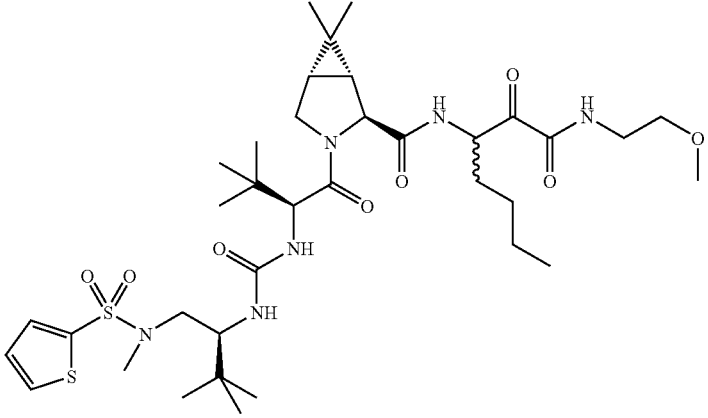 | B |
| 11263 | 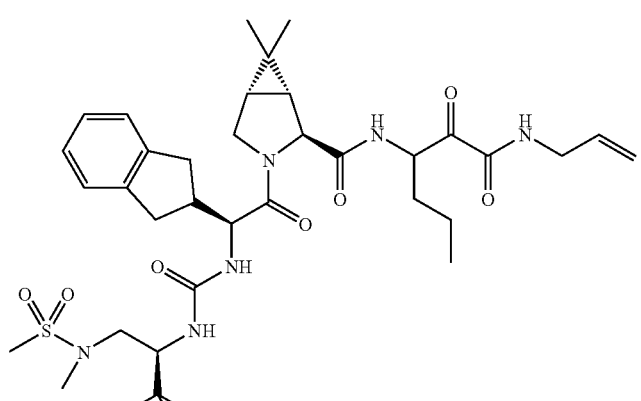 | A |

TABLE 2-continued

| Entry | Structure | Ki* |
|---|---|---|
| 11264 | 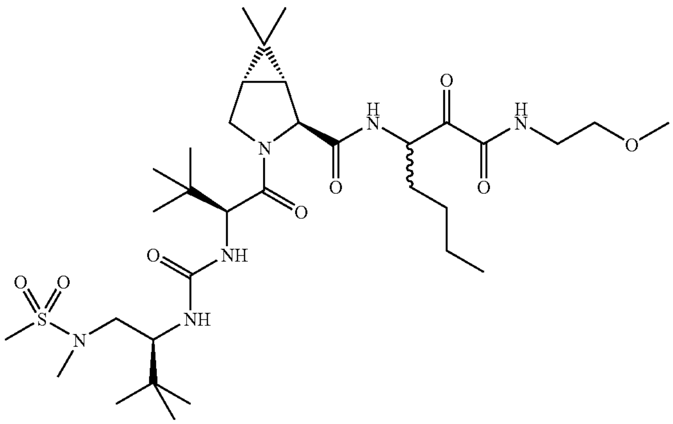 | A |
| 11265 | 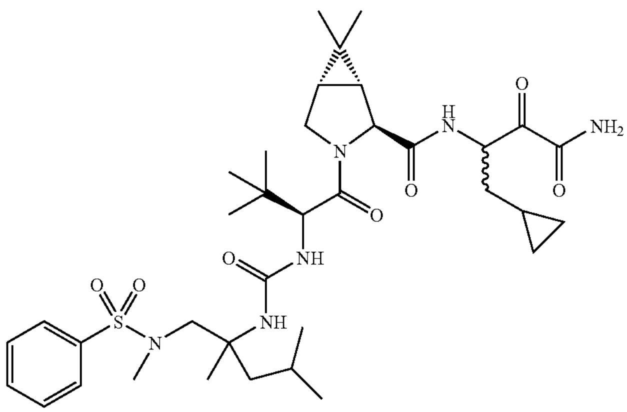 | A |
| 11266 | 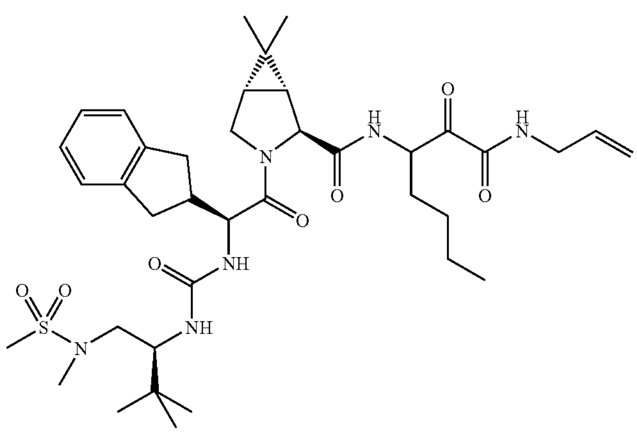 | A |

TABLE 2-continued

| Entry | Structure | Ki* |
|---|---|---|
| 11267 | 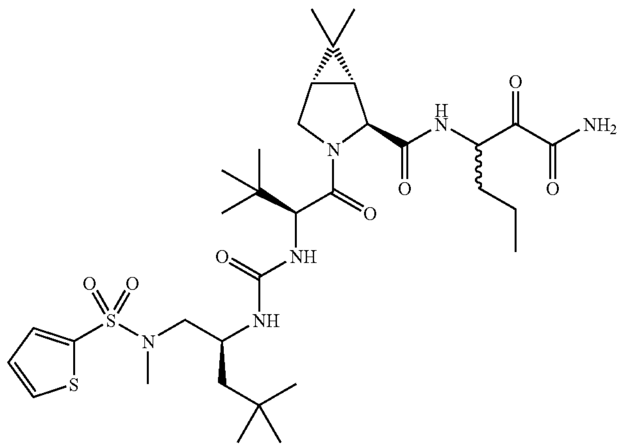 | A |
| 11268 | 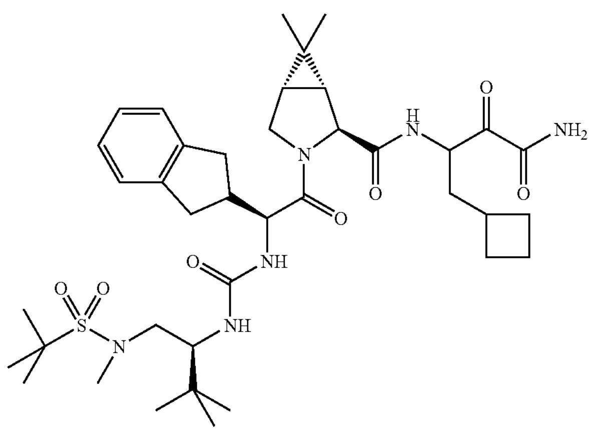 | A |
| 11269 | 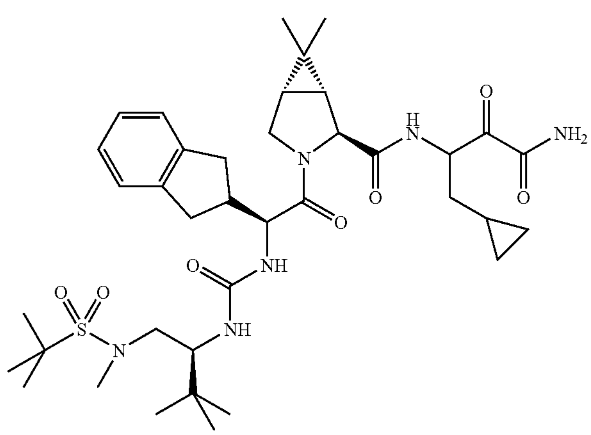 | A |

TABLE 2-continued

| Entry | Structure | Ki* |
|---|---|---|
| 11270 | 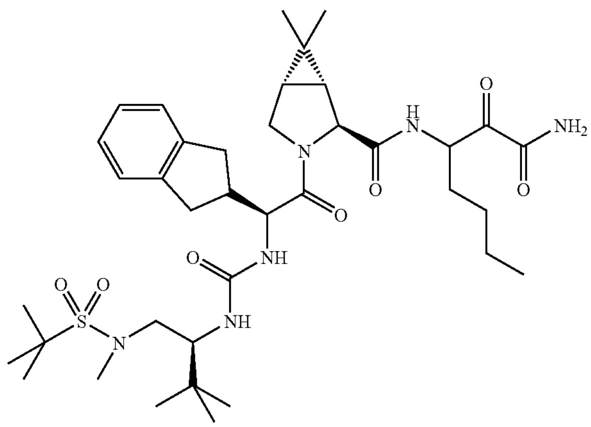 | A |
| 11271 | 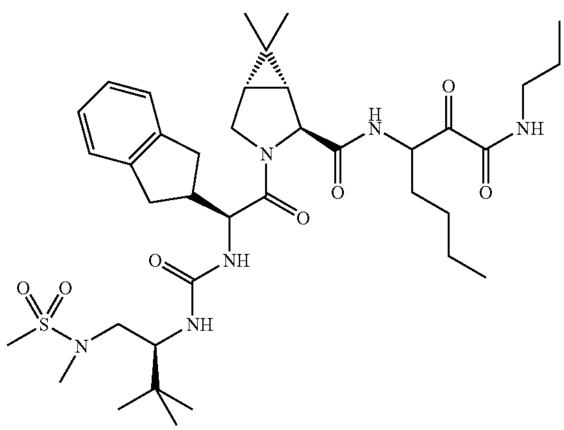 | A |
| 11272 | 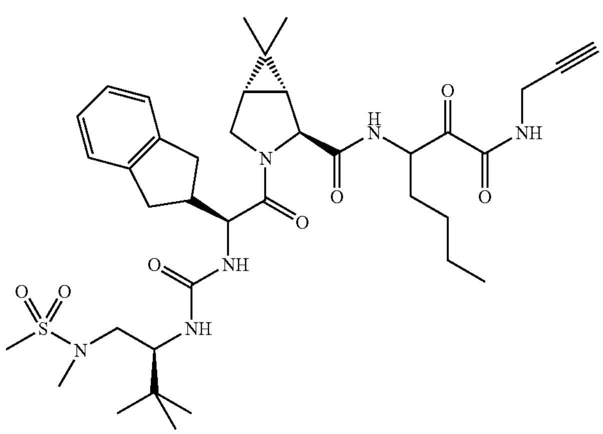 | A |

TABLE 2-continued
| Entry | Structure | Ki* |
|---|---|---|
| 11273 | 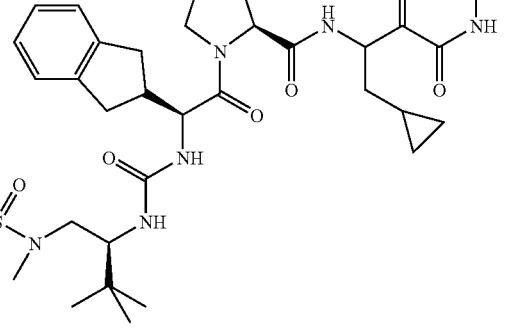 | B |
| 11274 | 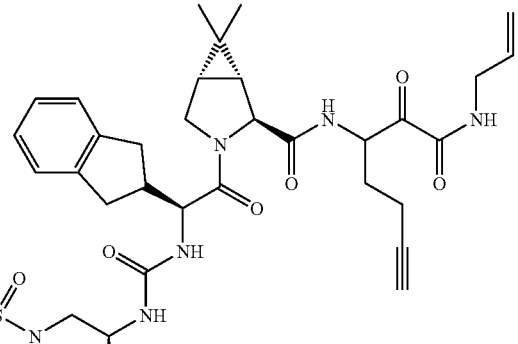 | A |
| 11275 | 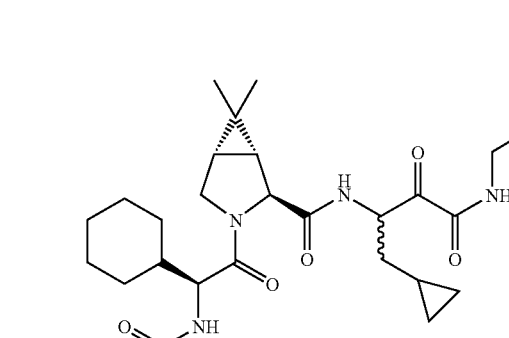 | A |

TABLE 2-continued

| Entry | Structure | Ki* |
|---|---|---|
| 11276 | 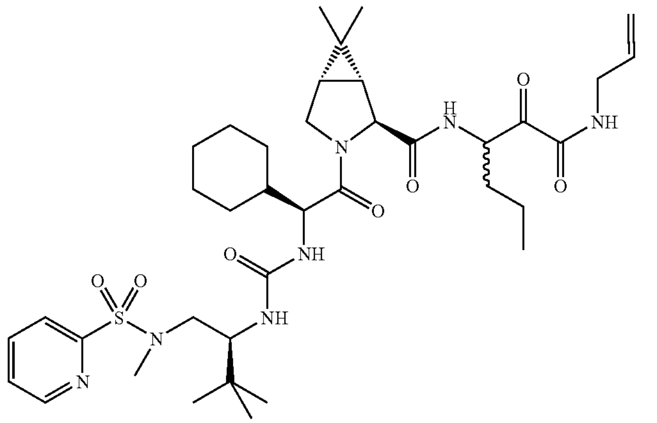 | A |
| 11277 | 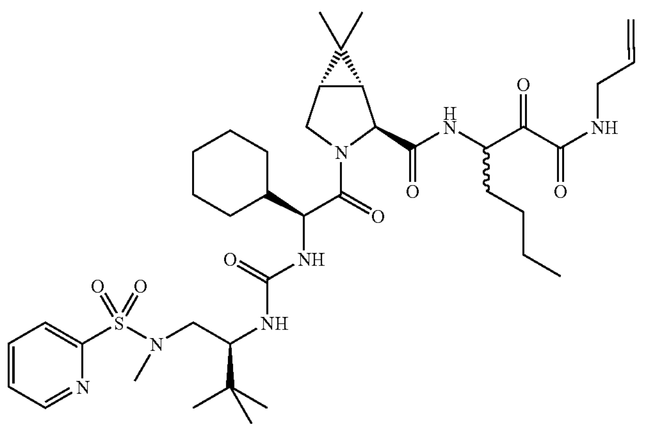 | A |
| 11278 | 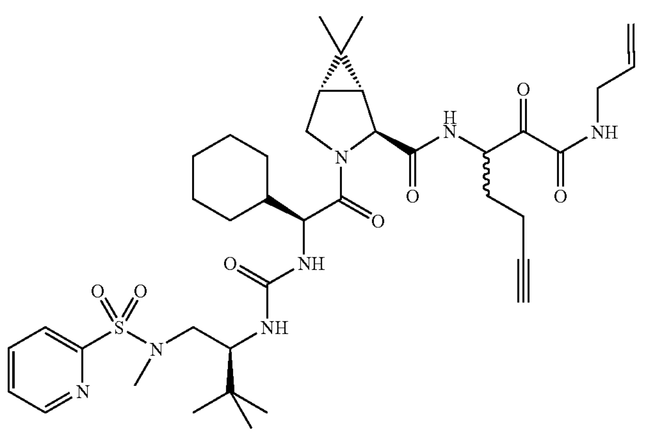 | A |

TABLE 2-continued
| Entry | Structure | Ki* |
|---|---|---|
| 11279 | 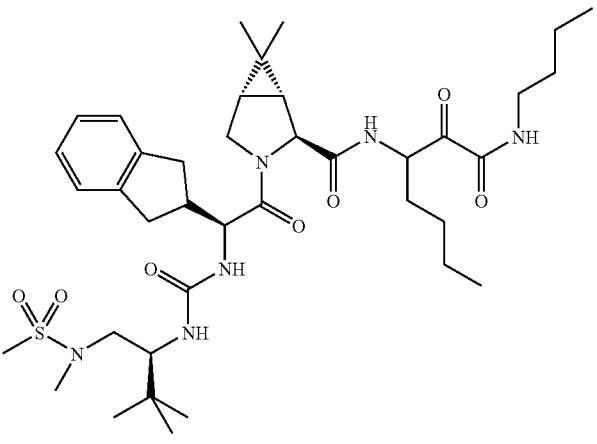 | A |
| 11280 | 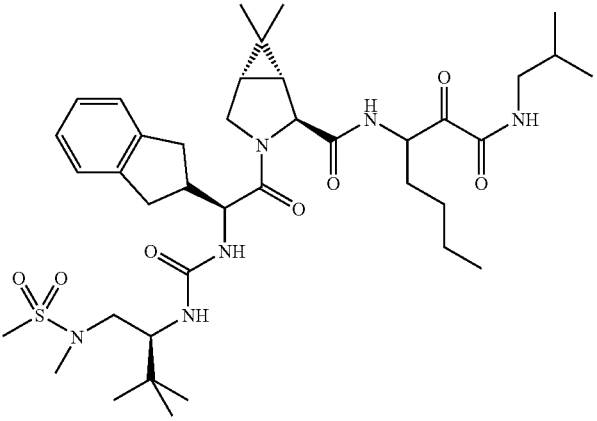 | A |
| 11281 | 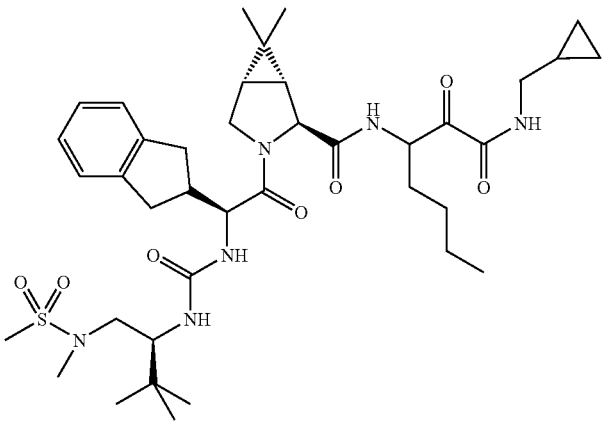 | A |

TABLE 2-continued

| Entry | Structure | Ki* |
|---|---|---|
| 11282 | 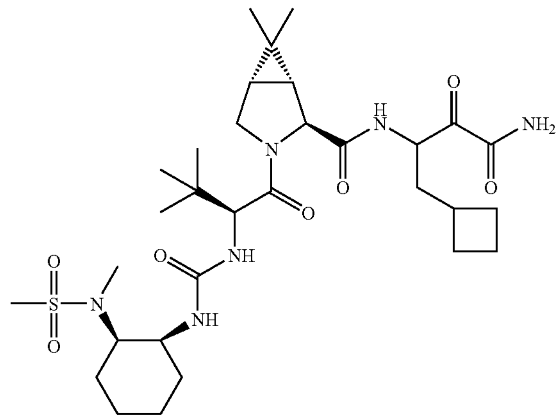 | B |
| 11283 | 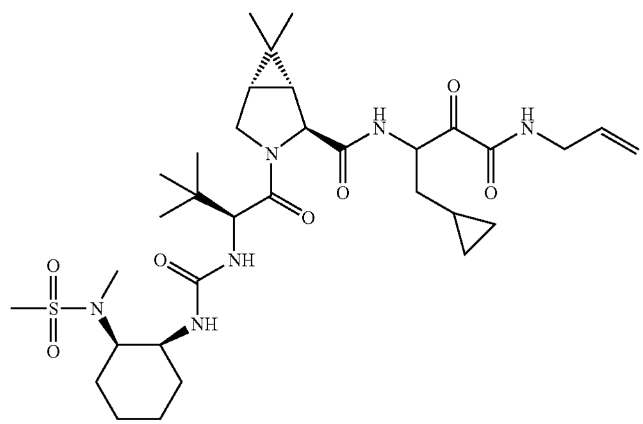 | C |
| 11284 | 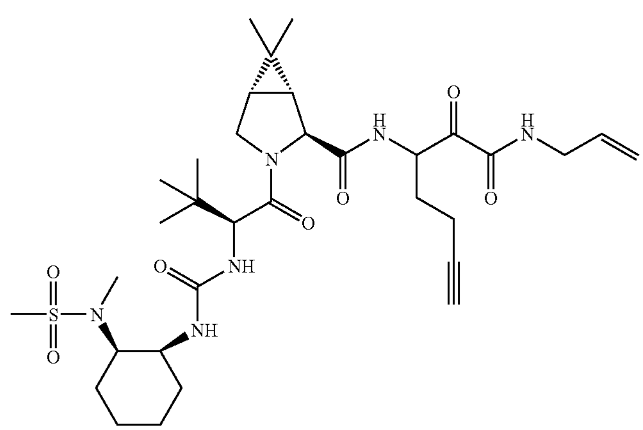 | B |

TABLE 2-continued

| Entry | Structure | Ki* |
|---|---|---|
| 11285 | 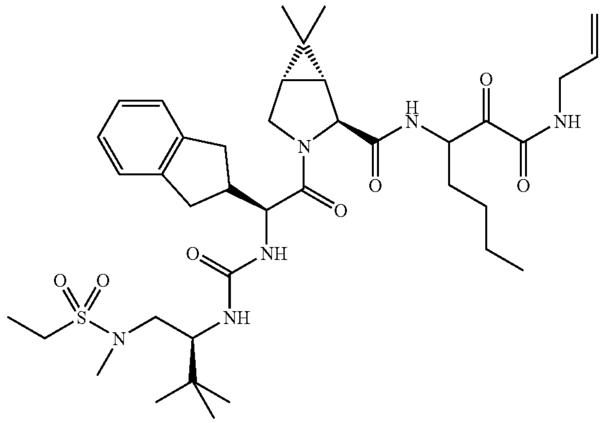 | A |
| 11286 | 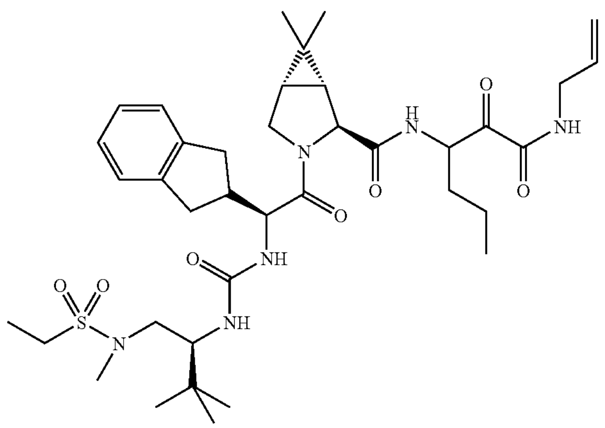 | A |
| 11287 | 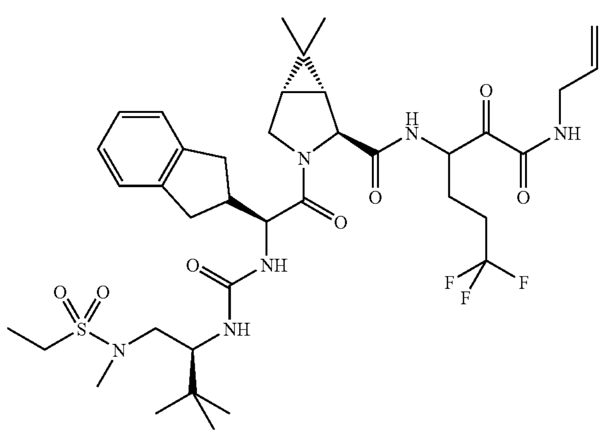 | A |

TABLE 2-continued

| Entry | Structure | Ki* |
|---|---|---|
| 11288 | 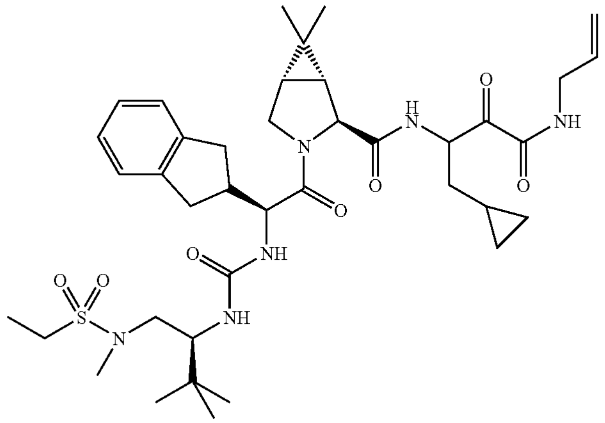 | A |
| 11289 | 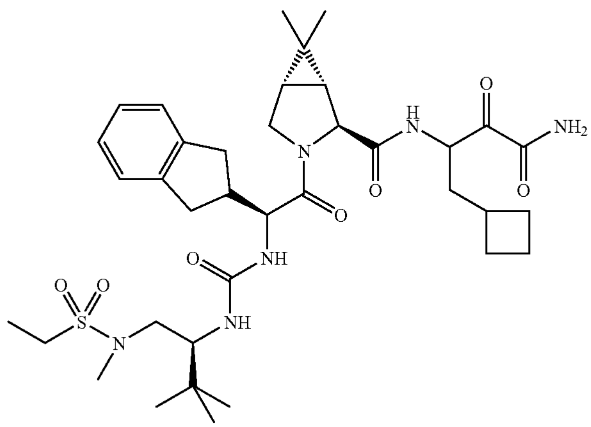 | A |
| 11290 | 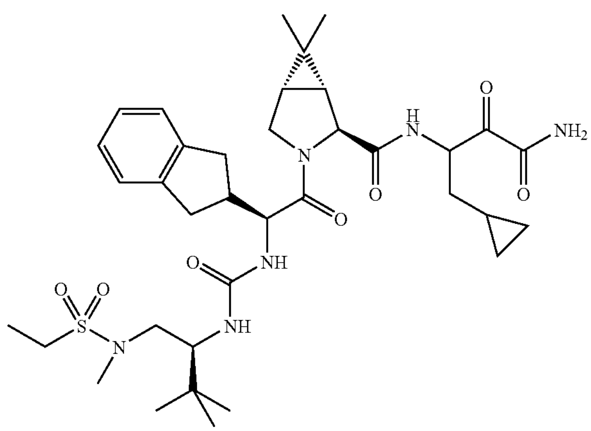 | A |

TABLE 2-continued

| Entry | Structure | Ki* |
|---|---|---|
| 11291 | 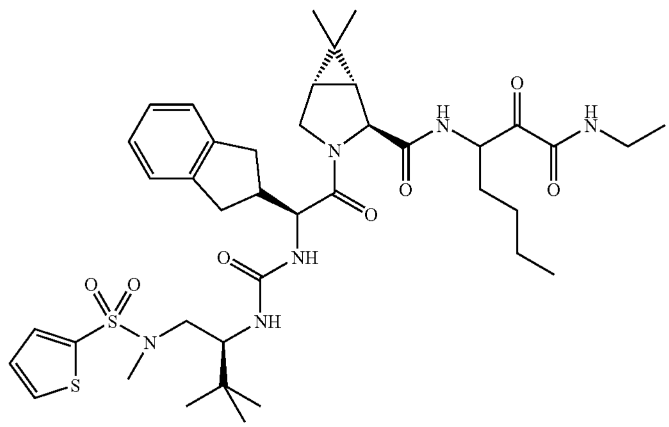 | A |
| 11292 | 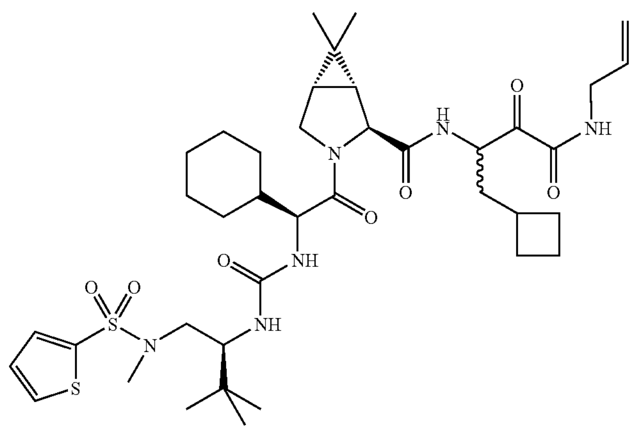 | A |
| 11293 | 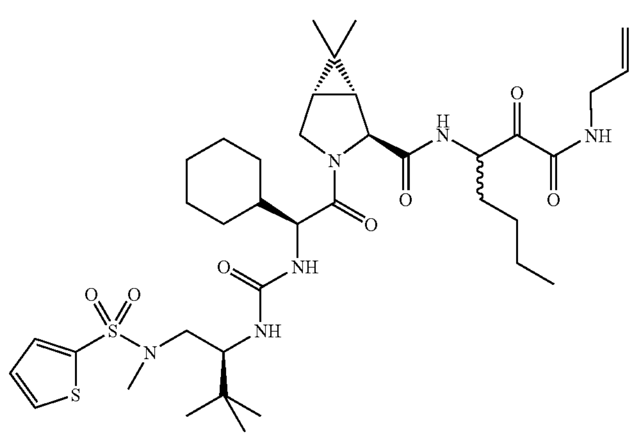 | A |

TABLE 2-continued

| Entry | Structure | Ki* |
|-------|-----------|-----|
| 11294 | 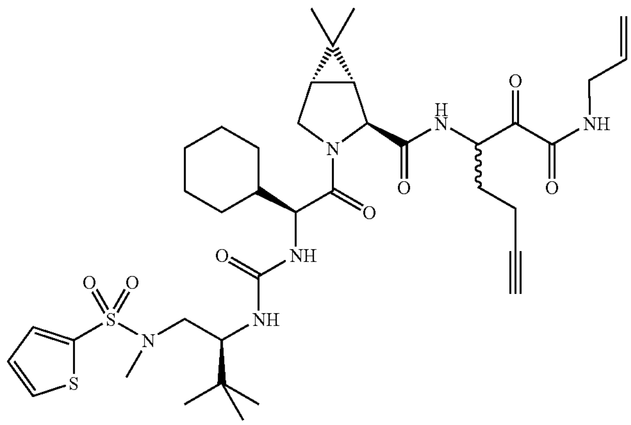 | A |
| 11295 | 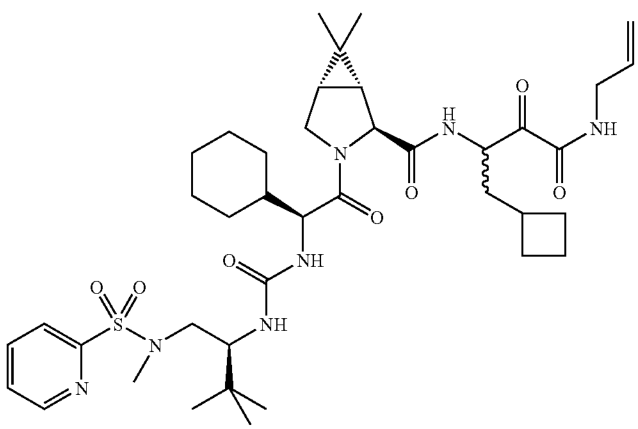 | A |
| 11296 | 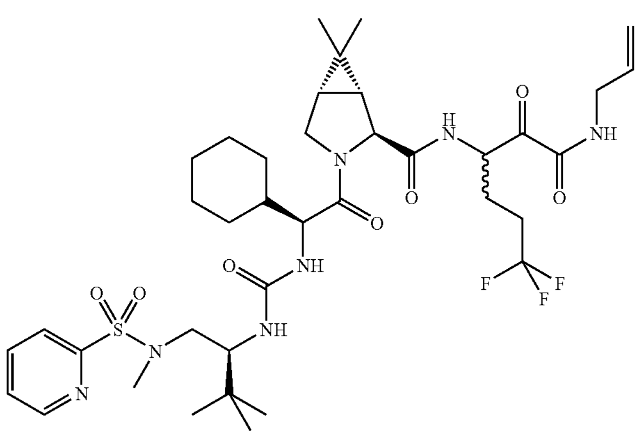 | A |

TABLE 2-continued

| Entry | Structure | Ki* |
|---|---|---|
| 11297 | 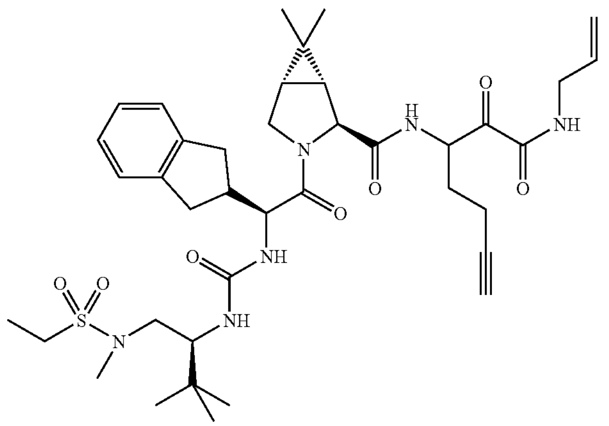 | A |
| 11298 | 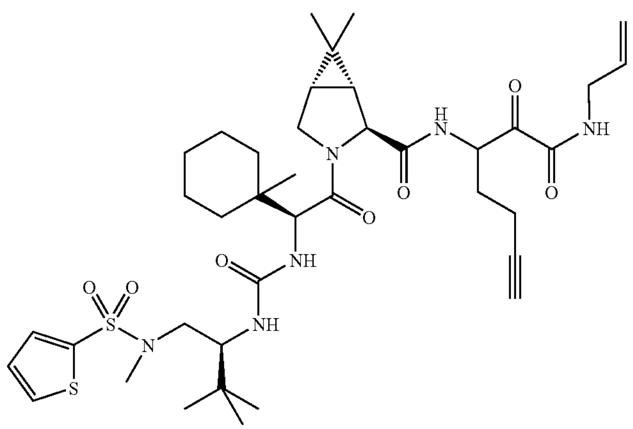 | A |
| 11299 | 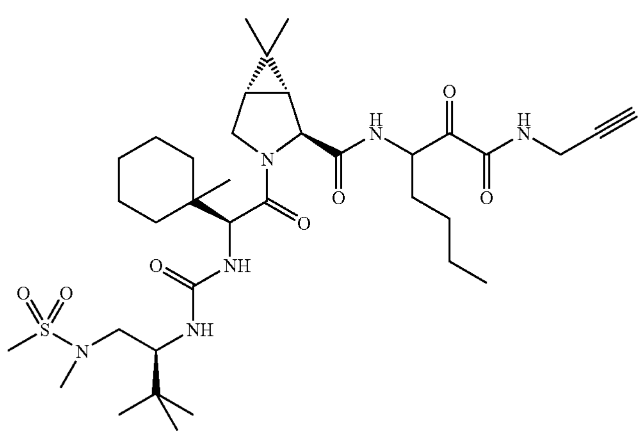 | A |

TABLE 2-continued

| Entry | Structure | Ki* |
|-------|-----------|-----|
| 11300 | 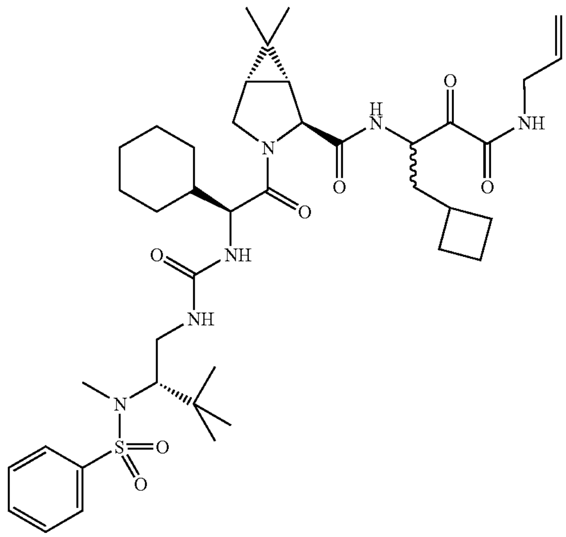 | C |
| 11311 | 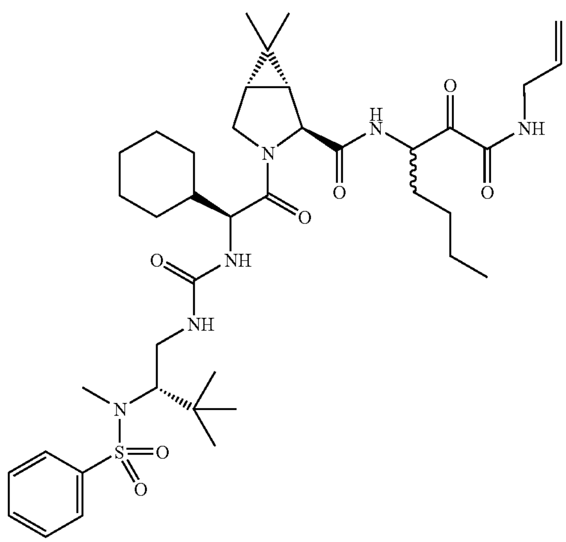 | C |
| 11312 | 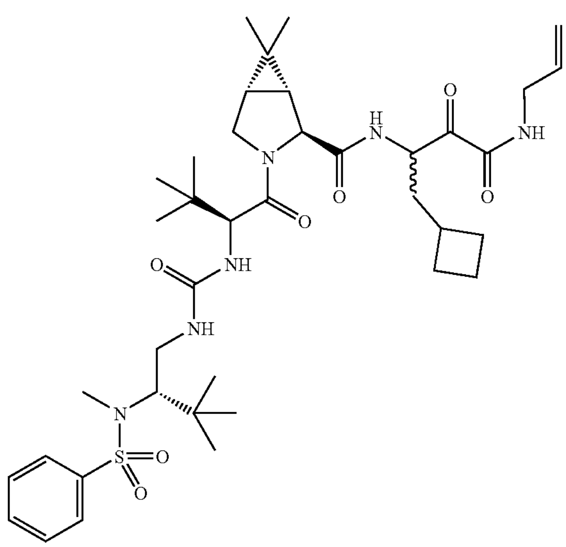 | C |

TABLE 2-continued

| Entry | Structure | Ki* |
|-------|-----------|-----|
| 11313 | 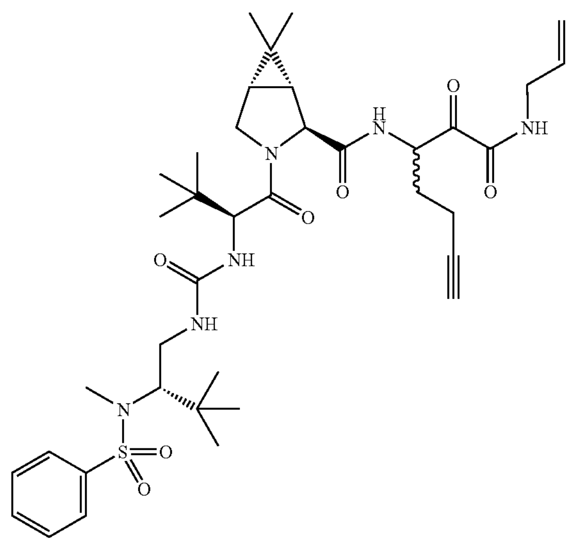 | C |
| 11314 | 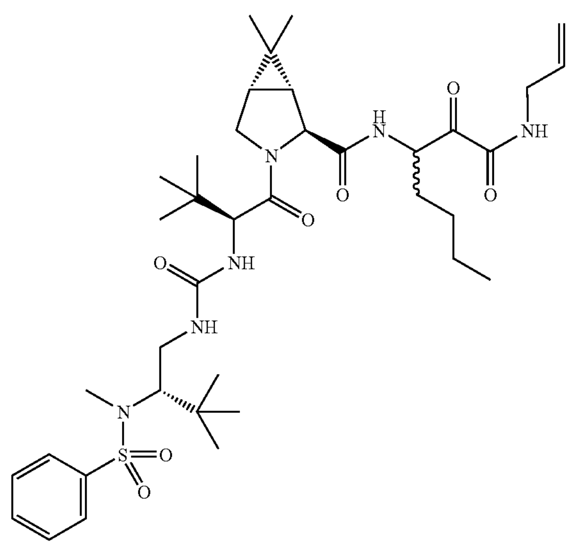 | C |
| 11315 | 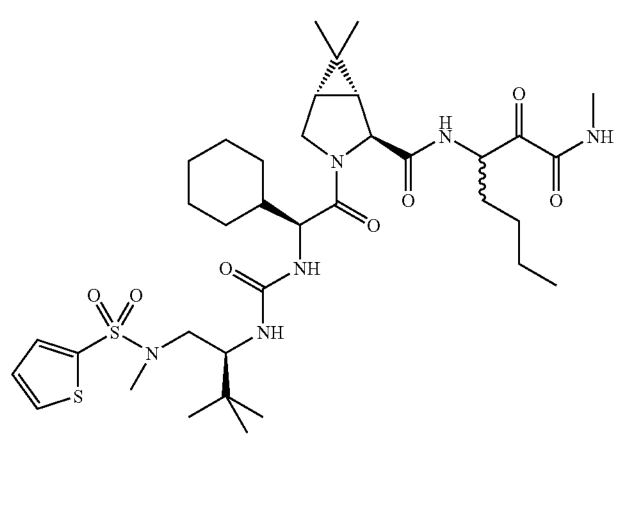 | A |

TABLE 2-continued

| Entry | Structure | Ki* |
|-------|-----------|-----|
| 11316 | 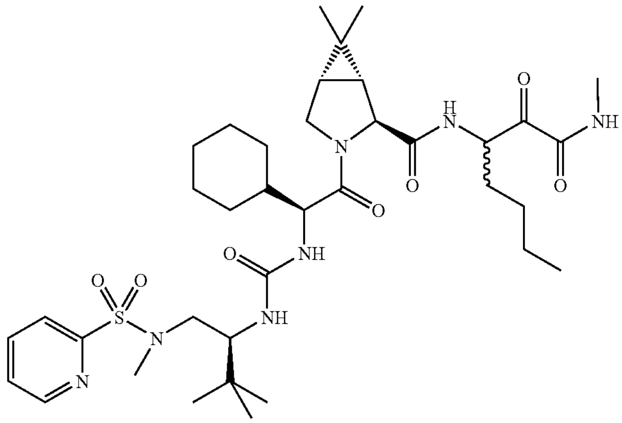 | A |
| 11317 | 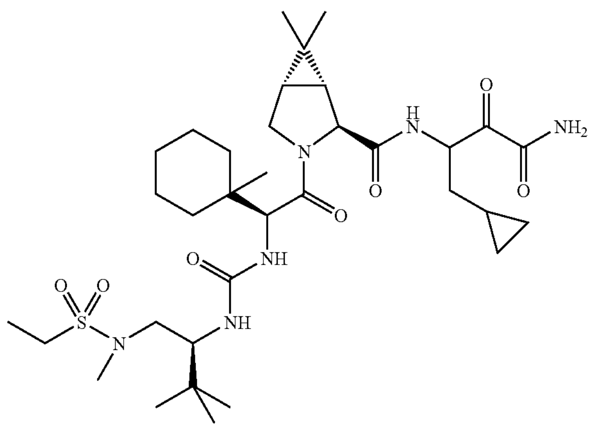 | A |
| 11318 | 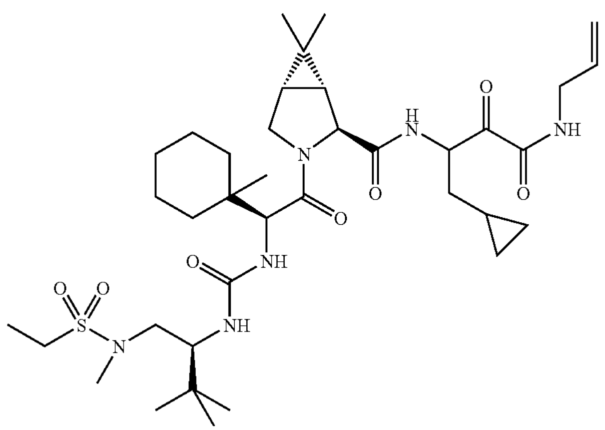 | A |

TABLE 2-continued

| Entry | Structure | Ki* |
|---|---|---|
| 11319 | 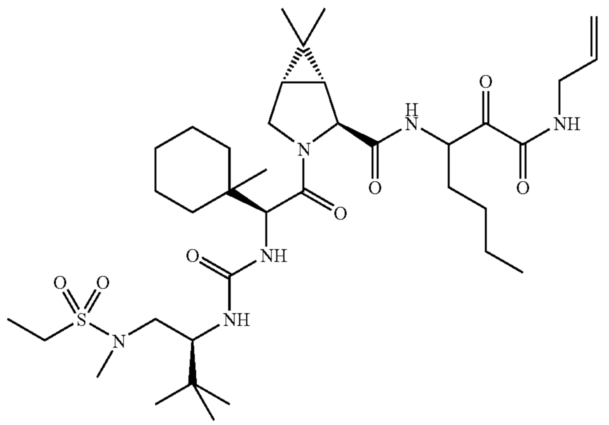 | A |
| 11320 | 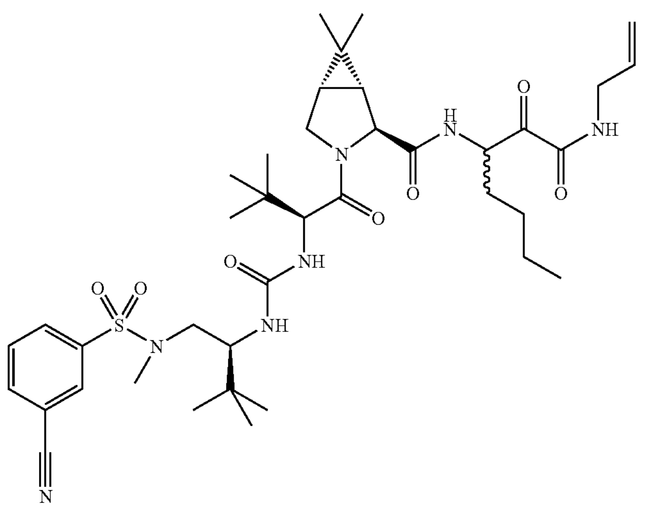 | A |
| 11321 | 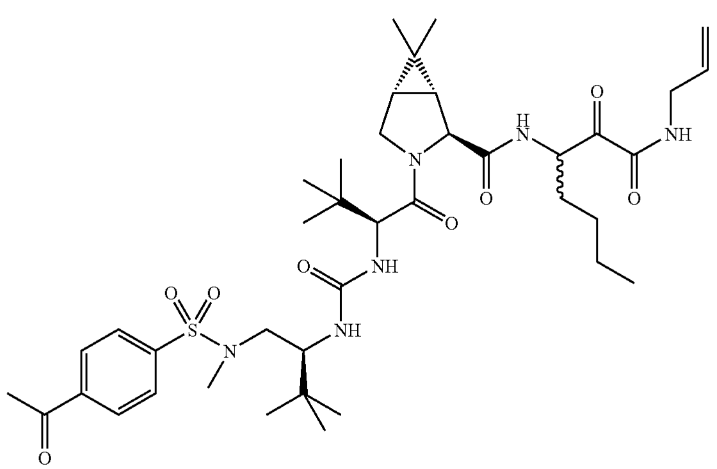 | A |

TABLE 2-continued
| Entry | Structure | Ki* |
|---|---|---|
| 11322 | 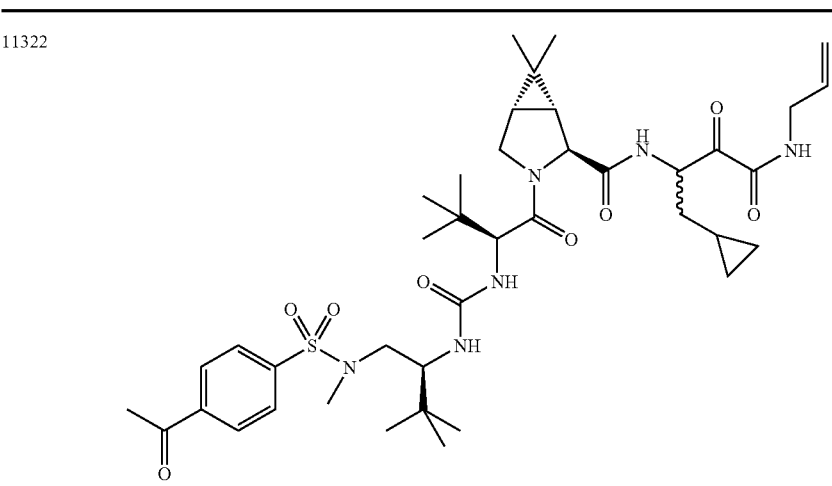 | A |
| 11323 | 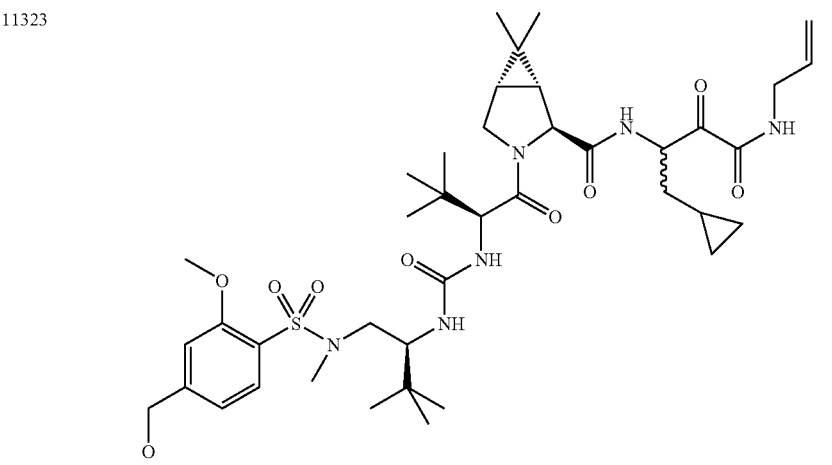 | A |
| 11324 | 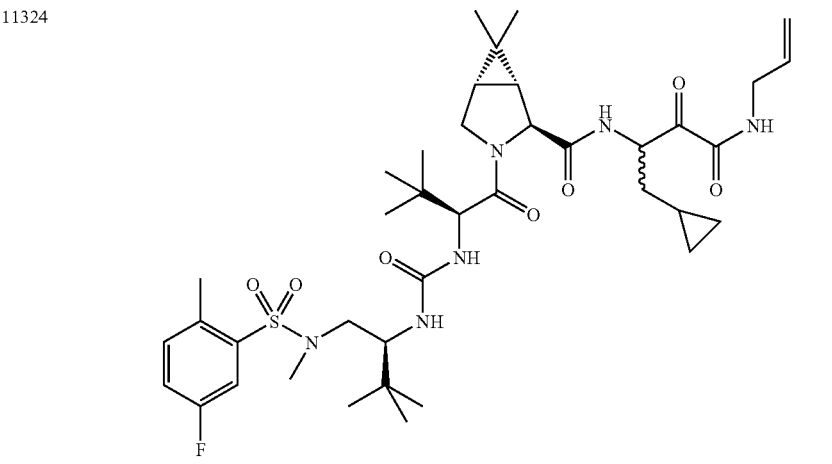 | A |

TABLE 2-continued

| Entry | Structure | Ki* |
|---|---|---|
| 11325 | 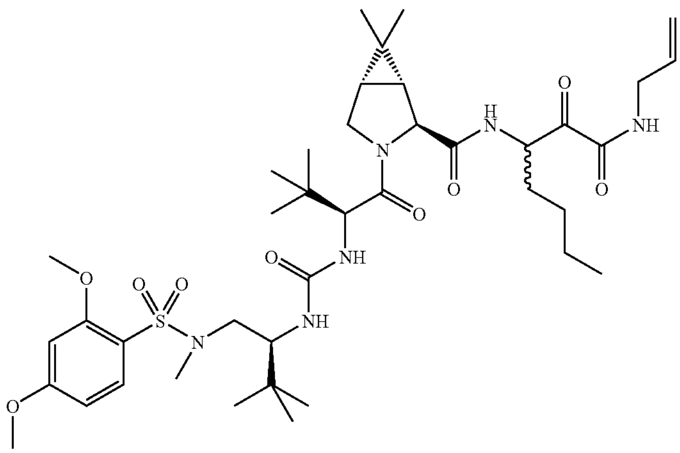 | A |
| 11326 | 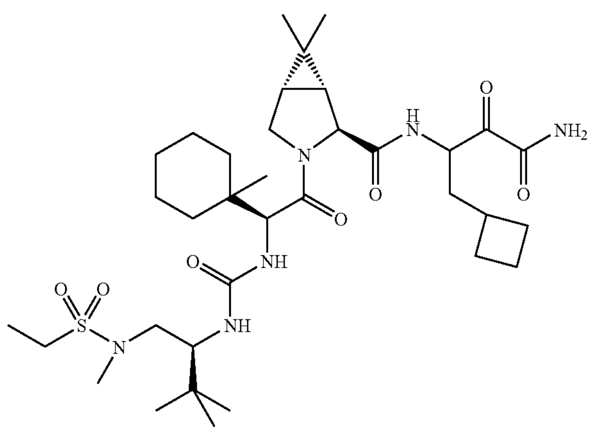 | A |
| 11327 | 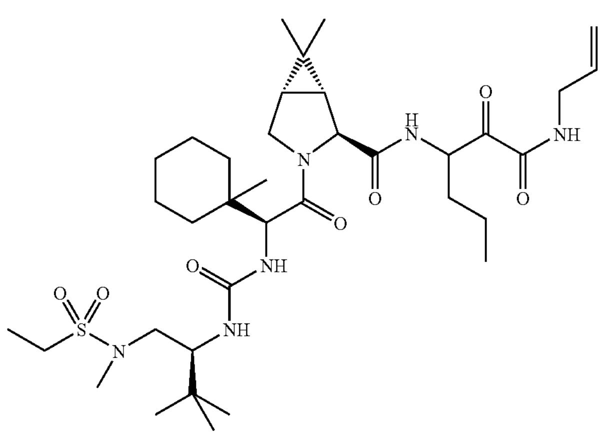 | A |

TABLE 2-continued

| Entry | Structure | Ki* |
|---|---|---|
| 11328 | 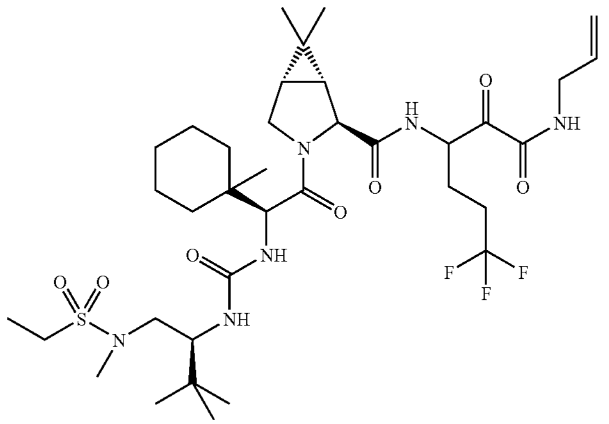 | A |
| 11329 | 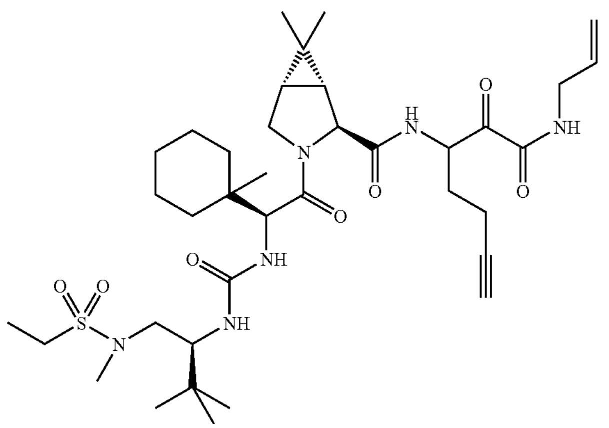 | A |
| 11330 | 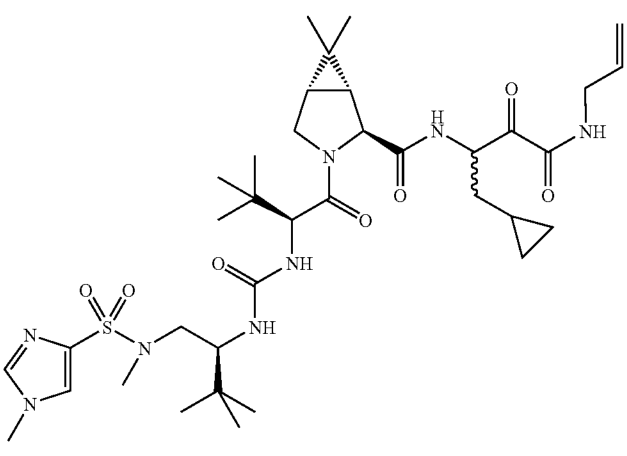 | A |

TABLE 2-continued
| Entry | Structure | Ki* |
|---|---|---|
| 11331 | 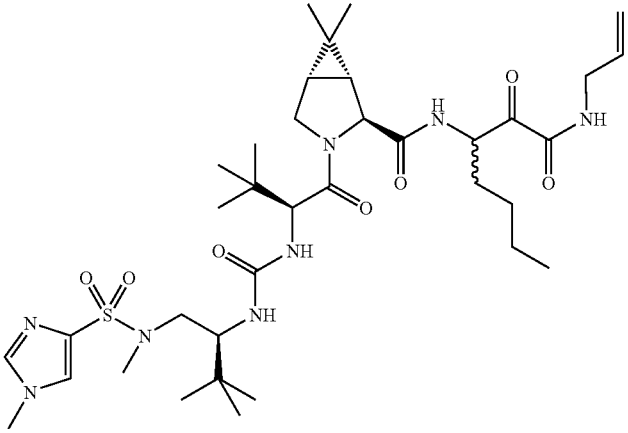 | A |
| 11332 | 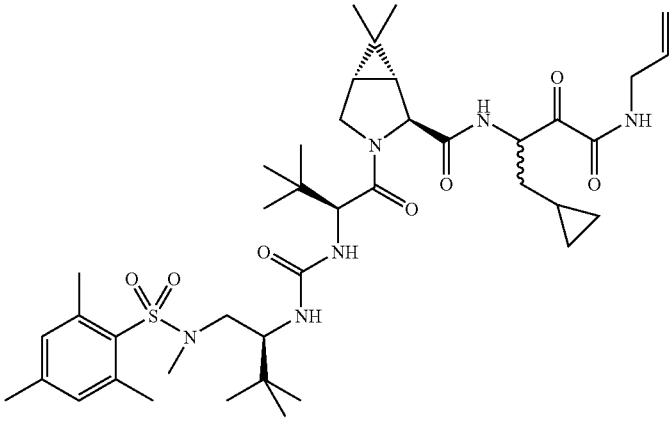 | B |
| 11333 | 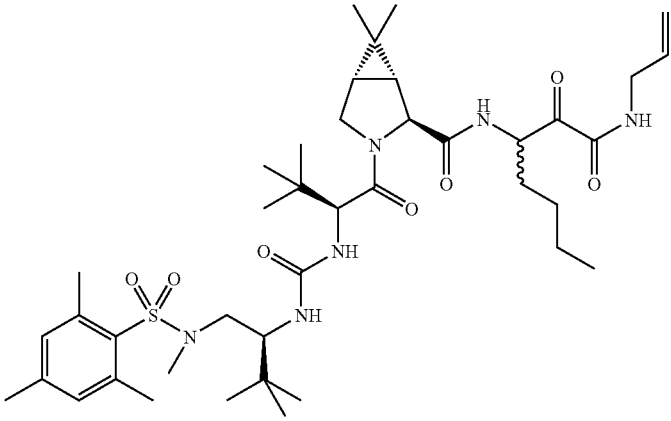 | B |

TABLE 2-continued
| Entry | Structure | Ki* |
|---|---|---|
| 11334 | 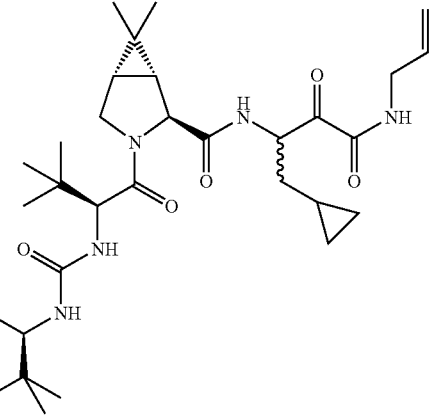 | A |
| 11335 | 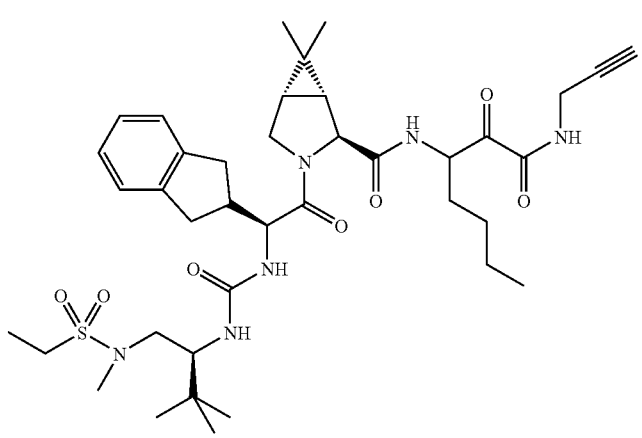 | A |
| 11336 | 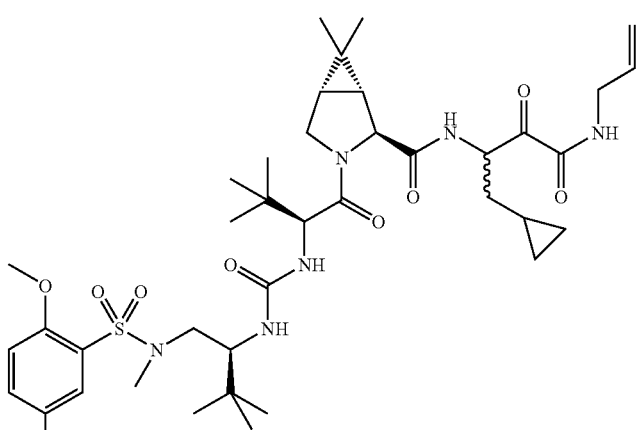 | A |

TABLE 2-continued
| Entry | Structure | Ki* |
|---|---|---|
| 11337 | 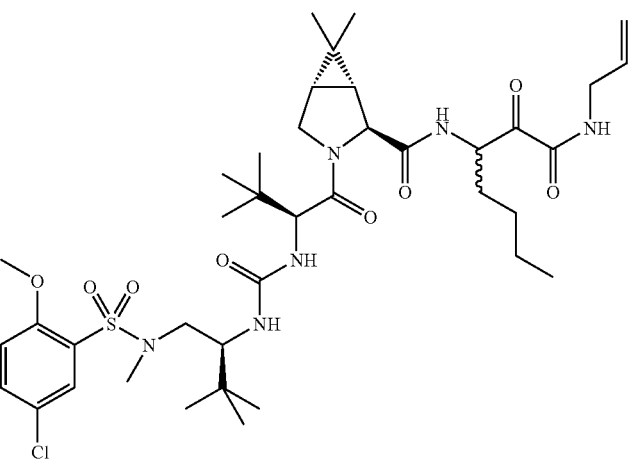 | A |
| 11338 | 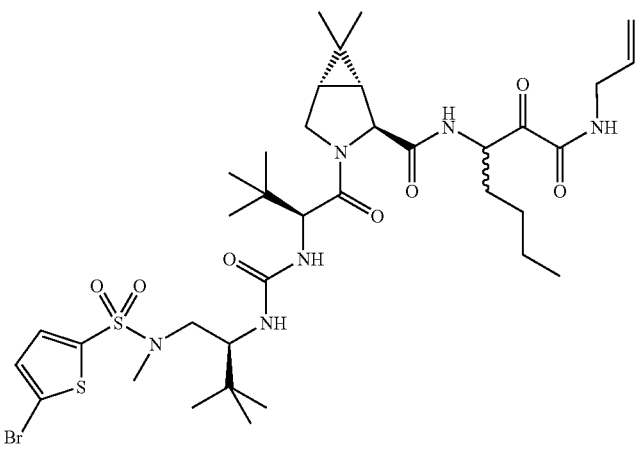 | A |
| 11339 | 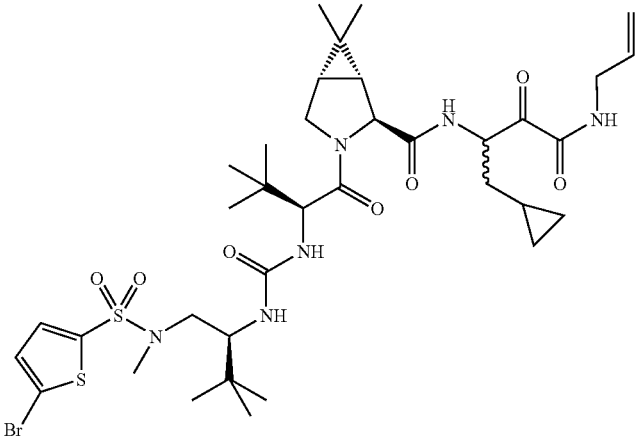 | A |

TABLE 2-continued
| Entry | Structure | Ki* |
|---|---|---|
| 11340 | 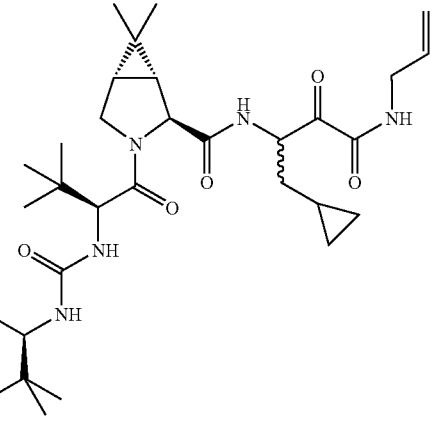 | A |
| 11341 | 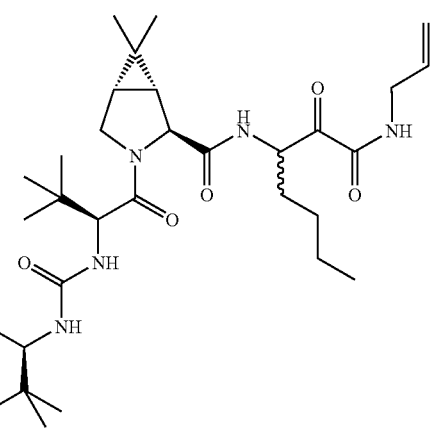 | A |
| 11342 | 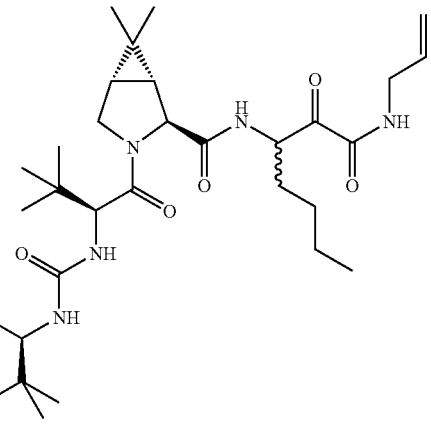 | A |

TABLE 2-continued
| Entry | Structure | Ki* |
|---|---|---|
| 11343 | 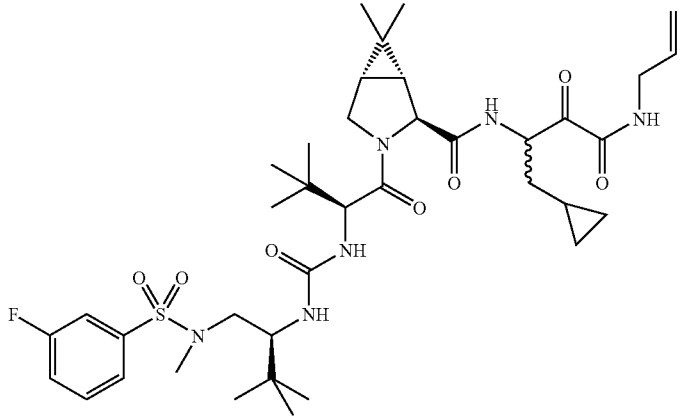 | A |
| 11344 | 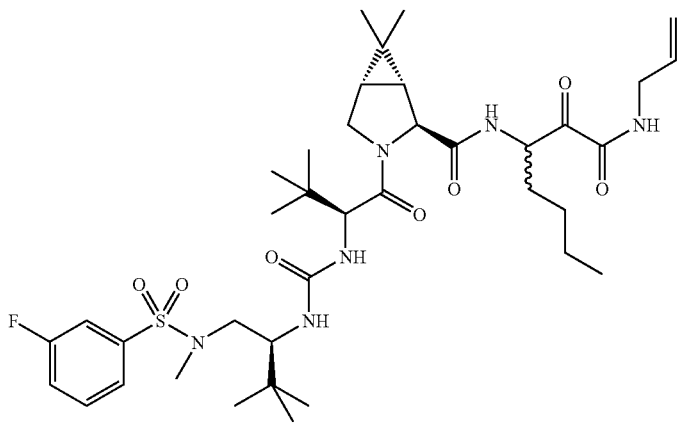 | A |
| 11345 | 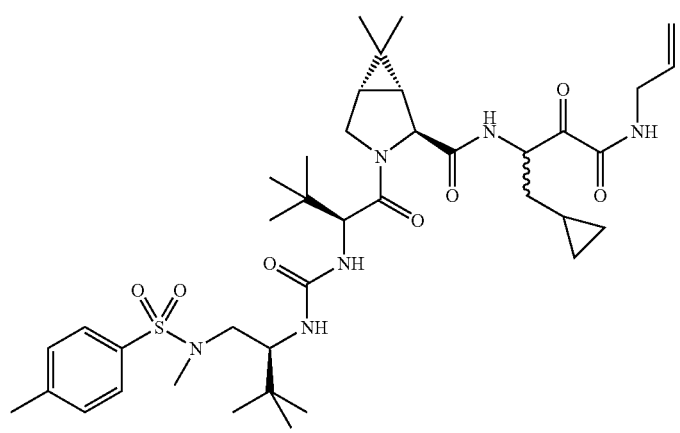 | A |

TABLE 2-continued
| Entry | Structure | Ki* |
|---|---|---|
| 11346 | 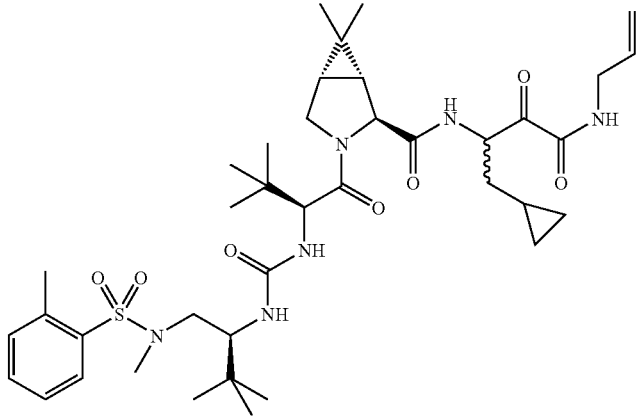 | A |
| 11347 | 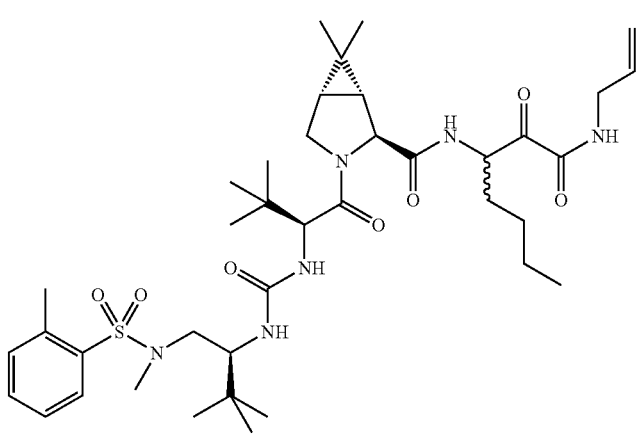 | A |
| 11348 | 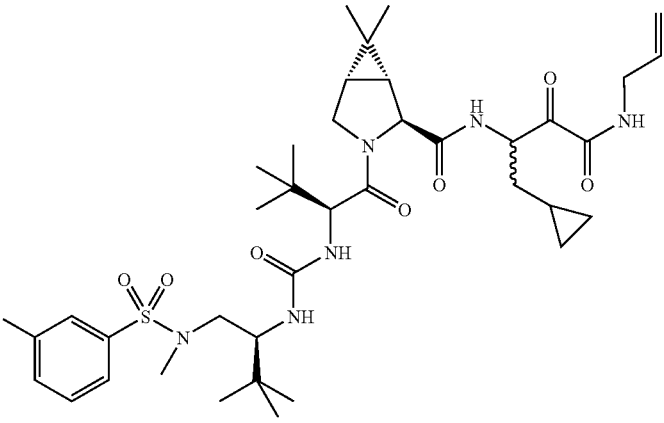 | A |

TABLE 2-continued
| Entry | Structure | Ki* |
|---|---|---|
| 11349 | 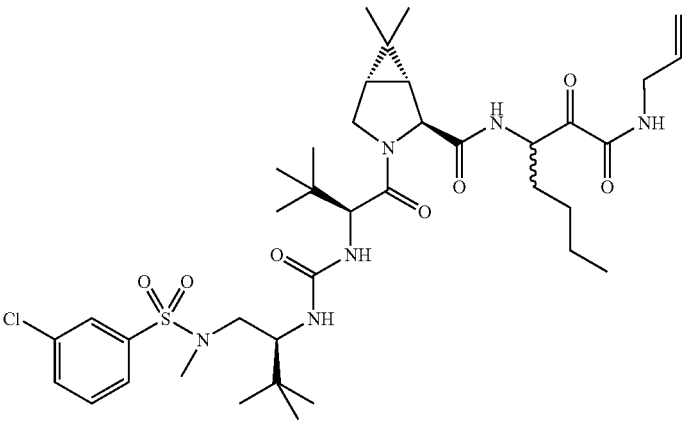 | A |
| 11350 | 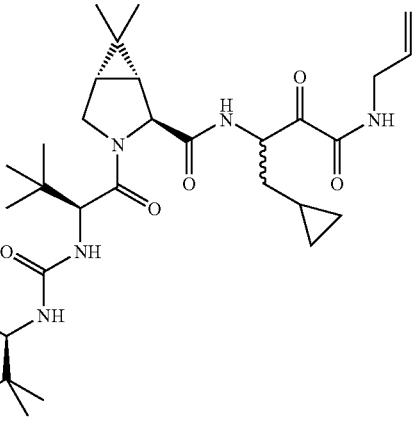 | A |
| 11351 | 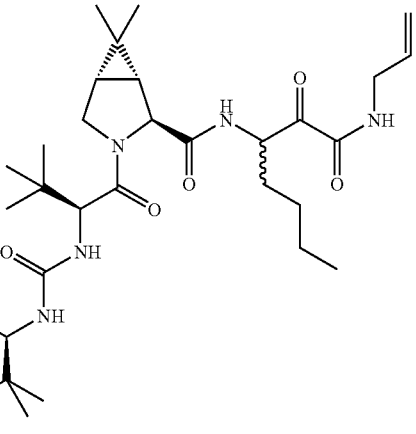 | A |

TABLE 2-continued
| Entry | Structure | Ki* |
|---|---|---|
| 11352 | 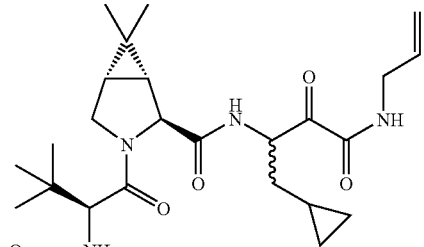 | A |
| 11353 | 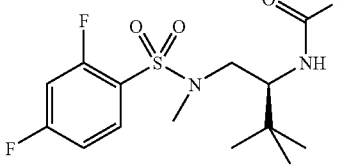 | A |
| 11354 | 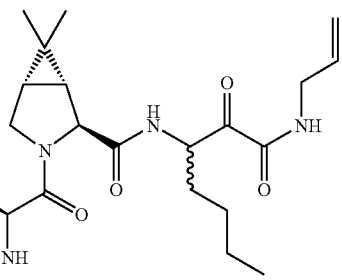 | A |

TABLE 2-continued

| Entry | Structure | Ki* |
|---|---|---|
| 11355 | 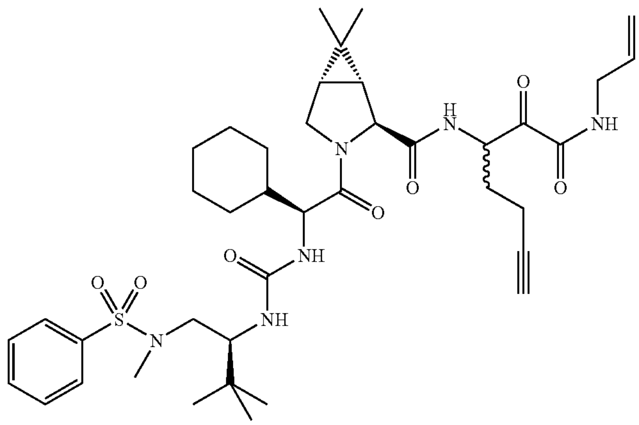 | A |
| 11356 | 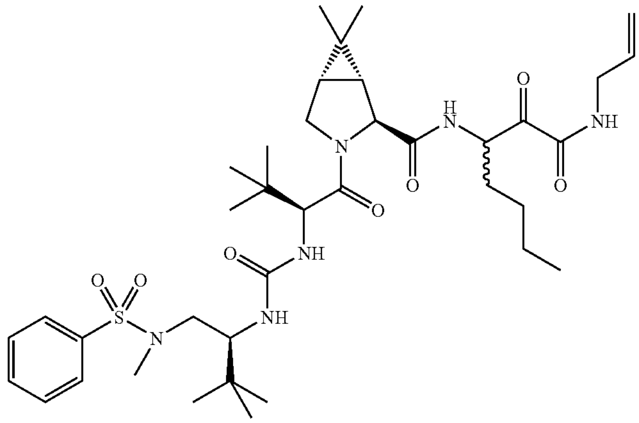 | A |
| 11357 | 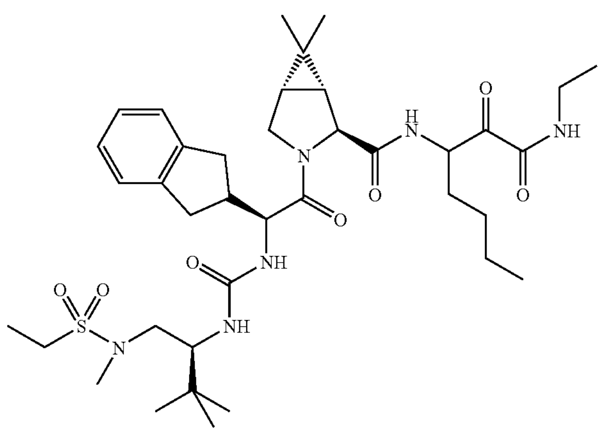 | A |

TABLE 2-continued

| Entry | Structure | Ki* |
|---|---|---|
| 11358 | 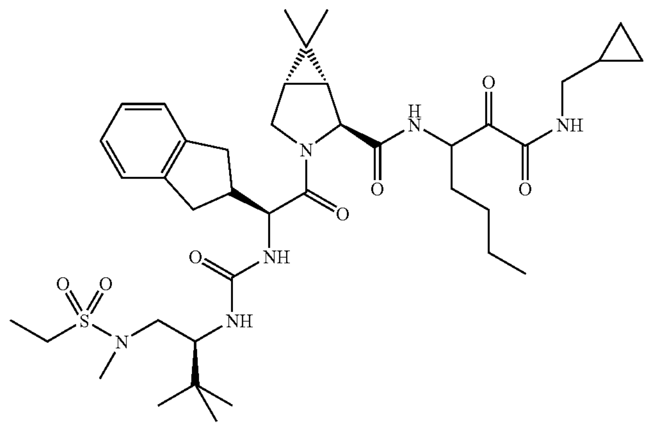 | A |
| 11359 | 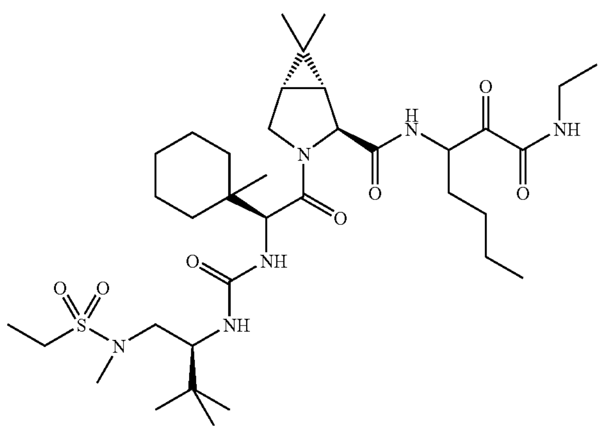 | A |
| 11360 | 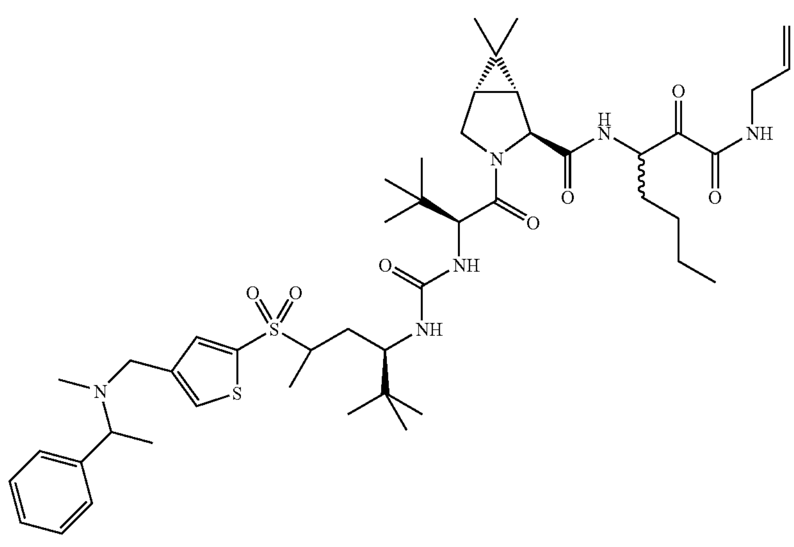 | A |

TABLE 2-continued

| Entry | Structure | Ki* |
|---|---|---|
| 11361 | 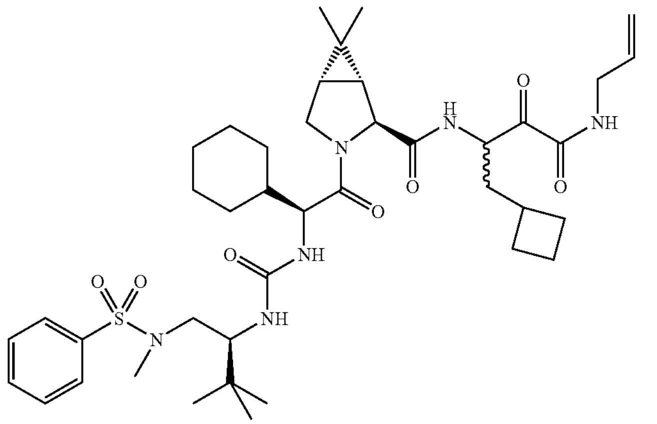 | A |
| 11362 | 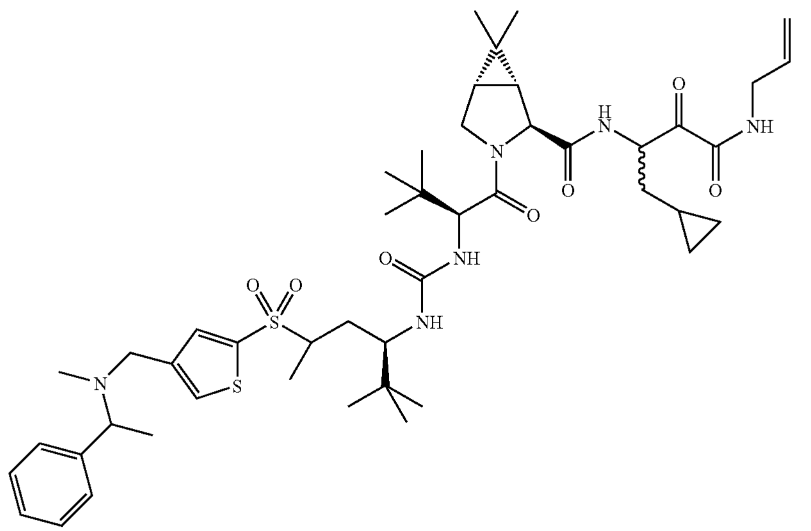 | A |
| 11363 | 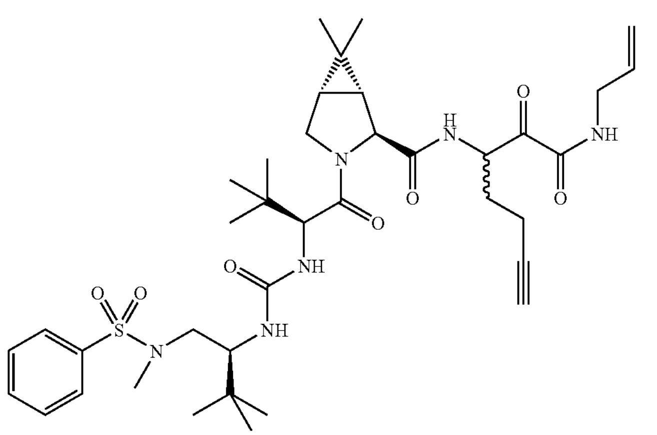 | A |

TABLE 2-continued
| Entry | Structure | Ki* |
|---|---|---|
| 11364 | 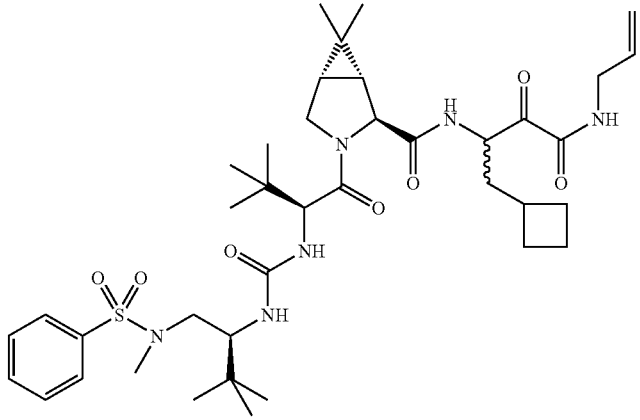 | B |
| 11365 | 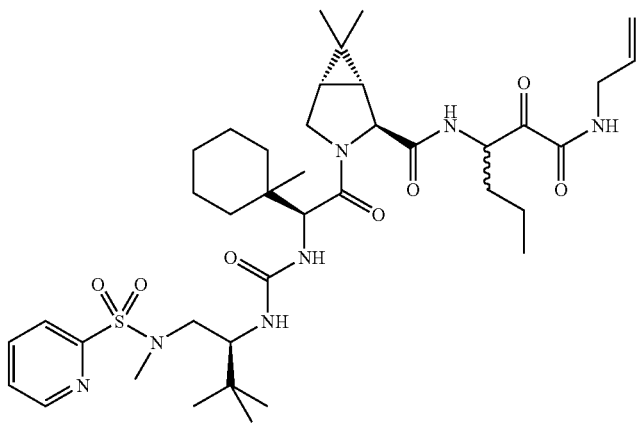 | A |
| 11366 | 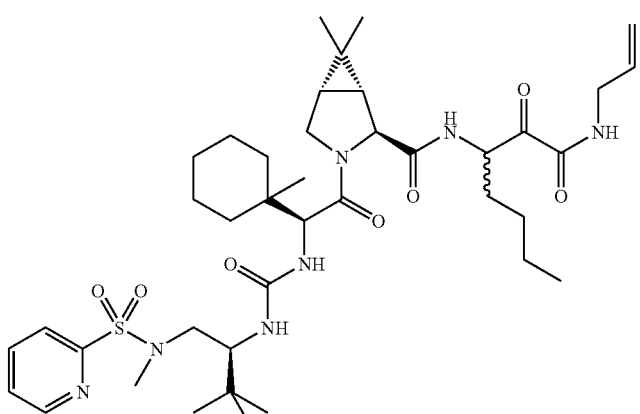 | A |

TABLE 2-continued
| Entry | Structure | Ki* |
|---|---|---|
| 11367 | 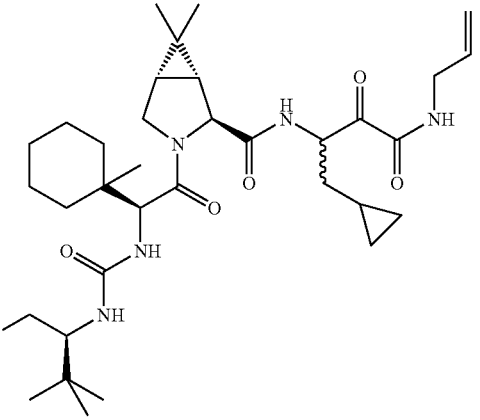 | A |
| 11368 | 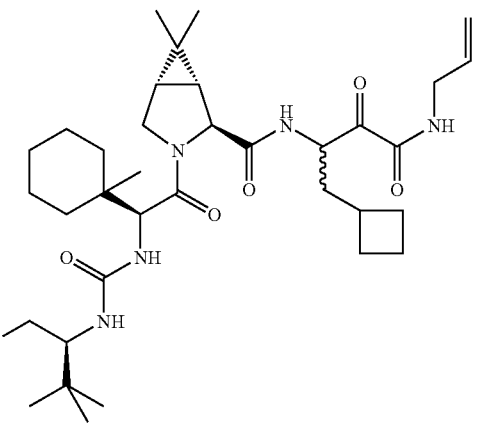 | A |
| 11369 | 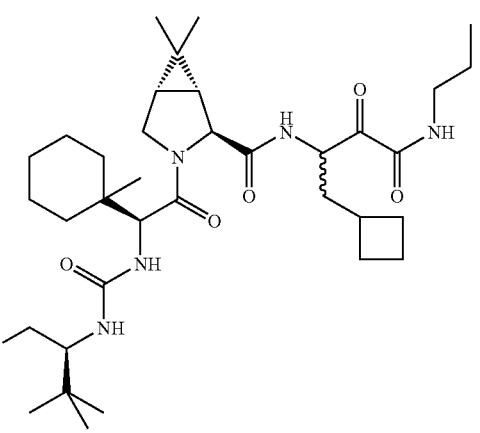 | B |

TABLE 2-continued

| Entry | Structure | Ki* |
|-------|-----------|-----|
| 11370 | 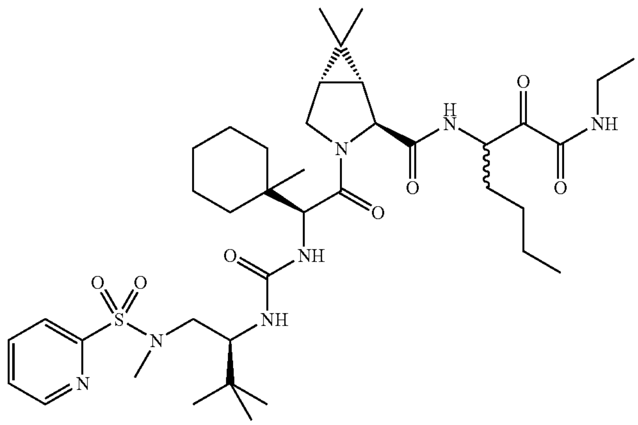 | A |
| 11371 | 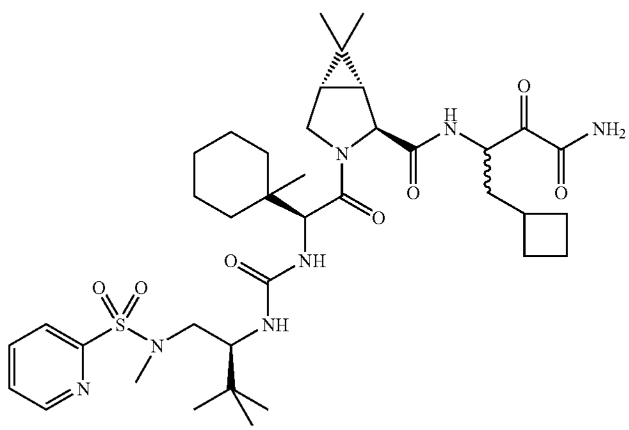 | A |
| 11372 | 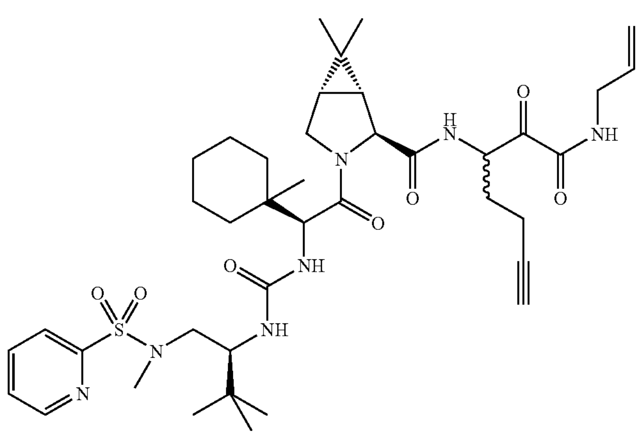 | A |

TABLE 2-continued
| Entry | Structure | Ki* |
|---|---|---|
| 11373 | 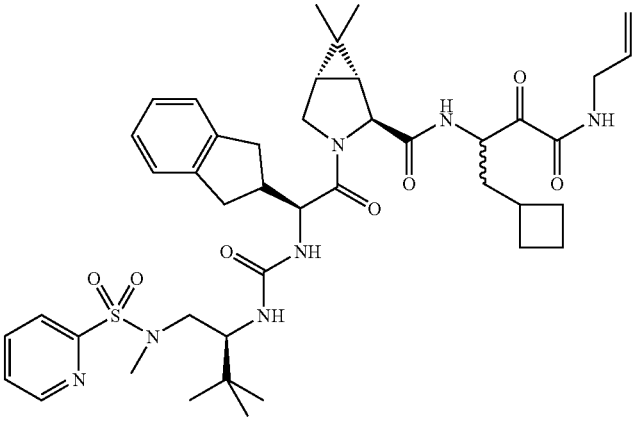 | A |
| 11374 | 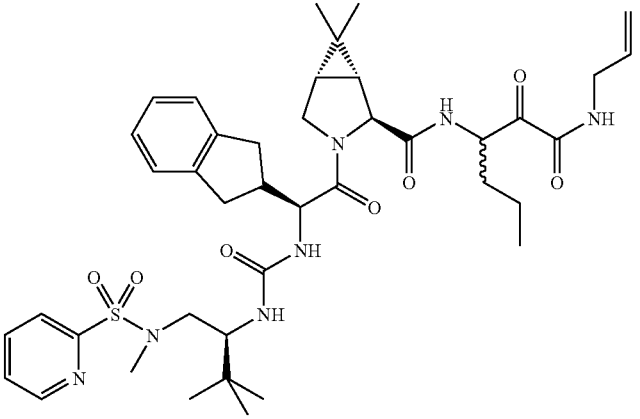 | A |
| 11375 | 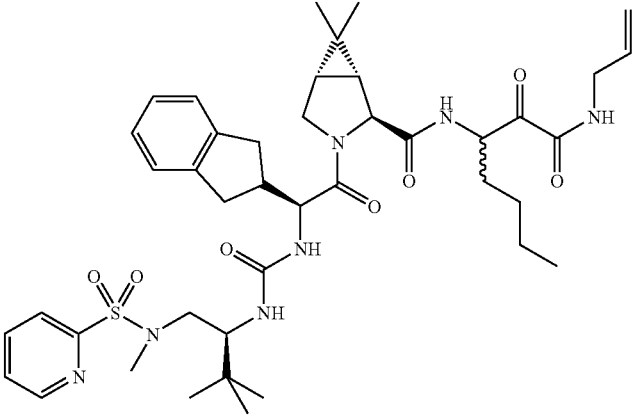 | A |

TABLE 2-continued

| Entry | Structure | Ki* |
|---|---|---|
| 11376 | 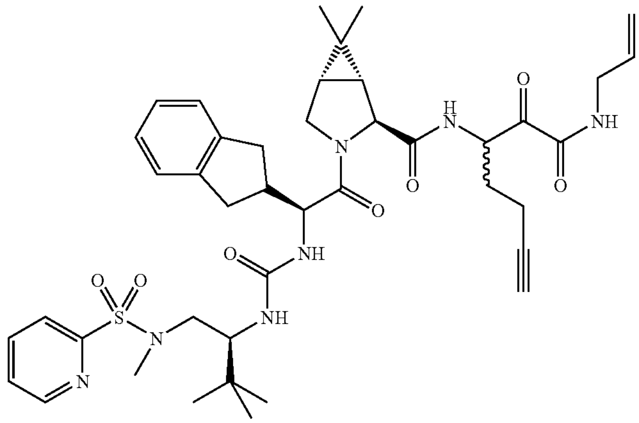 | A |
| 11377 | 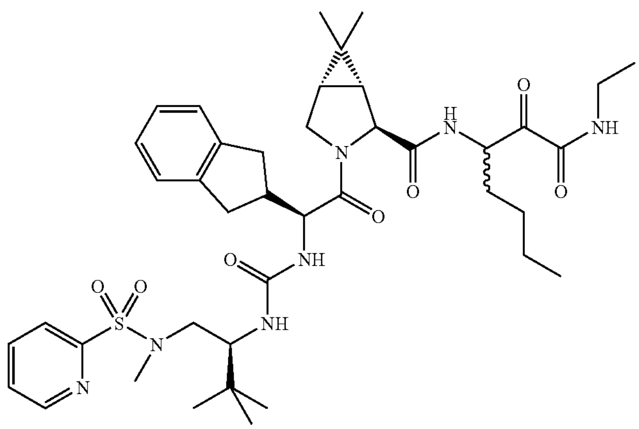 | A |
| 11378 | 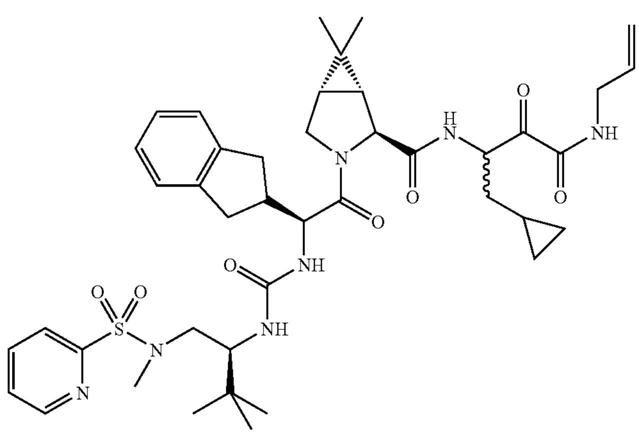 | B |

TABLE 2-continued

| Entry | Structure | Ki* |
|---|---|---|
| 11379 | 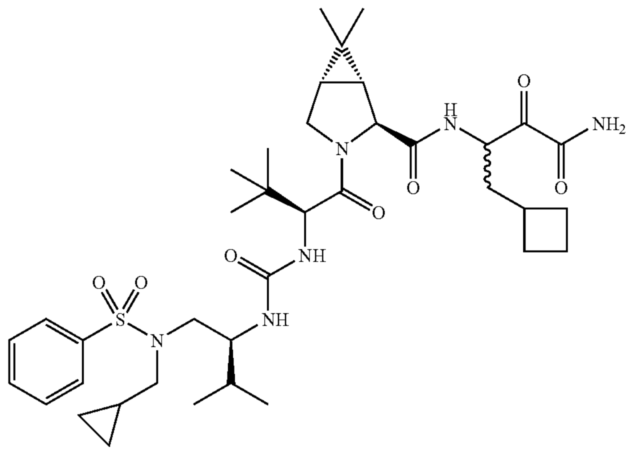 | A |
| 11380 | 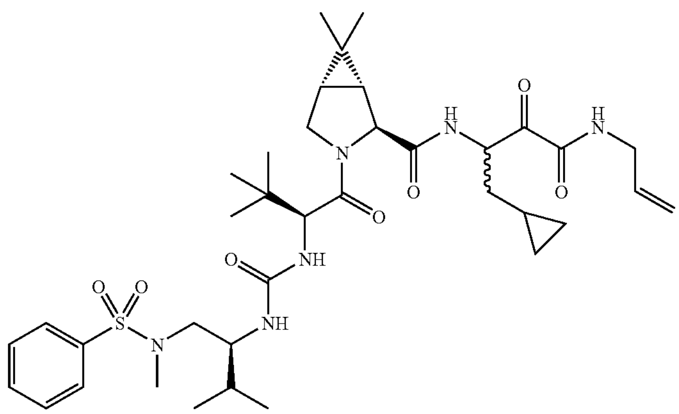 | A |
| 11381 | 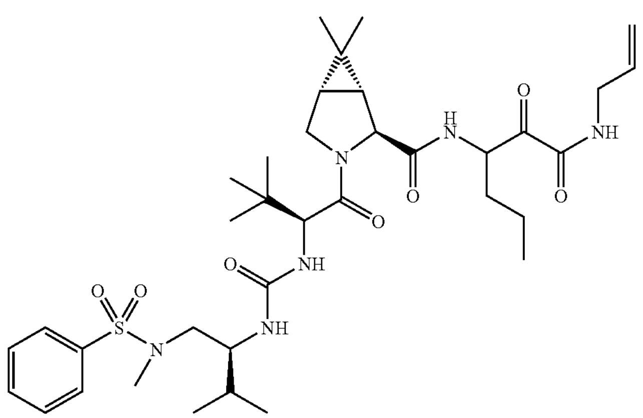 | A |

TABLE 2-continued

| Entry | Structure | Ki* |
|---|---|---|
| 11382 | 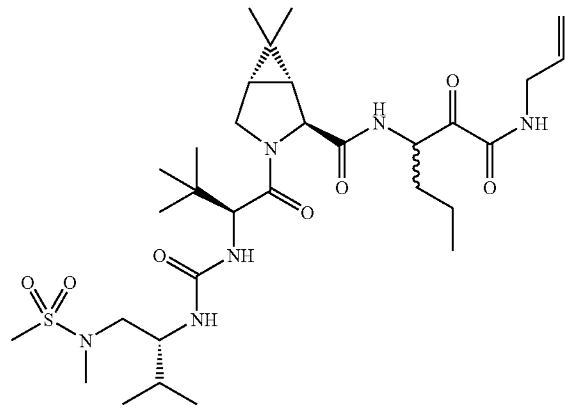 | A |
| 11383 | 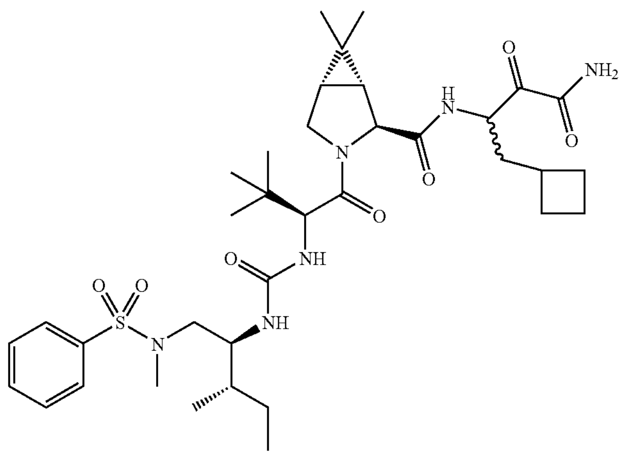 | A |
| 11384 | 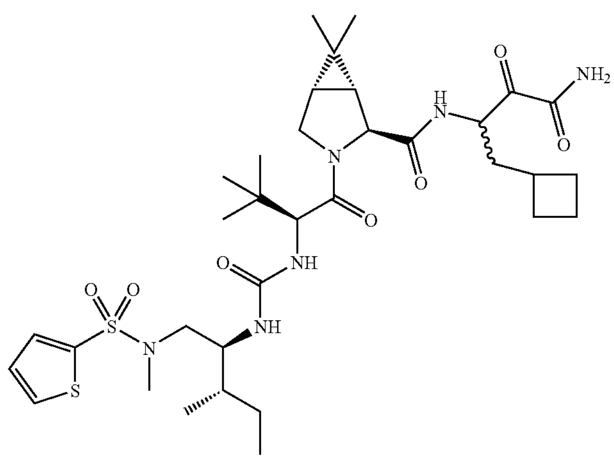 | A |

TABLE 2-continued

| Entry | Structure | Ki* |
|-------|-----------|-----|
| 11385 | 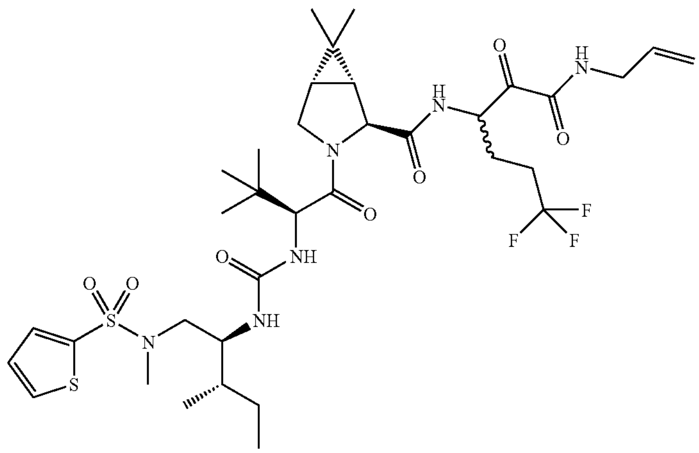 | A |
| 11386 | 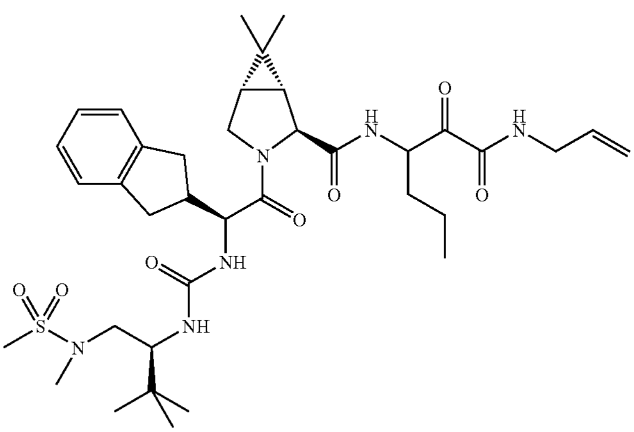 | A |
| 11387 | 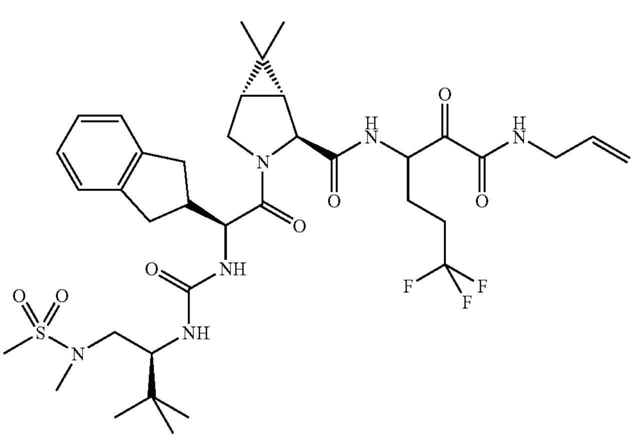 | A |

TABLE 2-continued
| Entry | Structure | Ki* |
|---|---|---|
| 11388 | 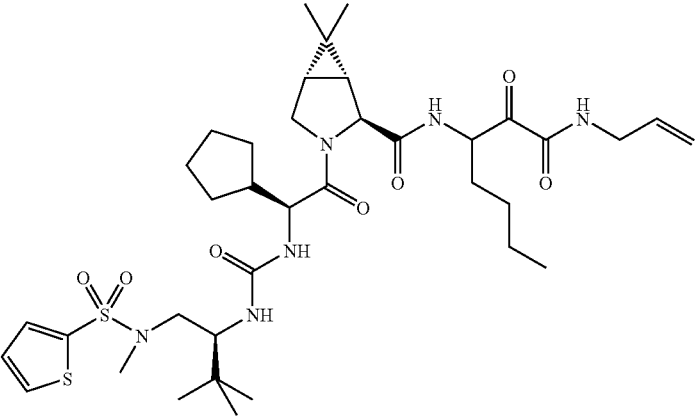 | A |
| 11389 | 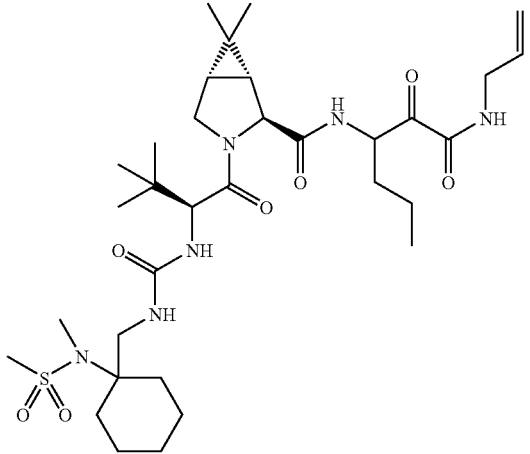 | C |
| 11390 | 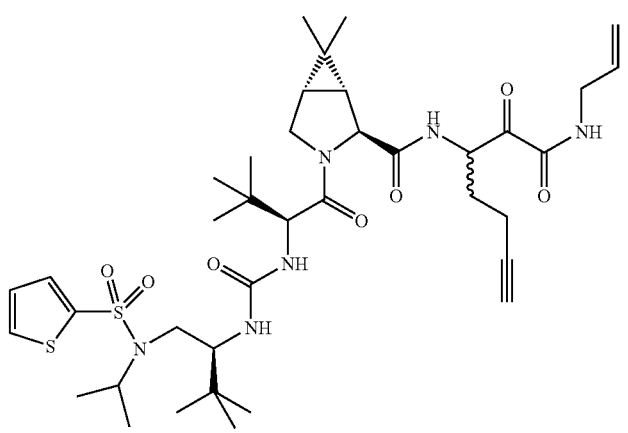 | A |

TABLE 2-continued

| Entry | Structure | Ki* |
|---|---|---|
| 11391 | 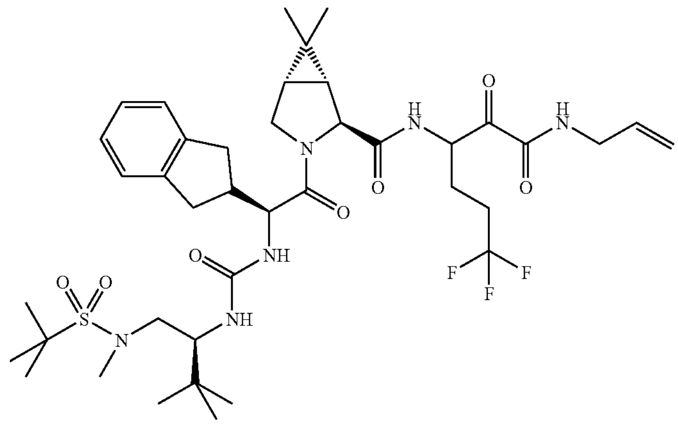 | B |

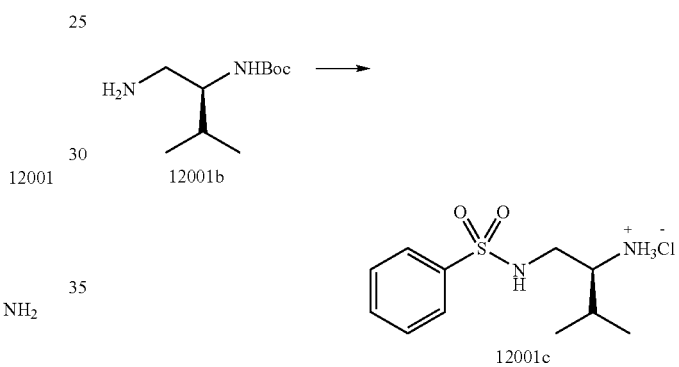

Example 10

Synthesis of Compound of Formula 12001

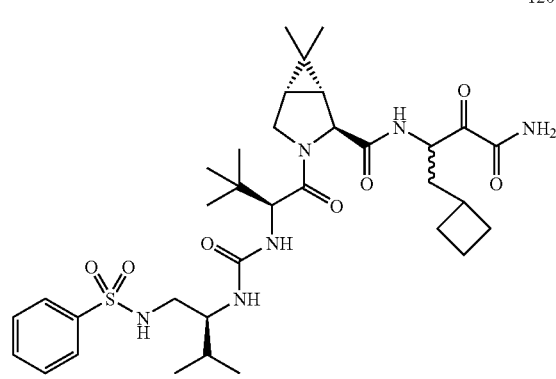

12001

Step A:

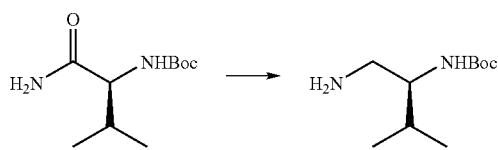

12001a  12001b

A solution of 12001a (2.0 g, 9.2 mmol, Indofine chemicals) in toluene (150 mL) was treated with BH$_3$.DMS (~10 M, 3 mL) and heated at 90° C. for 2 h. The reaction mixture was cooled to 0° C. and diluted with 2 M aq. NaOH. The organic layer was extracted with CH$_2$Cl$_2$ and the combined organic layers were dried (MgSO$_4$) filtered concentrated in vacuo to yield 1.1 g of 12001 b.

Step B:

H$_2$N–⟨⟩–NHBoc ⟶

12001b

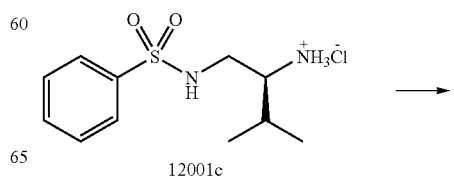

12001c

A solution of amine 12001b (500 mg, 2.5 mmol) in CH$_2$Cl$_2$ (10 mL) was treated with benzene sulfonyl chloride (669 mg, 3.8 mmol) and Et$_3$N (384 mg, 3.8 mmol) and stirred overnight at 0° C. The reaction mixture was diluted with aq. 1 M HCl and extracted with CH$_2$Cl$_2$. The combined organic layer was dried, filtered and concentrated in vacuo. The residue was purified by chromatography (SiO$_2$, EtOAc/Hexanes 1:3) to yield 552 mg of boc protected phenyl sulfonamide compound.

A solution of Boc-compound (552 mg, 1.6 mmol) in 4M HCl in dioxane at rt. was stirred for 1 h and concentrated in vacuo. The residue was triturated with ether and the solid separating out was isolated by decanting the ether layer and dried in vacuum to yield 12001c.

Step C:

12001c

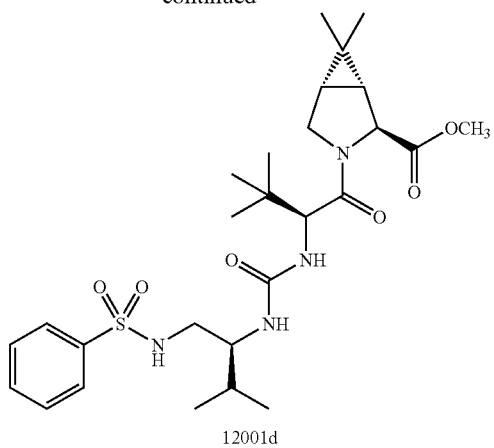

12001d

A solution of deprotected amine 12001c (139 mg, 0.5 mmol) in CH$_2$Cl$_2$/DMF (1:1, 20 mL) was treated with 4-nitrophenylcarbamate 1.16 (1.879 g, 4.20 mmol), NMM (1.062 g, 10.5 mmol) and stirred at rt. overnight. The reaction mixture was concentrated in vacuo diluted with CH$_2$Cl$_2$ (200 mL) and washed with aq. HCl (1M, 2×125 mL), aq. saturated NaHCO$_3$ (2×125 mL), brine (100 mL), dried (MgSO$_4$), filtered, and purified by chromatography (SiO$_2$, Hexanes/EtOAc 1:2) to yield 12001d.

Step D:

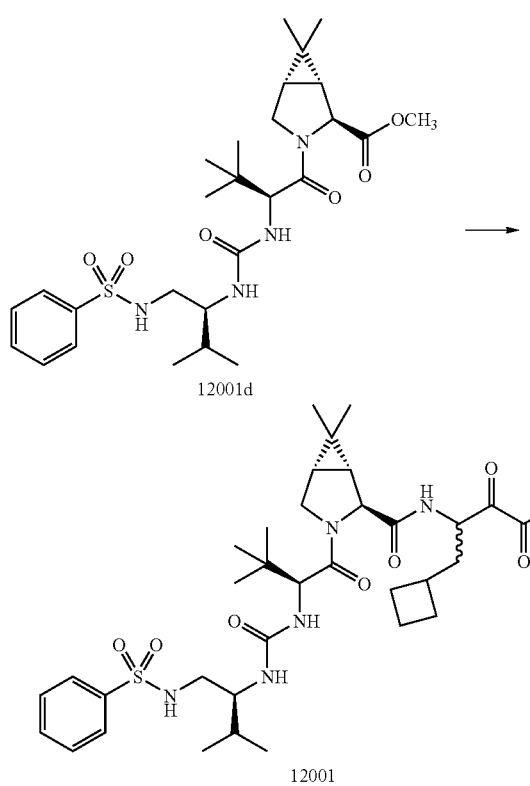

12001d

12001

Intermediate 12001d was converted to 12001 by coupling to intermediate 10.11 followed by Moffett oxidation identical to the procedures described in preparative example-6 of synthesis of 11001, Step D and Step E.

Example 11

Synthesis of Compound of Formula 12002

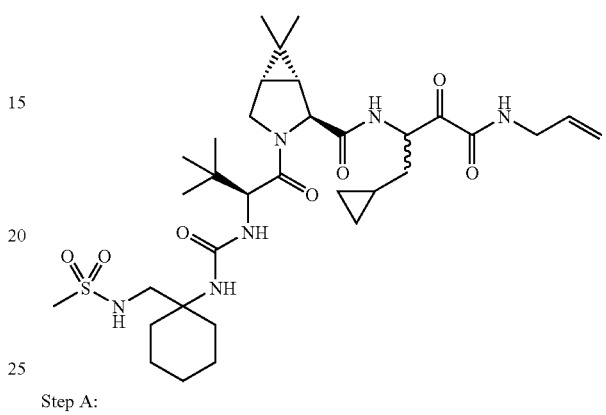

12002

Step A:

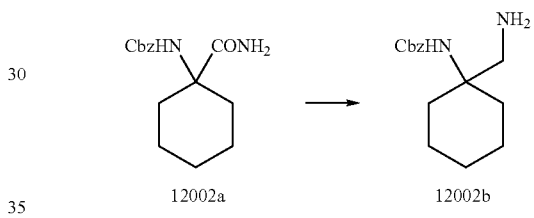

12002a      12002b

A solution 12002a (Gregory, H. et al.; *J. Chem. Soc.* 1968; 531) (11.62 g, 42.08 mmol) in dry toluene was treated with BH$_3$.DMS (~10 M soln, 6.3 mL) and heated at 70° C. overnight. The reaction mixture was cooled to rt and quenched with aq. NaOH and extracted with CH$_2$Cl$_2$. The combined organic layers were extracted with brine and concentrated in vacuo to yield 12002b 8.77 g (80%).

Step B:

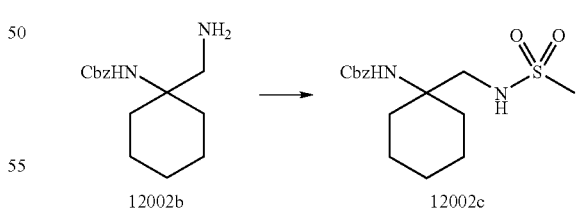

12002b      12002c

A solution of 12002b (2 g, 7.24 mmol) in methylene chloride was treated with pyridine (7.9 g, 100 mmol) and methanesulfonyl chloride (1.24 g, 10.86 mmol) and stirred at rt. for 24 h. The reaction mixture was washed with aq HCl, saturated NaHCO$_3$ and brine. The organic layer was dried (MgSO$_4$) filtered, concentrated in vacuo and purified by chromatography (SiO$_2$, acetone/Hexanes 1:2) to yield 12002c.

Step C:

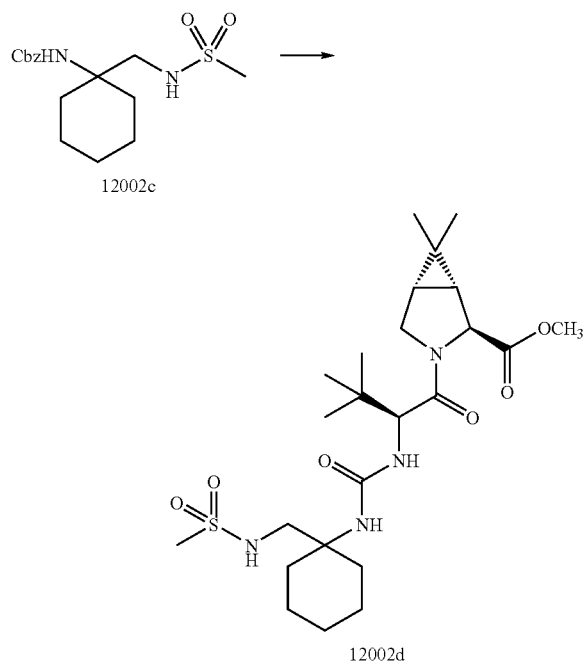

A solution of 12002c (465 mg, 1.37 mmol) in methanol was treated with palladium on carbon and hydrogenated for 2 h at 50 psi. The reaction mixture was filtered through a plug of Celite® and concentrated in vacuo to isolate the deprotected amine which was used in the next reaction without further purification.

A solution of deprotected amine in $CH_2Cl_2$/DMF (1:1) was treated with 4-nitrophenylcarbamate 1.16 (612 mg, 1.37 mmol), NMM (548 mg, 5.48 mmol) and stirred at rt. for 12 h. The reaction mixture was concentrated in vacuo diluted with $CH_2Cl_2$ (200 mL) and washed with aq. HCl (1M, 2×125 mL), aq. saturated $NaHCO_3$ (2×125 mL), brine (100 mL), dried ($MgSO_4$), filtered, and purified by chromatography ($SiO_2$, Hexanes/acetone 1:4) to yield 12002d (560 mg).

Step D:

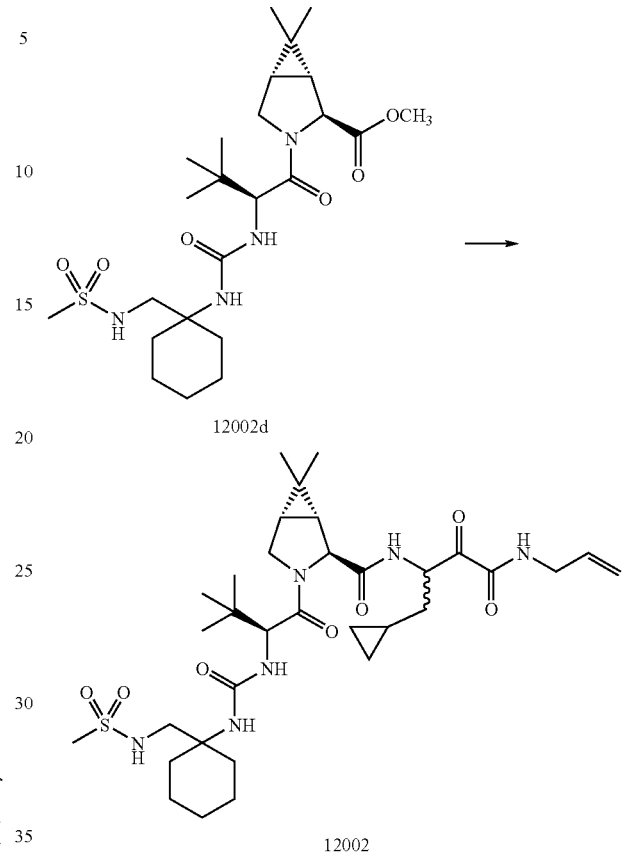

Intermediate 12002d was converted to 12002 by coupling to intermediate 12.04 followed by Dess-Martin oxidation identical to the procedures described in preparative example of synthesis of 11003, Step C and Step D.

Compounds shown in the following Table 3 were synthesized using similar reactions as shown in Examples above. Range of Ki* indicated: A≦75 nM; 75<B≦250 nM; C>250 nM.

TABLE 3

| Entry | Structure | Ki* |
|---|---|---|
| 12001 | 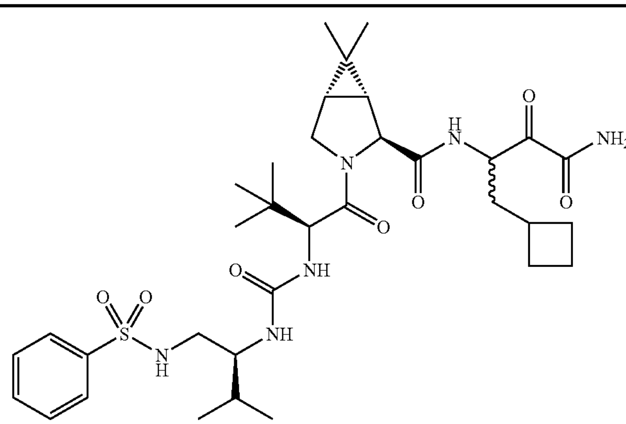 | A |

TABLE 3-continued

| Entry | Structure | Ki* |
|---|---|---|
| 12002 | 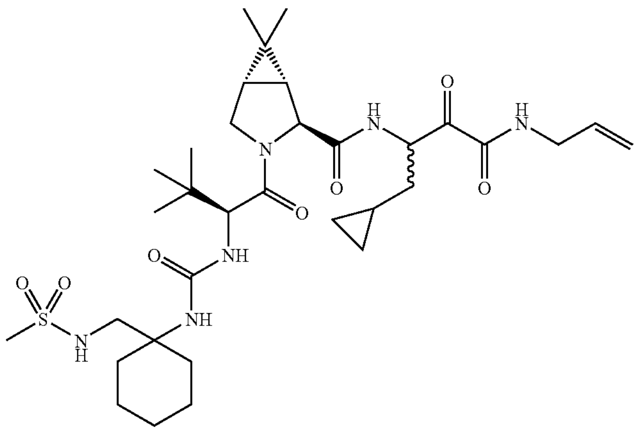 | A |
| 12003 | 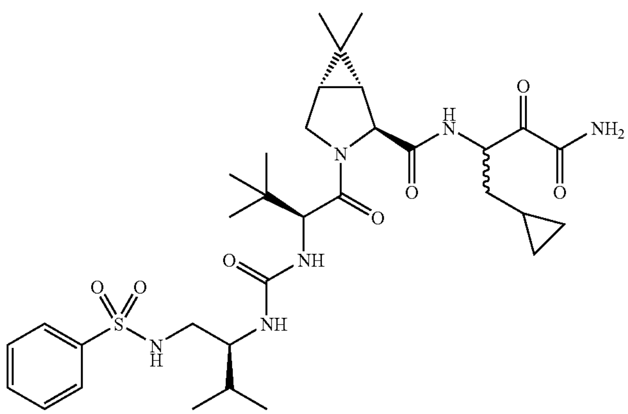 | A |
| 12005 | 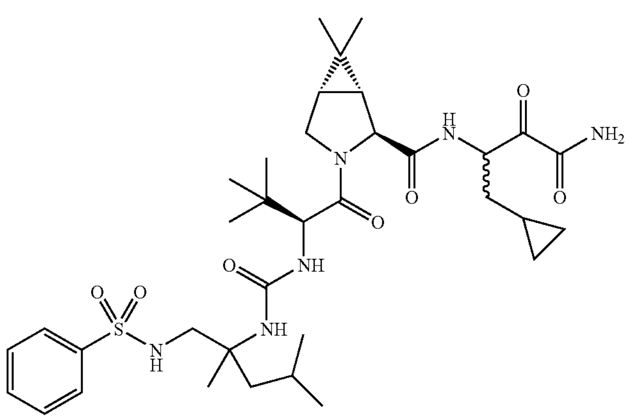 | B |

TABLE 3-continued

| Entry | Structure | Ki* |
|---|---|---|
| 12006 | 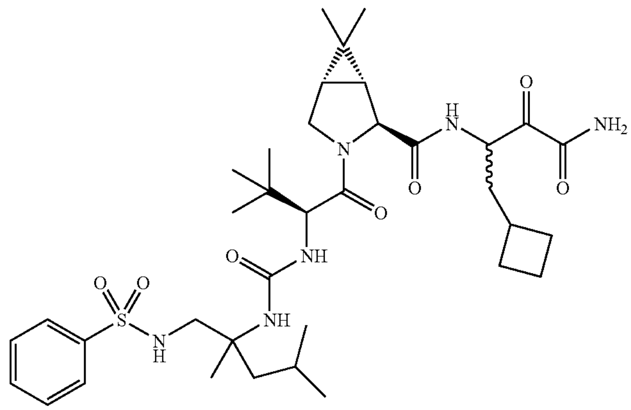 | B |
| 12007 | 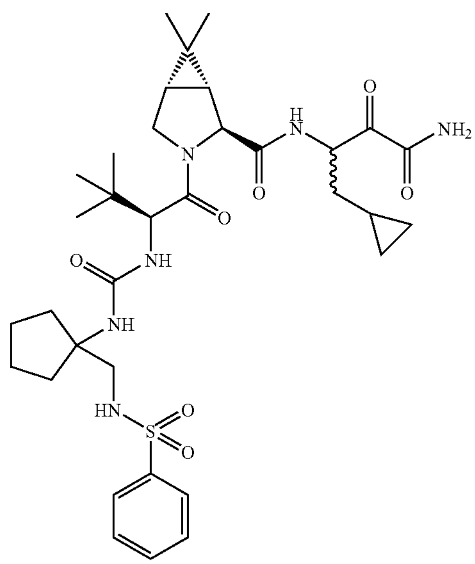 | A |
| 12008 | 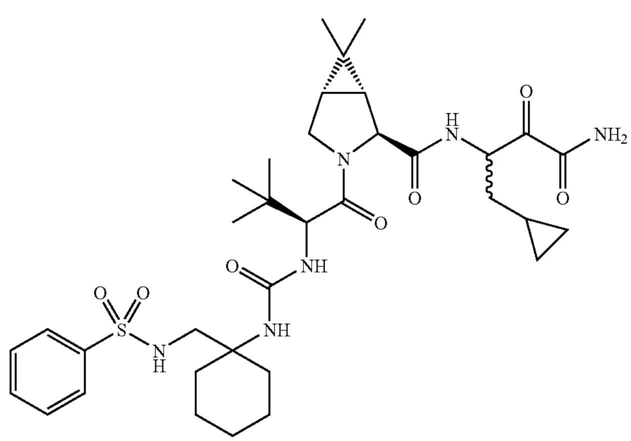 | A |

TABLE 3-continued
| Entry | Structure | Ki* |
|---|---|---|
| 12009 | 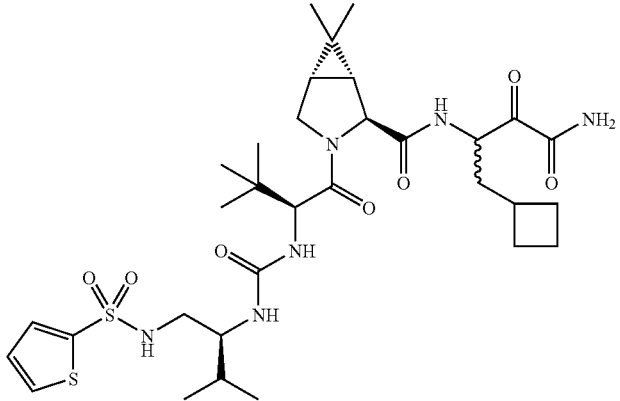 | A |
| 12010 | 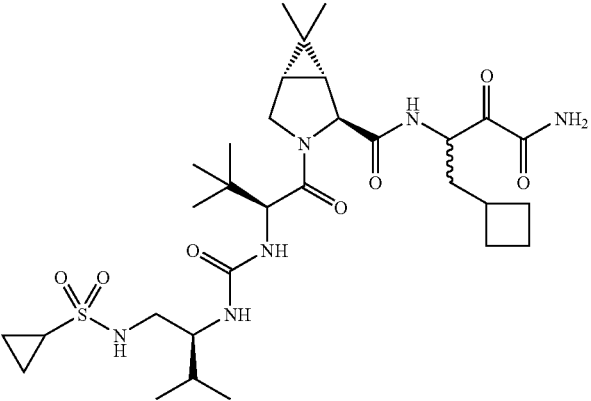 | A |
| 12012 | 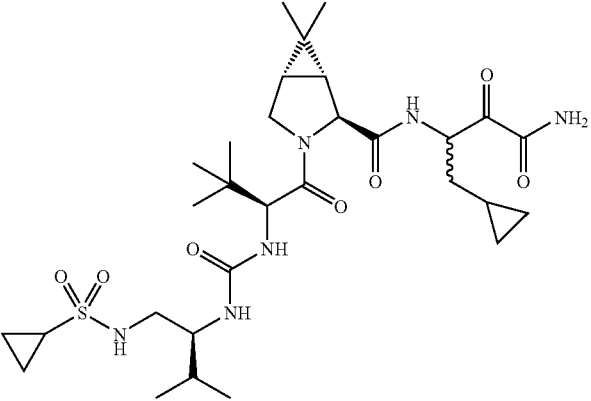 | A |

TABLE 3-continued

| Entry | Structure | Ki* |
|---|---|---|
| 12013 | 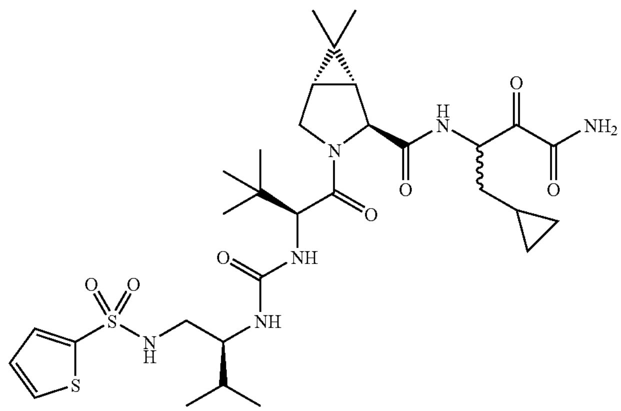 | A |
| 12014 | 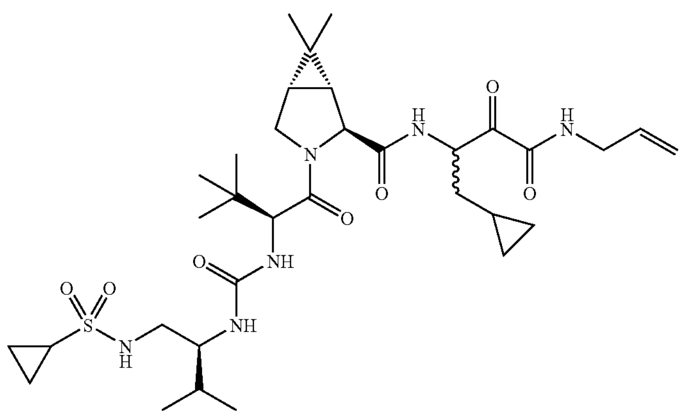 | C |
| 12015 | 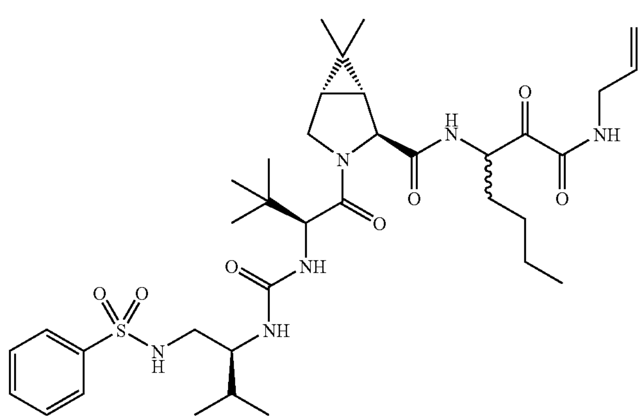 | C |

TABLE 3-continued

| Entry | Structure | Ki* |
|---|---|---|
| 12016 | 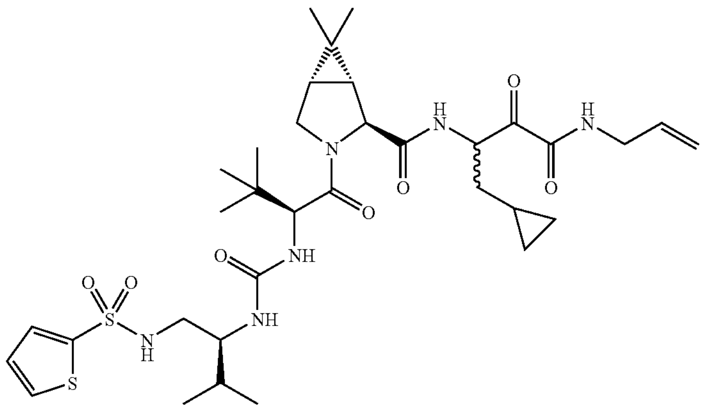 | B |
| 12017 | 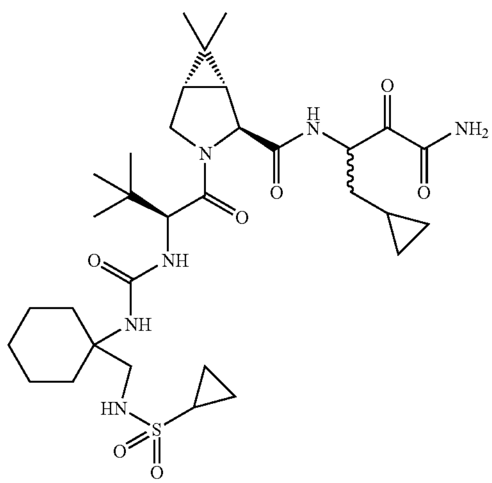 | A |
| 12018 | 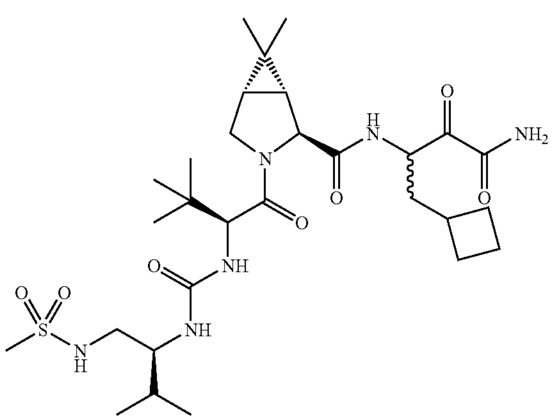 | A |

TABLE 3-continued

| Entry | Structure | Ki* |
|---|---|---|
| 12019 | 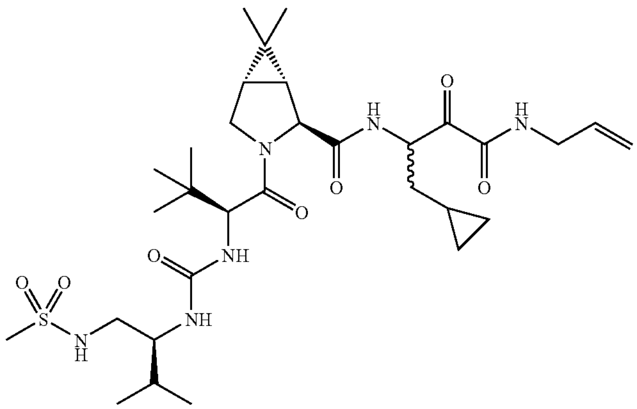 | A |
| 12020 | 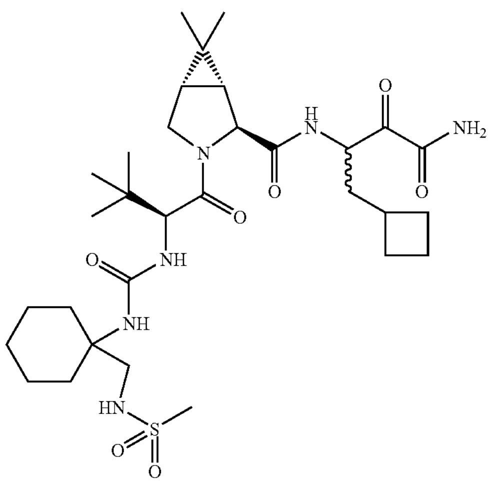 | A |
| 12021 | 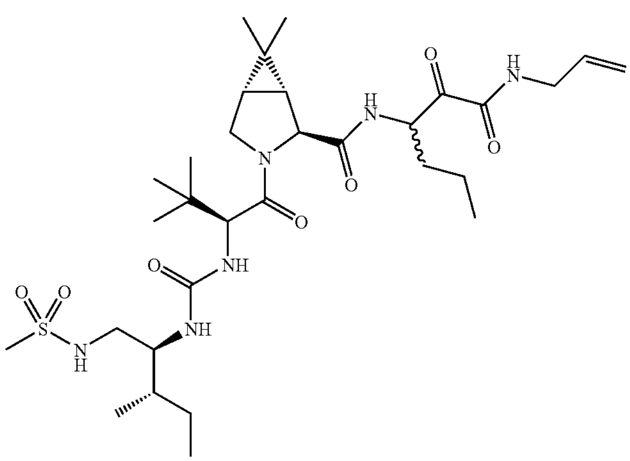 | A |

TABLE 3-continued

| Entry | Structure | Ki* |
|---|---|---|
| 12022 | 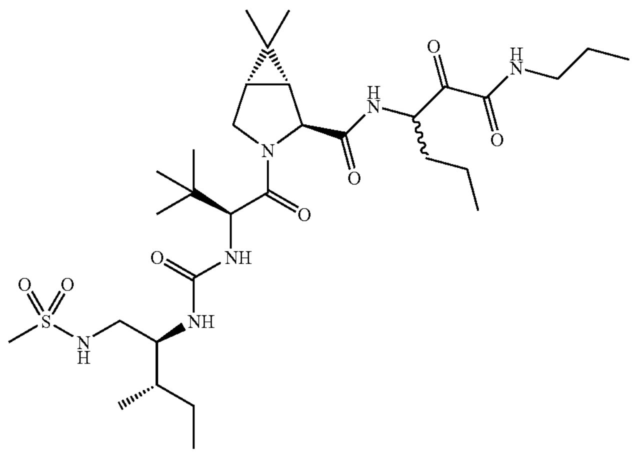 | C |
| 12023 | 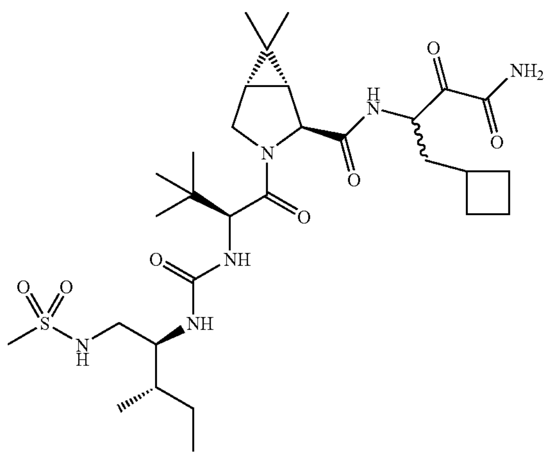 | A |
| 12024 | 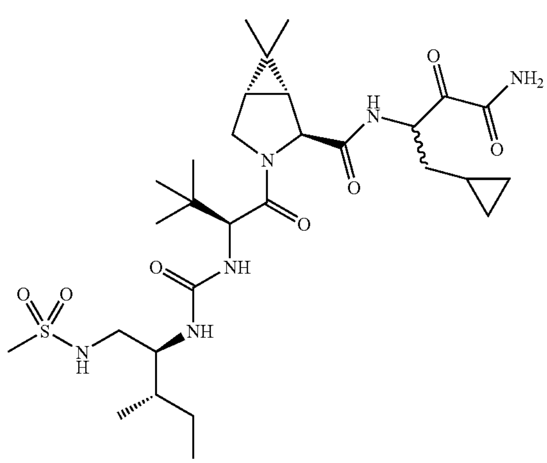 | B |

TABLE 3-continued

| Entry | Structure | Ki* |
|---|---|---|
| 12025 | 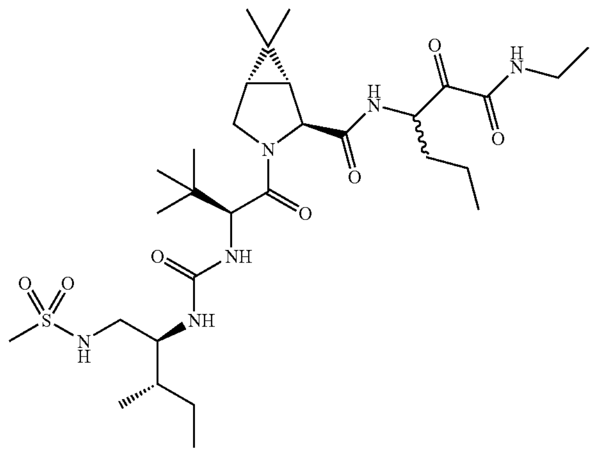 | C |

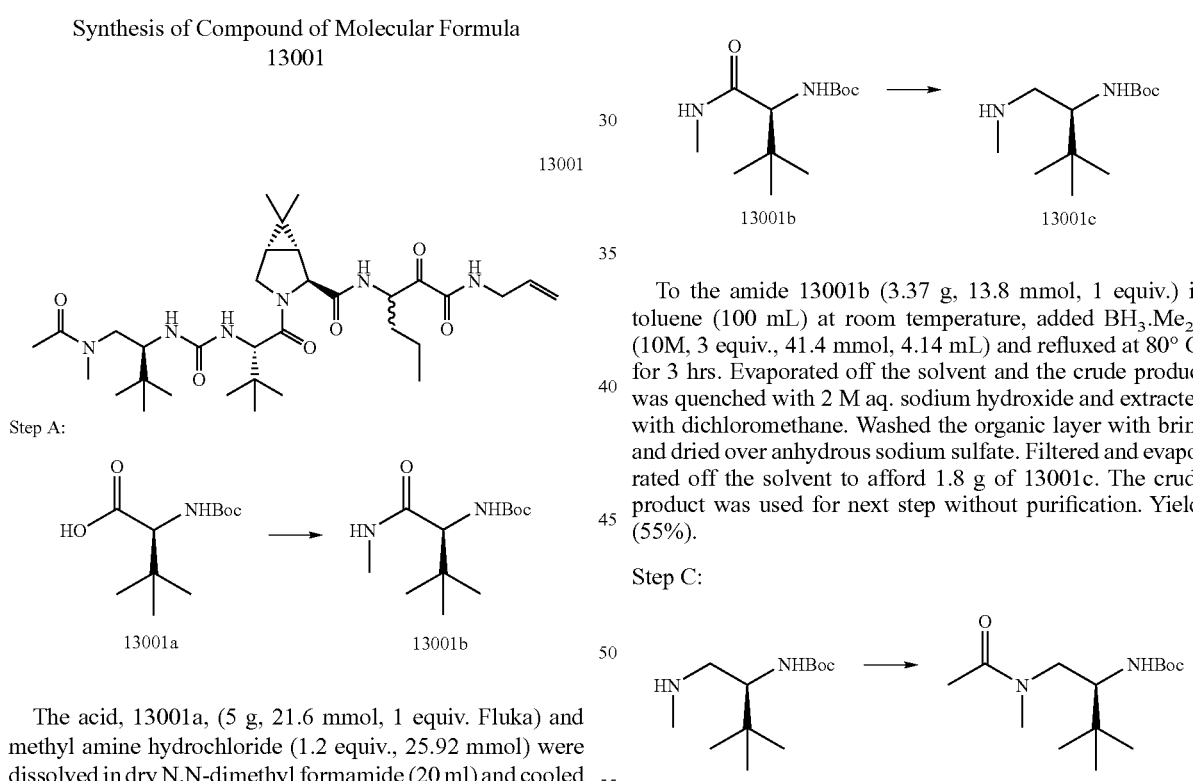

Example-12

Synthesis of Compound of Molecular Formula 13001

Step A:

The acid, 13001a, (5 g, 21.6 mmol, 1 equiv. Fluka) and methyl amine hydrochloride (1.2 equiv., 25.92 mmol) were dissolved in dry N,N-dimethyl formamide (20 ml) and cooled to 0° C. Added HATU (1.2 equiv., 25.92 mmol) followed by DIPEA (Sigma-Aldrich), (172.8 mmol., 8 equiv.) under $N_2$ atmosphere. The temperature was slowly raised to room temperature and stirred further for 4 h at room temperature. Diluted with EtOAc and washed with 1N HCl, $NaHCO_3$ and finally with brine. Dried over anhydrous sodium sulfate, filtered, and evaporated off the solvent. Crude product isolated was purified via flash column (10-50% EtOAc-Hexane) to afford 5.27 g of 13001b. Yield, (99%).

$^1$H NMR ($CDCl_3$, 300 MHz) δ, 6.0 (bs, 1H), 5.35 (d, 1H), 3.82 (d, 1H), 2.8 (s, 3H), 1.4 (s, 9H), 0.98 (s, 9H).

Step B:

To the amide 13001b (3.37 g, 13.8 mmol, 1 equiv.) in toluene (100 mL) at room temperature, added $BH_3.Me_2S$ (10M, 3 equiv., 41.4 mmol, 4.14 mL) and refluxed at 80° C. for 3 hrs. Evaporated off the solvent and the crude product was quenched with 2 M aq. sodium hydroxide and extracted with dichloromethane. Washed the organic layer with brine and dried over anhydrous sodium sulfate. Filtered and evaporated off the solvent to afford 1.8 g of 13001c. The crude product was used for next step without purification. Yield, (55%).

Step C:

To the Boc-protected amino compound 13001c (540 mg, 1 equiv.) in dichloromethane (25 mL) at ice temp was added triethylamine (3 equiv.) and acetyl chloride (3 equiv.). Stirred for 1 hr at ice temperature and then at room temperature for overnight Quenched with aq. sodium bicarbonate and extracted with EtOAc. Washed with 1N HCl and then with brine. The organic layer were dried over anhydrous sodium sulfate, filtered and evaporated off the solvent. The crude product was purified via flash column (20-40% EtOAc-Hexane). Yield=230 mg (38%).

Step D:

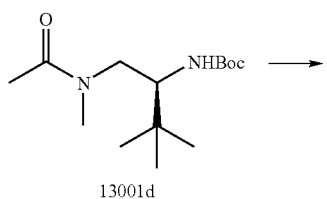

13001d

To the amide 13001d (28 mg, 1 equiv.) added 4M HCl/dioxane (2 mL) at room temperature. Stirred for 1 hr. TLC showed no starting material. Evaporated off the solvent and azeotroped with hexane and then with ether. Washed out the non polar material with ether and kept under high vac. over the week end. Used the salt without purification; Product isolated (pale yellow solid)=22 mg (100%).

Step E:

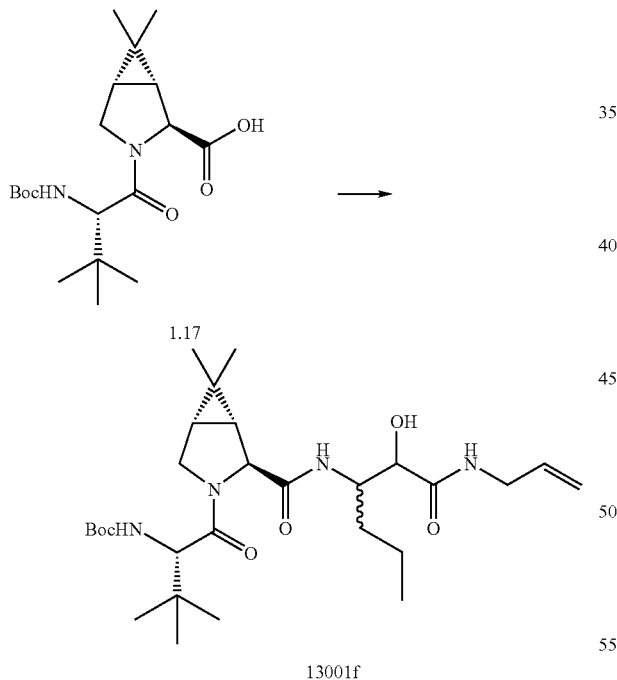

To a mixture of acid, 1.17 (860 mg, 2.33 mmol, 1 equiv.) and amine hydrochloride 13.01 (570 mg, 2.56 mmol, 1.1 equiv.) in DMF (15 mL) at ice temperature was added HATU (1.2 equiv., 1.066 g, 2.796 mmol) and DIPEA (8 equiv., 18.69 mmol, 3.26 mL) under $N_2$ and stirred at 0° C. overnight. The temperature was slowly allowed to rise to room temperature. Quenched with 1N HCl and extracted with EtOAc. The combined organic layer were washed with aq. NaHCO$_3$ (sat) and then with brine. Washed with ice cold water (5×20 ml) and again with brine. Dried over anhydrous Na$_2$SO$_4$, filtered, and evaporated off the solvent to afford 1.25 g of 13001f. Yield, 100%.

Step F:

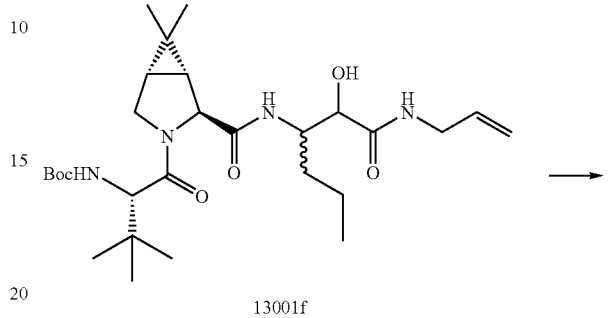

13001f

To the crude hydroxy amide, 13001f (2.71 mmol, 1.45 mg, 1 equiv.) in DCM (50 mL) at room temperature, was added Dess-Martin periodinane (2.30 mg, 5.42 mmol, 2 equiv.) and stirred at rt. for 5 hrs. TLC showed complete consumption of starting material and the appearance of product. Quenched with sat. NaHCO$_3$ aq thiosulfate solution and extracted with EtOAc. The organic layer was washed with brine and dried over anhydrous sodium sulfate. Filtered and evaporated off the solvent. Crude product was purified by silica gel flash column (10-40% acetone-hexane) to afford 860 mg of 13001g; Yield, 62%.

Step G:

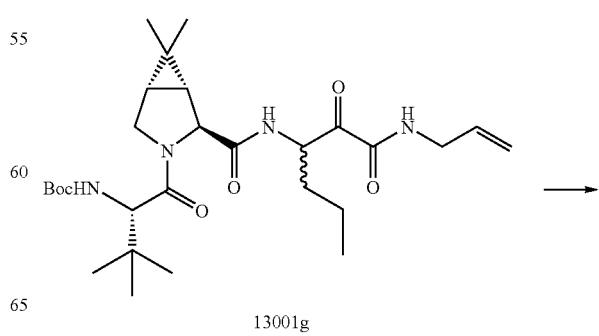

13001g

-continued

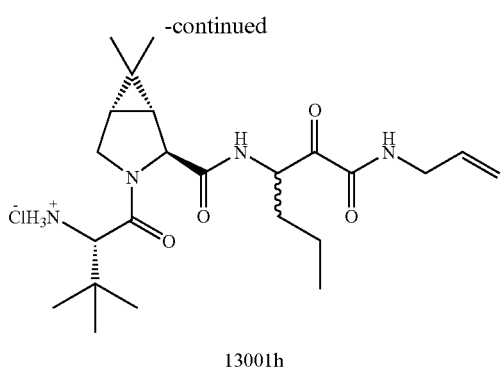

13001h

To the Boc amino compound 13001g (860 mg, 1 equiv.) added 4M HCl in dioxane (25 mL) at room temperature. Stirred for 1 hr. TLC showed no starting material. Evaporated off the solvent and azeotroped with hexane and then with ether. Washed out the non polar material with ether and kept under high vacuum over the week end. Used the salt without further purification; Product isolated (pale yellow solid)=750 mg (99%).

Step H:

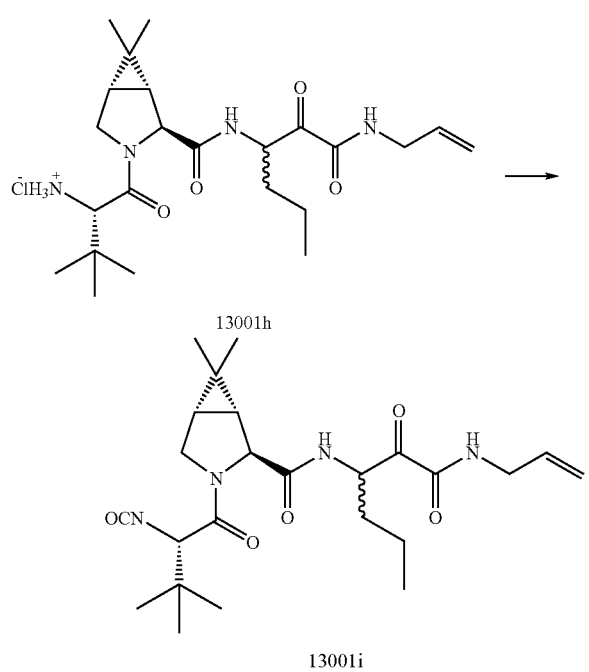

13001h

13001i

To the ammonium salt, 13001 h, (150 mg, 0.318 mmol, 1 equiv.) in DCM (5 ml) was added 5 ml of aq. sat. NaHCO$_3$. Stirred vigorously at ice temperature for 5 min. Stopped stirring and phosgene (2 equiv. 20% in toluene, 0.318 mL) was syringed out to the lower layer and restored the vigorous stirring immediately. Checked the TLC at times and after 2 hrs it showed complete consumption of starting material and then separated the layers. Washed the water layer one more time with DCM (3 ml) and the combined organic layers were dried over sodium sulfate. The organic layer was filtered and concentrated in vacuo to half the volume. Used 13001i as a stock solution of 0.01M by diluting to 30 mL of dichloromethane.

Step F:

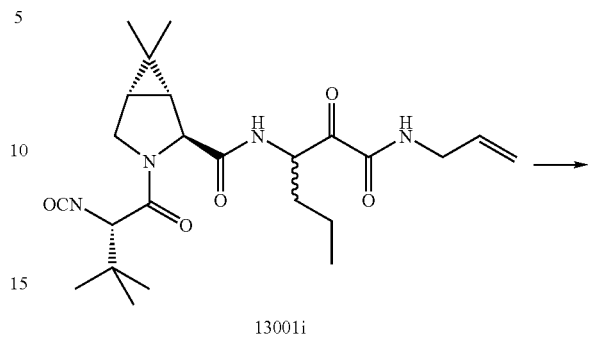

13001i

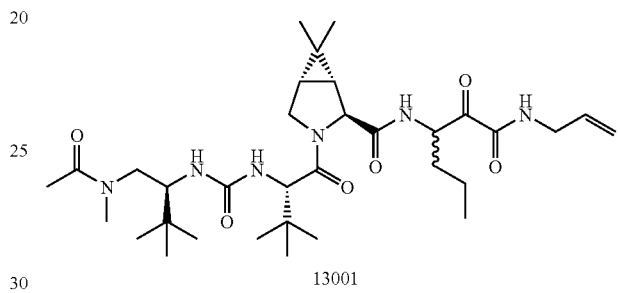

13001

To the ammonium salt 13001e (22 mg, 0.102 mmol, 1.1 equiv.) in DCM (10 ml) was added DIPEA (6 equiv., 135 µL) at ice temperature. Added isocyanate 13001i (1 equiv, 9 ml of 0.01M soln) under N$_2$ atm. and stirred for 30 min at ice temperature and 90 min at room temperature. Quenched with citric acid and extracted with EtOAc and washed with brine. Dried over anhydrous sodium sulfate, filtered and evaporated off the solvent. The crude product was purified via flash column (SiO$_2$, 10-50% acetone-hexane) to afford 50 mg of 13001 as a colorless solid. Yield, (78%)

MS (ESI), m/z, 633 (M+1), 312.

Example 13

Synthesis of Compound of Molecular Formula 13002

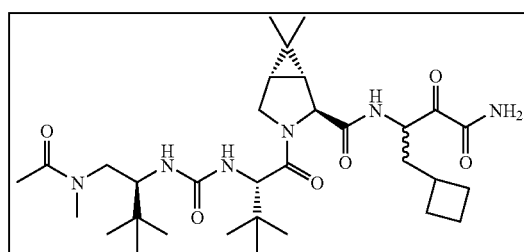

13002

Step A:

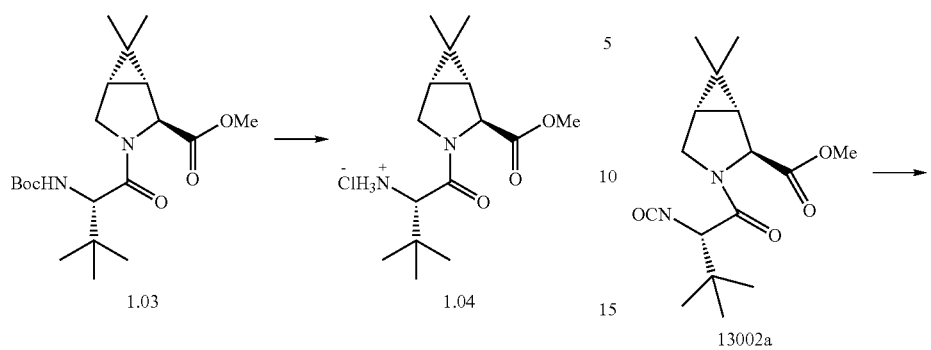

To the Boc protected dipeptide 1.03 (3.6 g, 9.42 mmol, 1 equiv.) added 4M HCl/dioxane (60 mL) at room temp. Stirred for 2 h. TLC showed no starting material. Evaporated off the solvent and azeotroped with hexane and then with ether. Washed out the non polar material with ether and kept under high vac. over night. Used the salt, 1.04, without purification.

Product isolated=3 g (100%).

Step B:

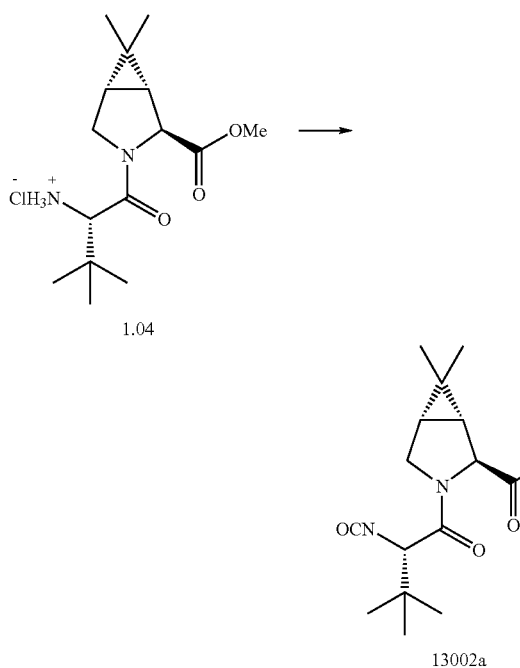

To the amine hydrochloride 1.04 (3 g, 9.4 mmol) in dichloromethane (50 ml) was added 50 ml of sat. NaHCO$_3$. Stirred vigorously at ice temperature for 5 min. Stopped stirring and phosgene (2 equiv. 20% in toluene, 10 mL) was syringed out to the lower layer and restored the vigorous stirring immediately. Checked the TLC at times and after 2 hrs it showed complete consumption of starting material and then separated the layers. Washed the water layer one more time with dichloromethane (3 ml) and dried over anhydrous sodium sulfate. Filtered and evaporated off the solvent using rotary evaporator under reduced pressure to half the volume and then flushed N$_2$ for 15 minutes. Diluted to 33.5 mL with dichloromethane and used as 0.28 M solution for further couplings.

Step C

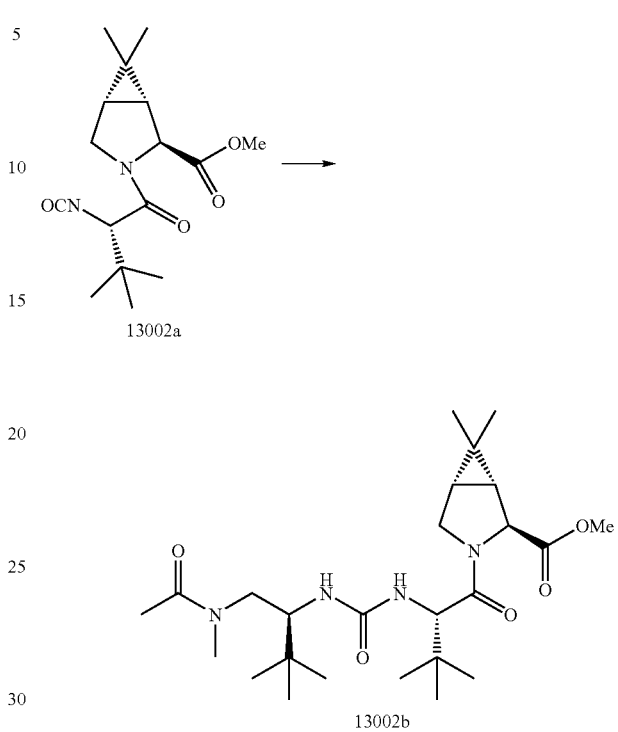

To the amine salt, 13001e, prepared as described before (151 mg, 0.73 mmol, 1 equiv.) in DCM (10 ml) was added DIPEA (8 equiv., 1.01 mL, 5.84 mmol) at ice temperature. Added isocyanate 13002a (1 equiv, 13 ml of 0.02M soln) under N$_2$ atm. and stirred for 30 min at ice temperature and 90 min at room temperature. Quenched with 10% citric acid and extracted with EtOAc and washed with brine. Dried over anhydrous sodium sulfate and filtered and evaporated off the solvent. The crude product was purified via flash column (20-80% EtOAC-hexane) to afford 270 mg of 13002b as a white solid. Yield, (76%).

$^1$H NMR (CDCl$_3$, 300 MHz) δ, 5.8 (bs, NH), 5.4 (bs, NH), 5.2 (d, 1H), 4.4 (d, 1H), 4-4.2 (m, 2H), 3.8-4 (m, 3H), 3.01 (s, 3H), 2.01 (bs, 6H), 1.6 (m, 1H), 1.4 (m, 1H), 1.02-0.98 (m, 24H).

Step D

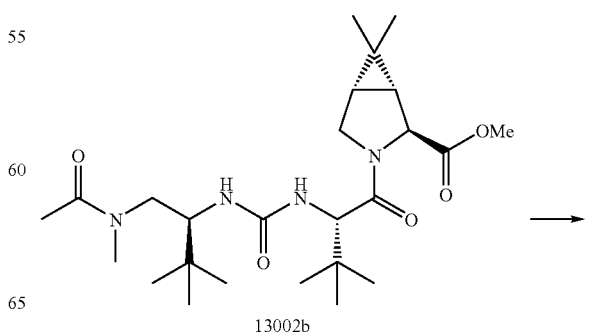

-continued

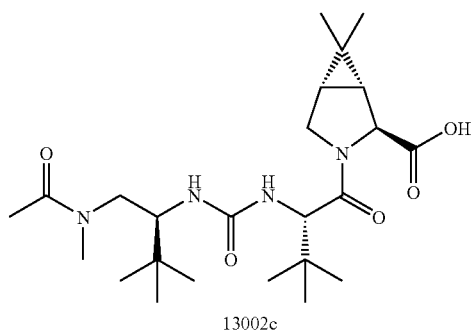

13002c

To the methyl ester, 13002b (270 mg, 0.562 mmol, 1 equiv.) in dioxane (10 ml) was added a solution of LiOH (10 equiv., 6 mL of 1N soln. in water) and stirred overnight. Quenched with 1N HCl and extracted with EtOAC. Washed with brine and dried over anhydrous sodium sulfate. Filtered and evaporated off the solvent. crude yield 260 mg (99%).

Step E:

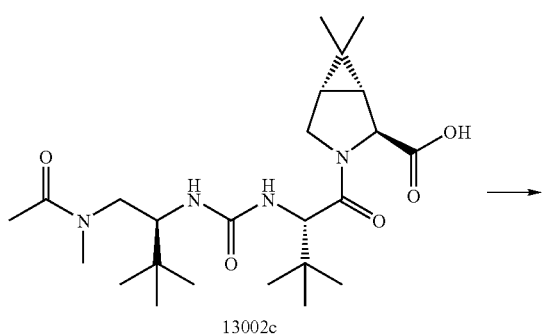

13002c

-continued

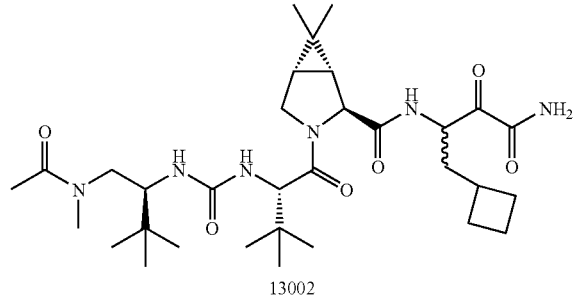

13002

To the ammonium salt, 10.11 (16.06 mg, 0.077 mmol, 1.2 equiv.) in DCM (10 ml) was added 13002 c (30 mg, 0.064 mmol, 1 equiv.) and cooled to −20° C. and added HATU (1.2 equiv., 0.077 mmol, 29.37 mg) followed by DIPEA (8 equiv., 89.94 µL, 0.515 mmol). The reaction mixture was stirred overnight at that temperature. Quenched with 1N HCl and extracted with EtOAC. Washed the organic layer with aq. saturated sodium bicarbonate and then with brine. Dried over anhydrous sodium sulfate, filtered, and evaporated off the solvent. Purified via flash column (SiO$_2$, 10-90% EtOAc-Hexane) to afford 40 mg of hydroxyamide Yield, (100%).

To the hydroxyl amide (40 mg, 0.0645 mmol, 1 equiv.) in 1:1 mixture of DMF/toluene (6 mL) at ice temperature was added EDCl.HCl (123 mg, 10 equiv., 0.645 mmol) and dichloroacetic acid (27 µL, 5 equiv., 0.322 mmol) and stirred for 5 min. and room temperature for 3 h. Quenched with brine and washed with 1N HCl followed by aq. sat. NaHCO$_3$ and again with brine. Dried over anhydrous sodium sulfate, filtered and evaporated off the solvent. Purified via silica gel preparative TLC (50% acetone-hexane) to afford 30 mg of 13002. Yield (75%).

MS (ESI), m/z, 619 (M+1), 312.

Compounds shown in the following Table 4 were synthesized using similar reactions as shown in Examples above. Range of Ki* indicated A≦75 nM; 75<B≦250 nM; C>250 nM.

TABLE 4

| Entry | Structure | Ki* |
|---|---|---|
| 13001 | 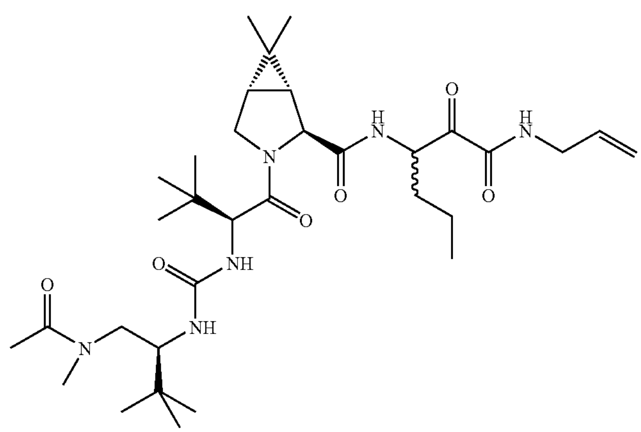 | A |

TABLE 4-continued

| Entry | Structure | Ki* |
|---|---|---|
| 13002 | 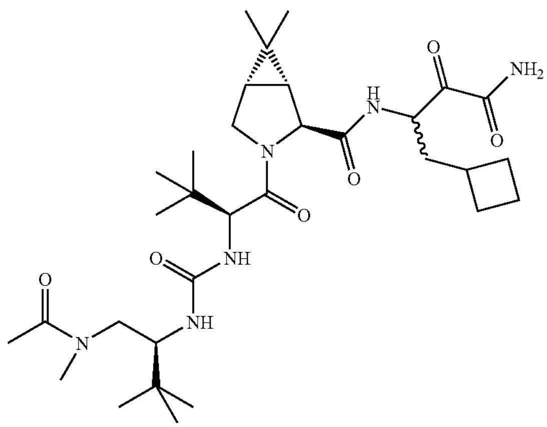 | A |
| 13003 | 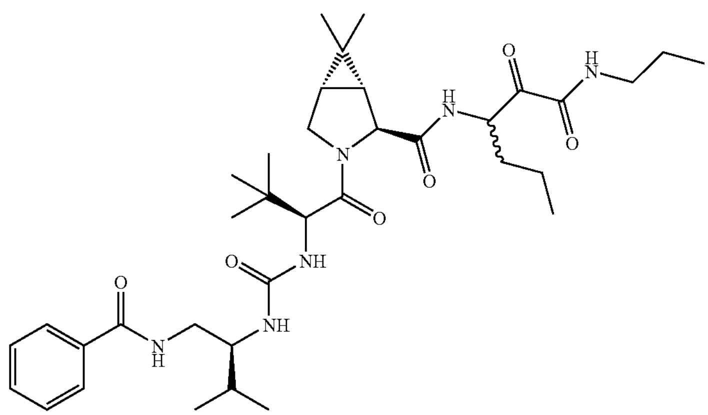 | B |
| 13004 | 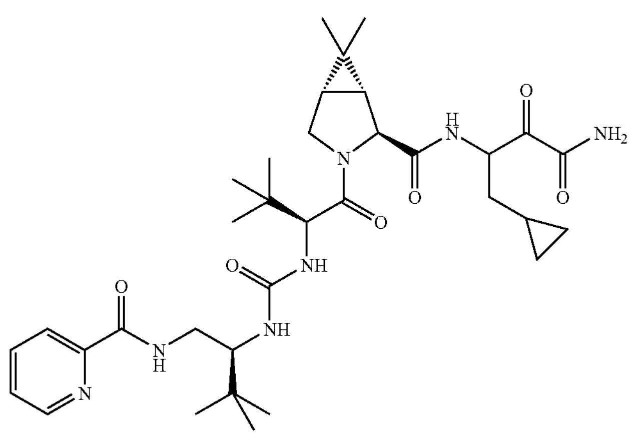 | A |

TABLE 4-continued
| Entry | Structure | Ki* |
|---|---|---|
| 13008 | 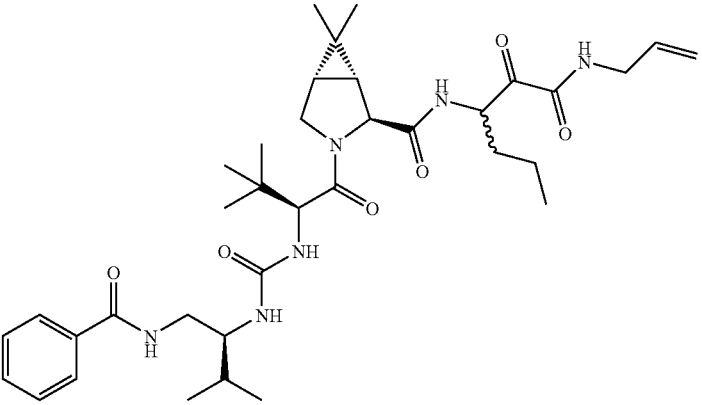 | A |
| 13009 | 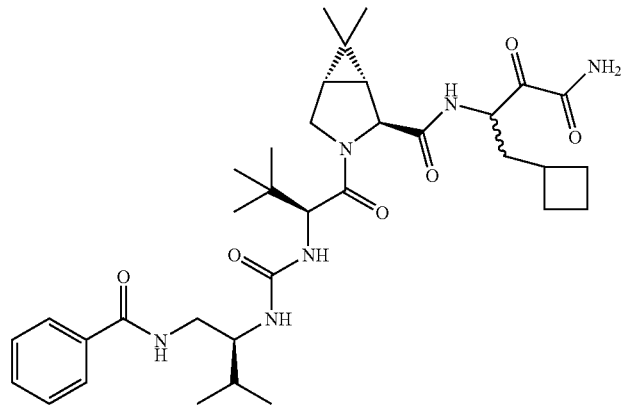 | A |
| 13010 | 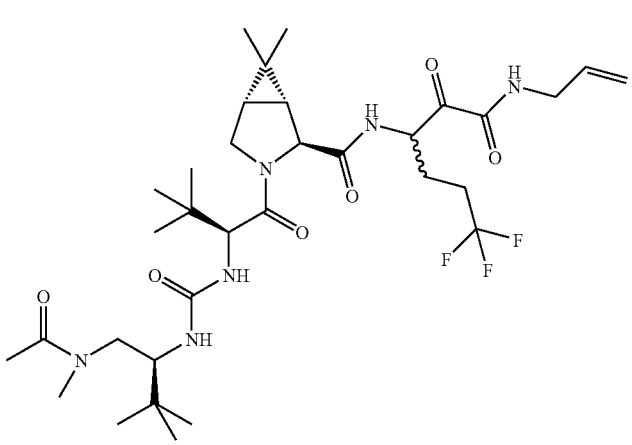 | A |

TABLE 4-continued

| Entry | Structure | Ki* |
|-------|-----------|-----|
| 13011 | 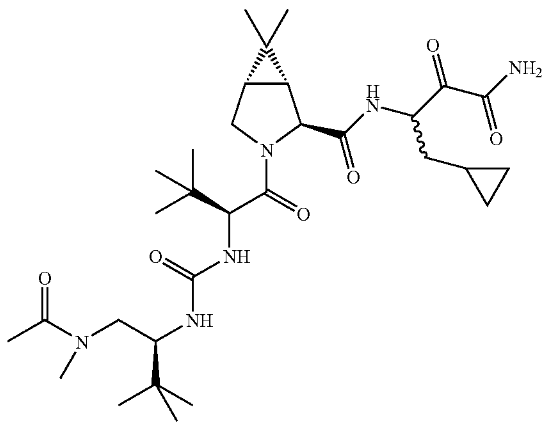 | A |
| 13012 | 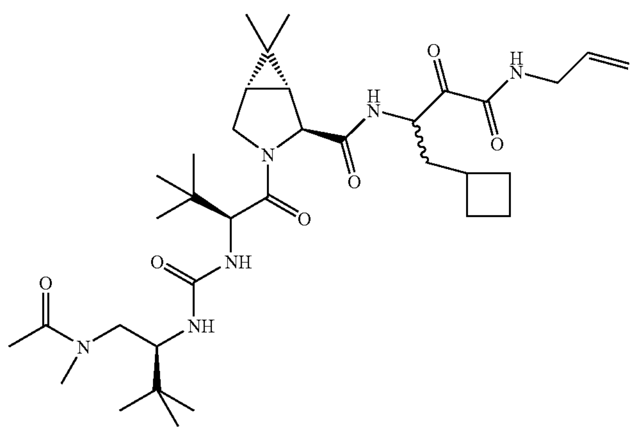 | B |
| 13013 | 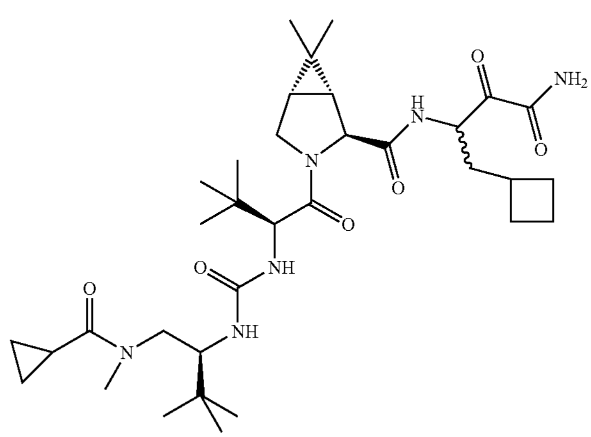 | A |

TABLE 4-continued
| Entry | Structure | Ki* |
|---|---|---|
| 13014 | 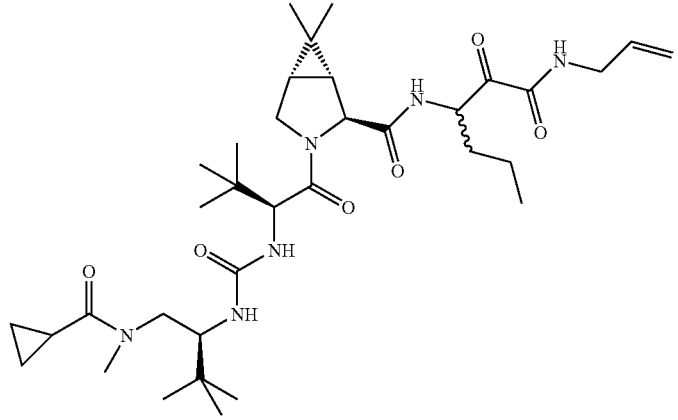 | B |
| 13015 | 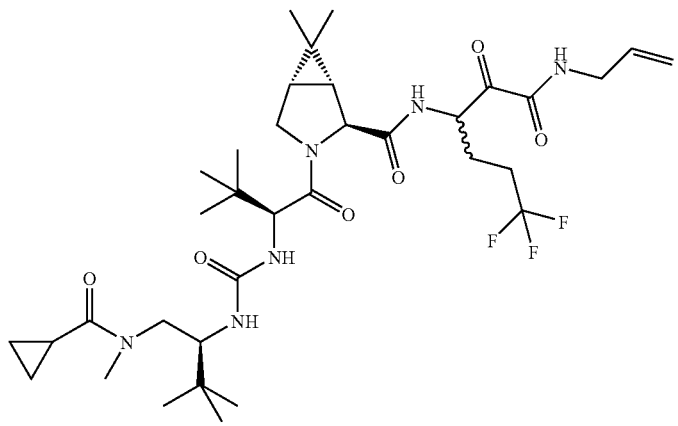 | B |
| 13016 | 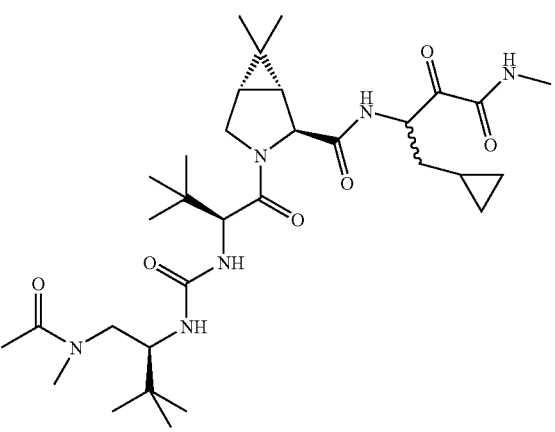 | A |

TABLE 4-continued

| Entry | Structure | Ki* |
|---|---|---|
| 13017 | 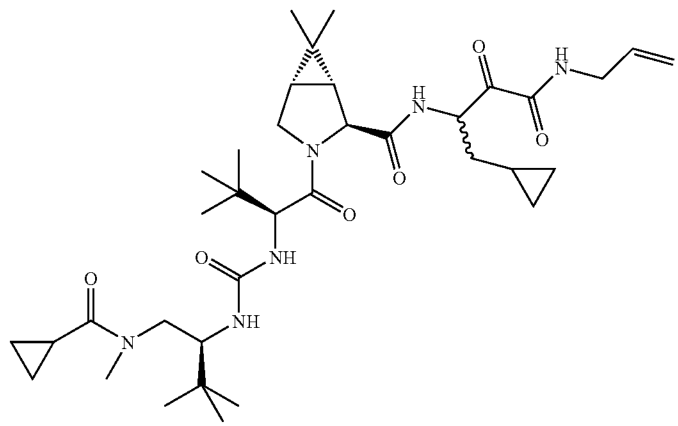 | C |
| 13018 | 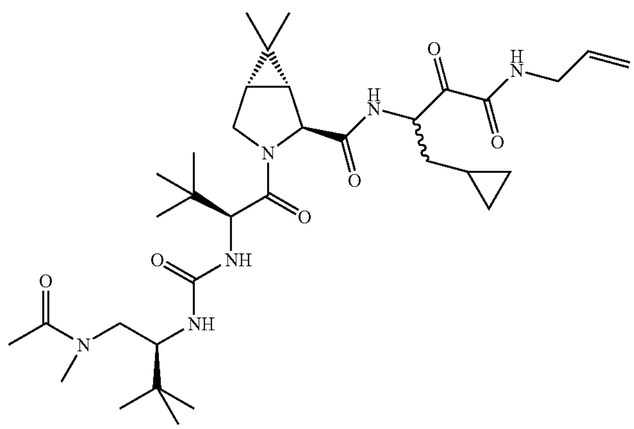 | A |
| 13019 | 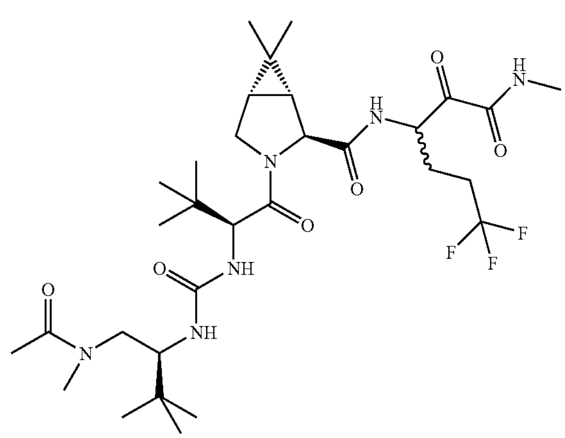 | A |

TABLE 4-continued

| Entry | Structure | Ki* |
|---|---|---|
| 13020 | 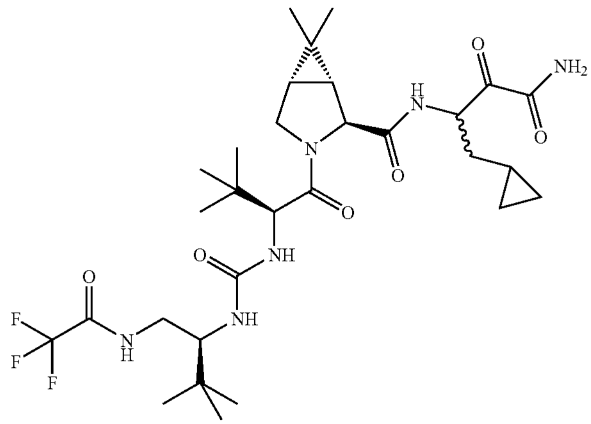 | A |
| 13021 | 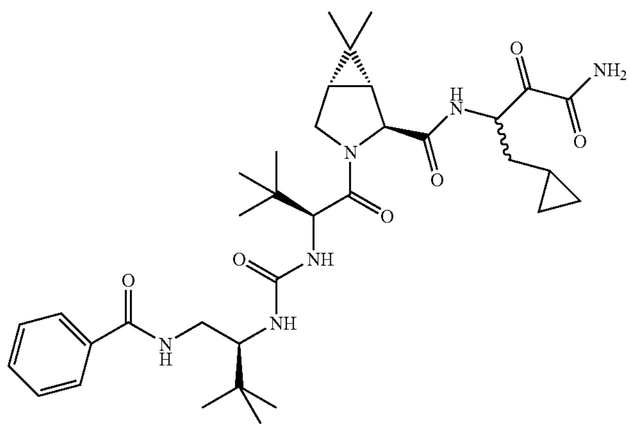 | A |
| 13022 | 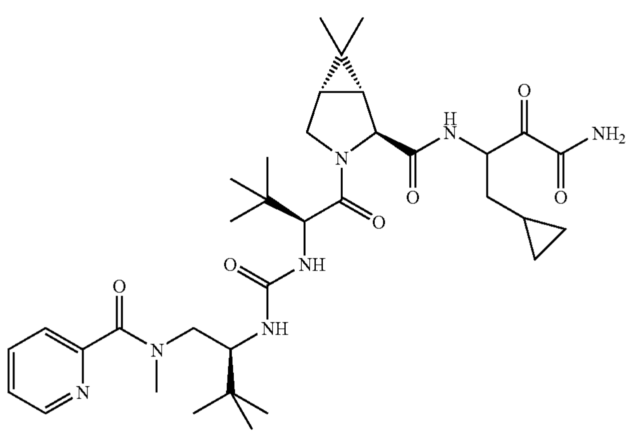 | A |

TABLE 4-continued

| Entry | Structure | Ki* |
|---|---|---|
| 13023 | 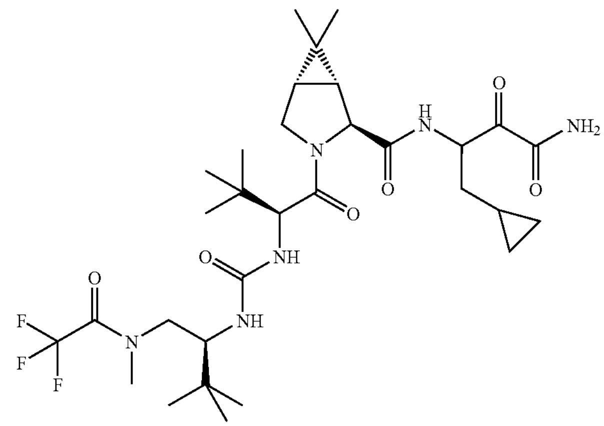 | A |
| 13024 | 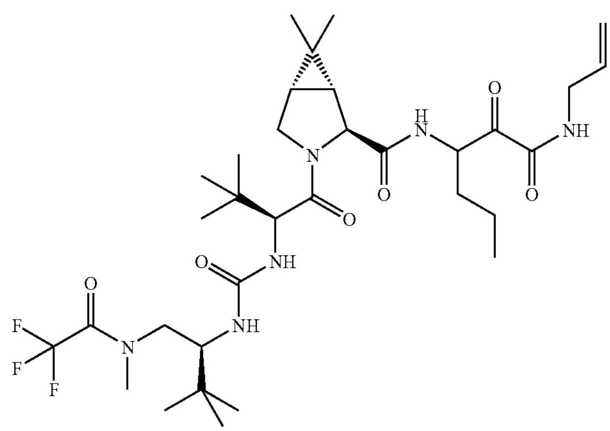 | A |
| 13025 | 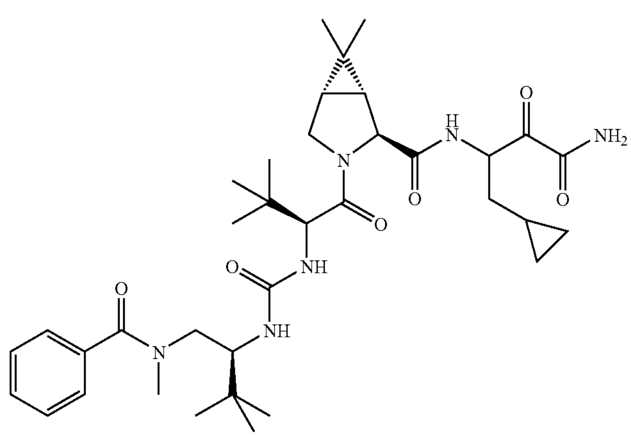 | A |

TABLE 4-continued

| Entry | Structure | Ki* |
|---|---|---|
| 13026 | 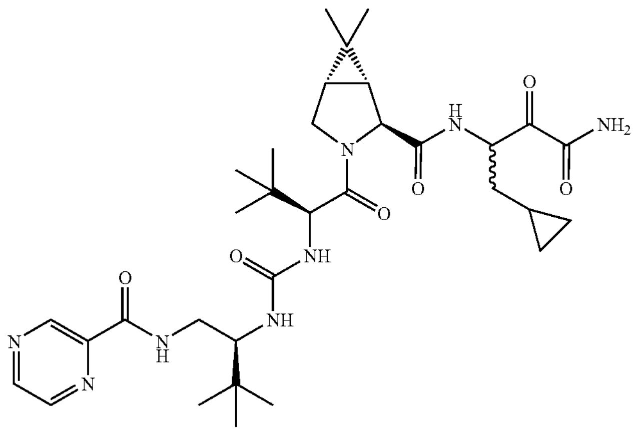 | A |
| 13027 | 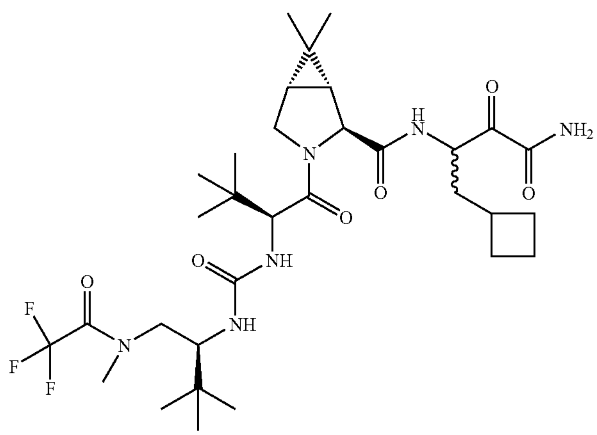 | A |
| 13028 | 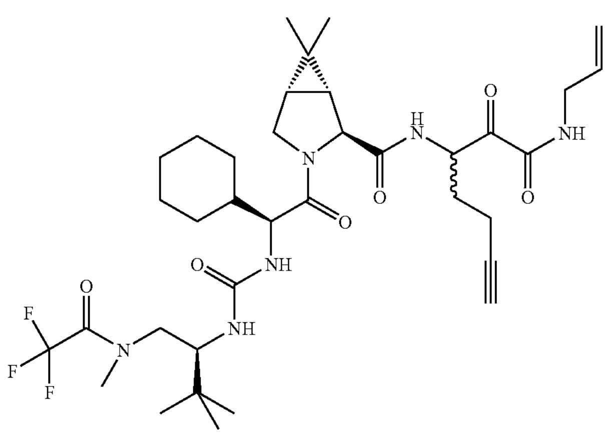 | A |

TABLE 4-continued

| Entry | Structure | Ki* |
|---|---|---|
| 13029 | 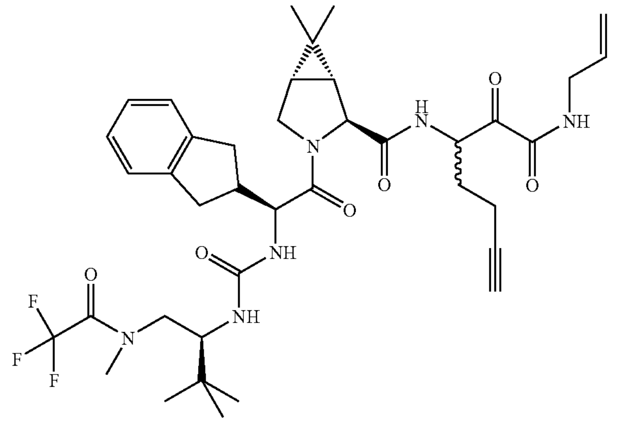 | A |
| 13030 | 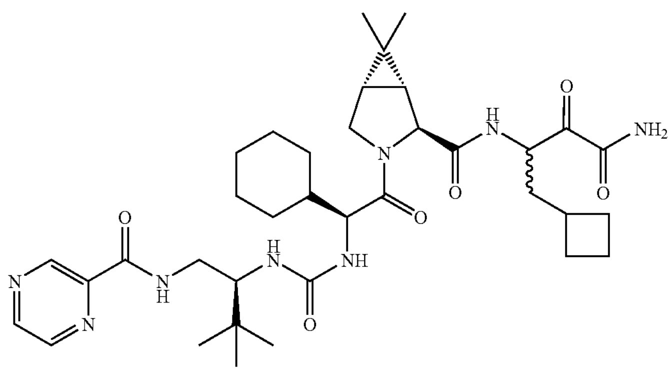 | A |
| 13031 | 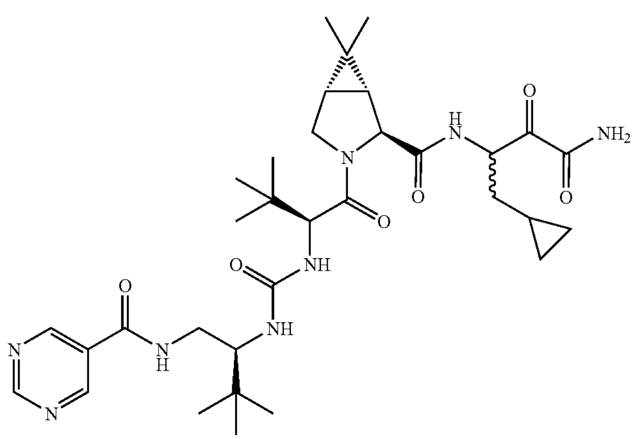 | A |

TABLE 4-continued

| Entry | Structure | Ki* |
|---|---|---|
| 13032 | 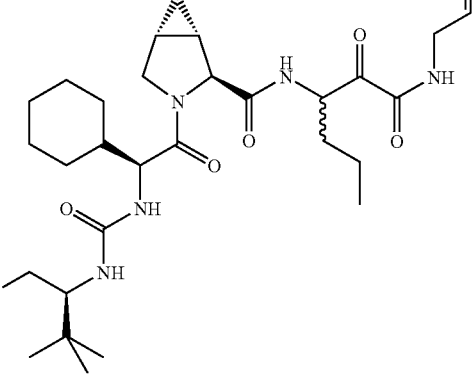 | A |
| 13033 | 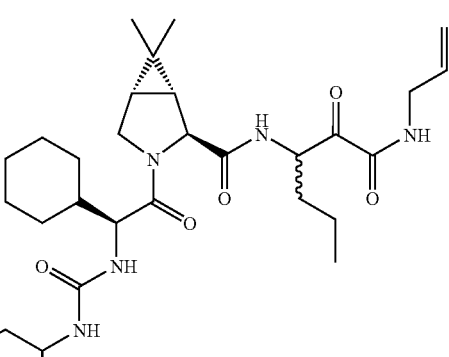 | A |

Example 14

Synthesis of Compound of Formula 14001

14001

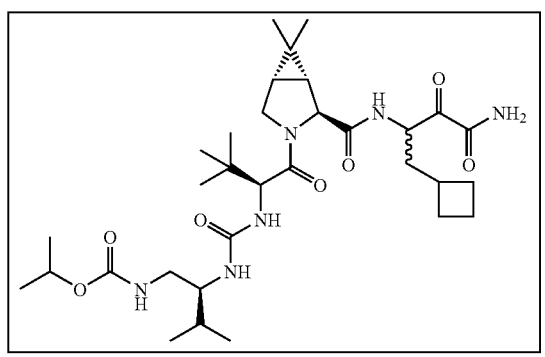

Step A:

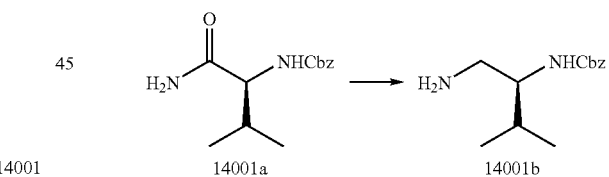

A solution of 14001a (10.0 g, 40.0 mmol Indofine chemicals) in toluene (150 mL) was treated with BH$_3$.DMS (~2 M, 40 mL) and heated at 90° C. overnight. The reaction mixture was cooled to 0° C. and diluted with 2 M aq. NaOH. The reaction mixture was heated at 90° C. for 15 min. The aqueous layer was extracted with CH$_2$Cl$_2$ and the combined organic layers were dried (MgSO$_4$) filtered concentrated in vacuo to yield 11 g of 14001b.

Step B:

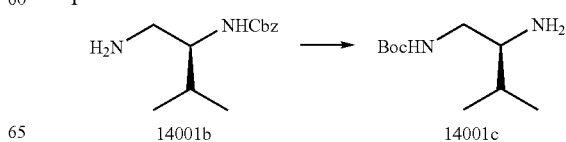

A solution of amine 14001b (10 g, 42.0 mmol) in CH₂Cl₂/DMF (1:5) was cooled to −78° C. and treated with di-tert-butyldicarbonate (13.8 g, 63 mmol). The reaction mixture was stirred at rt for 48 h and diluted with aq. 1 M HCl and extracted with EtOAc. The combined organic layer was washed with aq. NaHCO₃, brine, dried, filtered and concentrated in vacuo. The residue was purified by chromatography (SiO₂, EtOAc/Hexanes 1:3) to yield 4 g of Boc protected compound.

A solution of Boc-compound (6 g, 17.8 mmol) in methanol was treated with Pd(OH)₂/C (1.89 g, 20% on C) and hydrogenated for 1 h. The reaction mixture was filtered through a plug of celite and concentrated in vacuo. The residue 14001c was used further reaction without purification.

Step C:

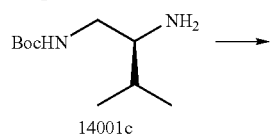

14001c

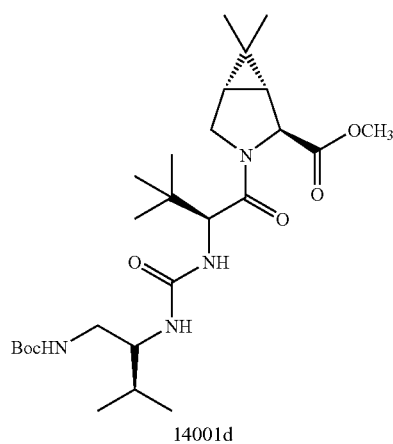

14001d

A solution of deprotected amine 14001c (3.6 g, 17.8 mmol) in CH₂Cl₂/DMF (1:1, 20 mL) was treated with 4-nitrophenylcarbamate 1.16 (7.97 g, 17.8 mmol), NMM (4 g, 14.0 mmol) and stirred at rt. overnight. The reaction mixture was concentrated in vacuo diluted with EtOAc and washed with aq. HCl, aq. saturated NaHCO₃, brine, dried (MgSO₄), filtered, and purified by chromatography (SiO₂, Hexanes/EtOAc 3:7) to yield 14001 d Step D:

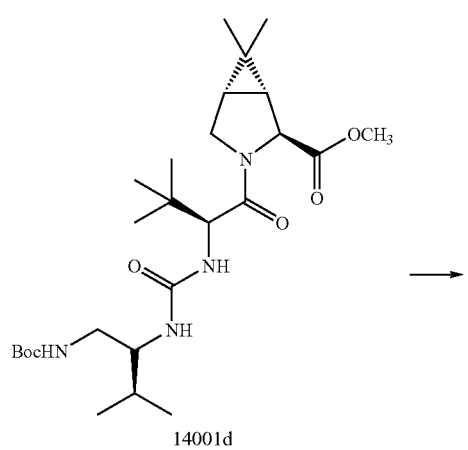

14001d

-continued

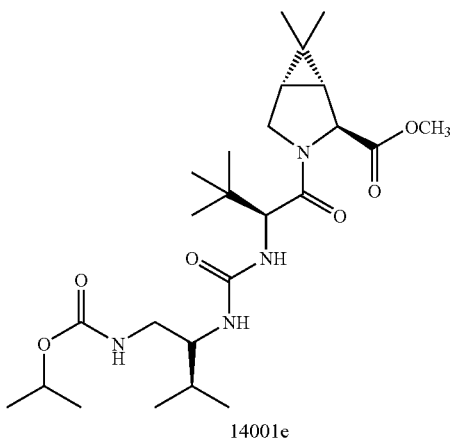

14001e

A solution of 14001d was dissolved in 4 M HCl in dioxane and stirred at rt for 2 h. The reaction mixture was concentrated in vacuo and used in further reactions without purification.

The ammonium salt (100 mg, 0.224 mmol) dissolved in DMF/CH₂Cl₂ (1:1) was treated with isopropylchloroformate (54 mg, 0.448 mmol) and Et₃N (45 mg, 0.448 mmol) at 0° C. and stirred at rt. overnight. The reaction mixture was diluted with EtOAc and the organic layer was washed with aq. 1M HCl, aq. saturated NaHCO₃, and brine. It was dried (MgSO₄) filtered, concentrated in vacuo and used as it is in the next reaction.

Step E:

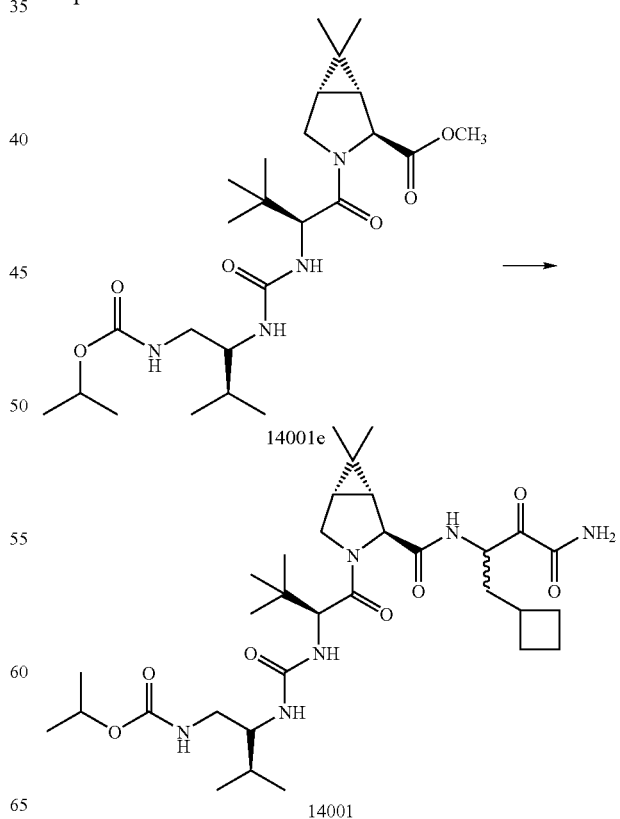

14001e

14001

Intermediate 14001e was converted to 14001 by coupling to intermediate 10.11 followed by Moffett oxidation identical to the procedures described in preparative example 6 of synthesis of 11001, Step D and Step E.

Example 15

Synthesis of Compound of Formula 14002

A solution of 14001d was dissolved in 4 M HCl in dioxane and stirred at rt for 2 h. The reaction mixture was concentrated in vacuo and used in further reactions without purification.

The ammonium salt (100 mg, 0.224 mmol) dissolved in DMF/CH$_2$Cl$_2$ (1:1) was treated with phenylisocyanate (53 mg, 0.448 mmol) and Et$_3$N (45 mg, 0.448 mmol) at 0° C. and stirred at rt. overnight. The reaction mixture was diluted with EtOAc and the organic layer was washed with aq. 1M HCl, aq. saturated NaHCO$_3$, and brine. It was dried (MgSO$_4$) filtered, concentrated in vacuo and purified by chromatography (SiO$_2$, EtOAc/Hex 2:3) to yield 14002a.

Step B:

Step A:

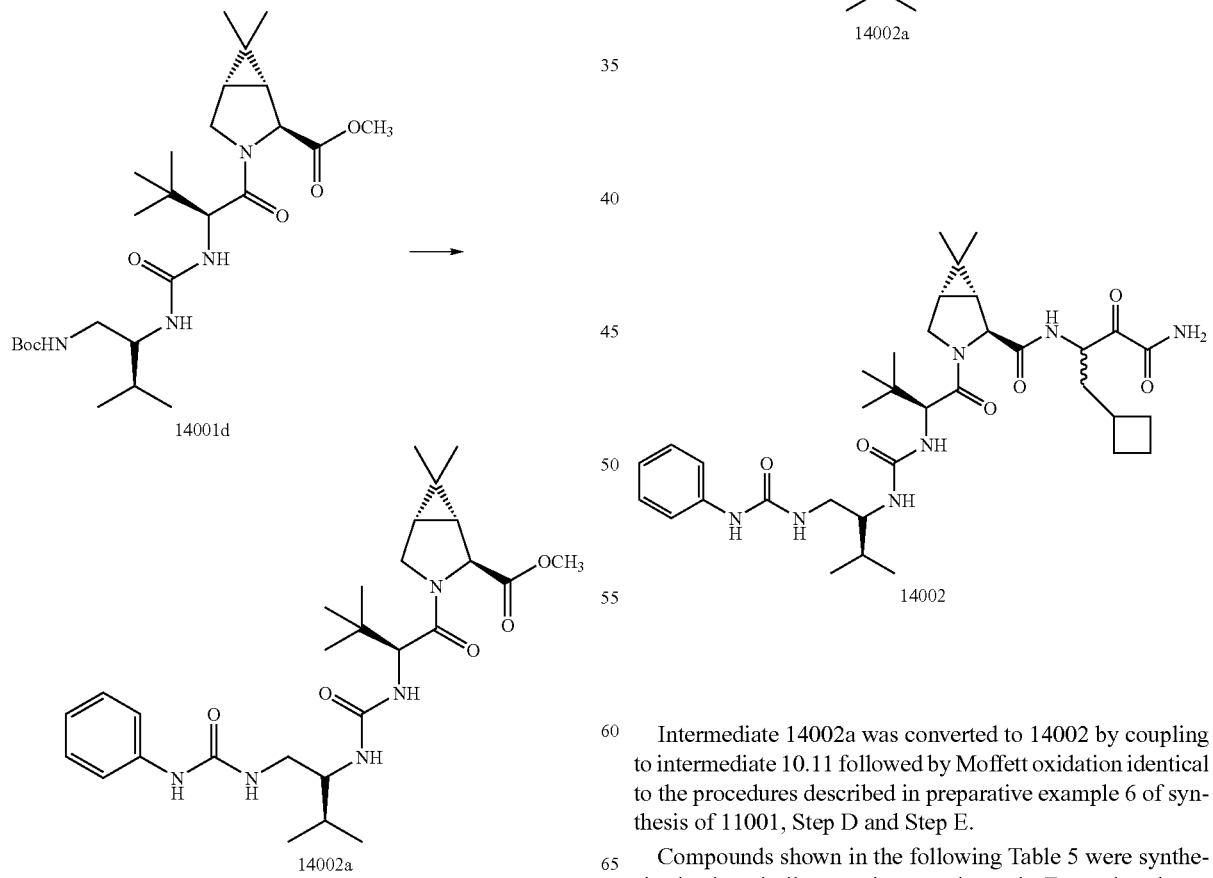

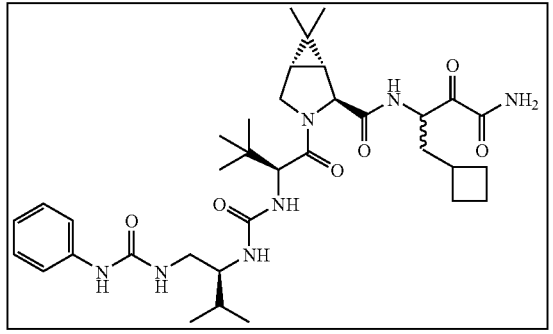

Intermediate 14002a was converted to 14002 by coupling to intermediate 10.11 followed by Moffett oxidation identical to the procedures described in preparative example 6 of synthesis of 11001, Step D and Step E.

Compounds shown in the following Table 5 were synthesized using similar reactions as shown in Examples above. Ki* Range Indicated A≦75 nM; 75<B≦250 nM; C>250 nM.

TABLE 5
| Entry | Structure | $K_i$* |
|---|---|---|
| 14001 | 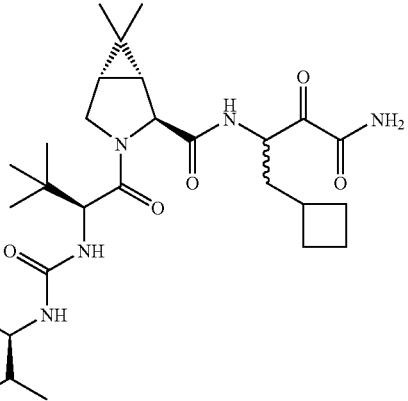 | A |
| 14002 | 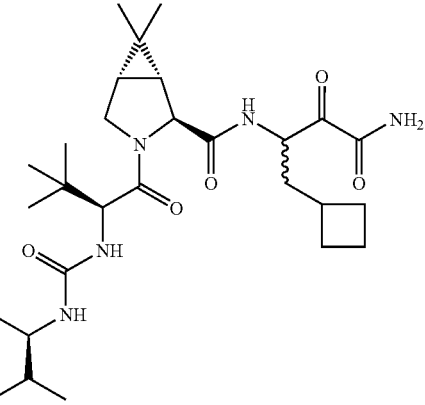 | A |
| 14003 | 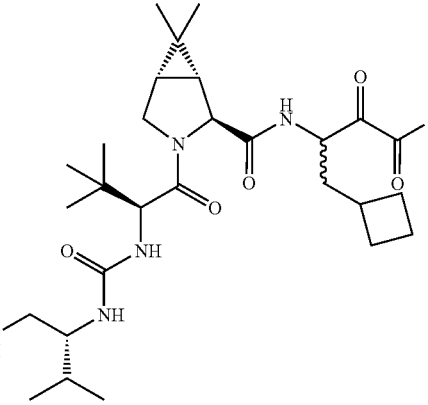 | B |

TABLE 5-continued

| Entry | Structure | $K_i$* |
|---|---|---|
| 14004 | 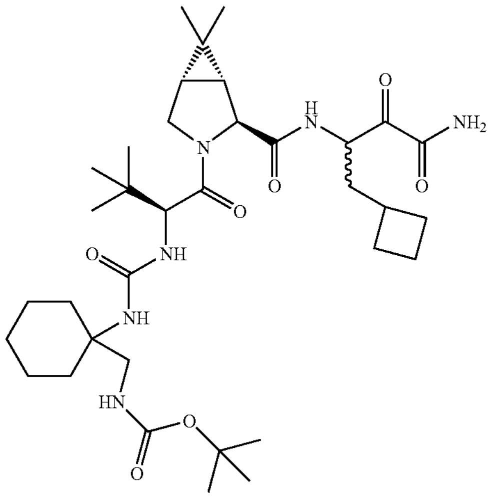 | A |
| 14005 | 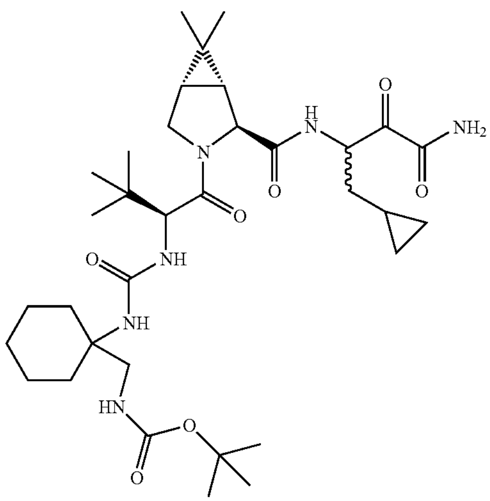 | A |
| 14009 | 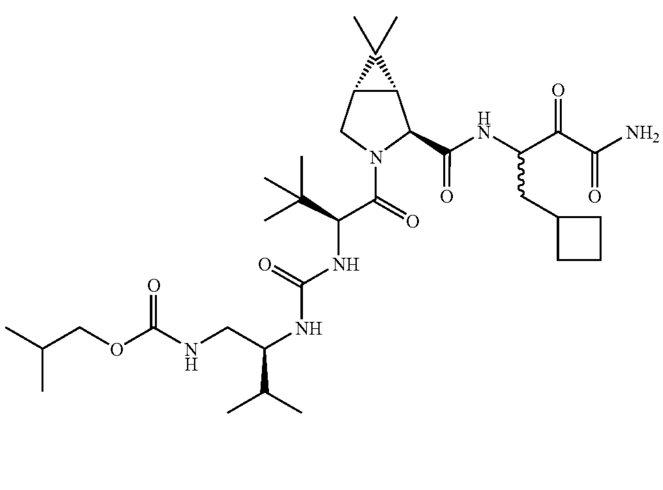 | A |

TABLE 5-continued

| Entry | Structure | $K_i$* |
|---|---|---|
| 14010 | 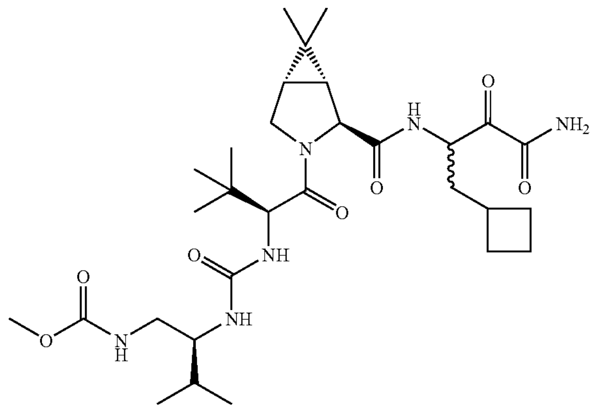 | A |
| 14011 | 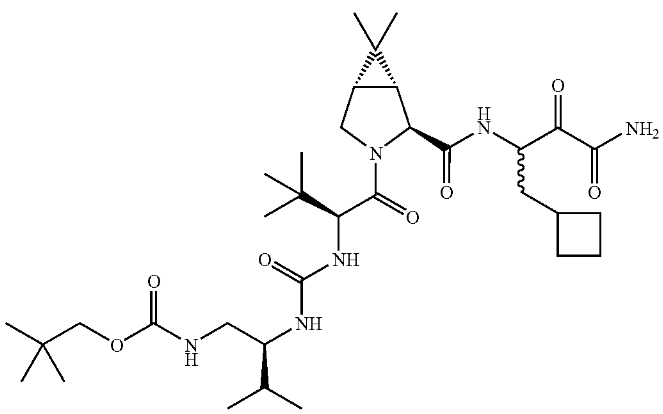 | A |
| 14012 | 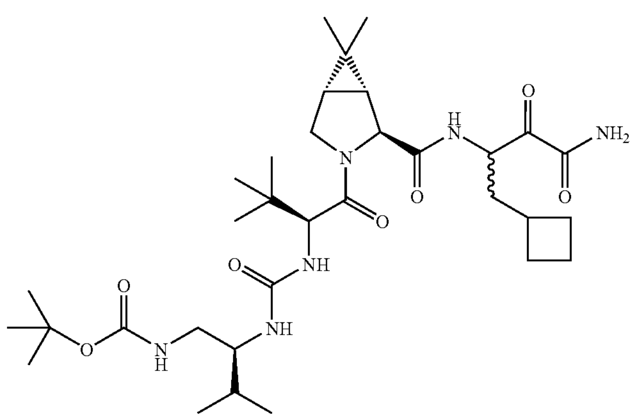 | B |

TABLE 5-continued

| Entry | Structure | $K_i$* |
|---|---|---|
| 14016 | 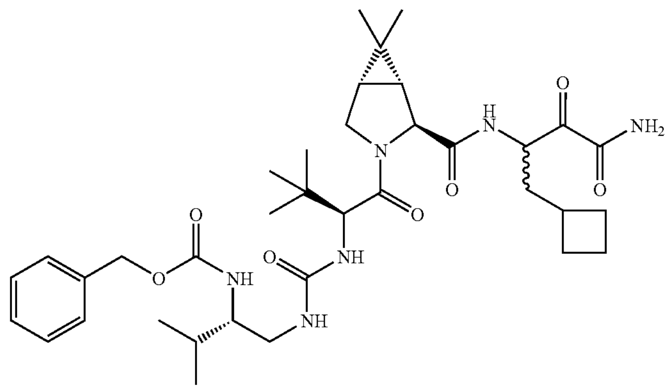 | B |
| 14017 | 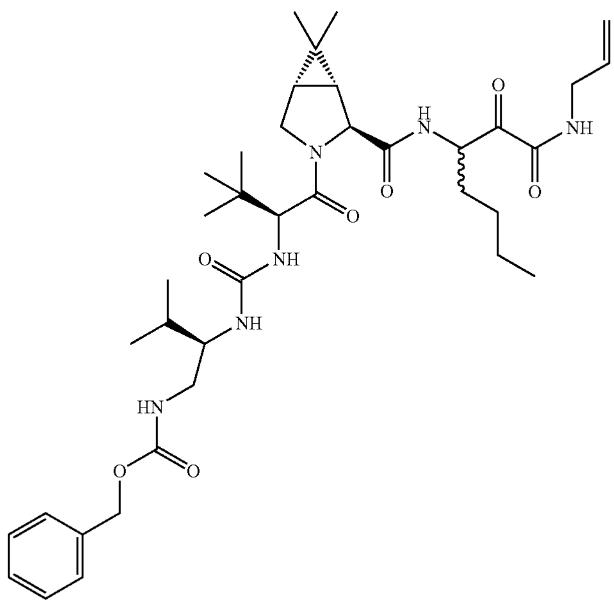 | B |
| 14019 | 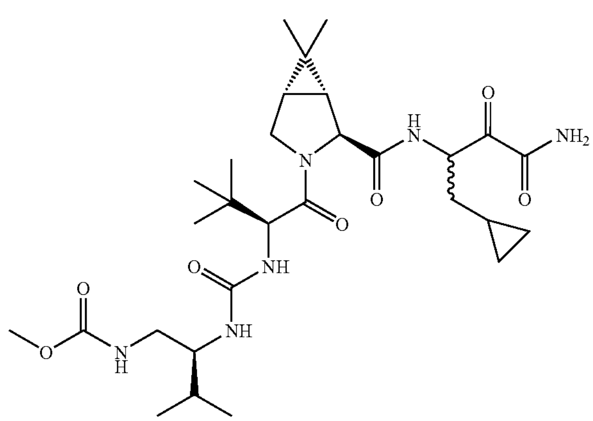 | A |

TABLE 5-continued

| Entry | Structure | $K_i$* |
|---|---|---|
| 14020 | 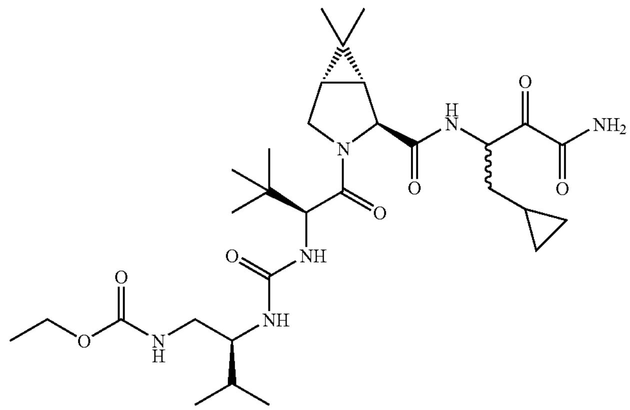 | A |
| 14021 | 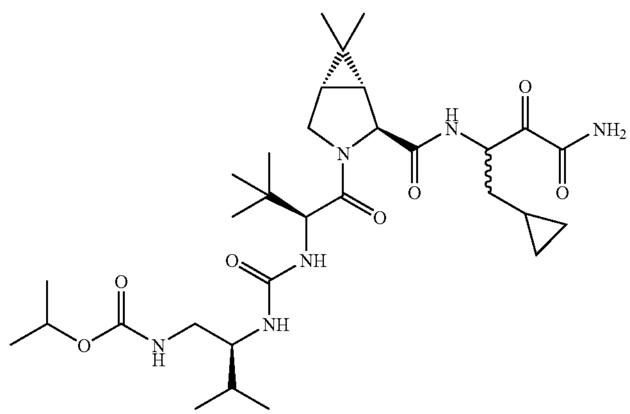 | A |
| 14022 | 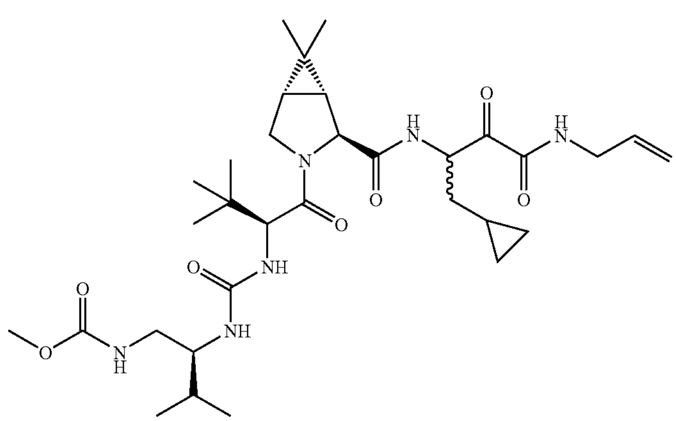 | A |

TABLE 5-continued

| Entry | Structure | $K_i^*$ |
|---|---|---|
| 14023 | 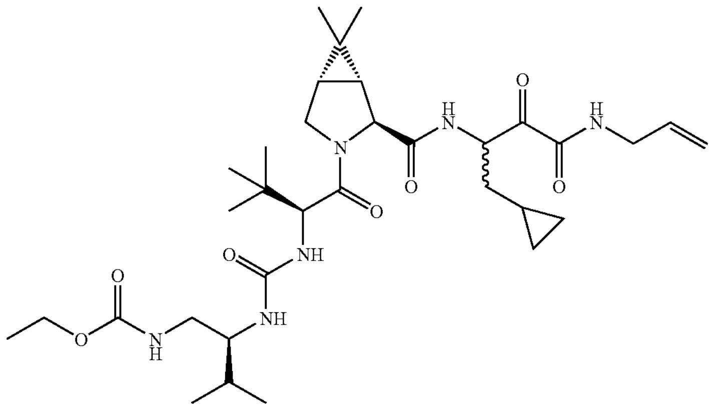 | B |
| 14024 | 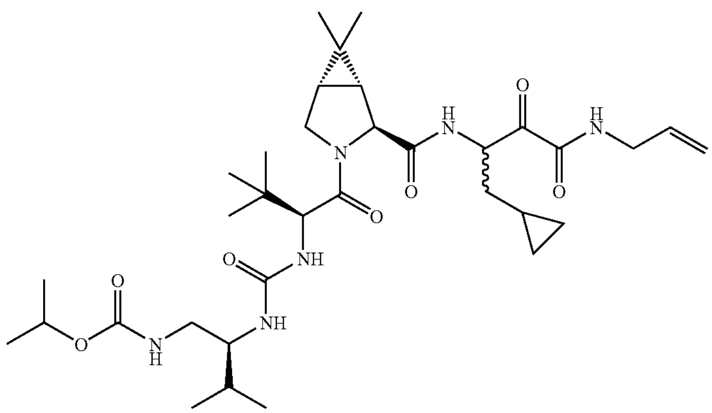 | B |
| 14025 | 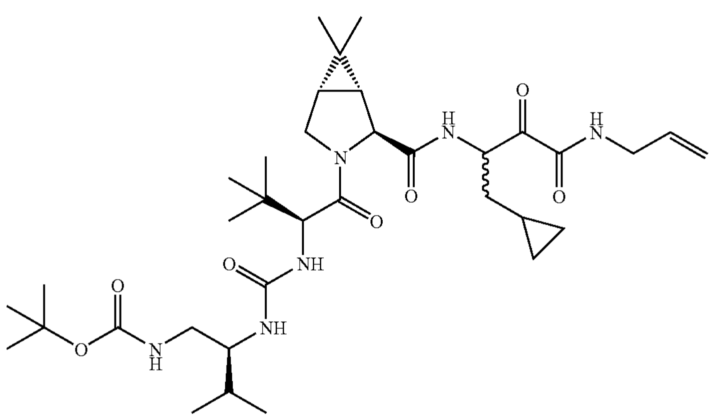 | C |

TABLE 5-continued
| Entry | Structure | $K_i$* |
|---|---|---|
| 14026 | 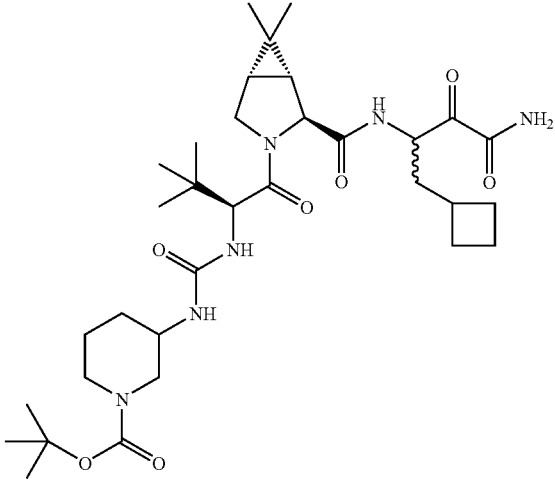 | C |
| 14027 | 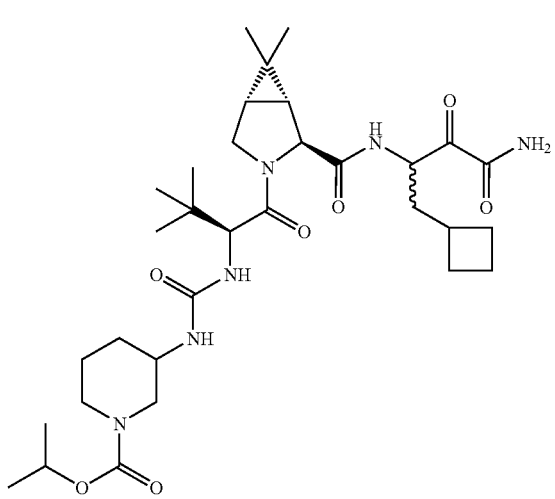 | B |
| 14028 | 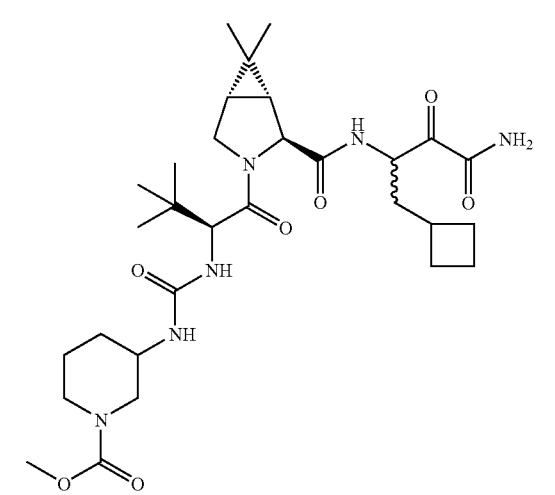 | B |

TABLE 5-continued

| Entry | Structure | $K_i^*$ |
|---|---|---|
| 14029 | 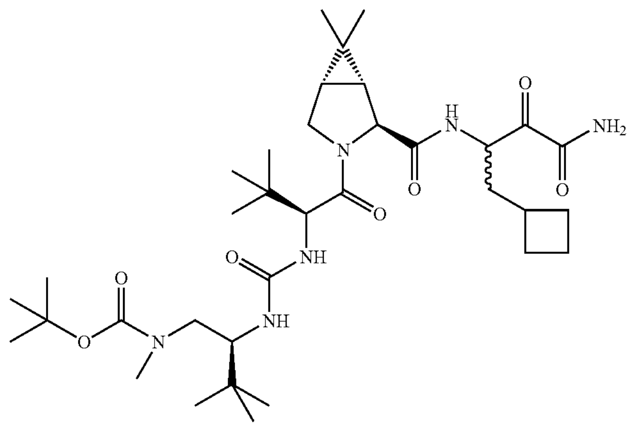 | C |
| 14030 | 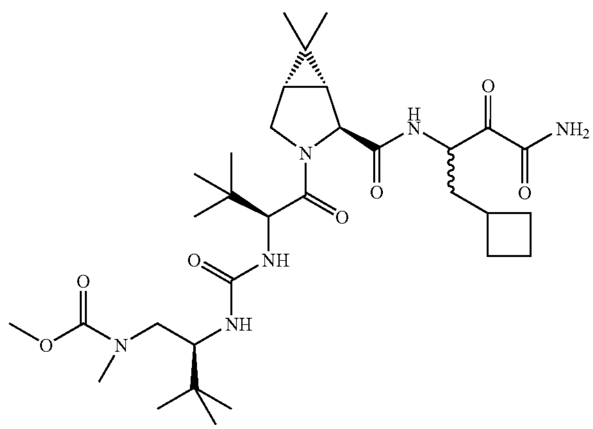 | A |
| 14031 | 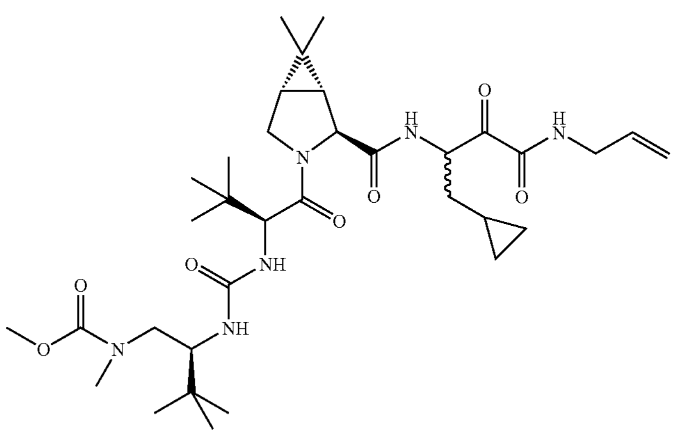 | B |

TABLE 5-continued

| Entry | Structure | $K_i$* |
|---|---|---|
| 14032 | 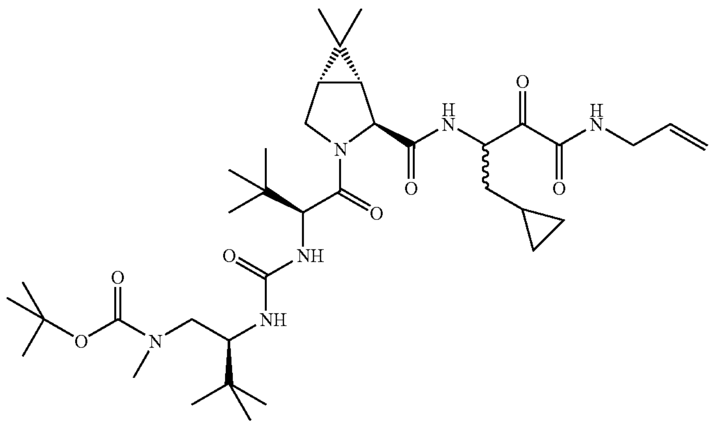 | C |
| 14033 | 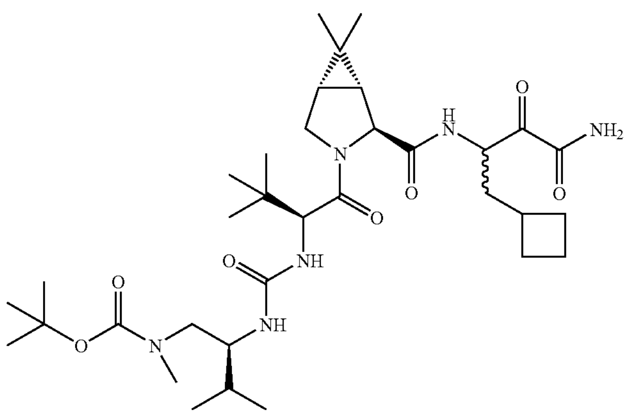 | B |
| 14034 | 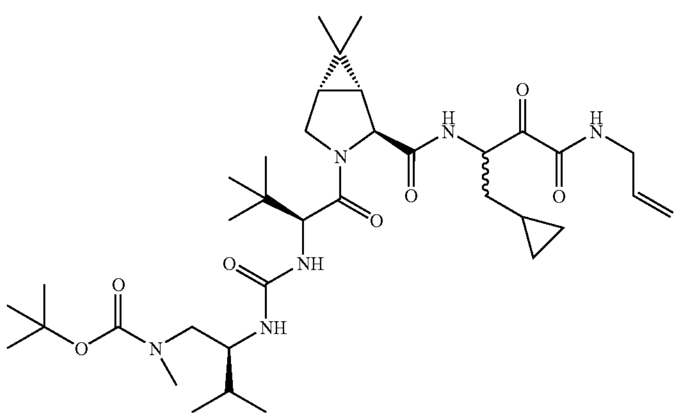 | C |

TABLE 5-continued

| Entry | Structure | $K_i$* |
|---|---|---|
| 14035 | 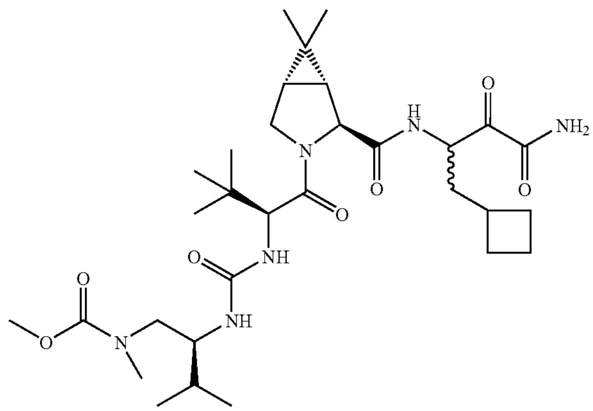 | A |
| 14036 | 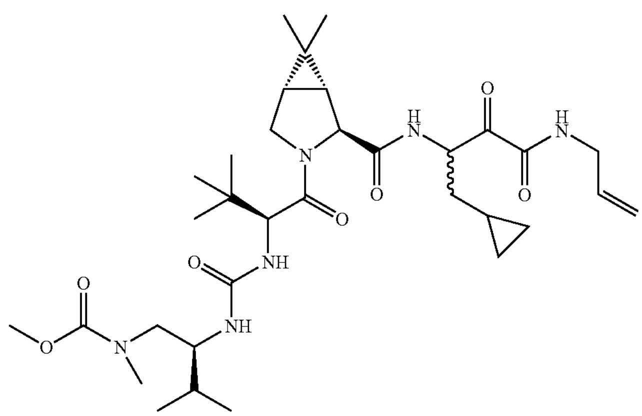 | B |
| 14037 | 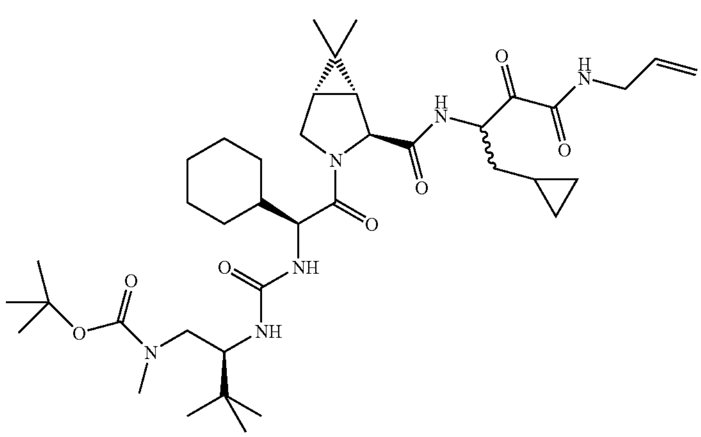 | C |

TABLE 5-continued

| Entry | Structure | $K_i{}^*$ |
|---|---|---|
| 14038 | 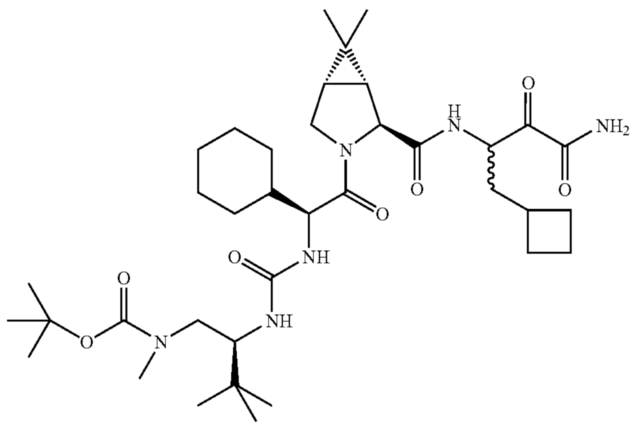 | B |
| 14039 | 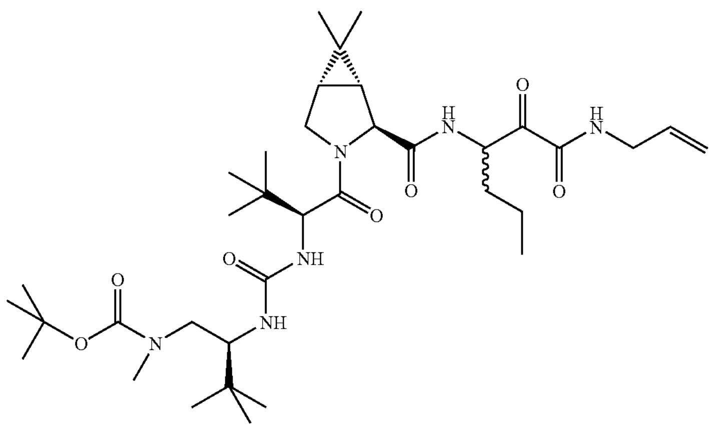 | C |
| 14040 | 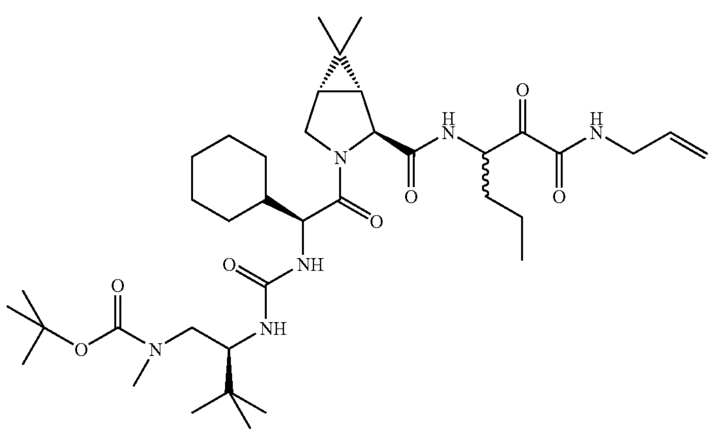 | C |

TABLE 5-continued

| Entry | Structure | $K_i^*$ |
|---|---|---|
| 14041 | 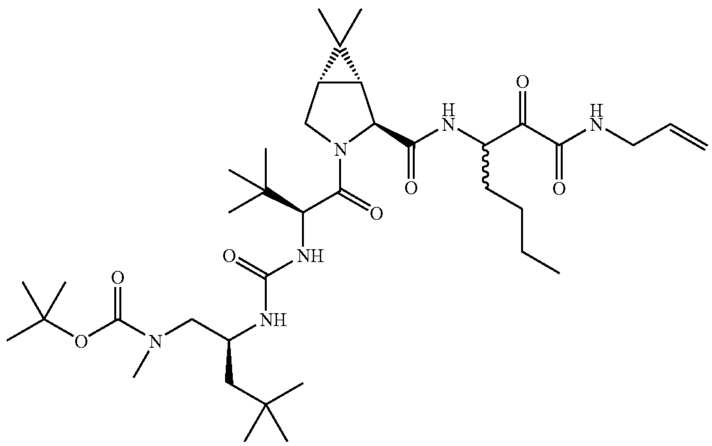 | C |
| 14042 | 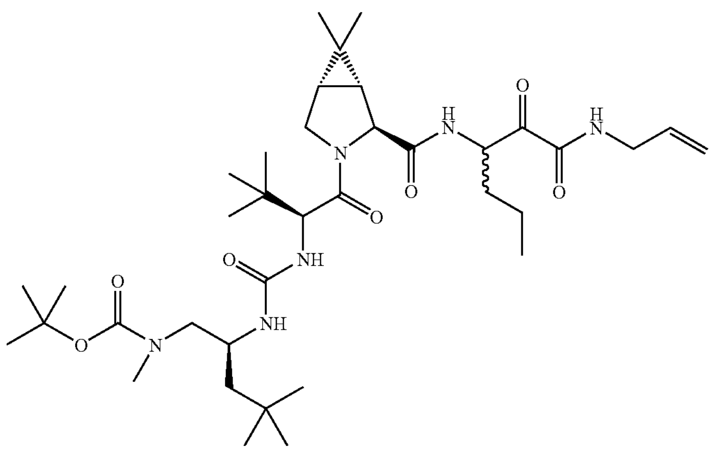 | C |
| 14043 | 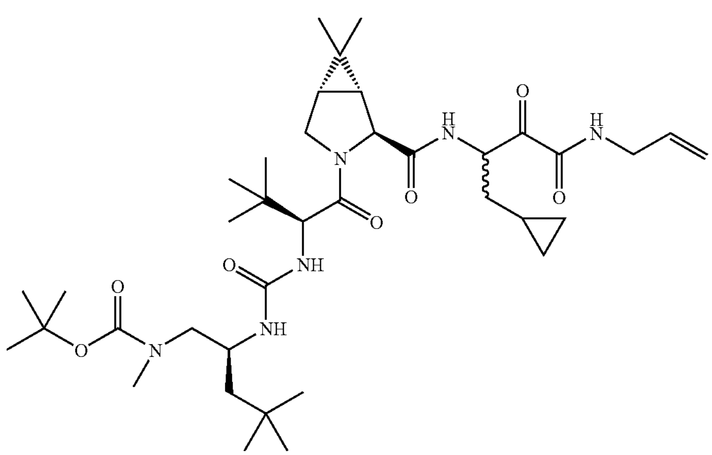 | C |

TABLE 5-continued
| Entry | Structure | $K_i$* |
|---|---|---|
| 14044 | 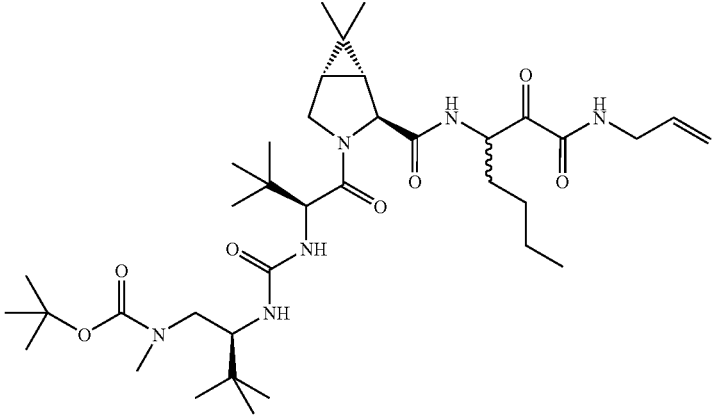 | C |
| 14045 | 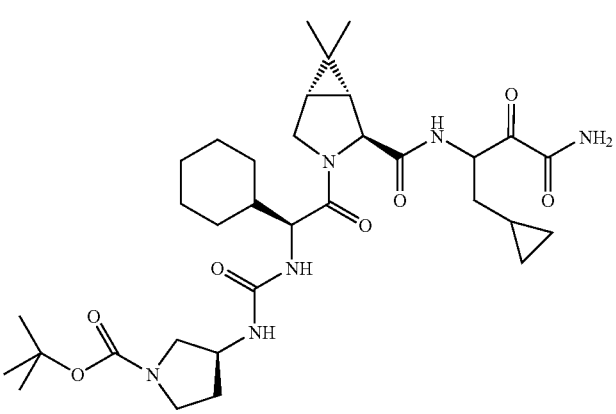 | C |
| 14046 | 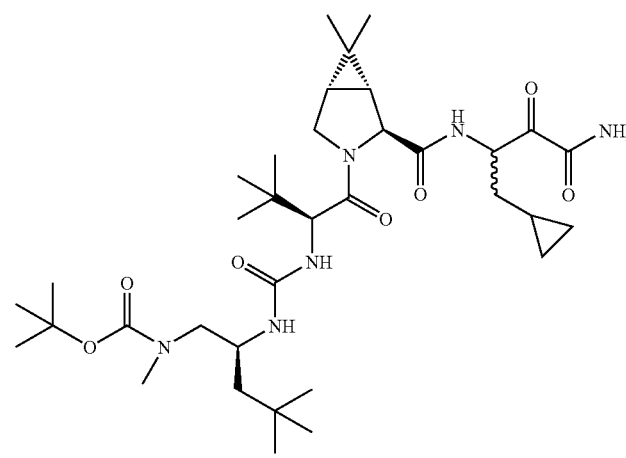 | C |

TABLE 5-continued

| Entry | Structure | $K_i$* |
|---|---|---|
| 14047 | 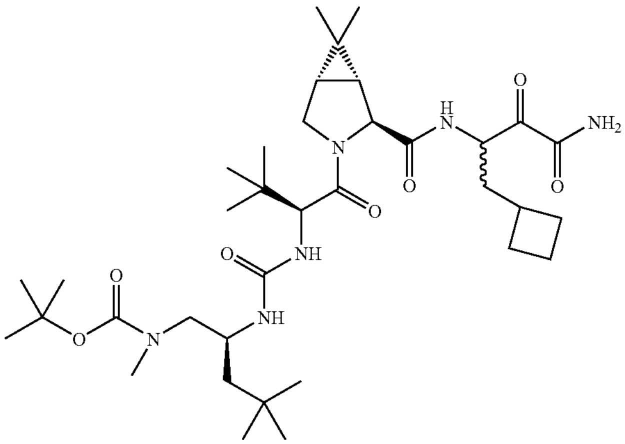 | C |
| 14048 | 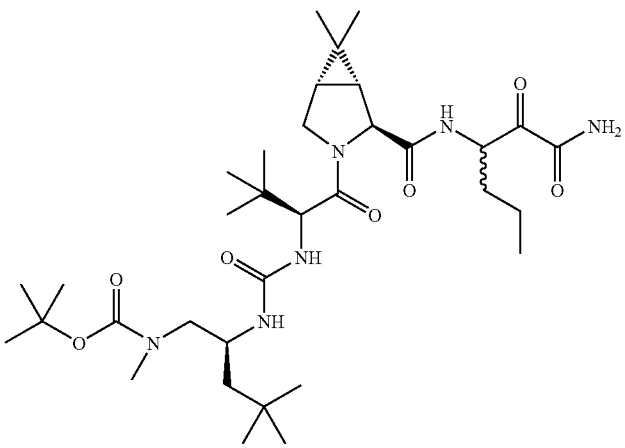 | C |
| 14049 | 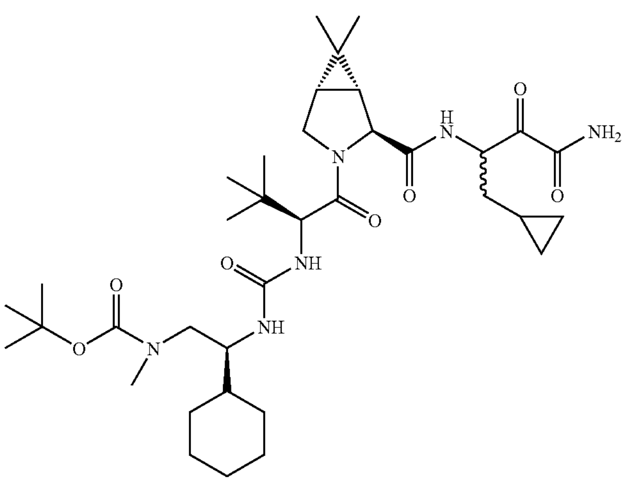 | C |

TABLE 5-continued

| Entry | Structure | $K_i$* |
|---|---|---|
| 14050 | 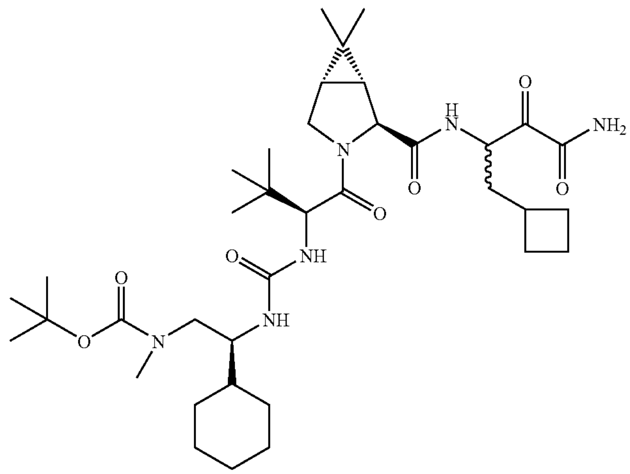 | C |
| 14051 | 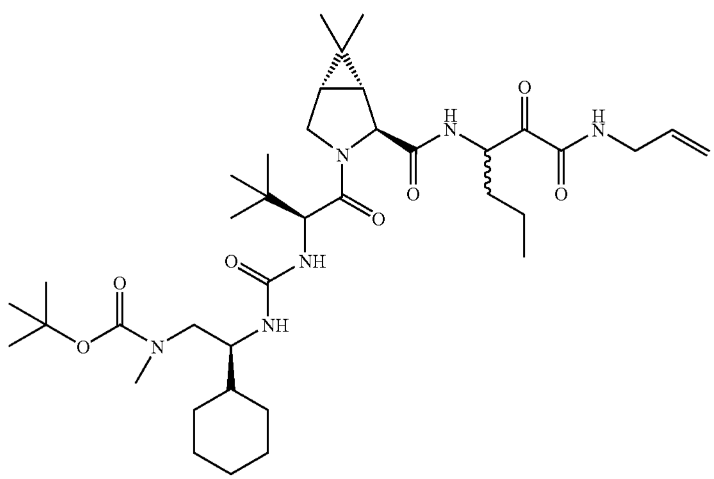 | C |
| 14052 | 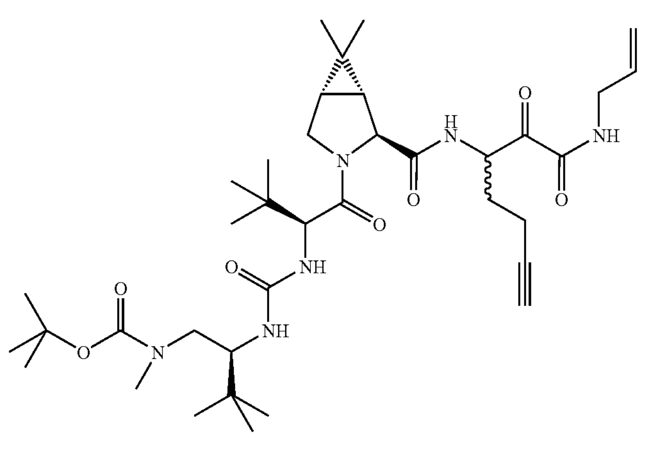 | C |

TABLE 5-continued

| Entry | Structure | $K_i$* |
|---|---|---|
| 14053 | 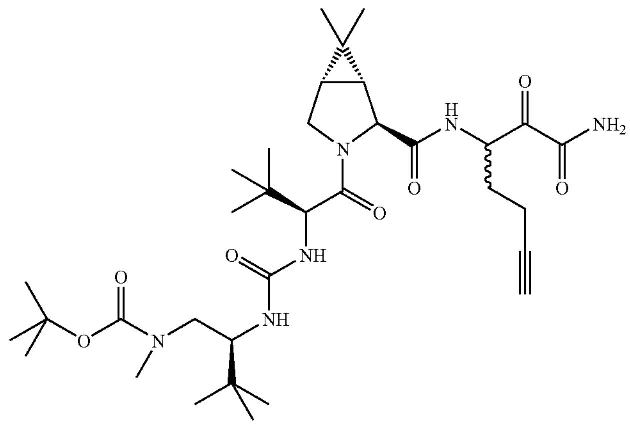 | C |
| 14054 | 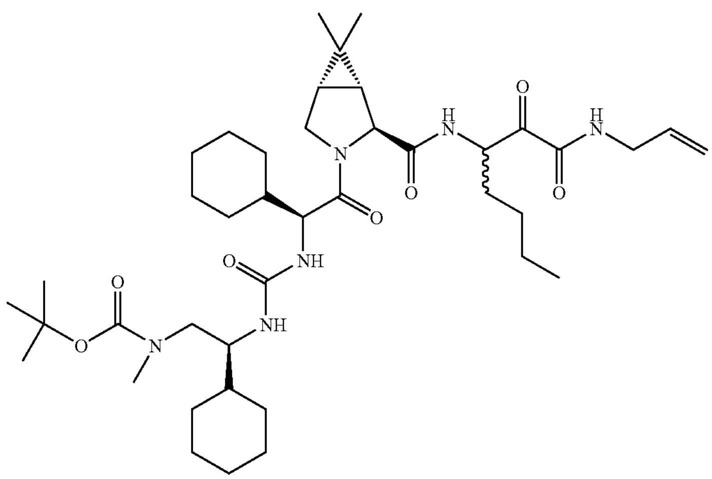 | C |
| 14055 | 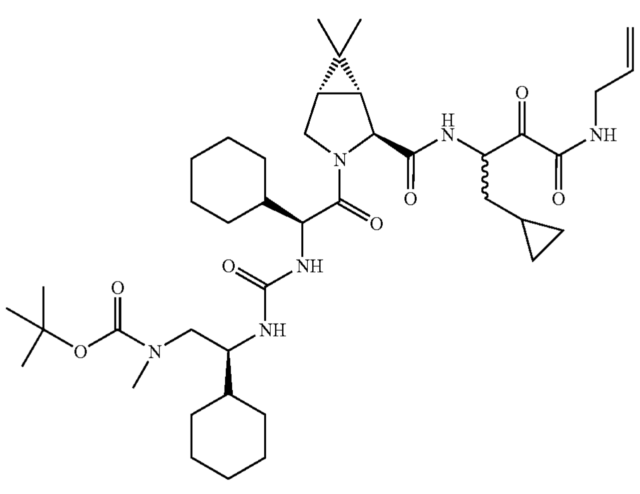 | C |

TABLE 5-continued

| Entry | Structure | $K_i^*$ |
|---|---|---|
| 14056 | 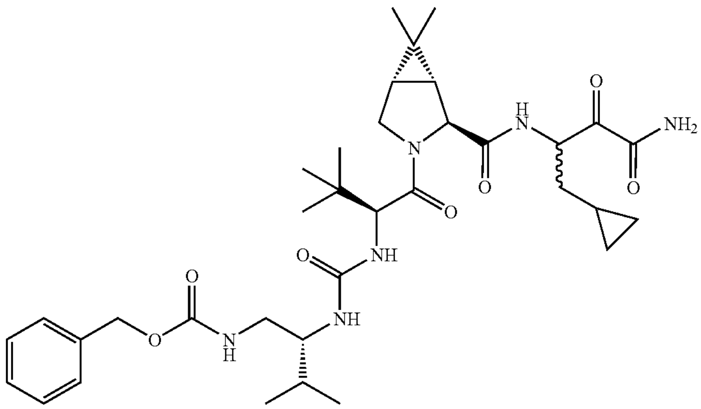 | A |
| 14057 | 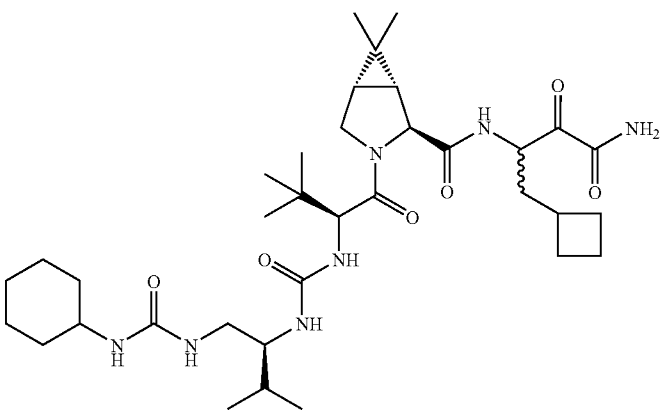 | A |
| 14058 | 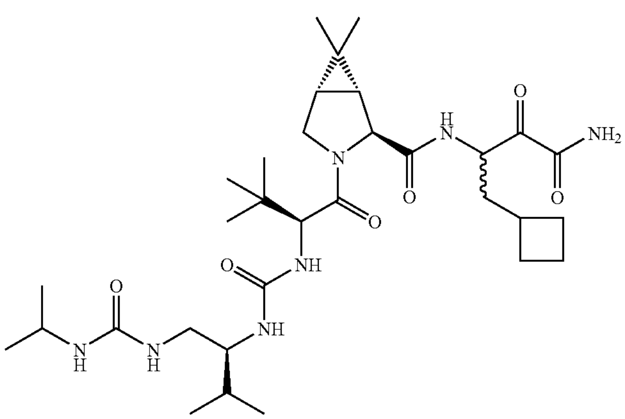 | A |

TABLE 5-continued
| Entry | Structure | $K_i^*$ |
|---|---|---|
| 14059 | 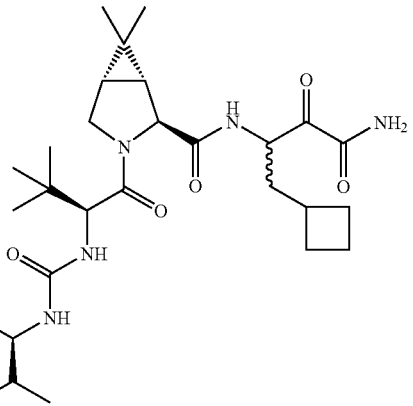 | A |
Additional compounds of the present invention are shown in Table 5A:
TABLE 5A
| Entry | Structure | $K_i^*$ |
|---|---|---|
| 11392 | 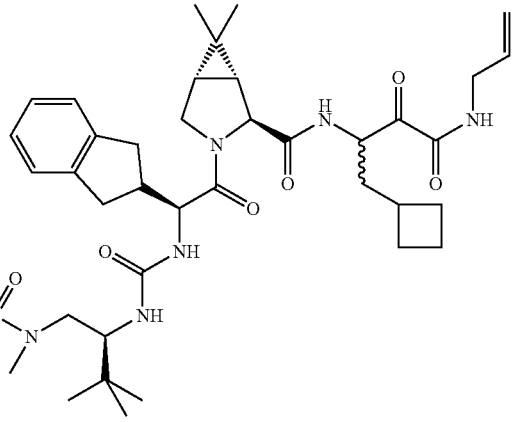 | A |
| 11393 | 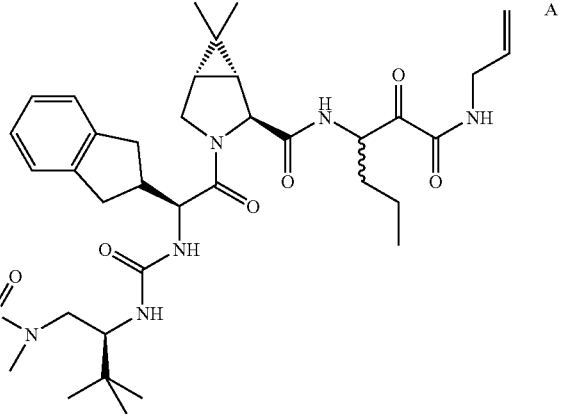 | A |

TABLE 5A-continued

| Entry | Structure | $K_i$* |
|---|---|---|
| 11394 | 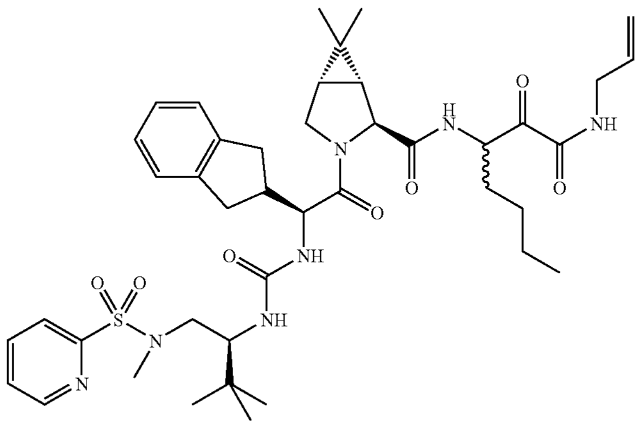 | A |
| 11395 | 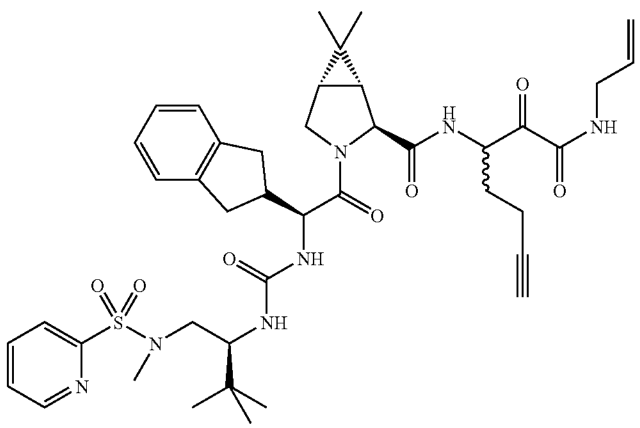 | A |
| 11396 | 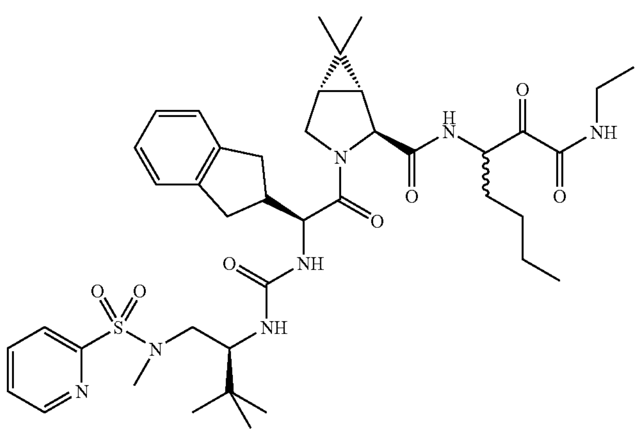 | A |

TABLE 5A-continued
| Entry | Structure | $K_i$* |
|---|---|---|
| 11397 | 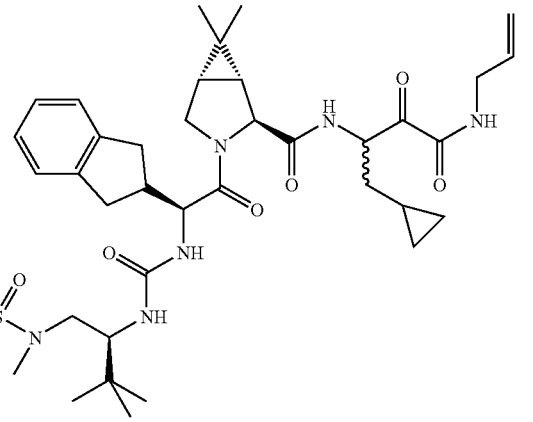 | B |
| 11398 | 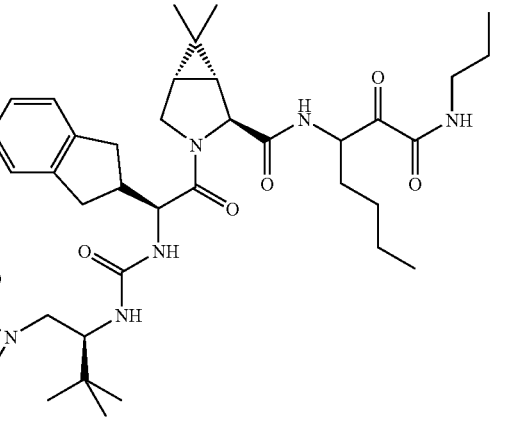 | A |
| 11399 | 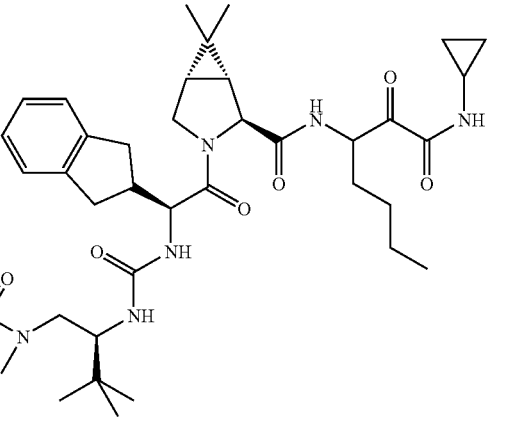 | A |

TABLE 5A-continued
| Entry | Structure | $K_i$* |
|---|---|---|
| 11400 | 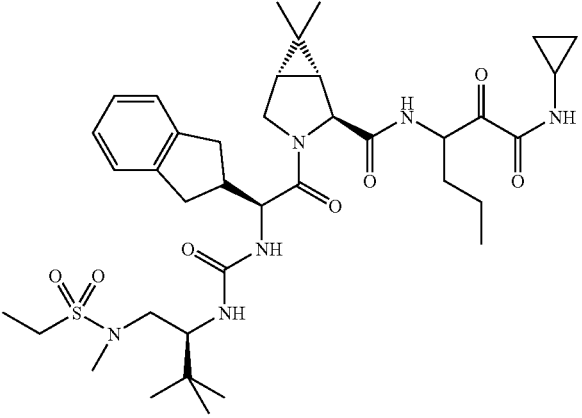 | A |
| 11401 | 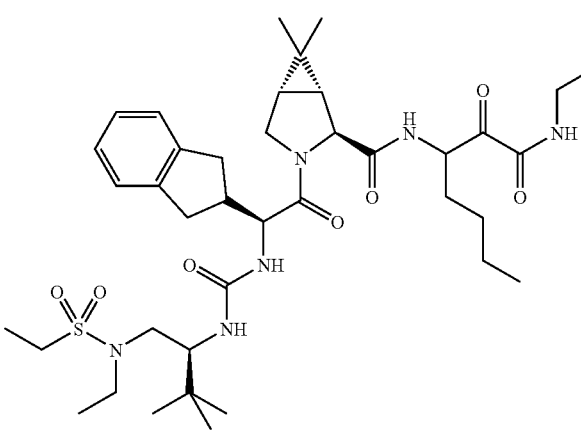 | A |
| 11402 | 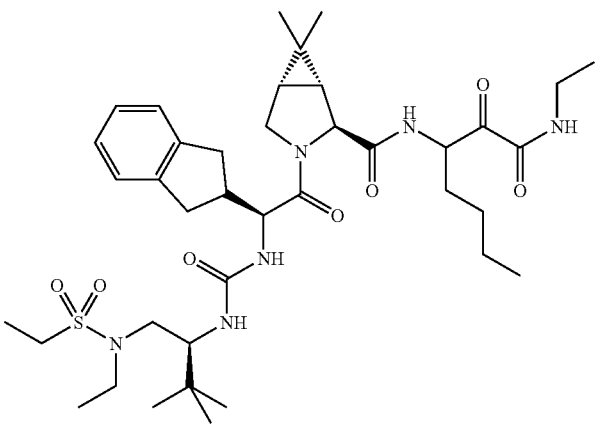 | A |

TABLE 5A-continued

| Entry | Structure | $K_i$* |
|---|---|---|
| 11403 | 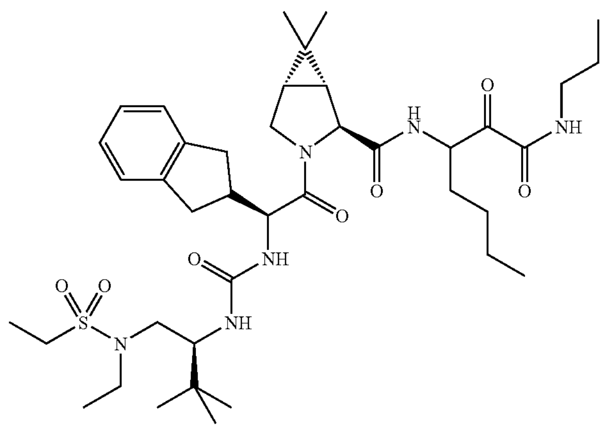 | A |
| 11404 | 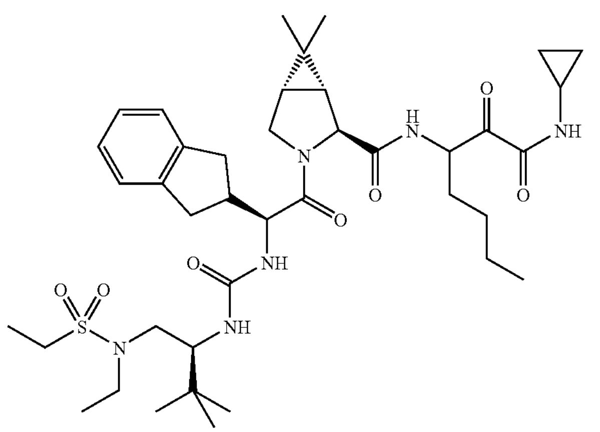 | A |
| 11405 | 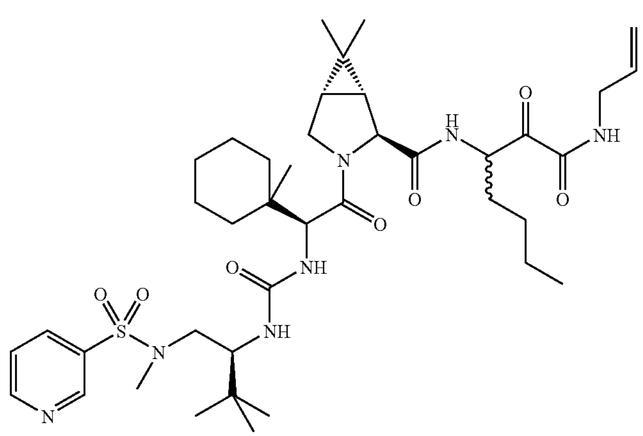 | A |

TABLE 5A-continued

| Entry | Structure | K_i* |
|---|---|---|
| 11406 | 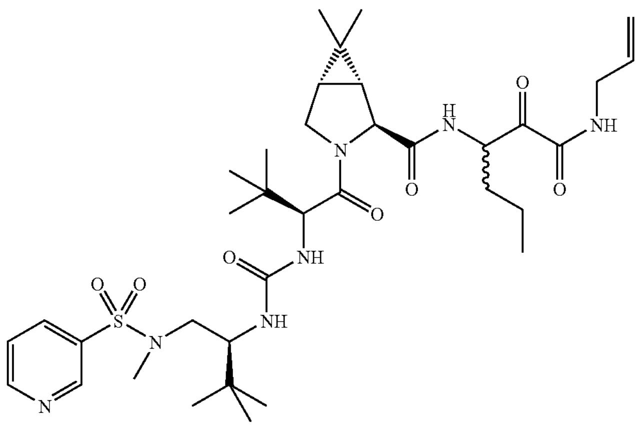 | A |
| 11407 | 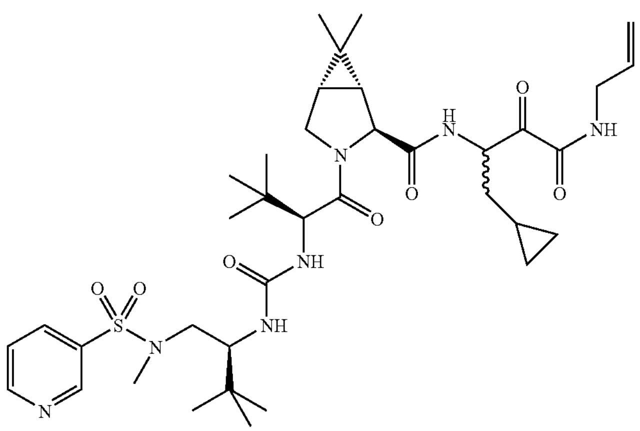 | A |
| 11408 | 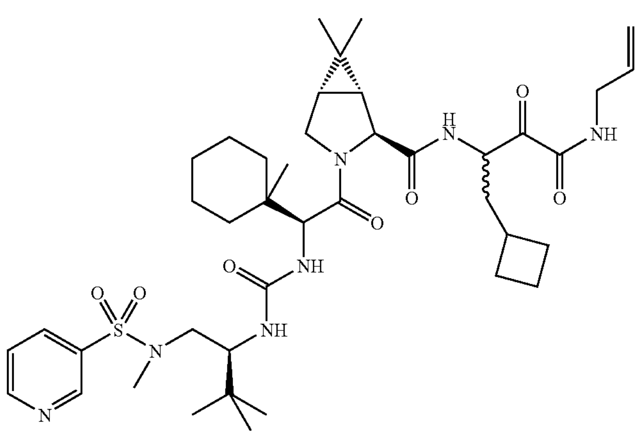 | A |

TABLE 5A-continued

| Entry | Structure | $K_i$* |
|---|---|---|
| 11409 | 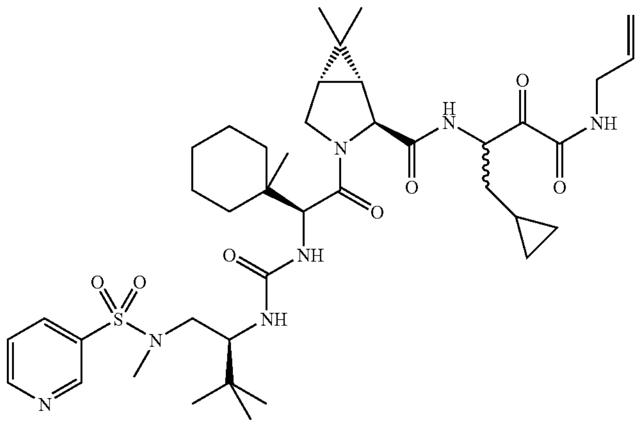 | A |
| 11410 | 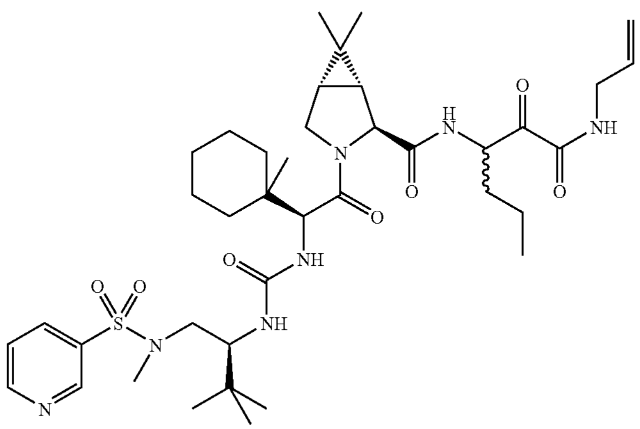 | A |
| 11411 | 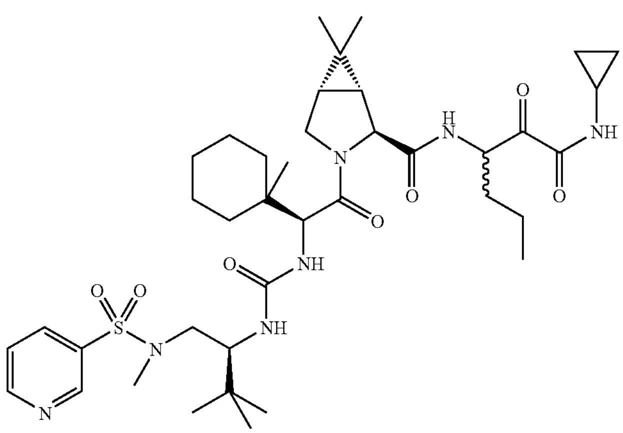 | A |

TABLE 5A-continued

| Entry | Structure | $K_i$* |
|---|---|---|
| 11412 | 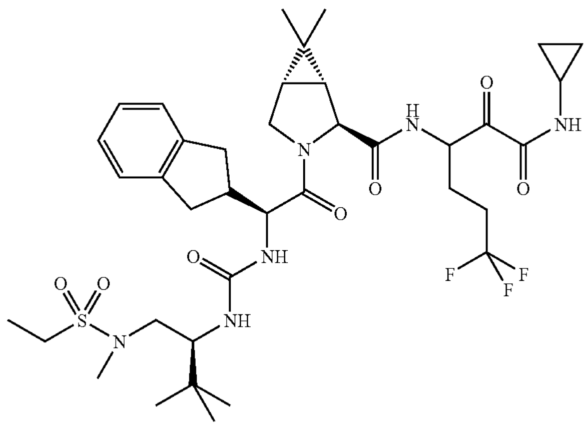 | A |
| 11413 | 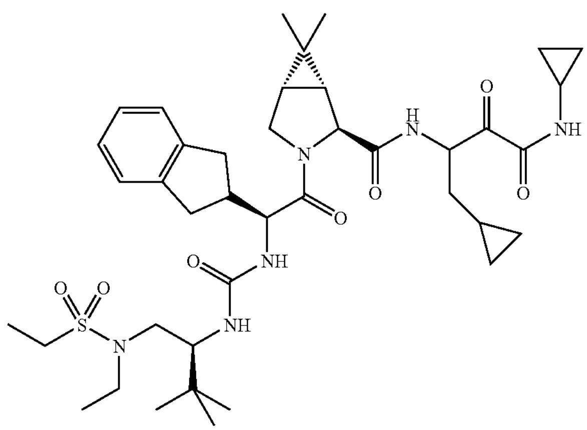 | A |
| 11414 | 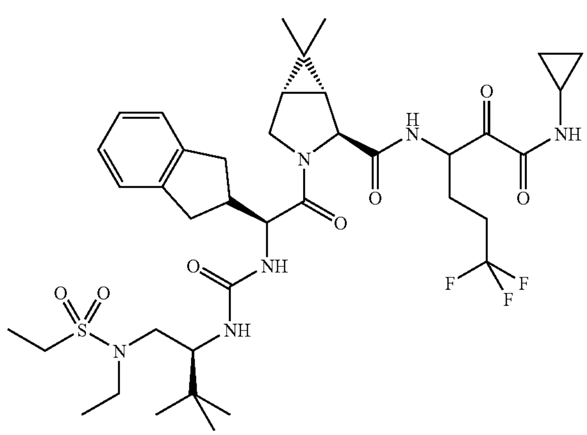 | A |

TABLE 5A-continued
| Entry | Structure | $K_i$* |
|---|---|---|
| 11415 | 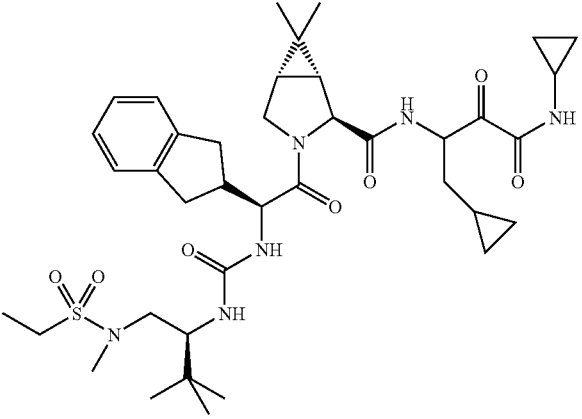 | A |
| 11416 | 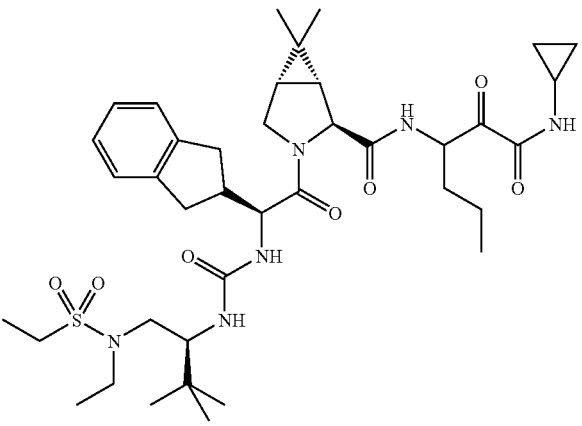 | A |
| 11417 | 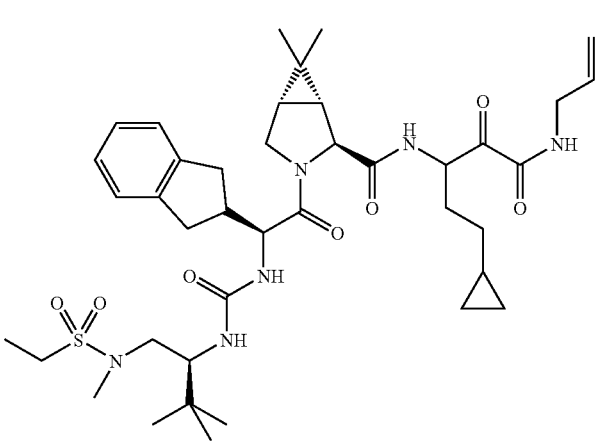 | A |

TABLE 5A-continued
| Entry | Structure | $K_i$* |
|---|---|---|
| 11418 | 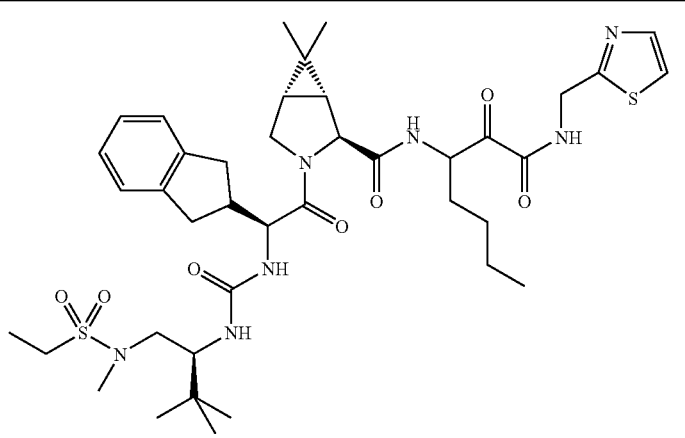 | A |
| 11419 | 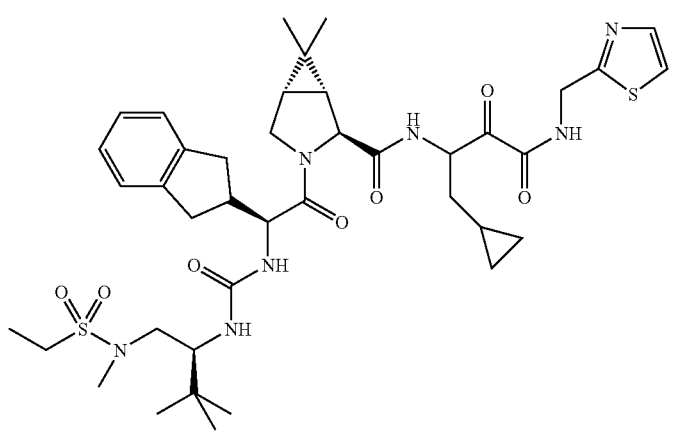 | A |
| 11420 | 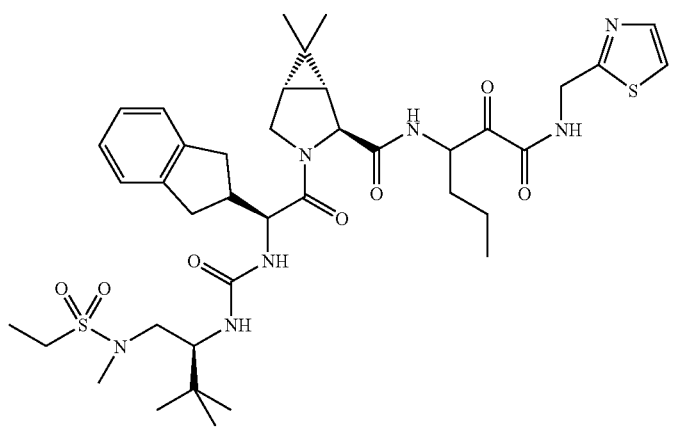 | A |

TABLE 5A-continued

| Entry | Structure | K_i* |
|---|---|---|
| 11421 | 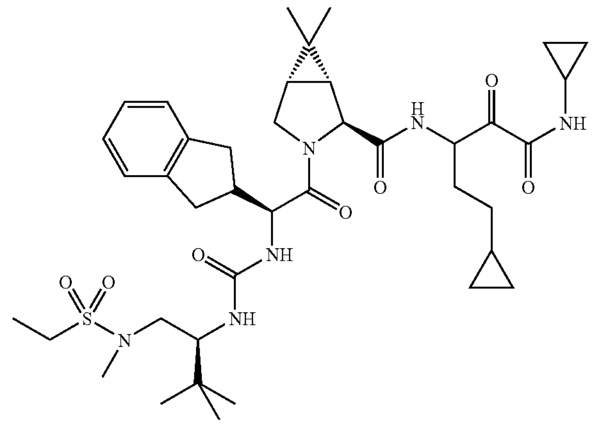 | A |
| 11422 | 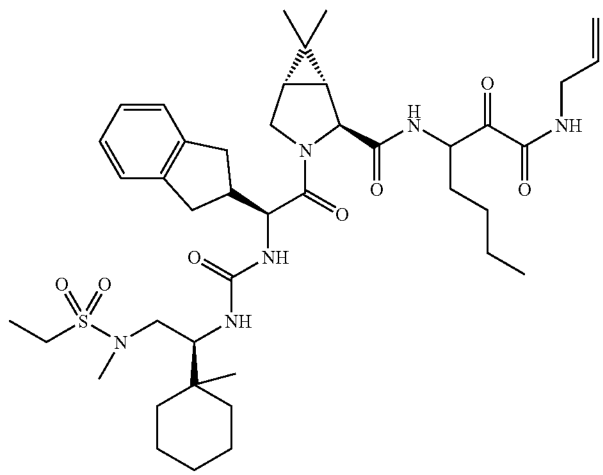 | A |
| 11423 | 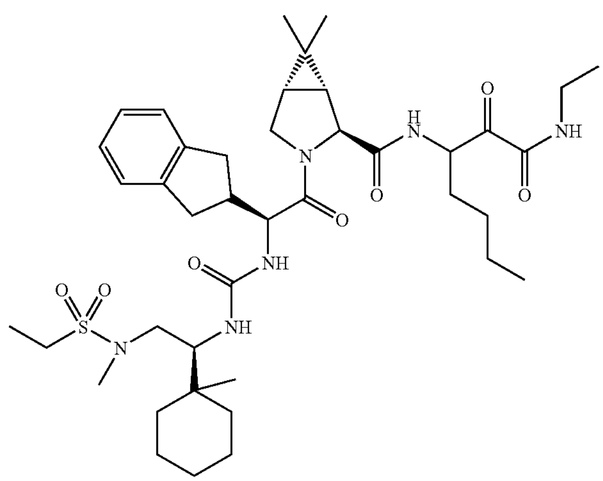 | A |

TABLE 5A-continued

| Entry | Structure | $K_i^*$ |
|---|---|---|
| 11424 | 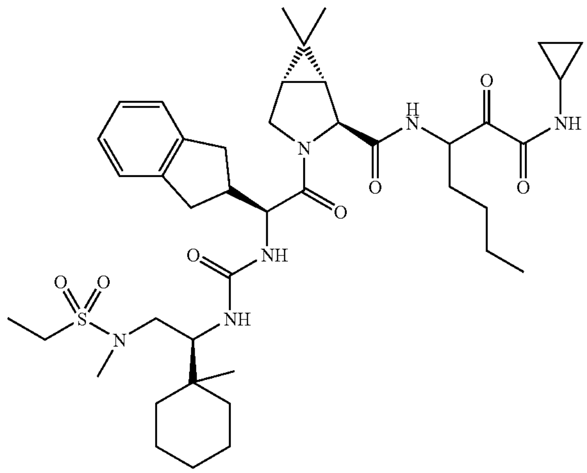 | A |
| 11425 | 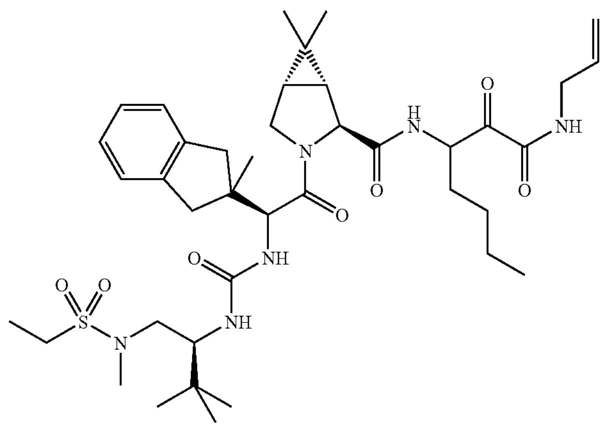 | A |
| 11426 | 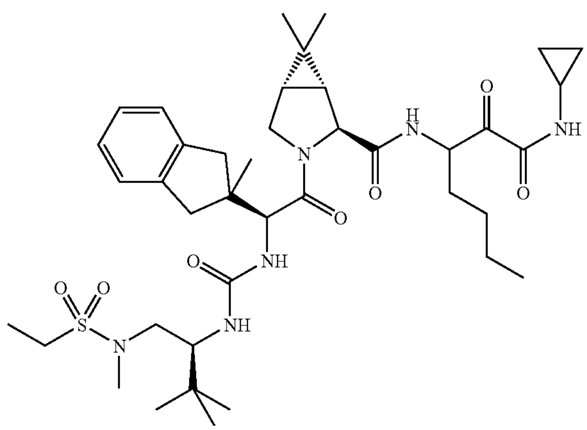 | A |

Range of $K_i^*$ indicated A ≦ 75 nM; 75 < B ≦ 250 nM; C > 250 nM.

The present invention relates to novel HCV protease inhibitors. This utility can be manifested in their ability to inhibit the HCV NS2/NS4a serine protease. A general procedure for such demonstration is illustrated by the following in vitro assay.

Assay for HCV Protease Inhibitory Activity:

Spectrophotometric Assay: Spectrophotometric assay for the HCV serine protease can be performed on the inventive compounds by following the procedure described by R. Zhang et al, Analytical Biochemistry, 270 (1999) 268-275, the disclosure of which is incorporated herein by reference. The assay based on the proteolysis of chromogenic ester substrates is suitable for the continuous monitoring of HCV NS3 protease activity. The substrates are derived from the P side of the NS5A-NS5B junction sequence (Ac-DTEDVVX(Nva), where X=A or P) whose C-terminal carboxyl groups are esterified with one of four different chromophoric alcohols (3- or 4-nitrophenol, 7-hydroxy-4-methyl-coumarin, or 4-phenylazophenol). Illustrated below are the synthesis, characterization and application of these novel spectrophotometric ester substrates to high throughput screening and detailed kinetic evaluation of HCV NS3 protease inhibitors.

Materials and Methods:

Materials: Chemical reagents for assay related buffers are obtained from Sigma Chemical Company (St. Louis, Mo.). Reagents for peptide synthesis were from Aldrich Chemicals, Novabiochem (San Diego, Calif.), Applied Biosystems (Foster City, Calif.) and Perseptive Biosystems (Framingham, Mass.). Peptides are synthesized manually or on an automated ABI model 431A synthesizer (from Applied Biosystems). UV/VIS Spectrometer model LAMBDA 12 was from Perkin Elmer (Norwalk, Conn.) and 96-well UV plates were obtained from Corning (Corning, N.Y.). The prewarming block can be from USA Scientific (Ocala, Fla.) and the 96-well plate vortexer is from Labline Instruments (Melrose Park, Ill.). A Spectramax Plus microtiter plate reader with monochrometer is obtained from Molecular Devices (Sunnyvale, Calif.).

Enzyme Preparation: Recombinant heterodimeric HCV NS3/NS4A protease (strain 1a) is prepared by using the procedures published previously (D. L. Sali et al, *Biochemistry*, 37 (1998) 3392-3401). Protein concentrations are determined by the Biorad dye method using recombinant HCV protease standards previously quantified by amino acid analysis. Prior to assay initiation, the enzyme storage buffer (50 mM sodium phosphate pH 8.0, 300 mM NaCl, 10% glycerol, 0.05% lauryl maltoside and 10 mM DTT) is exchanged for the assay buffer (25 mM MOPS pH 6.5, 300 mM NaCl, 10% glycerol, 0.05% lauryl maltoside, 5 µM EDTA and 5 µM DTT) utilizing a Biorad Bio-Spin P-6 prepacked column.

Substrate Synthesis and Purification: The synthesis of the substrates is done as reported by R. Zhang et al, (ibid.) and is initiated by anchoring Fmoc-Nva-OH to 2-chlorotrityl chloride resin using a standard protocol (K. Barlos et al, *Int. J. Pept. Protein Res.*, 37 (1991), 513-520). The peptides are subsequently assembled, using Fmoc chemistry, either manually or on an automatic ABI model 431 peptide synthesizer. The N-acetylated and fully protected peptide fragments are cleaved from the resin either by 10% acetic acid (HOAc) and 10% trifluoroethanol (TFE) in dichloromethane (DCM) for 30 min, or by 2% trifluoroacetic acid (TFA) in DCM for 10 min. The combined filtrate and DCM wash is evaporated azeotropically (or repeatedly extracted by aqueous $Na_2CO_3$ solution) to remove the acid used in cleavage. The DCM phase is dried over $Na_2SO_4$ and evaporated.

The ester substrates are assembled using standard acid-alcohol coupling procedures (K. Holmber et al, *Acta Chem. Scand.*, B33 (1979) 410-412). Peptide fragments are dissolved in anhydrous pyridine (30-60 mg/ml) to which 10 molar equivalents of chromophore and a catalytic amount (0.1 eq.) of para-toluenesulfonic acid (pTSA) were added. Dicyclohexylcarbodiimide (DCC, 3 eq.) is added to initiate the coupling reactions. Product formation is monitored by HPLC and can be found to be complete following 12-72 hour reaction at room temperature. Pyridine solvent is evaporated under vacuum and further removed by azeotropic evaporation with toluene. The peptide ester is deprotected with 95% TFA in DCM for two hours and extracted three times with anhydrous ethyl ether to remove excess chromophore. The deprotected substrate is purified by reversed phase HPLC on a C3 or C8 column with a 30% to 60% acetonitrile gradient (using six column volumes). The overall yield following HPLC purification can be approximately 20-30%. The molecular mass can be confirmed by electrospray ionization mass spectroscopy. The substrates are stored in dry powder form under desiccation.

Spectra of Substrates and Products: Spectra of substrates and the corresponding chromophore products are obtained in the pH 6.5 assay buffer. Extinction coefficients are determined at the optimal off-peak wavelength in 1-cm cuvettes (340 nm for 3-Np and HMC, 370 nm for PAP and 400 nm for 4-Np) using multiple dilutions. The optimal off-peak wavelength is defined as that wavelength yielding the maximum fractional difference in absorbance between substrate and product (product OD−substrate OD)/substrate OD).

Protease Assay: HCV protease assays are performed at 30° C. using a 200 µl reaction mix in a 96-well microtiter plate. Assay buffer conditions (25 mM MOPS pH 6.5, 300 mM NaCl, 10% glycerol, 0.05% lauryl maltoside, 5 µM EDTA and 5 µM DTT) are optimized for the NS3/NS4A heterodimer (D. L. Sali et al, ibid.)). Typically, 150 µl mixtures of buffer, substrate and inhibitor are placed in wells (final concentration of DMSO≦4% v/v) and allowed to preincubate at 30° C. for approximately 3 minutes. Fifty µls of prewarmed protease (12 nM, 30° C.) in assay buffer, is then used to initiate the reaction (final volume 200 µl). The plates are monitored over the length of the assay (60 minutes) for change in absorbance at the appropriate wavelength (340 nm for 3-Np and HMC, 370 nm for PAP, and 400 nm for 4-Np) using a Spectromax Plus microtiter plate reader equipped with a monochrometer (acceptable results can be obtained with plate readers that utilize cutoff filters). Proteolytic cleavage of the ester linkage between the Nva and the chromophore is monitored at the appropriate wavelength against a no enzyme blank as a control for non-enzymatic hydrolysis. The evaluation of substrate kinetic parameters is performed over a 30-fold substrate concentration range (~6-200 µM). Initial velocities are determined using linear regression and kinetic constants are obtained by fitting the data to the Michaelis-Menten equation using non-linear regression analysis (Mac Curve Fit 1.1, K. Raner). Turnover numbers ($k_{cat}$) are calculated assuming the enzyme is fully active.

Evaluation of Inhibitors and Inactivators: The inhibition constants ($K_i$) for the competitive inhibitors Ac-D-(D-Gla)-L-I-(Cha)-C—OH (27), Ac-DTEDVVA(Nva)-OH and Ac-DTEDVVP(Nva)-OH are determined experimentally at fixed concentrations of enzyme and substrate by plotting $v_o/v_i$ vs. inhibitor concentration ($[I]_o$) according to the rearranged Michaelis-Menten equation for competitive inhibition kinetics: $v_o/v_i = 1 + [I]_o/(K_i (1+[S]_o/K_m))$, where $v_o$ is the uninhibited initial velocity, $v_i$ is the initial velocity in the presence of inhibitor at any given inhibitor concentration ($[I]_o$) and $[S]_o$ is the substrate concentration used. The resulting data are fitted using linear regression and the resulting slope, $1/(K_i(1+[S]_o/K_m))$, is used to calculate the $K_i$ value. The KI* values for some of the inventive compounds are given in Table 6.

While the present invention has been described with in conjunction with the specific embodiments set forth above, many alternatives, modifications and other variations thereof will be apparent to those of ordinary skill in the art. All such alternatives, modifications and variations are intended to fall within the spirit and scope of the present invention.

What is claimed is:

1. A compound, or enantiomer, stereoisomer, rotamer, tautomer, diastereomer and racemate of said compound, or a pharmaceutically acceptable salt or ester of said compound, said compound of the general structure shown in Formula I:

551

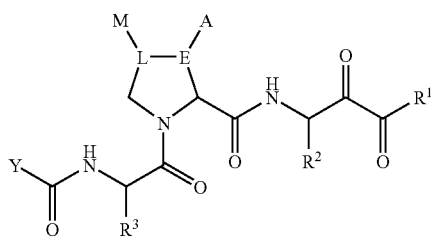

Formula I wherein:
R¹ is OR⁸, NR⁹R¹⁰, or CHR⁹R¹⁰, wherein R⁸, R⁹ and R¹⁰ can be the same or different, each being independently selected from the group consisting of H, alkyl-, alkenyl-, alkynyl-, aryl-, heteroalkyl-, cycloalkyl-, and arylalkyl-; or R¹⁰ is R¹⁴, wherein R¹⁴ is selected from the group consisting of:

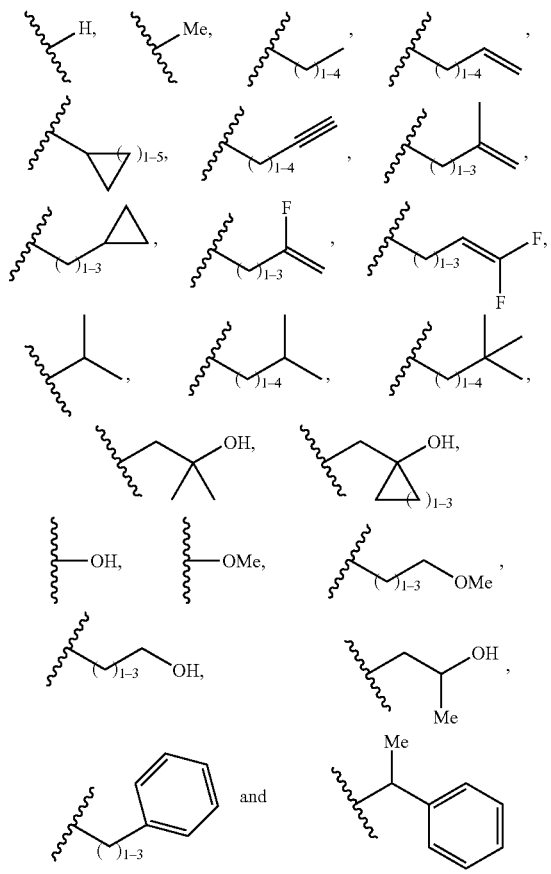

A and M are connected to each other (in other words, A-E-L-M taken together) such that the moiety:

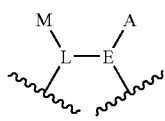

shown above in Formula I forms either a three, four, six, seven or eight-membered cycloalkyl;

E is C(H) or C(R);
L is C(H) or C(R);
R, R², and R³ can be the same or different, each being independently selected from the group consisting of H, alkyl-, alkenyl-, alkynyl-, cycloalkyl-, heteroalkyl-, aryl-, (cycloalkyl)alkyl-, and aryl-alkyl-;

Y is:

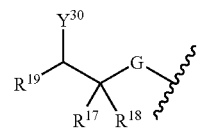

wherein Y³⁰ and Y³¹ are selected from

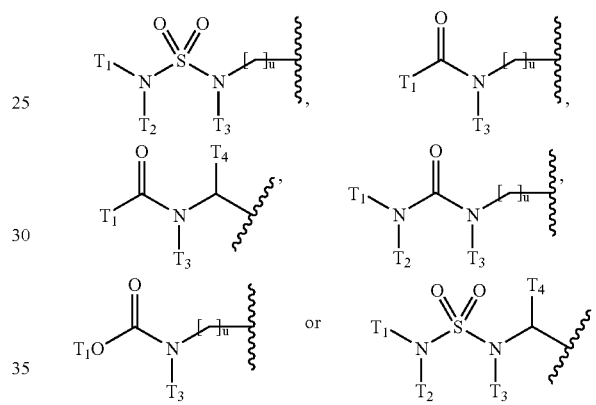

where u is a number 0-6;

G is NH or O; and
R¹⁵, R¹⁶, R¹⁷, R¹⁸, R¹⁹, T₁, T₂, T₃ and T₄ can be the same or different, each being independently selected from the group consisting of H, alkyl, heteroalkyl, alkenyl, heteroalkenyl, alkynyl, heteroalkynyl, cycloalkyl, aryl, and arylalkyl, or alternately, R¹⁷ and R¹⁸ are connected to each other to form a three to eight-membered cycloalkyl; wherein each of said alkyl, aryl, or cycloalkyl or can be unsubstituted or optionally independently substituted with one or more moieties selected from the group consisting of: hydroxy, alkoxy, aryloxy, thio, alkylthio arylthio, amino, amido, alkylamino, arylamino, alkylsulfonyl, arylsulfonyl, sulfonamido, alkyl, aryl, heteroaryl, alkylsulfonamido, arylsulfonamido, keto, carboxy, carbalkoxy, carboxamido, alkoxycarbonylamino, alkoxycarbonyloxy, alkylureido, arylureido, halo, cyano, and nitro.

2. The compound of claim 1, wherein R¹ is NR⁹R¹⁰, and R⁹ is H, R¹⁰ is H, or R¹⁴ wherein R¹⁴ is selected from the group consisting of

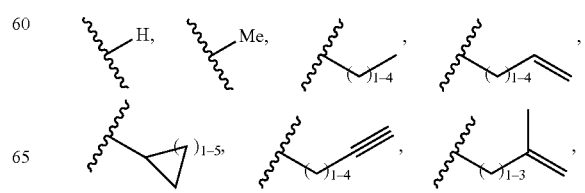

-continued
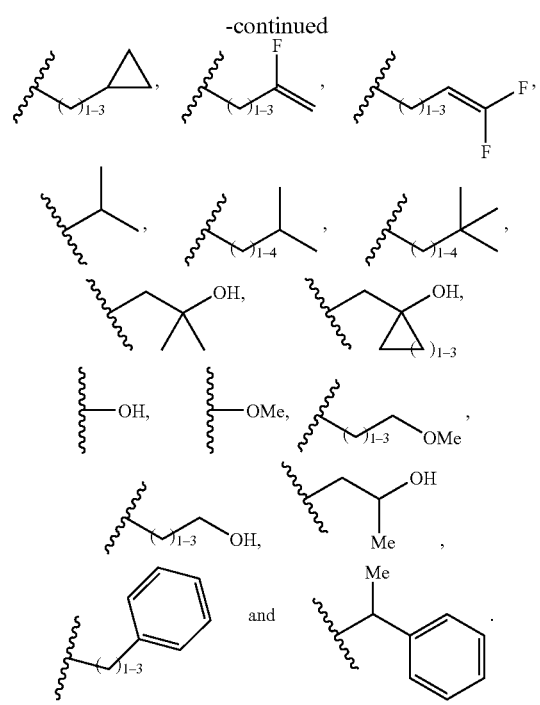
3. The compound of claim 1, wherein $R^2$ is selected from the group consisting of the following moieties:
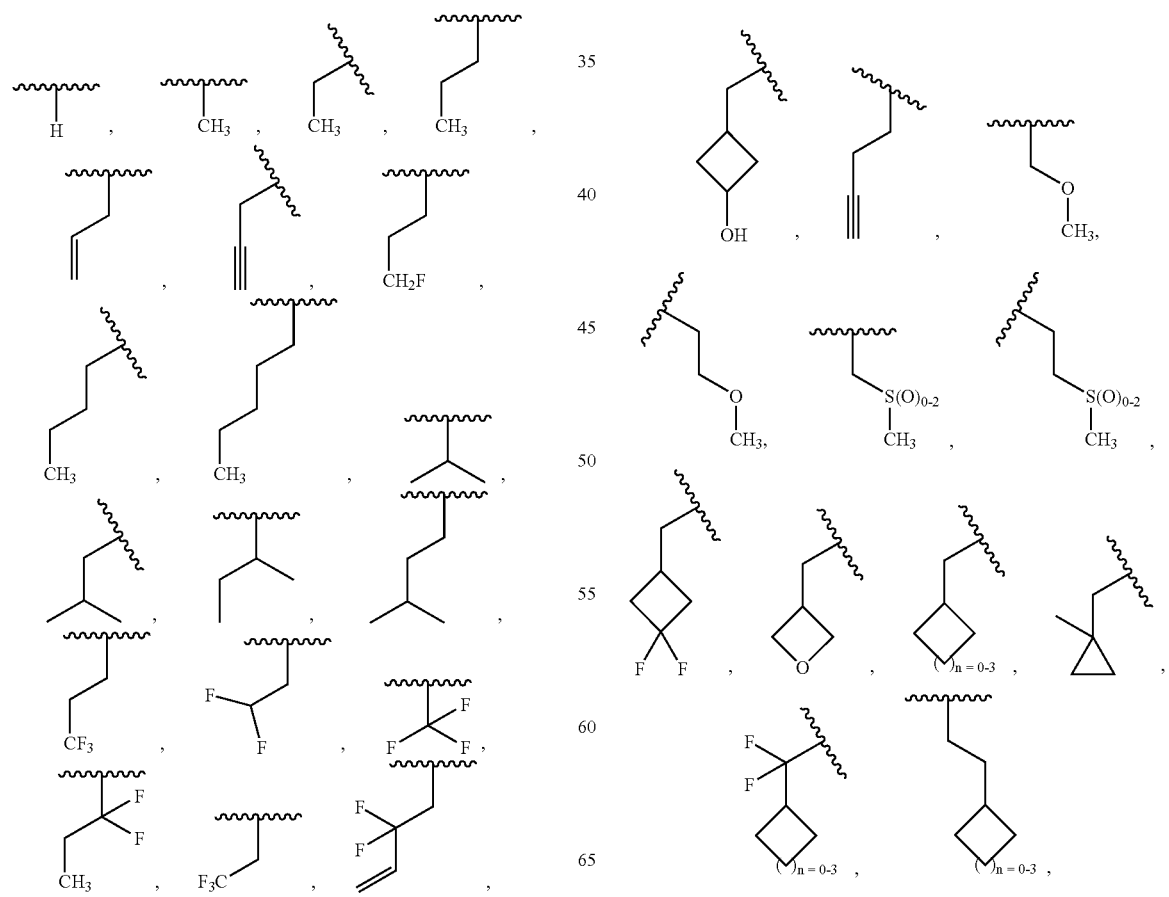
-continued
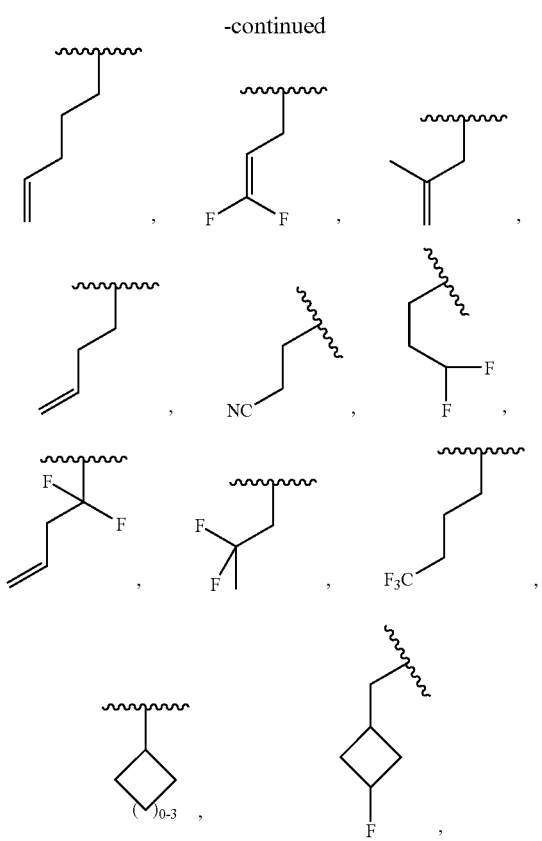

4. The compound of claim 1, wherein $R^3$ is selected from the group consisting of:

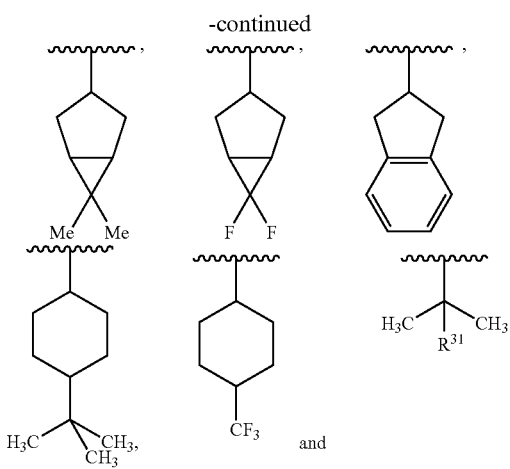
wherein R³¹ is OH or O-alkyl; and
R³² is H, O(O)CH₃, C(O)OtBu or C(O)N(H)tBu.
5. The compound of claim 4, wherein R³ is selected from the group consisting of the following moieties:
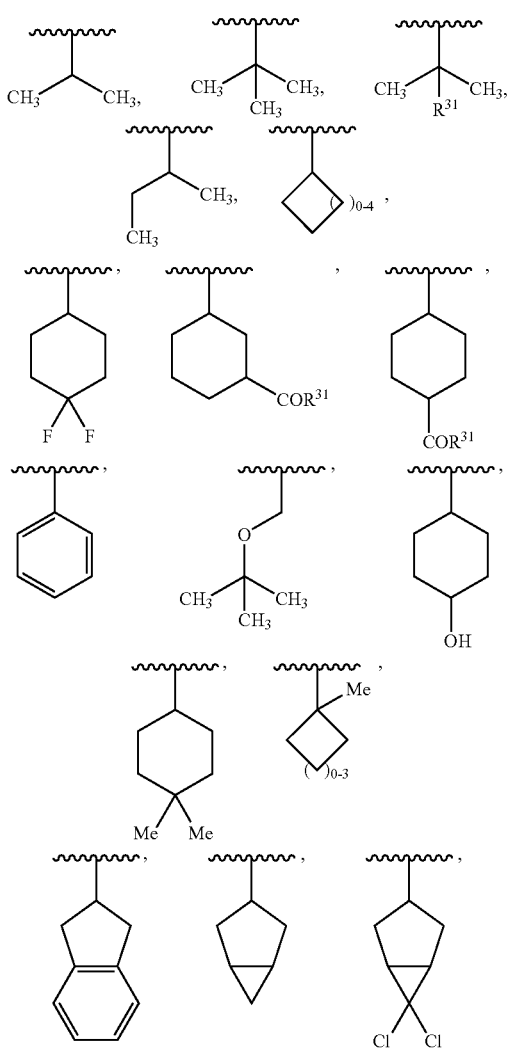
6. The compound of claim 1, wherein G is NH.
7. The compound of claim 6, wherein Y is selected from the following moieties:
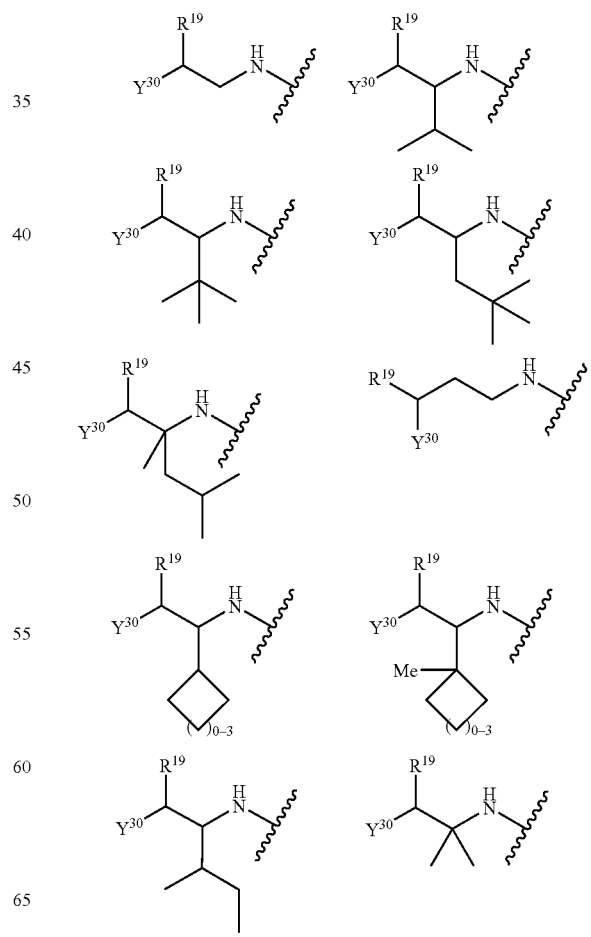

-continued
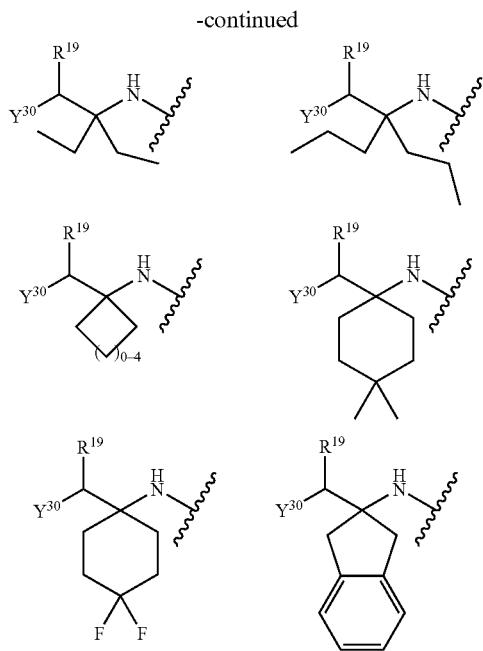
wherein Y³² is selected from the group consisting of:
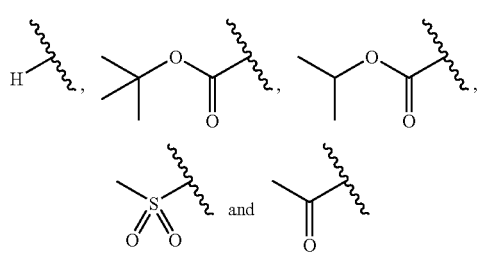
Y³⁰ and Y³¹ is selected from
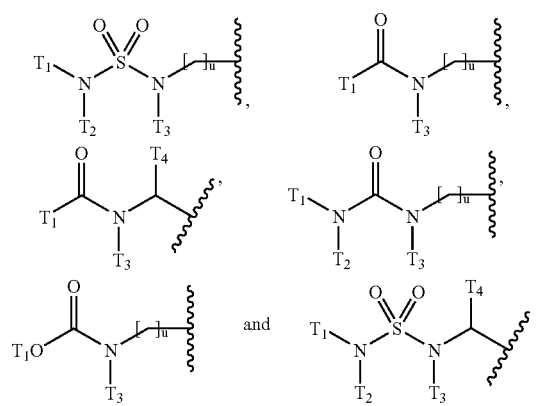
wherein u is a number 0-6; and
R¹⁹ is selected from H, alkyl, phenyl or benzyl.
8. The compound of claim 7, wherein $T_1$, $T_2$ and $T_3$ can be the same or different, each being independently selected from the group consisting of:
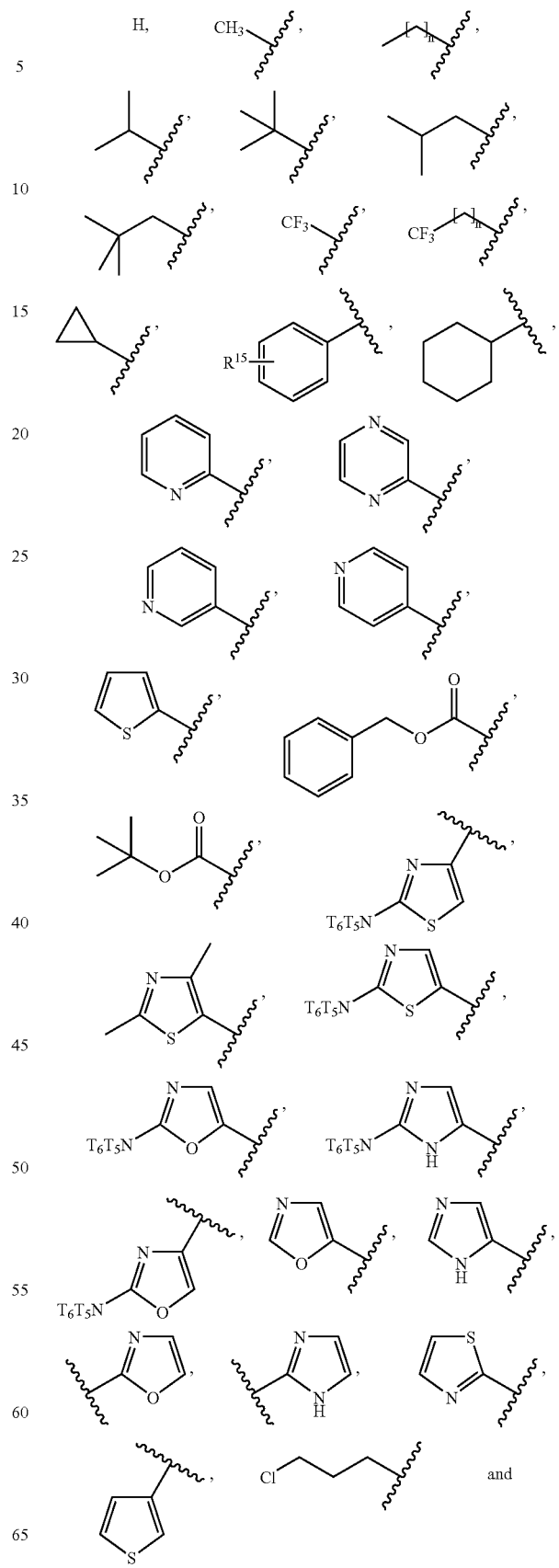

-continued
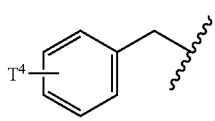
9. The compound of claim 1, wherein the moiety:
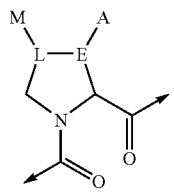
is selected from the following structures:
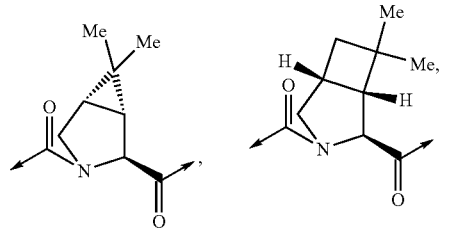
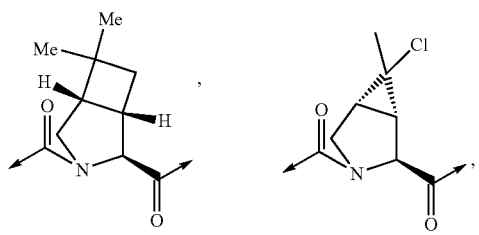
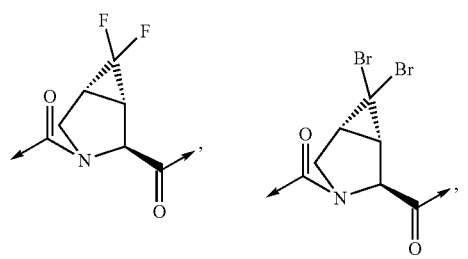
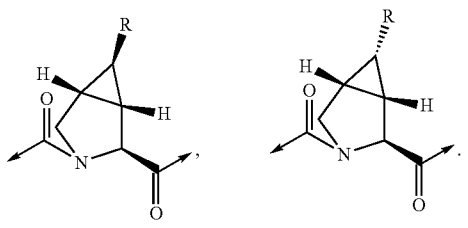
10. The compound of claim 9, wherein the moiety:
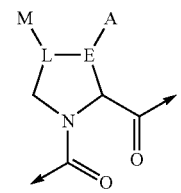
is selected from the following structures:
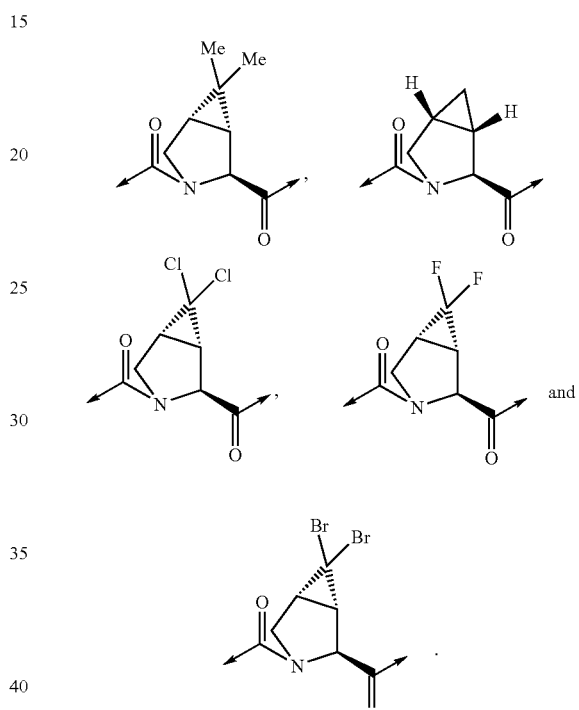
11. The compound of claim 10, wherein the moiety:
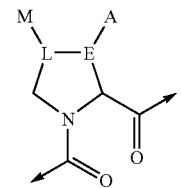
is selected from the following structures:
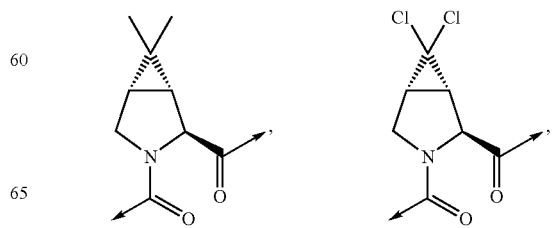

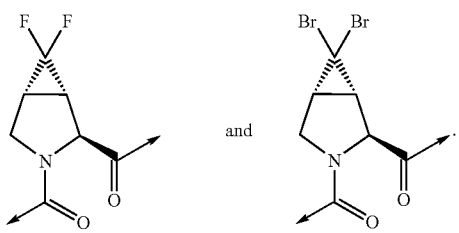
12. The compound of claim 1, wherein $R^1$ is $NHR^{14}$, where $R^{14}$ is selected from the group consisting of:
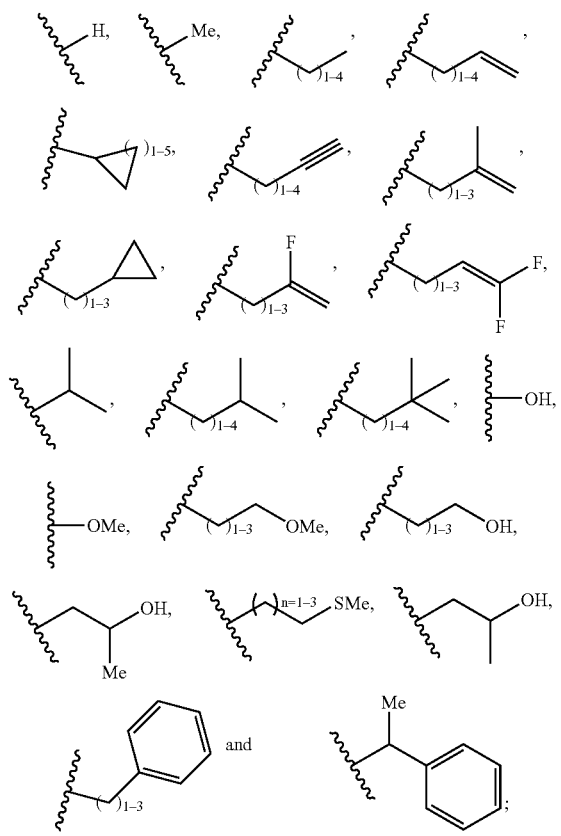
$R^2$ is selected from the group consisting of the following moieties:
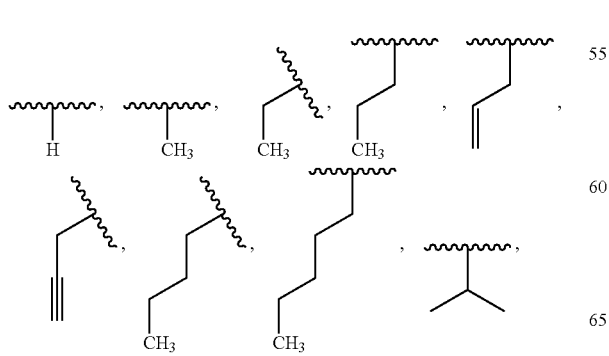
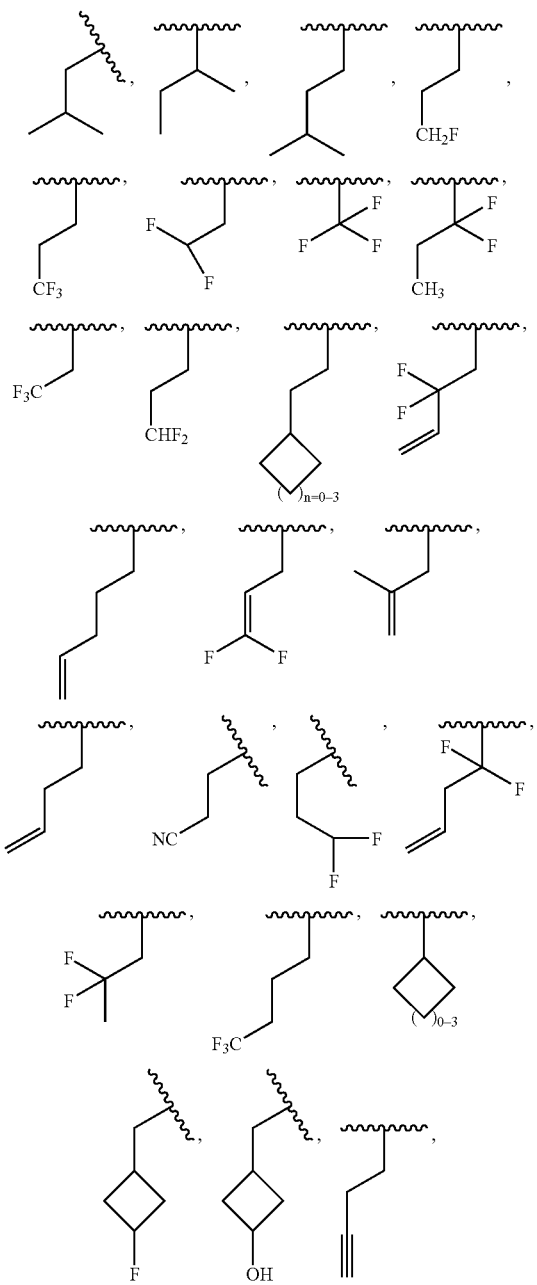
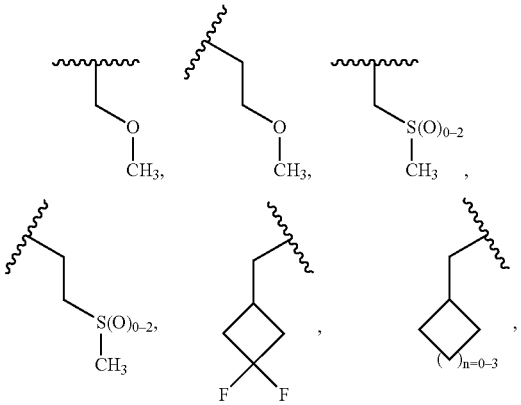

-continued
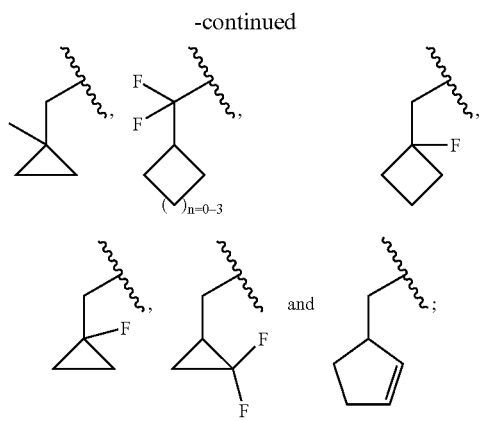
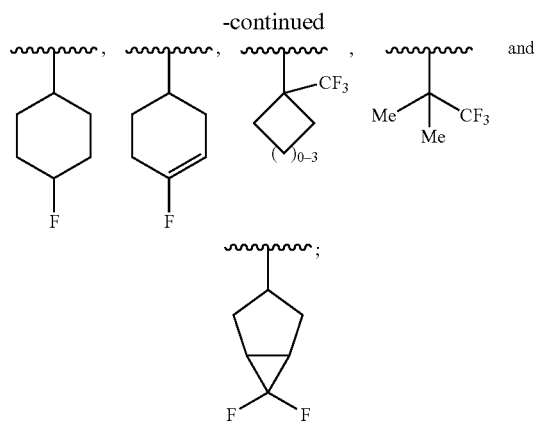
R³ is selected from the group consisting of the following moieties:
Y is selected from the group consisting of:
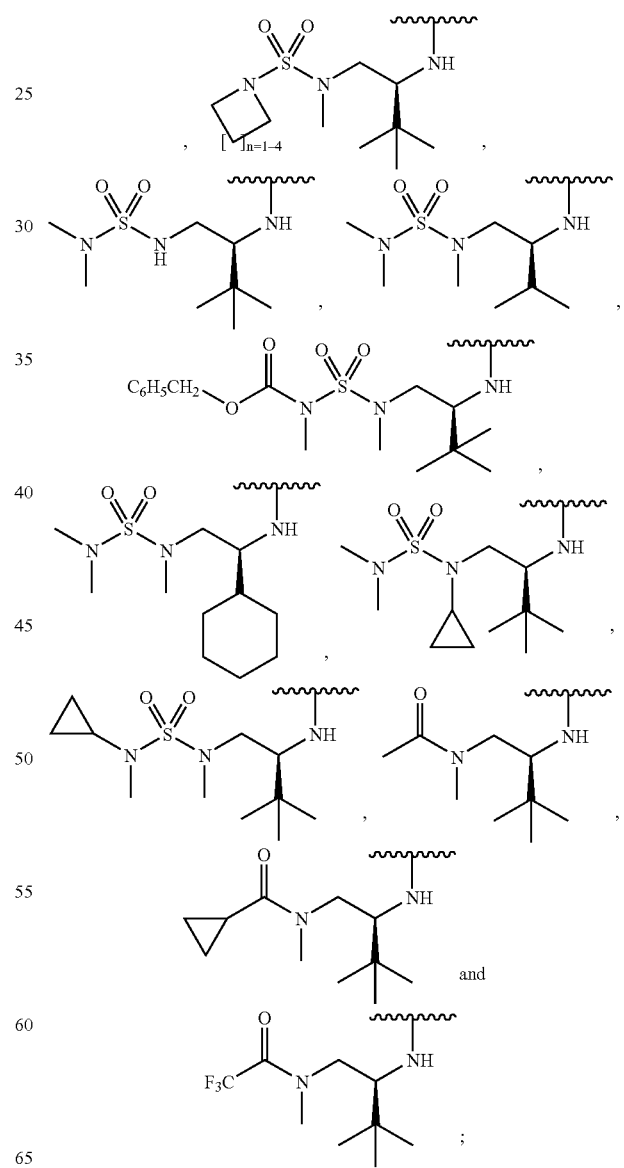

and the moiety:

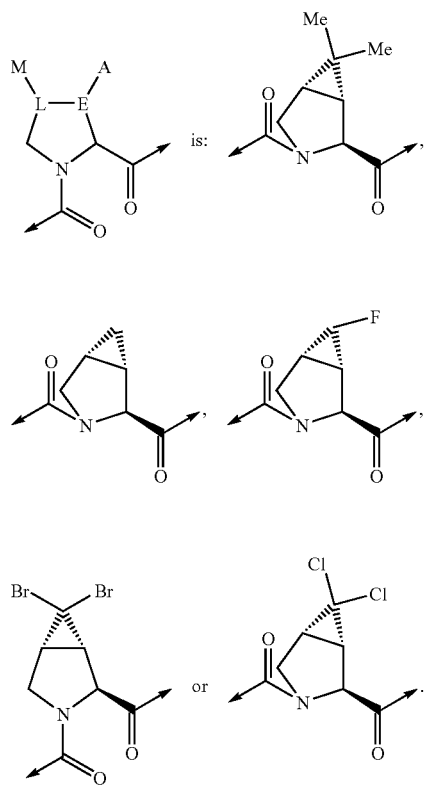

is:

13. A pharmaceutical composition comprising as an active ingredient at east one compound of claim 1.

14. The pharmaceutical composition of claim 13 for use in treating an infection of Hepatitis C Virus ("HCV").

15. The pharmaceutical composition of claim 14 additionally comprising at least one pharmaceutically acceptable carrier.

16. The pharmaceutical composition of claim 15, additionally containing at least one antiviral agent.

17. The pharmaceutical composition of claim 16, additionally containing at least one interferon.

18. The pharmaceutical composition of claim 17, wherein said at least one antiviral agent is ribavirin and said at least one interferon is α-interferon or pegylated interferon.

19. A method of treating an infection of Hepatitis C Virus ("HCV"), said method comprising administering to a patient in need of such treatment a pharmaceutical composition which comprises therapeutically effective amounts of at least one compound of claim 1.

20. The method of claim 19, wherein said administration is oral or subcutaneous.

21. A method of preparing a pharmaceutical composition for treating an infection of Hepatitis C Virus ("HCV"), said method comprising bringing into intimate physical contact at least one compound of claim 1 and at least one pharmaceutically acceptable carrier.

22. A compound exhibiting Hepatitis C Virus ("HCV") protease inhibitory activity, or enantiomer, stereoisomer, rotamer, tautomer, diastereomer, and racemate of said compound, or a pharmaceutically acceptable salt or ester of said compound, said compound being selected from the compounds of structures listed below:

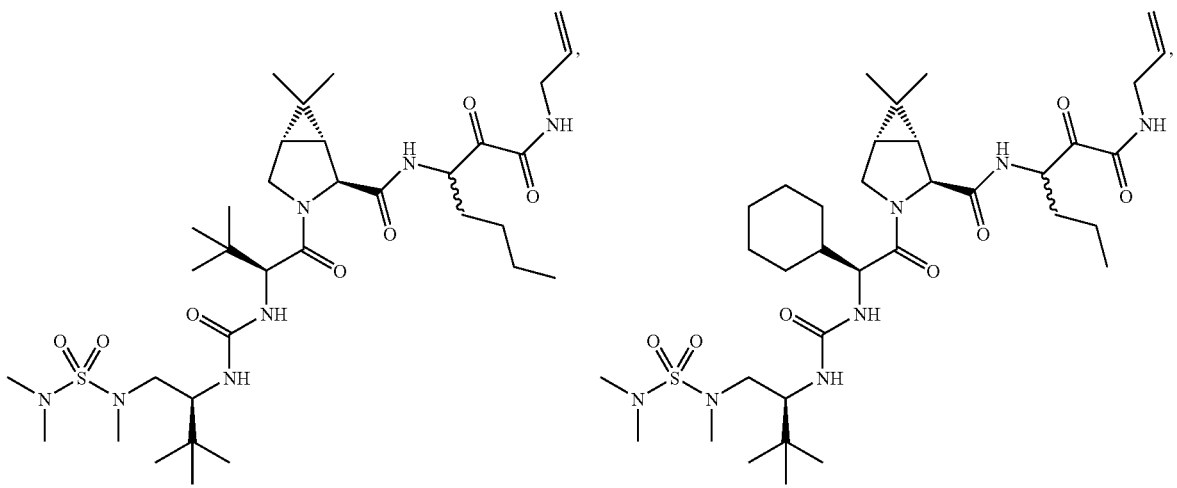

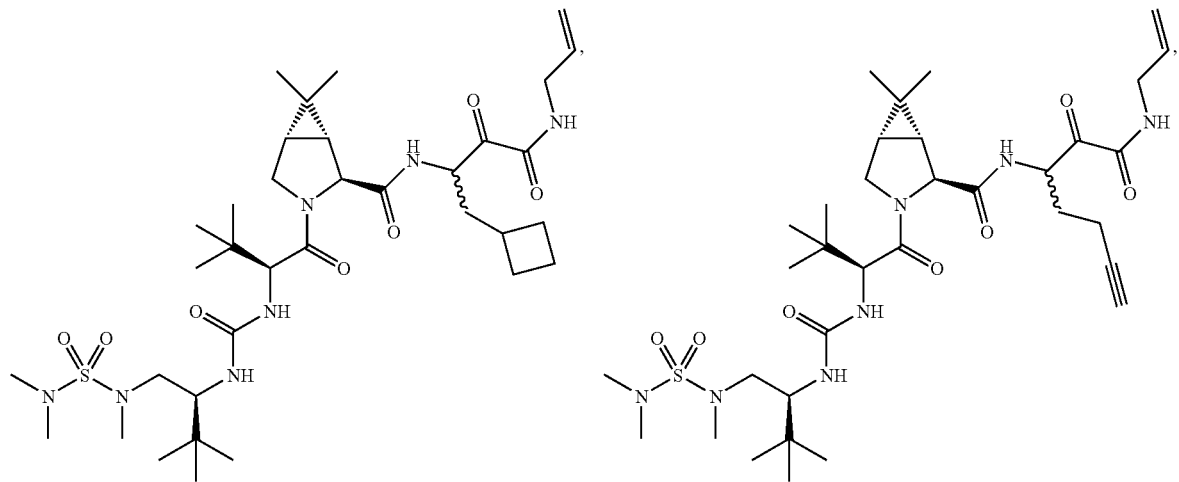
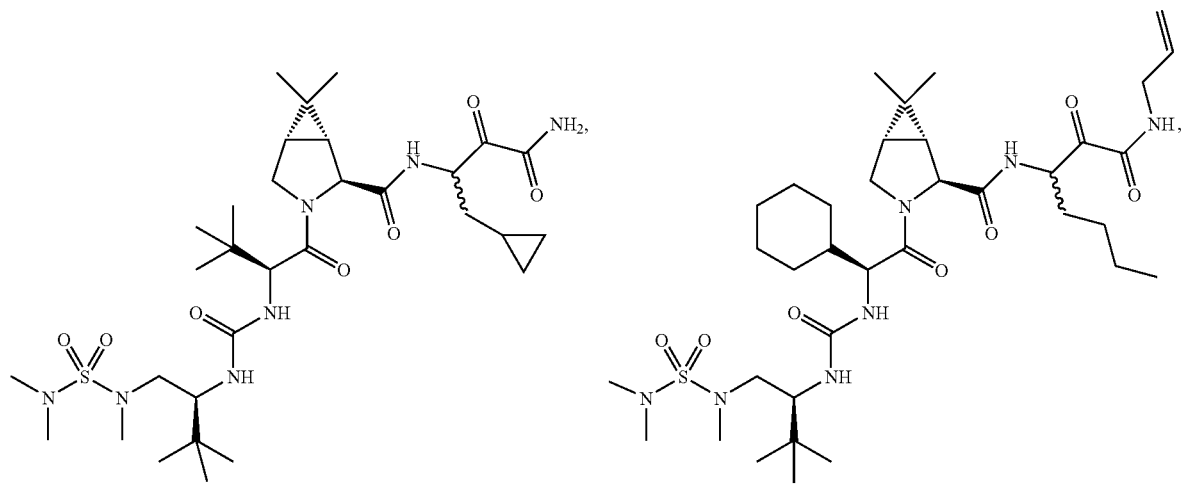
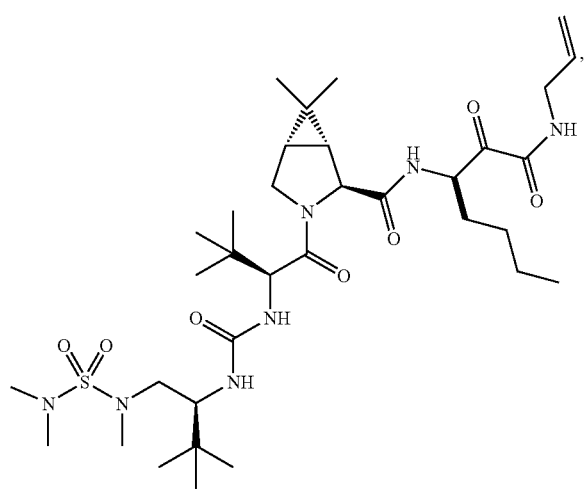

-continued
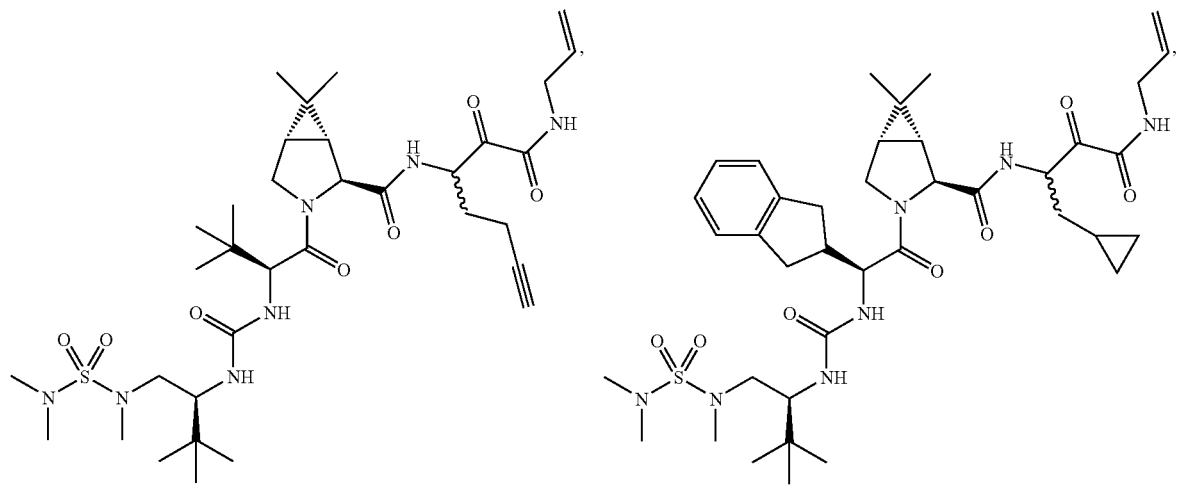
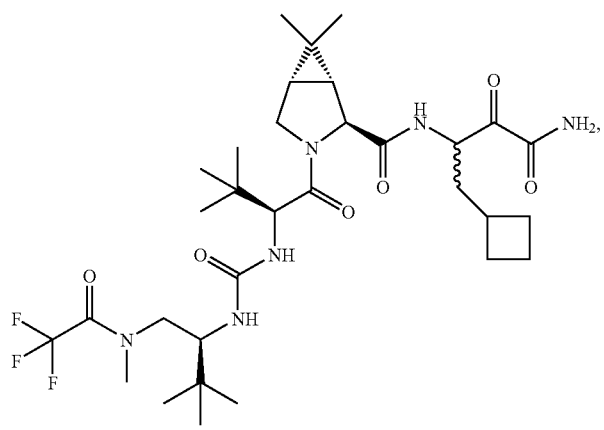
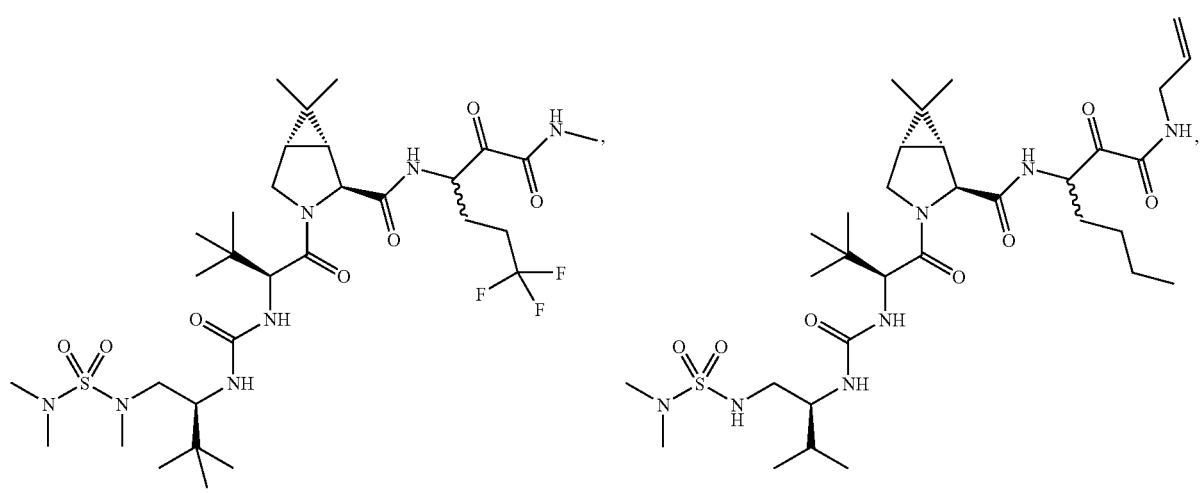

-continued
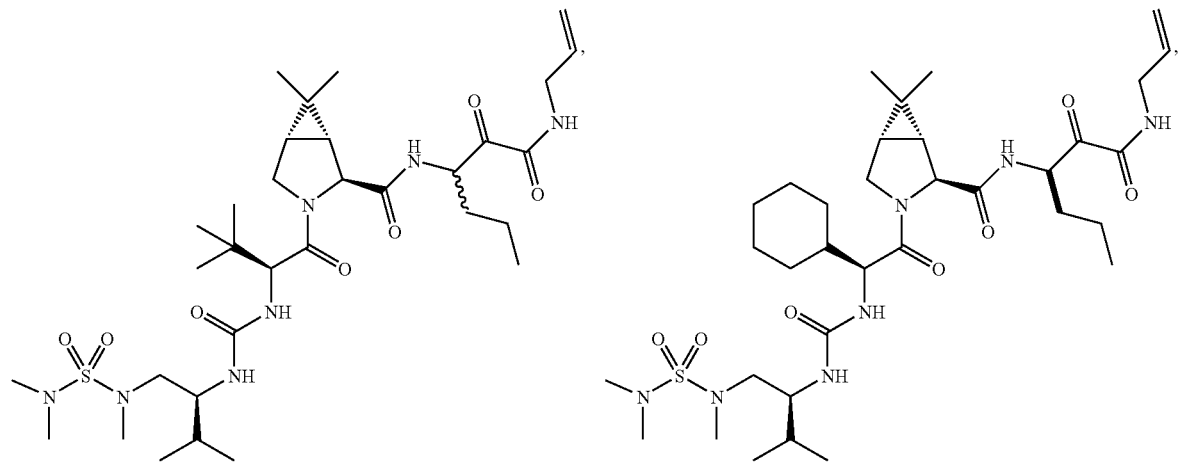
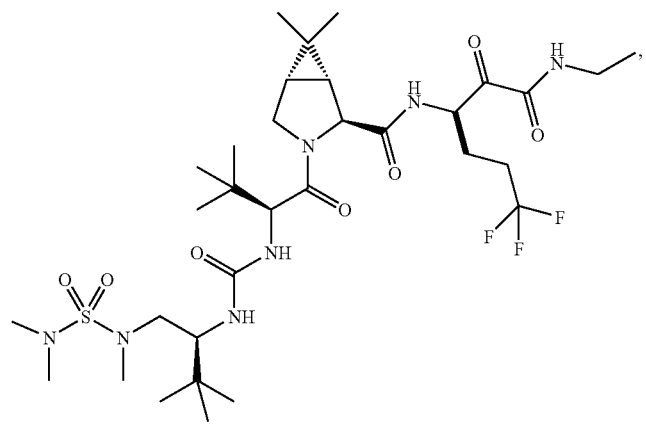
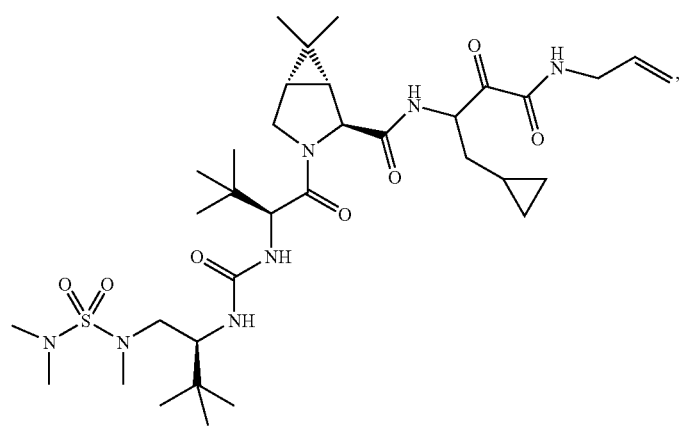

-continued
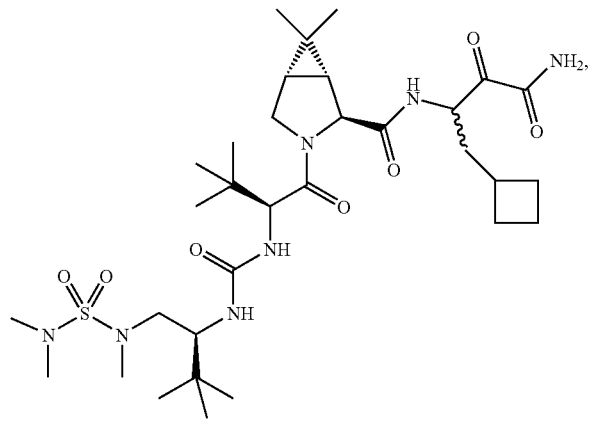
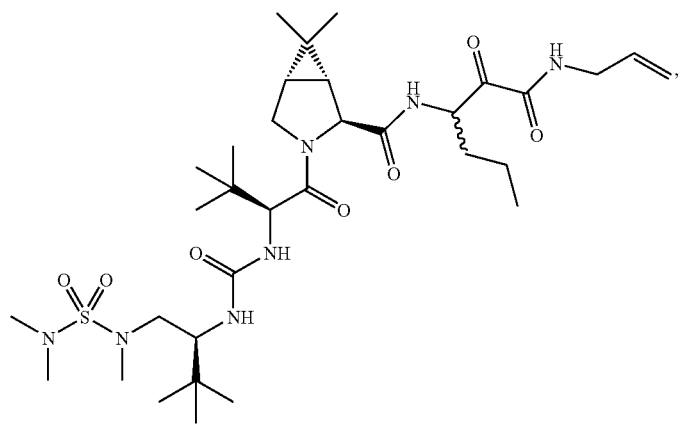
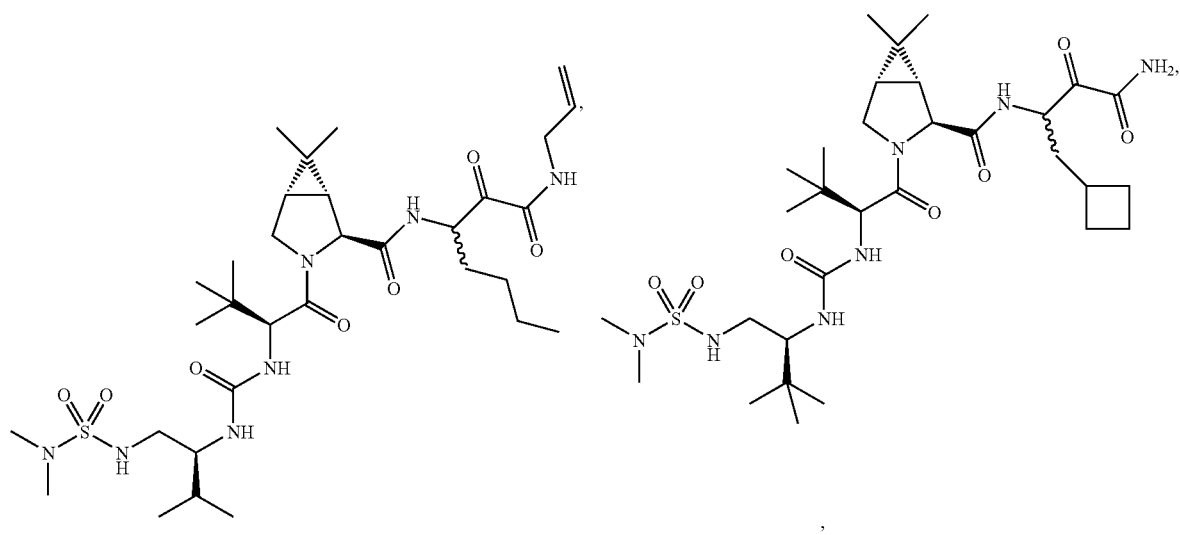

-continued
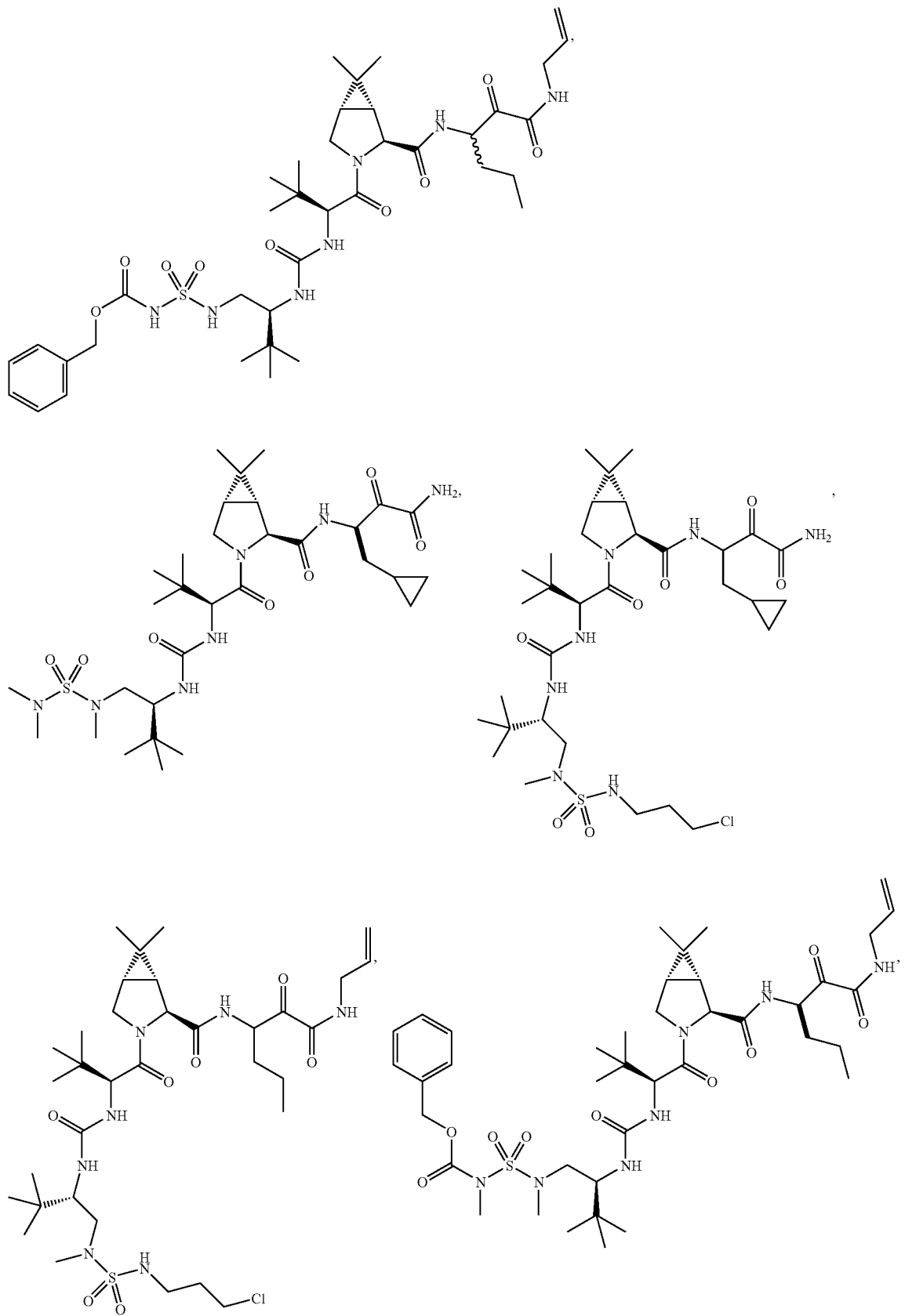

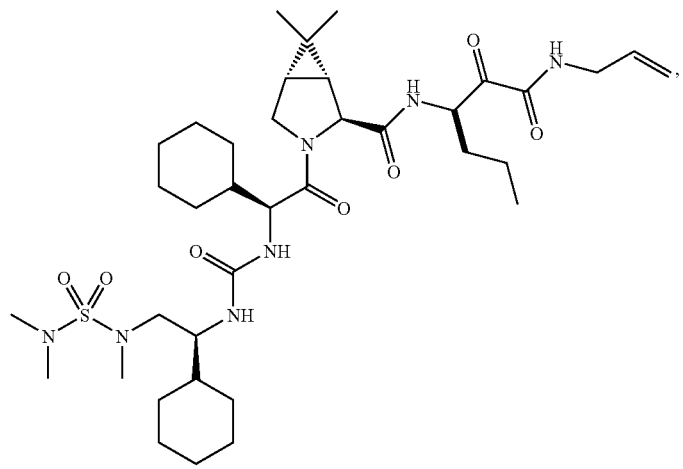
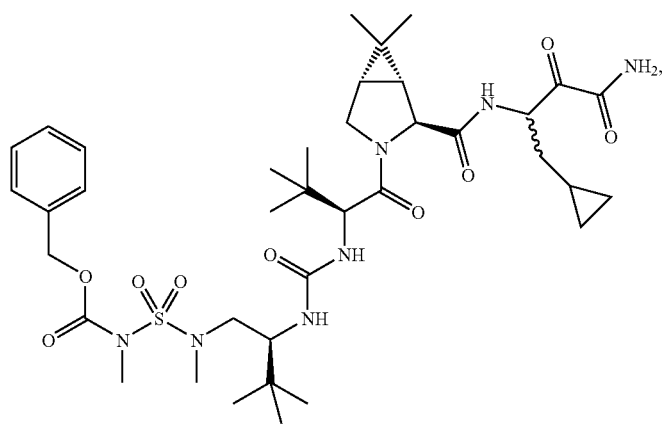
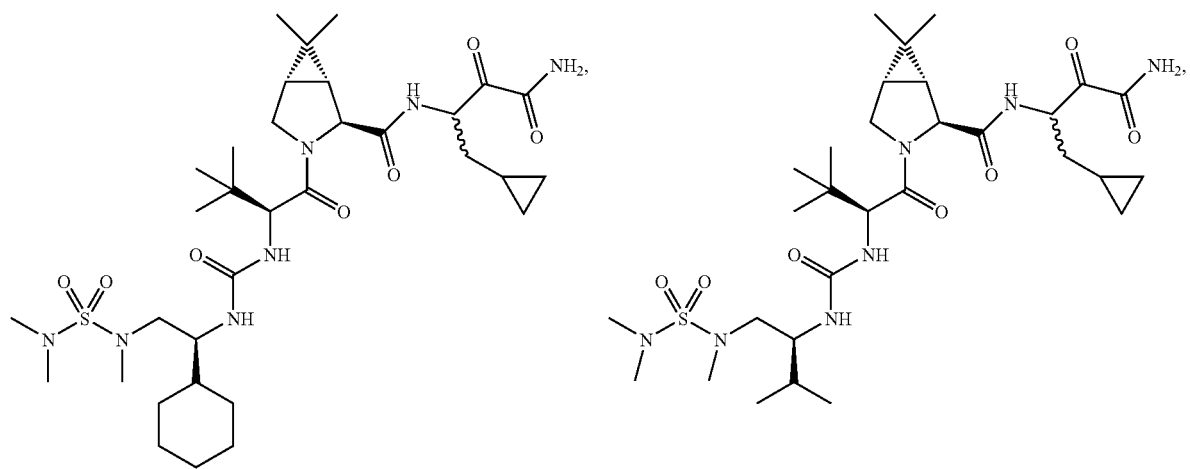

-continued
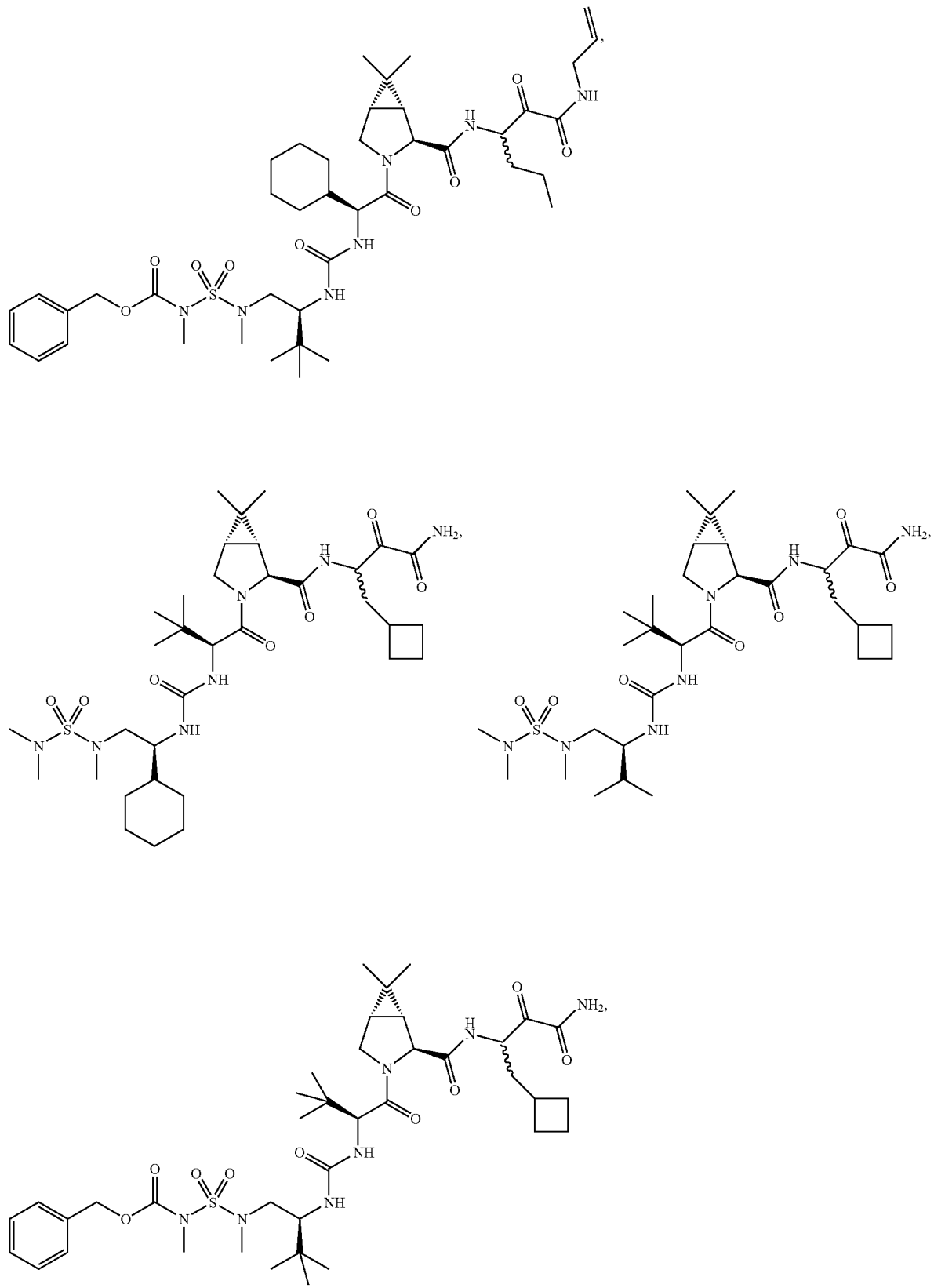

-continued
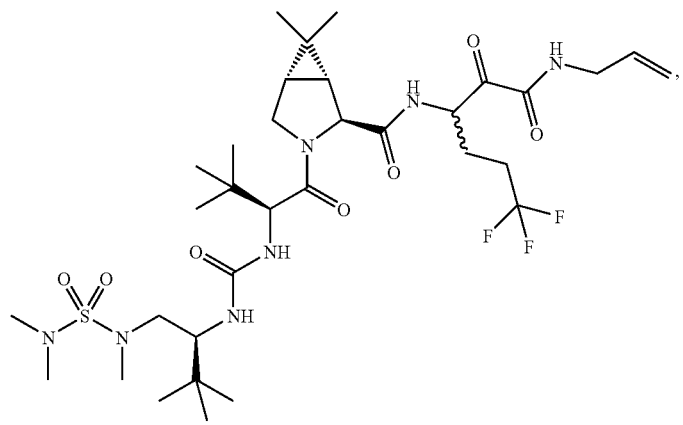
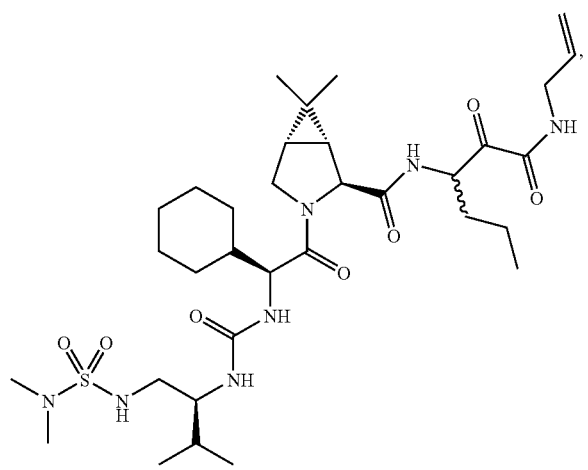
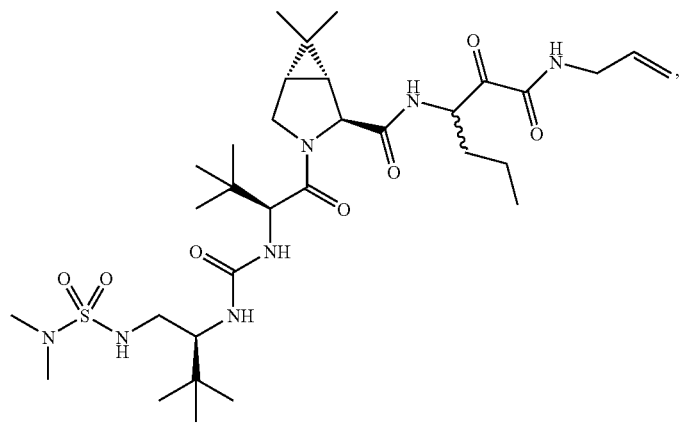

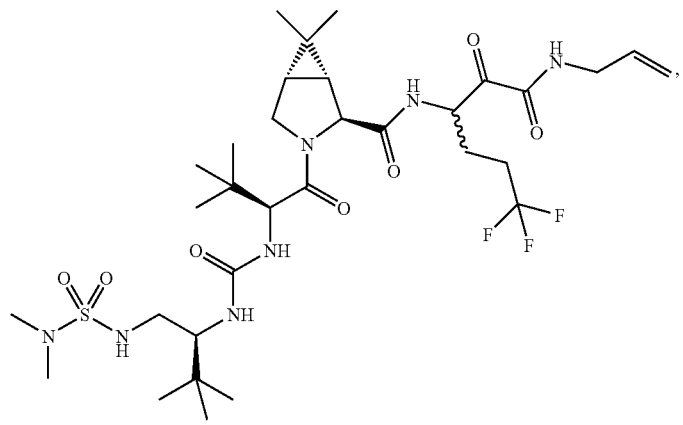
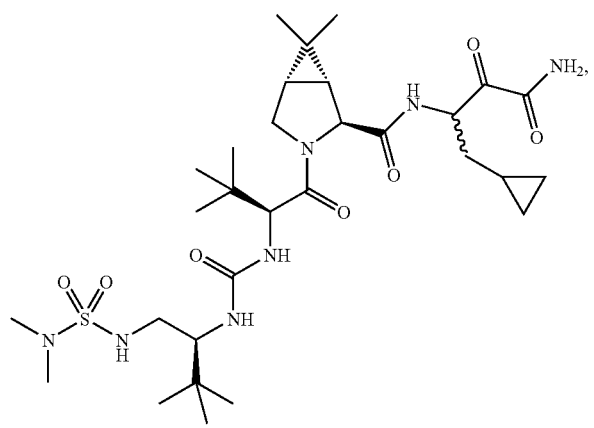
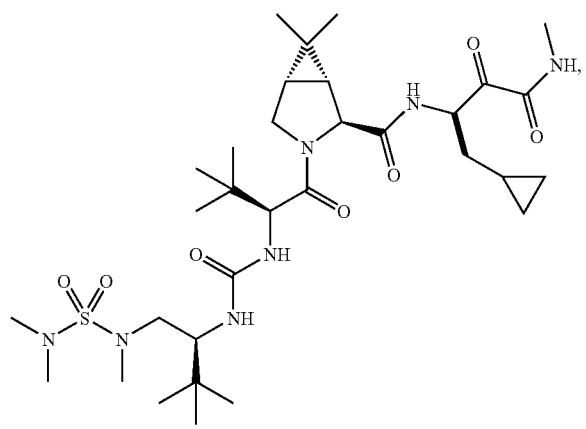

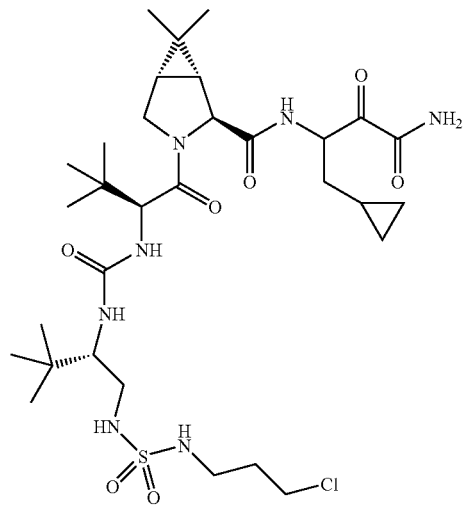
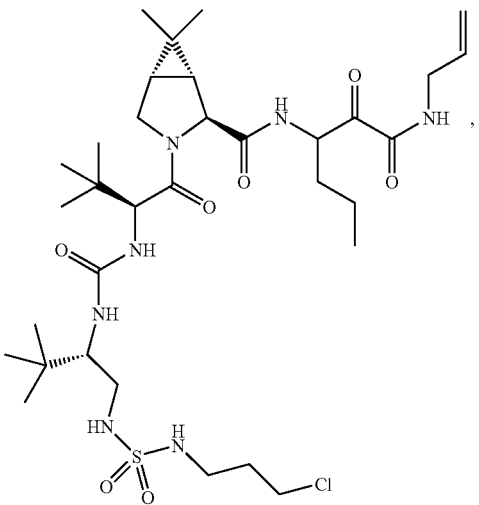
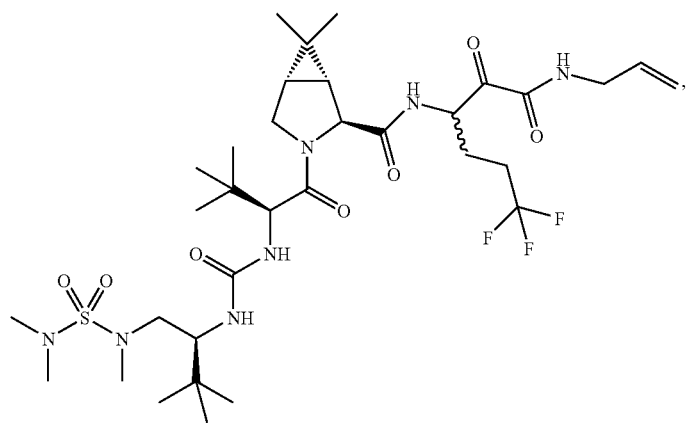
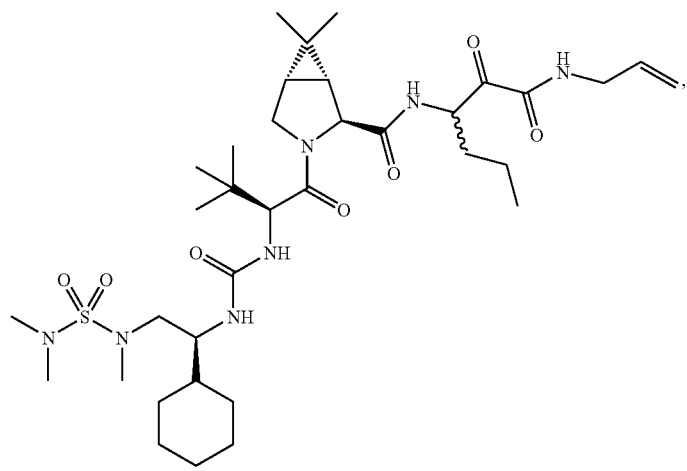

-continued
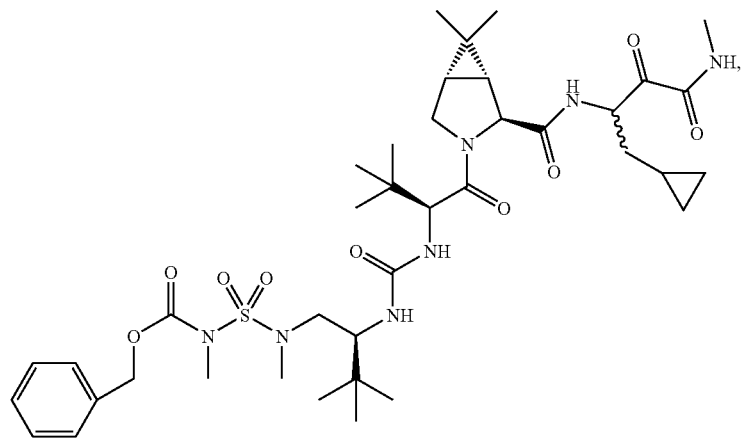
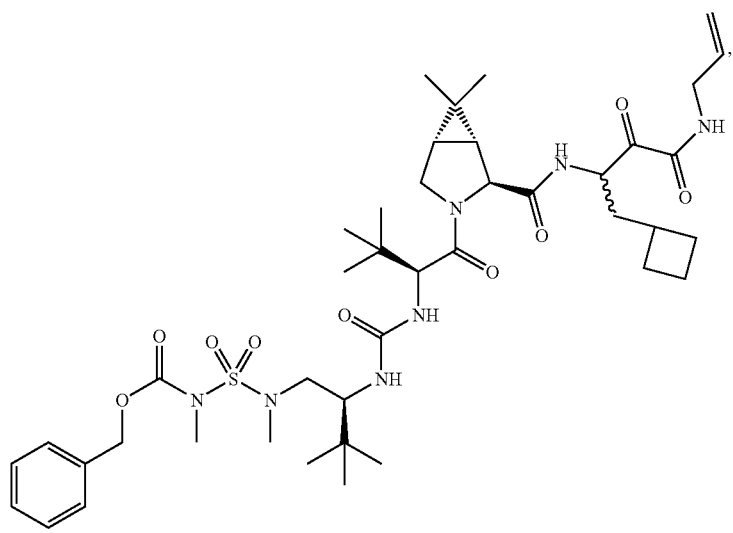
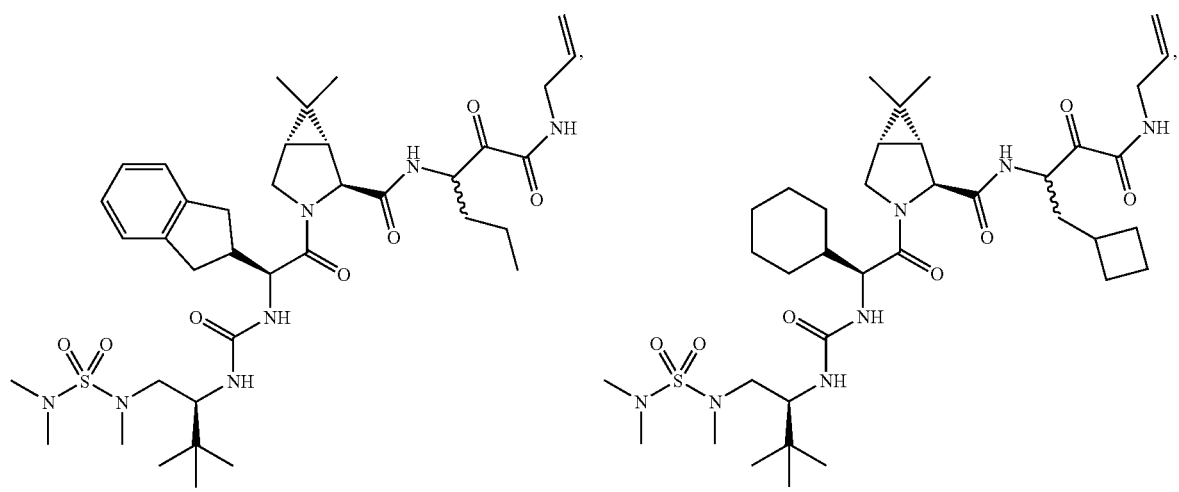

591 592
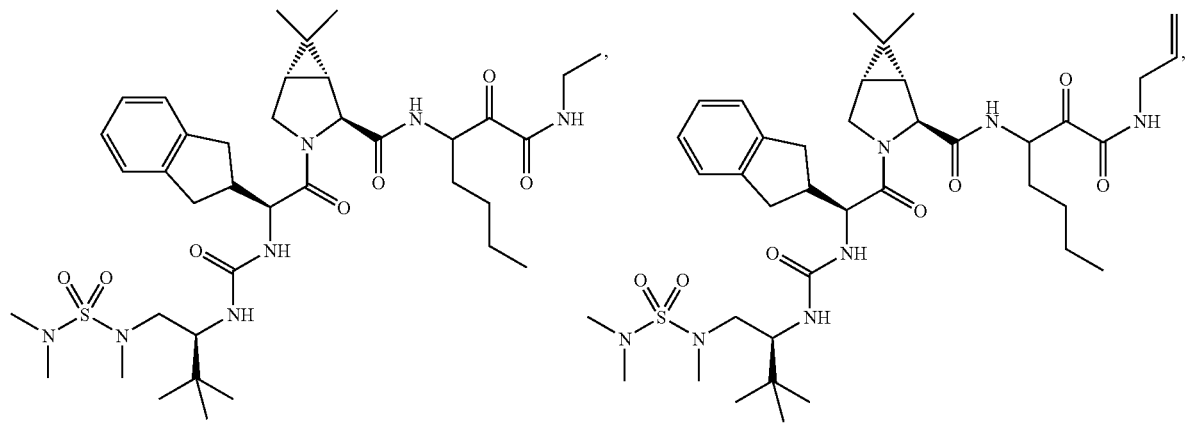
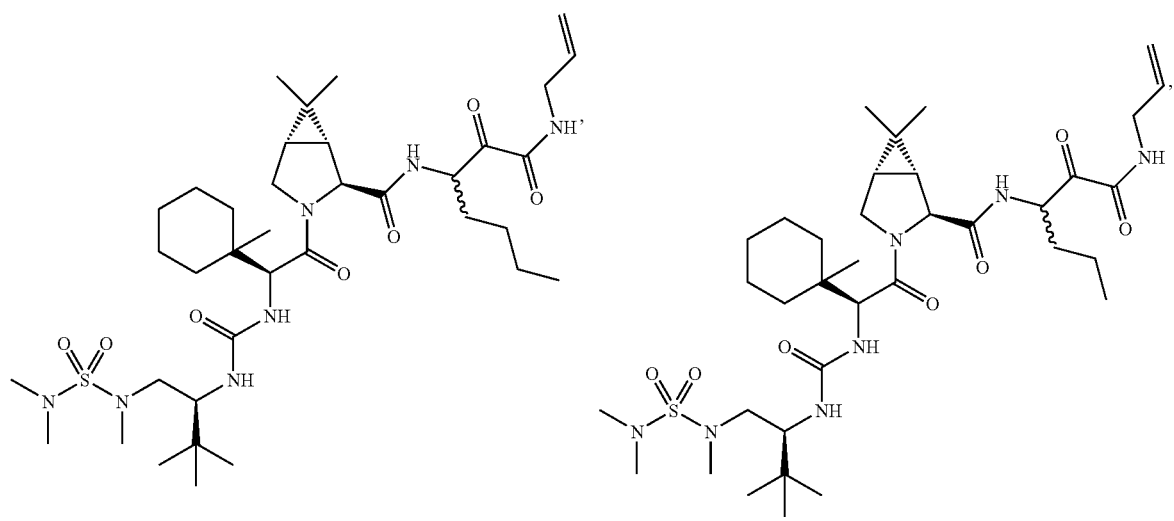
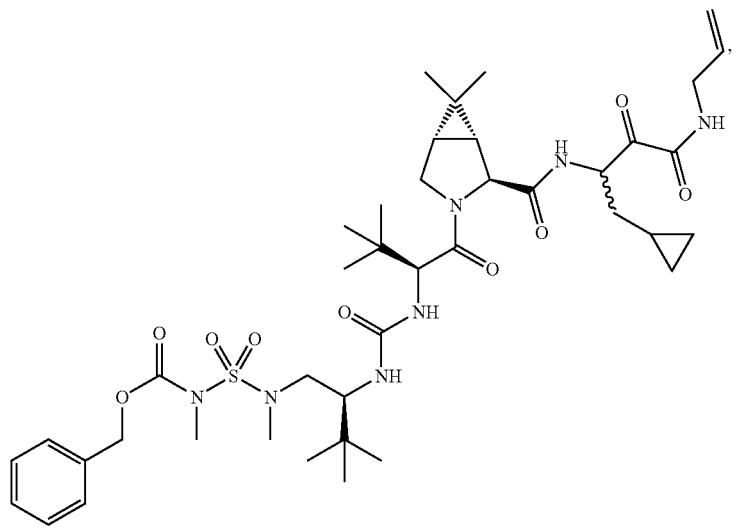

-continued
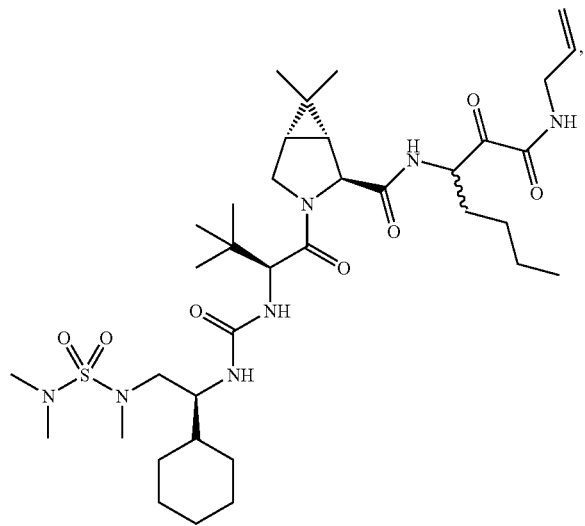
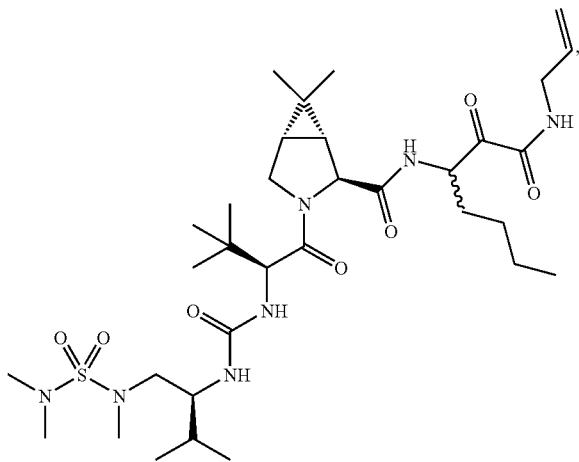
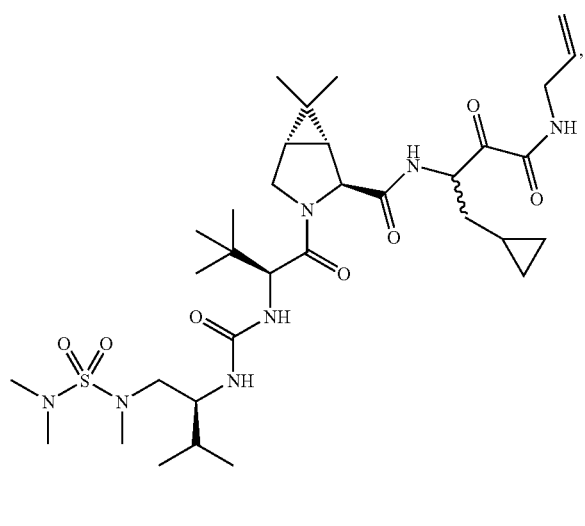
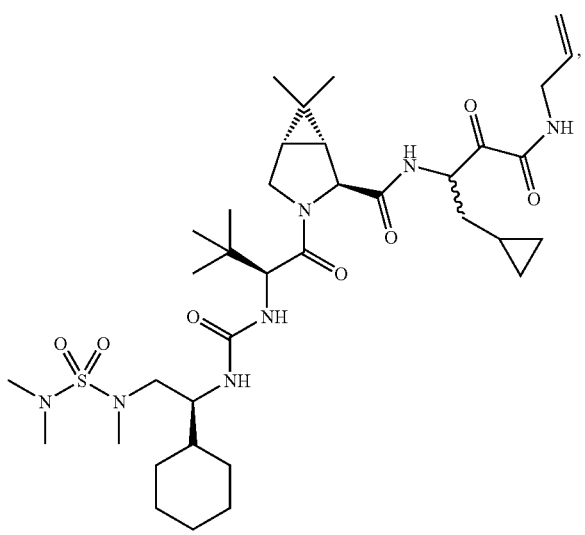
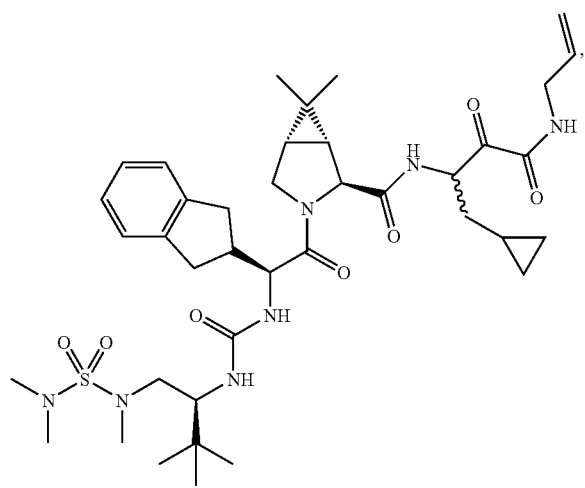

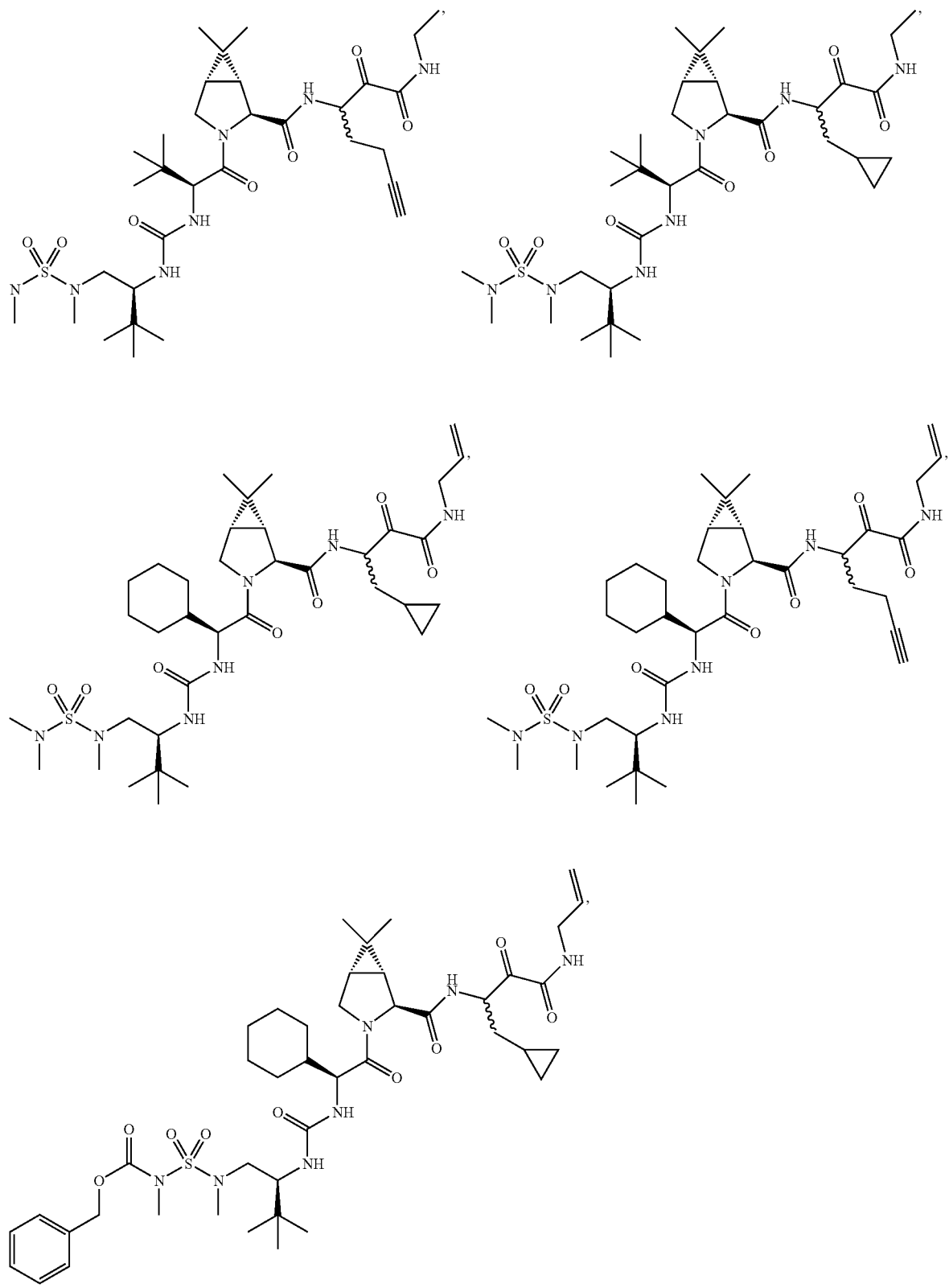

-continued
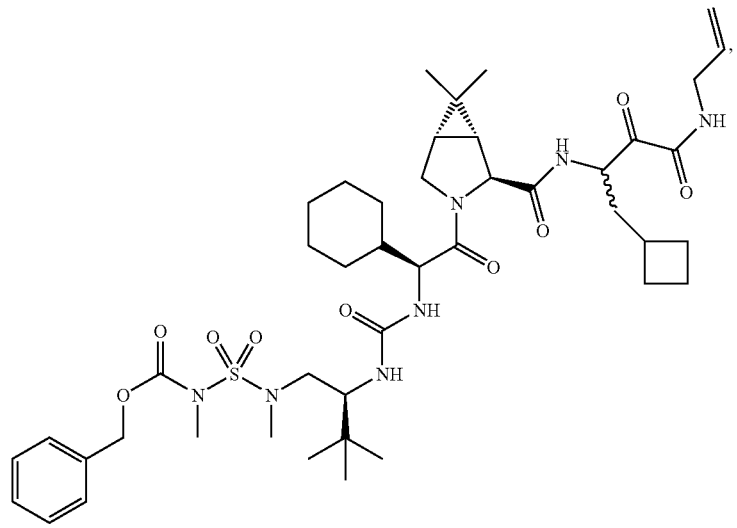
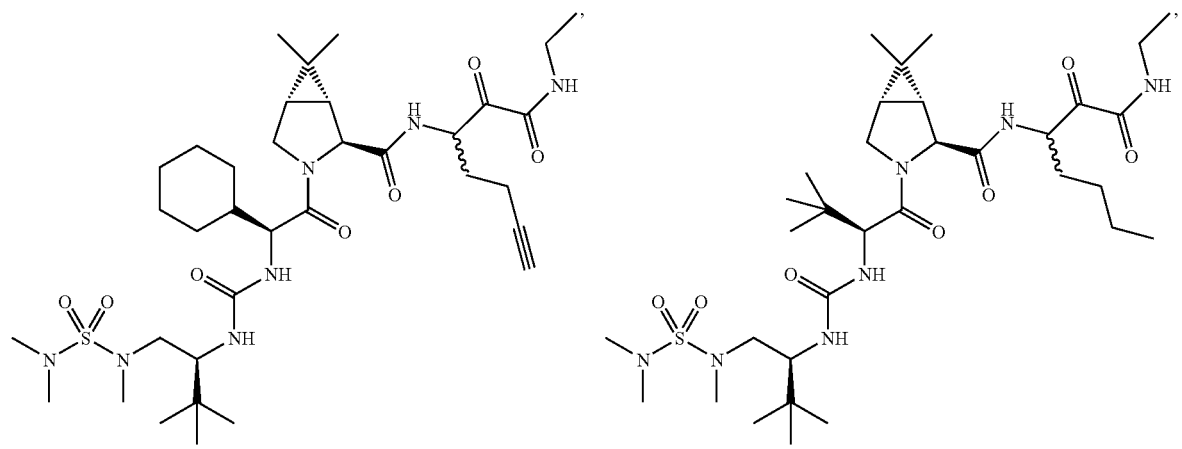
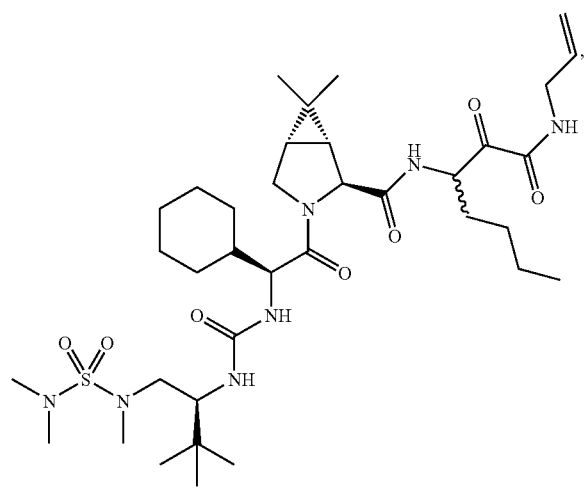

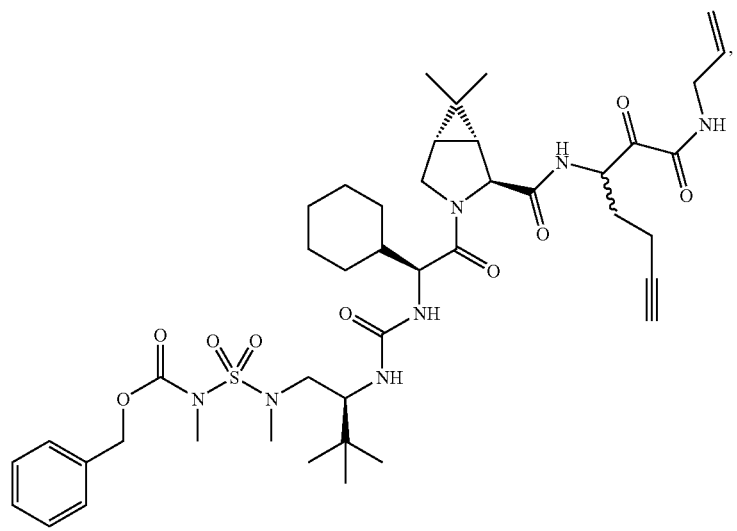
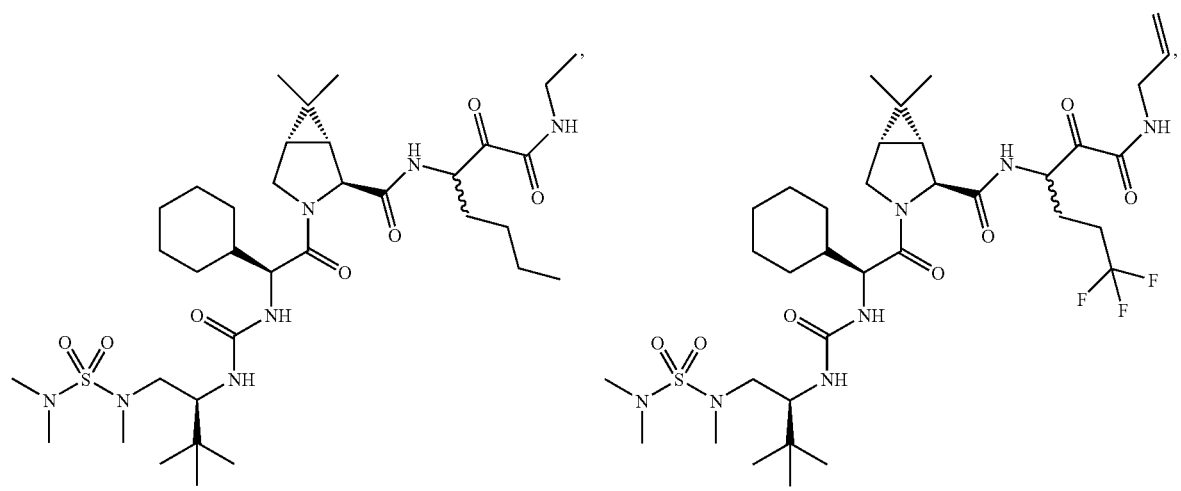
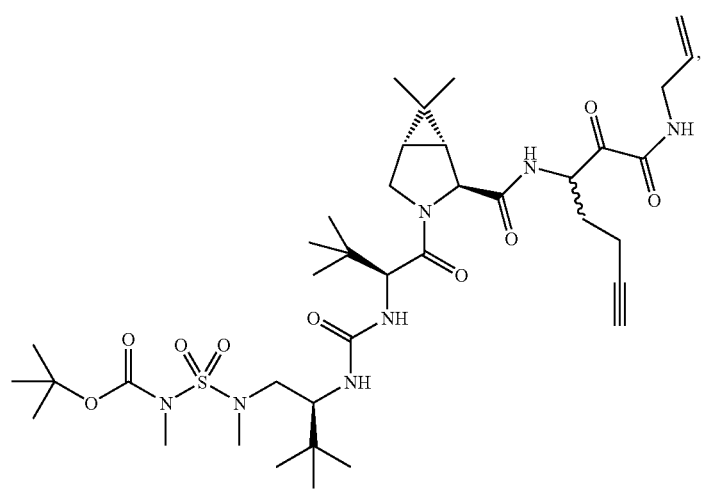

-continued
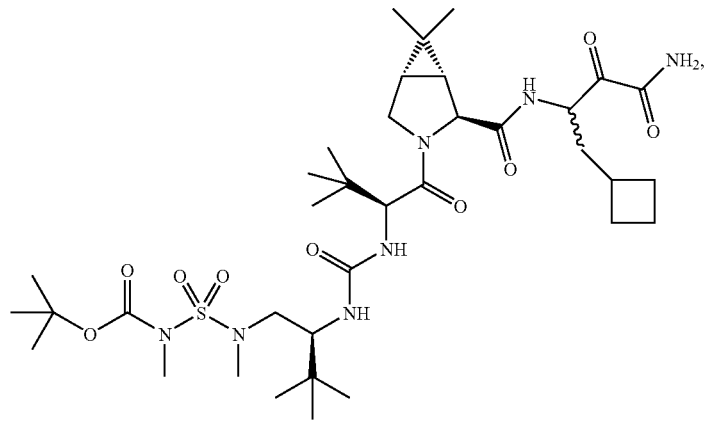
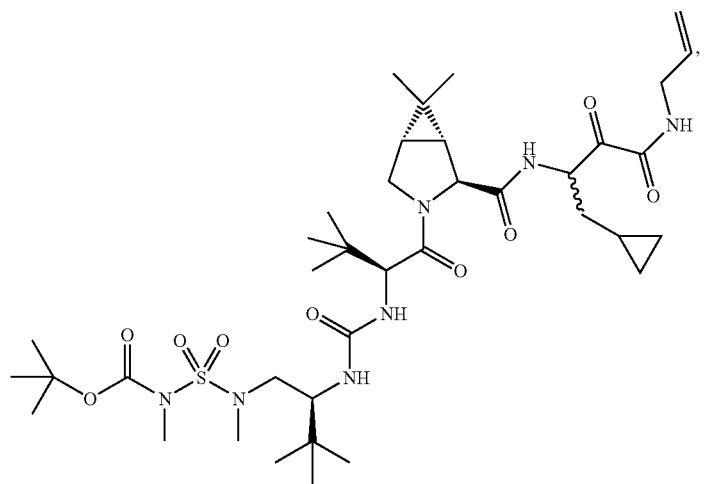
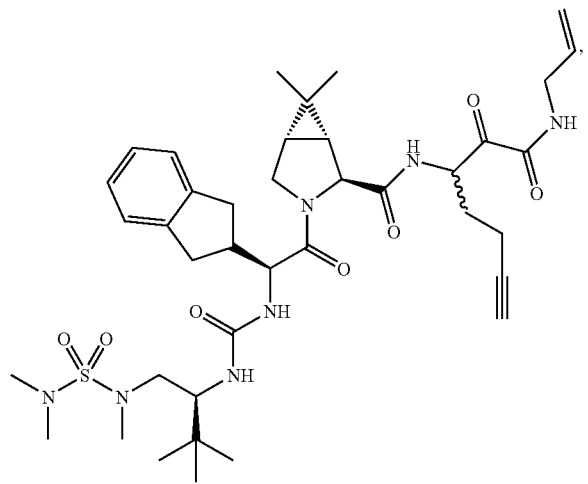

-continued
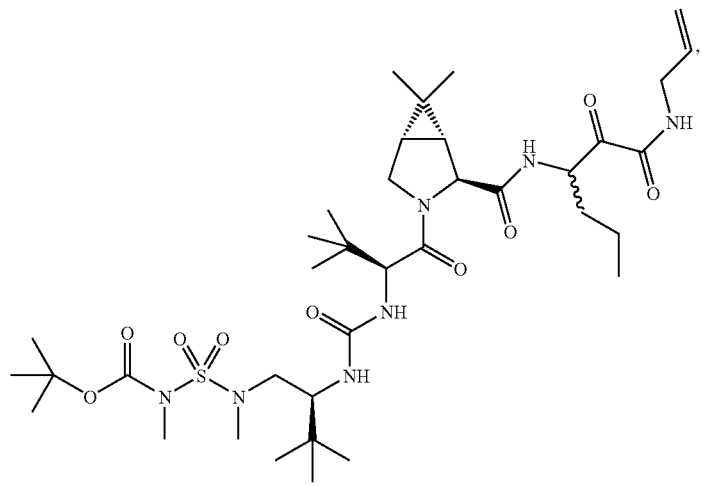
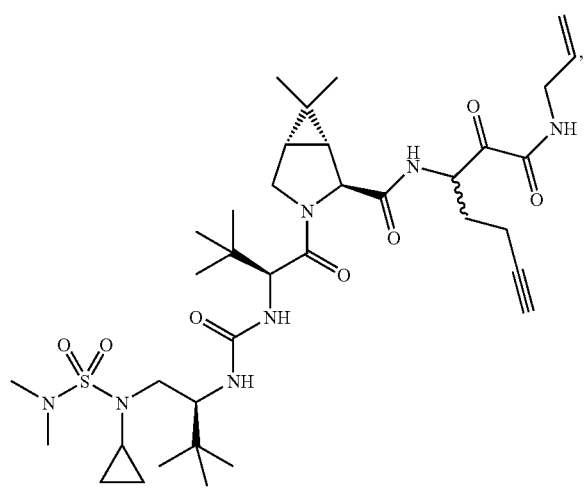
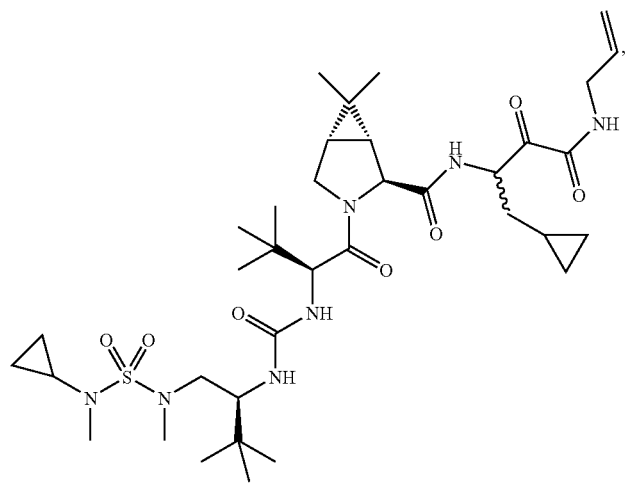

-continued
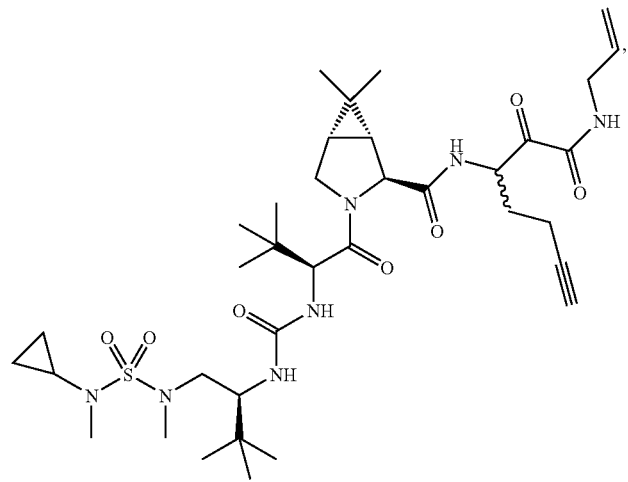
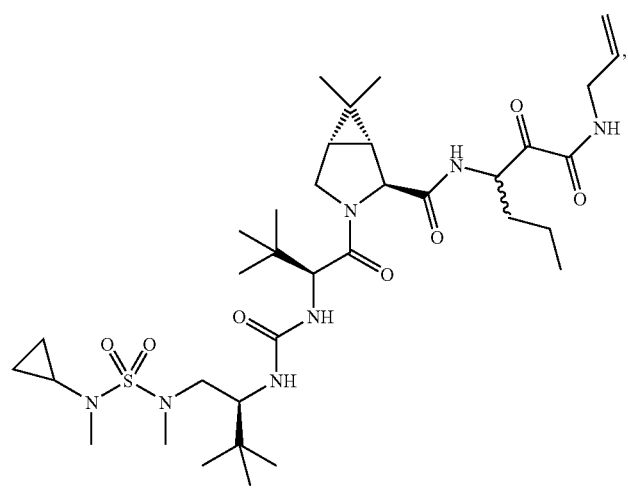
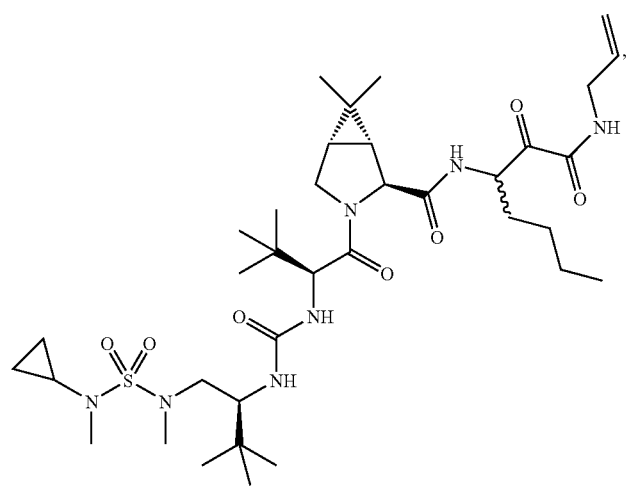

-continued
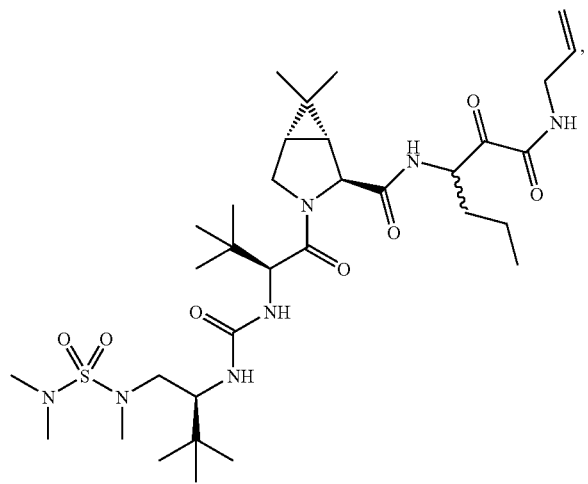
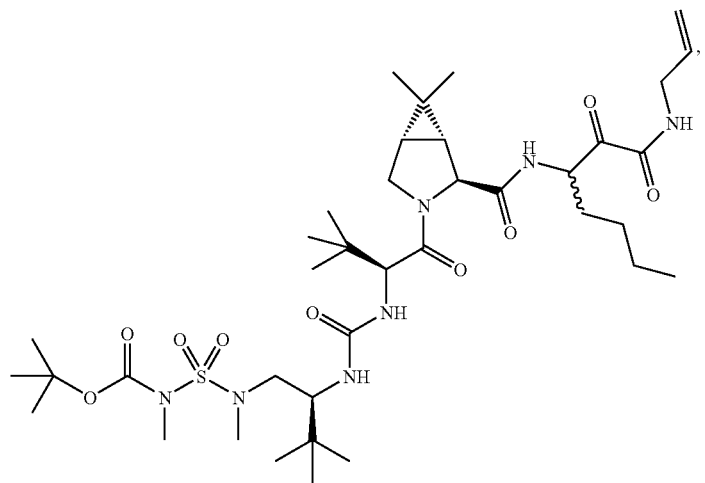
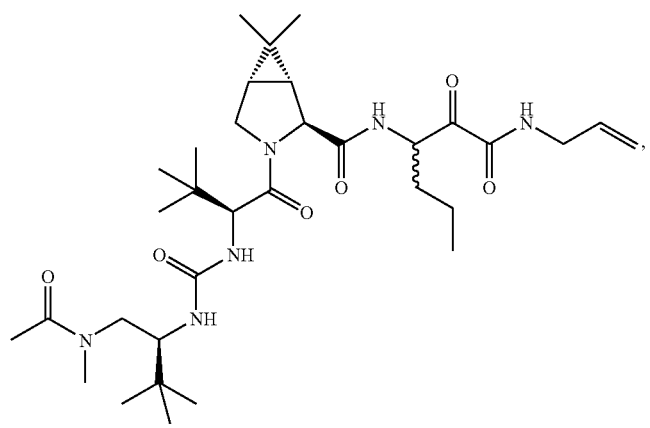

-continued
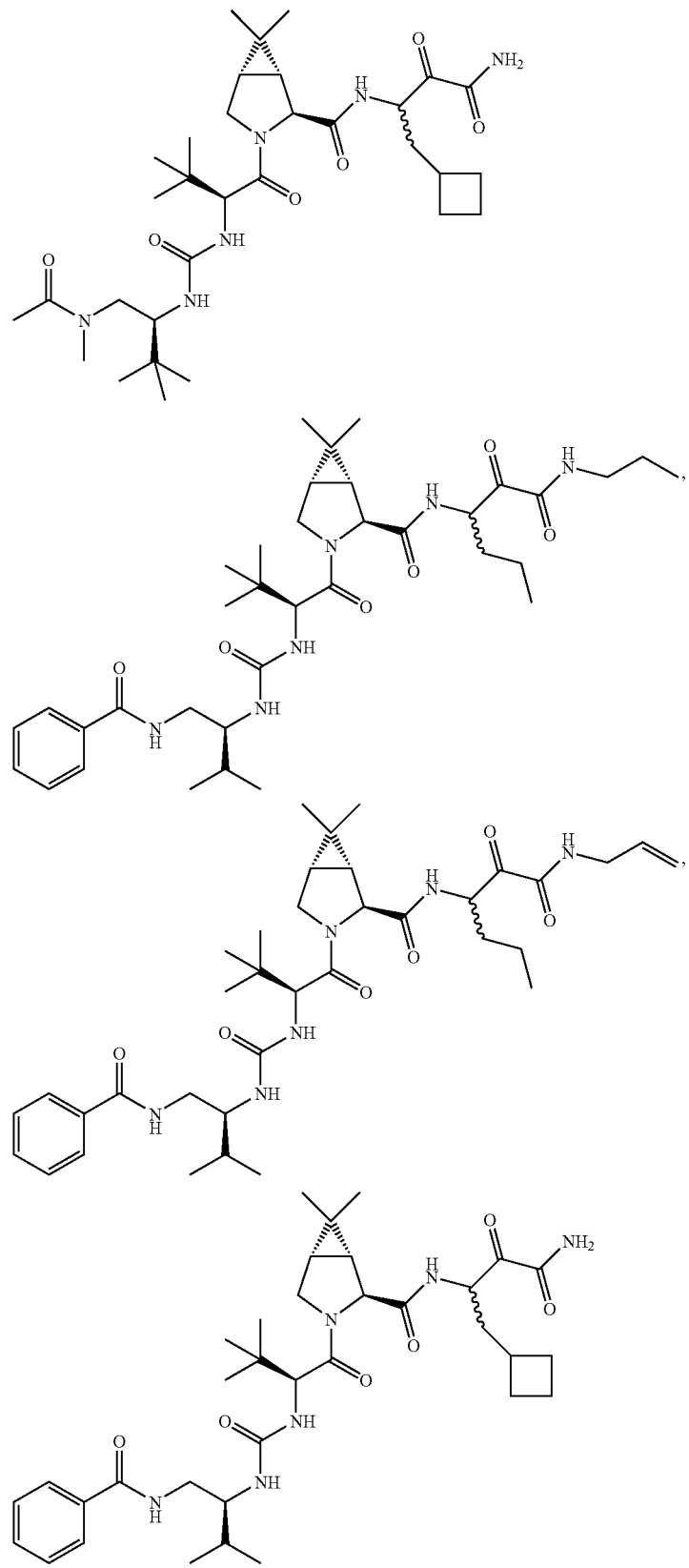

611     612
-continued
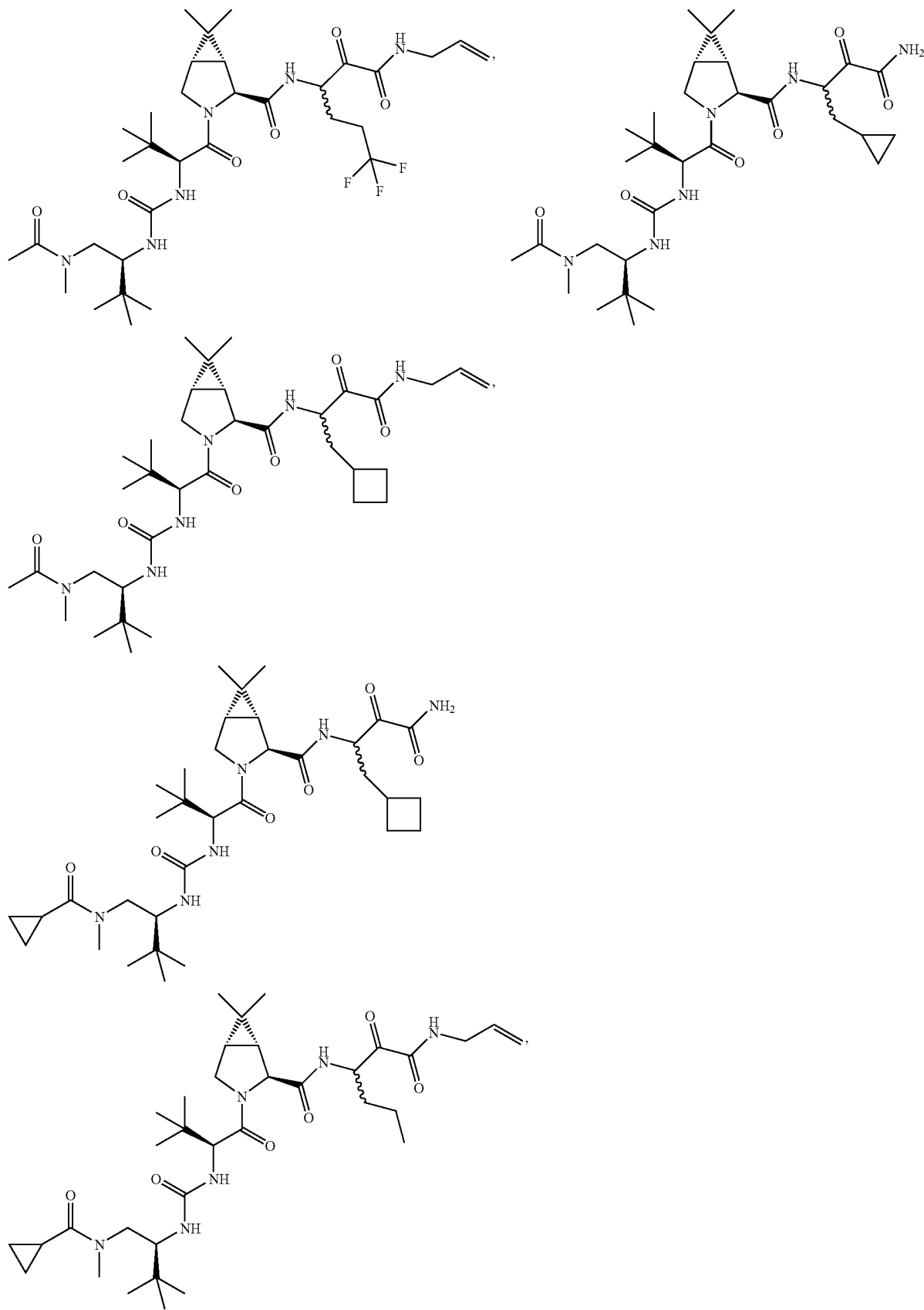

-continued
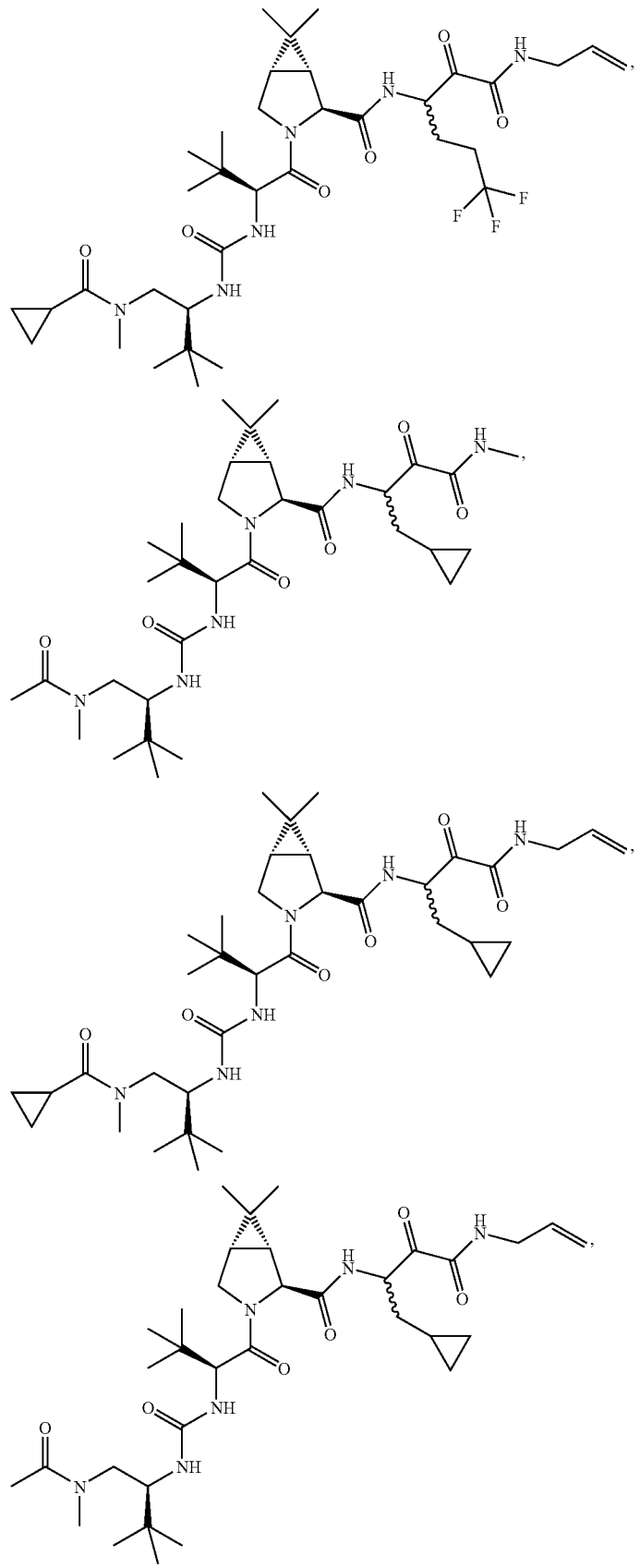

-continued
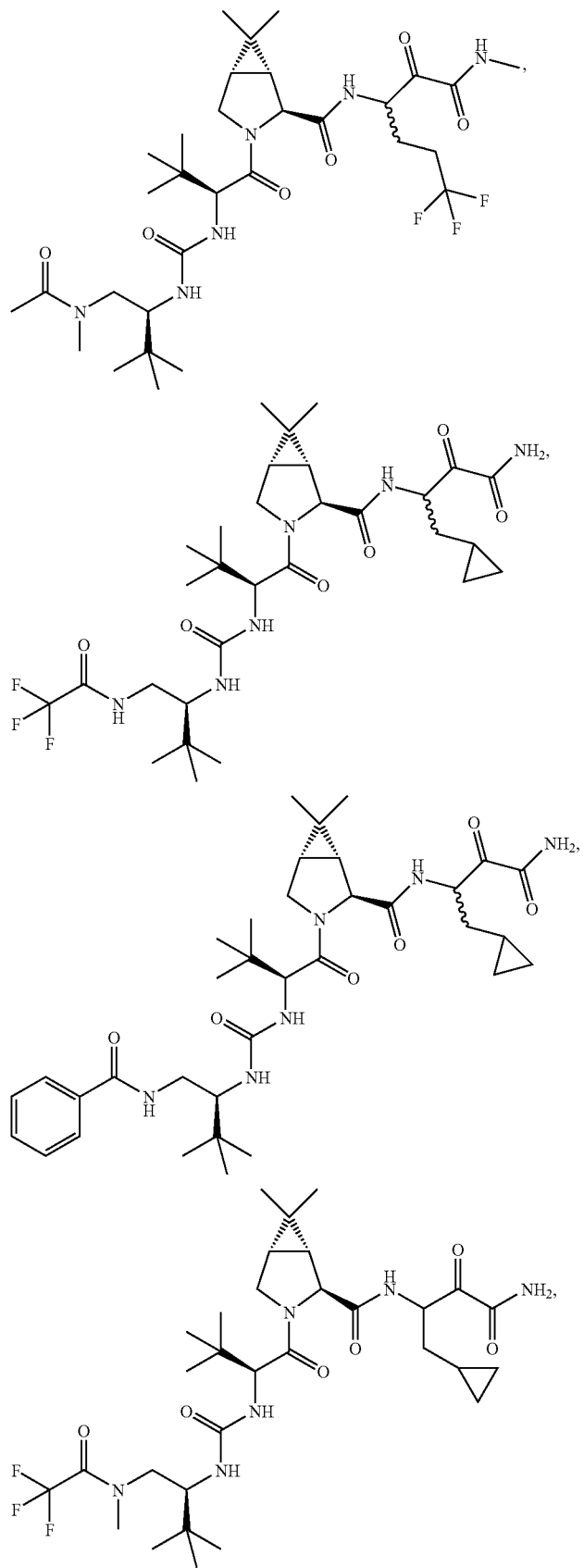

-continued
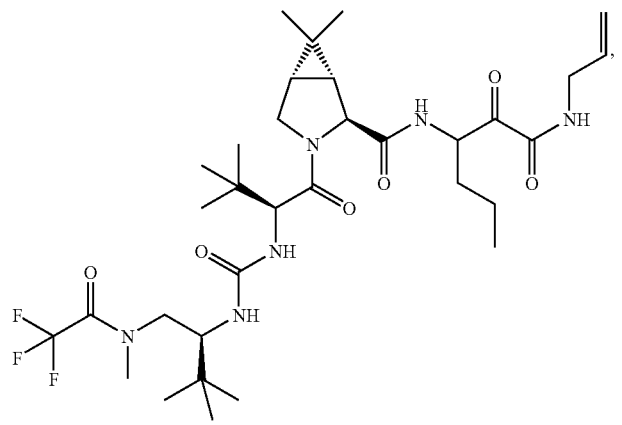
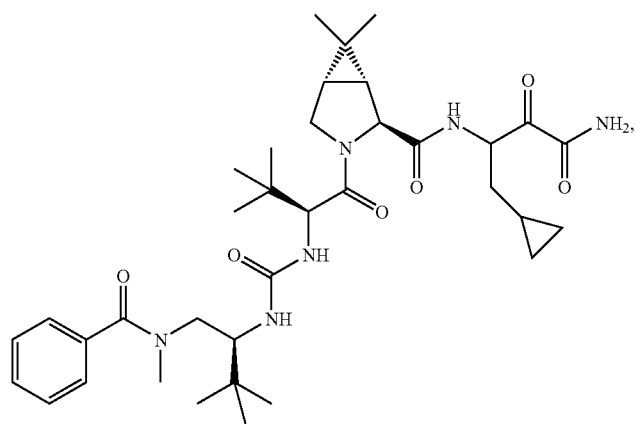
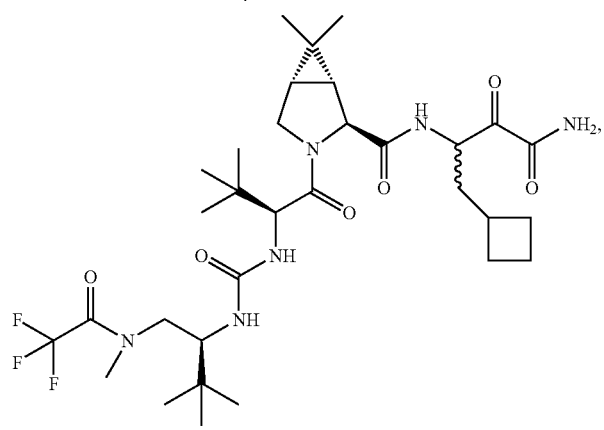
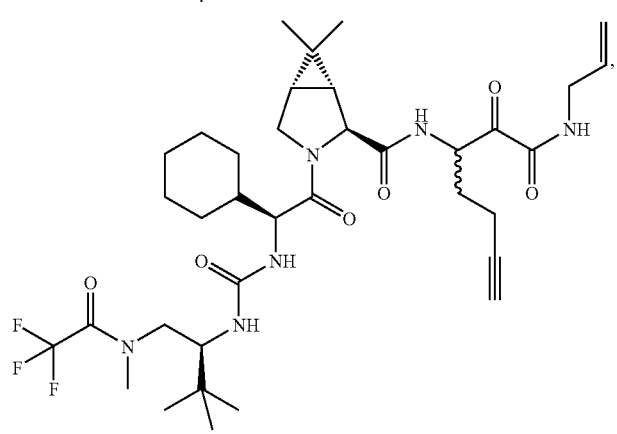

-continued
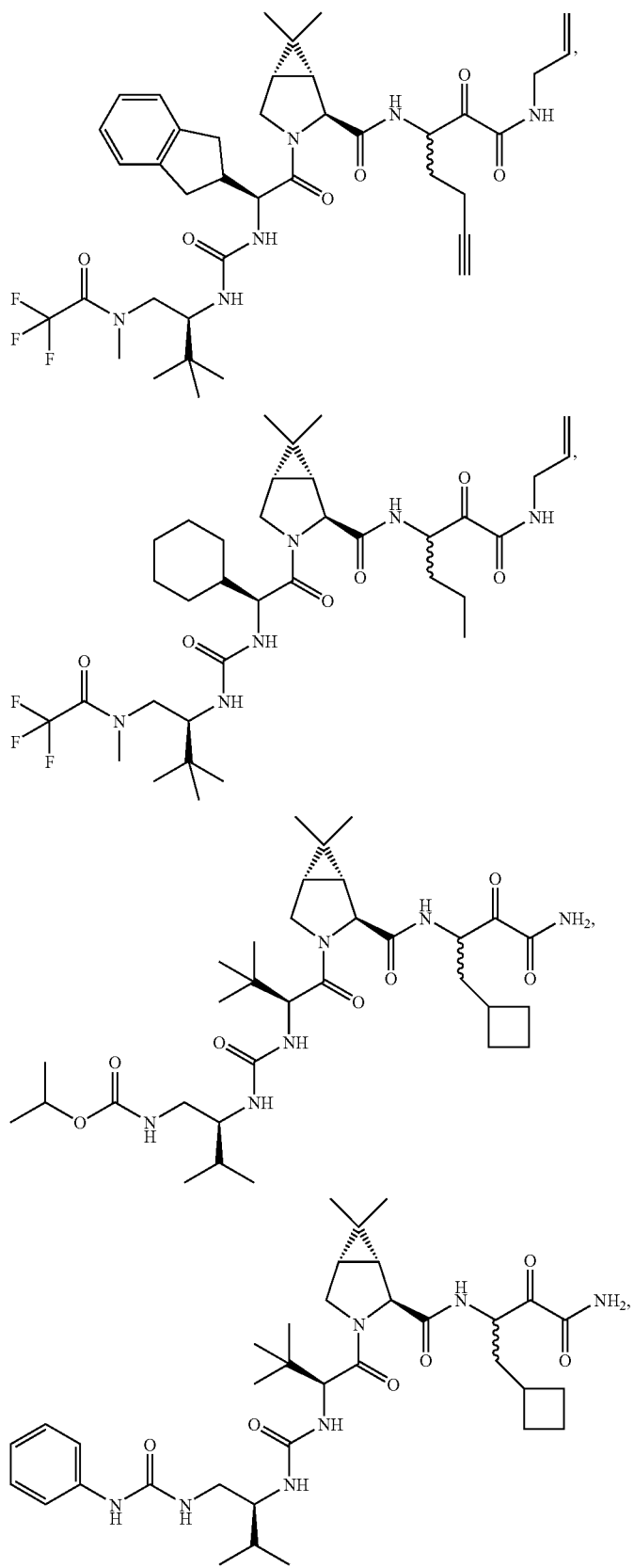

-continued
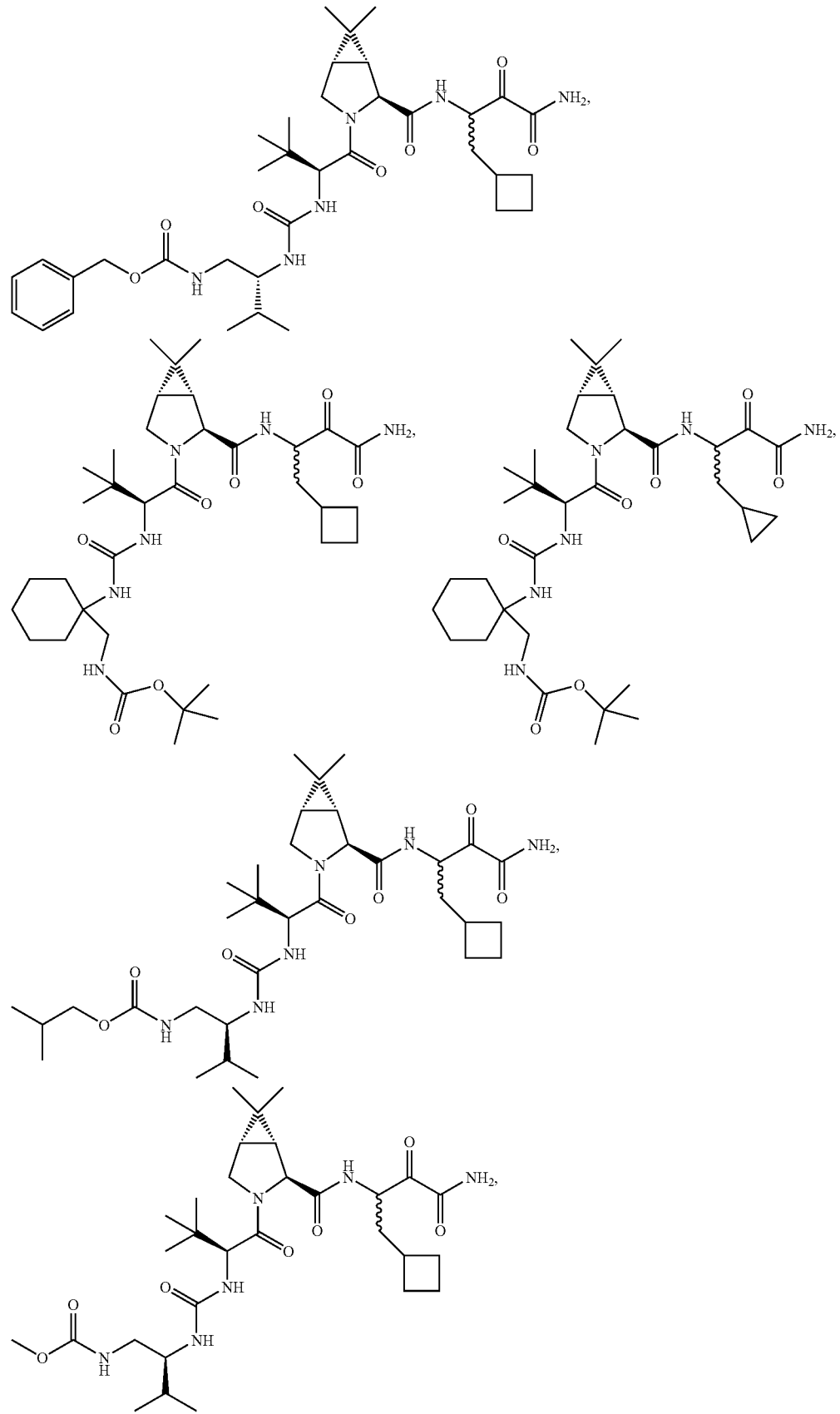

-continued
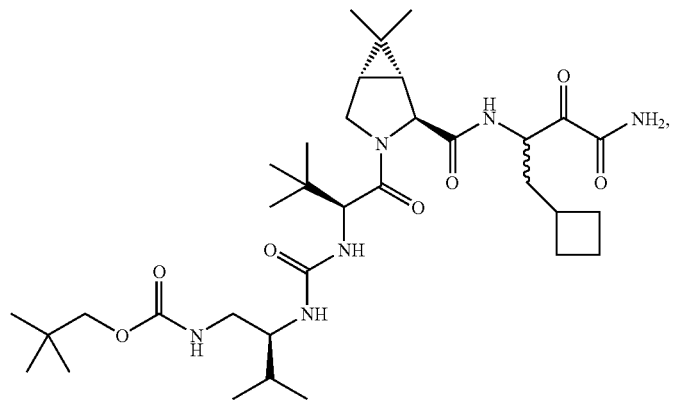
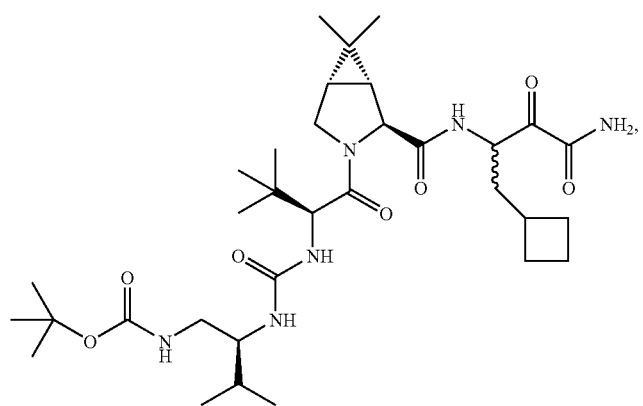
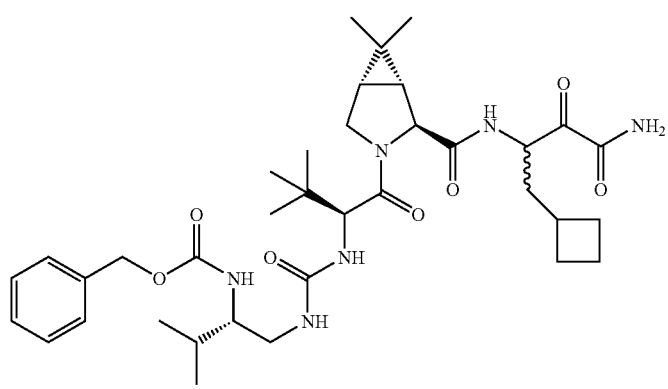

-continued
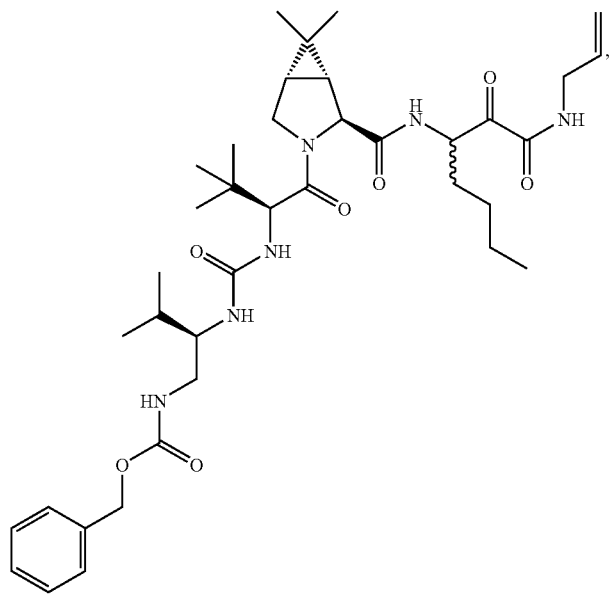
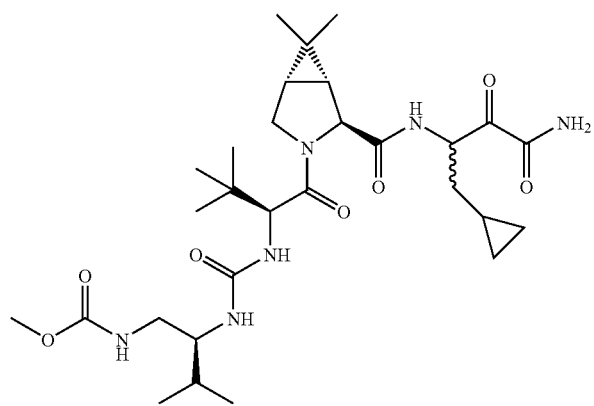
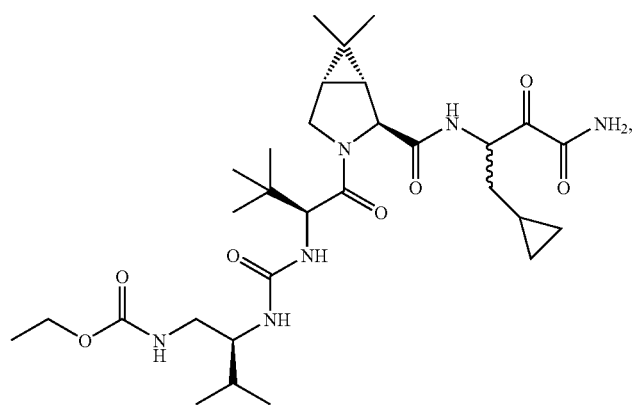

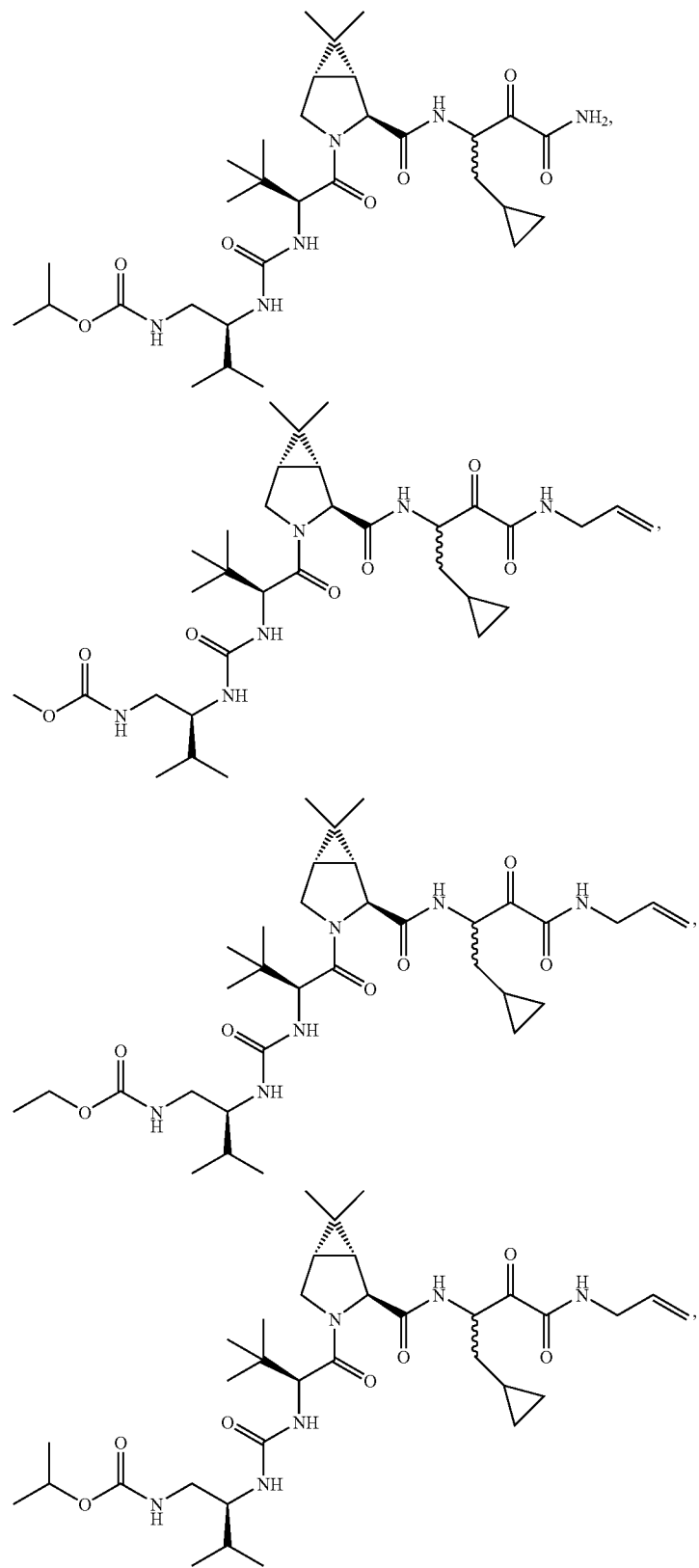

-continued
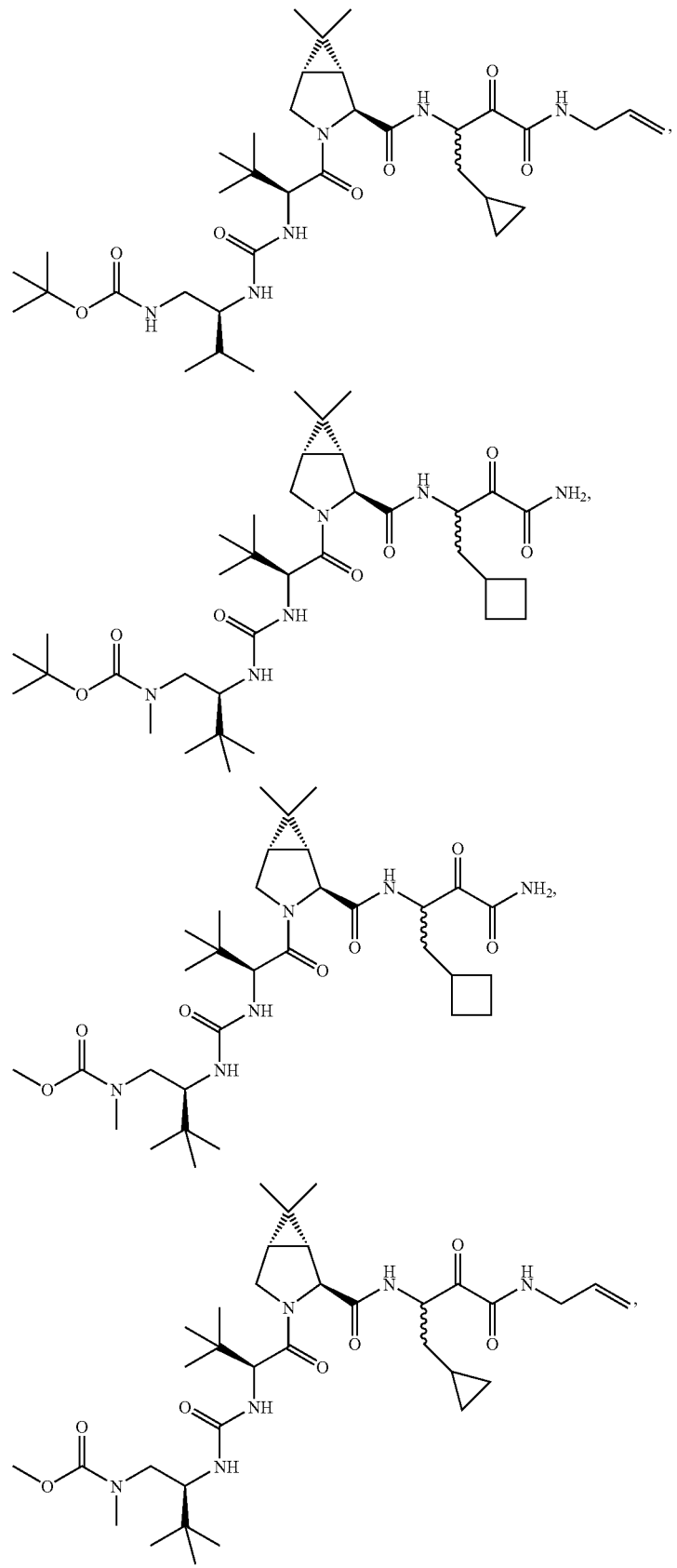

-continued
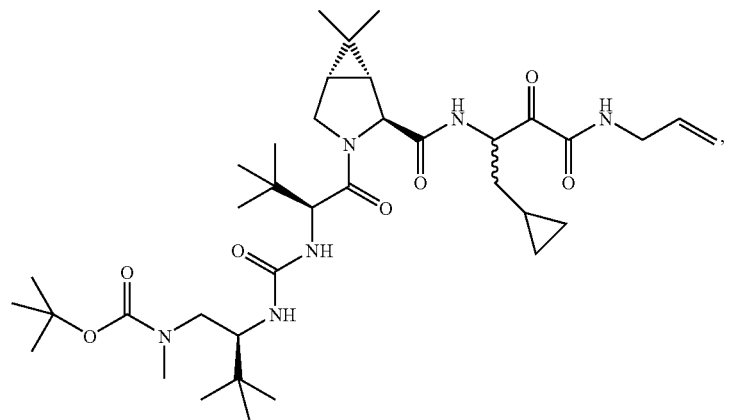
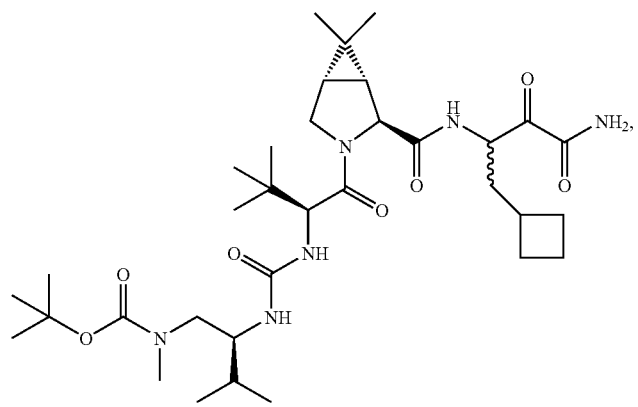
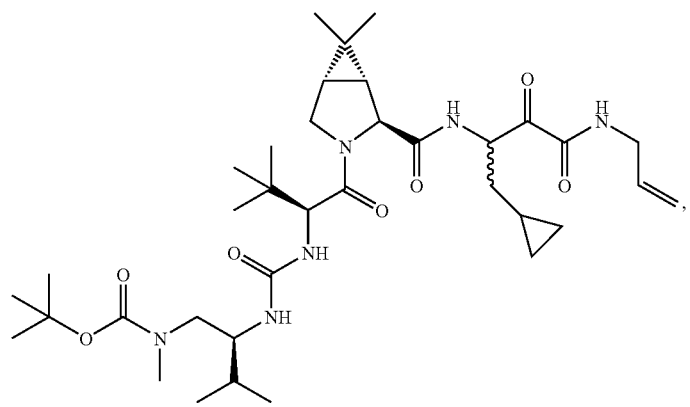
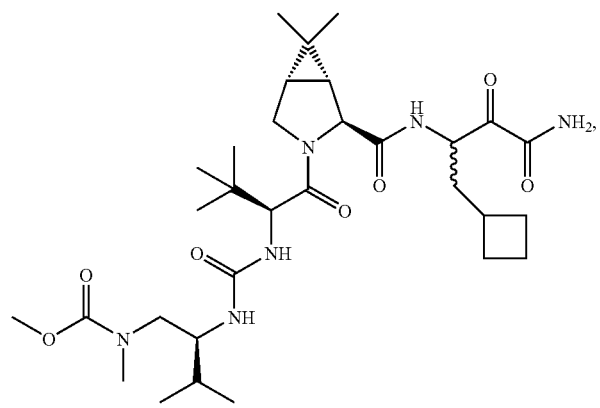

-continued
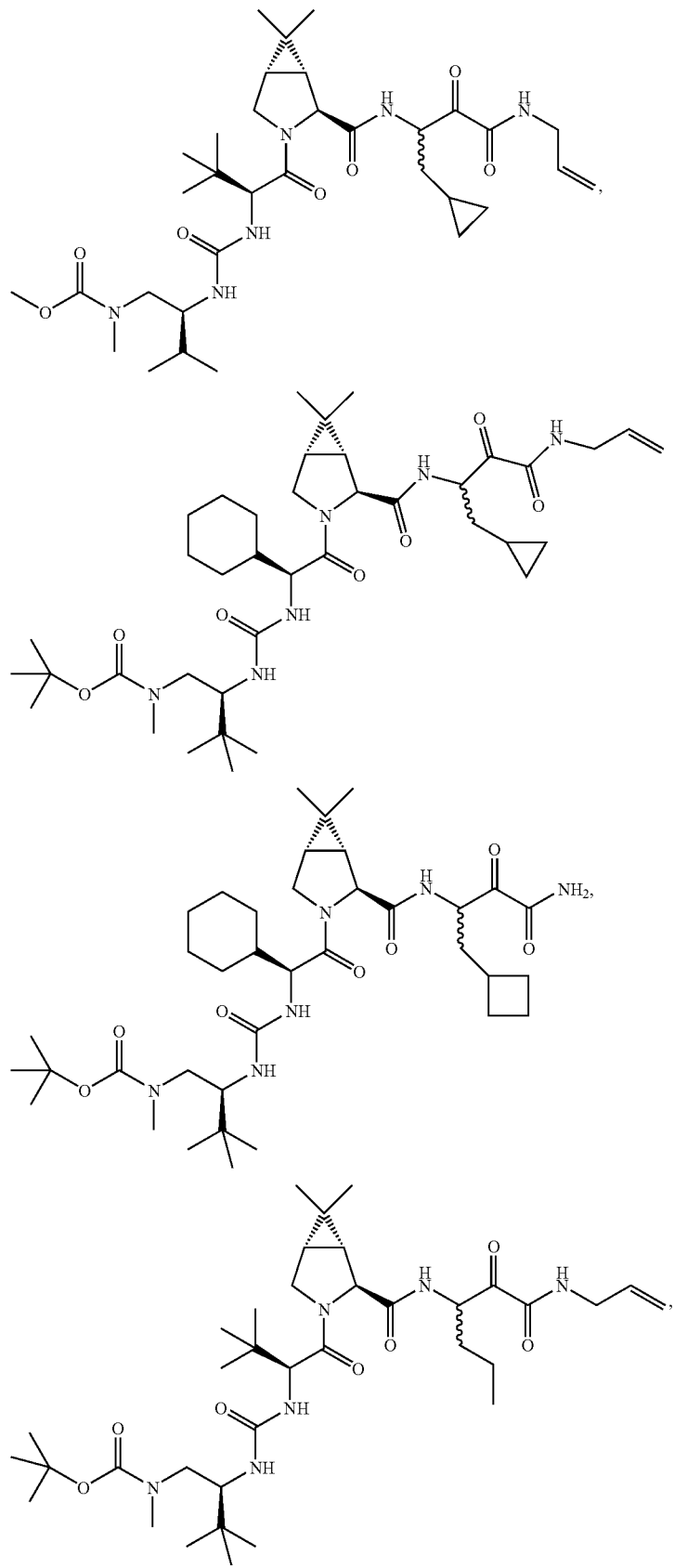

-continued
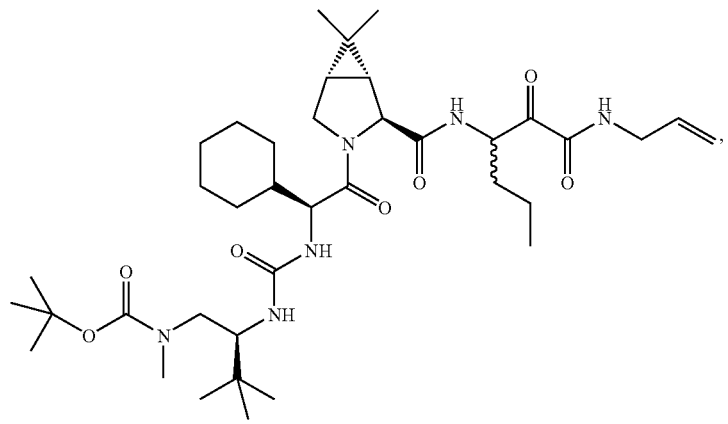
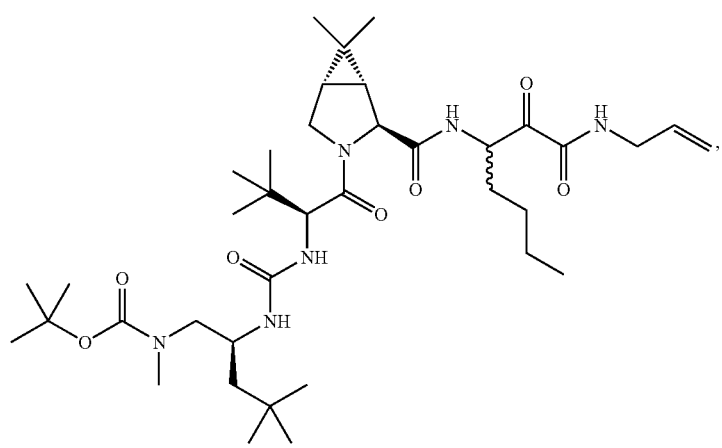
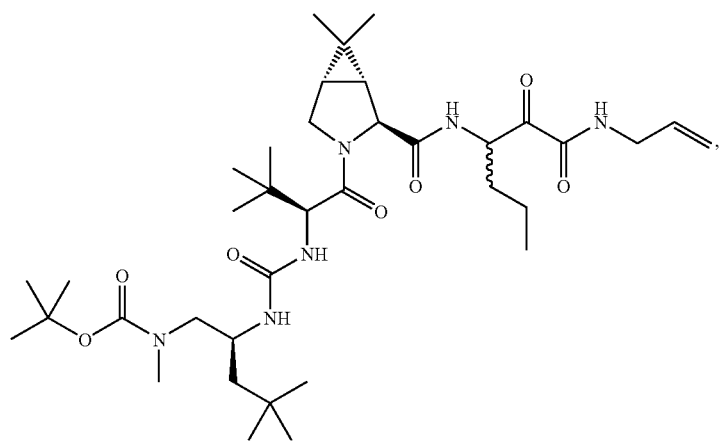

-continued
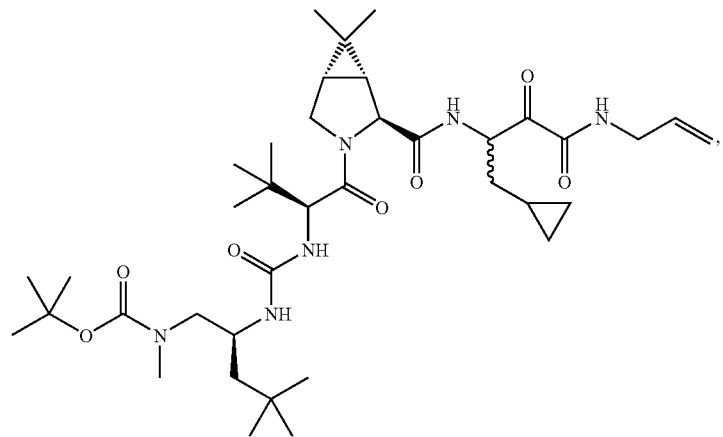
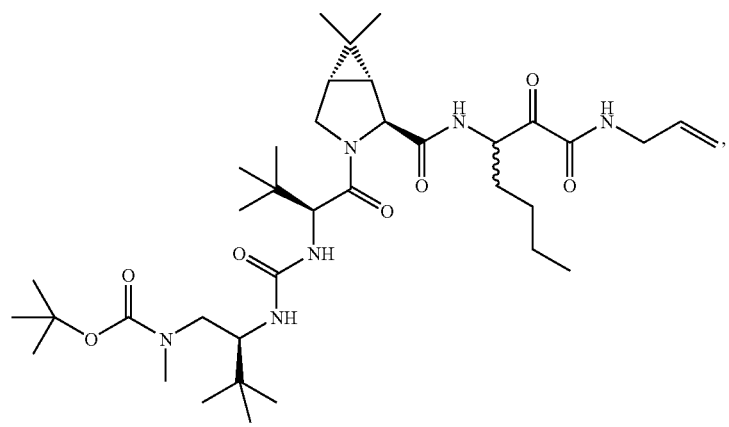
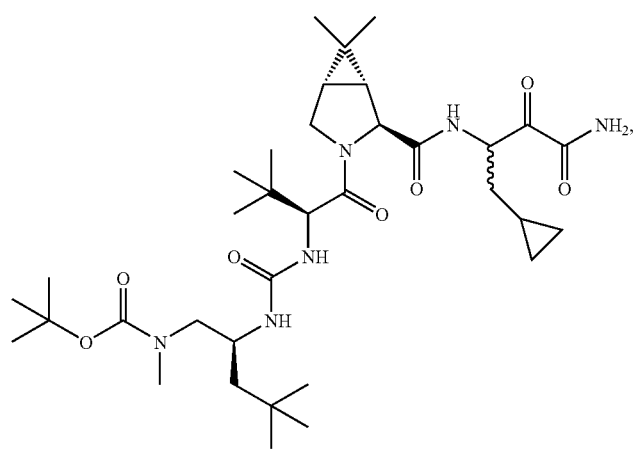

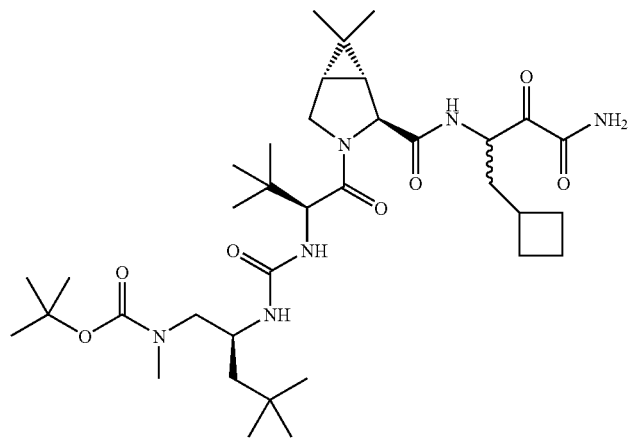
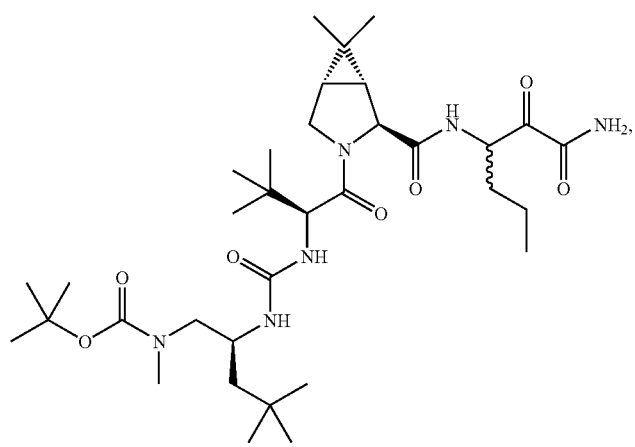
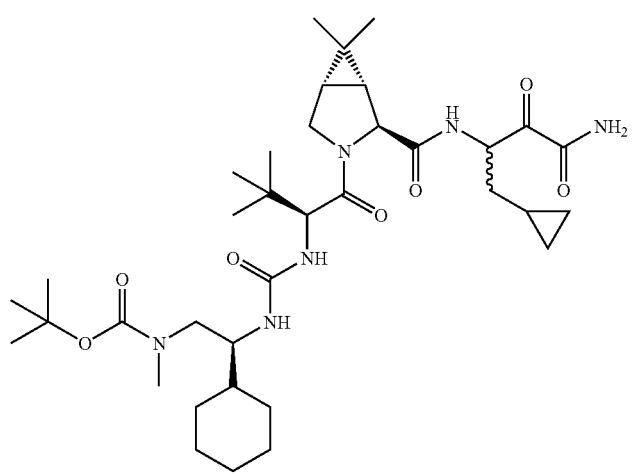

-continued
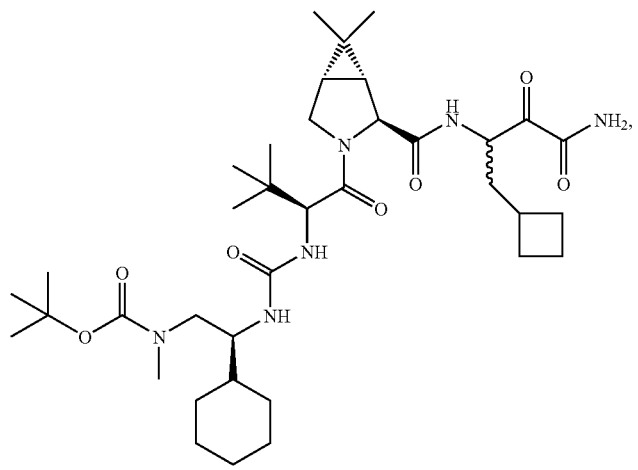
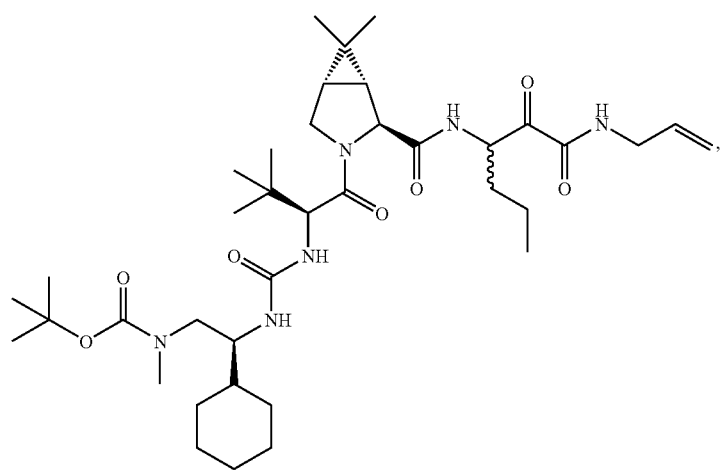
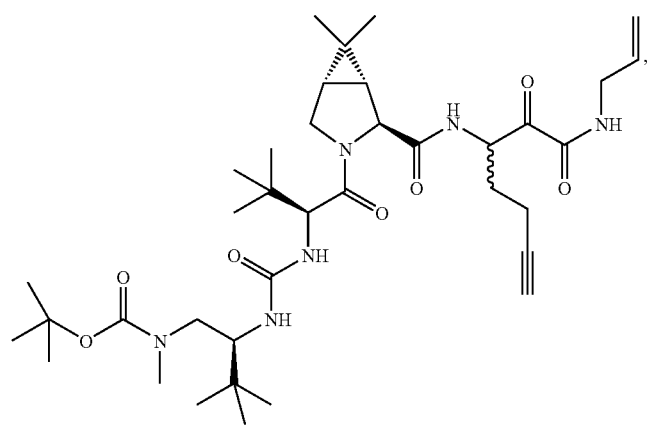

-continued
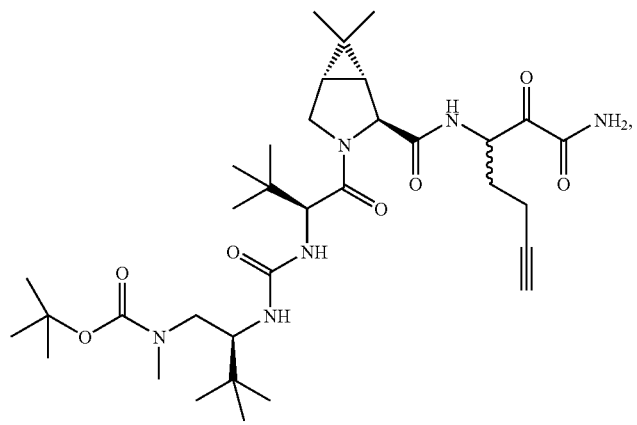
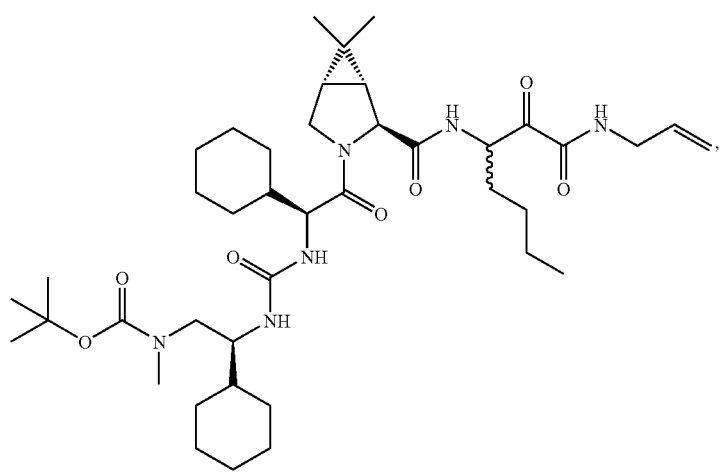
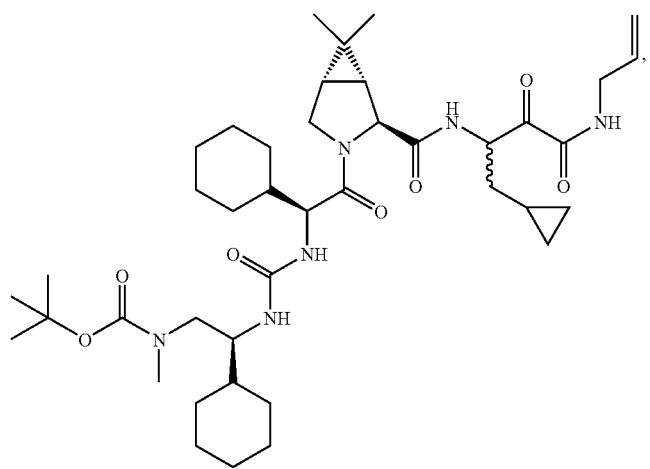

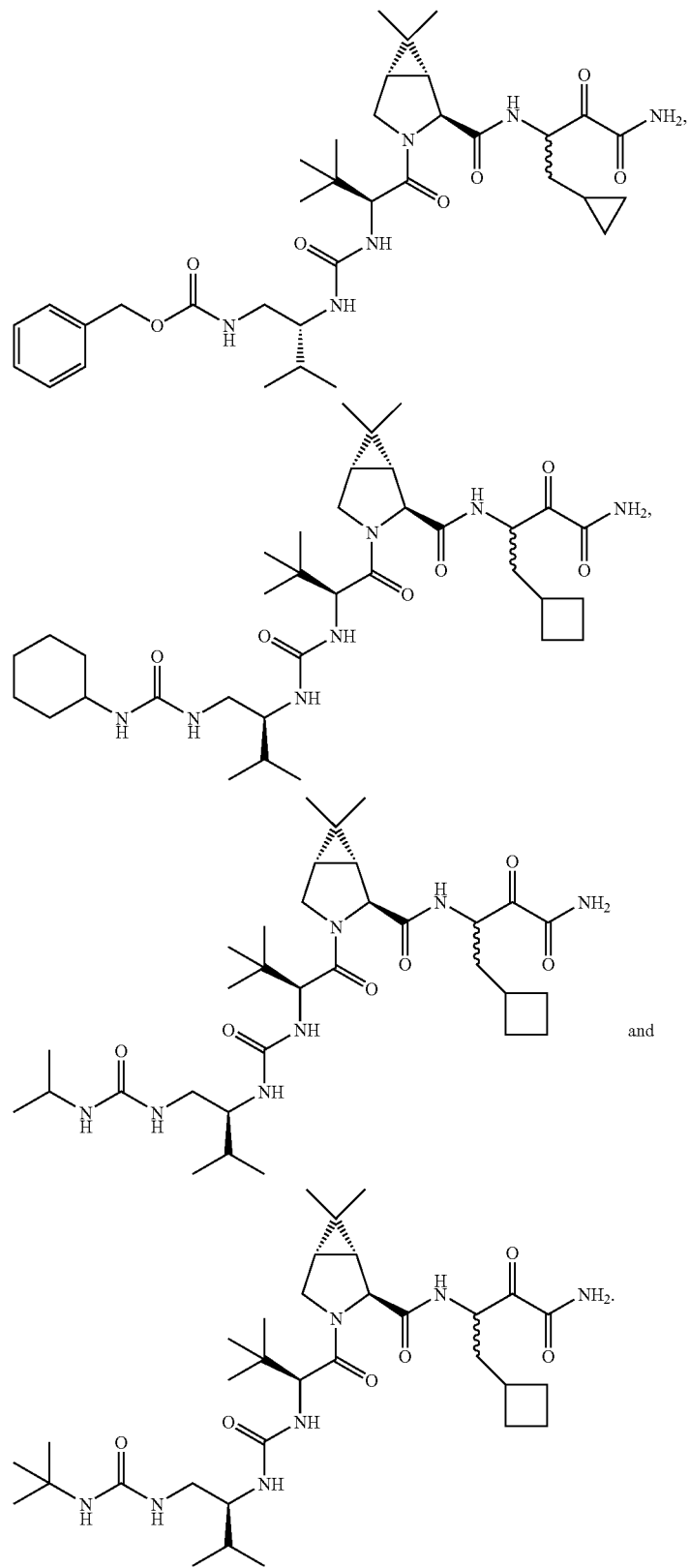

23. A pharmaceutical composition for treating an infection of Hepatitis C Virus ("HCV"), said composition comprising therapeutically effective amount of one or more compounds in claim 22 and a pharmaceutically acceptable carrier.

24. The pharmaceutical composition of claim 23, additionally containing at least one antiviral agent.

25. The pharmaceutical composition of claim 24, additionally containing at least one interferon or PEG-interferon alpha conjugate.

26. The pharmaceutical composition of claim 25, wherein said at least one antiviral agent is ribavirin and said at least one interferon is α-interferon or pegylated interferon.

27. A method of treatment of an infection of Hepatitis C Virus ("HCV"), comprising administering an effective amount of one or more compounds of claim 22.

28. A method of treating, or ameliorating one or more symptoms of hepatitis C, comprising administering a therapeutically effective amount of one or more compounds of claim 22.

29. The method of claim 28, wherein the HCV protease is the NS3/NS4a protease.

30. The method of claim 29, wherein the compound or compounds inhibit HCV NS3/NS4a protease.

31. A method of treating an infection of hepatitis C Virus ("HCV"), said method comprising administering to a patient in need of such treatment, a pharmaceutical composition which comprises therapeutically effective amounts of at least one compound, or enantiomers, stereoisomers, rotamers, tautomers, diastereomers, and racemates of said compound, or a pharmaceutically acceptable salt- or ester of said compound, said compound being selected from the following:

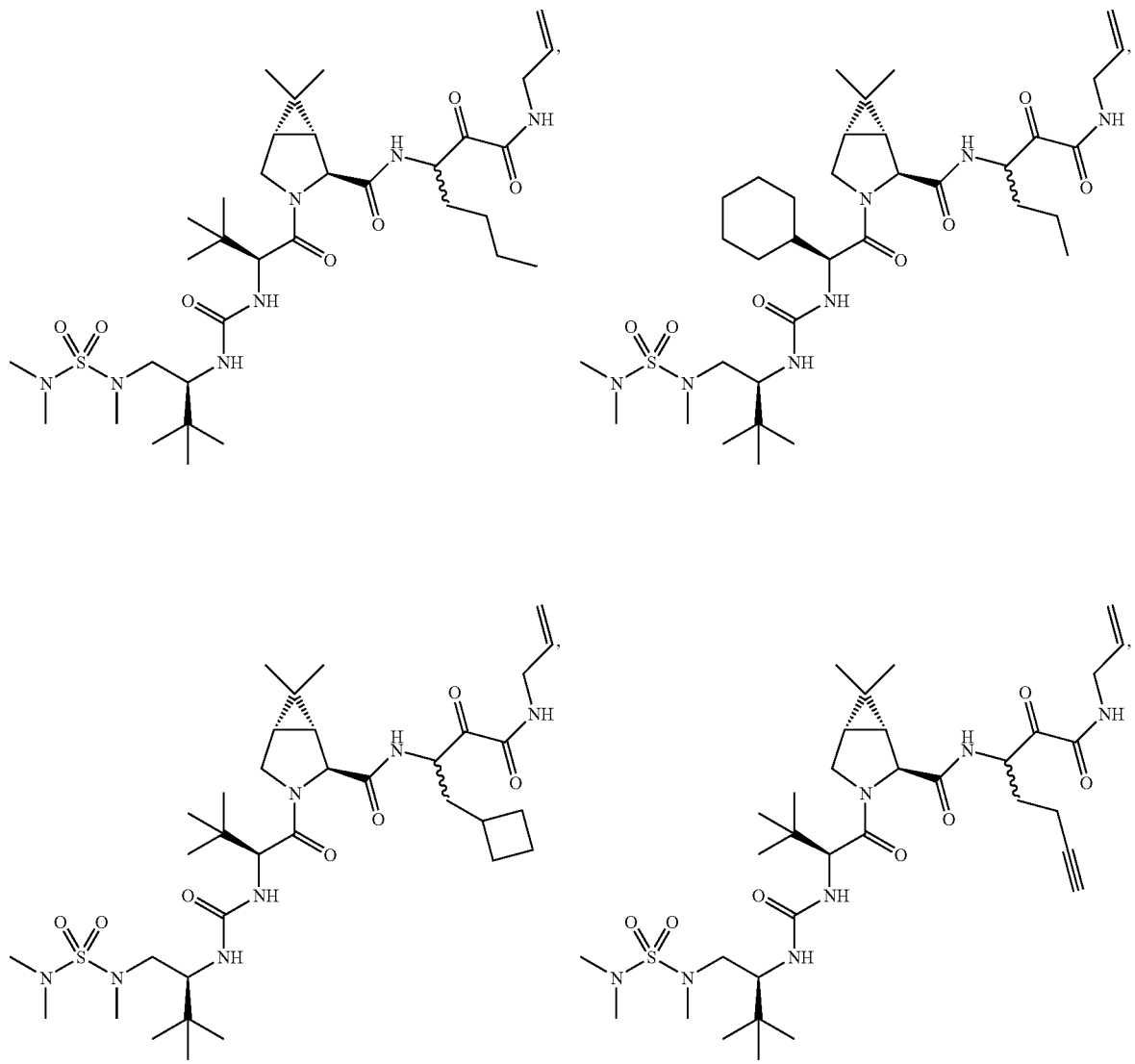

649
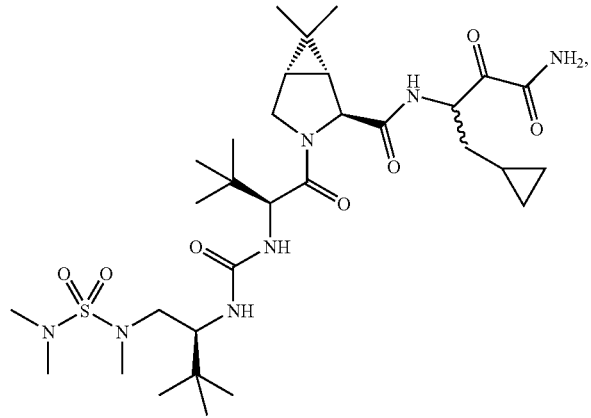
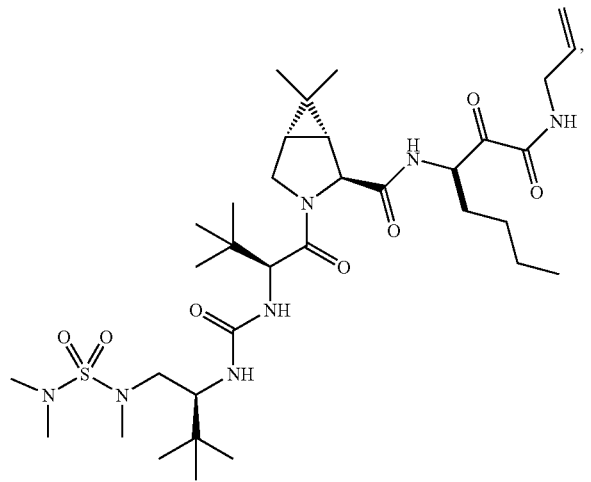
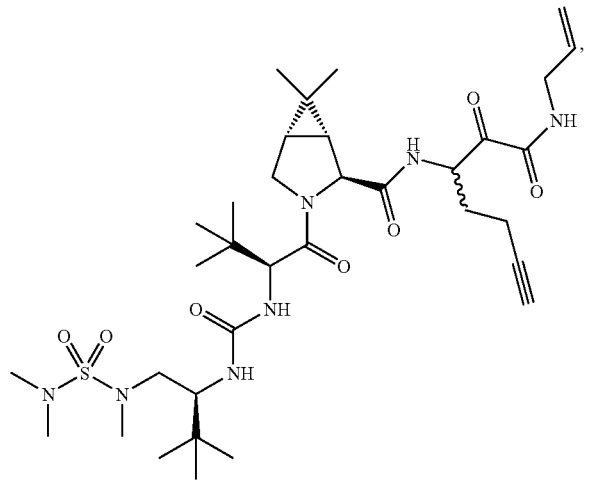
650
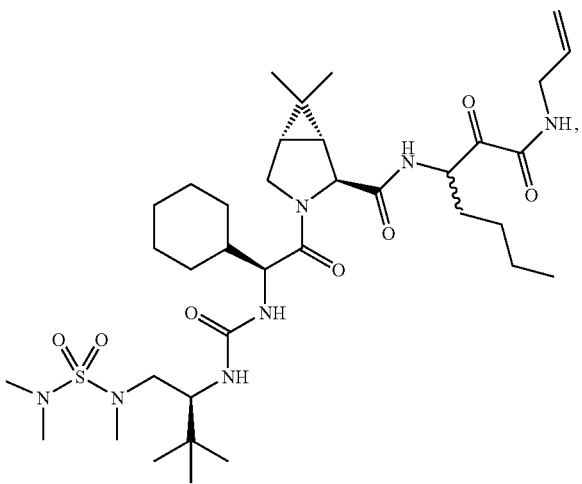
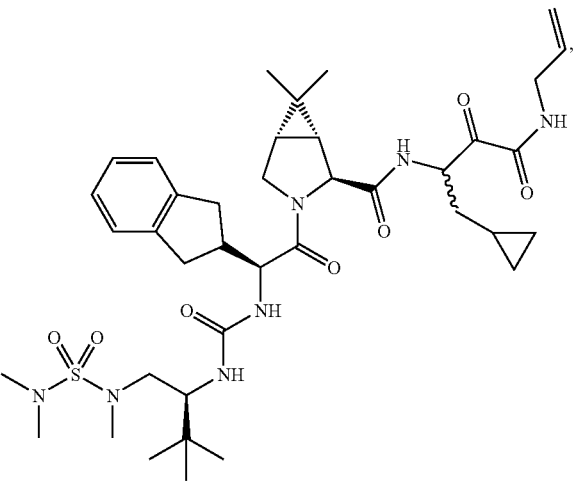

-continued
651
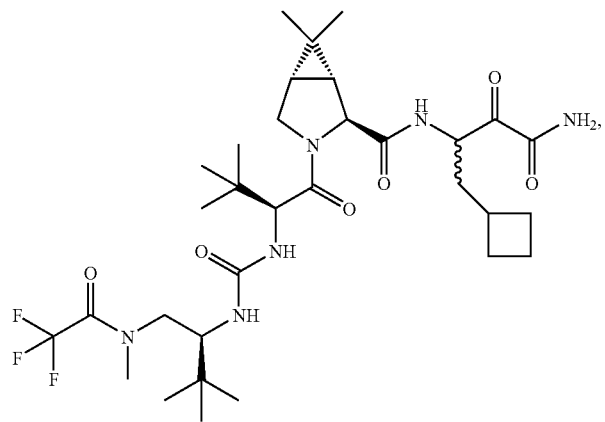
652
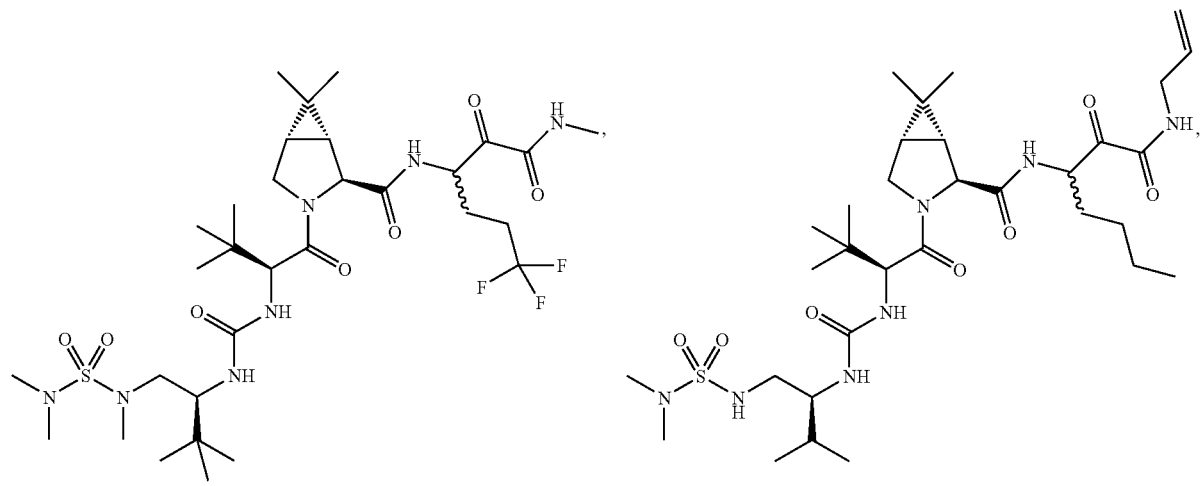
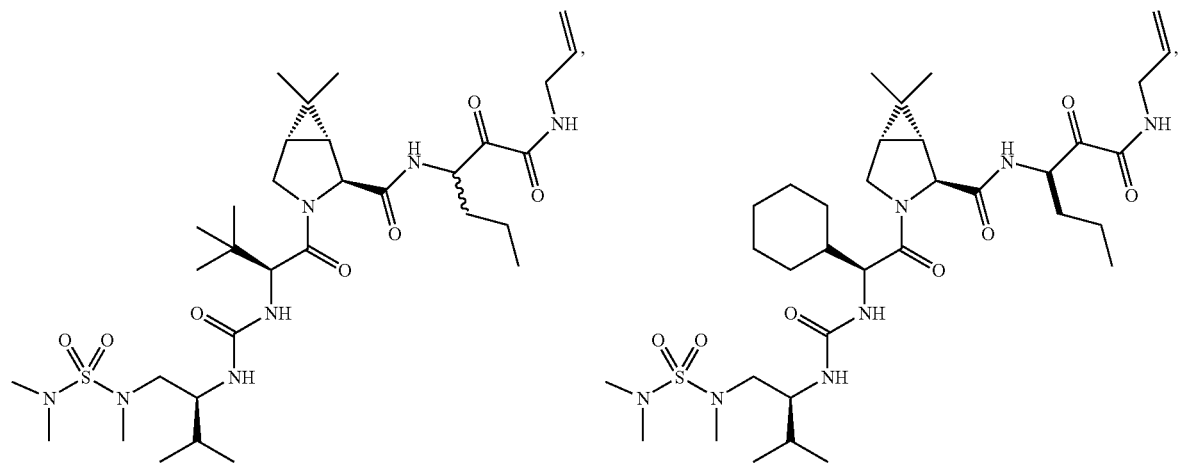

-continued
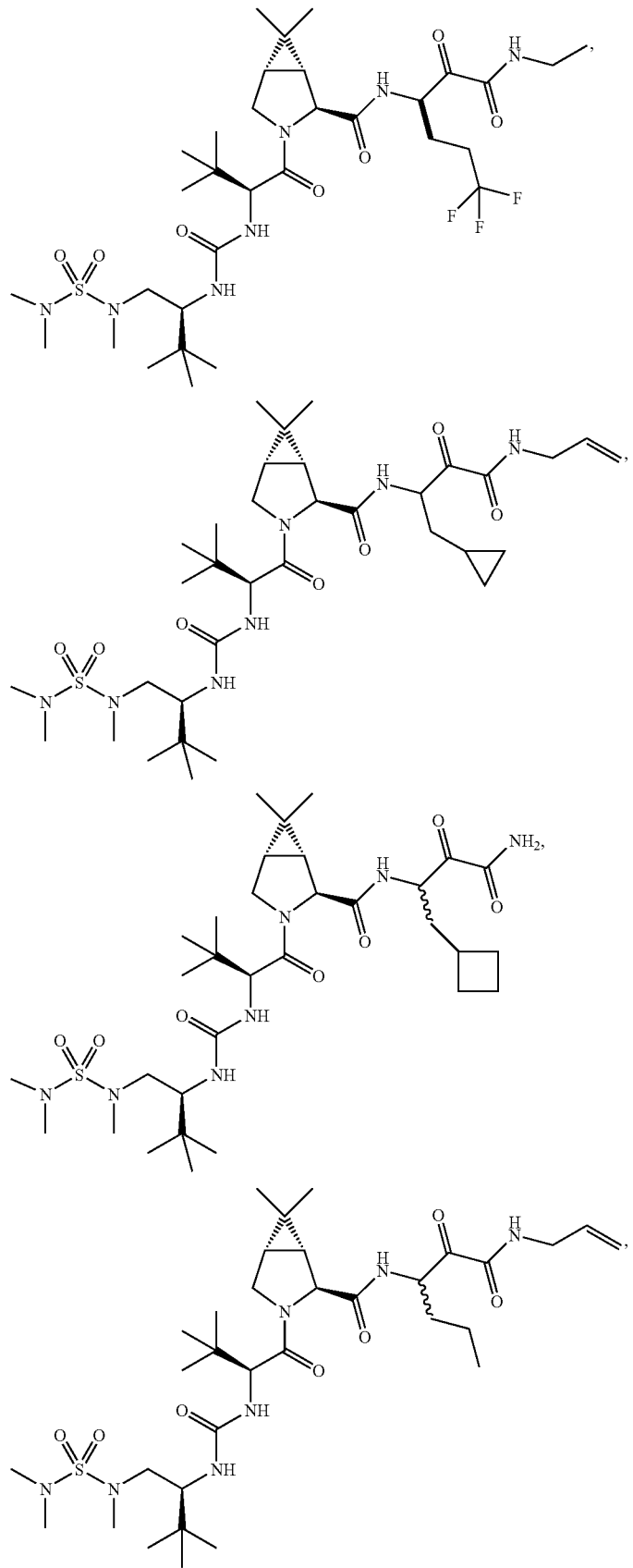

-continued
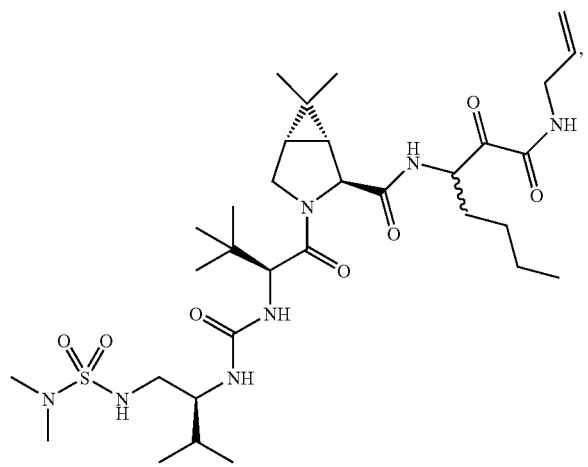
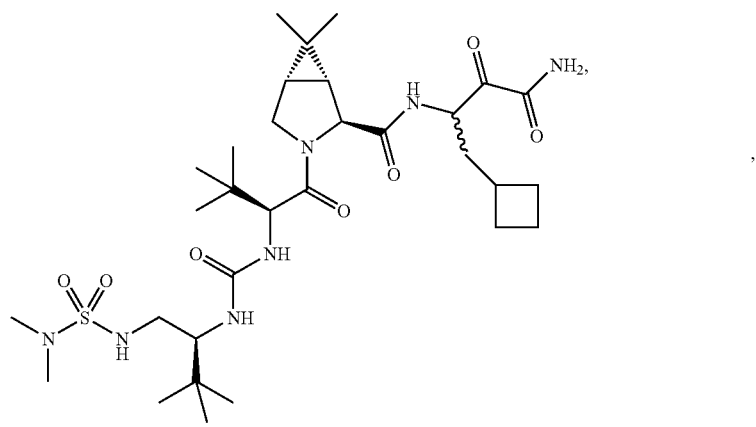
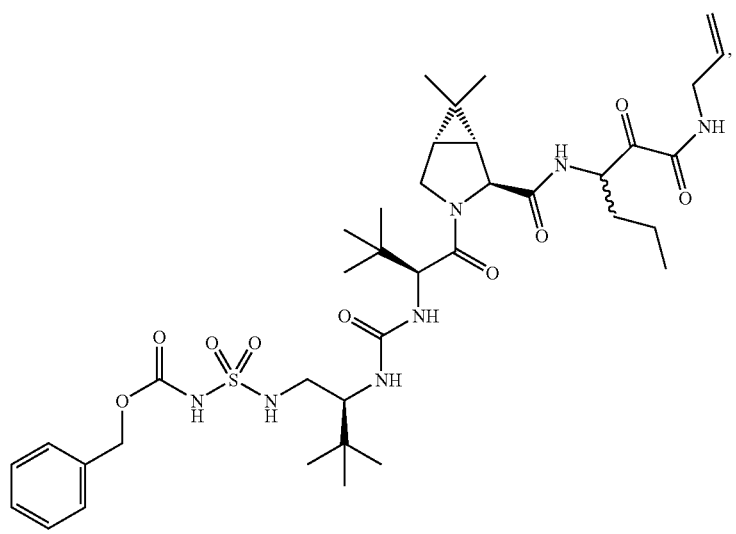

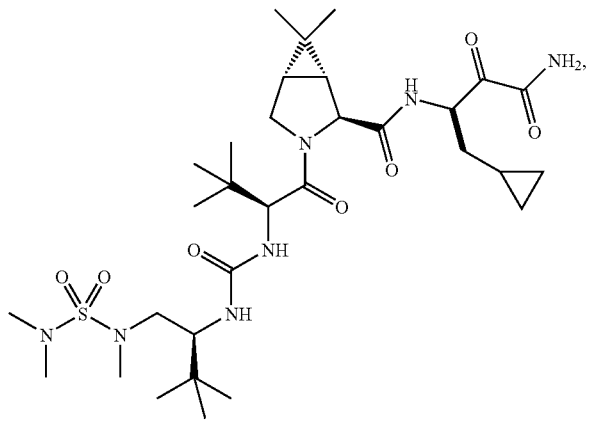
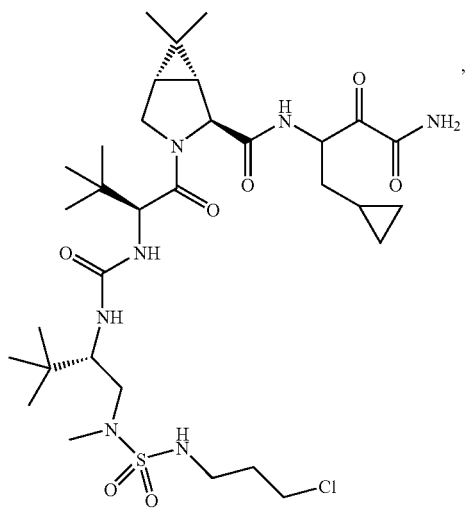
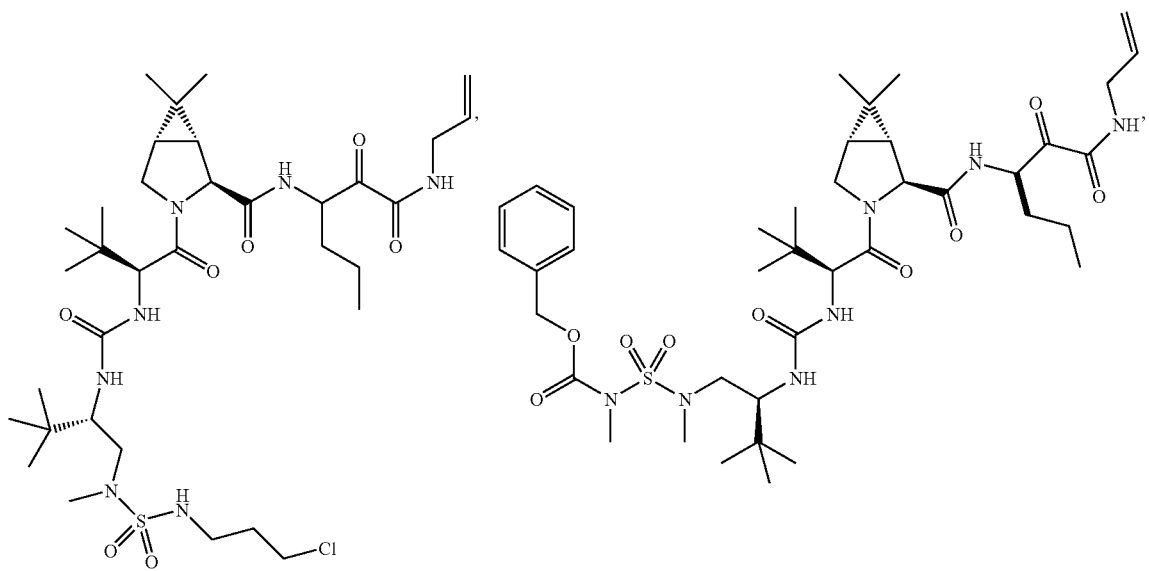

-continued
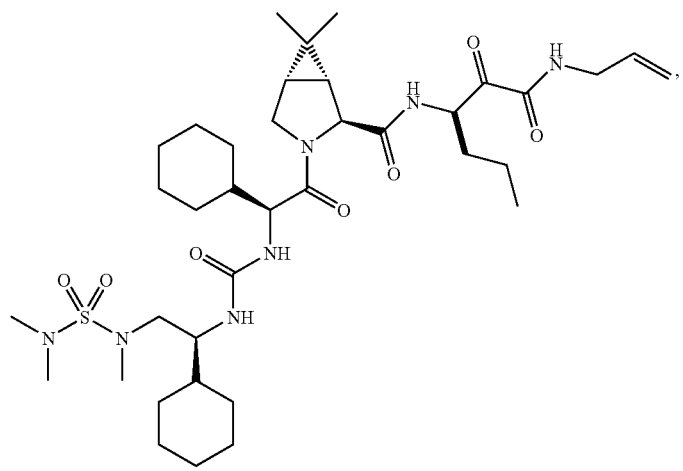
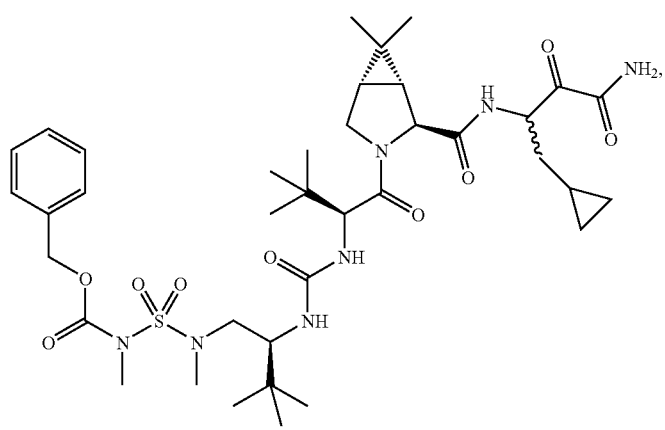
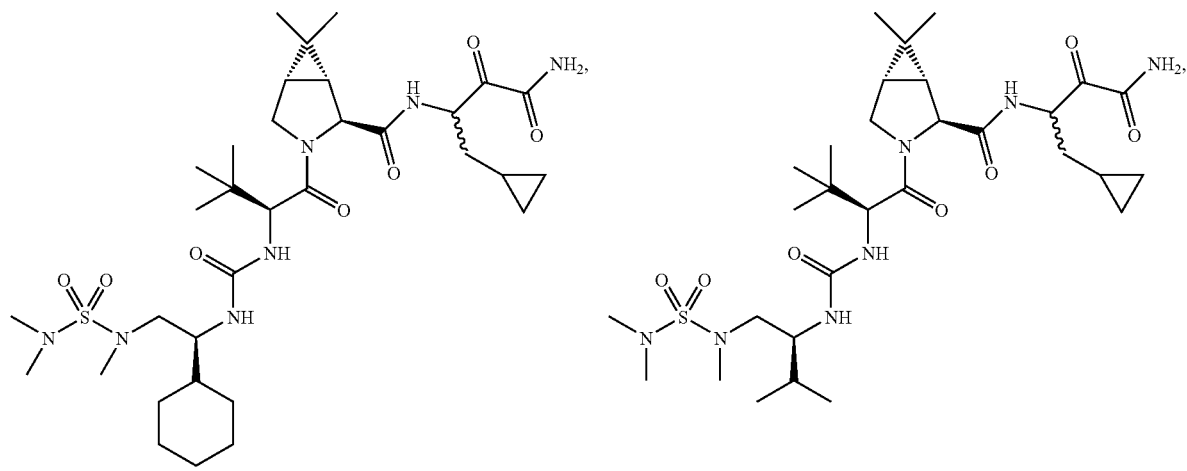

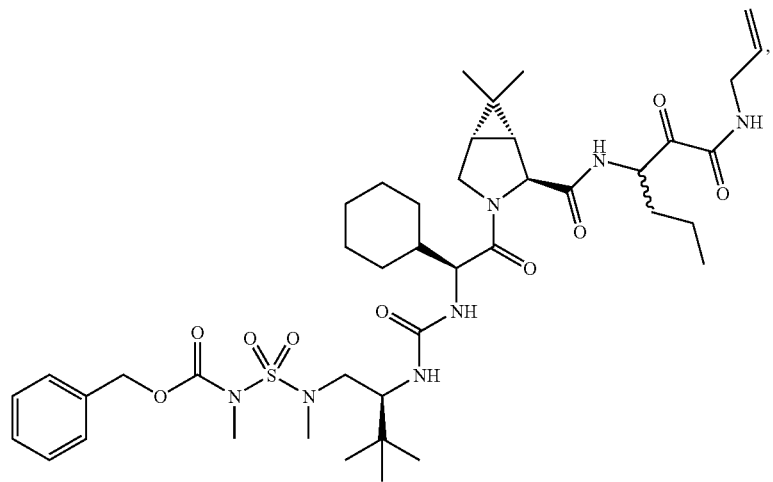
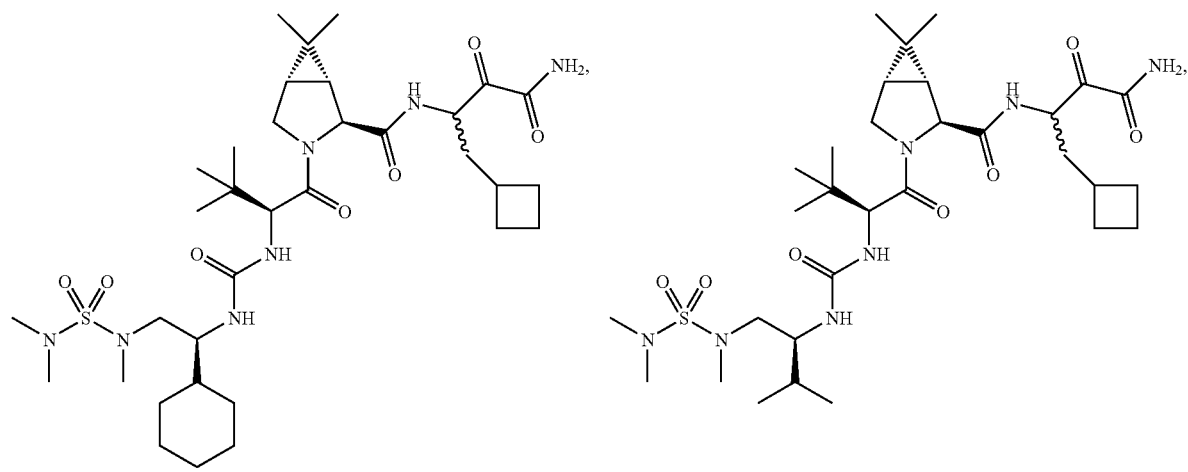
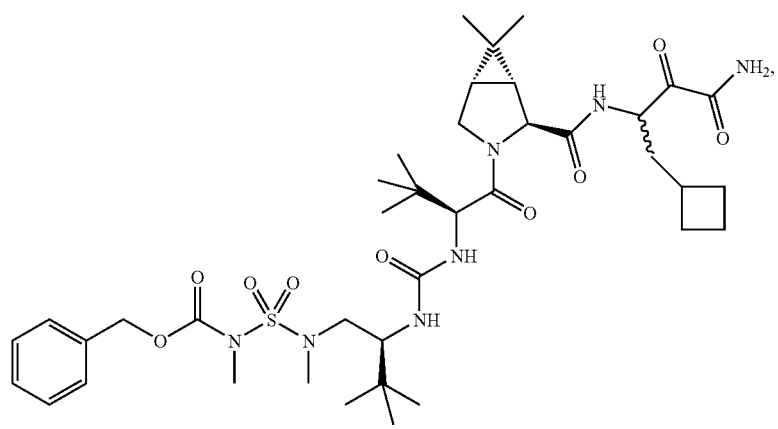

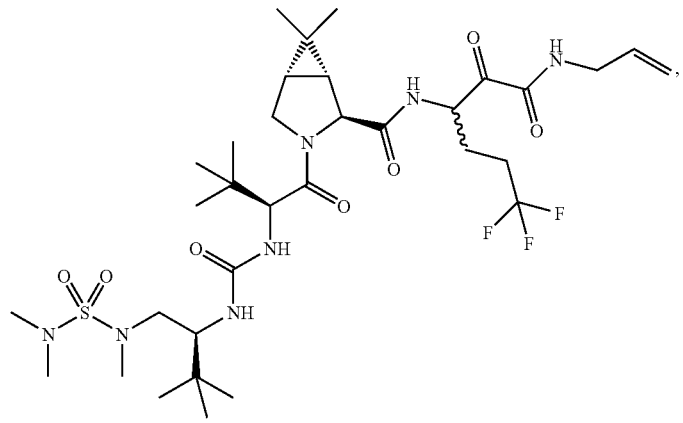
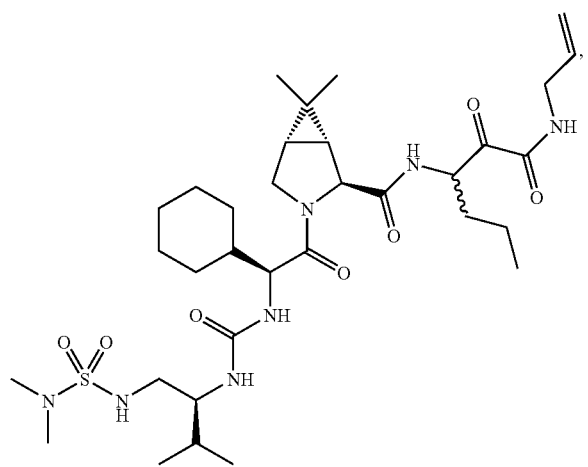
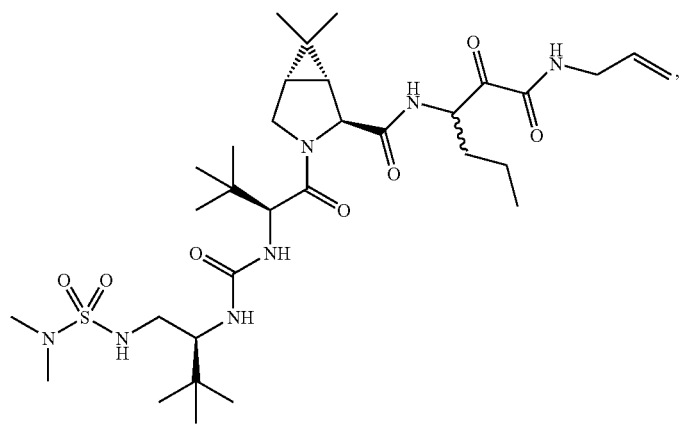

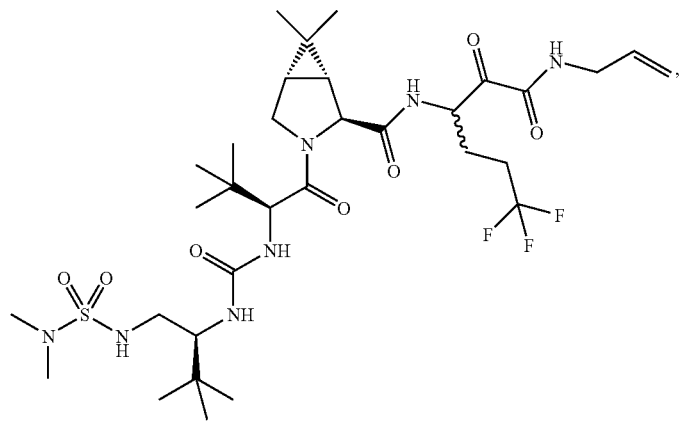
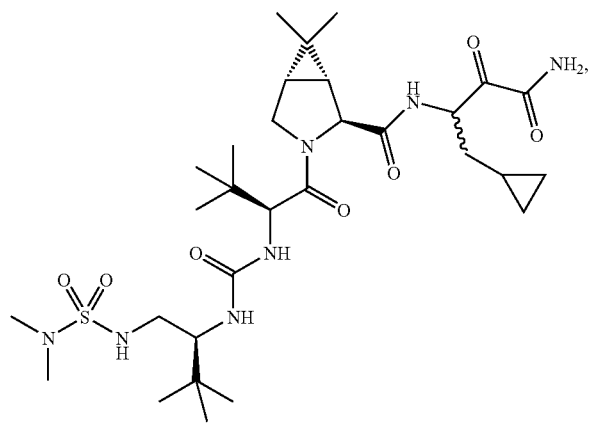
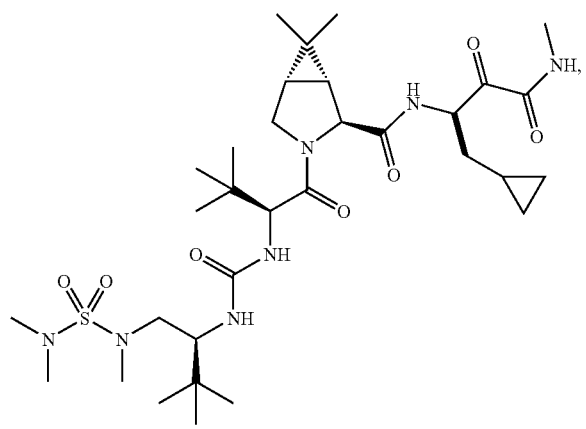

-continued
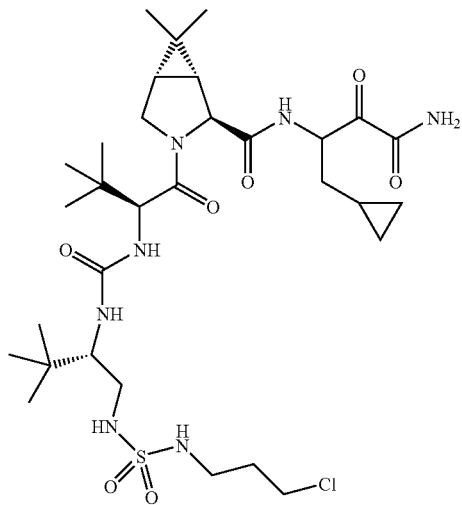
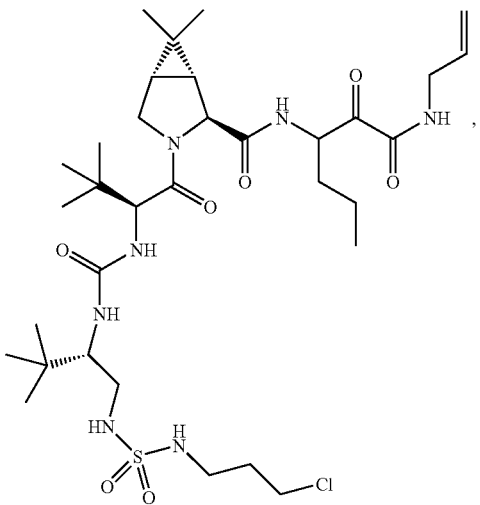
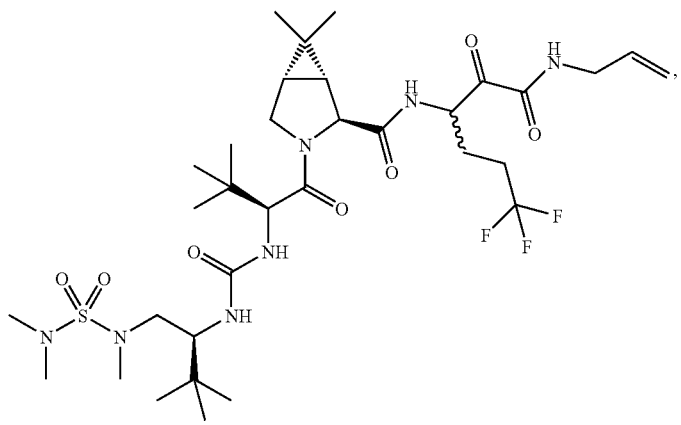
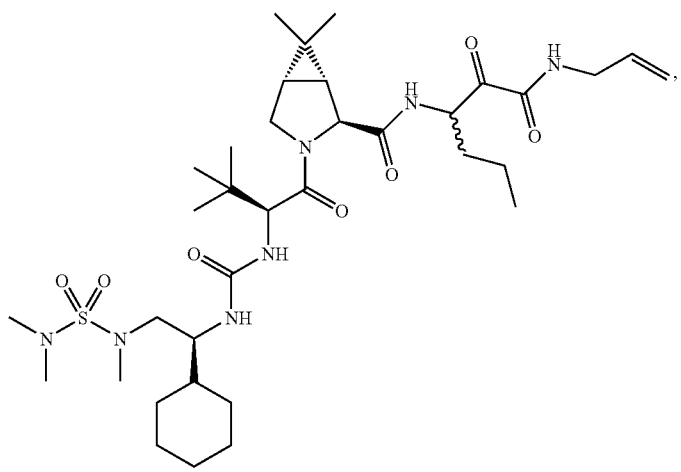

-continued
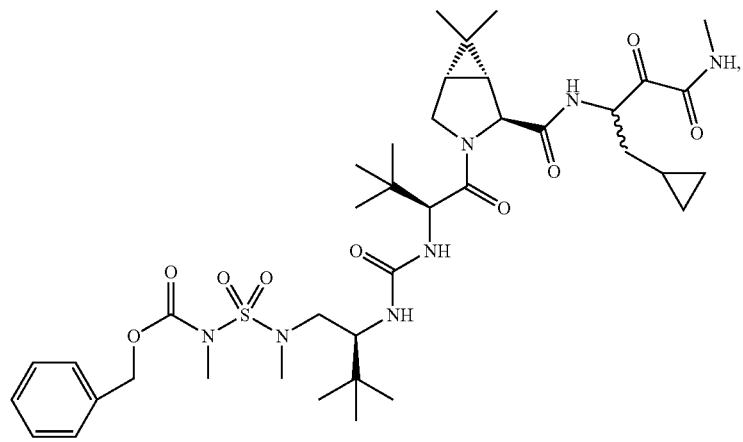
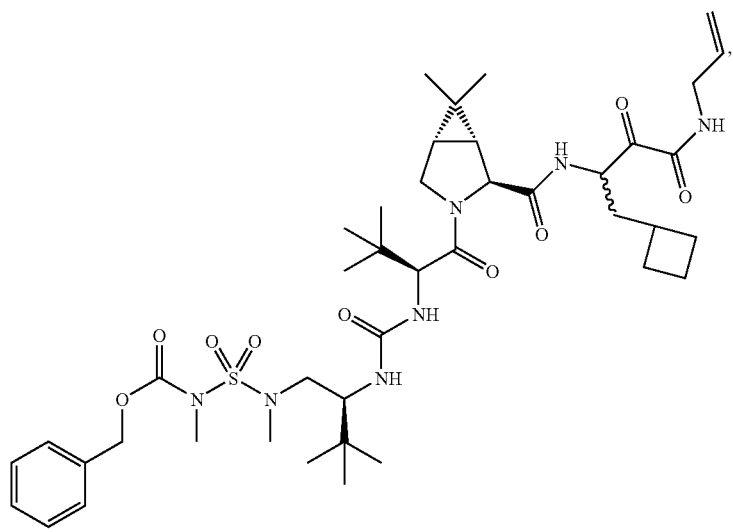
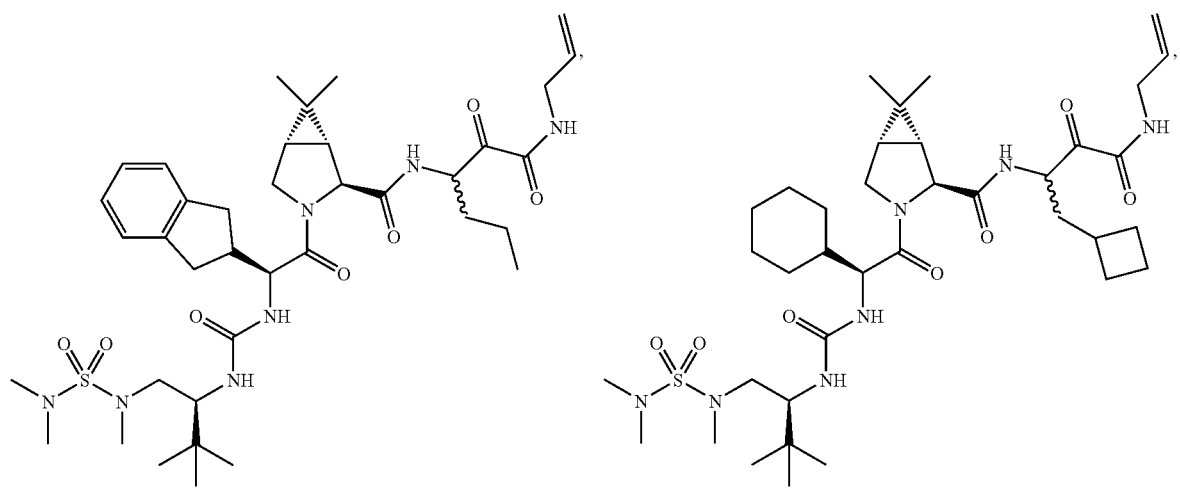

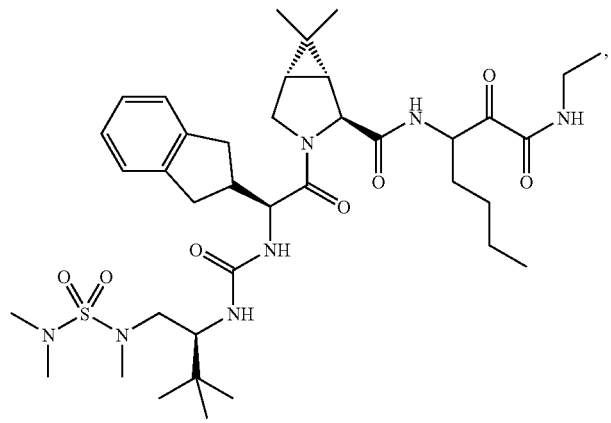
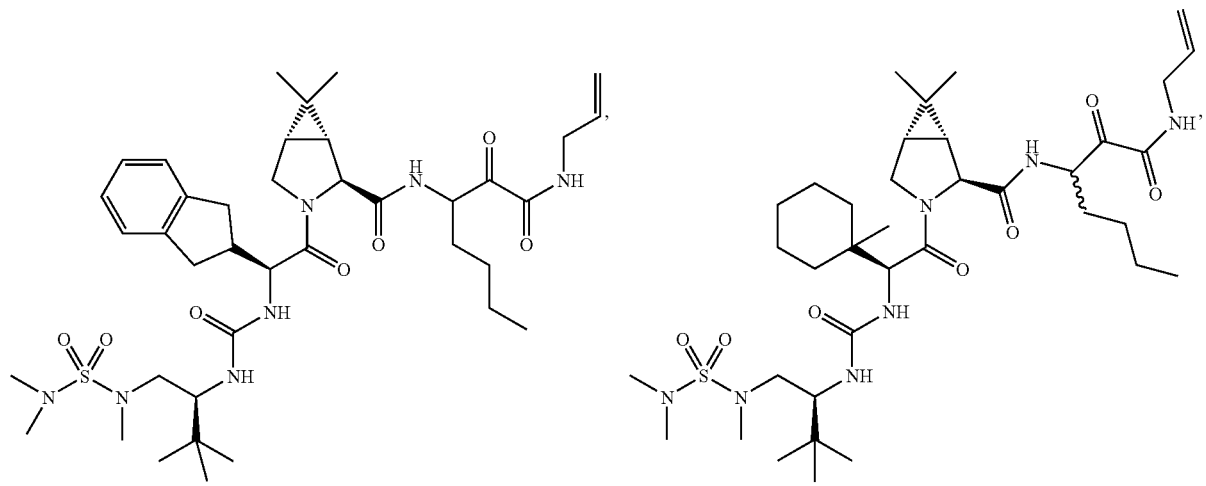
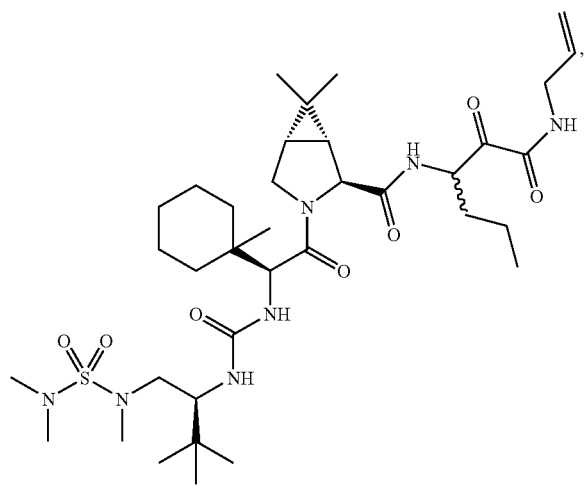

-continued
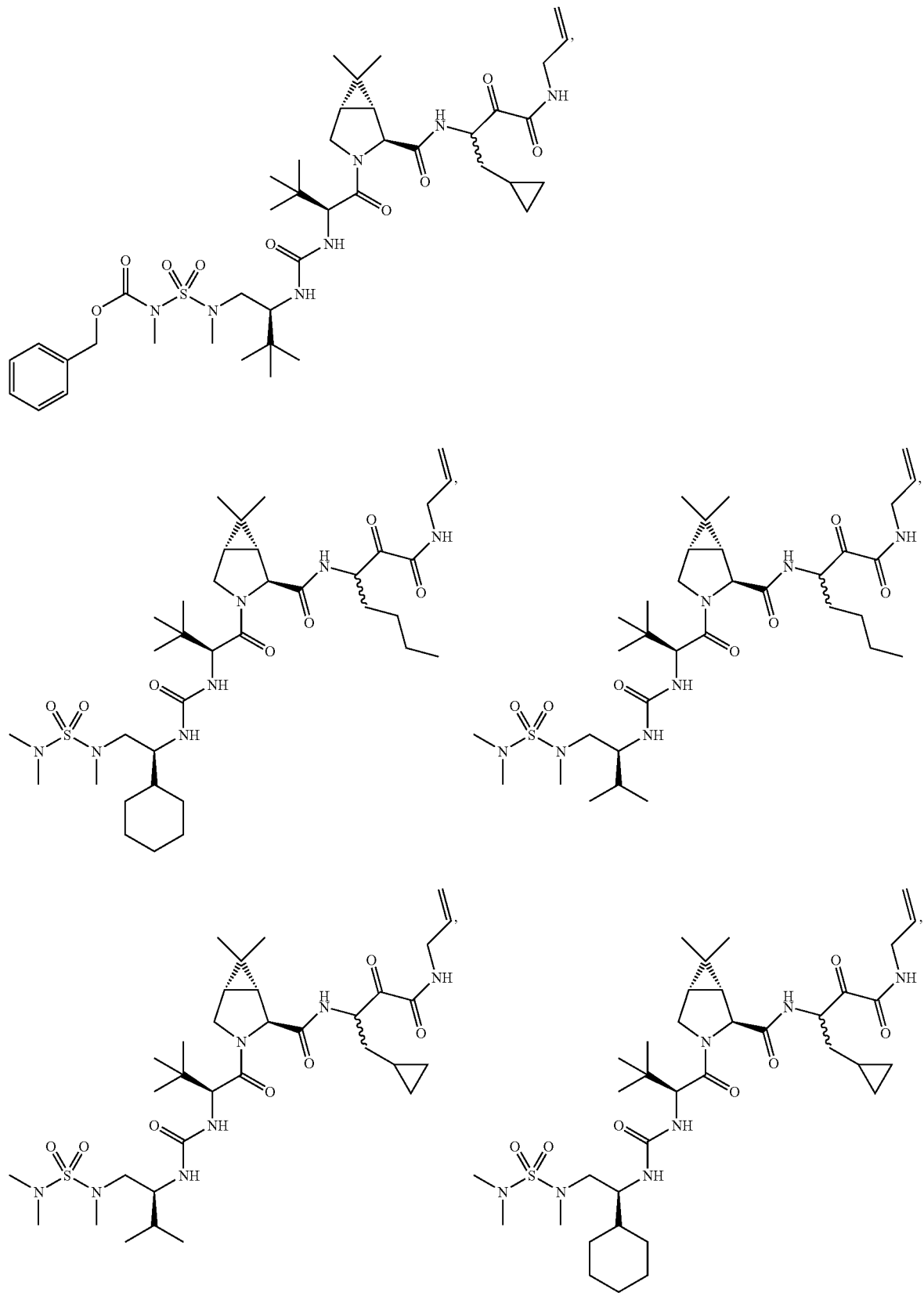

-continued
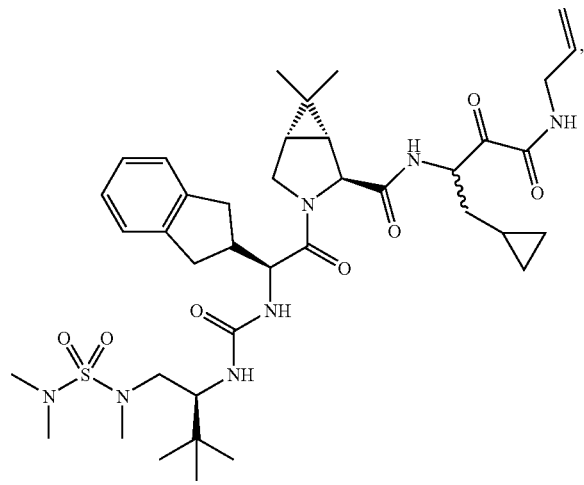
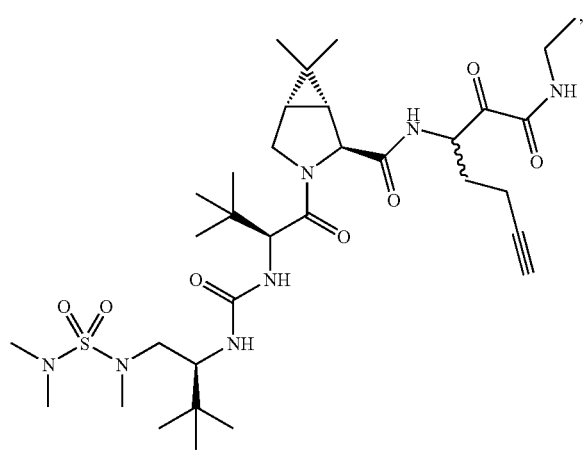
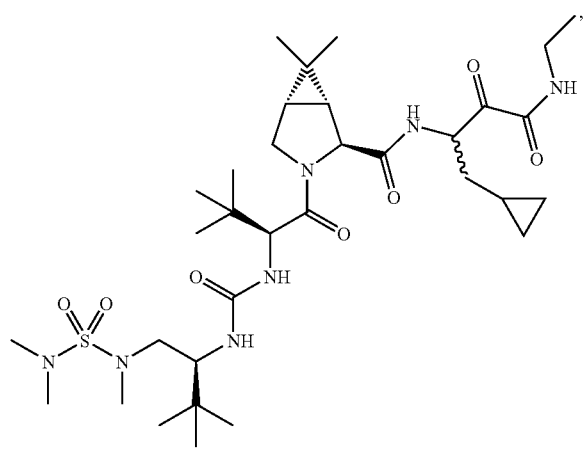

677 678
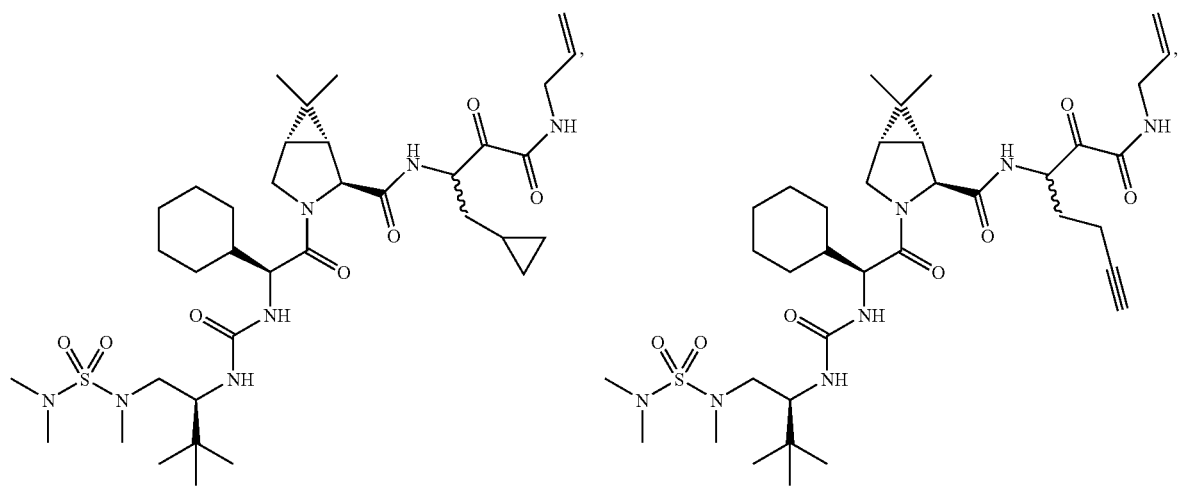
-continued
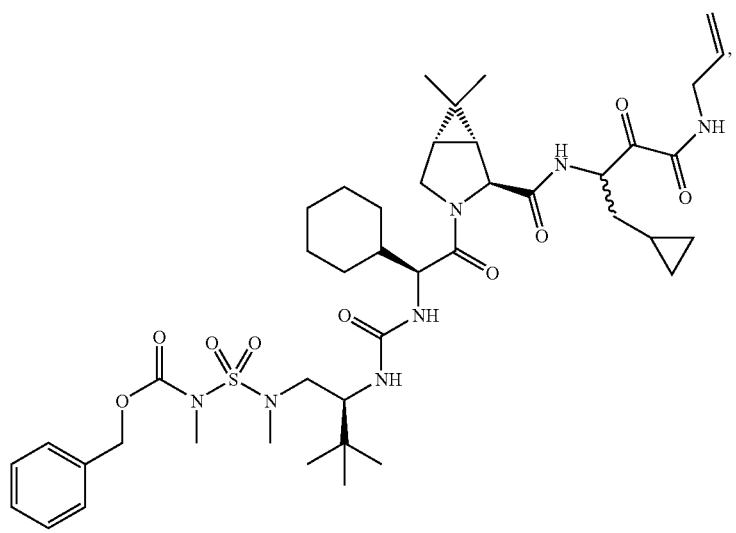
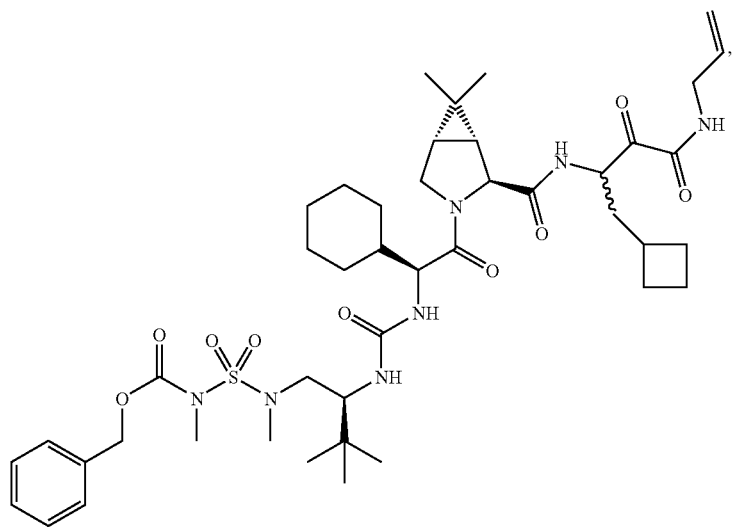

-continued
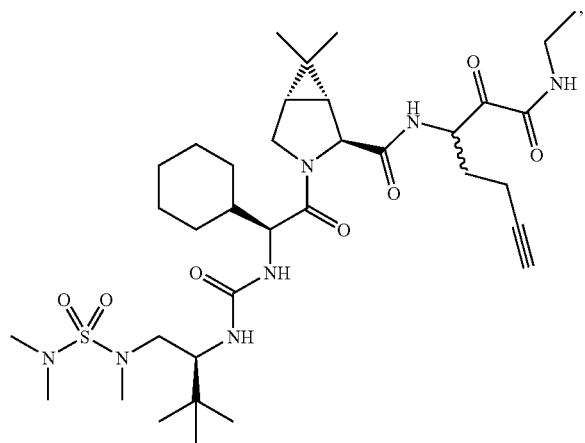
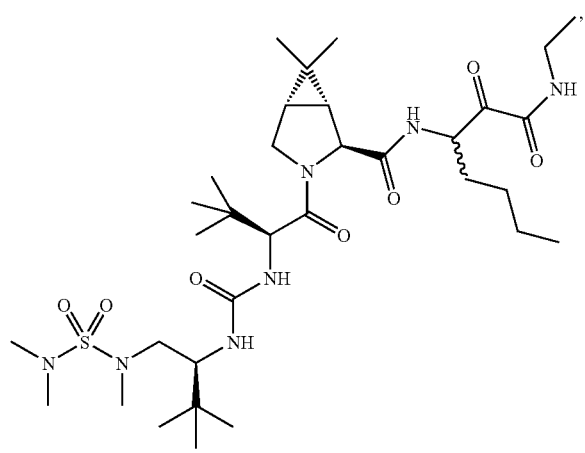
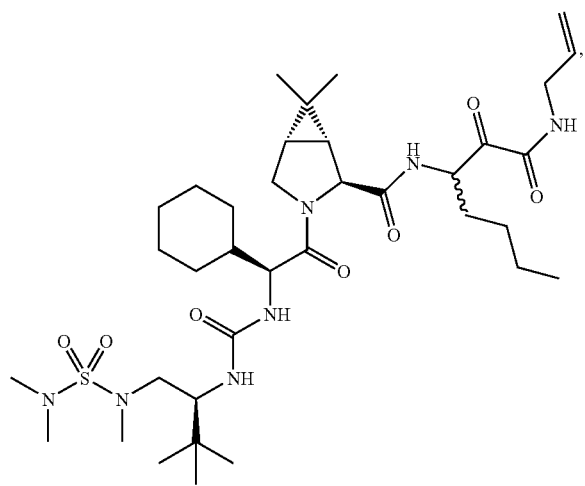

-continued
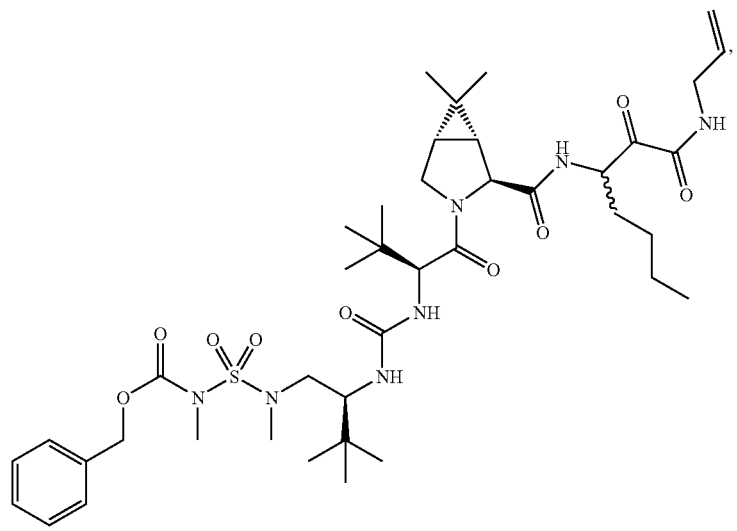
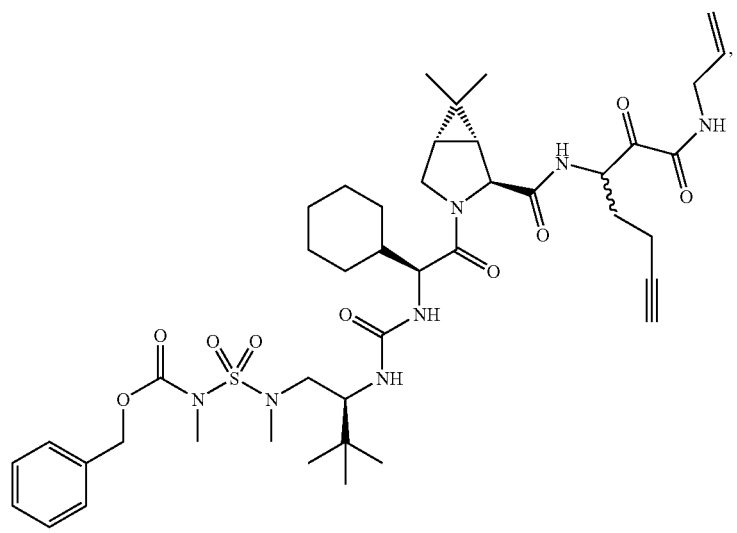
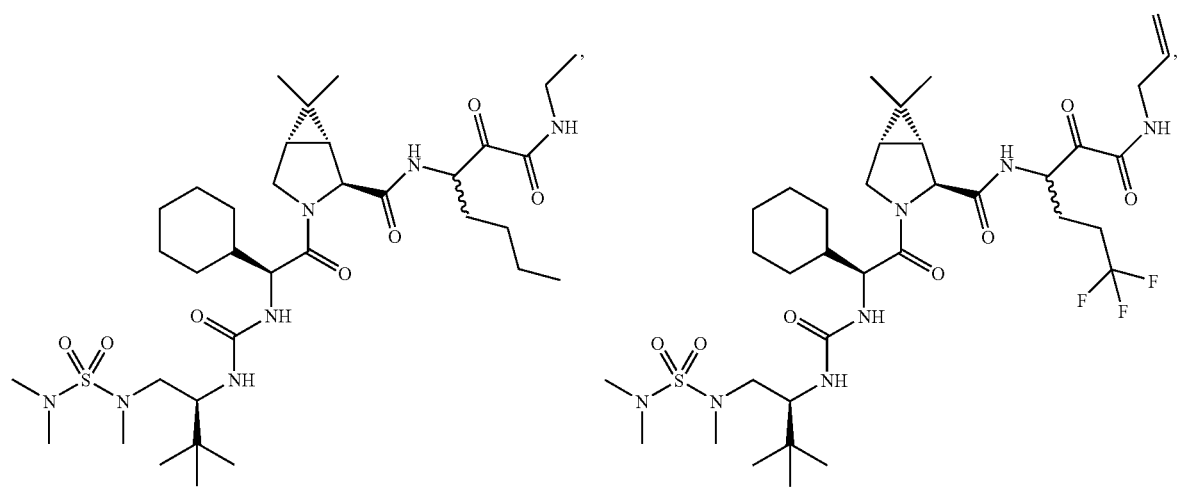

-continued
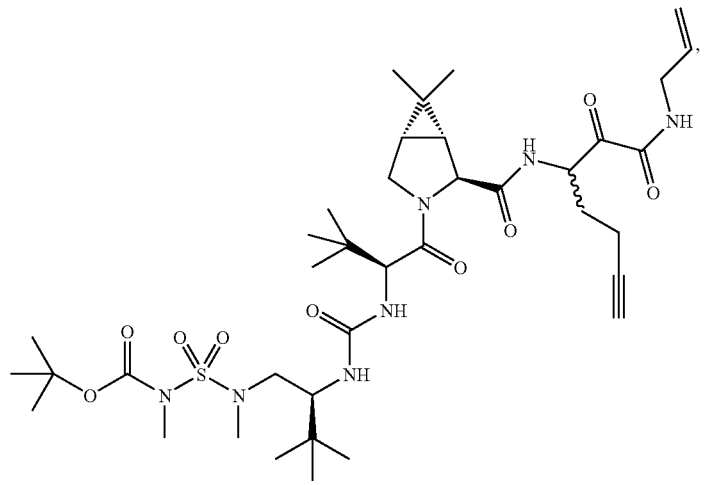
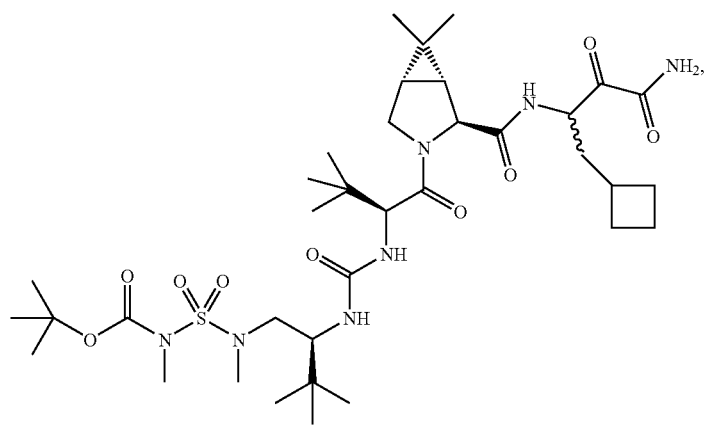
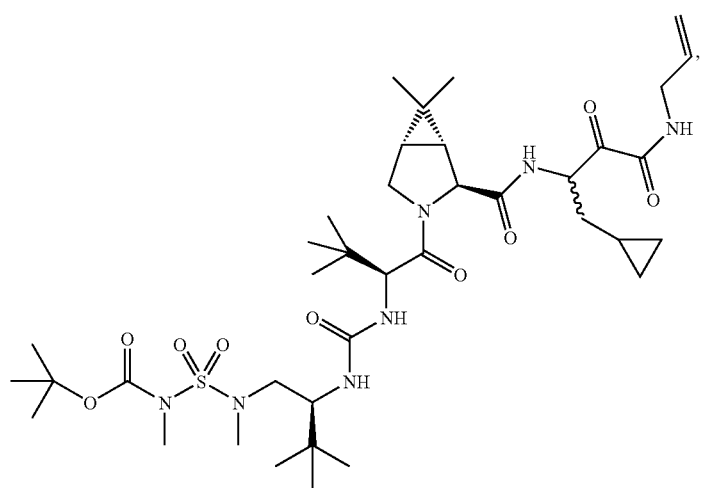

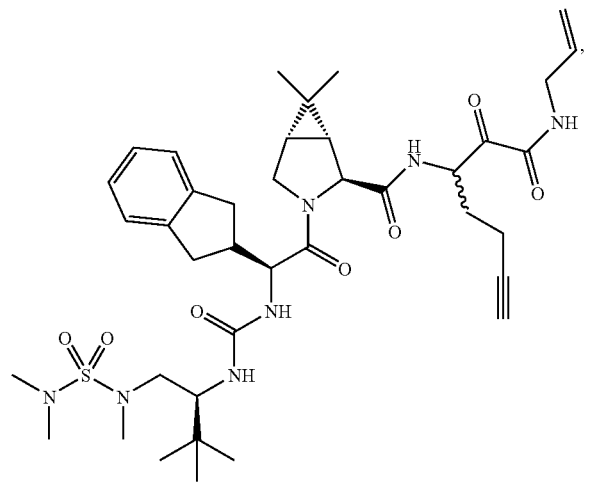
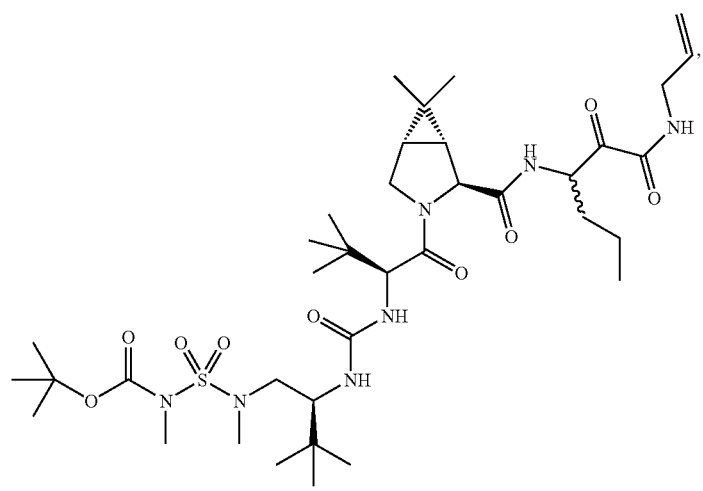
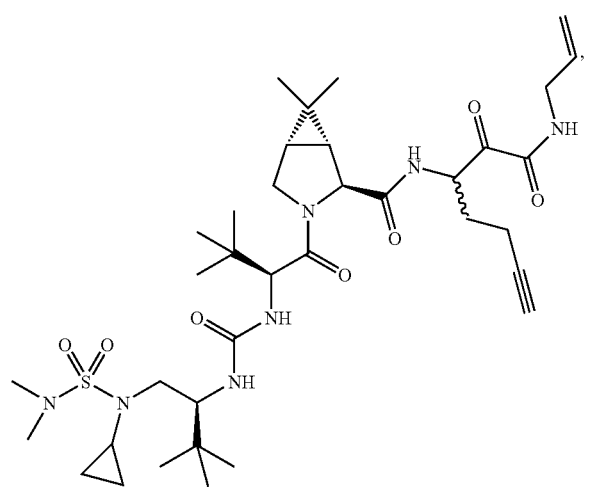

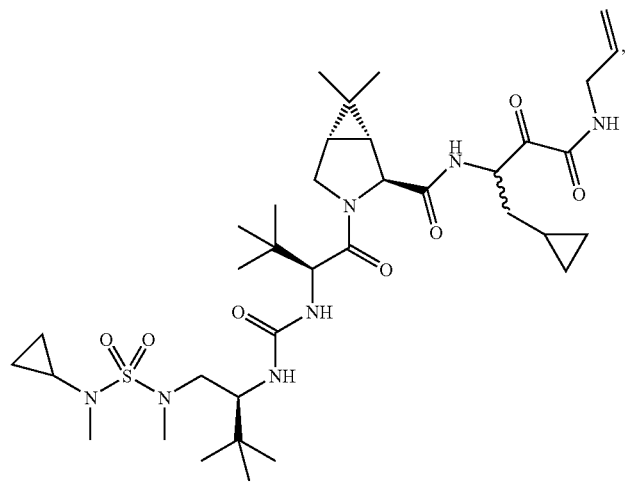
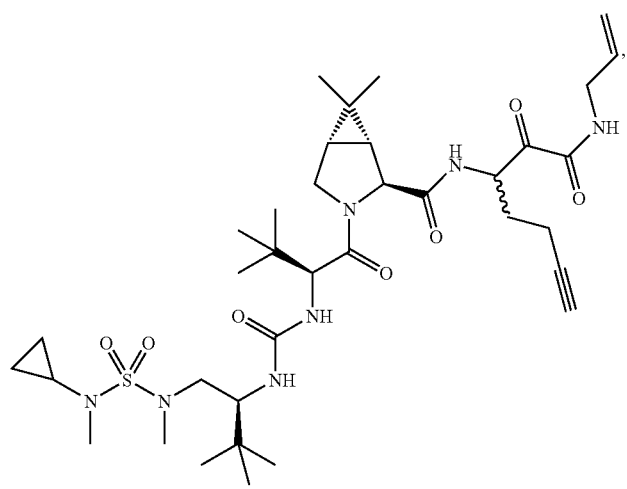
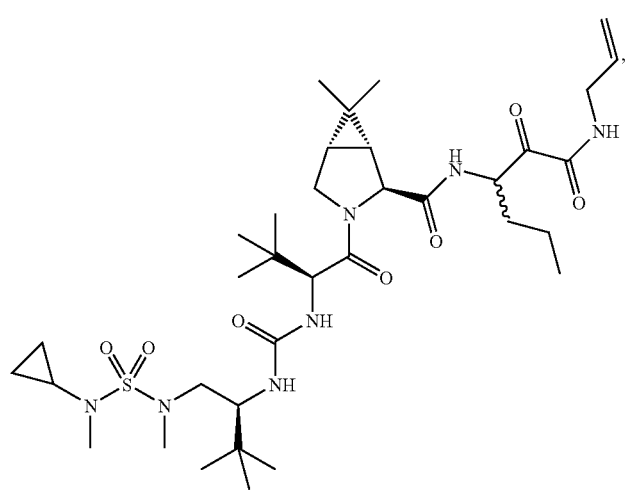

-continued
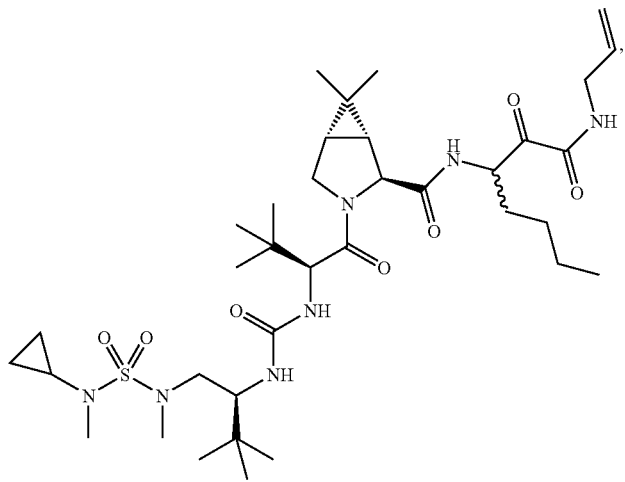
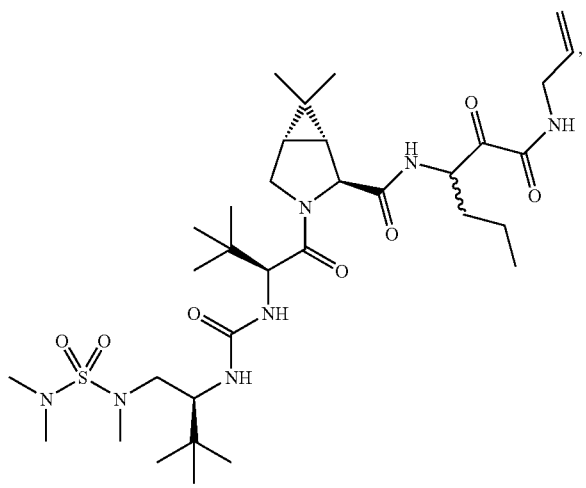
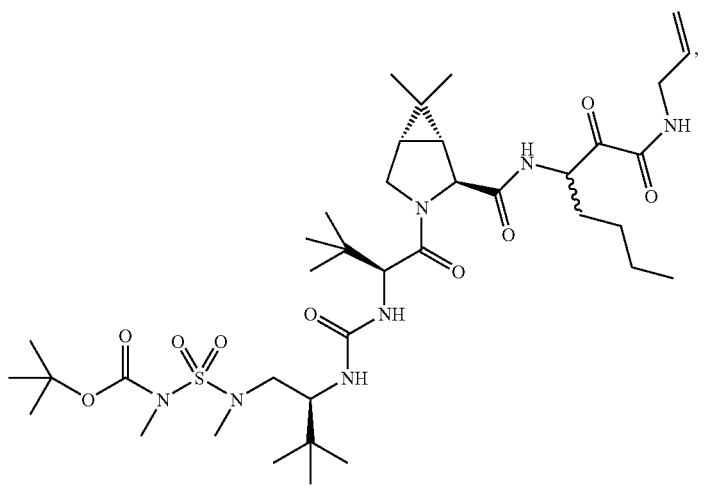

-continued
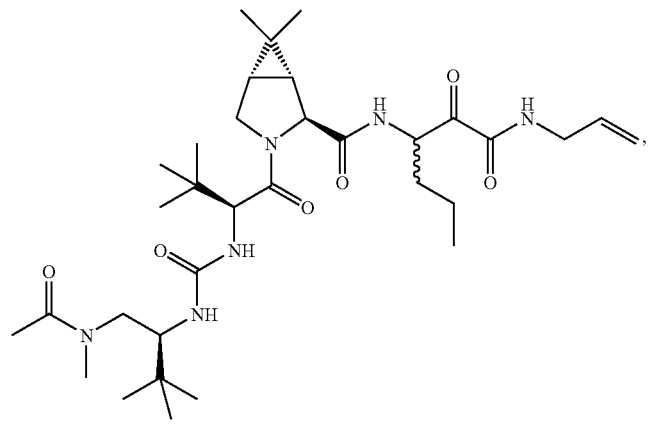
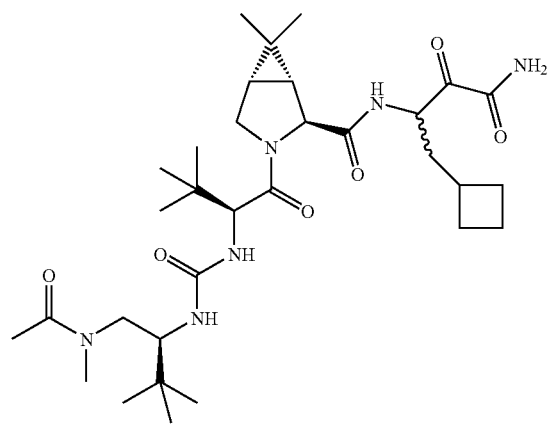
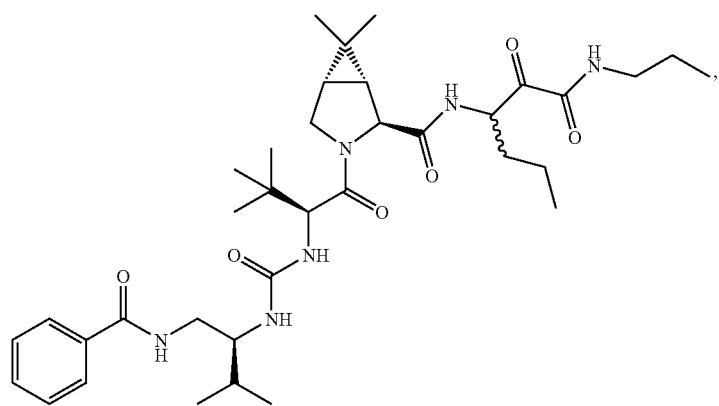
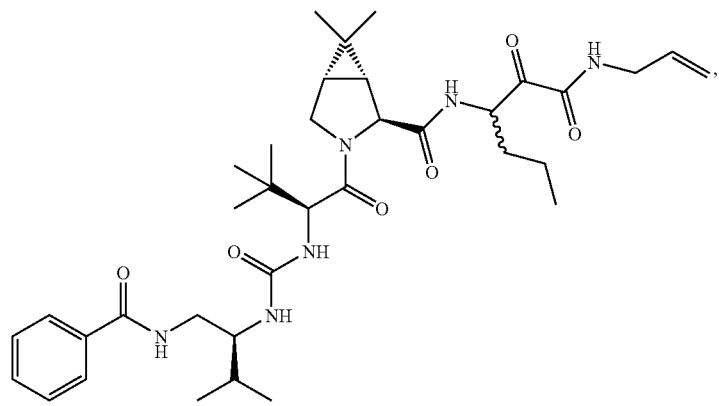

-continued
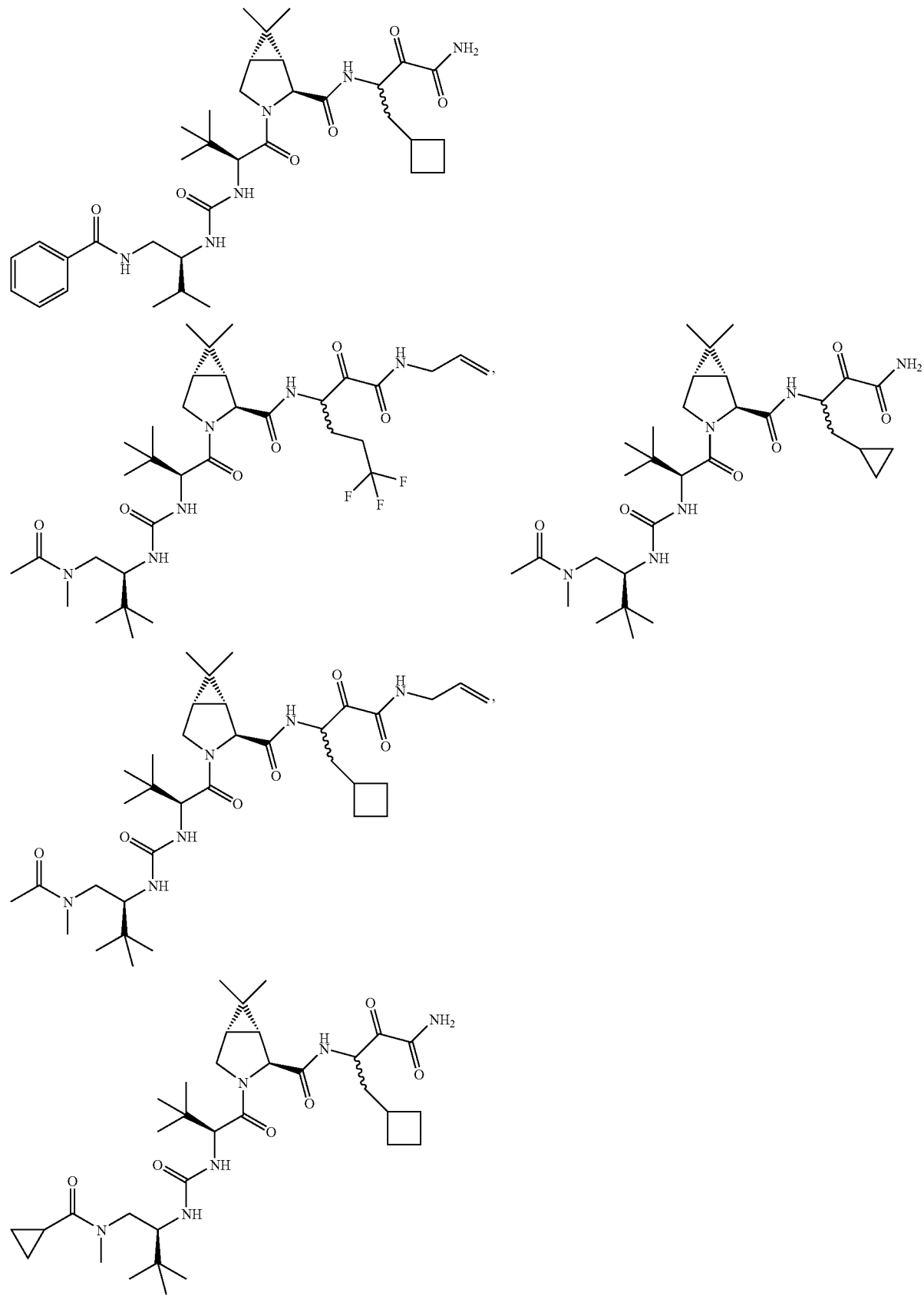

-continued
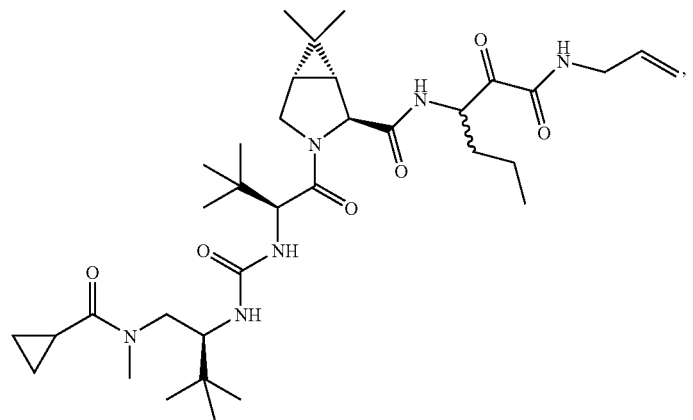
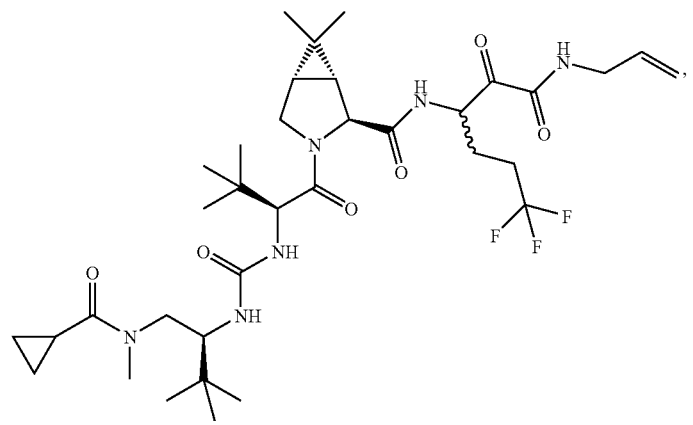
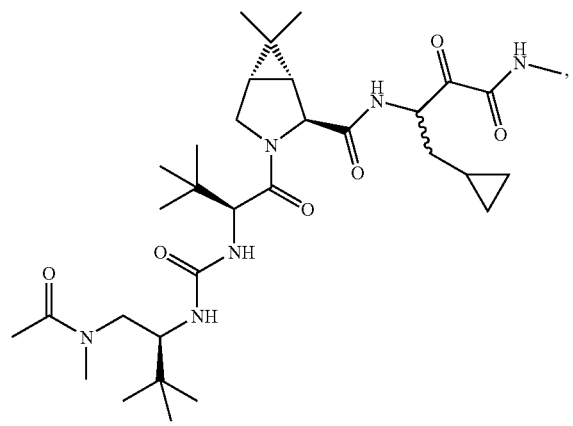
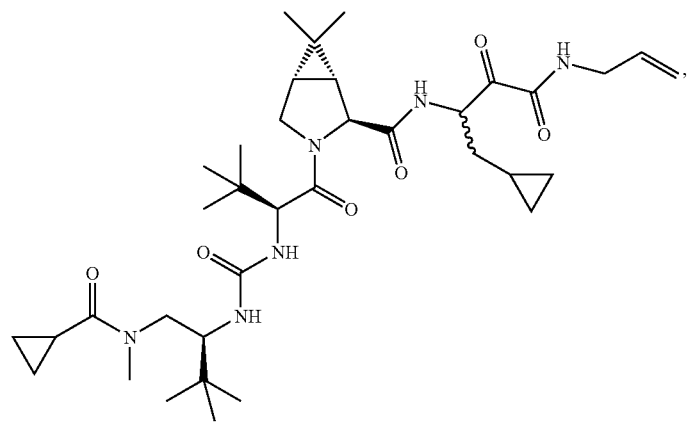

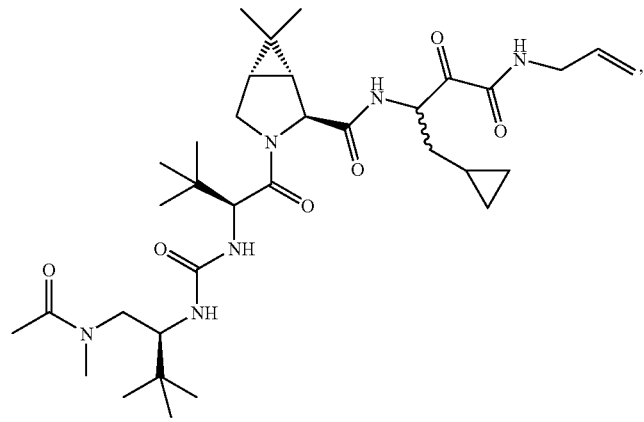
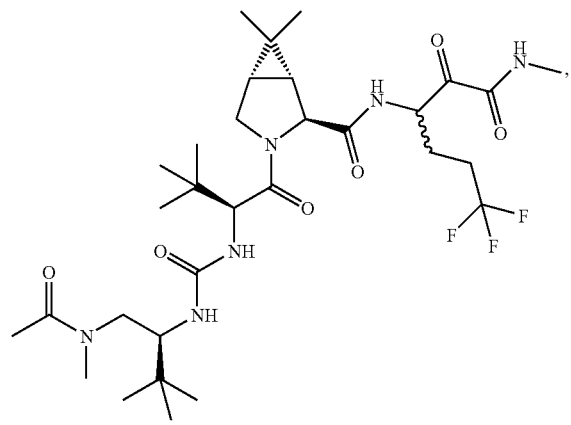
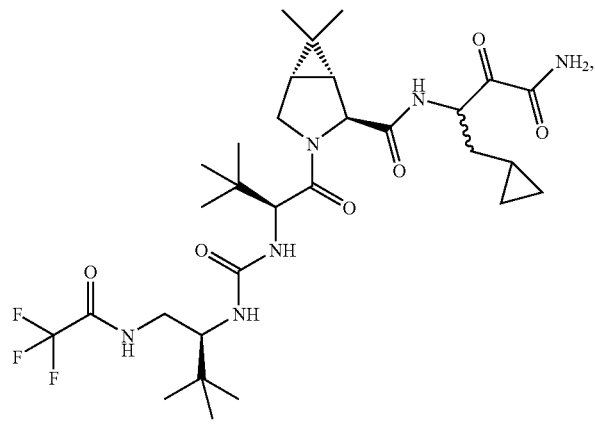
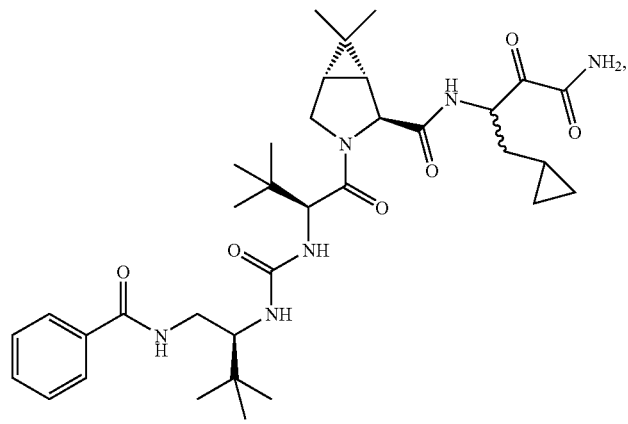

-continued
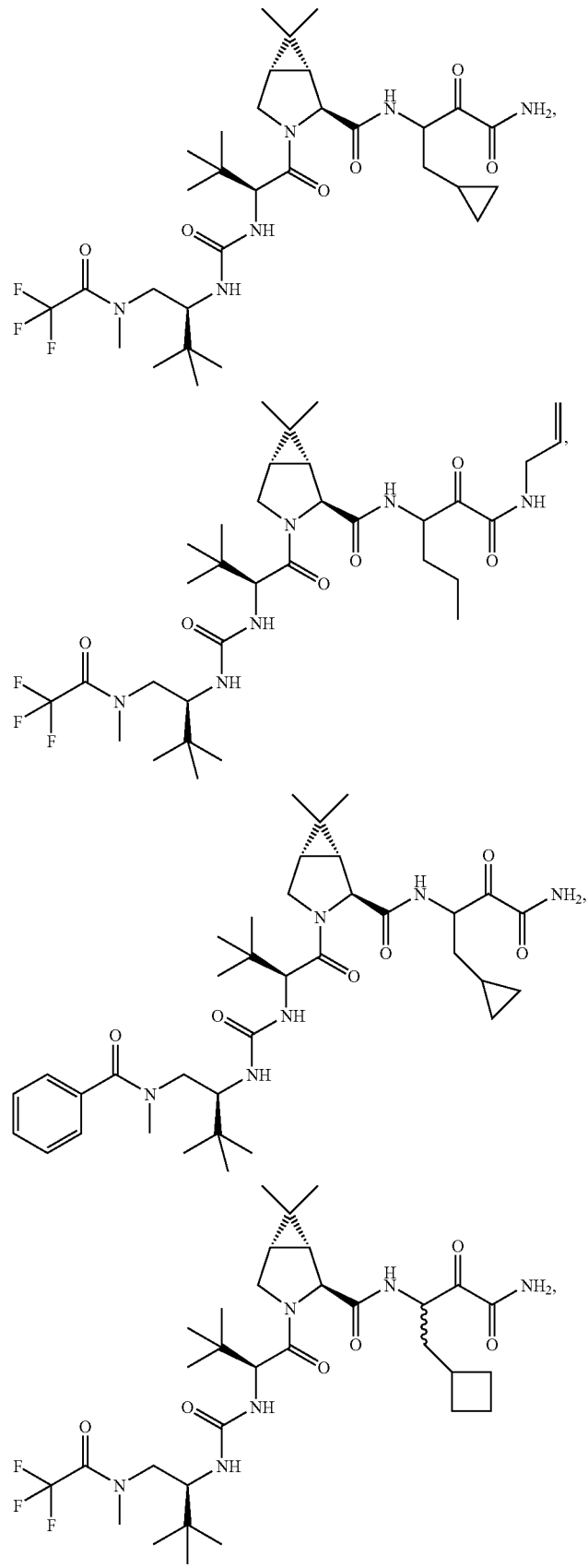

-continued
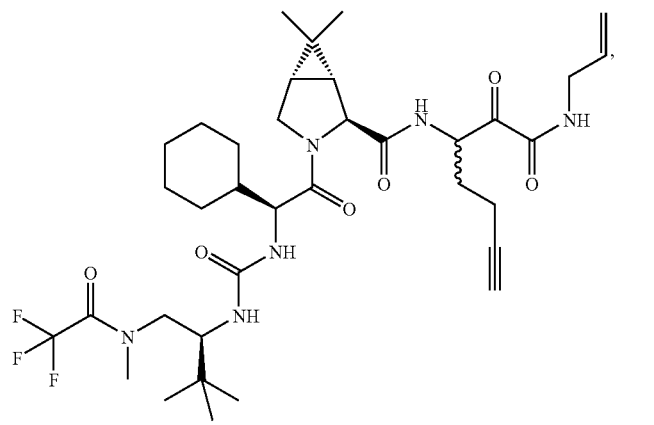
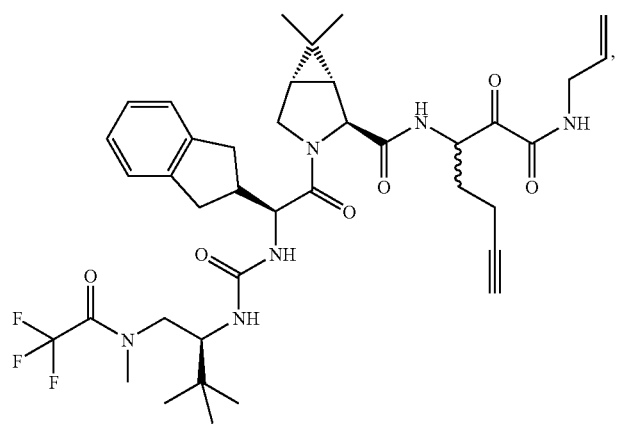
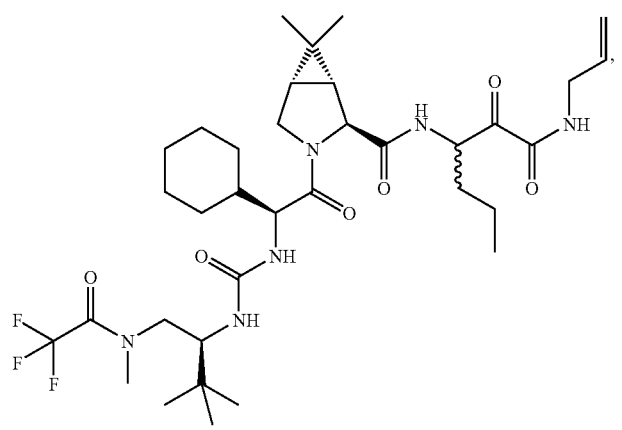
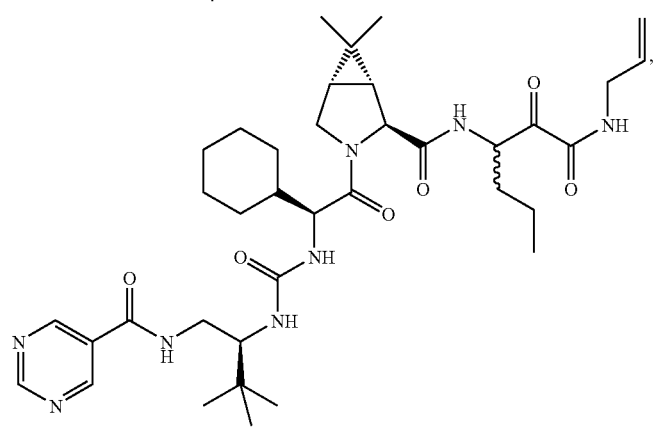

-continued
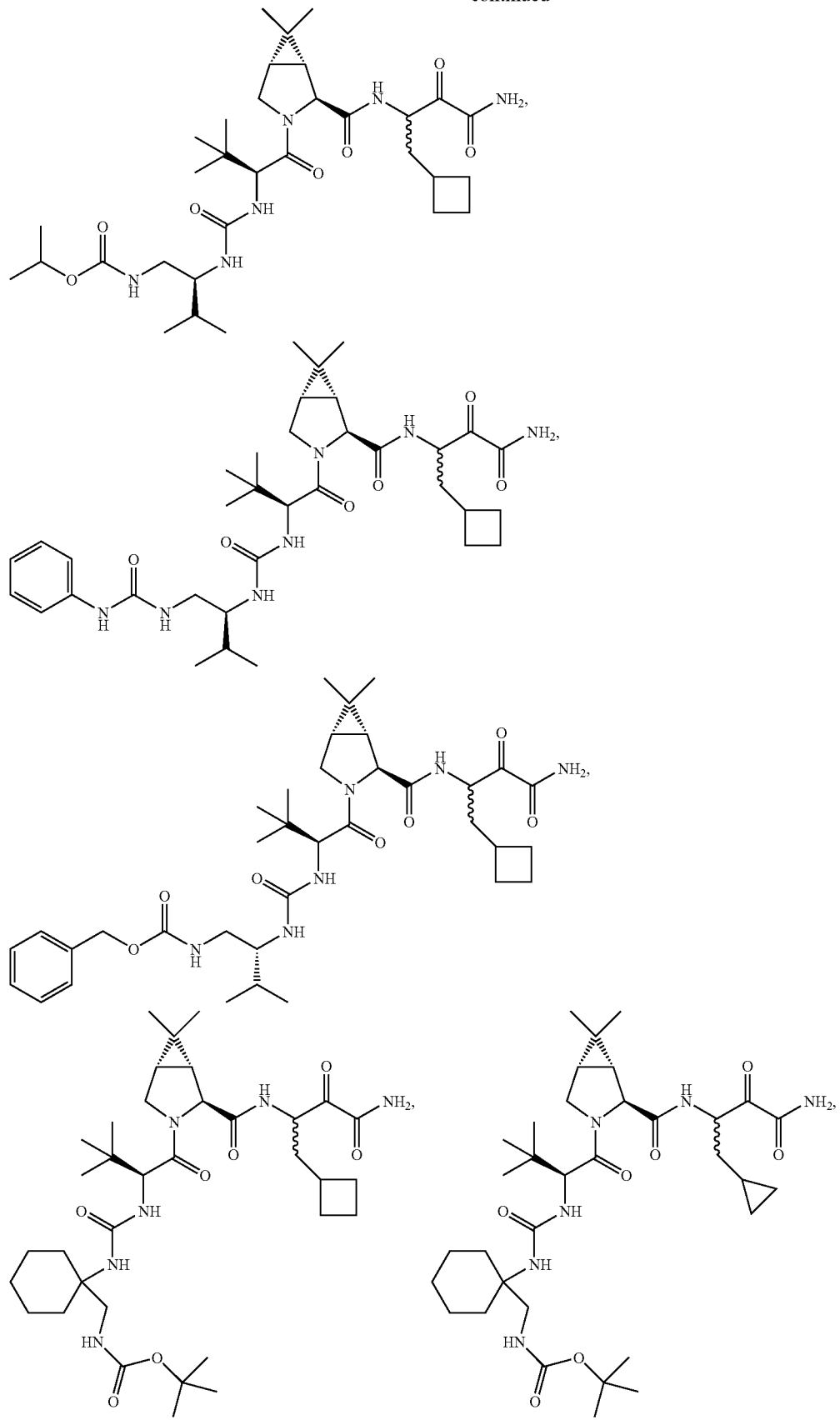

-continued
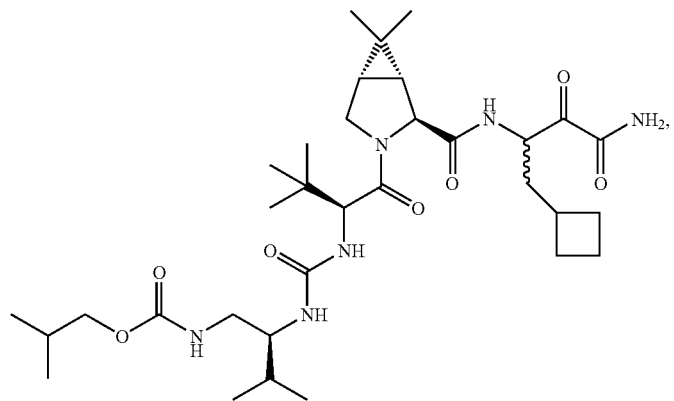
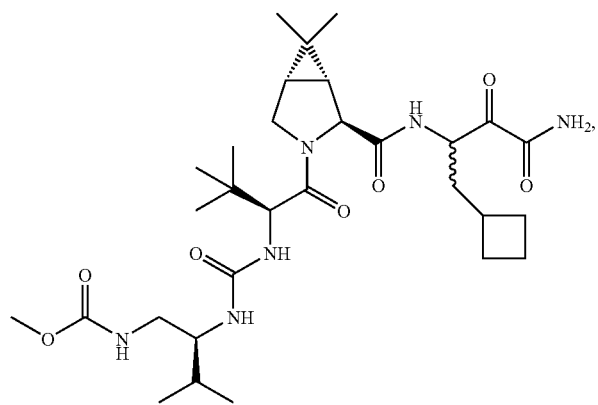
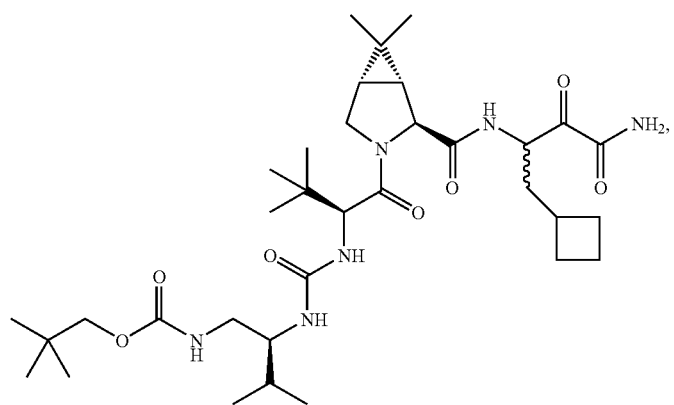
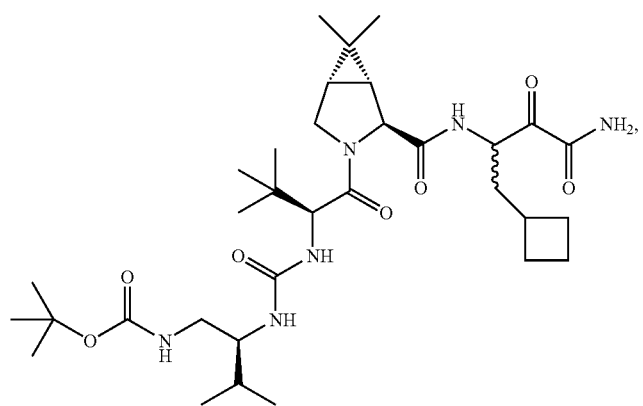

-continued
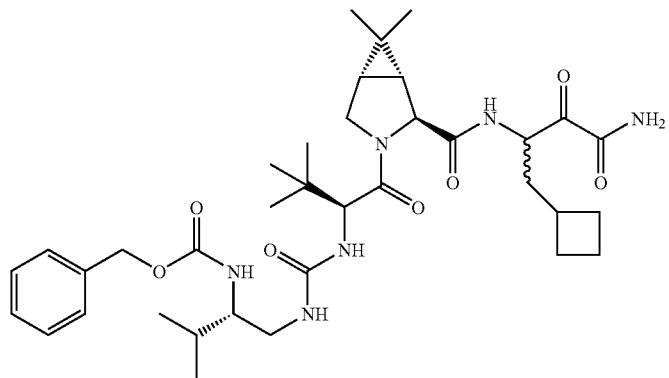
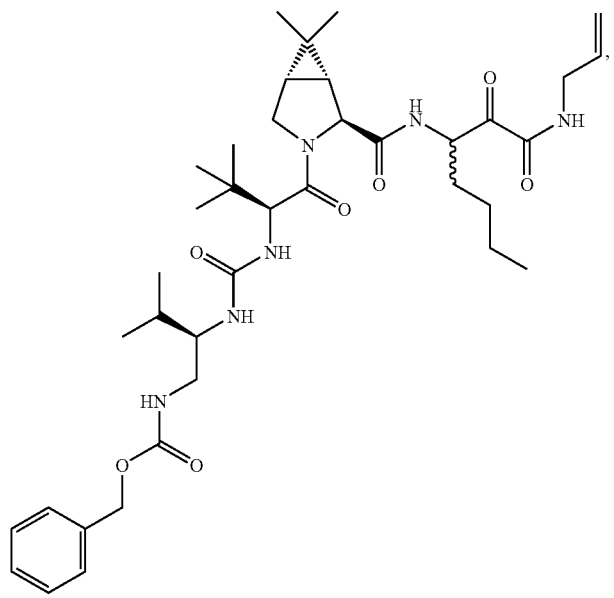
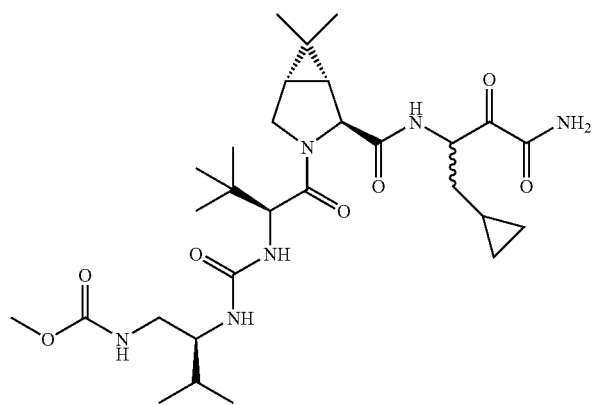

-continued
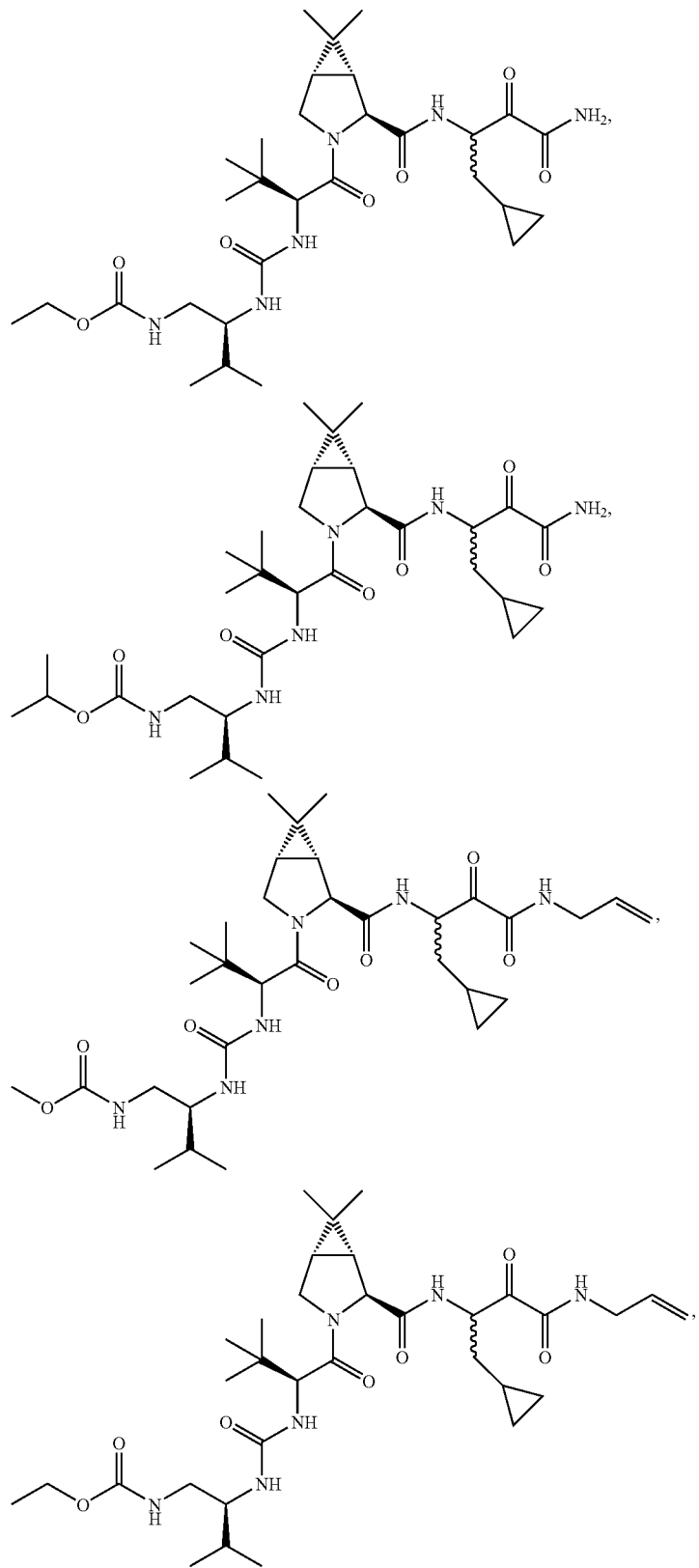

711
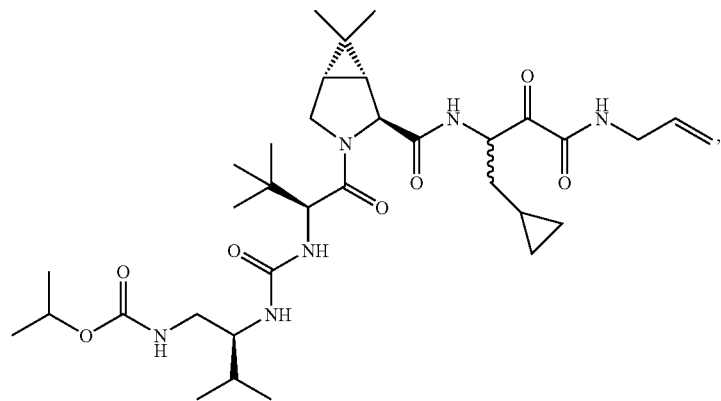
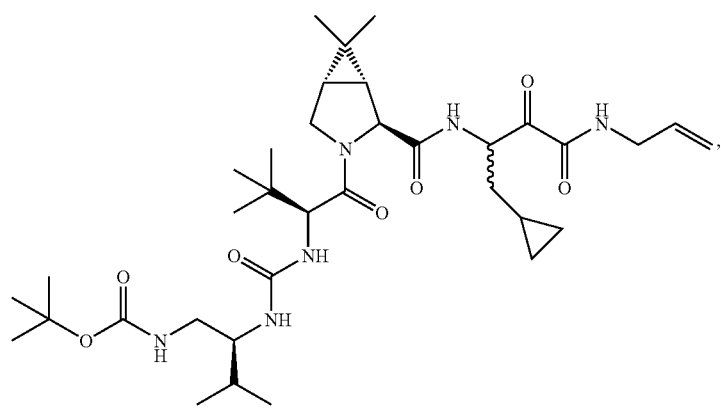
712
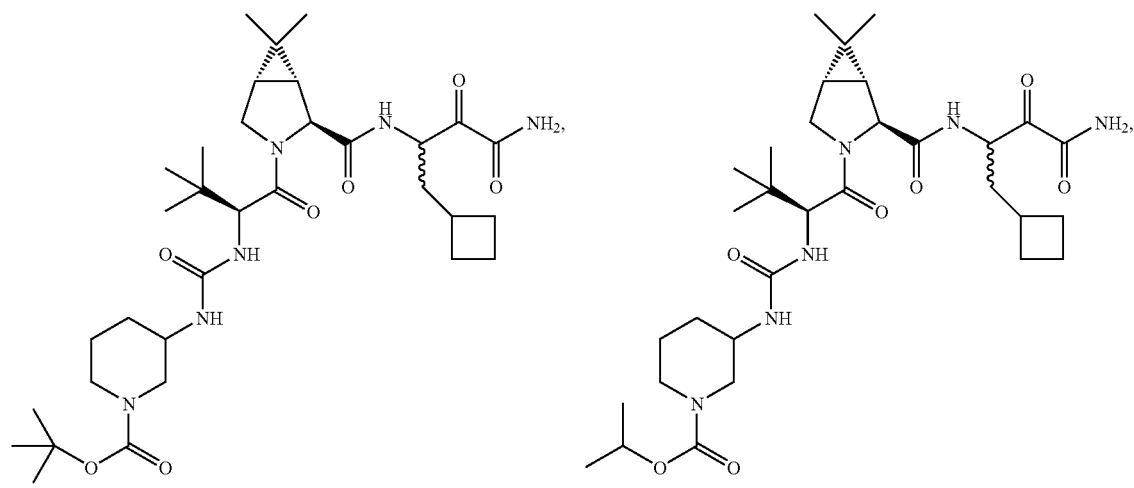

-continued
| 713 | 714 |
|---|---|
| 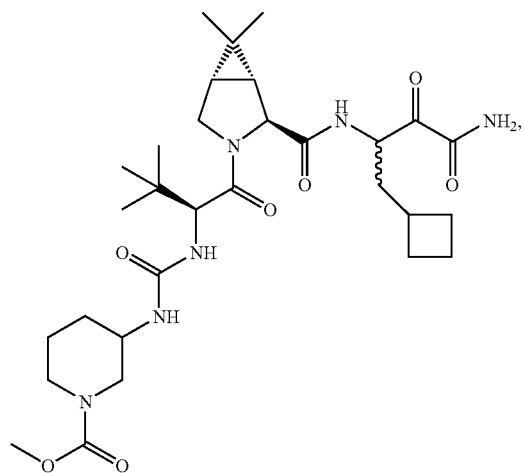 | 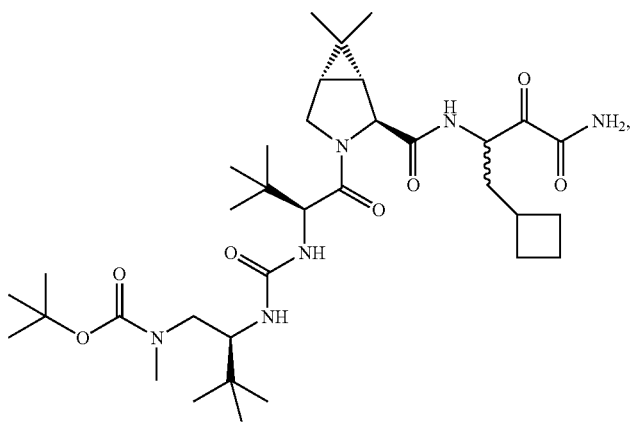 |
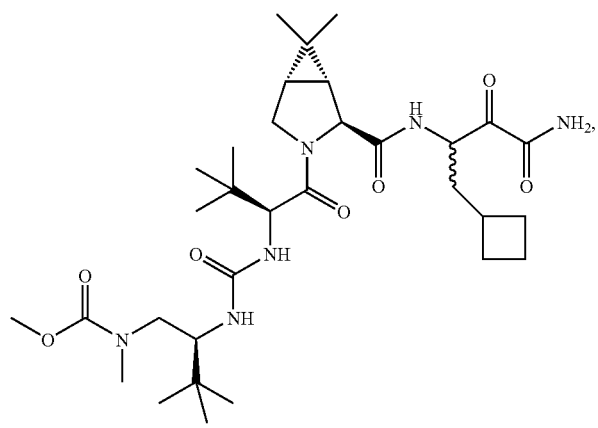
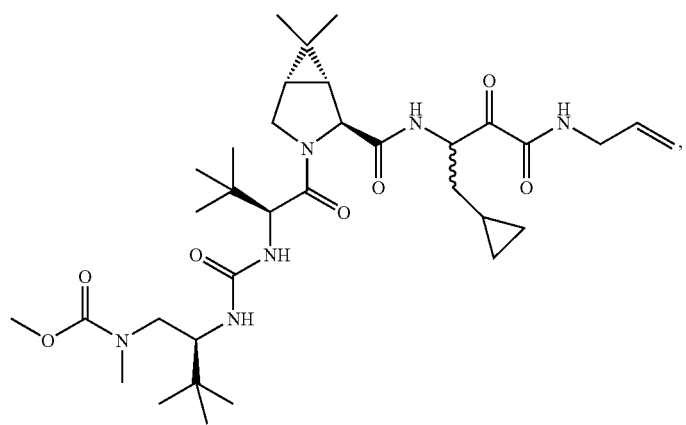

-continued
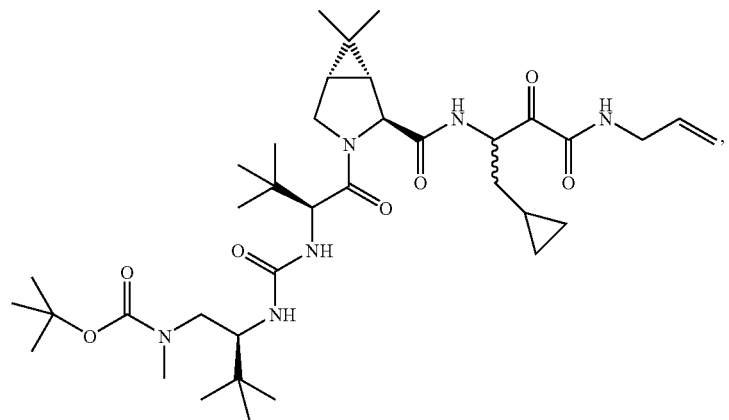
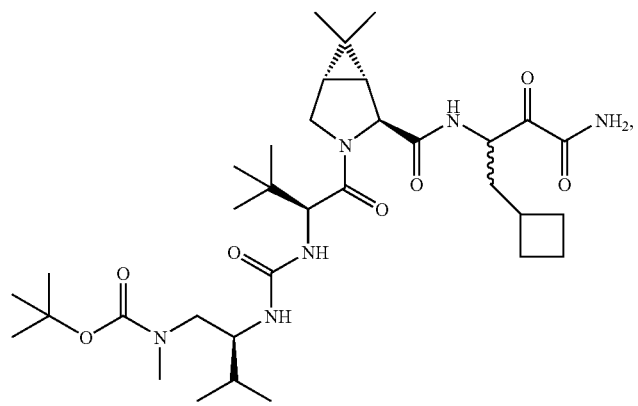
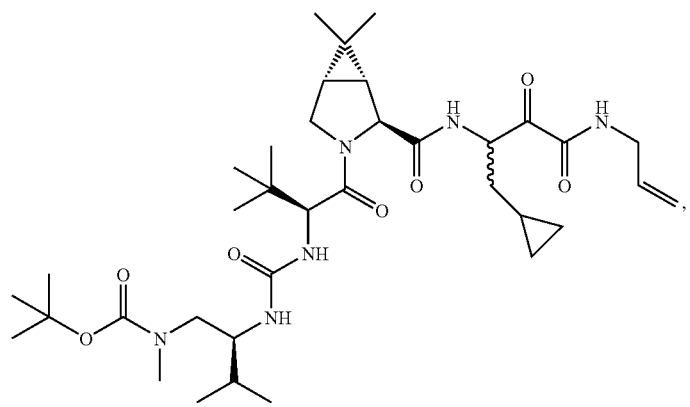
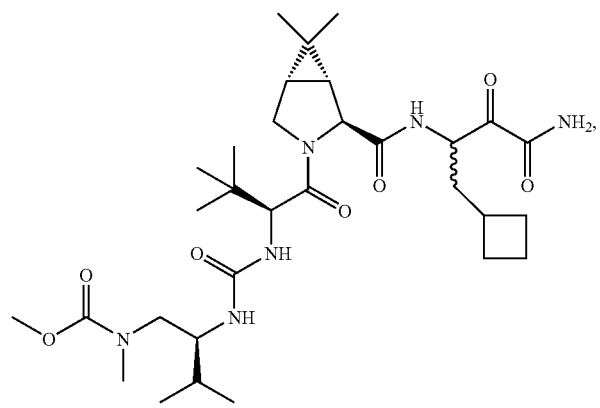

-continued
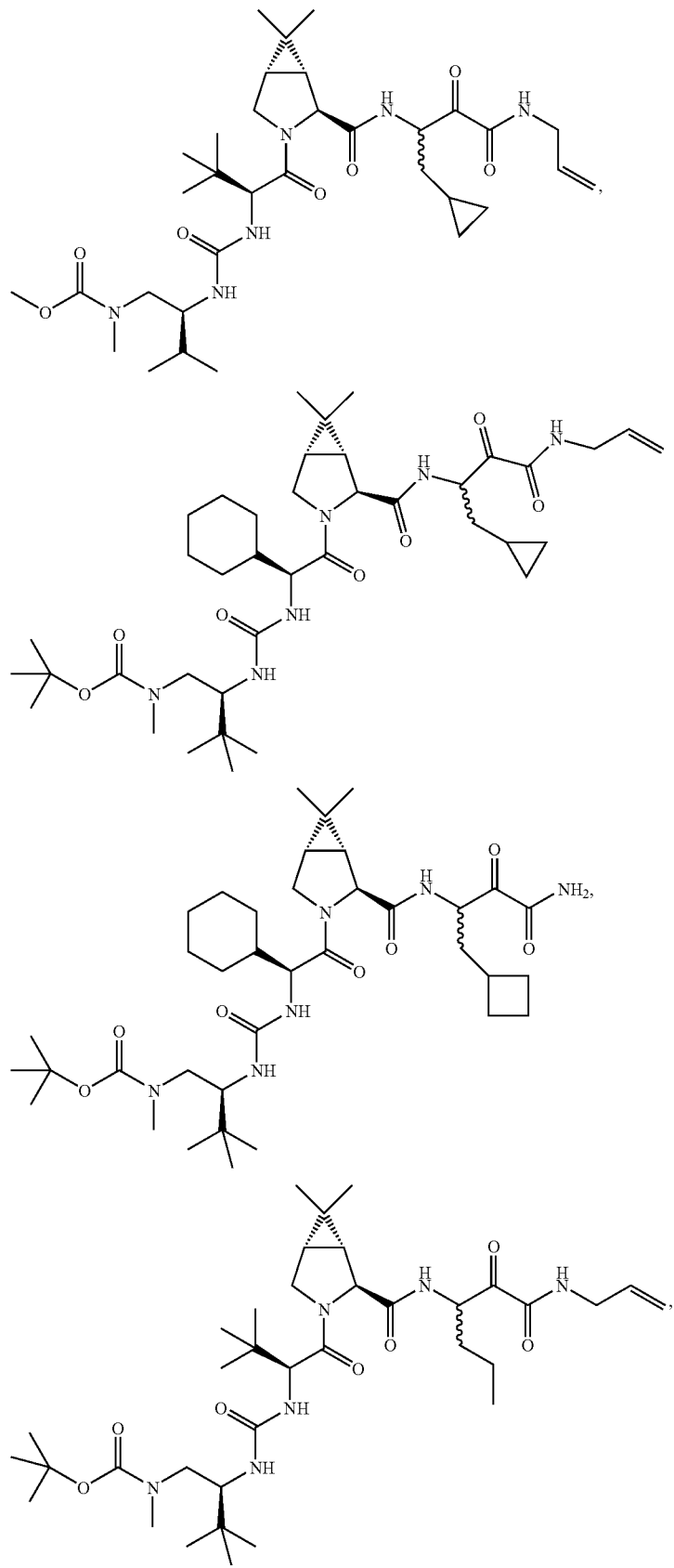

-continued
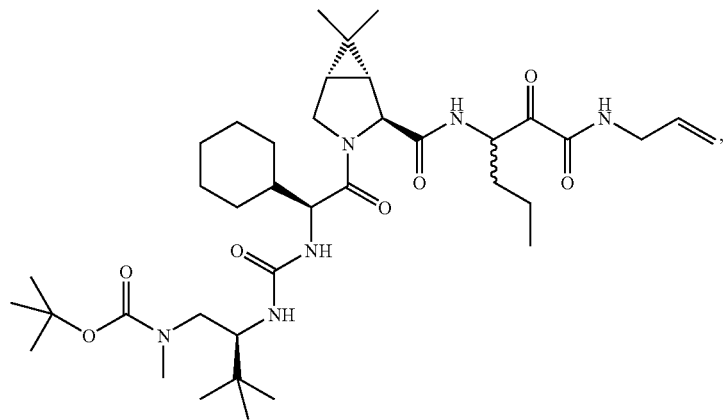
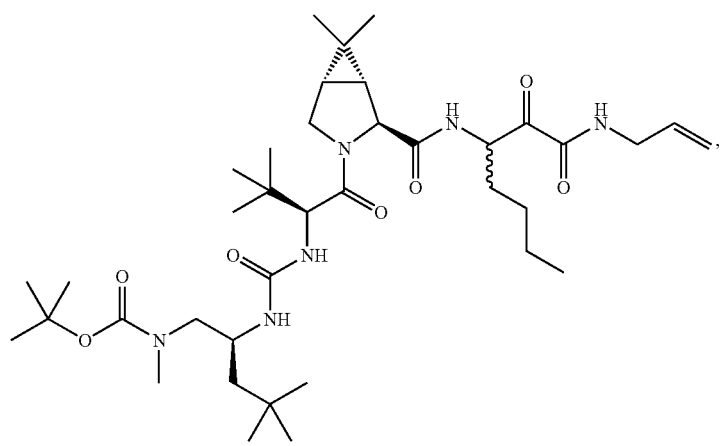
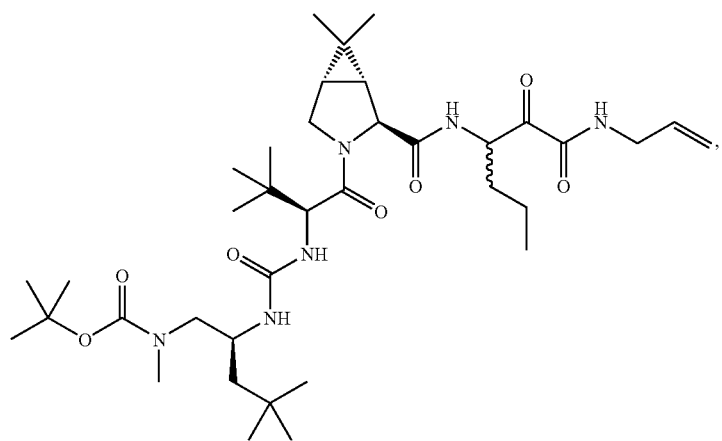

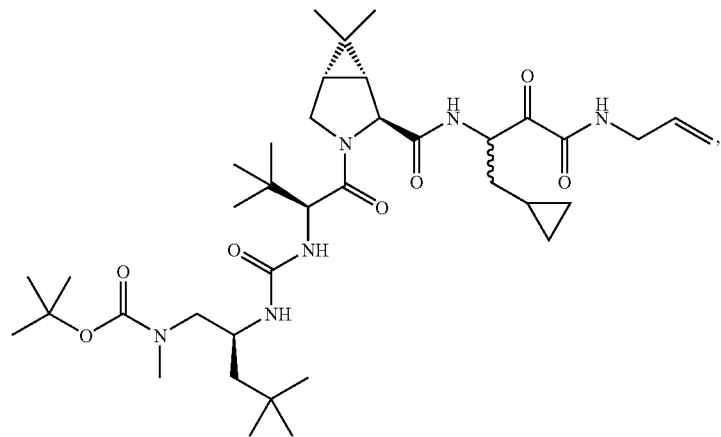
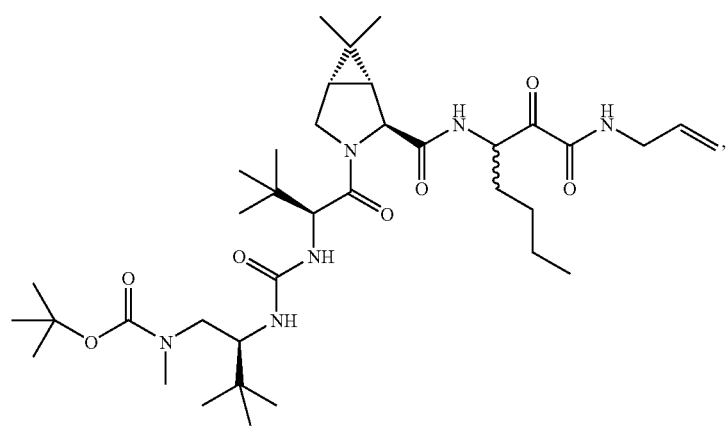
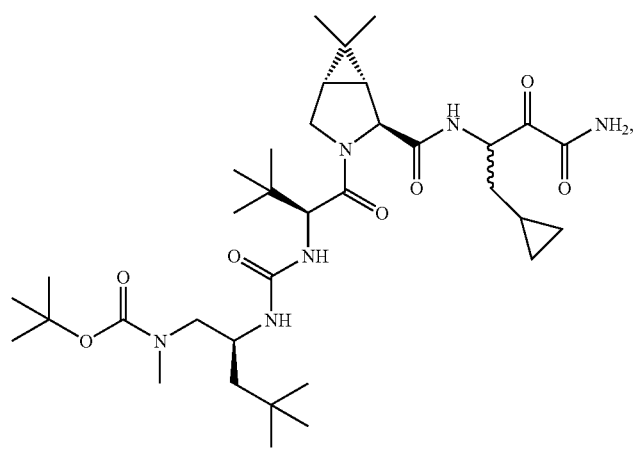

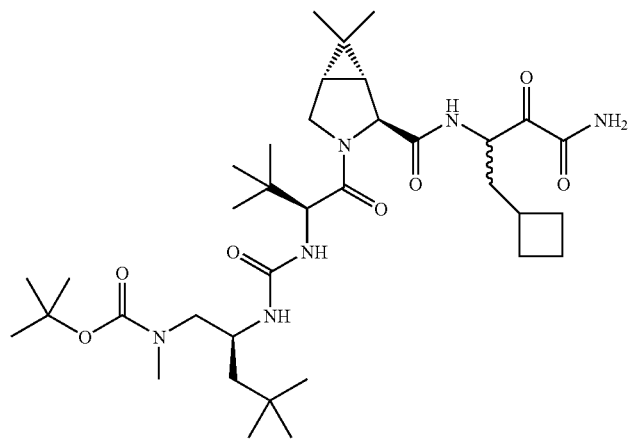
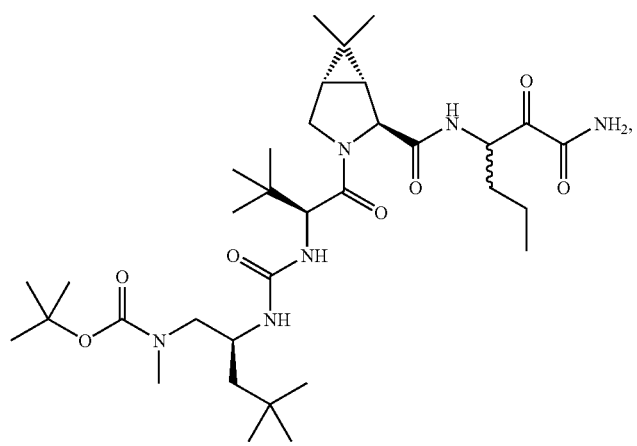
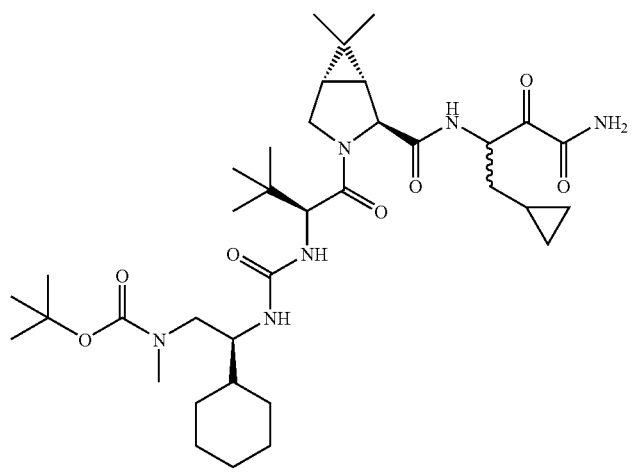

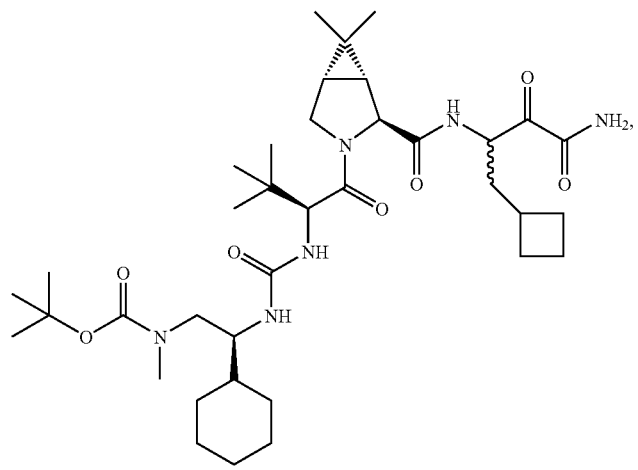
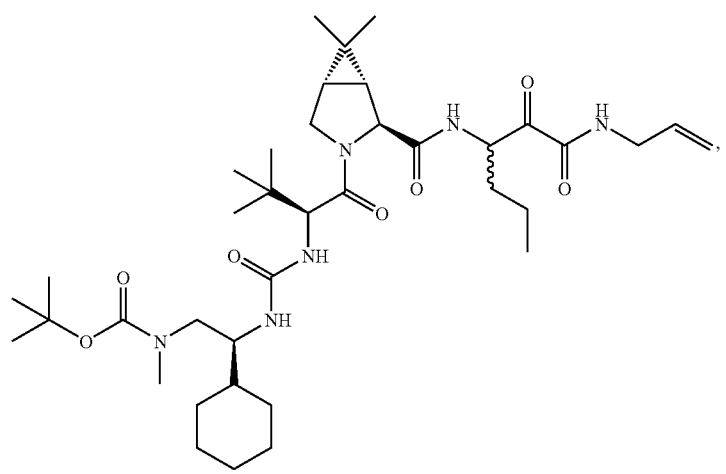
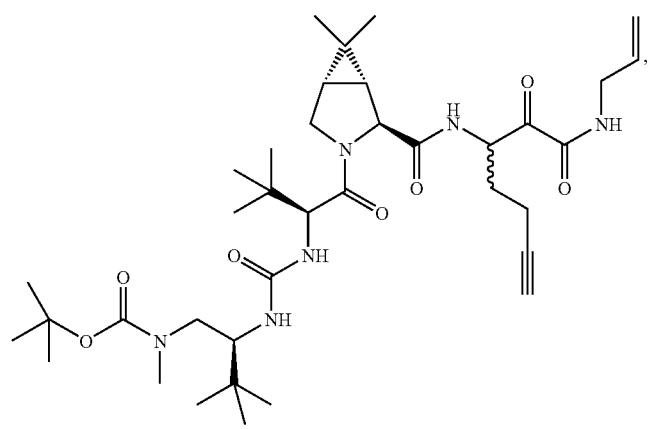

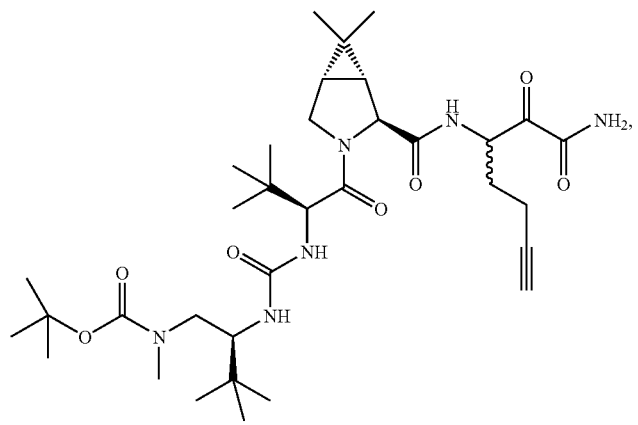
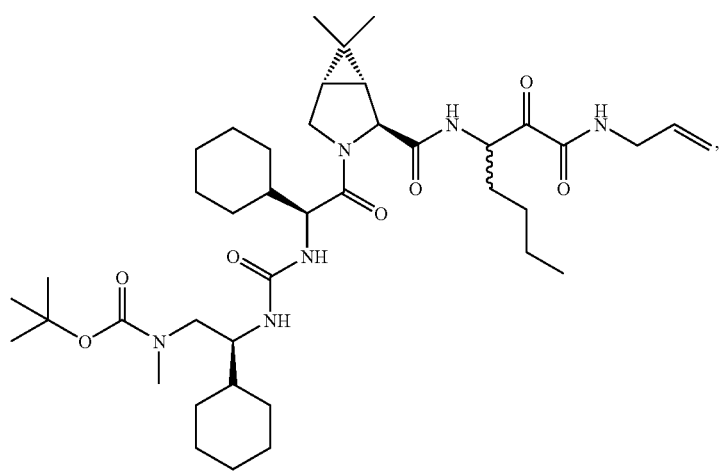
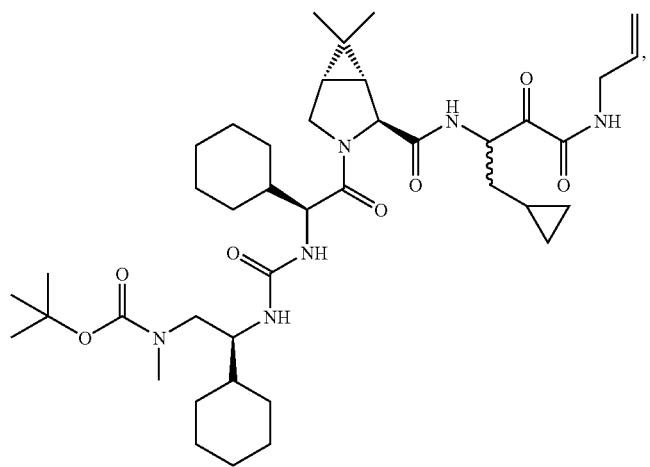

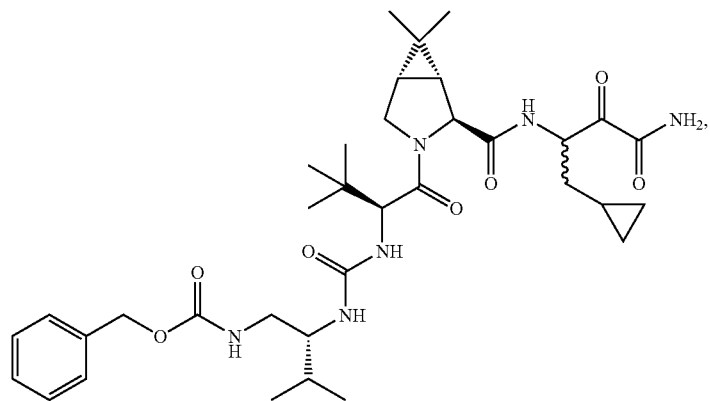
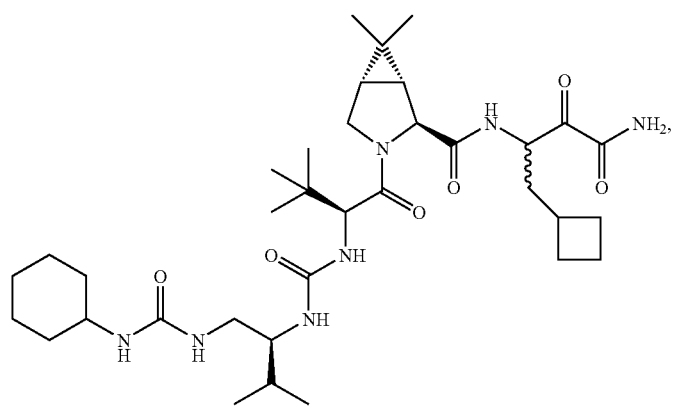
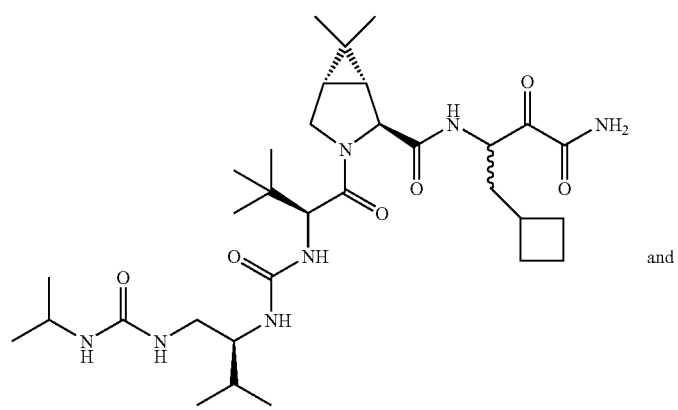

-continued
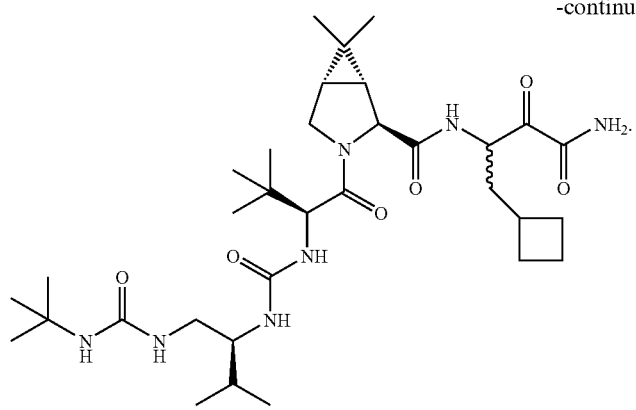
32. A compound of claim 1 in purified form.
33. The compound of claim 1, wherein Y is:
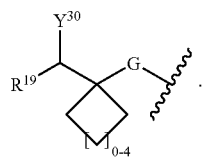
* * * * *

UNITED STATES PATENT AND TRADEMARK OFFICE
CERTIFICATE OF CORRECTION

PATENT NO. : 7,718,691 B2  
APPLICATION NO. : 11/542228  
DATED : May 18, 2010  
INVENTOR(S) : Srikanth Venkatraman et al.

It is certified that error appears in the above-identified patent and that said Letters Patent is hereby corrected as shown below:

On the Title Page Left hand column, under Item (75) Inventors: Line 4:  
Please correct "Wanil Wu" to -- Wanli Wu --

On the Title Page Left hand column, under Item (75) Inventors: Line 11:  
Please correct "Viyyor M. Girijavallabhan" to -- Viyyoor M. Girijavallabhan --

Signed and Sealed this

Twenty-third Day of November, 2010

David J. Kappos  
*Director of the United States Patent and Trademark Office*